United States Patent
Donald et al.

(10) Patent No.: US 11,267,825 B2
(45) Date of Patent: Mar. 8, 2022

(54) HIGHLY ACTIVE AMINO-THIAZOLE SUBSTITUTED INDOLE-2-CARBOXAMIDES ACTIVE AGAINST THE HEPATITIS B VIRUS (HBV)

(71) Applicant: AICURIS GMBH & CO. KG, Wuppertal (DE)

(72) Inventors: Alastair Donald, Wuppertal (DE); Andreas Urban, Sprockhovel (DE); Susanne Bonsmann, Cologne (DE); Anita Wegert, Aldenhofen (DE); Christiaan Gremmen, Velserbroek (NL); Jasper Springer, Diepenveen (NL)

(73) Assignee: AICURIS GMBH & CO. KG, Wuppertal (DE)

( * ) Notice: Subject to any disclaimer, the term of this patent is extended or adjusted under 35 U.S.C. 154(b) by 58 days.

(21) Appl. No.: 16/761,189

(22) PCT Filed: Nov. 2, 2018

(86) PCT No.: PCT/EP2018/000502
§ 371 (c)(1),
(2) Date: May 1, 2020

(87) PCT Pub. No.: WO2019/086141
PCT Pub. Date: May 9, 2019

(65) Prior Publication Data
US 2020/0354379 A1  Nov. 12, 2020

(30) Foreign Application Priority Data
Nov. 2, 2017 (EP) .................... 17199687

(51) Int. Cl.
*C07D 519/00* (2006.01)
*C07D 513/04* (2006.01)

(52) U.S. Cl.
CPC ......... *C07D 519/00* (2013.01); *C07D 513/04* (2013.01)

(58) Field of Classification Search
CPC ..................... C07D 519/00; C07D 513/04

USPC ................................... 514/210.18
See application file for complete search history.

(56) References Cited

U.S. PATENT DOCUMENTS

| | | |
|---|---|---|
| 2014/0221423 A1 | 8/2014 | Sun et al. |
| 2016/0185777 A1 | 6/2016 | Hartman et al. |

FOREIGN PATENT DOCUMENTS

| | | |
|---|---|---|
| WO | 2012174488 A2 | 12/2012 |
| WO | 2016109689 A2 | 7/2016 |

OTHER PUBLICATIONS

International Search Report for PCT/EP2018/000502 dated Feb. 14, 2019.
Liudi Tang et al., "The current status and future directions of hepatitis B antiviral drug discovery," Exper Opinion on Drug Discovery, Nov. 11, 2016, vol. 12, No. 1, pp. 5-15.
Zhi Chen et al., "patents and development of HBV and HCV clinical treatment: form 2001 to Apr. 2005" Expert Opinion on Therapeutic Patents, Informa Healthcare, Jan. 1, 2005, vol. 15, No. 8, pp. 1027-1039.
Database Registry Online, Chemical Abstracts Service, XP002776814, Jul. 6, 2015.
Database Registry Online, Chemical Abstracts Service, XP002776815, May 17, 2015.
Database Registry Online, Chemical Abstracts Service, XP002776816, May 15, 2015.
Database Registry Online, Chemical Abstract Serivice, XP002776817, Jul. 3, 2012.
Database Registry Online, Chemical Abstract Service, XP002776818, Feb. 24, 2009.

*Primary Examiner* — Kahsay Habte
(74) *Attorney, Agent, or Firm* — Millen White Zelano and Branigan, PC; Csaba Henter

(57) ABSTRACT

The present invention relates generally to novel antiviral agents. Specifically, the present invention relates to compounds which can inhibit the protein(s) encoded by hepatitis B virus (HBV) or interfere with the function of the HBV replication cycle, compositions comprising such compounds, methods for inhibiting HBV viral replication, methods for treating or preventing HBV infection, and processes and intermediates for making the compounds.

20 Claims, No Drawings

Specification includes a Sequence Listing.

SEQUENCE LISTING

<160> NUMBER OF SEQ ID NOS: 7

<210> SEQ ID NO 1
<211> LENGTH: 21
<212> TYPE: DNA
<213> ORGANISM: Hepatitis B virus

<400> SEQUENCE: 1
ctgtaccaaa ccttcggacg g                    21

```
<210> SEQ ID NO 2
<211> LENGTH: 18
<212> TYPE: DNA
<213> ORGANISM: Hepatitis B virus

<400> SEQUENCE: 2
aggagaaacg ggctgagg                                                 18

<210> SEQ ID NO 3
<211> LENGTH: 26
<212> TYPE: DNA
<213> ORGANISM: Hepatitis B virus

<400> SEQUENCE: 3
ccatcatcct gggctttcgg aaaatt                                        26

<210> SEQ ID NO 4
<211> LENGTH: 24
<212> TYPE: DNA
<213> ORGANISM: Hepatitis B virus

<400> SEQUENCE: 4
tgcagaggtg aagcgaagtg caca                                          24

<210> SEQ ID NO 5
<211> LENGTH: 24
<212> TYPE: DNA
<213> ORGANISM: Hepatitis B virus

<400> SEQUENCE: 5
gacgtccttt gtttacgtcc cgtc                                          24

<210> SEQ ID NO 6
<211> LENGTH: 25
<212> TYPE: DNA
<213> ORGANISM: Hepatitis B virus

<400> SEQUENCE: 6
acggggcgca cctctcttta cgcgg                                         25

<210> SEQ ID NO 7
<211> LENGTH: 26
<212> TYPE: DNA
<213> ORGANISM: Hepatitis B virus

<400> SEQUENCE: 7
ctccccgtct gtgccttctc atctgc                                        26
```

HIGHLY ACTIVE AMINO-THIAZOLE SUBSTITUTED INDOLE-2-CARBOXAMIDES ACTIVE AGAINST THE HEPATITIS B VIRUS (HBV)

INTRODUCTION

A series of novel, highly active amino-thiazole substituted indole-2-carboxamides active against the hepatitis B virus (HBV), having general structure I were identified. This novel class of anti-HBV agent demonstrates excellent in vitro potency, along with good metabolic stability, acceptable solubility, high permeability and in vivo activity.

TECHNICAL FIELD

The present invention relates generally to novel antiviral agents. Specifically, the present invention relates to compounds which can inhibit the protein(s) encoded by hepatitis B virus (HBV) or interfere with the function of the HBV replication cycle, compositions comprising such compounds, methods for inhibiting HBV viral replication, methods for treating or preventing HBV infection, and processes and intermediates for making the compounds.

BACKGROUND OF THE INVENTION

Chronic HBV infection is a significant global health problem, affecting over 5% of the world population (over 350 million people worldwide and 1.25 million individuals in the US). Despite the availability of a prophylactic HBV vaccine, the burden of chronic HBV infection continues to be a significant unmet worldwide medical problem, due to suboptimal treatment options and sustained rates of new infections in most parts of the developing world. Current treatments do not provide a cure and are limited to only two classes of agents (interferon alpha and nucleoside analogues/inhibitors of the viral polymerase); drug resistance, low efficacy, and tolerability issues limit their impact.

The low cure rates of HBV are attributed at least in part to the fact that complete suppression of virus production is difficult to achieve with a single antiviral agent, and to the presence and persistence of covalently closed circular DNA (cccDNA) in the nucleus of infected hepatocytes. However, persistent suppression of HBV DNA slows liver disease progression and helps to prevent hepatocellular carcinoma (HCC).

Current therapy goals for HBV-infected patients are directed to reducing serum HBV DNA to low or undetectable levels, and to ultimately reducing or preventing the development of cirrhosis and HCC.

The HBV is an enveloped, partially double-stranded DNA (dsDNA) virus of the hepadnavirus family (Hepadnaviridae). HBV capsid protein (HBV-CP) plays essential roles in HBV replication. The predominant biological function of HBV-CP is to act as a structural protein to encapsidate pre-genomic RNA and form immature capsid particles, which spontaneously self-assemble from many copies of capsid protein dimers in the cytoplasm.

HBV-CP also regulates viral DNA synthesis through differential phosphorylation states of its C-terminal phosphorylation sites. Also, HBV-CP might facilitate the nuclear translocation of viral relaxed circular genome by means of the nuclear localization signals located in the arginine-rich domain of the C-terminal region of HBV-CP.

In the nucleus, as a component of the viral cccDNA mini-chromosome, HBV-CP could play a structural and regulatory role in the functionality of cccDNA mini-chromosomes. HBV-CP also interacts with viral large envelope protein in the endoplasmic reticulum (ER), and triggers the release of intact viral particles from hepatocytes.

HBV-CP related anti-HBV compounds have been reported. For example, phenylpropenamide derivatives, including compounds named AT-61 and AT-130 (Feld J. et al. Antiviral Res. 2007, 76, 168), and a class of thiazolidin-4-ones from Valeant (WO2006/033995), have been shown to inhibit pre-genomic RNA (pgRNA) packaging.

F. Hoffmann-La Roche AG have disclosed a series of 3-substituted tetrahydro-pyrazolo[1,5-a]pyrazines for the therapy of HBV (WO2016/113273, WO2017/198744, WO2018/011162, WO2018/011160, WO2018/011163).

Heteroaryldihydropyrimidines (HAPs) were discovered in a tissue culture-based screening (Weber et al., Antiviral Res. 2002, 54, 69). These HAP analogs act as synthetic allosteric activators and are able to induce aberrant capsid formation that leads to degradation of HBV-CP (WO 99/54326, WO 00/58302, WO 01/45712, WO 01/6840). Further HAP analogs have also been described (J. Med. Chem. 2016, 59 (16), 7651-7666).

A subclass of HAPs from F. Hoffman-La Roche also shows activity against HBV (WO2014/184328, WO2015/132276, and WO2016/146598). A similar subclass from Sunshine Lake Pharma also shows activity against HBV (WO2015/144093). Further HAPs have also been shown to possess activity against HBV (WO2013/102655, Bioorg. Med. Chem. 2017, 25(3) pp. 1042-1056, and a similar subclass from Enanta Therapeutics shows similar activity (WO2017/011552). A further subclass from Medshine Discovery shows similar activity (WO2017/076286). A further subclass (Janssen Pharma) shows similar activity (WO2013/102655).

A subclass of pyridazones and triazinones (F. Hoffman-La Roche) also show activity against HBV (WO2016/023877), as do a subclass of tetrahydropyridopyridines (WO2016/177655). A subclass of tricyclic 4-pyridone-3-carboxylic acid derivatives from Roche also show similar anti-HBV activity (WO2017/013046).

A subclass of sulfamoyl-arylamides from Novira Therapeutics (now part of Johnson & Johnson Inc.) also shows activity against HBV (WO2013/006394, WO2013/096744, WO2014/165128, WO2014/184365, WO2015/109130, WO2016/089990, WO2016/109663, WO2016/109684, WO2016/109689, WO2017/059059). A similar subclass of thioether-arylamides (also from Novira Therapeutics) shows activity against HBV (WO2016/089990). Additionally, a subclass of aryl-azepanes (also from Novira Therapeutics) shows activity against HBV (WO2015/073774). A similar subclass of arylamides from Enanta Therapeutics show activity against HBV (WO2017/015451).

Sulfamoyl derivatives from Janssen Pharma have also been shown to possess activity against HBV (WO2014/033167, WO2014/033170, WO2017001655, J. Med. Chem, 2018, 61(14) 6247-6260). A similar class of glyoxamide substituted pyrrolamides (Gilead Sciences) has also been described (WO2018039531).

A subclass of glyoxamide substituted pyrrolamide derivatives also from Janssen Pharma have also been shown to possess activity against HBV (WO2015/011281). A similar class of glyoxamide substituted pyrrolamides (Gilead Sciences) has also been described (WO2018039531).

A subclass of sulfamoyl- and oxalyl-heterobiaryls from Enanta Therapeutics also show activity against HBV (WO2016/161268, WO2016/183266, WO2017/015451, WO2017/136403 & US20170253609).

A subclass of aniline-pyrimidines from Assembly Biosciences also show activity against HBV (WO2015/057945, WO2015/172128). A subclass of fused tri-cycles from Assembly Biosciences (dibenzo-thiazepinones, dibenzo-diazepinones, dibenzo-oxazepinones) show activity against HBV (WO2015/138895, WO2017/048950).

A series of cyclic sulfamides has been described as modulators of HBV-CP function by Assembly Biosciences (WO2018/160878).

Arbutus Biopharma have disclosed a series of benzamides for the therapy of HBV (WO2018/052967, WO2018/172852).

It was also shown that the small molecule bis-ANS acts as a molecular 'wedge' and interferes with normal capsid-protein geometry and capsid formation (Zlotnick A et al. J. Virol. 2002, 4848).

WO2012/031024 claims compounds of the Formula shown below as allosteric modulators of mGluR5 receptors

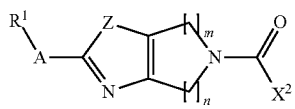

WO2010/114971 claims compounds of the Formula shown below, as modulators of mGuR5 receptors

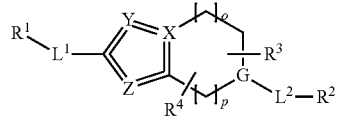

WO 9840385 claims compounds of Formula shown below as inhibitors of glucose-6-phosphatase

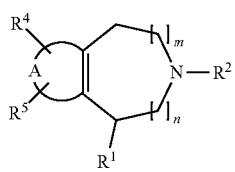

Problems that HBV direct acting antivirals may encounter are toxicity, mutagenicity, lack of selectivity, poor efficacy, poor bioavailability, low solubility and difficulty of synthesis. There is a thus a need for additional inhibitors for the treatment, amelioration or prevention of HBV that may overcome at least one of these disadvantages or that have additional advantages such as increased potency or an increased safety window.

Administration of such therapeutic agents to an HBV infected patient, either as monotherapy or in combination with other HBV treatments or ancillary treatments, will lead to significantly reduced virus burden, improved prognosis, diminished progression of the disease and/or enhanced seroconversion rates.

SUMMARY OF THE INVENTION

Provided herein are compounds useful for the treatment or prevention of HBV infection in a subject in need thereof, and intermediates useful in their preparation. The subject matter of the invention is a compound of Formula I:

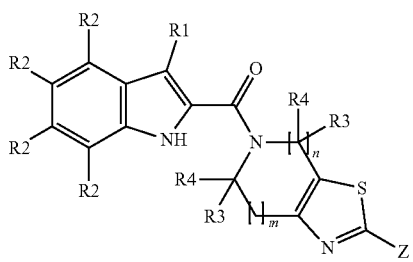

in which

Z is H, D, O(R5), $CH_3$, C≡N, Cl, C(=O)$NH_2$, N(R5)(R6), N(R5)C(=O)(R6), NHC(=O)N(R5)(R6), N(R5)$SO_2$(R6), NHC(=O)O(R5), NHC(=O)C(=O)O(R5), NHC(=O)C(=O)N(R5)(R6), NHC(=O)NHSO$_2$R5, $CH_2$—N(R5)(R6), aryl, and heteroaryl R1 is H, D, F, Cl, Br, $NH_2$ R2 is for each position independently selected from the group comprising H, $CF_2H$, $CF_3$, $CF_2CH_3$, F, Cl, Br, $CH_3$, Et, i-Pr, c-Pr, D, $CH_2OH$, $CH(CH_3)OH$, $CH_2F$, C(F)$CH_3$, I, C=C, C≡C, C≡N, C($CH_3$)$_2$OH, Si($CH_3$)$_3$, SMe, OH, $OCH_3$ R3 and R4 are for each position independently selected from the group comprising H, methyl and ethyl R3 and R4 are optionally connected to form a C3-C5-cycloalkyl ring R5 and R6 are independently selected from the group comprising H, D, C1-C6-alkyl, C3-C6-cycloalkyl, C4-C7-heterocycloalkyl, C2-C6-aminoalkyl, and C2-C6-hydroxyalkyl, optionally substituted with 1, 2, or 3 groups each independently selected from OH, halo, acyl, $SO_2Me$, carboxy, carboxy ester, carbamoyl, substituted carbamoyl, C6-aryl, heteroaryl, C1-C6-alkyl, C3-C6-cycloalkyl, C3-C7-heterocycloalkyl, C1-C6-haloalkyl, C1-C6-alkoxy, C1-C6-hydroxyalkyl, and C1-C6 alkenyloxy R5 and R6 are optionally connected to form a C4-C7-heterocyclic ring containing 1 or 2 nitrogen or oxygen atoms n is 1 or 2 m is 0 or 1

In one embodiment of the invention subject matter of the invention is a compound of Formula I in which:

Z is N(R5)(R6), N(R5)C(=O)(R6), NHC(=O)N(R5)(R6), and N(R5)$SO_2$(R6)

R1 is H

R2 is for each position independently selected from the group comprising H, $CF_2H$, $CF_3$, $CF_2CH_3$, F, Cl, Br, $CH_3$, Et, i-Pr R3 and R4 are for each position independently selected from the group comprising H and methyl R3 and R4 are optionally connected to form a cyclopropyl ring R5 and R6 are independently selected from the group comprising H, C1-C6-alkyl, C3-C6-cycloalkyl, C4-C7-heterocycloalkyl and C2-C6-hydroxyalkyl optionally substituted with OH, C1-C6-alkoxy, C1-C6-hydroxyalkyl and C3-C7-heterocycloalkyl R5 and R6 are optionally connected to form a C4-C7-heterocyclic ring containing 1 or 2 nitrogen or oxygen atoms n is 1 m is 1

In one embodiment of the invention subject matter of the invention is a compound of Formula I in which:

Z is N(R5)(R6)

R1 is H

R2 is for each position independently selected from the group comprising H, $CF_2H$, $CF_3$, $CF_2CH_3$, F, Cl, $CH_3$, and Et R3 and R4 are H R5 and R6 are independently selected from the group comprising H, C1-C6-alkyl, C3-C6-cycloalkyl, C4-C7-heterocycloalkyl and C2-C6-hydroxyalkyl optionally substituted with OH, C1-C6-alkoxy, C1-C6-hydroxyalkyl and C3-C7-heterocycloalkyl n is 1 m is 1

In one embodiment subject matter of the present invention is a compound according to Formula I in which Z is H, D, O(R5), $CH_3$, C≡N, Cl, C(=O)$NH_2$, N(R5)(R6), N(R5)C(=O)(R6), NHC(=O)N(R5)(R6), and N(R5)$SO_2$(R6), NHC(=O)O(R5), NHC(=O)C(=O)O(R5), NHC(=O)C(=O)N(R5)(R6), $CH_2$—N(R5)(R6), aryl, heteroaryl, preferably N(R5)(R6), N(R5)C(=O)(R6), NHC(=O)N(R5)(R6), and N(R5)$SO_2$(R6), and most preferably N(R5)(R6).

In one embodiment subject matter of the present invention is a compound according to Formula I in which R1 is H, D, F, Cl, Br, $NH_2$, preferably H.

In a preferred embodiment subject matter of the present invention is a compound according to Formula I in which Z is N(R5)(R6) and R1 is H.

In a more preferred embodiment subject matter of the present invention is a compound according to Formula I in which Z is N(R5)(R6), R1 is H, and R2 is for each position independently selected from the group comprising H, $CF_2H$, $CF_3$, $CF_2CH_3$, F, Cl, $CH_3$, and Et.

In another preferred embodiment subject matter of the present invention is a compound according to Formula I in which Z is N(R5)C(=O)(R6) and R1 is H.

In another more preferred embodiment subject matter of the present invention is a compound according to Formula I in which Z is N(R5)C(=O)(R6), R1 is H, and R2 is for each position independently selected from the group comprising H, $CF_2H$, $CF_3$, $CF_2CH_3$, F, Cl, $CH_3$, and Et.

In one embodiment subject matter of the present invention is a compound according to Formula I in which R2 is for each position independently selected from the group comprising H, $CF_2H$, $CF_3$, $CF_2CH_3$, F, Cl, Br, $CH_3$, Et, i-Pr, c-Pr, D, $CH_2OH$, $CH(CH_3)OH$, $CH_2F$, $C(F)CH_3$, I, C=C, C≡C, C≡N, $C(CH_3)_2OH$, $Si(CH_3)_3$, SMe, OH, $OCH_3$, preferably H, $CF_2H$, $CF_3$, $CF_2CH_3$, F, Cl, Br, $CH_3$, Et, i-Pr, and most preferably H, $CF_2H$, $CF_3$, $CF_2CH_3$, F, Cl, $CH_3$, and Et.

In one embodiment subject matter of the present invention is a compound according to Formula I in which R3 and R4 are for each position independently selected from the group comprising H, methyl and ethyl, preferably H and methyl, most preferably H.

In a preferred embodiment subject matter of the present invention is a compound according to Formula I in which Z is N(R5)(R6), R3 is H, and R4 is H.

In a more preferred embodiment subject matter of the present invention is a compound according to Formula I in which Z is N(R5)(R6), R2 is for each position independently selected from the group comprising H, $CF_2H$, $CF_3$, $CF_2CH_3$, F, Cl, $CH_3$, and Et, R3 is H, and R4 is H.

In another preferred embodiment subject matter of the present invention is a compound according to Formula I in which Z is N(R5)C(=O)(R6), R3 is H, and R4 is H.

In another more preferred embodiment subject matter of the present invention is a compound according to Formula I in which Z is N(R5)C(=O)(R6), R2 is for each position independently selected from the group comprising H, $CF_2H$, $CF_3$, $CF_2CH_3$, F, Cl, $CH_3$, and Et, R3 is H, and R4 is H.

In one embodiment subject matter of the present invention is a compound according to Formula I in which R5 and R6 are independently selected from the group comprising H, D, C1-C6-alkyl, C3-C6-cycloalkyl, C4-C7-heterocycloalkyl, C2-C6-aminoalkyl, and C2-C6-hydroxyalkyl, optionally substituted with 1, 2, or 3 groups each independently selected from OH, halo, acyl, SO2Me, carboxy, carboxyl ester, carbamoyl, substituted carbamoyl, C6-aryl, heteroaryl, C1-C6-alkyl, C3-C6-cycloalkyl, C3-C7-heterocycloalkyl, C1-C6-haloalkyl, C1-C6-alkoxy, C1-C6-hydroxyalkyl, or C1-C6 alkenyloxy, preferably H, C1-C6-alkyl, C3-C6-cycloalkyl, C4-C7-heterocycloalkyl and C2-C6-hydroxyalkyl optionally substituted with OH, C1-C6-alkoxy, C1-C6-hydroxyalkyl and C3-C7-heterocycloalkyl.

In a preferred embodiment subject matter of the present invention is a compound according to Formula I in which R5 is H, and R6 is selected from C1-C6-alkyl, C3-C6-cycloalkyl, C4-C7-heterocycloalkyl, C2-C6-aminoalkyl, and C2-C6-hydroxyalkyl, optionally substituted with 1, 2, or 3 groups each independently selected from OH, halo, acyl, $SO_2Me$, carboxy, carboxyl ester, carbamoyl, substituted carbamoyl, C6-aryl, heteroaryl, C1-C6-alkyl, C3-C6-cycloalkyl, C3-C7-heterocycloalkyl, C1-C6-haloalkyl, C1-C6-alkoxy, C1-C6-hydroxyalkyl, and C1-C6 alkenyloxy, preferably H, C1-C6-alkyl, C3-C6-cycloalkyl, C4-C7-heterocycloalkyl and C2-C6-hydroxyalkyl optionally substituted with OH, C1-C6-alkoxy, C1-C6-hydroxyalkyl or C3-C7-heterocycloalkyl.

In a more preferred embodiment subject matter of the present invention is a compound according to Formula I in which R5 is H and R6 is selected from the group comprising C1-C6-alkyl, C3-C6-cycloalkyl, C4-C7-heterocycloalkyl, C2-C6-aminoalkyl, and C2-C6-hydroxyalkyl optionally substituted with one or two groups selected from OH, halo, C3-C6-cycloalkyl, and C3-C7-heterocycloalkyl.

In an even more preferred embodiment subject matter of the present invention is a compound according to Formula I in which R2 is for each position independently selected from the group comprising H, $CF_2H$, $CF_3$, $CF_2CH_3$, F, Cl, $CH_3$, and Et, R5 is H, and R6 is selected from the group comprising C1-C6-alkyl, C3-C6-cycloalkyl, C4-C7-heterocycloalkyl, C2-C6-aminoalkyl, and C2-C6-hydroxyalkyl optionally substituted with one or two groups selected from OH, halo, C3-C6-cycloalkyl, and C3-C7-heterocycloalkyl.

In one embodiment subject matter of the present invention is a compound according to Formula I in which n is 1.

In one embodiment subject matter of the present invention is a compound according to Formula I in which m is 1.

In a preferred embodiment subject matter of the present invention is a compound according to Formula I in which n is 1 and m is 1.

In a more preferred embodiment subject matter of the present invention is a compound according to Formula I in which Z is N(R5)(R6), n is 1 and m is 1.

In an even more preferred embodiment subject matter of the present invention is a compound according to Formula I in which Z is N(R5)(R6), n is 1, m is 1, and R2 is for each position independently selected from the group comprising H, $CF_2H$, $CF_3$, $CF_2CH_3$, F, Cl, $CH_3$, and Et.

In another even more preferred embodiment subject matter of the present invention is a compound according to Formula I in which Z is N(R5)C(=O)(R6), n is 1, m is 1, and R2 is for each position independently selected from the group comprising H, CF$_2$H, CF$_3$, CF$_2$CH$_3$, F, Cl, CH$_3$, and Et.

One embodiment of the invention is a pharmaceutical composition comprising a compound of Formula I or a pharmaceutically acceptable salt thereof according to the present invention, together with a pharmaceutically acceptable carrier.

One embodiment of the invention is a method of treating an HBV infection in an individual in need thereof, comprising administering to the individual a therapeutically effective amount of a compound of Formula I or a pharmaceutically acceptable salt thereof according to the present invention.

A further embodiment of the invention is a compound of Formula II or a pharmaceutically acceptable salt thereof according to the invention, for use in the prevention or treatment of an HBV infection in subject in need thereof.

II in which
Y is N(R5)SO$_2$(R6), N(R5)(R6), or N(R5)C(=O)(R6)
R1 is H
R2 is for each position independently selected from the group comprising H, CF$_2$H, CF$_3$, CF$_2$CH$_3$, F, Cl, Br, CH$_3$, Et, i-Pr
R3 and R4 are for each position independently selected from the group comprising H and methyl
R5 and R6 are independently selected from the group comprising H, D, C1-C6-alkyl, C3-C6-cycloalkyl, C4-C7-heterocycloalkyl, C2-C6-aminoalkyl, and C2-C6-hydroxyalkyl, optionally substituted with 1, 2, or 3 groups each independently selected from OH, halo, acyl, SO$_2$Me, carboxy, carboxyl ester, carbamoyl, substituted carbamoyl, C6-aryl, heteroaryl, C1-C6-alkyl, C3-C6-cycloalkyl, C3-C7-heterocycloalkyl, C1-C6-haloalkyl, C1-C6-alkoxy, C1-C6-hydroxyalkyl, or C1-C6 alkenyloxy
R5 and R6 are optionally connected to form a C4-C7-heterocyclic ring containing 1 or 2 nitrogen or oxygen atoms
n is 1 or 2
m is 0 or 1
In one embodiment subject matter of the present invention is a compound according to Formula II in which:
Y is N(R5)(R6)
R1 is H
R2 is for each position independently selected from the group comprising H, CF$_2$H, CF$_3$, CF$_2$CH$_3$, F, Cl, CH$_3$, and Et
R3 and R4 are H
R5 and R6 are independently selected from the group comprising H, C1-C6-alkyl, C3-C6-cycloalkyl, C4-C7-heterocycloalkyl and C2-C6-hydroxyalkyl optionally substituted with OH, C1-C6-alkoxy, C1-C6-hydroxyalkyl and C3-C7-heterocycloalkyl
R5 and R6 are optionally connected to form a C4-C7-heterocyclic ring containing 1 or 2 nitrogen or oxygen atoms
n is 1
m is 1

In one embodiment subject matter of the present invention is a compound according to Formula II in which Y is N(R5)SO$_2$(R6), N(R5)(R6), or N(R5)C(=O)(R6), preferably N(R5)(R6).

In one embodiment subject matter of the present invention is a compound according to Formula II in which R1 is H.

In a preferred embodiment subject matter of the present invention is a compound according to Formula II in which Y is N(R5)(R6) and R1 is H.

In another preferred embodiment subject matter of the present invention is a compound according to Formula II in which Y is N(R5)C(=O)R6 and R1 is H.

In one embodiment subject matter of the present invention is a compound according to Formula II in which R2 is for each position independently selected from the group comprising H, CF$_2$H, CF$_3$, CF$_2$CH$_3$, F, Cl, Br, CH$_3$, Et, i-Pr, preferably H, CF$_2$H, CF$_3$, CF$_2$CH$_3$, F, Cl, CH$_3$, and Et.

In a preferred embodiment subject matter of the present invention is a compound according to Formula II in which Y is N(R5)(R6) and R2 is for each position independently selected from the group comprising H, CF$_2$H, CF$_3$, CF$_2$CH$_3$, F, Cl, CH$_3$, and Et.

In another preferred embodiment subject matter of the present invention is a compound according to Formula II in which Y is N(R5)C(=O)(R6) and R2 is for each position independently selected from the group comprising H, CF$_2$H, CF$_3$, CF$_2$CH$_3$, F, Cl, CH$_3$, and Et.

In one embodiment subject matter of the present invention is a compound according to Formula II in which R3 and R4 are for each position independently selected from the group comprising H and methyl, preferably H.

In a preferred embodiment subject matter of the present invention is a compound according to Formula II in which Y is N(R5)(R6), and R3 is H.

In a more preferred embodiment subject matter of the present invention is a compound according to Formula II in which Y is N(R5)(R6), R3 is H, and R4 is H.

In an even more preferred embodiment of the present invention is a compound according to Formula II in which Y is N(R5)(R6), R2 is for each position independently selected from the group comprising H, CF$_2$H, CF$_3$, CF$_2$CH$_3$, F, Cl, CH$_3$, and Et, R3 is H, and R4 is H.

In another preferred embodiment subject matter of the present invention is a compound according to Formula II in which Y is N(R5)C(=O)(R6), and R3 is H.

In another more preferred embodiment subject matter of the present invention is a compound according to Formula II in which Y is N(R5)C(=O)(R6), R3 is H, and R4 is H.

In another even more preferred embodiment subject matter of the present invention is a compound according to Formula II in which Y is N(R5)C(=O)(R6), R2 is for each position independently selected from the group comprising H, CF$_2$H, CF$_3$, CF$_2$CH$_3$, F, Cl, CH$_3$, and Et, R3 is H, and R4 is H.

In one embodiment subject matter of the present invention is a compound according to Formula II in which R5 and R6 are independently selected from the group comprising H, D, C1-C6-alkyl, C3-C6-cycloalkyl, C4-C7-heterocycloalkyl, C2-C6-aminoalkyl, and C2-C6-hydroxyalkyl, optionally substituted with 1, 2, or 3 groups each independently selected from OH, halo, acyl, $SO_2Me$, carboxy, carboxyl ester, carbamoyl, substituted carbamoyl, C6-aryl, heteroaryl, C1-C6-alkyl, C3-C6-cycloalkyl, C3-C7-heterocycloalkyl, C1-C6-haloalkyl, C1-C6-alkoxy, C1-C6-hydroxyalkyl, or C1-C6 alkenyloxy, preferably H, C1-C6-alkyl, C3-C6-cycloalkyl, C4-C7-heterocycloalkyl and C2-C6-hydroxyalkyl optionally substituted with OH, C1-C6-alkoxy, C1-C6-hydroxyalkyl and C3-C7-heterocycloalkyl.

In a preferred embodiment subject matter of the present invention is a compound according to Formula II in which Y is N(R5)(R6), and R5 is H.

In a more preferred embodiment subject matter of the present invention is a compound according to Formula II in which Y is N(R5)(R6), R5 is H, and R2 is for each position independently selected from the group comprising H, $CF_2H$, $CF_3$, $CF_2CH_3$, F, Cl, $CH_3$, and Et.

In another preferred embodiment subject matter of the present invention is a compound according to Formula II in which Y is N(R5)C(=O)(R6), and R5 is H.

In another more preferred embodiment subject matter of the present invention is a compound according to Formula II in which Y is N(R5)C(=O)R6, R5 is H, and R2 is for each position independently selected from the group comprising H, $CF_2H$, $CF_3$, $CF_2CH_3$, F, Cl, $CH_3$, and Et.

In another preferred embodiment subject matter of the present invention is a compound according to Formula II in which Y is N(R5)(R6), and R6 is is selected from C1-C6-alkyl, C3-C6-cycloalkyl, C4-C7-heterocycloalkyl, C2-C6-aminoalkyl, and C2-C6-hydroxyalkyl, optionally substituted with 1, 2, or 3 groups each independently selected from OH, halo, acyl, $SO_2Me$, carboxy, carboxyl ester, carbamoyl, substituted carbamoyl, C6-aryl, heteroaryl, C1-C6-alkyl, C3-C6-cycloalkyl, C3-C7-heterocycloalkyl, C1-C6-haloalkyl, C1-C6-alkoxy, C1-C6-hydroxyalkyl, and C1-C6 alkenyloxy, preferably H, C1-C6-alkyl, C3-C6-cycloalkyl, C4-C7-heterocycloalkyl and C2-C6-hydroxyalkyl optionally substituted with OH, C1-C6-alkoxy, C1-C6-hydroxyalkyl or C3-C7-heterocycloalkyl.

In another more preferred embodiment subject matter of the present invention is a compound according to Formula II in which Y is N(R5)(R6), R5 is H, R6 is selected from the group comprising C1-C6-alkyl, C3-C6-cycloalkyl, C4-C7-heterocycloalkyl, C2-C6-aminoalkyl, and C2-C6-hydroxyalkyl optionally substituted with one or two groups selected from OH, halo, C3-C6-cycloalkyl, and C3-C7-heterocycloalkyl, and R2 is for each position independently selected from the group comprising H, $CF_2H$, $CF_3$, $CF_2CH_3$, F, Cl, $CH_3$, and Et.

In another preferred embodiment subject matter of the present invention is a compound according to Formula II in which Y is N(R5)C(=O)(R6), and R6 is selected from C1-C6-alkyl, C3-C6-cycloalkyl, C4-C7-heterocycloalkyl, C2-C6-aminoalkyl, and C2-C6-hydroxyalkyl, optionally substituted with 1, 2, or 3 groups each independently selected from OH, halo, acyl, $SO_2Me$, carboxy, carboxyl ester, carbamoyl, substituted carbamoyl, C6-aryl, heteroaryl, C1-C6-alkyl, C3-C6-cycloalkyl, C3-C7-heterocycloalkyl, C1-C6-haloalkyl, C1-C6-alkoxy, C1-C6-hydroxyalkyl, or C1-C6 alkenyloxy, preferably H, C1-C6-alkyl, C3-C6-cycloalkyl, C4-C7-heterocycloalkyl and C2-C6-hydroxyalkyl optionally substituted with OH, C1-C6-alkoxy, C1-C6-hydroxyalkyl or C3-C7-heterocycloalkyl.

In another more preferred embodiment subject matter of the present invention is a compound according to Formula II in which Y is N(R5)C(=O)(R6), R5 is H, R6 is selected from the group comprising C1-C6-alkyl, C3-C6-cycloalkyl, C4-C7-heterocycloalkyl, C2-C6-aminoalkyl, and C2-C6-hydroxyalkyl optionally substituted with one or two groups selected from OH, halo, C3-C6-cycloalkyl, and C3-C7-heterocycloalkyl, and R2 is for each position independently selected from the group comprising H, $CF_2H$, $CF_3$, $CF_2CH_3$, F, Cl, $CH_3$, and Et.

In one embodiment subject matter of the present invention is a compound according to Formula II in which n is 1.

In one embodiment subject matter of the present invention is a compound according to Formula II in which m is 1.

In a preferred embodiment subject matter of the present invention is a compound according to Formula II in which n is 1 and m is 1.

In a more preferred embodiment subject matter of the present invention is a compound according to Formula II in which n is 1, m is 1 and Y is N(R5)(R6).

In an even more preferred embodiment subject matter of the present invention is a compound according to Formula II in which n is 1, m is 1, Y is N(R5)(R6), and R5 is H.

In another more preferred embodiment subject matter of the present invention is a compound according to Formula II in which n is 1, m is 1 and Y is N(R5)C(=O)(R6).

In another even more preferred embodiment subject matter of the present invention is a compound according to Formula II in which n is 1, m is 1, Y is N(R5)C(=O)(R6), and R5 is H.

One embodiment of the invention is a pharmaceutical composition comprising a compound of Formula II or a pharmaceutically acceptable salt thereof according to the present invention, together with a pharmaceutically acceptable carrier.

One embodiment of the invention is a method of treating an HBV infection in an individual in need thereof, comprising administering to the individual a therapeutically effective amount of a compound of Formula II or a pharmaceutically acceptable salt thereof according to the present invention.

A further embodiment of the invention is a compound of Formula III or a pharmaceutically acceptable salt thereof according to the invention, for use in the prevention or treatment of an HBV infection in subject.

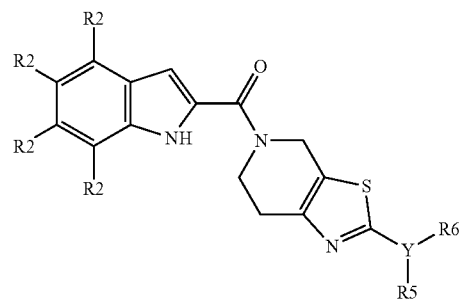

III in which
R2 is for each position independently selected from the group comprising H, $CF_2H$, $CF_3$, $CF_2CH_3$, F, Cl, Br, $CH_3$, Et, i-Pr
R5 and R6 are independently selected from the group comprising H, D, C1-C6-alkyl, C3-C6-cycloalkyl, C4-C7-heterocycloalkyl, C2-C6-aminoalkyl, and C2-C6-hydroxyalkyl, optionally substituted with 1, 2, or 3 groups each independently selected from OH, halo, acyl, SO₂Me, carboxy, carboxyl ester, carbamoyl, substituted carbamoyl, C6-aryl, heteroaryl, C1-C6-alkyl, C3-C6-cycloalkyl, C3-C7-heterocycloalkyl, C1-C6-haloalkyl, C1-C6-alkoxy, C1-C6-hydroxyalkyl, or C1-C6 alkenyloxy.

In one embodiment subject matter of the present invention is a compound according to Formula III in which:
R2 is for each position independently selected from the group comprising H, CF₂H, CF₃, CF₂CH₃, F, Cl, CH₃, and Et.
R5 and R6 are independently selected from the group comprising H, C1-C6-alkyl, C3-C6-cycloalkyl, C4-C7-heterocycloalkyl and C2-C6-hydroxyalkyl optionally substituted with OH, C1-C6-alkoxy, C1-C6-hydroxyalkyl and C3-C7-heterocycloalkyl.

In one embodiment subject matter of the present invention is a compound according to Formula III in which R2 is for each position independently selected from the group comprising H, CF₂H, CF₃, CF₂CH₃, F, Cl, Br, CH₃, Et, i-Pr, preferably H, CF₂H, CF₃, CF₂CH₃, F, Cl, CH₃, and Et.

In one embodiment subject matter of the present invention is a compound according to Formula III in which R5 and R6 are independently selected from the group comprising H, D, C1-C6-alkyl, C3-C6-cycloalkyl, C4-C7-heterocycloalkyl, C2-C6-aminoalkyl, and C2-C6-hydroxyalkyl, optionally substituted with 1, 2, or 3 groups each independently selected from OH, halo, acyl, SO₂Me, carboxy, carboxyl ester, carbamoyl, substituted carbamoyl, C6-aryl, heteroaryl, C1-C6-alkyl, C3-C6-cycloalkyl, C3-C7-heterocycloalkyl, C1-C6-haloalkyl, C1-C6-alkoxy, C1-C6-hydroxyalkyl, or C1-C6 alkenyloxy, preferably H, C1-C6-alkyl, C3-C6-cycloalkyl, C4-C7-heterocycloalkyl and C2-C6-hydroxyalkyl optionally substituted with OH, C1-C6-alkoxy, C1-C6-hydroxyalkyl and C3-C7-heterocycloalkyl.

In a preferred embodiment subject matter of the present invention is a compound according to Formula III in which R2 is for each position independently selected from the group comprising H, CF₂H, CF₃, CF₂CH₃, F, Cl, CH₃, and Et, and R5 is H.

In another preferred embodiment subject matter of the present invention is a compound according to Formula III in which R2 is for each position independently selected from the group comprising H, CF₂H, CF₃, CF₂CH₃, F, Cl, CH₃, and Et, and R6 is selected from the group comprising H, D, C1-C6-alkyl, C3-C6-cycloalkyl, C4-C7-heterocycloalkyl, C2-C6-aminoalkyl, and C2-C6-hydroxyalkyl, optionally substituted with 1, 2, or 3 groups each independently selected from OH, halo, acyl, SO₂Me, carboxy, carboxyl ester, carbamoyl, substituted carbamoyl, C6-aryl, heteroaryl, C1-C6-alkyl, C3-C6-cycloalkyl, C3-C7-heterocycloalkyl, C1-C6-haloalkyl, C1-C6-alkoxy, C1-C6-hydroxyalkyl, and C1-C6 alkenyloxy, preferably H, C1-C6-alkyl, C3-C6-cycloalkyl, C4-C7-heterocycloalkyl and C2-C6-hydroxyalkyl optionally substituted with OH, C1-C6-alkoxy, C1-C6-hydroxyalkyl or C3-C7-heterocycloalkyl.

In a more preferred embodiment subject matter of the present invention is a compound according to Formula III in which R2 is for each position independently selected from the group comprising H, CF₂H, CF₃, CF₂CH₃, F, Cl, CH₃, and Et, R5 is H, and R6 is selected from the group comprising C1-C6-alkyl, C3-C6-cycloalkyl, C4-C7-heterocycloalkyl, C2-C6-aminoalkyl, and C2-C6-hydroxyalkyl optionally substituted with one or two groups selected from OH, halo, C3-C6-cycloalkyl, and C3-C7-heterocycloalkyl.

One embodiment of the invention is a pharmaceutical composition comprising a compound of Formula III or a pharmaceutically acceptable salt thereof according to the present invention, together with a pharmaceutically acceptable carrier.

One embodiment of the invention is a method of treating an HBV infection in an individual in need thereof, comprising administering to the individual a therapeutically effective amount of a compound of Formula III or a pharmaceutically acceptable salt thereof according to the present invention.

A further embodiment of the invention is a compound of Formula IVa or IVb or a pharmaceutically acceptable salt thereof according to the invention, for use in the prevention or treatment of an HBV infection in subject.

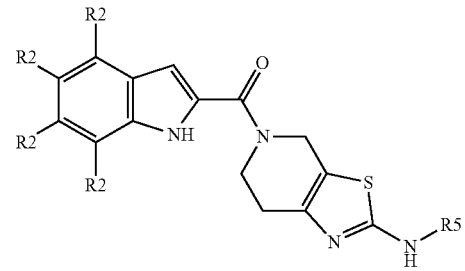

IVa

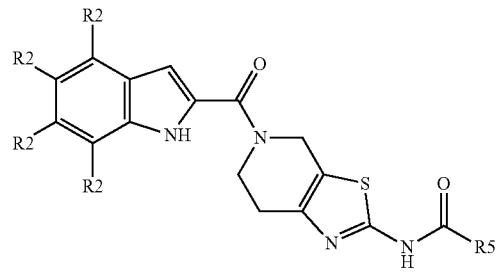

IVb in which
R2 is for each position independently selected from the group comprising H, CH₂F, CF₂H, CF₃, C(F)CH₃, CF₂CH₃, F, Cl, Br, CH₃, Et
R5 is selected from the group comprising H, D, C1-C6-alkyl, C3-C6-cycloalkyl, C4-C7-heterocycloalkyl, C2-C6-aminoalkyl, and C2-C6-hydroxyalkyl, optionally substituted with 1, 2, or 3 groups each independently selected from OH, halo, acyl, SO₂Me, carboxy, carboxyl ester, carbamoyl, substituted carbamoyl, C6-aryl, heteroaryl, C1-C6-alkyl, C3-C6-cycloalkyl, C3-C7-heterocycloalkyl, C1-C6-haloalkyl, C1-C6-alkoxy, C1-C6-hydroxyalkyl, or C1-C6 alkenyloxy, preferably C1-C6-alkyl, C3-C6-cycloalkyl, C4-C7-heterocycloalkyl and C2-C6-hydroxyalkyl optionally substituted with OH, C1-C6-alkoxy, C1-C6-hydroxylalkyl and C3-C7-heterocycloalkyl.

In one embodiment subject matter of the present invention is a compound according to Formula IVa or IVb in which R2 is H, CH₂F, CF₂H, CF₃, CF₂CH₃, F, Cl, Br, CH₃, Et.

In one embodiment subject matter of the present invention is a compound according to Formula IVa or IVb in which R5 is C1-C6-alkyl, C3-C6-cycloalkyl, C4-C7-heterocycloalkyl, C2-C6-aminoalkyl, and C2-C6-hydroxyalkyl, optionally substituted with 1, 2, or 3 groups each independently selected from OH, halo, acyl, SO₂Me, carboxy, carboxyl ester, carbamoyl, substituted carbamoyl, C6-aryl, heteroaryl, C1-C6-alkyl, C3-C6-cycloalkyl, C3-C7-heterocycloalkyl, C1-C6-haloalkyl, C1-C6-alkoxy, C1-C6-hydroxyalkyl, or C1-C6 alkenyloxy, preferably C1-C6-alkyl, C3-C6-cycloalkyl, C4-C7-heterocycloalkyl and C2-C6-hydroxyalkyl optionally substituted with OH, C1-C6-alkoxy, C1-C6-hydroxylalkyl and C3-C7-heterocycloalkyl.

In a preferred embodiment subject matter of the present invention is a compound according to Formula IVa or IVb in which R2 is for each position independently selected from the group comprising H, $CF_2H$, $CF_3$, $CF_2CH_3$, F, Cl, $CH_3$, and Et, and R5 is selected from the group comprising C1-C6-alkyl, C3-C6-cycloalkyl, C4-C7-heterocycloalkyl, C2-C6-aminoalkyl, and C2-C6-hydroxyalkyl, optionally substituted with 1, 2, or 3 groups each independently selected from OH, halo, acyl, $SO_2Me$, carboxy, carboxyl ester, carbamoyl, substituted carbamoyl, C6-aryl, heteroaryl, C1-C6-alkyl, C3-C6-cycloalkyl, C3-C7-heterocycloalkyl, C1-C6-haloalkyl, C1-C6-alkoxy, C1-C6-hydroxyalkyl, and C1-C6 alkenyloxy, preferably C1-C6-alkyl, C3-C6-cycloalkyl, C4-C7-heterocycloalkyl and C2-C6-hydroxyalkyl optionally substituted with OH, C1-C6-alkoxy, C1-C6-hydroxylalkyl or C3-C7-heterocycloalkyl.

In a more preferred embodiment subject matter of the present invention is a compound according to Formula IVa or IVb in which R2 is for each position independently selected from the group comprising H, $CF_2H$, $CF_3$, $CF_2CH_3$, F, Cl, $CH_3$, and Et, and R5 is selected from C1-C6-alkyl, C3-C6-cycloalkyl, C4-C7-heterocycloalkyl, C2-C6-aminoalkyl, and C2-C6-hydroxyalkyl optionally substituted with one or two groups selected from OH, halo, C3-C6-cycloalkyl, and C3-C7-heterocycloalkyl.

One embodiment of the invention is a pharmaceutical composition comprising a compound of Formula IVa or IVb or a pharmaceutically acceptable salt thereof according to the present invention, together with a pharmaceutically acceptable carrier.

One embodiment of the invention is a method of treating an HBV infection in an individual in need thereof, comprising administering to the individual a therapeutically effective amount of a compound of Formula IVa or IVb or a pharmaceutically acceptable salt thereof according to the present invention.

In some embodiments, the dose of a compound of the invention is from about 1 mg to about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound (i.e., another drug for HBV treatment) as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof. All before mentioned doses refer to daily doses per patient.

The compounds of the invention may, depending on their structure, exist as salts, solvates or hydrates. The invention therefore also encompasses the salts, solvates or hydrates and respective mixtures thereof.

The compounds of the invention may, depending on their structure, exist in tautomeric or stereoisomeric forms (enantiomers, diastereomers). The invention therefore also encompasses the tautomers, enantiomers or diastereomers and respective mixtures thereof. The stereoisomerically uniform constituents can be isolated in a known manner from such mixtures of enantiomers and/or diastereomers.

A further embodiment of the invention is a compound of Formula I or a pharmaceutically acceptable salt thereof according to the invention, for use in the prevention or treatment of an HBV infection in subject

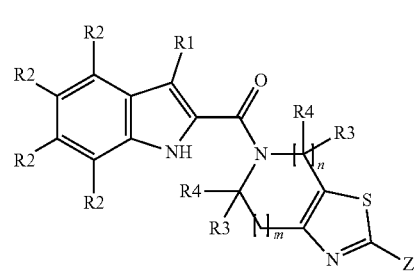

in which

Z is H, D, O(R5), $CH_3$, C≡N, Cl, C(=O)$NH_2$, N(R5)(R6), N(R5)C(=O)(R6), NHC(=O)N(R5)(R6), N(R5)$SO_2$(R6), NHC(=O)C(=O)O(R5), NHC(=O)C(=O)N(R5)(R6), NHC(=O)NH$SO_2$R5, $CH_2$—N(R5)(R6), or heteroaryl R1 is H, D, F, Cl, Br, or $NH_2$ R2 is for each position independently selected from the group comprising H, $CF_2H$, $CF_3$, $CF_2CH_3$, F, Cl, Br, $CH_3$, Et, i-Pr, c-Pr, D, $CH_2OH$, $CH(CH_3)OH$, $CH_2F$, $C(F)CH_3$, I, C=C, C≡C, C≡N, $C(CH_3)_2OH$, $Si(CH_3)_3$, SMe, OH, and $OCH_3$ R3 and R4 are for each position independently selected from the group comprising H, methyl and ethyl R3 and R4 are optionally connected to form a C3-C5-cycloalkyl ring R5 and R6 are independently selected from the group comprising H, D, C1-C6-alkyl, C3-C6-cycloalkyl, C4-C7-heterocycloalkyl, C2-C6-aminoalkyl, and C2-C6-hydroxyalkyl, optionally substituted with 1, 2, or 3 groups each independently selected from OH, halo, C≡N, acyl, $SO_2Me$, carboxy, carboxyl ester, carbamoyl, substituted carbamoyl, C6-aryl, heteroaryl, C1-C6-alkyl, C3-C6-cycloalkyl, C3-C7-heterocycloalkyl, C3-C7-heterocycloalkyl substituted with acyl or carboxyl ester, C1-C6-haloalkyl, C1-C6-alkoxy, C1-C6-alkyl-O-C1-C6-alkyl, C1-C6-hydroxyalkyl, C1-C6-alkylamino, and C1-C6 alkenyloxy R5 and R6 are optionally connected to form a C4-C7-heterocyclic ring containing 1 or 2 nitrogen or oxygen atoms, optionally substituted with 1, 2, or 3 groups each independently selected from OH, halo, acyl, $SO_2Me$, carboxy, carboxyl ester, carbamoyl, substituted carbamoyl, C6-aryl, heteroaryl, C1-C6-alkyl, C3-C6-cycloalkyl, C3-C7-heterocycloalkyl, C1-C6-haloalkyl, C1-C6-alkoxy, C1-C6-hydroxyalkyl, and C1-C6 alkenyloxy n is 1 or 2 m is 0 or 1 with the proviso that when Z is NHC(=O)N(R5)(R6), neither R5, nor R6 is cyclopentyl or isopropyl, and when Z is N(R5)C(=O)(R6) and R5 is H, R6 is not unsubstituted cyclopropyl, unsubstituted cyclobutyl, $CH_3$, or tetrahydrofuranyl.

In one embodiment of the invention subject matter of the invention is a compound of Formula I in which
- Z is N(R5)(R6), N(R5)C(=O)(R6), NHC(=O)N(R5)(R6), or N(R5)$SO_2$(R6)
- R1 is H
- R2 is for each position independently selected from the group comprising H, $CF_2H$, $CF_3$, $CF_2CH_3$, F, Cl, Br, $CH_3$, Et, and i-Pr
- R3 and R4 are for each position independently selected from the group comprising H and methyl
- R3 and R4 are optionally connected to form a cyclopropyl ring
- R5 and R6 are independently selected from the group comprising H, D, C1-C6-alkyl, C3-C6-cycloalkyl, C4-C7-heterocycloalkyl, C2-C6-aminoalkyl, and C2-C6-hydroxyalkyl, optionally substituted with 1, 2, or 3 groups each independently selected from OH, halo, C≡N, acyl, $SO_2Me$, carboxy, carboxyl ester, carbamoyl, substituted carbamoyl, C6-aryl, heteroaryl, C1-C6-alkyl, C3-C6-cycloalkyl, C3-C7-heterocycloalkyl, C3-C7-heterocycloalkyl substituted with acyl or carboxyl ester, C1-C6-haloalkyl, C1-C6-alkoxy, C1-C6-alkyl-O-C1-C6-alkyl, C1-C6-hydroxyalkyl, C1-C6-alkylamino, and C1-C6 alkenyloxy
- R5 and R6 are optionally connected to form a C4-C7-heterocyclic ring containing 1 or 2 nitrogen or oxygen atoms, optionally substituted with 1, 2, or 3 groups each independently selected from OH, halo, acyl, $SO_2Me$, carboxy, carboxyl ester, carbamoyl, substituted carbamoyl, C6-aryl, heteroaryl, C1-C6-alkyl, C3-C6-cycloalkyl, C3-C7-heterocycloalkyl, C1-C6-haloalkyl, C1-C6-alkoxy, C1-C6-hydroxyalkyl, and C1-C6 alkenyloxy
- n is 1 or 2
- m is 0 or 1 with the proviso that
when Z is NHC(=O)N(R5)(R6), neither R5, nor R6 is cyclopentyl or isopropyl, and
when Z is N(R5)C(=O)(R6) and R5 is H, R6 is not unsubstituted cyclopropyl, unsubstituted cyclobutyl, $CH_3$, or tetrahydrofuranyl.

In one embodiment of the invention subject matter of the invention is a compound of Formula I in which:
- Z is N(R5)(R6)
- R1 is H
- R2 is for each position independently selected from the group comprising H, $CF_2H$, $CF_3$, $CF_2CH_3$, F, Cl, $CH_3$, and Et
- R3 and R4 are H
- R5 and R6 are independently selected from the group comprising H, D, C1-C6-alkyl, C3-C6-cycloalkyl, C4-C7-heterocycloalkyl, C2-C6-aminoalkyl, and C2-C6-hydroxyalkyl, optionally substituted with 1, 2, or 3 groups each independently selected from OH, halo, C≡N, acyl, $SO_2Me$, carboxy, carboxyl ester, carbamoyl, substituted carbamoyl, C6-aryl, heteroaryl, C1-C6-alkyl, C3-C6-cycloalkyl, C3-C7-heterocycloalkyl, C3-C7-heterocycloalkyl substituted with acyl or carboxyl ester, C1-C6-haloalkyl, C1-C6-alkoxy, C1-C6-alkyl-O-C1-C6-alkyl, C1-C6-hydroxyalkyl, C1-C6-alkylamino, and C1-C6 alkenyloxy
- n is 1
- m is 1

In one embodiment subject matter of the present invention is a compound according to Formula I in which Z is H, D, O(R5), $CH_3$, C≡N, Cl, C(=O)$NH_2$, N(R5)(R6), N(R5)C(=O)(R6), NHC(=O)N(R5)(R6), N(R5)$SO_2$(R6), NHC(=O)C(=O)O(R5), NHC(=O)C(=O)N(R5)(R6), $CH_2$—N(R5)(R6), heteroaryl, preferably N(R5)(R6), N(R5)C(=O)(R6), NHC(=O)N(R5)(R6), or N(R5)$SO_2$(R6), and most preferably N(R5)(R6).

In one embodiment subject matter of the present invention is a compound according to Formula I in which R1 is H, D, F, Cl, Br, or $NH_2$, preferably H.

In a preferred embodiment subject matter of the present invention is a compound according to Formula I in which Z is N(R5)(R6) and R1 is H.

In another preferred embodiment subject matter of the present invention is a compound according to Formula I in which Z is N(R5)C(=O)(R6) and R1 is H with the proviso that when R5 is H, R6 is not unsubstituted cyclopropyl, unsubstituted cyclobutyl, $CH_3$, or tetrahydrofuranyl.

In one embodiment subject matter of the present invention is a compound according to Formula I in which R2 is for each position independently selected from the group comprising H, $CF_2H$, $CF_3$, $CF_2CH_3$, F, Cl, Br, $CH_3$, Et, i-Pr, c-Pr, D, $CH_2OH$, $CH(CH_3)OH$, $CH_2F$, $C(F)CH_3$, I, C═C, C≡C, C≡N, $C(CH_3)_2OH$, $Si(CH_3)_3$, SMe, OH, and $OCH_3$, preferably H, $CF_2H$, $CF_3$, $CF_2CH_3$, F, Cl, Br, $CH_3$, Et, and i-Pr, and most preferably H, $CF_2H$, $CF_3$, $CF_2CH_3$, F, Cl, $CH_3$, and Et.

In a more preferred embodiment subject matter of the present invention is a compound according to Formula I in which Z is N(R5)(R6), R1 is H, and R2 is for each position independently selected from the group comprising H, $CF_2H$, $CF_3$, $CF_2CH_3$, F, Cl, $CH_3$, and Et.

In another more preferred embodiment of the present invention is a compound according to Formula I in which Z is N(R5)C(=O)(R6), R1 is H, and R2 is for each position independently selected from the group comprising H, $CF_2H$, $CF_3$, $CF_2CH_3$, F, Cl, $CH_3$, and Et with the proviso that when R5 is H, R6 is not unsubstituted cyclopropyl, unsubstituted cyclobutyl, $CH_3$, or tetrahydrofuranyl.

In one embodiment subject matter of the present invention is a compound according to Formula I in which R3 and R4 are for each position independently selected from the group comprising H, methyl and ethyl, preferably H and methyl, most preferably H.

In a preferred embodiment subject matter of the present invention is a compound according to Formula I in which Z is N(R5)(R6), R3 is H, and R4 is H.

In a more preferred embodiment subject matter of the present invention is a compound according to Formula I in which Z is N(R5)(R6), R2 is for each position independently selected from the group comprising H, $CF_2H$, $CF_3$, $CF_2CH_3$, F, Cl, $CH_3$, and Et, R3 is H, and R4 is H.

In another preferred embodiment subject matter of the present invention is a compound according to Formula I in which Z is N(R5)C(=O)(R6), R3 is H, and R4 is H with the proviso that when R5 is H, R6 is not unsubstituted cyclopropyl, unsubstituted cyclobutyl, $CH_3$, or tetrahydrofuranyl.

In another more preferred embodiment subject matter of the present invention is a compound according to Formula I in which Z is N(R5)C(=O)(R6), R2 is for each position independently selected from the group comprising H, $CF_2H$, $CF_3$, $CF_2CH_3$, F, Cl, $CH_3$, and Et, R3 is H, and R4 is H with the proviso that when R5 is H, R6 is not unsubstituted cyclopropyl, unsubstituted cyclobutyl, $CH_3$, or tetrahydrofuranyl.

In one embodiment subject matter of the present invention is a compound according to Formula I in which R5 and R6 are independently selected from the group comprising H, D, C1-C6-alkyl, C3-C6-cycloalkyl, C4-C7-heterocycloalkyl, C2-C6-aminoalkyl, and C2-C6-hydroxyalkyl, optionally substituted with 1, 2, or 3 groups each independently selected from OH, halo, C≡N, acyl, SO$_2$Me, carboxy, carboxyl ester, carbamoyl, substituted carbamoyl, C6-aryl, heteroaryl, C1-C6-alkyl, C3-C6-cycloalkyl, C3-C7-heterocycloalkyl, C3-C7-heterocycloalkyl substituted with acyl or carboxyl ester, C1-C6-haloalkyl, C1-C6-alkoxy, C1-C6-alkyl-O-C1-C6-alkyl, C1-C6-hydroxyalkyl, C1-C6-alkylamino and C1-C6 alkenyloxy, preferably H, C1-C6-alkyl, C3-C6-cycloalkyl, C4-C7-heterocycloalkyl and C2-C6-hydroxyalkyl optionally substituted with OH, C1-C6-alkoxy, C1-C6-hydroxyalkyl or C3-C7-heterocycloalkyl.

In a preferred embodiment subject matter of the present invention is a compound according to Formula I in which R5 is H, and R6 is selected from C1-C6-alkyl, C3-C6-cycloalkyl, C4-C7-heterocycloalkyl, C2-C6-aminoalkyl, and C2-C6-hydroxyalkyl, optionally substituted with 1, 2, or 3 groups each independently selected from OH, halo, acyl, SO$_2$Me, carboxy, carboxyl ester, carbamoyl, substituted carbamoyl, C6-aryl, heteroaryl, C1-C6-alkyl, C3-C6-cycloalkyl, C3-C7-heterocycloalkyl, C1-C6-haloalkyl, C1-C6-alkoxy, C1-C6-hydroxyalkyl, and C1-C6 alkenyloxy, preferably H, C1-C6-alkyl, C3-C6-cycloalkyl, C4-C7-heterocycloalkyl and C2-C6-hydroxyalkyl optionally substituted with OH, C1-C6-alkoxy, C1-C6-hydroxyalkyl or C3-C7-heterocycloalkyl with the proviso that when Z is NHC(=O)N(R5)(R6), R6 is not cyclopentyl or isopropyl, and when Z is N(R5)C(=O)(R6), R6 is not unsubstituted cyclopropyl, unsubstituted cyclobutyl, CH$_3$, or tetrahydrofuranyl.

In a more preferred embodiment subject matter of the present invention is a compound according to Formula I in which R5 is H and R6 is selected from the group comprising C1-C6-alkyl, C3-C6-cycloalkyl, C4-C7-heterocycloalkyl, C2-C6-aminoalkyl, and C2-C6-hydroxyalkyl optionally substituted with one or two groups selected from OH, halo, C3-C6-cycloalkyl, and C3-C7-heterocycloalkyl with the proviso that when Z is NHC(=O)N(R5)(R6), R6 is not cyclopentyl or isopropyl, and when Z is N(R5)C(=O)(R6), R6 is not unsubstituted cyclopropyl, unsubstituted cyclobutyl, CH$_3$, or tetrahydrofuranyl.

In an even more preferred embodiment subject matter of the present invention is a compound according to Formula I in which R2 is for each position independently selected from the group comprising H, CF$_2$H, CF$_3$, CF$_2$CH$_3$, F, Cl, CH$_3$, and Et, R5 is H, and R6 is selected from the group comprising C1-C6-alkyl, C3-C6-cycloalkyl, C4-C7-heterocycloalkyl, C2-C6-aminoalkyl, and C2-C6-hydroxyalkyl optionally substituted with one or two groups selected from OH, halo, C3-C6-cycloalkyl, and C3-C7-heterocycloalkyl with the proviso that when Z is NHC(=O)N(R5)(R6), R6 is not cyclopentyl or isopropyl, and when Z is N(R5)C(=O)(R6), R6 is not unsubstituted cyclopropyl, unsubstituted cyclobutyl, CH$_3$, or tetrahydrofuranyl.

In one embodiment subject matter of the present invention is a compound according to Formula I in which n is 1.

In one embodiment subject matter of the present invention is a compound according to Formula I in which m is 1.

In a preferred embodiment subject matter of the present invention is a compound according to Formula I in which n is 1 and m is 1 with the proviso that when Z is NHC(=O)N(R5)(R6), neither R5, nor R6 is cyclopentyl or isopropyl, and when Z is N(R5)C(=O)(R6) and R5 is H, R6 is not unsubstituted cyclopropyl, unsubstituted cyclobutyl, CH$_3$, or tetrahydrofuranyl.

In a more preferred embodiment subject matter of the present invention is a compound according to Formula I in which Z is N(R5)(R6), n is 1 and m is 1.

In a an even more preferred embodiment subject matter of the present invention is a compound according to Formula I in which Z is N(R5)(R6), n is 1, m is 1, and R2 is for each position independently selected from the group comprising H, CF$_2$H, CF$_3$, CF$_2$CH$_3$, F, Cl, CH$_3$, and Et.

In another even more preferred embodiment subject matter of the present invention is a compound according to Formula I in which Z is N(R5)C(=O)(R6), n is 1, m is 1, and R2 is for each position independently selected from the group comprising H, CF$_2$H, CF$_3$, CF$_2$CH$_3$, F, Cl, CH$_3$, and Et with the proviso that when R5 is H, R6 is not unsubstituted cyclopropyl, unsubstituted cyclobutyl, CH$_3$, or tetrahydrofuranyl.

One embodiment of the invention is a pharmaceutical composition comprising a compound of Formula I or a pharmaceutically acceptable salt thereof according to the present invention, together with a pharmaceutically acceptable carrier.

One embodiment of the invention is a method of treating an HBV infection in an individual in need thereof, comprising administering to the individual a therapeutically effective amount of a compound of Formula I or a pharmaceutically acceptable salt thereof according to the present invention.

A further embodiment of the invention is a compound of Formula II or a pharmaceutically acceptable salt thereof according to the invention, for use in the prevention or treatment of an HBV infection in subject in need thereof

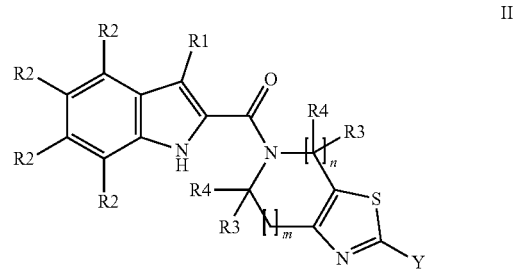

II in which
Y is N(R5)SO$_2$(R6), N(R5)(R6), or N(R5)C(=O)(R6)
R1 is H
R2 is for each position independently selected from the group comprising H, CF$_2$H, CF$_3$, CF$_2$CH$_3$, F, Cl, Br, CH$_3$, Et, and i-Pr
R3 and R4 are for each position independently selected from the group comprising H and methyl
R5 and R6 are independently selected from the group comprising H, D, C1-C6-alkyl, C3-C6-cycloalkyl, C4-C7-heterocycloalkyl, C2-C6-aminoalkyl, and C2-C6-hydroxyalkyl, optionally substituted with 1, 2, or 3 groups each independently selected from OH, halo, acyl, SO$_2$Me, carboxy, carboxyl ester, carbamoyl, substituted carbamoyl, C6-aryl, heteroaryl, C1-C6-alkyl, C3-C6-cycloalkyl, C3-C7-heterocycloalkyl, C3-C7-heterocycloalkyl substituted with acyl or carboxyl ester, C1-C6-haloalkyl, C1-C6-alkoxy, C1-C6-alkyl-O-C1-C6-alkyl, C1-C6-hydroxyalkyl, and C1-C6 alkenyloxy R5 and R6 are optionally connected to form a C4-C7-heterocyclic ring containing 1 or 2 nitrogen or oxygen atoms, optionally substituted with 1, 2, or 3 groups each independently selected from OH, halo, acyl, $SO_2Me$, carboxy, carboxyl ester, carbamoyl, substituted carbamoyl, C6-aryl, heteroaryl, C1-C6-alkyl, C3-C6-cycloalkyl, C3-C7-heterocycloalkyl, C1-C6-haloalkyl, C1-C6-alkoxy, C1-C6-hydroxyalkyl, and C1-C6 alkenyloxy n is 1 or 2
m is 0 or 1
with the proviso that
when Y is N(R5)C(=O)(R6) and R5 is H, R6 is not unsubstituted cyclopropyl, unsubstituted cyclobutyl, $CH_3$, or tetrahydrofuranyl, In one embodiment subject matter of the present invention is a compound according to Formula II in which:
Y is N(R5)(R6)
R1 is H
R2 is for each position independently selected from the group comprising H, $CF_2H$, $CF_3$, $CF_2CH_3$, F, Cl, $CH_3$, and Et
R3 and R4 are H
R5 and R6 are independently selected from the group comprising H, D, C1-C6-alkyl, C3-C6-cycloalkyl, C4-C7-heterocycloalkyl, C2-C6-aminoalkyl, and C2-C6-hydroxyalkyl, optionally substituted with 1, 2, or 3 groups each independently selected from OH, halo, acyl, $SO_2Me$, carboxy, carboxyl ester, carbamoyl, substituted carbamoyl, C6-aryl, heteroaryl, C1-C6-alkyl, C3-C6-cycloalkyl, C3-C7-heterocycloalkyl, C3-C7-heterocycloalkyl substituted with acyl or carboxyl ester, C1-C6-haloalkyl, C1-C6-alkoxy, C1-C6-alkyl-O-C1-C6-alkyl, C1-C6-hydroxyalkyl, and C1-C6 alkenyloxy R5 and R6 are optionally connected to form a C4-C7-heterocyclic ring containing 1 or 2 nitrogen or oxygen atoms, optionally substituted with 1, 2, or 3 groups each independently selected from OH, halo, acyl, $SO_2Me$, carboxy, carboxyl ester, carbamoyl, substituted carbamoyl, C6-aryl, heteroaryl, C1-C6-alkyl, C3-C6-cycloalkyl, C3-C7-heterocycloalkyl, C1-C6-haloalkyl, C1-C6-alkoxy, C1-C6-hydroxyalkyl, and C1-C6 alkenyloxy n is 1
m is 1

In one embodiment subject matter of the present invention is a compound according to Formula II in which Y is $N(R5)SO_2(R6)$, N(R5)(R6), or N(R5)C(=O)(R6), preferably N(R5)(R6).

In one embodiment subject matter of the present invention is a compound according to Formula II in which R1 is H.

In a preferred embodiment subject matter of the present invention is a compound according to Formula II in which Y is N(R5)(R6) and R1 is H.

In another preferred embodiment subject matter of the present invention is a compound according to Formula II in which Y is N(R5)C(=O)R6 and R1 is H with the proviso that when R5 is H, R6 is not unsubstituted cyclopropyl, unsubstituted cyclobutyl, $CH_3$, or tetrahydrofuranyl.

In one embodiment subject matter of the present invention is a compound according to Formula II in which R2 is for each position independently selected from the group comprising H, $CF_2H$, $CF_3$, $CF_2CH_3$, F, Cl, Br, $CH_3$, Et, and i-Pr, preferably H, $CF_2H$, $CF_3$, $CF_2CH_3$, F, Cl, $CH_3$, and Et.

In a preferred embodiment subject matter of the present invention is a compound according to Formula II in which Y is N(R5)(R6) and R2 is for each position independently selected from the group comprising H, $CF_2H$, $CF_3$, $CF_2CH_3$, F, Cl, $CH_3$, and Et.

In a preferred embodiment subject matter of the present invention is a compound according to Formula II in which Y is N(R5)C(=O)(R6) and R2 is for each position independently selected from the group comprising H, $CF_2H$, $CF_3$, $CF_2CH_3$, F, Cl, $CH_3$, and Et with the proviso that when R5 is H, R6 is not unsubstituted cyclopropyl, unsubstituted cyclobutyl, $CH_3$, or tetrahydrofuranyl.

In one embodiment subject matter of the present invention is a compound according to Formula II in which R3 and R4 are for each position independently selected from the group comprising H and methyl, preferably H.

In a preferred embodiment subject matter of the present invention is a compound according to Formula II in which Y is N(R5)(R6), and R3 is H.

In a more preferred embodiment subject matter of the present invention is a compound according to Formula II in which Y is N(R5)(R6), R3 is H, and R4 is H.

In an even more preferred embodiment subject matter of the present invention is a compound according to Formula II in which Y is N(R5)(R6), R2 is for each position independently selected from the group comprising H, $CF_2H$, $CF_3$, $CF_2CH_3$, F, Cl, $CH_3$, and Et, R3 is H, and R4 is H.

In another preferred embodiment subject matter of the present invention is a compound according to Formula II in which Y is N(R5)C(=O)(R6), and R3 is H with the proviso that when R5 is H, R6 is not unsubstituted cyclopropyl, unsubstituted cyclobutyl, $CH_3$, or tetrahydrofuranyl.

In another more preferred embodiment subject matter of the present invention is a compound according to Formula II in which Y is N(R5)C(=O)(R6), R3 is H, and R4 is H with the proviso that when R5 is H, R6 is not unsubstituted cyclopropyl, unsubstituted cyclobutyl, $CH_3$, or tetrahydrofuranyl.

In another even more preferred embodiment of the present invention is a compound according to Formula II in which Y is N(R5)C(=O)(R6), R2 is for each position independently selected from the group comprising H, $CF_2H$, $CF_3$, $CF_2CH_3$, F, Cl, $CH_3$, and Et, R3 is H, and R4 is H with the proviso that when R5 is H, R6 is not unsubstituted cyclopropyl, unsubstituted cyclobutyl, $CH_3$, or tetrahydrofuranyl.

In one embodiment subject matter of the present invention is a compound according to Formula II in which R5 and R6 are independently selected from the group comprising H, D, C1-C6-alkyl, C3-C6-cycloalkyl, C4-C7-heterocycloalkyl, C2-C6-aminoalkyl, and C2-C6-hydroxyalkyl, optionally substituted with 1, 2, or 3 groups each independently selected from OH, halo, acyl, $SO_2Me$, carboxy, carboxyl ester, carbamoyl, substituted carbamoyl, C6-aryl, heteroaryl, C1-C6-alkyl, C3-C6-cycloalkyl, C3-C7-heterocycloalkyl, C3-C7-heterocycloalkyl substituted with acyl or carboxyl ester, C1-C6-haloalkyl, C1-C6-alkoxy, C1-C6-alkyl-O-C1-C6-alkyl, C1-C6-hydroxyalkyl, and C1-C6 alkenyloxy, preferably H, C1-C6-alkyl, C3-C6-cycloalkyl, C4-C7-heterocycloalkyl and C2-C6-hydroxyalkyl optionally substituted with OH, C1-C6-alkoxy, C1-C6-hydroxyalkyl or C3-C7-heterocycloalkyl.

In a preferred embodiment subject matter of the present invention is a compound according to Formula II in which Y is N(R5)(R6), and R5 is H.

In a more preferred embodiment subject-matter of the present invention is a compound according to Formula II in which Y is N(R5)(R6), R5 is H, and R2 is for each position independently selected from the group comprising H, CF$_2$H, CF$_3$, CF$_2$CH$_3$, F, Cl, CH$_3$, and Et.

In another preferred embodiment subject matter of the present invention is a compound according to Formula II in which Y is N(R5)C(=O)(R6), and R5 is H with the proviso that R6 is not unsubstituted cyclopropyl, unsubstituted cyclobutyl, CH$_3$, or tetrahydrofuranyl.

In another more preferred embodiment subject matter of the present invention is a compound according to Formula II in which Y is N(R5)C(=O)R6, R5 is H, and R2 is for each position independently selected from the group comprising H, CF$_2$H, CF$_3$, CF$_2$CH$_3$, F, Cl, CH$_3$, and Et with the proviso that R6 is not unsubstituted cyclopropyl, unsubstituted cyclobutyl, CH$_3$, or tetrahydrofuranyl.

In another preferred embodiment subject matter of the present invention is a compound according to Formula II in which Y is N(R5)(R6), and R6 is selected from C1-C6-alkyl, C3-C6-cycloalkyl, C4-C7-heterocycloalkyl, C2-C6-aminoalkyl, and C2-C6-hydroxyalkyl, optionally substituted with 1, 2, or 3 groups each independently selected from OH, halo, acyl, SO$_2$Me, carboxy, carboxyl ester, carbamoyl, substituted carbamoyl, C6-aryl, heteroaryl, C1-C6-alkyl, C3-C6-cycloalkyl, C3-C7-heterocycloalkyl, C1-C6-haloalkyl, C1-C6-alkoxy, C1-C6-hydroxyalkyl, and C1-C6 alkenyloxy, preferably H, C1-C6-alkyl, C3-C6-cycloalkyl, C4-C7-heterocycloalkyl and C2-C6-hydroxyalkyl optionally substituted with OH, C1-C6-alkoxy, C1-C6-hydroxyalkyl or C3-C7-heterocycloalkyl.

In another more preferred embodiment subject matter of the present invention is a compound according to Formula II in which Y is N(R5)(R6), R5 is H, R6 is selected from the group comprising C1-C6-alkyl, C3-C6-cycloalkyl, C4-C7-heterocycloalkyl, C2-C6-aminoalkyl, and C2-C6-hydroxyalkyl optionally substituted with one or two groups selected from OH, halo, C3-C6-cycloalkyl, and C3-C7-heterocycloalkyl, and R2 is for each position independently selected from the group comprising H, CF$_2$H, CF$_3$, CF$_2$CH$_3$, F, Cl, CH$_3$, and Et.

In another more preferred embodiment subject matter of the present invention is a compound according to Formula II in which Y is N(R5)C(=O)(R6), and R6 is is selected from C1-C6-alkyl, C3-C6-cycloalkyl, C4-C7-heterocycloalkyl, C2-C6-aminoalkyl, and C2-C6-hydroxyalkyl, optionally substituted with 1, 2, or 3 groups each independently selected from OH, halo, acyl, SO$_2$Me, carboxy, carboxyl ester, carbamoyl, substituted carbamoyl, C6-aryl, heteroaryl, C1-C6-alkyl, C3-C6-cycloalkyl, C3-C7-heterocycloalkyl, C1-C6-haloalkyl, C1-C6-alkoxy, C1-C6-hydroxyalkyl, and C1-C6 alkenyloxy, preferably H, C1-C6-alkyl, C3-C6-cycloalkyl, C4-C7-heterocycloalkyl and C2-C6-hydroxyalkyl optionally substituted with OH, C1-C6-alkoxy, C1-C6-hydroxyalkyl or C3-C7-heterocycloalkyl with the proviso that when R5 is H, R6 is not unsubstituted cyclopropyl, unsubstituted cyclobutyl, CH$_3$, or tetrahydrofuranyl.

In another more preferred embodiment subject matter of the present invention is a compound according to Formula II in which Y is N(R5)C(=O)(R6), R5 is H, R6 is selected from the group comprising C1-C6-alkyl, C3-C6-cycloalkyl, C4-C7-heterocycloalkyl, C2-C6-aminoalkyl, and C2-C6-hydroxyalkyl optionally substituted with one or two groups selected from OH, halo, C3-C6-cycloalkyl, and C3-C7-heterocycloalkyl, and R2 is for each position independently selected from the group comprising H, CF$_2$H, CF$_3$, CF$_2$CH$_3$, F, Cl, CH$_3$, and Et with the proviso that R6 is not unsubstituted cyclopropyl, unsubstituted cyclobutyl, CH$_3$, or tetrahydrofuranyl.

In one embodiment subject matter of the present invention is a compound according to Formula II in which n is 1.

In one embodiment subject matter of the present invention is a compound according to Formula II in which m is 1.

In a preferred embodiment subject matter of the present invention is a compound according to Formula II in which n is 1 and m is 1 with the proviso that when Y is N(R5)C(=O)(R6) and R5 is H, R6 is not unsubstituted cyclopropyl, unsubstituted cyclobutyl, CH$_3$, or tetrahydrofuranyl.

In a more preferred subject matter of the present invention is a compound according to Formula II in which n is 1, m is 1 and Y is N(R5)(R6).

In an even more preferred embodiment subject matter of the present invention is a compound according to Formula II in which n is 1, m is 1, Y is N(R5)(R6), and R5 is H.

In another more preferred embodiment subject matter of the present invention is a compound according to Formula II in which n is 1, m is 1 and Y is N(R5)C(=O)(R6) with the proviso that when R5 is H, R6 is not unsubstituted cyclopropyl, unsubstituted cyclobutyl, CH$_3$, or tetrahydrofuranyl.

In another even more preferred embodiment subject matter of the present invention is a compound according to Formula II in which n is 1, m is 1, Y is N(R5)C(=O)(R6), and R5 is H with the proviso that R6 is not unsubstituted cyclopropyl, unsubstituted cyclobutyl, CH$_3$, or tetrahydrofuranyl.

One embodiment of the invention is a pharmaceutical composition comprising a compound of Formula II or a pharmaceutically acceptable salt thereof according to the present invention, together with a pharmaceutically acceptable carrier.

One embodiment of the invention is a method of treating an HBV infection in an individual in need thereof, comprising administering to the individual a therapeutically effective amount of a compound of Formula II or a pharmaceutically acceptable salt thereof according to the present invention.

A further embodiment of the invention is a compound of Formula III or a pharmaceutically acceptable salt thereof according to the invention, for use in the prevention or treatment of an HBV infection in subject

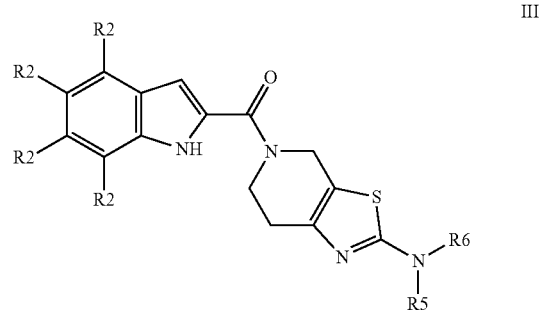

III in which
R2 is for each position independently selected from the group comprising H, CF$_2$H, CF$_3$, CF$_2$CH$_3$, F, Cl, Br, CH$_3$, Et, and i-Pr
R5 and R6 are independently selected from the group comprising H, D, C1-C6-alkyl, C3-C6-cycloalkyl, C4-C7-heterocycloalkyl, C2-C6-aminoalkyl, and C2-C6-hydroxyalkyl, optionally substituted with 1, 2, or 3 groups each independently selected from OH, halo, acyl, SO$_2$Me, carboxy, carboxyl ester, carbamoyl, substituted carbamoyl, C6-aryl, heteroaryl, C1-C6-alkyl, C3-C6-cycloalkyl, C3-C7-heterocycloalkyl, C3-C7-heterocycloalkyl substituted with acyl or carboxyl ester, C1-C6-haloalkyl, C1-C6-alkoxy, C1-C6-alkyl-O-C1-C6-alkyl, C1-C6-hydroxyalkyl, and C1-C6 alkenyloxy In one embodiment subject matter of the present invention is a compound according to Formula III in which:
R2 is for each position independently selected from the group comprising H, CF$_2$H, CF$_3$, CF$_2$CH$_3$, F, Cl, CH$_3$, and Et.
R5 and R6 are independently selected from the group comprising H, C1-C6-alkyl, C3-C6-cycloalkyl, C4-C7-heterocycloalkyl and C2-C6-hydroxyalkyl optionally substituted with OH, C1-C6-alkoxy, C1-C6-hydroxyalkyl and C3-C7-heterocycloalkyl.

In one embodiment subject matter of the present invention is a compound according to Formula III in which R2 is for each position independently selected from the group comprising H, CF$_2$H, CF$_3$, CF$_2$CH$_3$, F, Cl, Br, CH$_3$, Et, and i-Pr, preferably H, CF$_2$H, CF$_3$, CF$_2$CH$_3$, F, Cl, CH$_3$, and Et.

In one embodiment subject matter of the present invention is a compound according to Formula III in which R5 and R6 are independently selected from the group comprising H, D, C1-C6-alkyl, C3-C6-cycloalkyl, C4-C7-heterocycloalkyl, C2-C6-aminoalkyl, and C2-C6-hydroxyalkyl, optionally substituted with 1, 2, or 3 groups each independently selected from OH, halo, acyl, SO$_2$Me, carboxy, carboxyl ester, carbamoyl, substituted carbamoyl, C6-aryl, heteroaryl, C1-C6-alkyl, C3-C6-cycloalkyl, C3-C7-heterocycloalkyl, C3-C7-heterocycloalkyl substituted with acyl or carboxyl ester, C1-C6-haloalkyl, C1-C6-alkoxy, C1-C6-alkyl-O-C1-C6-alkyl, C1-C6-hydroxyalkyl, and C1-C6 alkenyloxy, preferably H, C1-C6-alkyl, C3-C6-cycloalkyl, C4-C7-heterocycloalkyl and C2-C6-hydroxyalkyl optionally substituted with OH, C1-C6-alkoxy, C1-C6-hydroxyalkyl or C3-C7-heterocycloalkyl.

In a preferred embodiment subject matter of the present invention is a compound according to Formula III in which R2 is for each position independently selected from the group comprising H, CF$_2$H, CF$_3$, CF$_2$CH$_3$, F, Cl, CH$_3$, and Et, and R5 is H.

In another preferred embodiment subject matter of the present invention is a compound according to Formula III in which R2 is for each position independently selected from the group comprising H, CF$_2$H, CF$_3$, CF$_2$CH$_3$, F, Cl, CH$_3$, and Et, and R6 is selected from the group comprising H, D, C1-C6-alkyl, C3-C6-cycloalkyl, C4-C7-heterocycloalkyl, C2-C6-aminoalkyl, and C2-C6-hydroxyalkyl, optionally substituted with 1, 2, or 3 groups each independently selected from OH, halo, acyl, SO$_2$Me, carboxy, carboxyl ester, carbamoyl, substituted carbamoyl, C6-aryl, heteroaryl, C1-C6-alkyl, C3-C6-cycloalkyl, C3-C7-heterocycloalkyl, C1-C6-haloalkyl, C1-C6-alkoxy, C1-C6-hydroxyalkyl, and C1-C6 alkenyloxy, preferably H, C1-C6-alkyl, C3-C6-cycloalkyl, C4-C7-heterocycloalkyl and C2-C6-hydroxyalkyl optionally substituted with OH, C1-C6-alkoxy, C1-C6-hydroxyalkyl or C3-C7-heterocycloalkyl.

In another even more preferred embodiment subject matter of the present invention is a compound according to Formula III in which R2 is for each position independently selected from the group comprising H, CF$_2$H, CF$_3$, CF$_2$CH$_3$, F, Cl, CH$_3$, and Et, R5 is H, and R6 is selected from the group comprising C1-C6-alkyl, C3-C6-cycloalkyl, C4-C7-heterocycloalkyl, C2-C6-aminoalkyl, and C2-C6-hydroxyalkyl optionally substituted with one or two groups selected from OH, halo, C3-C6-cycloalkyl, and C3-C7-heterocycloalkyl.

One embodiment of the invention is a pharmaceutical composition comprising a compound of Formula III or a pharmaceutically acceptable salt thereof according to the present invention, together with a pharmaceutically acceptable carrier.

One embodiment of the invention is a method of treating an HBV infection in an individual in need thereof, comprising administering to the individual a therapeutically effective amount of a compound of Formula III or a pharmaceutically acceptable salt thereof according to the present invention.

A further embodiment of the invention is a compound of Formula IVa or IVb or a pharmaceutically acceptable salt thereof according to the invention, for use in the prevention or treatment of an HBV infection in subject.

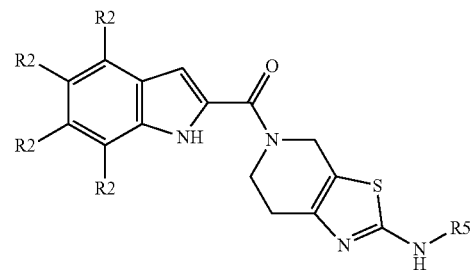

IVa

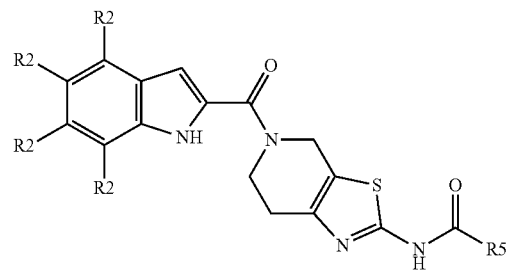

IVb in which
R2 is for each position independently selected from the group comprising H, CH$_2$F, CF$_2$H, CF$_3$, C(F)CH$_3$, CF$_2$CH$_3$, F, Cl, Br, CH$_3$, and Et
R5 is selected from the group comprising H, D, C1-C6-alkyl, C3-C6-cycloalkyl, C4-C7-heterocycloalkyl, C2-C6-aminoalkyl, and C2-C6-hydroxyalkyl, optionally substituted with 1, 2, or 3 groups each independently selected from OH, halo, acyl, SO$_2$Me, carboxy, carboxyl ester, carbamoyl, substituted carbamoyl, C6-aryl, heteroaryl, C1-C6-alkyl, C3-C6-cycloalkyl, C3-C7-heterocycloalkyl, C1-C6-haloalkyl, C1-C6-alkoxy, C1-C6-hydroxyalkyl, or C1-C6 alkenyloxy, preferably C1-C6-alkyl, C3-C6-cycloalkyl, C4-C7-heterocycloalkyl and C2-C6-hydroxyalkyl optionally substituted with OH, C1-C6-alkoxy, C1-C6-hydroxylalkyl and C3-C7-heterocycloalkyl
with the proviso that
when the said compound is a compound of Formula IVb, R5 is not unsubstituted cyclopropyl, unsubstituted cyclobutyl, CH$_3$, or tetrahydrofuranyl.

In one embodiment subject matter of the present invention is a compound according to Formula IVa or IVb in which R2 is H, CH$_2$F, CF$_2$H, CF$_3$, CF$_2$CH$_3$, F, Cl, Br, CH$_3$, or Et.

In one embodiment subject matter of the present invention is a compound according to Formula IVa or IVb in which R5 is C1-C6-alkyl, C3-C6-cycloalkyl, C4-C7-heterocycloalkyl, C2-C6-aminoalkyl, or C2-C6-hydroxyalkyl, optionally substituted with 1, 2, or 3 groups each independently selected from OH, halo, acyl, SO$_2$Me, carboxy, carboxyl ester, carbamoyl, substituted carbamoyl, C6-aryl, heteroaryl, C1-C6-alkyl, C3-C6-cycloalkyl, C3-C7-heterocycloalkyl, C1-C6-haloalkyl, C1-C6-alkoxy, C1-C6-hydroxyalkyl, and C1-C6 alkenyloxy, preferably C1-C6-alkyl, C3-C6-cycloalkyl, C4-C7-heterocycloalkyl and C2-C6-hydroxyalkyl optionally substituted with OH, C1-C6-alkoxy, C1-C6-hydroxylalkyl or C3-C7-heterocycloalkyl.

In a preferred embodiment subject matter of the present invention is a compound according to Formula IVa or IVb in which R2 is for each position independently selected from the group comprising H, CF$_2$H, CF$_3$, CF$_2$CH$_3$, F, Cl, CH$_3$, and Et, and R5 is selected from the group comprising C1-C6-alkyl, C3-C6-cycloalkyl, C4-C7-heterocycloalkyl, C2-C6-aminoalkyl, and C2-C6-hydroxyalkyl, optionally substituted with 1, 2, or 3 groups each independently selected from OH, halo, acyl, SO$_2$Me, carboxy, carboxyl ester, carbamoyl, substituted carbamoyl, C6-aryl, heteroaryl, C1-C6-alkyl, C3-C6-cycloalkyl, C3-C7-heterocycloalkyl, C1-C6-haloalkyl, C1-C6-alkoxy, C1-C6-hydroxyalkyl, and C1-C6 alkenyloxy, preferably C1-C6-alkyl, C3-C6-cycloalkyl, C4-C7-heterocycloalkyl and C2-C6-hydroxyalkyl optionally substituted with OH, C1-C6-alkoxy, C1-C6-hydroxylalkyl or C3-C7-heterocycloalkyl with the proviso that when the said compound is a compound of Formula IVb, R5 is not unsubstituted cyclopropyl, unsubstituted cyclobutyl, CH$_3$, or tetrahydrofuranyl.

In a more preferred embodiment subject matter of the present invention is a compound according to Formula IVa or IVb in which R2 is for each position independently selected from the group comprising H, CF$_2$H, CF$_3$, CF$_2$CH$_3$, F, Cl, CH$_3$, and Et, and R5 is selected from C1-C6-alkyl, C3-C6-cycloalkyl, C4-C7-heterocycloalkyl, C2-C6-aminoalkyl, and C2-C6-hydroxyalkyl optionally substituted with one or two groups selected from OH, halo, C3-C6-cycloalkyl, and C3-C7-heterocycloalkyl with the proviso that when the said compound is a compound of Formula IVb, R5 is not unsubstituted cyclopropyl, unsubstituted cyclobutyl, CH$_3$, or tetrahydrofuranyl.

One embodiment of the invention is a pharmaceutical composition comprising a compound of Formula IVa or IVb or a pharmaceutically acceptable salt thereof according to the present invention, together with a pharmaceutically acceptable carrier.

One embodiment of the invention is a method of treating an HBV infection in an individual in need thereof, comprising administering to the individual a therapeutically effective amount of a compound of Formula IVa or IVb or a pharmaceutically acceptable salt thereof according to the present invention.

In some embodiments, the dose of a compound of the invention is from about 1 mg to about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound (i.e., another drug for HBV treatment) as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof. All before mentioned doses refer to daily doses per patient.

The compounds of the invention may, depending on their structure, exist as salts, solvates or hydrates. The invention therefore also encompasses the salts, solvates or hydrates and respective mixtures thereof.

The compounds of the invention may, depending on their structure, exist in tautomeric or stereoisomeric forms (enantiomers, diastereomers). The invention therefore also encompasses the tautomers, enantiomers or diastereomers and respective mixtures thereof. The stereoisomerically uniform constituents can be isolated in a known manner from such mixtures of enantiomers and/or diastereomers.

Further embodiments within the scope of the present invention are set out below:

1. Compound of Formula I

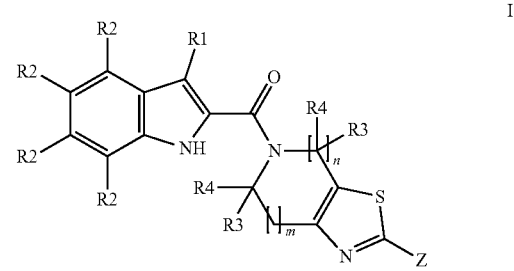

I in which
Z is H, D, O(R5), CH$_3$, C≡N, Cl, C(═O)NH$_2$, N(R5)(R6), N(R5)C(═O)(R6), NHC(═O)N(R5)(R6), N(R5)SO$_2$(R6), NHC(═O)O(R5), NHC(═O)C(═O)O(R5), NHC(═O)C(═O)N(R5)(R6), NHC(═O)NHSO$_2$R5, CH$_2$—N(R5)(R6), aryl, and heteroaryl
R1 is H, D, F, Cl, Br, NH$_2$
R2 is for each position independently selected from the group comprising H, CF$_2$H, CF$_3$, CF$_2$CH$_3$, F, Cl, Br, CH$_3$, Et, i-Pr, c-Pr, D, CH$_2$OH, CH(CH$_3$)OH, CH$_2$F, C(F)CH$_3$, I, C═C, C≡C, C≡N, C(CH$_3$)$_2$OH, Si(CH$_3$)$_3$, SMe, OH, OCH$_3$
R3 and R4 are for each position independently selected from the group comprising H, methyl and ethyl
R3 and R4 are optionally connected to form a C3-C5-cycloalkyl ring
R5 and R6 are independently selected from the group comprising H, D, C1-C6-alkyl, C3-C6-cycloalkyl, C4-C7-heterocycloalkyl, C2-C6-aminoalkyl, and C2-C6-hydroxyalkyl, optionally substituted with 1, 2, or 3 groups each independently selected from OH, halo, acyl, SO$_2$Me, carboxy, carboxyl ester, carbamoyl, substituted carbamoyl, C6-aryl, heteroaryl, C1-C6-alkyl, C3-C6-cycloalkyl, C3-C7-heterocycloalkyl, C1-C6-haloalkyl, C1-C6-alkoxy, C1-C6-hydroxyalkyl, and C1-C6 alkenyloxy
R5 and R6 are optionally connected to form a C4-C7-heterocyclic ring containing 1 or 2 nitrogen or oxygen atoms.

n is 1 or 2 m is 0 or 1 or a pharmaceutically acceptable salt thereof or a solvate of a compound of Formula I or the pharmaceutically acceptable salt thereof or a prodrug of a compound of Formula I or a pharmaceutically acceptable salt or a solvate thereof.

2. A compound of Formula I according to embodiment 1 that is a compound of Formula II

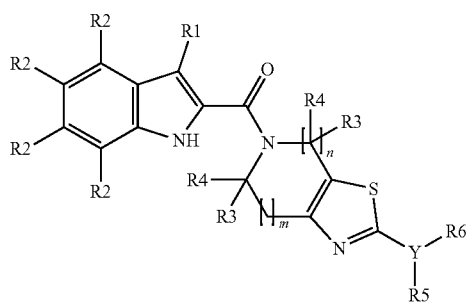

in which
- Y is N(R5)SO$_2$(R6), N(R5)(R6), or N(R5)C(=O)(R6)
- R1 is H
- R2 is for each position independently selected from the group comprising H, CF$_2$H, CF$_3$, CF$_2$CH$_3$, F, Cl, Br, CH$_3$, Et, i-Pr
- R3 and R4 are for each position independently selected from the group comprising H and methyl
- R5 and R6 are independently selected from the group comprising H, D, C1-C6-alkyl, C3-C6-cycloalkyl, C4-C7-heterocycloalkyl, C2-C6-aminoalkyl, and C2-C6-hydroxyalkyl, optionally substituted with 1, 2, or 3 groups each independently selected from OH, halo, acyl, SO$_2$Me, carboxy, carboxyl ester, carbamoyl, substituted carbamoyl, C6-aryl, heteroaryl, C1-C6-alkyl, C3-C6-cycloalkyl, C3-C7-heterocycloalkyl, C1-C6-haloalkyl, C1-C6-alkoxy, C1-C6-hydroxyalkyl, or C1-C6 alkenyloxy
- R5 and R6 are optionally connected to form a C4-C7-heterocyclic ring containing 1 or 2 nitrogen or oxygen atoms.
- n is 1 or 2
- m is 0 or 1 or a pharmaceutically acceptable salt thereof or a solvate of a compound of Formula II or the pharmaceutically acceptable salt thereof or a prodrug of a compound of Formula II or a pharmaceutically acceptable salt or a solvate thereof.

3. A compound of Formula I according to embodiments 1 or 2 that is a compound of Formula III

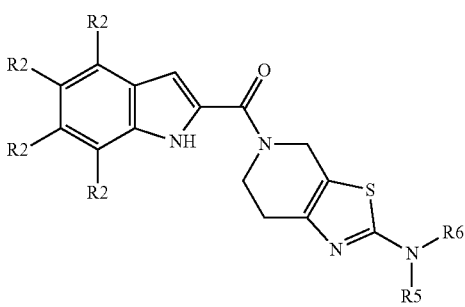

in which
- R2 is for each position independently selected from the group comprising H, CF$_2$H, CF$_3$, CF$_2$CH$_3$, F, Cl, Br, CH$_3$, Et, i-Pr
- R5 and R6 are independently selected from the group comprising H, D, C1-C6-alkyl, C3-C6-cycloalkyl, C4-C7-heterocycloalkyl, C2-C6-aminoalkyl, and C2-C6-hydroxyalkyl, optionally substituted with 1, 2, or 3 groups each independently selected from OH, halo, acyl, SO$_2$Me, carboxy, carboxyl ester, carbamoyl, substituted carbamoyl, C6-aryl, heteroaryl, C1-C6-alkyl, C3-C6-cycloalkyl, C3-C7-heterocycloalkyl, C1-C6-haloalkyl, C1-C6-alkoxy, C1-C6-hydroxyalkyl, or C1-C6 alkenyloxy or a pharmaceutically acceptable salt thereof or a solvate of a compound of Formula III or the pharmaceutically acceptable salt thereof or a prodrug of a compound of Formula III or a pharmaceutically acceptable salt or a solvate thereof.

4. A compound of Formula I according to any of embodiments 1-3 that is a compound of Formula IVa or IVb

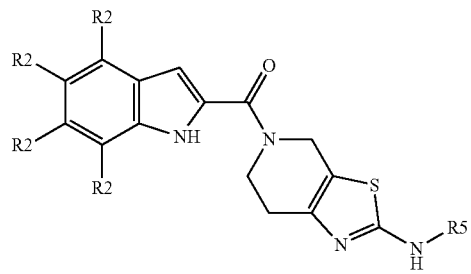

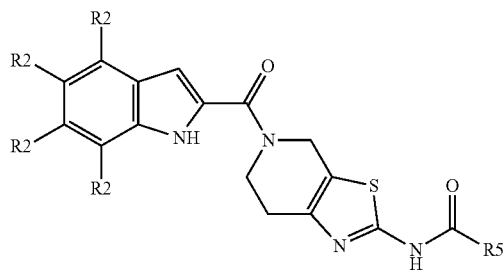

in which
- R2 is for each position independently selected from the group comprising H, CH$_2$F, CF$_2$H, CF$_3$, C(F)CH$_3$, CF$_2$CH$_3$, F, Cl, Br, CH$_3$, Et
- R5 is selected from the group comprising H, D, C1-C6-alkyl, C3-C6-cycloalkyl, C4-C7-heterocycloalkyl, C2-C6-aminoalkyl, and C2-C6-hydroxyalkyl, optionally substituted with 1, 2, or 3 groups each independently selected from OH, halo, acyl, SO$_2$Me, carboxy, carboxyl ester, carbamoyl, substituted carbamoyl, C6-aryl, heteroaryl, C1-C6-alkyl, C3-C6-cycloalkyl, C3-C7-heterocycloalkyl, C1-C6-haloalkyl, C1-C6-alkoxy, C1-C6-hydroxyalkyl, or C1-C6 alkenyloxy, preferably C1-C6-alkyl, C3-C6-cycloalkyl, C4-C7-heterocycloalkyl and C2-C6-hydroxyalkyl optionally substituted with OH, C1-C6-alkoxy, C1-C6-hydroxylalkyl and C3-C7-heterocycloalkyl.

or a pharmaceutically acceptable salt thereof or a solvate of a compound of Formula IVa or IVb or the pharmaceutically acceptable salt thereof or a prodrug of a compound of Formula IVa or IVb or a pharmaceutically acceptable salt or a solvate thereof.

5. A compound according to any of embodiments 1 to 4 or a pharmaceutically acceptable salt thereof or a solvate of said compound or the pharmaceutically acceptable salt thereof or a prodrug of said compound or a pharmaceutically acceptable salt or a solvate thereof for use in the prevention or treatment of an HBV infection in subject.

6. A pharmaceutical composition comprising a compound according to any of embodiments 1 to 4 or a pharmaceutically acceptable salt thereof or a solvate of said compound or the pharmaceutically acceptable salt thereof or a prodrug of said compound or a pharmaceutically acceptable salt or a solvate thereof, together with a pharmaceutically acceptable carrier.

7. A method of treating an HBV infection in an individual in need thereof, comprising administering to the individual a therapeutically effective amount of a compound according to any of embodiments 1 to 4 or a pharmaceutically acceptable salt thereof or a solvate of said compound or the pharmaceutically acceptable salt thereof or a prodrug of said compound or a pharmaceutically acceptable salt or a solvate thereof.

8. Method for the preparation of a compound of Formula I according to embodiment 1 by reacting a compound of Formula V

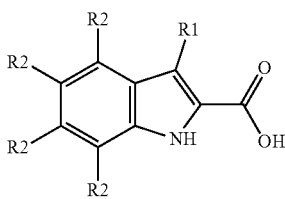

in which R and R2 are as defined in embodiment 1, with a compound of Formula VI

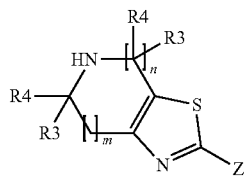

in which n, m, Z, R3 and R4 are as defined in embodiment 1.

Further embodiments within the scope of the present invention are set out below:

1. Compound of Formula I

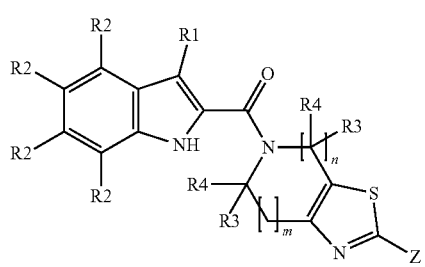

in which

Z is H, D, O(R5), $CH_3$, C≡N, Cl, C(=O)$NH_2$, N(R5)(R6), N(R5)C(=O)(R6), NHC(=O)N(R5)(R6), N(R5)$SO_2$(R6), NHC(=O)C(=O)O(R5), NHC(=O)C(=O)N(R5)(R6), NHC(=O)NH$SO_2$R5, $CH_2$—N(R5)(R6), or heteroaryl R1 is H, D, F, Cl, Br, or $NH_2$ R2 is for each position independently selected from the group comprising H, $CF_2H$, $CF_3$, $CF_2CH_3$, F, Cl, Br, $CH_3$, Et, i-Pr, c-Pr, D, $CH_2OH$, $CH(CH_3)OH$, $CH_2F$, C(F)$CH_3$, I, C=C, C≡C, C≡N, C($CH_3$)$_2$OH, Si($CH_3$)$_3$, SMe, OH, and $OCH_3$ R3 and R4 are for each position independently selected from the group comprising H, methyl and ethyl R3 and R4 are optionally connected to form a C3-C5-cycloalkyl ring R5 and R6 are independently selected from the group comprising H, D, C1-C6-alkyl, C3-C6-cycloalkyl, C4-C7-heterocycloalkyl, C2-C6-aminoalkyl, and C2-C6-hydroxyalkyl, optionally substituted with 1, 2, or 3 groups each independently selected from OH, halo, C≡N, acyl, $SO_2$Me, carboxy, carboxyl ester, carbamoyl, substituted carbamoyl, C6-aryl, heteroaryl, C1-C6-alkyl, C3-C6-cycloalkyl, C3-C7-heterocycloalkyl, C3-C7-heterocycloalkyl substituted with acyl or carboxyl ester, C1-C6-haloalkyl, C1-C6-alkoxy, C1-C6-alkyl-O-C1-C6-alkyl, C1-C6-hydroxyalkyl, C1-C6-alkylamino, and C1-C6 alkenyloxy R5 and R6 are optionally connected to form a C4-C7-heterocyclic ring containing 1 or 2 nitrogen or oxygen atoms, optionally substituted with 1, 2, or 3 groups each independently selected from OH, halo, acyl, $SO_2$Me, carboxy, carboxyl ester, carbamoyl, substituted carbamoyl, C6-aryl, heteroaryl, C1-C6-alkyl, C3-C6-cycloalkyl, C3-C7-heterocycloalkyl, C1-C6-haloalkyl, C1-C6-alkoxy, C1-C6-hydroxyalkyl, and C1-C6 alkenyloxy n is 1 or 2 m is 0 or 1 with the proviso that when Z is NHC(=O)N(R5)(R6), neither R5, nor R6 is cyclopentyl or isopropyl, and when Z is N(R5)C(=O)(R6) and R5 is H, R6 is not unsubstituted cyclopropyl, unsubstituted cyclobutyl, $CH_3$, or tetrahydrofuranyl, or a pharmaceutically acceptable salt thereof or a solvate of a compound of Formula I or the pharmaceutically acceptable salt thereof or a prodrug of a compound of Formula I or a pharmaceutically acceptable salt or a solvate thereof.

2. A compound of Formula I according to embodiment 1 that is a compound of Formula II

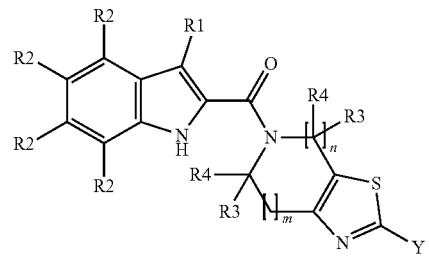

in which
- Y is N(R5)SO₂(R6), N(R5)(R6), or N(R5)C(=O)(R6)
- R1 is H
- R2 is for each position independently selected from the group comprising H, CF₂H, CF₃, CF₂CH₃, F, Cl, Br, CH₃, Et, and i-Pr
- R3 and R4 are for each position independently selected from the group comprising H and methyl
- R5 and R6 are independently selected from the group comprising H, D, C1-C6-alkyl, C3-C6-cycloalkyl, C4-C7-heterocycloalkyl, C2-C6-aminoalkyl, and C2-C6-hydroxyalkyl, optionally substituted with 1, 2, or 3 groups each independently selected from OH, halo, acyl, SO₂Me, carboxy, carboxyl ester, carbamoyl, substituted carbamoyl, C6-aryl, heteroaryl, C1-C6-alkyl, C3-C6-cycloalkyl, C3-C7-heterocycloalkyl, C3-C7-heterocycloalkyl substituted with acyl or carboxyl ester, C1-C6-haloalkyl, C1-C6-alkoxy, C1-C6-alkyl-O-C1-C6-alkyl, C1-C6-hydroxyalkyl, and C1-C6 alkenyloxy
- R5 and R6 are optionally connected to form a C4-C7-heterocyclic ring containing 1 or 2 nitrogen or oxygen atoms, optionally substituted with 1, 2, or 3 groups each independently selected from OH, halo, acyl, SO₂Me, carboxy, carboxyl ester, carbamoyl, substituted carbamoyl, C6-aryl, heteroaryl, C1-C6-alkyl, C3-C6-cycloalkyl, C3-C7-heterocycloalkyl, C1-C6-haloalkyl, C1-C6-alkoxy, C1-C6-hydroxyalkyl, and C1-C6 alkenyloxy
- n is 1 or 2
- m is 0 or 1 with the proviso that
when Y is N(R5)C(=O)(R6) and R5 is H, R6 is not unsubstituted cyclopropyl, unsubstituted cyclobutyl, CH₃, or tetrahydrofuranyl,
or a pharmaceutically acceptable salt thereof or a solvate of a compound of Formula II or the pharmaceutically acceptable salt thereof or a prodrug of a compound of Formula II or a pharmaceutically acceptable salt or a solvate thereof.

3. A compound of Formula I according to embodiments 1 or 2 that is a compound of Formula III

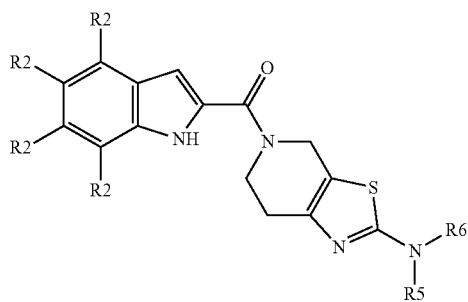

in which
- R2 is for each position independently selected from the group comprising H, CF₂H, CF₃, CF₂CH₃, F, Cl, Br, CH₃, Et, and i-Pr
- R5 and R6 are independently selected from the group comprising H, D, C1-C6-alkyl, C3-C6-cycloalkyl, C4-C7-heterocycloalkyl, C2-C6-aminoalkyl, and C2-C6-hydroxyalkyl, optionally substituted with 1, 2, or 3 groups each independently selected from OH, halo, acyl, SO₂Me, carboxy, carboxyl ester, carbamoyl, substituted carbamoyl, C6-aryl, heteroaryl, C1-C6-alkyl, C3-C6-cycloalkyl, C3-C7-heterocycloalkyl, C3-C7-heterocycloalkyl substituted with acyl or carboxyl ester, C1-C6-haloalkyl, C1-C6-alkoxy, C1-C6-alkyl-O-C1-C6-alkyl, C1-C6-hydroxyalkyl, and C1-C6 alkenyloxy or a pharmaceutically acceptable salt thereof or a solvate of a compound of Formula III or the pharmaceutically acceptable salt thereof or a prodrug of a compound of Formula III or a pharmaceutically acceptable salt or a solvate thereof.

4. A compound of Formula I according to any of embodiments 1-3 that is a compound of Formula IVa or IVb

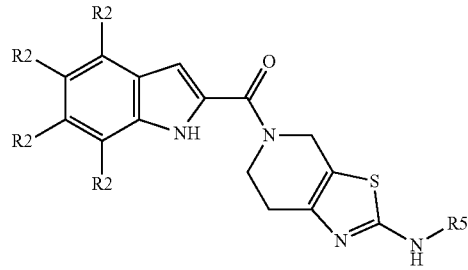

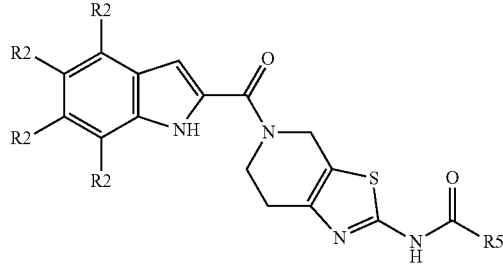

in which
- R2 is for each position independently selected from the group comprising H, CH₂F, CF₂H, CF₃, C(F)CH₃, CF₂CH₃, F, Cl, Br, CH₃, and Et.
- R5 is selected from the group comprising H, D, C1-C6-alkyl, C3-C6-cycloalkyl, C4-C7-heterocycloalkyl, C2-C6-aminoalkyl, and C2-C6-hydroxyalkyl, optionally substituted with 1, 2, or 3 groups each independently selected from OH, halo, acyl, SO₂Me, carboxy, carboxyl ester, carbamoyl, substituted carbamoyl, C6-aryl, heteroaryl, C1-C6-alkyl, C3-C6-cycloalkyl, C3-C7-heterocycloalkyl, C1-C6-haloalkyl, C1-C6-alkoxy, C1-C6-hydroxyalkyl, and C1-C6 alkenyloxy, preferably C1-C6-alkyl, C3-C6-cycloalkyl, C4-C7-heterocycloalkyl and C2-C6-hydroxyalkyl optionally substituted with OH, C1-C6-alkoxy, C1-C6-hydroxylalkyl or C3-C7-heterocycloalkyl.

with the proviso that
when the said compound is a compound of Formula IVb, R5 is not unsubstituted cyclopropyl, unsubstituted cyclobutyl, CH₃, or tetrahydrofuranyl,
or a pharmaceutically acceptable salt thereof or a solvate of a compound of Formula IVa or IVb or the pharmaceutically acceptable salt thereof or a prodrug of a compound of Formula IVa or IVb or a pharmaceutically acceptable salt or a solvate thereof.

5. A compound according to any of embodiments 1 to 4 or a pharmaceutically acceptable salt thereof or a solvate of said compound or the pharmaceutically acceptable salt thereof or a prodrug of said compound or a pharmaceutically acceptable salt or a solvate thereof for use in the prevention or treatment of an HBV infection in subject.

6. A pharmaceutical composition comprising a compound according to any of embodiments 1 to 4 or a pharmaceutically acceptable salt thereof or a solvate of said compound or the pharmaceutically acceptable salt thereof or a prodrug of said compound or a pharmaceutically acceptable salt or a solvate thereof, together with a pharmaceutically acceptable carrier.

7. A method of treating an HBV infection in an individual in need thereof, comprising administering to the individual a therapeutically effective amount of a compound according to any of embodiments 1 to 4 or a pharmaceutically acceptable salt thereof or a solvate of said compound or the pharmaceutically acceptable salt thereof or a prodrug of said compound or a pharmaceutically acceptable salt or a solvate thereof.

8. Method for the preparation of a compound of Formula I according to embodiment 1 by reacting a compound of Formula V

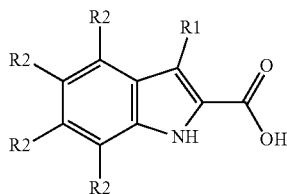

in which R1 and R2 are as defined in embodiment 1, with a compound of Formula VI

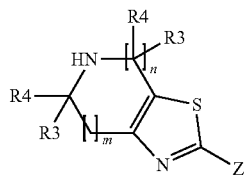

in which n, m, Z, R3 and R4 are as defined in embodiment 1.

DEFINITIONS

Listed below are definitions of various terms used to describe this invention. These definitions apply to the terms as they are used throughout this specification and claims unless otherwise limited in specific instances either individually or as part of a larger group.

Unless defined otherwise all technical and scientific terms used herein generally have the same meaning as commonly understood by one of ordinary skill in the art to which this invention belongs. Generally the nomenclature used herein and the laboratory procedures in cell culture, molecular genetics, organic chemistry and peptide chemistry are those well known and commonly employed in the art.

As used herein the articles "a" and "an" refer to one or to more than one (i.e. to at least one) of the grammatical object of the article. By way of example, "an element" means one element or more than one element. Furthermore, use of the term "including" as well as other forms such as "include", "includes" and "included", is not limiting.

As used herein the term "capsid assembly modulator" refers to a compound that disrupts or accelerates or inhibits or hinders or delays or reduces or modifies normal capsid assembly (e.g. during maturation) or normal capsid disassembly (e.g. during infectivity) or perturbs capsid stability, thereby inducing aberrant capsid morphology or aberrant capsid function. In one embodiment, a capsid assembly modulator accelerates capsid assembly or disassembly thereby inducing aberrant capsid morphology. In another embodiment a capsid assembly modulator interacts (e.g. binds at an active site, binds at an allosteric site or modifies and/or hinders folding and the like), with the major capsid assembly protein (HBV-CP), thereby disrupting capsid assembly or disassembly. In yet another embodiment a capsid assembly modulator causes a perturbation in the structure or function of HBV-CP (e.g. the ability of HBV-CP to assemble, disassemble, bind to a substrate, fold into a suitable conformation or the like which attenuates viral infectivity and/or is lethal to the virus).

As used herein the term "treatment" or "treating" is defined as the application or administration of a therapeutic agent i.e., a compound of the invention (alone or in combination with another pharmaceutical agent) to a patient, or application or administration of a therapeutic agent to an isolated tissue or cell line from a patient (e.g. for diagnosis or ex vivo applications) who has an HBV infection, a symptom of HBV infection, or the potential to develop an HBV infection with the purpose to cure, heal, alleviate, relieve, alter, remedy, ameliorate, improve or affect the HBV infection, the symptoms of HBV infection or the potential to develop an HBV infection. Such treatments may be specifically tailored or modified based on knowledge obtained from the field of pharmacogenomics.

As used herein the term "prevent" or "prevention" means no disorder or disease development if none had occurred, or no further disorder or disease development if there had already been development of the disorder or disease. Also considered is the ability of one to prevent some or all of the symptoms associated with the disorder or disease.

As used herein the term "patient", "individual" or "subject" refers to a human or a non-human mammal. Non-human mammals include for example livestock and pets such as ovine, bovine, porcine, feline, and murine mammals. Preferably the patient, subject, or individual is human.

As used herein the terms "effective amount", "pharmaceutically effective amount", and "therapeutically effective amount" refer to a nontoxic but sufficient amount of an agent to provide the desired biological result. That result may be reduction and/or alleviation of the signs, symptoms, or causes of a disease, or any other desired alteration of a biological system. An appropriate therapeutic amount in any individual case may be determined by one of ordinary skill in the art using routine experimentation.

As used herein the term "pharmaceutically acceptable" refers to a material such as a carrier or diluent which does not abrogate the biological activity or properties of the compound and is relatively non-toxic i.e. the material may be administered to an individual without causing undesirable biological effects or interacting in a deleterious manner with any of the components of the composition in which it is contained.

As used herein the term "pharmaceutically acceptable salt" refers to derivatives of the disclosed compounds wherein the parent compound is modified by converting an existing acid or base moiety to its salt form. Examples of pharmaceutically acceptable salts include but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent or in a mixture of the two; generally non-aqueous media like ether, ethyl acetate, ethanol, isopropanol, or acetonitrile are preferred. Lists of suitable salts are found in Remington's Pharmaceutical Sciences $17^{th}$ ed. Mack Publishing Company, Easton, Pa., 1985 p. 1418 and Journal of Pharmaceutical Science, 66, 2 (1977), each of which is incorporated herein by reference in its entirety.

As used herein the term "composition" or "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including but not limited to intravenous, oral, aerosol, rectal, parenteral, ophthalmic, pulmonary and topical administration.

As used herein the term "pharmaceutically acceptable carrier" means a pharmaceutically acceptable material, composition or carrier such as a liquid or solid filler, stabilizer, dispersing agent, suspending agent, diluent, excipient, thickening agent, solvent or encapsulating material involved in carrying or transporting a compound useful within the invention within or to the patient such that it may perform its intended function. Typically such constructs are carried or transported from one organ, or portion of the body, to another organ or portion of the body. Each carrier must be "acceptable" in the sense of being compatible with the other ingredients of the formulation including the compound use within the invention and not injurious to the patient. Some examples of materials that may serve as pharmaceutically acceptable carriers include: sugars, such as lactose, glucose and sucrose; starches such as corn starch and potato starch; cellulose and its derivatives such as sodium carboxymethyl cellulose, ethyl cellulose and cellulose acetate; powdered tragacanth; malt, gelatin, talc; excipients such as cocoa butter and suppository waxes; oils such as peanut oil, cottonseed oil, safflower oil, sesame oil, olive oil, corn oil and soybean oil; glycols such as propylene glycol; polyols such as glycerin, sorbitol, mannitol and polyethylene glycol; esters such as ethyl oleate and ethyl laurate; agar; buffering agents, such as magnesium hydroxide and aluminium hydroxide; surface active agents; alginic acid; pyrogen-free water; isotonic saline; Ringer's solution; ethyl alcohol; phosphate buffer solutions and other non-toxic compatible substances employed in pharmaceutical formulations.

As used herein "pharmaceutically acceptable carrier" also includes any and all coatings, antibacterial and antifungal agents and absorption delaying agents and the like that are compatible with the activity of the compound useful within the invention and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described for example in Remington's Pharmaceutical Sciences (Genaro, Ed., Mack Publishing Company, Easton, Pa., 1985) which is incorporated herein by reference.

As used herein, the term "substituted" means that an atom or group of atoms has replaced hydrogen as the substituent attached to another group.

As used herein, the term "comprising" also encompasses the option "consisting of".

As used herein, the term "alkyl" by itself or as part of another substituent means, unless otherwise stated, a straight or branched chain hydrocarbon having the number of carbon atoms designated (i.e. C1-C6-alkyl means one to six carbon atoms) and includes straight and branched chains. Examples include methyl, ethyl, propyl, isopropyl, butyl, isobutyl, tert-butyl, pentyl, neopentyl, and hexyl. In addition, the term "alkyl" by itself or as part of another substituent can also mean a C1-C3 straight chain hydrocarbon substituted with a C3-C5-carbocylic ring. Examples include (cyclopropyl)methyl, (cyclobutyl)methyl and (cyclopentyl)methyl. For the avoidance of doubt, where two alkyl moieties are present in a group, the alkyl moieties may be the same or different.

As used herein the term "alkenyl" denotes a monovalent group derived from a hydrocarbon moiety containing at least two carbon atoms and at least one carbon-carbon double bond of either E or Z stereochemistry. The double bond may or may not be the point of attachment to another group. Alkenyl groups (e.g. C2-C8-alkenyl) include, but are not limited to for example ethenyl, propenyl, prop-1-en-2-yl, butenyl, methyl-2-buten-1-yl, heptenyl and octenyl. For the avoidance of doubt, where two alkenyl moieties are present in a group, the alkyl moieties may be the same or different.

As used herein, a C2-C6-alkynyl group or moiety is a linear or branched alkynyl group or moiety containing from 2 to 6 carbon atoms, for example a C2-C4 alkynyl group or moiety containing from 2 to 4 carbon atoms. Exemplary alkynyl groups include —C≡CH or —CH$_2$—C≡C, as well as 1- and 2-butynyl, 2-pentynyl, 3-pentynyl, 4-pentynyl, 2-hexynyl, 3-hexynyl, 4-hexynyl and 5-hexynyl. For the avoidance of doubt, where two alkynyl moieties are present in a group, they may be the same or different.

As used herein, the term "halo" or "halogen" alone or as part of another substituent means unless otherwise stated a fluorine, chlorine, bromine, or iodine atom, preferably fluorine, chlorine, or bromine, more preferably fluorine or chlorine. For the avoidance of doubt, where two halo moieties are present in a group, they may be the same or different.

As used herein, an C1-C6-alkoxy group or C1-C6-alkenyloxy group is typically a said C1-C6-alkyl (e.g. a C1-C4 alkyl) group or a said C2-C6-alkenyl (e.g. a C2-4 alkenyl) group respectively which is attached to an oxygen atom.

As used herein the term "aryl" employed alone or in combination with other terms, means unless otherwise stated a carbocyclic aromatic system containing one or more rings (typically one, two or three rings) wherein such rings may be attached together in a pendant manner such as a biphenyl, or may be fused, such as naphthalene. Examples of aryl groups include phenyl, anthracyl, and naphthyl. Preferred examples are phenyl (e.g. C6-aryl) and biphenyl (e.g. C12-aryl). In some embodiments aryl groups have from six to sixteen carbon atoms. In some embodiments aryl groups have from six to twelve carbon atoms (e.g. C6-C12-aryl). In some embodiments, aryl groups have six carbon atoms (e.g. C6-aryl).

As used herein the terms "heteroaryl" and "heteroaromatic" refer to a heterocycle having aromatic character containing one or more rings (typically one, two or three rings). Heteroaryl substituents may be defined by the number of carbon atoms e.g. C1-C9-heteroaryl indicates the number of carbon atoms contained in the heteroaryl group without including the number of heteroatoms. For example a C1-C9-heteroaryl will include an additional one to four heteroatoms. A polycyclic heteroaryl may include one or more rings that are partially saturated. Non-limiting examples of heteroaryls include:

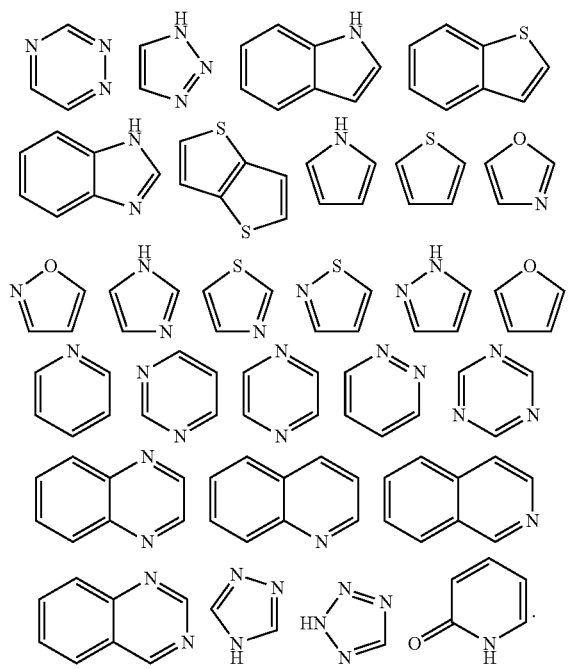

Additional non-limiting examples of heteroaryl groups include pyridyl, pyrazinyl, pyrimidinyl (including e.g. 2- and 4-pyrimidinyl), pyridazinyl, thienyl, furyl, pyrrolyl (including e.g., 2-pyrrolyl), imidazolyl, thiazolyl, oxazolyl, pyrazolyl (including e.g. 3- and 5-pyrazolyl), isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl. Non-limiting examples of polycyclic heterocycles and heteroaryls include indolyl (including 3-, 4-, 5-, 6- and 7-indolyl), indolinyl, quinolyl, tetrahydroquinolyl, isoquinolyl (including, e.g. 1- and 5-isoquinolyl), 1,2,3,4-tetrahydroisoquinolyl, cinnolinyl, quinoxalinyl (including, e.g. 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (including, e.g. 3-, 4-, 5-, 6-, and 7-benzofuryl), 2,3-dihydrobenzofuryl, 1,2-benzisoxazolyl, benzothienyl (including e.g. 3-, 4-, 5-, 6-, and 7-benzothienyl), benzoxazolyl, benzothiazolyl (including e.g. 2-benzothiazolyl and 5-benzothiazolyl), purinyl, benzimidazolyl (including e.g., 2-benzimidazolyl), benzotriazolyl, thioxanthinyl, carbazolyl, carbolinyl, acridinyl, pyrrolizidinyl and quinolizidinyl.

As used herein the term "haloalkyl" is typically a said alkyl, alkenyl, alkoxy or alkenoxy group respectively wherein any one or more of the carbon atoms is substituted with one or more said halo atoms as defined above. Haloalkyl embraces monohaloalkyl, dihaloalkyl, and polyhaloalkyl radicals. The term "haloalkyl" includes but is not limited to fluoromethyl, 1-fluoroethyl, difluoromethyl, 2,2-difluoroethyl, 2,2,2-trifluoroethyl, trifluoromethyl, chloromethyl, dichloromethyl, trichloromethyl, pentafluoroethyl, difluoromethoxy, and trifluoromethoxy.

As used herein, a C1-C6-hydroxyalkyl group is a said C1-C6 alkyl group substituted by one or more hydroxy groups. Typically, it is substituted by one, two or three hydroxyl groups. Preferably, it is substituted by a single hydroxy group.

As used herein, a C1-C6-aminoalkyl group is a said C1-C6 alkyl group substituted by one or more amino groups. Typically, it is substituted by one, two or three amino groups. Preferably, it is substituted by a single amino group.

As used herein the term "cycloalkyl" refers to a monocyclic or polycyclic nonaromatic group wherein each of the atoms forming the ring (i.e. skeletal atoms) is a carbon atom. In one embodiment, the cycloalkyl group is saturated or partially unsaturated. In another embodiment, the cycloalkyl group is fused with an aromatic ring. Cycloalkyl groups include groups having 3 to 10 ring atoms (C3-C10-cycloalkyl), groups having 3 to 8 ring atoms (C3-C8-cycloalkyl), groups having 3 to 7 ring atoms (C3-C7-cycloalkyl) and groups having 3 to 6 ring atoms (C3-C6-cycloalkyl). Illustrative examples of cycloalkyl groups include, but are not limited to the following moieties:

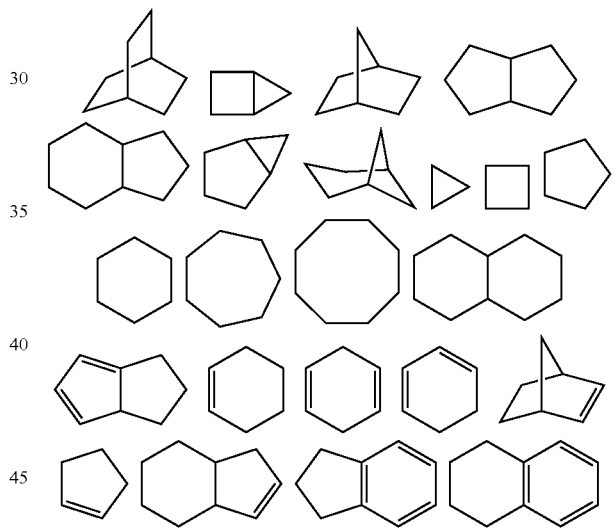

Monocyclic cycloalkyls include but are not limited to cyclopropyl, cyclobutyl, cyclopentyl, cyclohexyl, cycloheptyl, and cyclooctyl. Dicyclic cycloalkyls include but are not limited to tetrahydronaphthyl, indanyl, and tetrahydropentalene. Polycyclic cycloalkyls include adamantine and norbornane. The term cycloalkyl includes "unsaturated nonaromatic carbocyclyl" or "nonaromatic unsaturated carbocyclyl" groups both of which refer to a nonaromatic carbocycle as defined herein which contains at least one carbon-carbon double bond or one carbon-carbon triple bond.

As used herein the terms "heterocycloalkyl" and "heterocyclyl" refer to a heteroalicyclic group containing one or more rings (typically one, two or three rings), that contains one to four ring heteroatoms each selected from oxygen, sulfur and nitrogen. In one embodiment each heterocyclyl group has from 3 to 10 atoms in its ring system with the proviso that the ring of said group does not contain two adjacent oxygen or sulfur atoms. In one embodiment each heterocyclyl group has a fused bicyclic ring system with 3 to 10 atoms in the ring system, again with the proviso that the ring of said group does not contain two adjacent oxygen or sulfur atoms. In one embodiment each heterocyclyl group has a bridged bicyclic ring system with 3 to 10 atoms in the ring system, again with the proviso that the ring of said group does not contain two adjacent oxygen or sulfur atoms. In one embodiment each heterocyclyl group has a spiro-bicyclic ring system with 3 to 10 atoms in the ring system, again with the proviso that the ring of said group does not contain two adjacent oxygen or sulfur atoms. Heterocyclyl substituents may be alternatively defined by the number of carbon atoms e.g. C2-C8-heterocyclyl indicates the number of carbon atoms contained in the heterocyclic group without including the number of heteroatoms. For example a C2-C8-heterocyclyl will include an additional one to four heteroatoms. In another embodiment the heterocycloalkyl group is fused with an aromatic ring. In another embodiment the heterocycloalkyl group is fused with a heteroaryl ring. In one embodiment the nitrogen and sulfur heteroatoms may be optionally oxidized and the nitrogen atom may be optionally quaternized. The heterocyclic system may be attached, unless otherwise stated, at any heteroatom or carbon atom that affords a stable structure. An example of a 3-membered heterocyclyl group includes and is not limited to aziridine. Examples of 4-membered heterocycloalkyl groups include, and are not limited to azetidine and a beta-lactam. Examples of 5-membered heterocyclyl groups include, and are not limited to pyrrolidine, oxazolidine and thiazolidinedione. Examples of 6-membered heterocycloalkyl groups include, and are not limited to, piperidine, morpholine, piperazine, N-acetylpiperazine and N-acetylmorpholine. Other non-limiting examples of heterocyclyl groups are

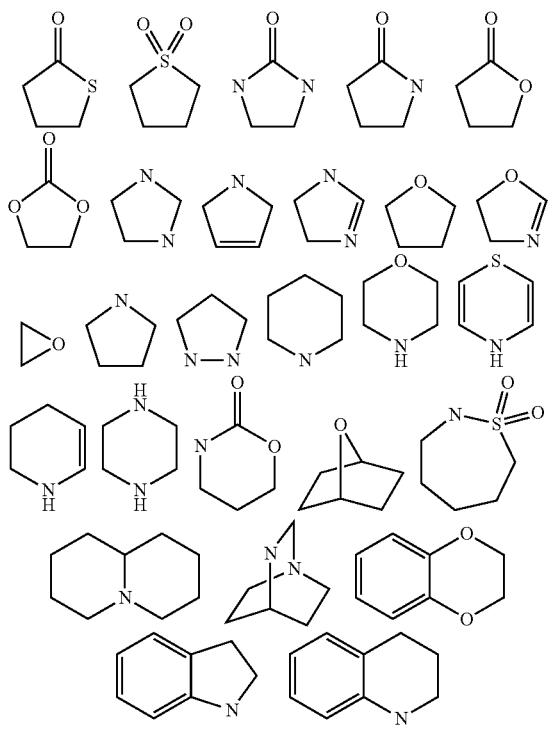

Examples of heterocycles include monocyclic groups such as aziridine, oxirane, thiirane, azetidine, oxetane, thietane, pyrrolidine, pyrroline, pyrazolidine, imidazoline, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, 1,3-dioxolane, homopiperazine, homopiperidine, 1,3-dioxepane, 47-dihydro-1,3-dioxepin, and hexamethyleneoxide.

As used herein, the term "aromatic" refers to a carbocycle or heterocycle with one or more polyunsaturated rings and having aromatic character i.e. having (4n+2) delocalized π (pi) electrons where n is an integer.

As used herein, the term "acyl", employed alone or in combination with other terms, means, unless otherwise stated, to mean to an alkyl, cycloalkyl, heterocycloalkyl, aryl or heteroaryl group linked via a carbonyl group.

As used herein, the terms "carbamoyl" and "substituted carbamoyl", employed alone or in combination with other terms, means, unless otherwise stated, to mean a carbonyl group linked to an amino group optionally mono or di-substituted by hydrogen, alkyl, cycloalkyl, heterocycloalkyl, aryl or heteroaryl. In some embodiments, the nitrogen substituents will be connected to form a heterocyclyl ring as defined above.

As used herein, the term "carboxy" and by itself or as part of another substituent means, unless otherwise stated, a group of formula C(═O)OH.

As used herein, the term "carboxyl ester" by itself or as part of another substituent means, unless otherwise stated, a group of formula C(═O)OX, wherein X is selected from the group consisting of C1-C6-alkyl, C3-C7-cycloalkyl, and aryl.

As used herein, a C1-C6-alkylamino group is typically one or two said C1-C6-alkyl (e.g. a C1-C4 alkyl) groups attached to a nitrogen atom. Alkylamino groups include, but are not limited to, for example, dimethylamino ((CH$_3$)$_2$N—), diethylamino ((CH$_3$CH$_2$)$_2$N—) and methylamino (CH$_3$NH—).

As used herein, a C1-C6-alkyl-O-C1-C6-alkyl group is typically a said C1-C6-alkoxy group attached to a said C1-C6-alkyl group, wherein any one or more of the carbon atoms is optionally substituted with one or more said halo atoms as defined above. C1-C6-alkyl-O-C1-C6-alkyl groups include, but are not limited to, for example, ethoxymethyl, methoxymethyl, methoxyethyl, difluoromethoxymethyl, difluoromethoxyethyl and trifluoromethoxymethyl.

As used herein the term "prodrug" represents a derivative of a compound of Formula I or Formula II or Formula III or Formula IVa or Formula IVb which is administered in a form which, once administered, is metabolised in vivo into an active metabolite also of Formula I or Formula II or Formula III or Formula IVa or Formula IVb.

Subject matter of the present invention are also the prodrugs of a compound of Formula I or Formula II or Formula III or Formula IVa or Formula IVb, whether in generalized form or in a specifically mentioned form below.

Various forms of prodrug are known in the art. For examples of such prodrugs see: Design of Prodrugs, edited by H. Bundgaard, (Elsevier, 1985) and Methods in Enzymology, Vol. 42, p. 309-396, edited by K. Widder, et al. (Academic Press, 1985); A Textbook of Drug Design and Development, edited by Krogsgaard-Larsen and H. Bundgaard, Chapter 5 "Design and Application of Prodrugs" by H. Bundgaard p. 113-191 (1991); H. Bundgaard, Advanced Drug Delivery Reviews 8, 1-38 (1992); H. Bundgaard, et al., Journal of Pharmaceutical Sciences, 77, 285 (1988); and N. Kakeya, et al., Chem. Pharm. Bull., 32, 692 (1984).

Examples of prodrugs include cleavable esters of compounds of Formula I, II, III, IVa and/or IVb. An in vivo cleavable ester of a compound of the invention containing a carboxy group is, for example, a pharmaceutically acceptable ester which is cleaved in the human or animal body to produce the parent acid. Suitable pharmaceutically acceptable esters for carboxy include C1-C6 alkyl ester, for example methyl or ethyl esters; C1-C6 alkoxymethyl esters, for example methoxymethyl ester; C1-C6 alkanoyloxymethyl esters; phthalidyl esters; C3-C8 cycloalkoxycarbonyloxyC1-C6 alkyl esters, for example 1-cyclohexylcarbonyloxyethyl; 1-3-dioxolan-2-ylmethylesters, for example 5-methyl-1,3-dioxolan-2-ylmethyl; C1-C6 alkoxycarbonyloxyethyl esters, for example 1-methoxycarbonyloxyethyl; aminocarbonylmethyl esters and mono- or di-N—(C1-C6 alkyl) versions thereof, for example N, N-dimethylaminocarbonylmethyl esters and N-ethylaminocarbonylmethyl esters; and may be formed at any carboxy group in the compounds of the invention.

An in vivo cleavable ester of a compound of the invention containing a hydroxy group is, for example, a pharmaceutically-acceptable ester which is cleaved in the human or animal body to produce the parent hydroxy group. Suitable pharmaceutically acceptable esters for hydroxy include C1-C6-alkanoyl esters, for example acetyl esters; and benzoyl esters wherein the phenyl group may be substituted with aminomethyl or N-substituted mono- or di-C1-C6 alkyl aminomethyl, for example 4-aminomethylbenzoyl esters and 4-N,N-dimethylaminomethylbenzoylesters.

Preferred prodrugs of the invention include acetyloxy and carbonate derivatives. For example, a hydroxy group of a compound of Formula I, II, III, IVa and/or IVb can be present in a prodrug as —O—COR$^i$ or —O—C(O)OR$^i$ where R$^i$ is unsubstituted or substituted C1-C4 alkyl. Substituents on the alkyl groups are as defined earlier. Preferably the alkyl groups in R$^i$ is unsubstituted, preferable methyl, ethyl, isopropyl or cyclopropyl.

Other preferred prodrugs of the invention include amino acid derivatives. Suitable amino acids include α-amino acids linked to compounds of Formula I, II, III, IVa and/or IVb via their C(O)OH group. Such prodrugs cleave in vivo to produce compounds of Formula I, II, III, IVa and/or IVb bearing a hydroxy group. Accordingly, such amino acid groups are preferably employed positions of Formula I, II, III, IVa and/or IVb where a hydroxy group is eventually required.

Exemplary prodrugs of this embodiment of the invention are therefore compounds of Formula I, II, III, IVa and/or IVb bearing a group of Formula —OC(O)—CH(NH$_2$)R$^{ii}$ where R$^{ii}$ is an amino acid side chain. Preferred amino acids include glycine, alanine, valine and serine. The amino acid can also be functionalised, for example the amino group can be alkylated. A suitable functionalised amino acid is N,N-dimethylglycine. Preferably the amino acid is valine.

Other preferred prodrugs of the invention include phosphoramidate derivatives. Various forms of phosphoramidate prodrugs are known in the art. For example of such prodrugs see Serpi et al., Curr. Protoc. Nucleic Acid Chem. 2013, Chapter 15, Unit 15.5 and Mehellou et al., ChemMedChem, 2009, 4 pp. 1779-1791. Suitable phosphoramidates include (phenoxy)-α-amino acids linked to compounds of Formula I via their —OH group. Such prodrugs cleave in vivo to produce compounds of Formula I bearing a hydroxy group. Accordingly, such phosphoramidate groups are preferably employed positions of Formula I where a hydroxy group is eventually required. Exemplary prodrugs of this embodiment of the invention are therefore compounds of Formula I bearing a group of Formula —OP(O)(OR$^{iii}$)R$^{iv}$ where R$^{iii}$ is alkyl, cycloalkyl, aryl or heteroaryl, and R$^{iv}$ is a group of Formula —NH—CH(R$^v$)C(O)OR$^{vi}$. wherein R$^v$ is an amino acid side chain and R$^{vi}$ is alkyl, cycloalkyl, aryl or heterocyclyl. Preferred amino acids include glycine, alanine, valine and serine. Preferably the amino acid is alanine. R$^v$ is preferably alkyl, most preferably isopropyl.

Subject matter of the present invention is also a method of preparing the compounds of the present invention. Subject matter of the invention is, thus, a method for the preparation of a compound of Formula I according to the present invention by reacting a compound of Formula V

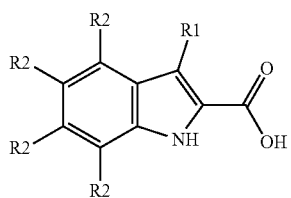

V in which R1 and R2 are as above-defined, with a compound of Formula VI

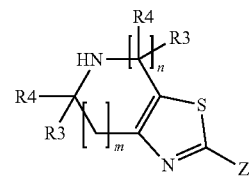

VI in which n, m, Z, R3 and R4 are as above-defined.

Subject matter of the invention is, also, a method for the preparation of a compound of Formula II, III, IV and V in the same manner, and as will be outlined in the Examples in more detail.

EXAMPLES

The invention is now described with reference to the following Examples. These Examples are provided for the purpose of illustration only, and the invention is not limited to these Examples, but rather encompasses all variations that are evident as a result of the teachings provided herein.

The HBV capsid assembly modulators can be prepared in a number of ways. Schemes 1-10 and Scheme 15 illustrate the main routes employed for their preparation for the purpose of this application. To the chemist skilled in the art it will be apparent that there are other methodologies that will also achieve the preparation of these intermediates and Examples.

In a preferred embodiment compounds of Formula I can be prepared as shown in General scheme 1 below.

General scheme1: Synthesis of compounds of Formula I

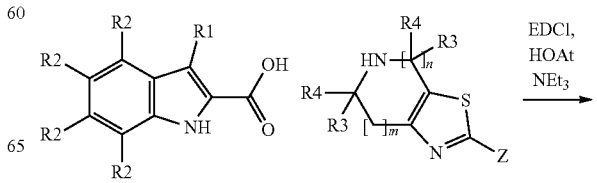

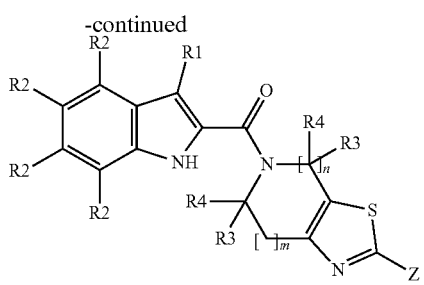

An amide coupling between an indole-2-carboxylic acid and an appropriate amine (e.g. a suitably substituted 4H,5H, 6H-pyrrolo[3,4-d][1,3]thiazole, a 4H,5H,6H,7H-[1,3]thiazolo[5,4-c]pyridine or a 4H,5H,6H,7H,8H-[1,3]thiazolo[4,5-d]azepine) with methods known in literature (A. El-Faham, F. Albericio, Chem. Rev. 2011, 111, 6557-6602) e.g. with HATU gives compounds of Formula I.

In another preferred embodiment the synthesis of compounds of Formula II follows General scheme 2.

Compound 1 shown in General scheme 2 is converted into bromide 2 in a Sandmeyer reaction (X. Cao et al., J. Med. Chem., 2014, 57, 3687-3706). In step 2 deprotection of the nitrogen protective group (A. Isidro-Lobet et al., Chem. Rev., 2009, 109, 2455-2504), drawn as (but not limited to Boc) e.g. with TFA gives amine 3. An amide coupling in step 3 with methods known in literature (El-Faham, F. Albericio, Chem. Rev. 2011, 111, 6557-6602), e.g. with EDCI results in a compound with the general structure 4. By methods known from the literature, the compounds with general structure 4 in step 4 are aminated (Y=N) (WO2014113191), alkoxylated (Y=O) (WO201229070), (hetero)arylated (X. Cao et al., J. Med. Chem., 2014, 57, 3687-3706), carboxylated under metal-halogen exchange conditions (N. Haginoya et al., Heterocycles, 2004, 63, 1555-1561), followed by amidation (Y=C(=O)N) (A. El-Faham, F. Albericio, Chem. Rev. 2011, 111, 6557-6602), formylated under metal-halogen exchange conditions (A. P. Jathoul, Angew. Chem., 2014, 53, 13059-13063), followed by reductive amination (Y=CH$_2$N) (WO2009147188) or cyanated (Y=CN) (EP1683800) to obtain compounds of Formula II.

General scheme 2: Synthesis of compounds of Formula II

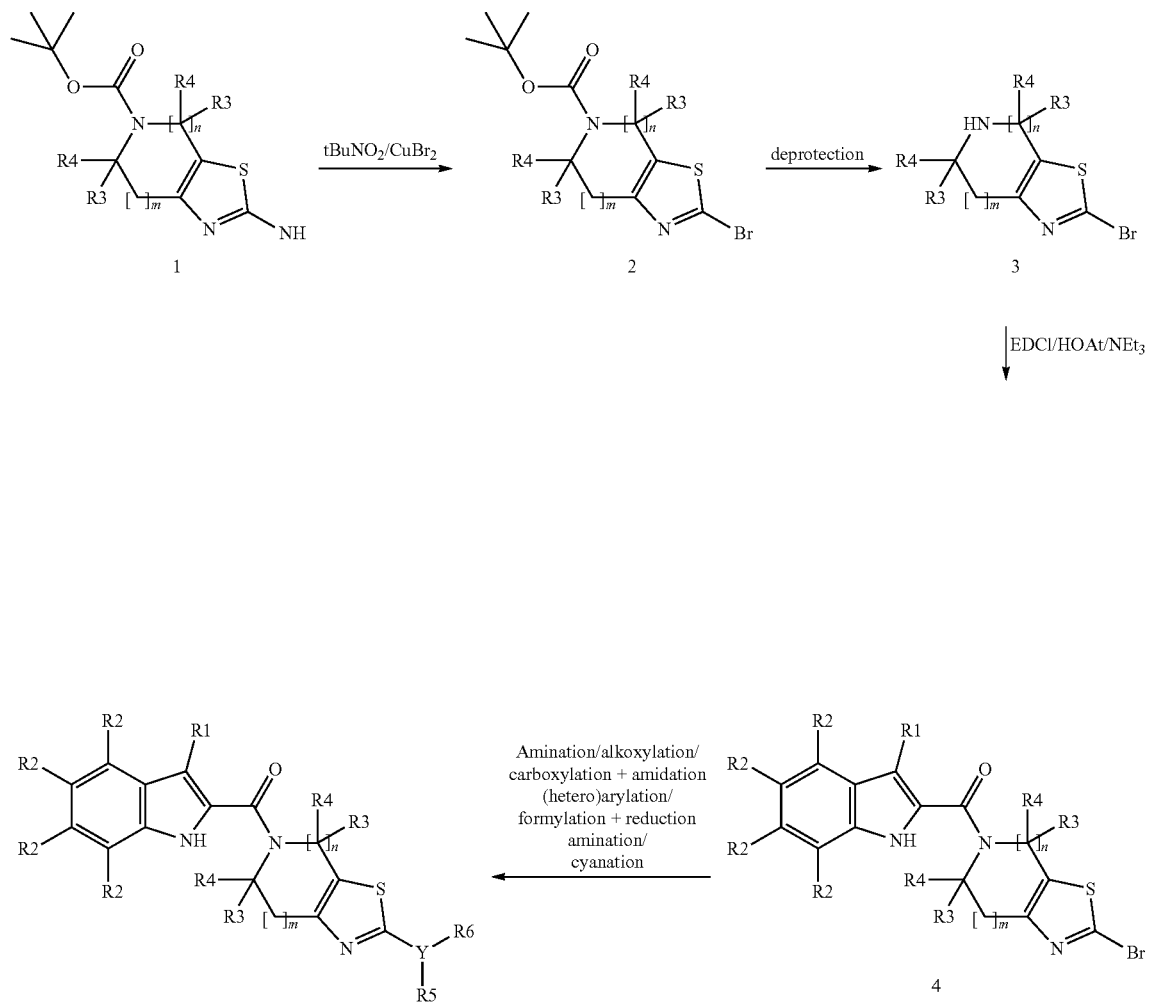

In another preferred embodiment the synthesis of compounds of Formula I and Formula II follows General scheme 3.

General scheme 3: Synthesis of compounds of Formula I and II

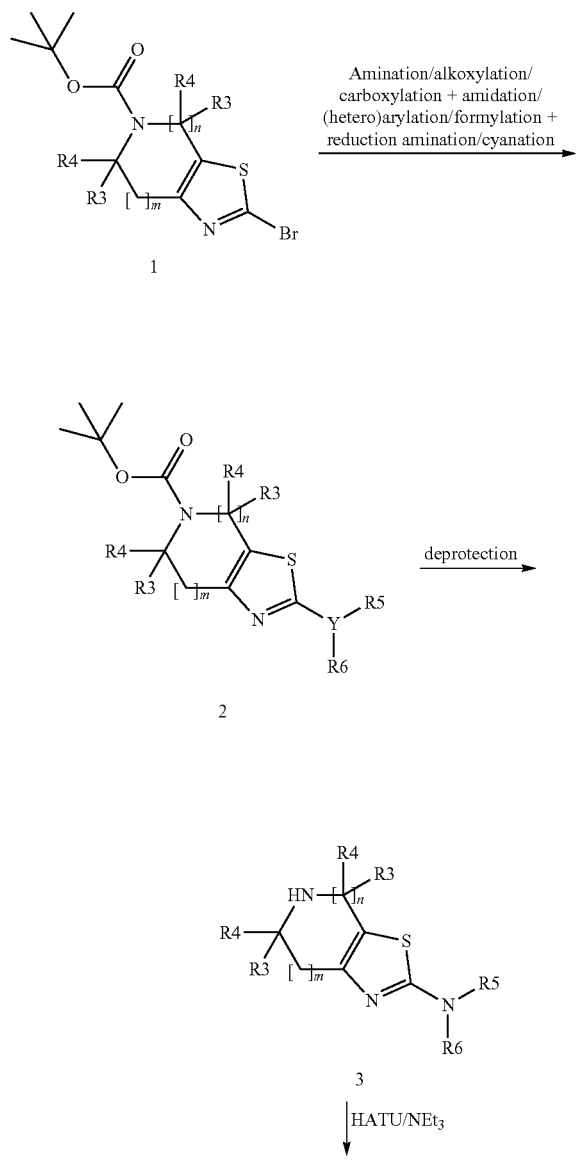

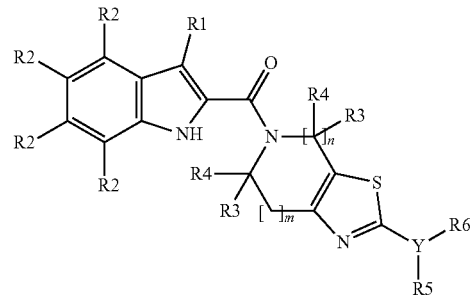

Compound 1 described in general scheme 3 is in step 1 aminated (Y=N) (WO2014113191), alkoxylated (Y=O) (WO201229070), (hetero)arylated (X. Cao et al., J. Med. Chem., 2014, 57, 3687-3706), carboxylated under metal-halogen exchange conditions (N. Haginoya et al., Heterocycles, 2004, 63, 1555-1561), followed by amidation (Y=C(=O)N) (A. El-Faham, F. Albericio, Chem. Rev. 2011, 111, 6557-6602), formylated under metal-halogen exchange conditions (A. P. Jathoul, Angew. Chem., 2014, 53, 13059-13063), followed by reductive amination (Y=CH$_2$N) (WO2009147188), or cyanated (Y=CN) (EP1683800) to obtain compounds with the general structure 2. In step 2 deprotection of the nitrogen protective group (A. Isidro-Llobet et al., Chem. Rev., 2009, 109, 2455-2504), drawn as but not limited to Boc, e.g. with HCl gives amine 3. An amide coupling in step 3 with methods known in literature (A. El-Faham, F. Albericio, Chem. Rev. 2011, 111, 6557-6602), e.g. with HATU results in compounds of Formula I and Formula II.

In another preferred embodiment the synthesis of compounds of Formula III and Formula IVa follows General scheme 4.

General scheme 4: Synthesis of compounds of Formula III and IVa

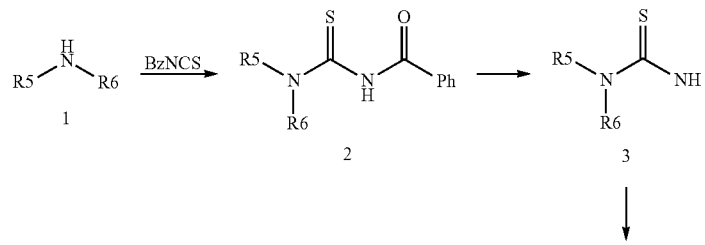

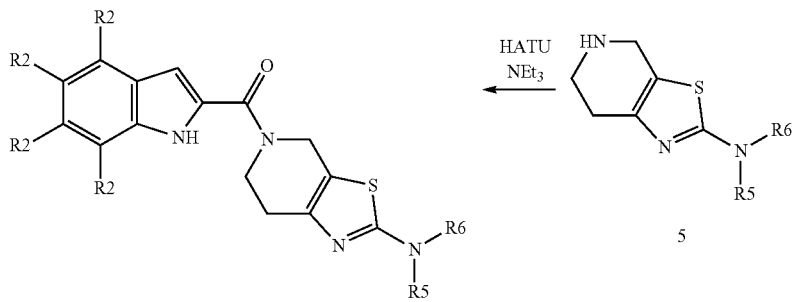

Compound 1 described in general scheme 4 is converted into the thioamide 2 by methods known from the literature (US2013123230) e.g. with benzoyl isothiocyanate. In step 2 deprotection of the thioamide (US2013123230), (drawn as but not limited to Bz) gives thioamide 3. Compound 3 is cyclized in step 3 to aminothiazole 4 (WO2012031024) under basic conditions. In step 4 deprotection of the nitrogen protective group (A. Isidro-Llobet et al., Chem. Rev., 2009, 109, 2455-2504), drawn as but not limited to Boc, e.g. with HCl gives amine 5. An amide coupling in step 4 with methods known in literature (A. El-Faham, F. Albericio, Chem. Rev. 2011, 111, 6557-6602), e.g. with HATU results in compounds of Formula III and Formula IVa.

In another preferred embodiment the synthesis of compounds of Formula IVb follows General scheme 5.

General scheme 5: Synthesis of compounds of Formula IVb

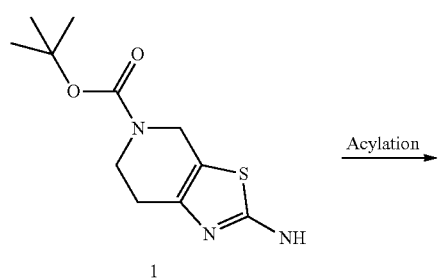

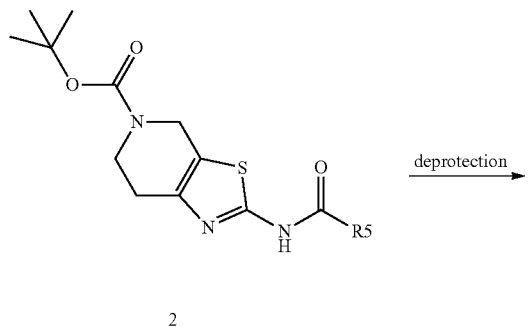

By methods known from the literature, in step 1 the compounds with general structure 1 described in general scheme 5 are acylated (P. N. Collier et al., J. Med. Chem., 2015, 58, 5684-5688). In step 2 deprotection of the nitrogen protective group (A. Isidro-Llobet et al., Chem. Rev., 2009, 109, 2455-2504), drawn as but not limited to Boc, e.g. with HCl gives amine 3. An amide coupling in step 3 with methods known in literature (A. El-Faham, F. Albericio, Chem. Rev. 2011, 111, 6557-6602), e.g. with HATU results in compounds of Formula IVb.

In another embodiment an alternative synthesis of compounds of Formula III follows General scheme 6.

General scheme 6: Synthesis of compounds of Formula III

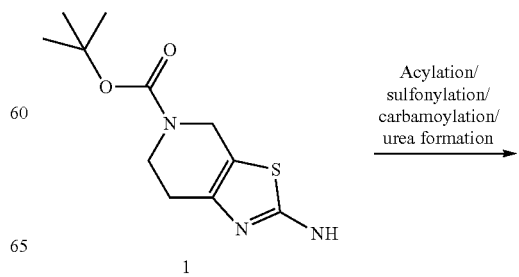

-continued

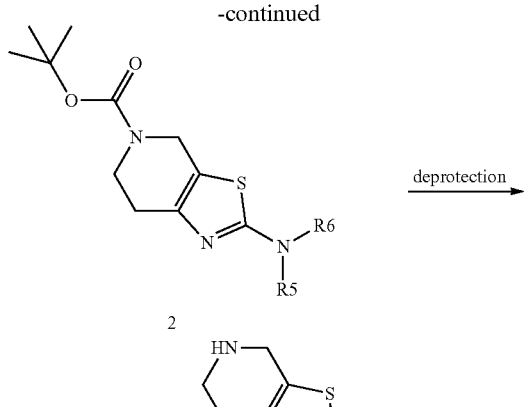

2

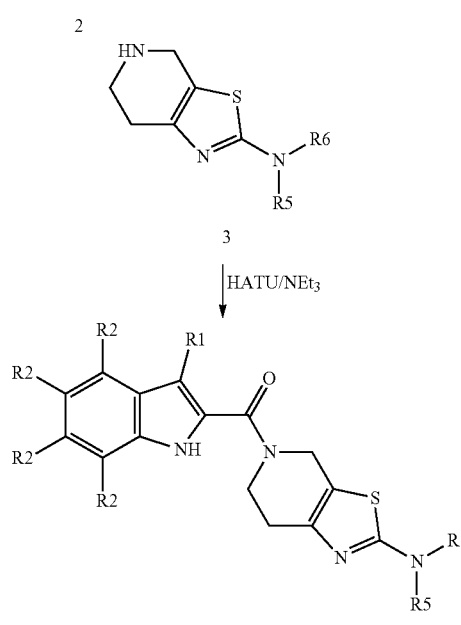

3

| HATU/NEt₃

-continued

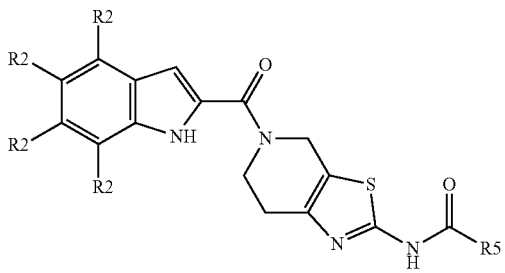

By methods known from the literature, the compounds described in general scheme 7 are acylated (P. N. Collier et al., J. Med. Chem., 2015, 58, 5684-5688) to give compounds of Formula IVb.

In another preferred embodiment the synthesis of compounds according to the invention follows General scheme 8.

General scheme 8: Synthesis of compounds of the invention

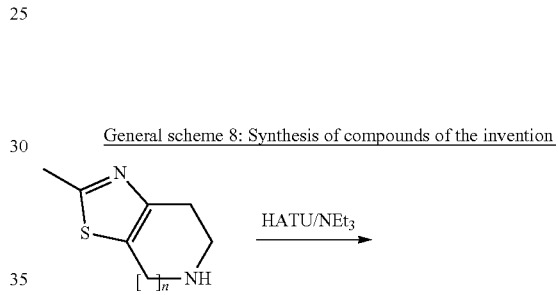

By methods known from the literature, in step 1 the compounds with general structure 1 described in general scheme 6 are acylated (P. N. Collier et al., J. Med. Chem., 2015, 58, 5684-5688), sulfonylated (J. Inoue et al., Bioorg. Med. Chem., 2000, 8, 2167-2173), carbamoylated (C. R. Moyes et al., J. Med. Chem., 2014, 57, 1437-1453) or transformed into a urea (EP2327704) to give compounds with the general structure 2. In step 2 deprotection of the nitrogen protective group (A. Isidro-Llobet et al., Chem. Rev., 2009, 109, 2455-2504), drawn as but not limited to Boc, e.g. with HCl gives amine 3. An amide coupling in step 3 with methods known in literature (A. El-Faham, F. Albericio, Chem. Rev. 2011, 111, 6557-6602), e.g. with HATU results in compounds of Formula III.

In another embodiment an alternative synthesis of compounds of Formula IVb follows General scheme 7.

General scheme 7: Synthesis of compounds of Formula IVb

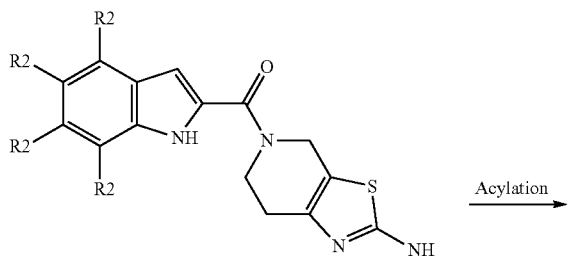

Acylation

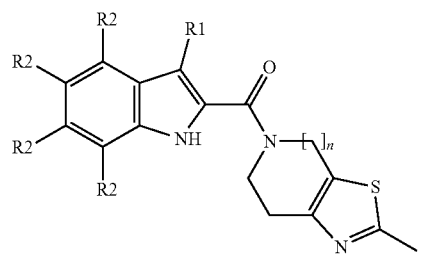

An amide coupling in with amines of structure shown with methods known in literature (A. El-Faham, F. Albericio, Chem. Rev. 2011, 111, 6557-6602), e.g. with HATU results in a compound with the general structure shown.

In another preferred embodiment the synthesis of the compounds according to the invention follows General scheme 9.

General scheme 9: Synthesis of compounds of the invention

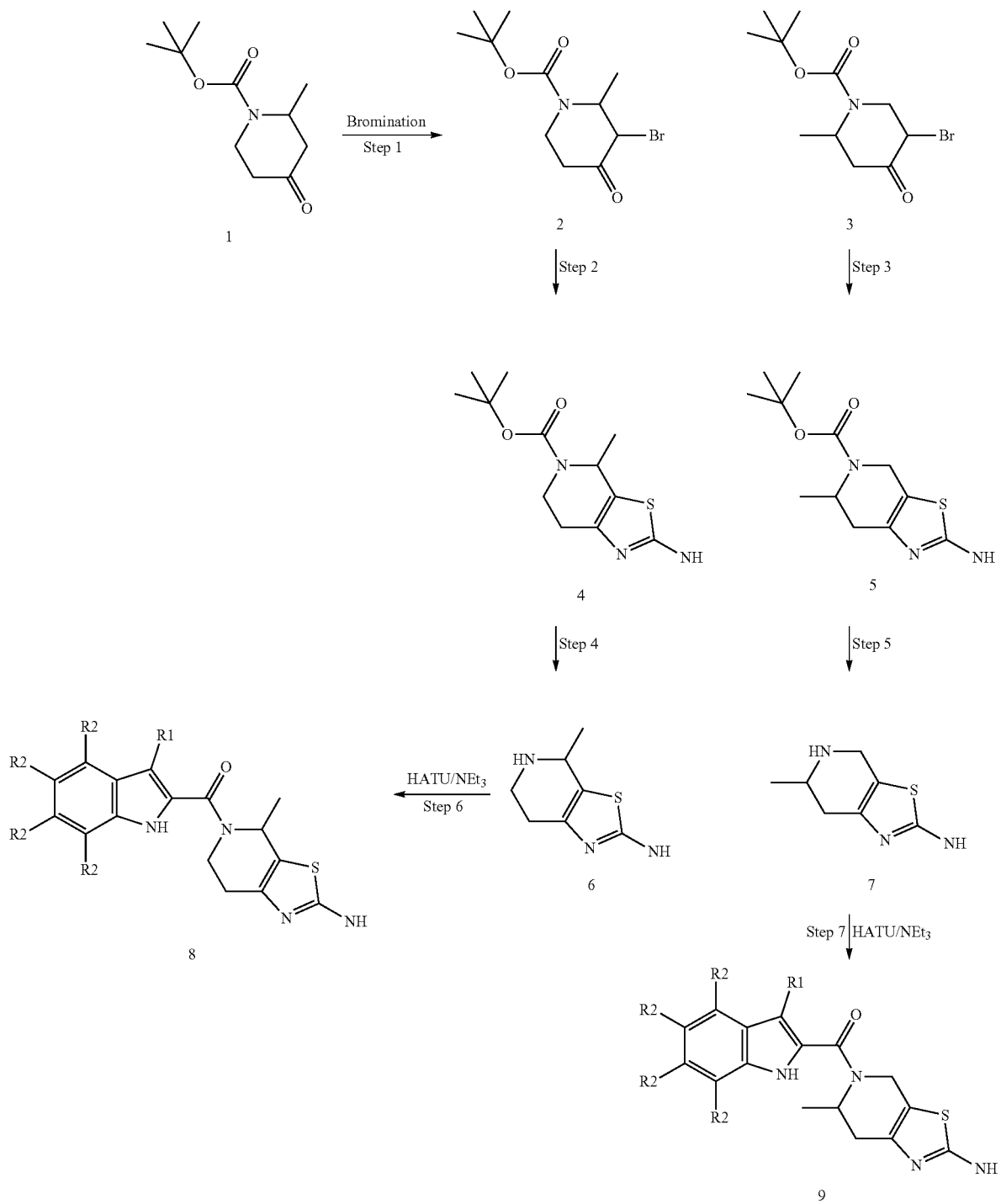

Ketone 1 shown in general scheme 9 is brominated to give the isomeric α-bromo-ketones 2 and 3 (Provins et al., ChemMedChem 2012, 7(12) pp. 2087-2092). In steps 2 and 3, these are then converted into aminothiazoles 4 and 5 respectively (X. Cao et al., J. Med. Chem., 2014, 57, 3687-3706). In steps 4 and 5 deprotection of the nitrogen protective groups (A. Isidro-Llobet et al., Chem. Rev., 2009, 109, 2455-2504), drawn as but not limited to Boc, e.g. with HCl gives amines 6 and 7. An amide coupling in steps 6 and 7 with methods known in literature (A. El-Faham, F. Albericio, Chem. Rev. 2011, 111, 6557-6602), e.g. with HATU results in a compound with the general structure 8 and a compound with the general structure 9.

In another preferred embodiment the synthesis of the compounds according to the invention follows General scheme 10.

General scheme 10: Synthesis of compounds of the invention

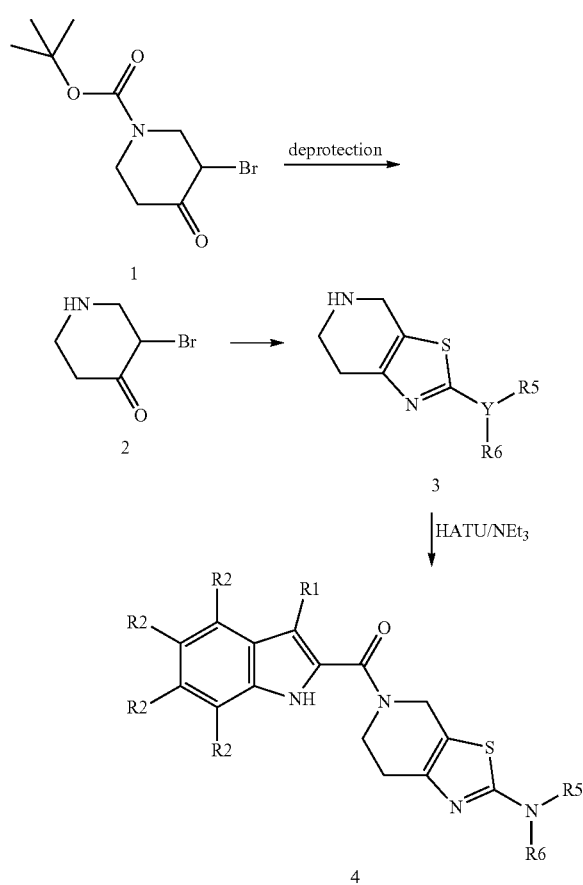

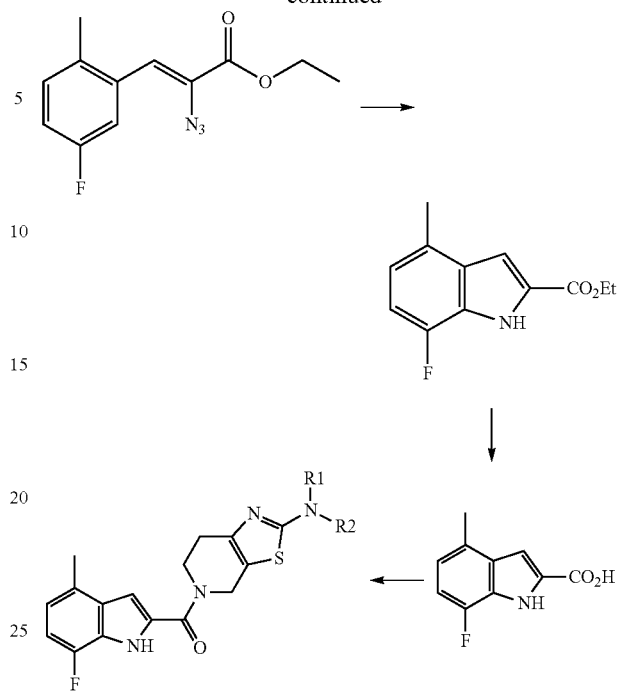

In step 1 deprotection of the nitrogen protective group of α-bromo-ketone 1 described in general scheme 10 (A. Isidro-Llobet et al., Chem. Rev., 2009, 109, 2455-2504), drawn as but not limited to Boc, e.g. with HBr gives amine 2. Compound 2 is cyclized in step 2 to aminothiazole 3 (WO201231024) under basic conditions. An amide coupling in step 3 with methods known in literature (A. El-Faham, F. Albericio, Chem. Rev. 2011, 111, 6557-6602), e.g. with HATU results in compounds of general structure 4.

The required substituted indole-2-carboxylic acids may be prepared in a number of ways; the main routes employed being outlined in Schemes 11-14. To the chemist skilled in the art it will be apparent that there are other methodologies that will also achieve the preparation of these intermediates.

Substituted indole-2-carboxylic acids can be prepared via the Hemetsberger-Knittel reaction (Organic Letters, 2011, 13(8) pp. 2012-2014, and Monatshefte für Chemie, 103(1), pp. 194-204) as shown in Scheme 11.

Scheme 11: Indoles from vinyl azides

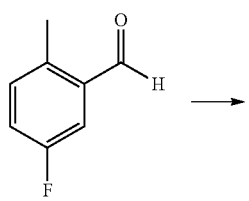

Substituted indoles may also be prepared using the Fischer method (Berichte der Deutschen Chemischen Gesellschaft. 17 (1), pp. 559-568) as shown in Scheme 12

Scheme 12: The Fischer indole synthesis

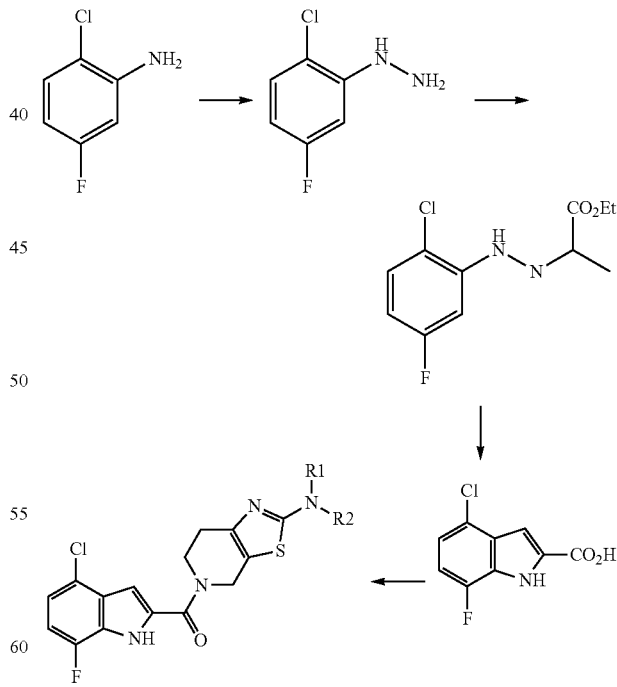

A further method for the preparation of substituted indoles is the palladium catalysed alkyne annulation reaction (Journal of the American Chemical Society, 1991, pp. 6690-6692) as shown in Scheme 13.

Scheme 13: Preparation of indoles via alkyne annulation

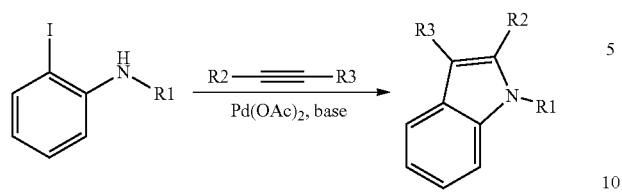

Additionally, indoles may be prepared from other suitably functionalized (halogenated) indoles (for example via palladium catalysed cross coupling or nucleophilic substitution reactions) as illustrated in Scheme 14.

Scheme 14: Palladium catalysed functionalization of halogenated indoles

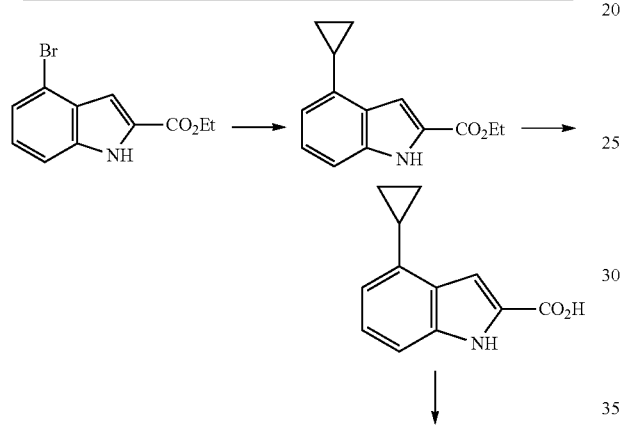

Chemists skilled in the art will appreciate that other methods are available for the synthesis of suitably functionalized indole-2-carboxylic acids and activated esters thereof.

In another preferred embodiment the synthesis of the compounds according to the invention follows General scheme 15.

General scheme 15: Synthesis of compounds of the invention

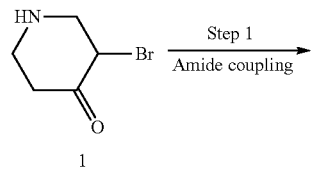

In step 1 an amid coupling with methods known in literature (A. El-Faham, F. Albericio, Chem. Rev. 2011, 111, 6557-6602), e.g. with an acid chloride results in compounds with the general structure 2. Compound 2 is cyclized with a thiourea in step 2 under basic conditions (WO201231024) to give compounds of general structure 3.

General Procedure—Synthesis of Thioureas

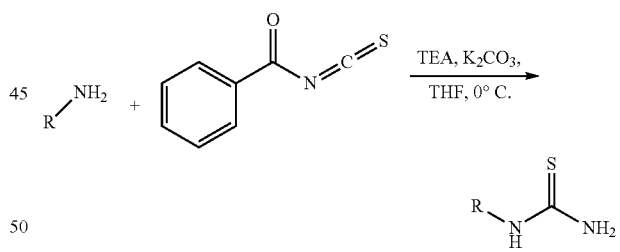

Triethylamine (7.66 mmol, 1.1 eq) was added to a solution of a corresponding amine hydrochloride (6.97 mmol, 1.0 eq) under an argon atmosphere in dry THF (10 mL) at 0° C. (ice bath). The resulting mixture was stirred for 10 min followed by the addition of benzoyl isothiocyanate (7.66 mmol, 1.1 eq). After removing the ice bath, the reaction mixture was allowed to warm to r.t. and stirred overnight. After the completion of reaction, the solution was concentrated under reduced pressure and the residue was re-suspended in a mixture of water (5 mL) and methanol (5 mL). Potassium carbonate (15.33 mmol, 2.2 eq) was added to the resulting suspension. The mixture was stirred overnight at r.t. and concentrated under reduced pressure (co-evaporation with ethylacetate). The obtained solid was re-suspended in 1:1 DCM/MeOH (150 mL) and filtered off.

The filtrate was concentrated under reduced pressure to afford a crude thiourea which was further purified by RP-HPLC.

The following thioureas were prepared as described above.

1-(3,3-Difluorocyclobutyl)thiourea

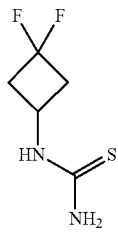

Yield 725.0 mg (62.6%).

1H NMR (500 MHz, DMSO-d6) δ (ppm) 2.48 (m, 2H), 2.90 (m, 2H), 4.37 (m, 1H), 6.93 (m, 1H), 7.44 (m, 1H), 7.97 (m, 1H).

LCMS(ESI): [M+H]+ m/z: calc. 167.0; found 167.2; Rt=0.72 min.

1-((1r,3r)-3-Fluorocyclobutyl)thiourea

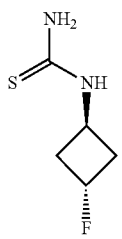

Yield 120.7 mg (16.8%).

1H NMR (500 MHz, DMSO-d6) δ (ppm) 2.28 (m, 2H), 2.43 (m, 2H), 4.61 (m, 1H), 5.16 (m, 1H), 6.96 (m, 1H), 7.52 (m, 1H), 8.03 (m, 1H).

LCMS(ESI): [M+H]+ m/z: calc. 149.0; found 149.0; Rt=0.49 min.

1-(2,2-Difluorocyclobutyl)thiourea

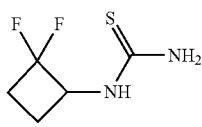

Yield 50.4 mg (41.4%).

1H NMR (400 MHz, DMSO-d6) δ (ppm) 1.56 (m, 1H), 2.15 (m, 1H), 2.30 (m, 2H), 5.18 (m, 1H), 7.23 (m, 2H), 8.02 (m, 1H).

LCMS(ESI): [M+H]+ m/z: calc. 167.0; found 166.9; Rt=0.71 min.

1-(3,3-Difluoro-1-methylcyclobutyl)thiourea

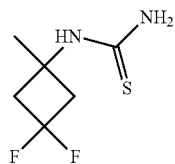

Yield 415.0 mg (72%).

1H NMR (500 MHz, DMSO-d6) δ (ppm) 1.59 (s, 3H), 2.63 (m, 2H), 2.90 (q, 2H), 6.78 (m, 2H), 7.93 (s, 1H).

LCMS(ESI): [M+H]+ m/z: calc. 181.0; found 181.2; Rt=0.87 min.

1-(3,3-Difluoro-1-(hydroxymethyl)cyclobutyl)thiourea

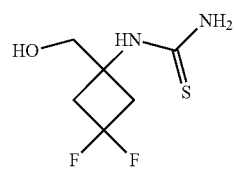 [SMILES: NC(=S)NC1(CO)CC(F)(F)C1]

Yield 184.0 mg (36.2%).

1H NMR (400 MHz, DMSO-d6) δ (ppm) 2.75 (m, 4H), 3.68 (m, 2H), 5.22 (m, 1H), 6.96 (m, 2H), 7.91 (s, 1H).

LCMS(ESI): [M+H]+ m/z: calc. 197.0; found 197.2; Rt=0.79 min.

1-(3,3-Difluoro-1-(methoxymethyl)cyclobutyl)thiourea

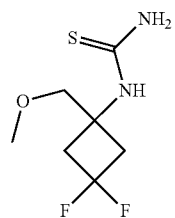

Yield 325.0 mg (38.7%).

1H NMR (500 MHz, DMSO-d6) δ (ppm) 2.78 (m, 4H), 3.34 (m, 3H), 3.75 (m, 2H), 6.90 (m, 2H), 7.95 (m, 1H).

LCMS(ESI): [M+H]+ m/z: calc. 211.0; found 211.0; Rt=0.90 min.

1-(1-(Trifluoromethyl)cyclobutyl)thiourea

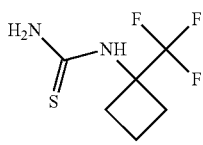 [SMILES: NC(=S)NC1(C(F)(F)F)CCC1]

Yield 94.0 mg (83.2%).

1H NMR (500 MHz, DMSO-d6) δ (ppm) 1.89 (m, 2H), 2.44 (m, 2H), 2.52 (m, 2H), 8.19 (m, 3H).

LCMS(ESI): [M+H]+ m/z: calc. 199.0; found 199.0; Rt=0.69 min.

1-(1-(Methoxymethyl)cyclobutyl)thiourea

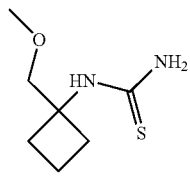

Yield 515.0 mg (44.8%).

1H NMR (500 MHz, DMSO-d6) δ (ppm) 1.79 (m, 2H), 2.16 (m, 4H), 3.35 (s, 3H), 3.77 (m, 2H), 6.59 (m, 2H), 7.55 (m, 1H).

LCMS(ESI): [M+H]+ m/z: calc. 175.0; found 175.2; Rt=0.79 min.

1-(1-(Methoxymethyl)cyclopropyl)thiourea

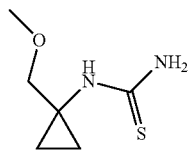

Yield 1.11 g (94.9%).

1H NMR (500 MHz, DMSO-d6) δ (ppm) 0.79 (m, 4H), 3.11 (s, 3H), 3.31 (m, 2H), 6.80 (m, 1H), 7.50 (m, 1H), 7.86 (m, 1H).

LCMS(ESI): [M+H]+ m/z: calc. 161.1; found 161.1; Rt=0.62 min.

1-(1-(Trifluoromethyl)cyclopropyl)thiourea

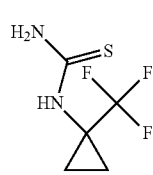

Yield 405.0 mg (35.5%).

1H NMR (400 MHz, DMSO-d6) δ (ppm) 1.11 (m, 2H), 1.26 (m, 2H), 7.13 (m, 1H), 7.94 (m, 1H), 8.39 (m, 1H).

LCMS(ESI): [M+H]+ m/z: calc. 185.0; found 185.2; Rt=0.63 min.

1-((3,3-Difluoro-1-hydroxycyclobutyl)methyl)thiourea

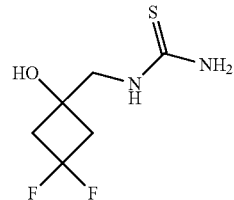 [SMILES: NC(=S)NCC1(O)CC(F)(F)C1]

Yield 35.7%.

1H NMR (500 MHz, DMSO-d6) δ (ppm) 2.42 (m, 2H), 2.74 (m, 2H), 3.60 (m, 2H), 7.26 (m, 2H), 7.76 (m, 2H).

LCMS(ESI): [M+H]+ m/z: calc. 197.0; found 197.0; Rt=0.69 min.

1-((3,3-Difluorocyclobutyl)methyl)thiourea

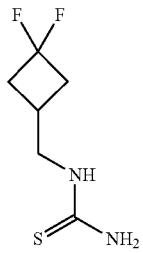

Yield 169.1 mg (24.7%).

1H NMR (500 MHz, CDCl3) δ (ppm) 2.29 (m, 2H), 2.48 (m, 1H), 2.74 (m, 2H), 3.56 (m, 2H), 5.80 (m, 2H), 6.26 (m, 1H).

LCMS(ESI): [M+H]+ m/z: calc. 181.0; found 181.0; Rt=0.81 min.

N-Methyl-1-(thioureidomethyl)cyclobutanecarboxamide

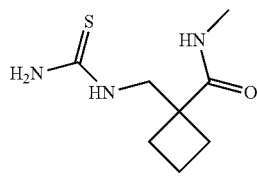

Yield 79.2 mg (17.6%).

1H NMR (400 MHz, DMSO-d6) δ (ppm) 1.70 (m, 2H), 1.88 (m, 2H), 2.17 (m, 2H), 2.61 (s, 3H), 3.75 (m, 2H), 7.09 (m, 2H), 7.29 (m, 1H), 7.67 (m, 1H).

LCMS(ESI): [M+H]+ m/z: calc. 202.1; found 202.2; Rt=0.68 min.

61

1-((1-Methoxycyclobutyl)methyl)thiourea

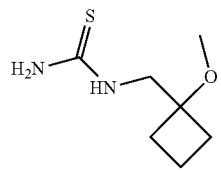

Yield 97.0 mg (64.1%).

1H NMR (400 MHz, DMSO-d6) δ (ppm) 1.56 (m, 1H), 1.62 (m, 1H), 1.82 (m, 2H), 2.02 (m, 2H), 3.09 (s, 3H), 3.66 (d, 2H), 7.05 (m, 2H), 7.39 (m, 1H).

LCMS(ESI): [M+H]+ m/z: calc. 175.1; found 175.2; Rt=0.87 min.

1-(Bicyclo[1.1.1]pentan-1-yl)thiourea

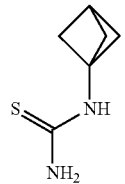

Yield 192.5 mg, (40.4%).

1H NMR (400 MHz, DMSO-d6) δ (ppm) 2.05 (s, 6H), 2.38 (m, 1H), 6.76 (m, 2H), 8.25 (m, 1H).

LCMS(ESI): [M+H]+ m/z: calc. 143.0; found 143.0; Rt=0.77 min.

1-((1s,3s)-3-Hydroxy-3-methylcyclobutyl)thiourea

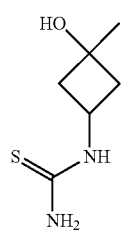

Yield 190.0 mg (32.6%).

1H NMR (500 MHz, DMSO-d6) δ (ppm) 1.89 (m, 4H), 2.27 (m, 3H), 4.04 (m, 1H), 4.92 (m, 1H), 6.84 (m, 2H), 7.80 (m, 1H).

LCMS(ESI): [M+H]+ m/z: calc. 161.0; found 161.1; Rt=0.49 min.

62

1-((1r,3r)-3-Methoxycyclobutyl)thiourea

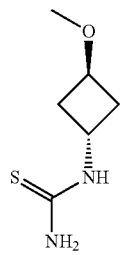

Yield 57.8 mg (49.8%).

1H NMR (400 MHz, DMSO-d6) δ (ppm) 2.18 (m, 4H), 3.11 (s, 3H), 3.89 (m, 1H), 4.48 (m, 1H), 6.88 (m, 1H), 7.37 (m, 1H), 7.92 (m, 1H).

LCMS(ESI): [M+H]+ m/z: calc. 161.0; found 161.2; Rt=0.62 min.

1-((1s,3s)-3-Methoxycyclobutyl)thiourea

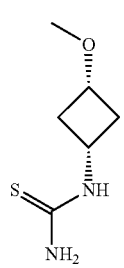

Yield 57.8 mg (49.8%).

1H NMR (500 MHz, DMSO-d6) δ (ppm) 2.58 (m, 2H), 3.10 (s, 3H), 3.54 (m, 1H), 4.10 (m, 1H), 6.87 (m, 1H), 7.39 (m, 1H), 7.90 (m, 1H).

LCMS(ESI): [M+H]+ m/z: calc. 161.0; found 161.0; Rt=0.68 min.

1-(3-(Difluoromethoxy)cyclobutyl)thiourea

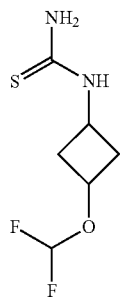

Yield 121.0 mg (14.4%).

1H NMR (500 MHz, DMSO-d6) δ (ppm) 2.06 (m, 2H), 2.26 (m, 1H), 2.68 (m, 2H), 4.32 (m, 2H), 6.61 (m, 1H), 7.96 (m, 2H). LCMS(ESI): [M+H]+ m/z: calc. 197.0; found 197.0; Rt=0.81 min.

concentrated under reduced pressure and the residue dissolved in 4:1 DCM/MeOH (10 mL) and filtered. The filtrate was concentrated and purified by HPLC to afford 3-cyanobicyclo[1.1.1]pentan-1-ylthiourea (39.1 mg, 233.81 μmol, 33.7% yield) as yellow solid.

Synthesis of [(1-methoxycyclopropyl)methyl]thiourea

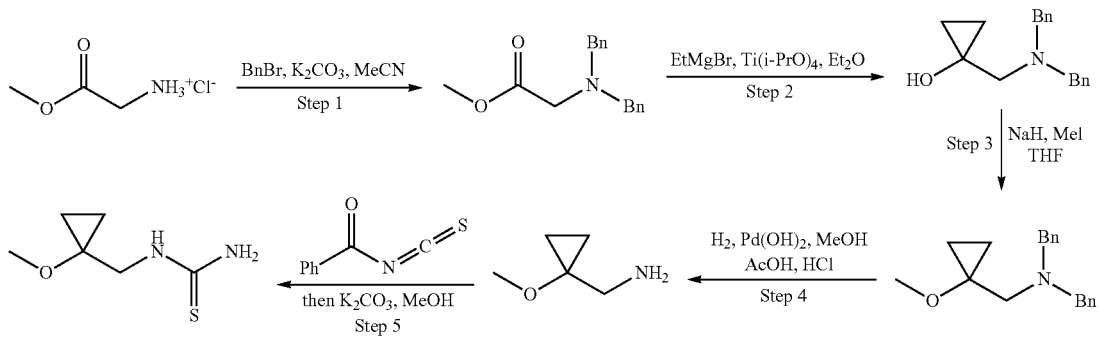

1-(2-Cyclopropyl-2,2-difluoroethyl)thiourea

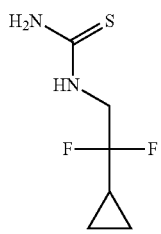

Yield 110.0 mg (20.5%).
1H NMR (400 MHz, CDCl₃) δ (ppm) 0.64 (m, 4H), 1.27 (m, 1H), 4.04 (m, 2H), 6.16 (m, 2H), 6.83 (m, 1H).
LCMS(ESI): [M+H]+ m/z: calc. 181.0; found 181.0; Rt=0.90 min.

Synthesis of {3-cyanobicyclo[1.1.1]pentan-1-yl}thiourea

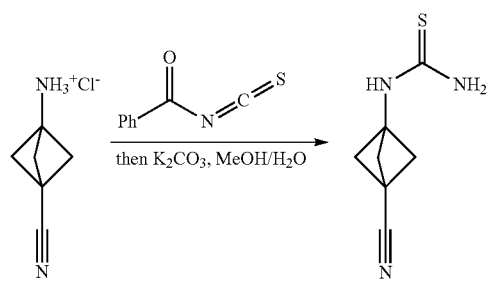

To a suspension of 3-aminobicyclo[1.1.1]pentane-1-carbonitrile hydrochloride (100.0 mg, 692 μmol) in dry DCM (5 ml) was added triethylamine (77.2 mg, 763 μmol) and benzoyl isothiocyanate (125 mg, 763 μmol). The reaction mixture was stirred at r.t. overnight. The reaction mixture was concentrated, the residue was dissolved in MeOH/H₂O (5 mL/1 mL) and potassium carbonate (240 mg, 1.73 mmol) was added. The reaction mixture was stirred for 10 h then Step 1: To a stirred suspension of methyl 2-aminoacetate hydrochloride (20.0 g, 159 mmol) in dry acetonitrile (350 ml) was added potassium carbonate (55.0 g, 398 mmol). To the stirred mixture was added dropwise (bromomethyl)benzene (54.5 g, 319 mmol, 38 ml). The reaction mixture was stirred at r.t. overnight, filtered and the filtrate was concentrated to afford methyl 2-(dibenzylamino)acetate (41.2 g, 153 mmol, 95.9% yield) as colorless oil.

Step 2: To a solution of methyl 2-(dibenzylamino)acetate (20.0 g, 74.3 mmol) in dry diethyl ether (250 ml) under a stream of argon was added dropwise a solution of titanium tetraisopropoxide (5.28 g, 18.6 mmol, 5.5 mL) in diethyl ether (50 mL). Ethylmagnesium bromide in diethyl ether (1M solution freshly prepared from bromoethane (24.3 g, 222 mmol, 16.6 mL) and magnesium (5.69 g, 234 mmol) was added dropwise at 15-20° C. under Ar. The reaction mixture was stirred overnight, then cooled to 0° C. and quenched by dropwise addition of sat. aq. NH₄Cl solution (300 mL). The reaction mixture was stirred at r.t. for 2 h and filtered. The organic phase was separated and the aqueous phase was extracted with MTBE (100 mL). The combined organic layers were dried over Na₂SO₄, filtered and concentrated to afford crude 1-[(dibenzylamino)methyl]cyclopropan-1-ol (17.5 g, 50.0% purity, 32.73 mmol, 44% yield) as yellow oil, that was used in the next step without purification.

Step 3: To a stirred solution of 1-[(dibenzylamino)methyl]cyclopropan-1-ol (13.5 g, 50.5 mmol) in dry THF (200 mL) at 0° C. under Ar was added portionwise sodium hydride (3.03 g, 126 mmol). The mixture was stirred for 1 h then iodomethane (10.8 g, 75.7 mmol, 4.71 mL) was added dropwise at 0° C. The reaction mixture was stirred at r.t. overnight and carefully poured into brine (200 mL). The mixture was extracted with EtOAc (2×100 mL), the combined organic phases were washed with brine, dried over sodium sulfate and concentrated. The residue was purified by column chromatography on silica with hexane-MTBE (40:1) as an eluent to afford dibenzyl[(1-methoxycyclopropyl)methyl]amine (2.0 g, 7.11 mmol, 14.1% yield) as a yellow oil.

Step 4: To a stirred solution of dibenzyl[(1-methoxycyclopropyl)methyl]amine (2.0 g, 7.11 mmol) in MeOH (30 ml) was added acetic acid (426 mg, 7.11 mmol, 410 μL) and palladium dihydroxide on charcoal (20%) (200 mg, 1.42 mmol). The mixture was stirred under an atmosphere of hydrogen overnight. The reaction mixture was filtered, HCl (4M solution in dixane, 1.8 ml) was added to the filtrate and the mixture was concentrated. The residue was triturated with MTBE, collected by filtration and dried to afford (1-methoxycyclopropyl)methanamine hydrochloride (850 mg, 6.18 mmol, 86.9% yield) as white solid.

Step 5: To a stirred suspension of (1-methoxycyclopropyl) methanamine hydrochloride (853 mg, 6.2 mmol) in dry DCM (20 mL) at 0° C. was added triethylamine (690 mg, 6.82 mmol, 950 μL). The reaction mixture was stirred for 15 min, cooled to 0° C. and benzoyl isothiocyanate (1.11 g, 6.82 mmol) was added dropwise. The reaction mixture was stirred at r.t. overnight. The reaction mixture was concentrated under reduced pressure and the residue was treated with water; the precipitate formed was filtered and suspended in MeOH-water (0 mL/10 mL). Potassium carbonate (1.97 g, 14.3 mmol) was added and the mixture was stirred at r.t. overnight. The mixture was concentrated under reduced pressure, the residue was dissolved in MeOH (20 mL), the precipitate formed was filtered off and the filtrate was concentrated under reduced pressure. The residue was purified by HPLC to afford [(1-methoxycyclopropyl) methyl]thiourea (399 mg, 2.49 mmol, 40.2% yield) as white solid.

Synthesis of 1-(carbamothioylamino)cyclopropane-1-carboxamide

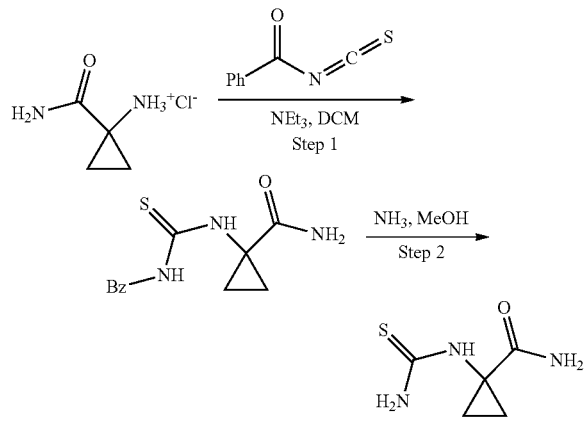

Step 1: To a stirred suspension of 1-aminocyclopropane-1-carboxamide hydrochloride (740 mg, 5.42 mmol) in dry DCM (15 mL) was added triethylamine (603 mg, 5.96 mmol, 830 μL). The mixture was stirred for 1 h at r.t. then cooled to 0° C. A solution of benzoyl isothiocyanate (972 mg, 5.96 mmol) in DCM (5 mL) was added dropwise. The mixture was stirred at r.t. overnight and concentrated. The residue was triturated with water, collected by filtration and dried in vacuo to afford 1-[(phenylformamido)methanethioyl]aminocyclopropane-1-carboxamide (1.38 g, 5.24 mmol, 96.7% yield) as yellow solid.

Step 2: To a suspension of 1-[(phenylformamido)methanethioyl]aminocyclopropane-1-carboxamide (1.18 g, 4.48 mmol) in MeOH (30 mL) was added 25% aq. ammonia (5 mL). The reaction mixture was stirred at r.t. for 2 h. The reaction mixture was concentrated to dryness and diluted with dry MeOH (10 mL). The precipitated solid was collected by filtration and dried to afford 1-(carbamothioylamino)cyclopropane-1-carboxamide (360.0 mg, 2.26 mmol, 50.5% yield) as white solid.

Synthesis of 3,3-difluoro-1-(1H-1,2,3-triazol-4-yl)cyclobutan-1-amine

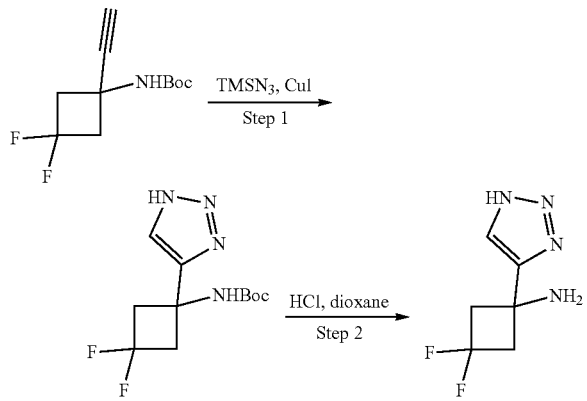

Step 1: Copper(I) iodide (89 mg, 467 μmol), tert-butyl N-(1-ethynyl-3,3-difluorocyclobutyl)carbamate (2.16 g, 9.34 mmol) and azidotrimethylsilane (1.61 g, 14.0 mmol, 1.86 mL) were added to round bottom flask containing DMF and $H_2O$ (50 mL, 9:1). The resulting mixture was stirred under an argon atmosphere at 100° C. for 14 h. The mixture was cooled to r.t., diluted with 200 mL of ethyl acetate and filtered through a thin layer of silica gel. The filtrate was washed with water (2×100 mL), dried over $Na_2SO_4$ and concentrated under reduced pressure to give tert-butyl N-[3,3-difluoro-1-(1H-1,2,3-triazol-4-yl)cyclobutyl]carbamate (2.11 g, 6.92 mmol, 74.1% yield) as light green solid.

Step 2: Tert-butyl N-[3,3-difluoro-1-(1H-1,2,3-triazol-4-yl)cyclobutyl]carbamate (2.0 g, 7.29 mmol) was dissolved in 4M HCl/dioxane (70 mL) at r.t. and the resulting mixture was stirred overnight. The resulting mixture was diluted with diethyl ether (70 mL), the precipitate was filtered and washed with 20 mL of diethyl ether before drying in vacuo to obtain 3,3-difluoro-1-(1H-1,2,3-triazol-4-yl)cyclobutan-1-amine dihydrochloride (1.37 g, 5.54 mmol, 76% yield) as light yellow powder.

Synthesis of 1-(1H-1,2,3-triazol-5-yl)cyclopropan-1-amine

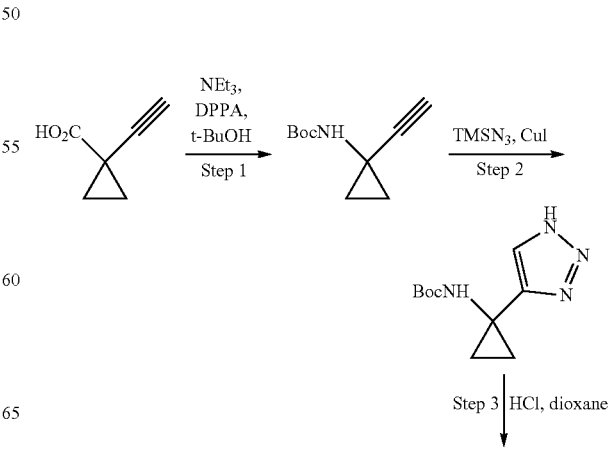

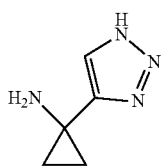

Step 1: 1-Ethynylcyclopropane-1-carboxylic acid (3.19 g, 29.0 mmol) was dissolved in t-BuOH (50 mL) and triethylamine (3.81 g, 37.66 mmol, 5.25 mL) was added in one portion, followed by addition of diphenoxyphosphoryl azide (8.77 g, 31.9 mmol, 6.87 ml). The resulting mixture was heated at 80° C. overnight. The mixture was concentrated under reduced pressure and the residue was stirred vigorously with 10% aqueous solution of NaOH for 1 h. The resulting mixture was extracted with MTBE (100 mL), and the organic phase washed with brine, dried over $Na_2SO_4$ and concentrated in vacuo to give tert-butyl N-(1-ethynylcyclopropyl)carbamate (3.92 g, 21.6 mmol, 74.7% yield) as light yellow crystalline solid.

Step 2: Copper(I) iodide (205.98 mg, 1.08 mmol), tert-butyl 1-ethynylcyclopropylcarbamate (3.92 g, 21.6 mmol) and azidotrimethylsilane (3.74 g, 32.5 mmol, 4.31 ml) were added to round bottom flask containing DMF and $H_2O$ (50 mL, 9:1). The resulting mixture was stirred under an argon atmosphere at 100° C. for 12 h. The mixture was cooled to r.t., diluted with ethyl acetate (200 mL) and filtered through a pad of silica gel. The filtrate was washed with water (3×300 mL), dried over $Na_2SO_4$ and concentrated under reduced pressure to give tert-butyl N-[1-(1H-1,2,3-triazol-5-yl)cyclopropyl]carbamate (3.46 g, 15.4 mmol, 71.3% yield) as brown solid.

Step 3: Tert-butyl N-[1-(1H-1,2,3-triazol-5-yl)cyclopropyl]carbamate (700 mg, 3.12 mmol) was dissolved in 4M HCl/dioxane (40 mL) and the resulting mixture was stirred overnight. The mixture was then concentrated under reduced pressure to obtain 1-(1H-1,2,3-triazol-5-yl)cyclopropan-1-amine dihydrochloride (500.0 mg, 2.54 mmol, 81.3% yield) as brown solid.

Synthesis of 1-amino-3,3-difluoro-N-methylcyclobutane-1-carboxamide

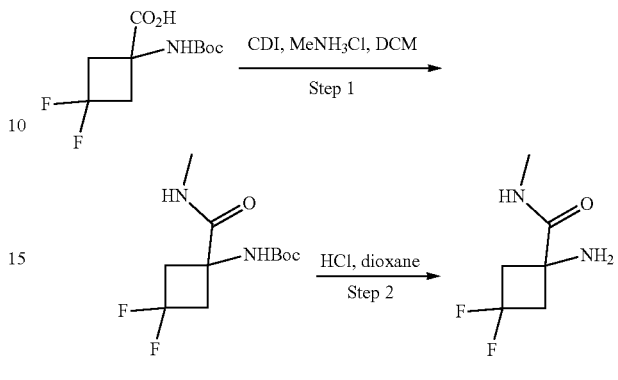

Step 1: To a solution of 1-[(tert-butoxy)carbonyl]amino-3,3-difluorocyclobutane-1-carboxylic acid (1.06 g, 4.2 mmol) in 30 mL of dry DCM at r.t. was added 1-(1H-imidazole-1-carbonyl)-1H-imidazole (1.02 g, 6.29 mmol). After gas release was complete (~30 min), methanamine hydrochloride (710 mg, 10.5 mmol) was added and the resulting mixture was stirred overnight. The mixture was diluted with DCM (20 mL), washed with water (2×30 mL) and brine (30 mL), dried over sodium sulfate and concentrated under reduced pressure to obtain tert-butyl N-[3,3-difluoro-1-(methylcarbamoyl)cyclobutyl]carbamate (1.08 g, 4.07 mmol, 96.9% yield) as a white solid.

Step 2: tert-Butyl N-[3,3-difluoro-1-(methylcarbamoyl)cyclobutyl]carbamate (1.05 g, 3.97 mmol) was dissolved in 4M HCl/dioxane (20 mL) at r.t. and the resulting mixture was stirred overnight. The resulting mixture was concentrated under reduced pressure to obtain 1-amino-3,3-difluoro-N-methylcyclobutane-1-carboxamide hydrochloride (670 mg, 3.34 mmol, 83.8% yield) as a colorless solid.

Synthesis of 1-ethynyl-3,3-difluorocyclobutan-1-amine

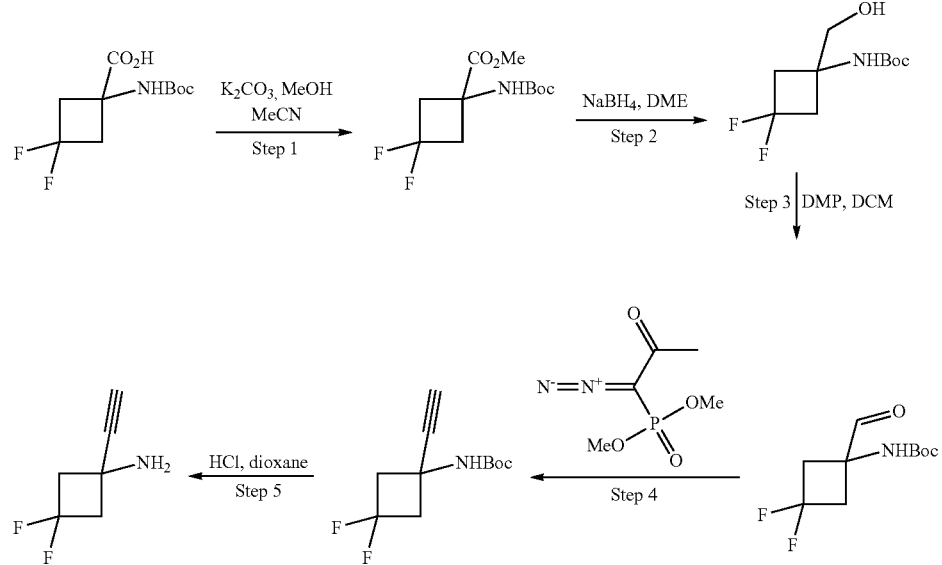

Step 1: To a solution of 1-[(tert-butoxy)carbonyl]amino-3,3-difluorocyclobutane-1-carboxylic acid (4.0 g, 16 mmol) in acetonitrile (200 mL) at r.t. was added potassium carbonate (3.3 g, 24 mmol). Iodomethane was then added portionwise (4.52 g, 31.84 mmol, 1.98 mL). The resulting viscous slurry was stirred overnight at r.t., then concentrated under reduced pressure. The residue was dissolved in MTBE (100 mL), and the resulting solution washed with water (2×100 mL), brine, then dried over Na₂SO₄ and concentrated in vacuo to give methyl 1-[(tert-butoxy)carbonyl]amino-3,3-difluorocyclobutane-1-carboxylate (3.87 g, 14.6 mmol, 91.6% yield) as colorless solid which was used for the next step without purification.

Step 2: To a vigorously stirred solution of methyl 1-[(tert-butoxy)carbonyl]amino-3,3-difluorocyclobutane-1-carboxylate (3.85 g, 14.5 mmol) in dry dimethoxyethane (90 mL) and dry methanol (10 mL) at 0° C. was added portionwise sodium borohydride (1.10 g, 29.0 mmol). The mixture was stirred at 0° C. for 2 h, then warmed to r.t. and stirred for a further 2 h at ambient temperature. The reaction was poured into stirred saturated aqueous Na₂CO₃ solution and extracted with MTBE (150 mL). The combined organic phases were washed with water (100 mL) and brine, dried over Na₂SO₄ and concentrated under reduced pressure to afford tert-butyl N-[3,3-difluoro-1-(hydroxymethyl)cyclobutyl]carbamate (3.42 g, 14.42 mmol, 99.3% yield) as white solid.

Step 3: To a solution of 1-(boc-amino)-3,3-difluorocyclobutane-1-methanol (3.42 g, 14.4 mmol) in DCM (100 mL) was added 1,1,1-tris(acetoxy)-1,1-dihydro-1,2-benziodoxol-3(1H)-one (7.34 g, 17.3 mmol) in few portions, (maintaining the temperature below 30° C. with water bath cooling). The mixture was poured into a stirred aqueous solution of Na₂CO₃ and Na₂S₂O₃ and stirred until the organic phase became transparent (~15 min). The layers were separated and the aqueous layer was extracted with DCM (30 mL). The combined organic extracts were washed with brine, dried over Na₂SO₄ and concentrated under reduced pressure to give tert-butyl N-(3,3-difluoro-1-formylcyclobutyl)carbamate (3.16 g, 12.8 mmol, 88.5% yield) as light yellow solid.

Step 4: To a solution of tert-butyl N-(3,3-difluoro-1-formylcyclobutyl)carbamate (3.14 g, 13.4 mmol) in dry methanol (50 mL) was added potassium carbonate (3.69 g, 26.7 mmol), followed by dropwise addition of dimethyl (1-diazo-2-oxopropyl)phosphonate (3.59 g, 18.7 mmol). After stirring for 2 h at r.t. the mixture was filtered, and the filtrate was concentrated under reduced pressure. The residue was treated with water (30 mL) and the resulting mixture was extracted with MTBE (2×50 mL). The combined organic layers were washed with brine, dried over Na₂SO₄ and concentrated under reduced pressure, to give tert-butyl N-(1-ethynyl-3,3-difluorocyclobutyl)carbamate (3.05 g, 90.0% purity, 11.9 mmol, 88.9% yield) as white solid.

Step 5: Tert-butyl N-(1-ethynyl-3,3-difluorocyclobutyl) carbamate (730 mg, 3.16 mmol) was dissolved in diethyl ether (10 mL) and 4M HCl solution in dioxane (10 mL) was added. The resulting mixture was stirred overnight, then diluted with diethyl ether (20 mL). The precipitate was collected by filtration, and washed with diethyl ether (10 mL), then dried in vacuo to give 1-ethynyl-3,3-difluorocyclobutan-1-amine hydrochloride (380 mg, 2.27 mmol, 71.8% yield) as white powder, containing ca. 1.5% of NH₄Cl by weight.

Synthesis of 1-amino-N-methylcyclopropane-1-carboxamide

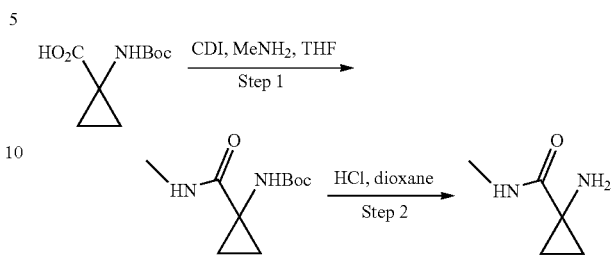

Step 1: 1-(1H-imidazole-1-carbonyl)-1H-imidazole (2.42 g, 14.9 mmol) was added to a solution of 1-((tert-butoxycarbonyl)amino)cyclopropanecarboxylic acid (2.0 g, 9.94 mmol) in 10 mL of dry THF at r.t. When the gas release completed (~20 min), a solution of methanamine (50 mL, 20% solution in methanol) was added dropwise. The resulting solution was was stirred overnight. The solvent was evaporated in vacuo and the residue was partitioned between DCM (30 mL) and water (10 mL). The organic phase was separated, washed with water, brine, dried over sodium sulfate and concentrated under reduced pressure to obtain tert-butyl N-[1-(methylcarbamoyl)cyclopropyl]carbamate (1.9 g, 8.89 mmol, 89.4% yield) as a white solid.

Step 2: Tert-butyl N-[1-(methylcarbamoyl)cyclopropyl] carbamate (1.9 g, 8.89 mmol) was dissolved in 25 mL of 4M HCl in dioxane. and the resulting mixture was stirred overnight. The mixture was concentrated under reduced pressure to obtain 1-amino-N-methylcyclopropane-1-carboxamide hydrochloride (1.29 g, 8.58 mmol, 96.4% yield) as a white solid.

Synthesis of [3,3-difluoro-1-(methoxymethyl)cyclobutyl]thiourea

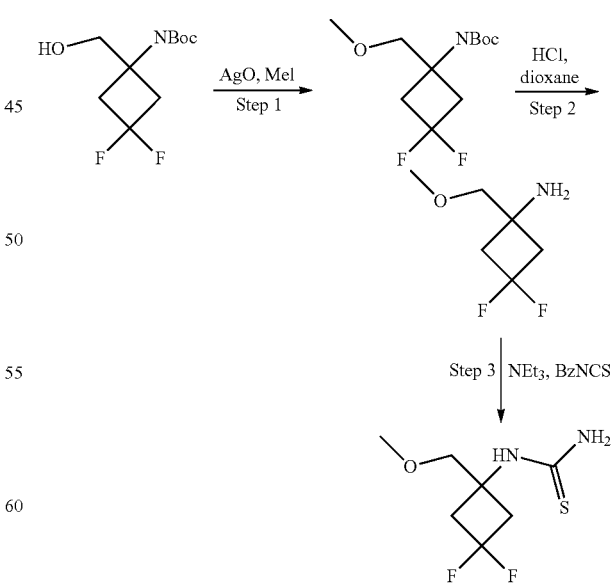

Step 1: To a solution of tert-butyl N-[3,3-difluoro-1-(hydroxymethyl)cyclobutyl]carbamate (940 mg, 3.96 mmol) and iodomethane (7.88 g, 55.49 mmol, 3.45 mL) in DCM (100 mL) was added silver oxide (6.43 g, 27.75 mmol). The reaction flask was covered with aluminum foil (protect from light) and the mixture was stirred at r.t. The mixture was stirred at room temperature for 10 days, then filtered and concentrated under reduced pressure, to obtain tert-butyl N-[3,3-difluoro-1-(methoxymethyl)cyclobutyl] carbamate (1.01 g, 95.0% purity, 3.82 mmol, 96.3% yield) as white crystalline solid.

Step 2: Tert-butyl N-[3,3-difluoro-1-(methoxymethyl)cyclobutyl]carbamate (1.0 g, 3.98 mmol) was dissolved in HCl (30 mL, 4M in dioxane). The resulting mixture was stirred overnight, then concentrated under reduced pressure to obtain 3,3-difluoro-1-(methoxymethyl)cyclobutan-1-amine hydrochloride (745.0 mg, 3.97 mmol, 99.7% yield) as a white powder.

Step 3: To a cooled (ice bath) solution of 3,3-difluoro-1-(methoxymethyl)cyclobutan-1-amine hydrochloride (750.0 mg, 4.0 mmol) in dry THF (30 mL) under argon was added triethylamine (444 mg, 4.4 mmol, 610 µL) followed by benzoyl isothiocyanate (718 mg, 4.4 mmol, 590 µL). The mixture was warmed to room temperature and stirred overnight. The reaction mixture was concentrated under reduced pressure. The residue was suspended in 1:2 water/MeOH (30 mL) and potassium carbonate (1.22 g, 8.79 mmol) was added. The mixture was stirred overnight at room temperature then concentrated under reduced pressure and co-evaporated with ethyl acetate. The solid obtained was suspended in MeOH (20 mL) and filtered. The filtrate was concentrated and purified by column chromatography (chloroform/acetonitrile with acetonitrile from 0-30%) to yield [3,3-difluoro-1-(methoxymethyl)cyclobutyl]thiourea (325 mg, 1.55 mmol, 38.7% yield) as a viscous yellow liquid.

Synthesis of [3,3-difluoro-1-(hydroxymethyl)cyclobutyl]thiourea

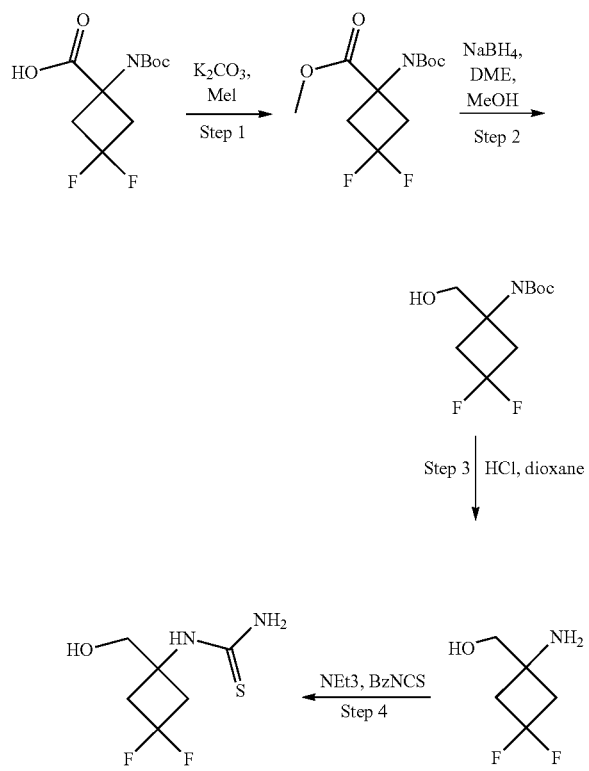

Step 1: To a solution of 1-[(tert-butoxy)carbonyl]amino-3,3-difluorocyclobutane-1-carboxylic acid (6.72 g, 26.75 mmol) in acetonitrile (300 mL) was added potassium carbonate (5.55 g, 40.12 mmol), followed by portionwise addition of iodomethane (7.59 g, 53.5 mmol, 3.33 ml). The resulting viscous slurry was stirred overnight at r.t., and progress of the reaction was monitored by 1H NMR. Once complete, the mixture was concentrated under reduced pressure. The residue was partitioned between MTBE (150 mL) and water (150 mL). The organic phase was washed with water (2×50 mL), brine, dried over $Na_2SO_4$ and concentrated to give methyl 1-[(tert-butoxy)carbonyl]amino-3,3-difluorocyclobutane-1-carboxylate (6.75 g, 25.45 mmol, 95.1% yield) as colorless solid. The material was used without further purification.

Step 2: To a cooled (0° C.), vigorously stirred solution of methyl 1-[(tert-butoxy)carbonyl]amino-3,3-difluorocyclobutane-1-carboxylate (6.73 g, 25.37 mmol) in dry dimethoxyethane (45 mL) and dry methanol (5 mL) was added portionwise sodium borohydride (1.92 g, 50.74 mmol). The mixture was stirred at 0° C. for 2 h, then allowed to warm up to r.t. and stirred overnight. The mixture was poured into stirred saturated aqueous $Na_2CO_3$ solution and extracted with MTBE (150 mL). The organic phase was washed with water (100 mL) and brine then dried over $Na_2SO_4$ and concentrated under reduced pressure to afford tert-butyl N-[3,3-difluoro-1-(hydroxymethyl)cyclobutyl]carbamate (5.65 g, 23.82 mmol, 93.9% yield) as white solid.

Step 3: Tert-Butyl N-[3,3-difluoro-1-(hydroxymethyl)cyclobutyl]carbamate (900 mg, 3.79 mmol) was dissolved in 25 mL of 4M HCl/dioxane at r.t. and the resulting mixture was stirred overnight. Upon completion of the reaction (monitored by 1H NMR), the resulting mixture was concentrated under reduced pressure, the residue was treated with 20 mL of acetonitrile, and filtered. The precipitate was washed with acetonitrile and dried in vacuo to obtain (1-amino-3,3-difluorocyclobutyl)methanol hydrochloride (550.0 mg, 3.17 mmol, 83.5% yield) as white powder.

Step 4: To a cooled (ice bath) solution of (1-amino-3,3-difluorocyclobutyl)methanol hydrochloride (450 mg, 2.59 mmol) in dry THF (10 mL) under argon was added triethylamine (289 mg, 2.85 mmol, 400 µL), followed by benzoyl isothiocyanate (465 mg, 2.85 mmol, 380 µL). The mixture was allowed to warm to room temperature and stirred overnight. The reaction mixture was then concentrated under reduced pressure. The residue was suspended in 1:1 water/MeOH (20 mL) and potassium carbonate (790 mg, 5.7 mmol) was added. The mixture was stirred overnight at room temperature then concentrated under reduced pressure and co-evaporated with ethyl acetate. The residue obtained was suspended in 1:1 DCM/MeOH (20 mL) and filtered. The filtrate was concentrated and purified by HPLC to yield the desired [3,3-difluoro-1-(hydroxymethyl)cyclobutyl]thiourea (184 mg, 937 µmol, 36.2% yield) as a white solid.

Synthesis of [(3,3-difluoro-1-hydroxycyclobutyl)methyl]thiourea

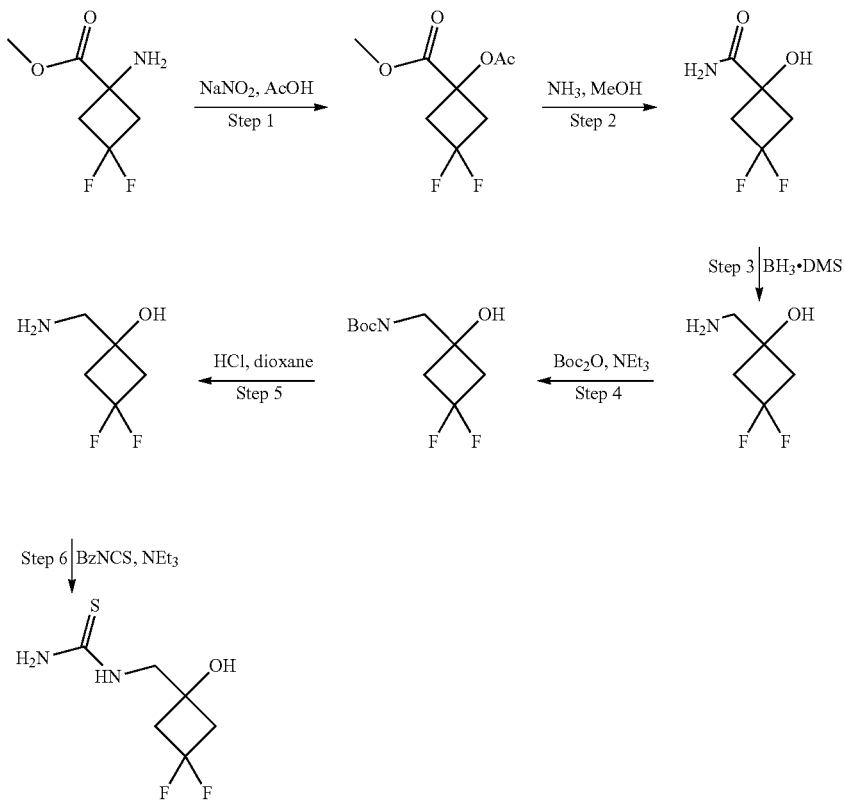

Step 1: To a solution of methyl 1-amino-3,3-difluorocyclobutane-1-carboxylate hydrochloride (6.25 g, 31.0 mmol) in glacial acetic acid (200 mL) was added sodium nitrite (4.28 g, 62.0 mmol). The mixture was heated at 45° C. overnight, cooled, then concentrated under reduced pressure. The residue was treated with acetyl chloride (60 mL), and the resulting mixture stirred at r.t. for 1 h. The mixture was concentrated then suspended in ethyl acetate (100 mL) and filtered. The filtrate was concentrated to give methyl 1-(acetyloxy)-3,3-difluorocyclobutane-1-carboxylate (3.52 g, 75.0% purity, 12.68 mmol, 40.9% yield) as white amorphous solid, which was used in next step without purification.

Step 2: Methyl 1-(acetyloxy)-3,3-difluorocyclobutane-1-carboxylate (3.5 g, 16.81 mmol) was dissolved in saturated $NH_3$ in MeOH (100 mL) and left to stir at r.t. for 7 d. The solution was concentrated under reduced pressure to obtain 3,3-difluoro-1-hydroxycyclobutane-1-carboxamide (3.0 g, 70% purity by H NMR, 6.95 mmol, 41.3% yield) as brown viscous liquid.

Step 3: To a solution of 3,3-difluoro-1-hydroxycyclobutane-1-carboxamide (3.0 g, 19.85 mmol) in dry THF (100 mL) under argon was added dropwise borane dimethyl sulfide complex (9.05 g, 119 mmol, 11.3 mL). The resulting mixture was stirred at 60° C. overnight, then poured into 300 mL of vigorously stirred dry methanol and the resulting solution was heated to reflux for 10 min and then concentrated under reduced pressure. The residue was treated with 2M HCl/MeOH (50 mL), stirred at r.t. for 10 minutes and concentrated under reduced pressure to give 1-(aminomethyl)-3,3-difluorocyclobutan-1-ol hydrochloride (3.8 g, 70% purity by 1H NMR, 8.76 mmol, 44.1% yield) as brown solid, which was used for the next step directly.

Step 4: Crude 1-(aminomethyl)-3,3-difluorocyclobutan-1-ol hydrochloride (3.8 g, 21.89 mmol) was suspended in DCM (100 mL). Triethylamine (6.64 g, 65.67 mmol) was added, followed by addition of di-tert-butyl dicarbonate (23.89 g, 109.44 mmol). The resulting mixture was left to stir overnight at r.t. The resulting solution was added in few portions to a stirred solution of 2-aminoacetic acid (8.22 g, 109.44 mmol) and sodium carbonate (11.6 g, 109.44 mmol) in water (100 mL). The resulting solution was stirred at r.t. overnight. The reaction mixture was concentrated in vacuo and the residue was partitioned between MTBE (100 mL) and water (300 mL). The organic phase was washed with aq. $Na_2CO_3$ (30 mL), aq. citric acid (30 mL), water (50 m), dried over $Na_2SO_4$ and concentrated in vacuum to give 3.2 g of brown liquid, which was purified by column chromatography to give tert-butyl N-[(3,3-difluoro-1-hydroxycyclobutyl)methyl]carbamate (870 mg, 3.67 mmol, 16.8% yield) as white crystalline solid.

Step 5: Tert-butyl N-[(3,3-difluoro-1-hydroxycyclobutyl)methyl]carbamate (740.0 mg, 3.12 mmol) was dissolved in 4M HCl/dioxane (20 mL) and the resulting mixture was stirred overnight then concentrated under reduced pressure to obtain 1-(aminomethyl)-3,3-difluorocyclobutan-1-ol hydrochloride (620.0 mg, 85.0% purity, 3.04 mmol, 97.3% yield) as solid residue.

Step 6: To a cooled (ice bath) solution of 1-(aminomethyl)-3,3-difluorocyclobutan-1-ol hydrochloride (620 mg, 3.57 mmol) in dry THF (20 mL) under argon was added triethylamine (397.56 mg, 3.93 mmol, 550.0 µL), followed by benzoyl isothiocyanate (641 mg, 3.93 mmol, 530 µL). The mixture was allowed to warm up to room temperature and stirred overnight. The reaction mixture was concentrated under reduced pressure. The residue was suspended in 1:1 water/MeOH (30 mL) and potassium carbonate (1.09 g, 7.86 mmol) was added. The mixture was stirred overnight at room temperature then concentrated under reduced pressure and co-evaporated with ethyl acetate. The solid obtained was suspended in MeOH (20 mL) and filtered. The filtrate was concentrated and purified by column chromatography to give [(3,3-difluoro-1-hydroxycyclobutyl)methyl]thiourea (250 mg, 1.27 mmol, 35.7% yield) as a white solid.

The following examples illustrate the preparation and properties of some specific compounds of the invention.

The following abbreviations are used:
A—DNA nucleobase adenine
ACN—acetonitrile
Ar—argon
BBQ—BlackBerry Quencher 650
BODIPY-FL—4,4-difluoro-5,7-dimethyl-4-bora-3a,4a-diaza-s-indacene-3-propionic acid (fluorescent dye)
Boc—tert-butoxycarbonyl
n-BuLi—n-butyl lithium
t-BuLi—t-butyl lithium
Bn—benzyl
Bz—benzoyl
C—DNA nucleobase cytosine
$CC_{50}$—half-maximal cytotoxic concentration
CDI—carbonyl diimidazole
$CO_2$—carbon dioxide
CuCN—copper (I) cyanide
DCE—dichloroethane
DCM—dichloromethane
Dess-Martin periodinane—1,1,1-triacetoxy-1,1-dihydro-1,2-benziodoxol-3(1H)-one
DIPEA—diisopropylethylamine
DIPE—di-isopropyl ether
DHBV—duck hepatitis B virus
DMAP—4-dimethylaminopyridine
DME—dimethoxyethane
DMF—N,N-dimethylformamide
DMP—Dess-Martin periodinane
DMSO—dimethyl sulfoxide
DNA—deoxyribonucleic acid
DPPA—diphenyl phosphoryl azide
DTT—dithiothreitol
$EC_{50}$—half-maximal effective concentration
EDCI—N-(3-dimethylaminopropyl)-N'-ethylcarbodiimide hydrochloride
$Et_2O$—diethyl ether
EtOAc—ethyl acetate
EtOH—ethanol
FAM—6-fluorescein amidite
FL—five prime end labeled with fluorescein
$NEt_3$—triethylamine
ELS—Evaporative Light Scattering
g—gram(s)
G—DNA nucleobase guanine
HBV—hepatitis B virus
HATU—2-(1H-7-azabenzotriazol-1-yl)-1,1,3,3-tetramethyl uronium hexafluorophosphate
HCl—hydrochloric acid
HDI—hydrodynamic injection
HEPES—4-(2-hydroxyethyl)-1-piperazineethanesulfonic acid
HOAt—1-hydroxy-7-azabenzotriazole
HOBt—1-hydroxybenzotriazole
HPLC—high performance liquid chromatography
$IC_{50}$—half-maximal inhibitory concentration
LC640—3 prime end modification with fluorescent dye LightCycler® Red 640
LC/MS—liquid chromatography/mass spectrometry
$LiAlH_4$—lithium aluminium hydride
LiGH—lithium hydroxide
MeOH—methanol
MeCN—acetonitrile
$MgSO_4$—magnesium sulfate
MTBE—methyl t-butyl ether
mg—milligram(s)
min—minutes
mol—moles
mmol—millimole(s)
mL—millilitre(s)
MTBE—methyl tert-butyl ether
$N_2$—nitrogen
$Na_2CO_3$—sodium carbonate
$NaHCO_3$—sodium hydrogen carbonate
$Na_2SO_4$—sodium sulfate
NdeI—restriction enzyme recognizes CA^TATG sites
$NEt_3$—triethylamine
NaH—sodium hydride
NaOH—sodium hydroxide
$NH_3$—ammonia
$NH_4Cl$—ammonium chloride
NMR—nuclear magnetic resonance
PAGE—polyacrylamide gel electrophoresis
PCR—polymerase chain reaction
qPCR—quantitative PCR
Pd/C—palladium on carbon
PEG 400—polyethylene glycol 400
PH—3 prime end phosphate modification
pTSA—4-toluene-sulfonic acid
Rt—retention time
r.t.—room temperature
sat.—saturated aqueous solution
SDS—sodium dodecyl sulfate
SI—selectivity index (=$CC_{50}/EC_{50}$)
STAB—sodium triacetoxyborohydride
T—DNA nucleobase thymine
TBAF—tetrabutylammonium fluoride
Tg—transgenic
TFA—trifluoroacetic acid
THF—tetrahydrofuran
TLC—thin layer chromatography
Tris—tris(hydroxymethyl)-aminomethane
WHV—woodchuck hepatitis virus
XhoI—restriction enzyme recognizes C^TCGAG sites
Compound Identification—NMR For a number of compounds, NMR spectra were recorded using a Bruker DPX400 spectrometer equipped with a 5 mm reverse triple-resonance probe head operating at 400 MHz for the proton and 100 MHz for carbon. Deuterated solvents were chloroform-d (deuterated chloroform, $CDCl_3$) or d6-DMSO (deuterated DMSO, d6-dimethylsulfoxide). Chemical shifts are reported in parts per million (ppm) relative to tetramethylsilane (TMS) which was used as internal standard.

Compound Identification—HPLC/MS

For a number of compounds, LC-MS spectra were recorded using the following analytical methods.

Method A
Column—Reverse phase Waters Xselect CSH C18 (50× 2.1 mm, 3.5 micron)
Flow—0.8 mL/min, 25 degrees Celsius
Eluent A—95% acetonitrile+5% 10 mM ammonium carbonate in water (pH 9)
Eluent B—10 mM ammonium carbonate in water (pH 9)
Linear gradient t=0 min 5% A, t=3.5 min 98% A. t=6 min 98% A
Method B
Column—Reverse phase Waters Xselect CSH C18 (50× 2.1 mm, 3.5 micron)
Flow—0.8 mL/min, 35 degrees Celsius
Eluent A—0.1% formic acid in acetonitrile
Eluent B—0.1% formic acid in water
Linear gradient t=0 min 5% A, t=3.5 min 98% A. t=6 min 98% A
Method C
Column—Reverse phase Waters Xselect CSH C18 (50× 2.1 mm, 3.5 micron)
Flow—1 mL/min, 35 degrees Celsius
Eluent A—0.1% formic acid in acetonitrile
Eluent B—0.1% formic acid in water
Linear gradient t=0 min 5% A, t=1.6 min 98% A. t=3 min 98% A
Method D
Column—Phenomenex Gemini NX C18 (50×2.0 mm, 3.0 micron)
Flow—0.8 mL/min, 35 degrees Celsius
Eluent A—95% acetonitrile+5% 10 mM ammonium bicarbonate in water
Eluent B—10 mM ammonium bicarbonate in water pH=9.0
Linear gradient t=0 min 5% A, t=3.5 min 98% A. t=6 min 98% A
Method E
Column—Phenomenex Gemini NX C18 (50×2.0 mm, 3.0 micron)
Flow—0.8 mL/min, 25 degrees Celsius
Eluent A—95% acetonitrile+5% 10 mM ammonium bicarbonate in water
Eluent B—10 mM ammonium bicarbonate in water (pH 9)
Linear gradient t=0 min 5% A, t=3.5 min 30% A. t=7 min 98% A, t=10 min 98% A
Method F
Column—Waters XSelect HSS C18 (150×4.6 mm, 3.5 micron)
Flow—1.0 mL/min, 25 degrees Celsius
Eluent A—0.1% TFA in acetonitrile
Eluent B—0.1% TFA in water
Linear gradient t=0 min 2% A, t=1 min 2% A, t=15 min 60% A, t=20 min 60% A
Method G
Column—Zorbax SB-C18 1.8 μm 4.6×15 mm Rapid Resolution cartridge (PN 821975-932)
Flow—3 mL/min
Eluent A—0.1% formic acid in acetonitrile
Eluent B—0.1% formic acid in water
Linear gradient t=0 min 0% A, t=1.8 min 100% A
Method H
Column—Waters Xselect CSH C18 (50×2.1 mm, 2.5 micron)
Flow—0.6 mL/min
Eluent A—0.1% formic acid in acetonitrile
Eluent B—0.1% formic acid in water
Linear gradient t=0 min 5% A, t=2.0 min 98% A, t=2.7 min 98% A Preparation of 4-chloro-7-fluoro-1H-indole-2-carboxylic Acid

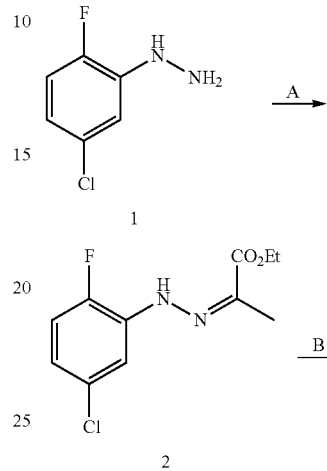

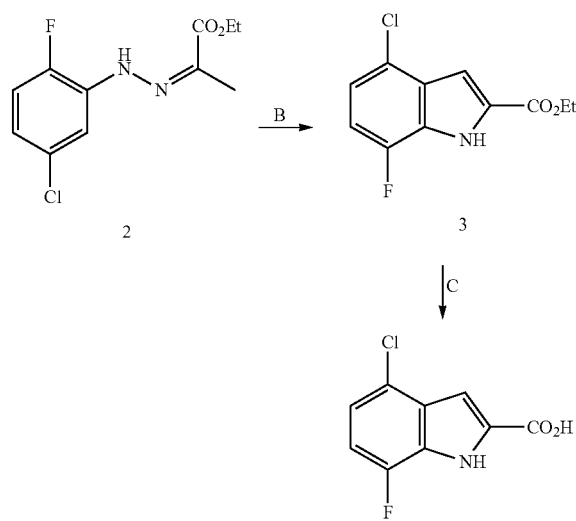

Step A: A mixture of compound 1-HCl (17.0 g, 86.2 mmol), sodium acetate (7.10 g, 86.6 mmol), and ethyl pyruvate (10.0 g, 86.1 mmol) in ethanol (100 mL) was refluxed for 1 h, cooled to r.t., and diluted with water (100 mL). The precipitated solid was collected by filtration and dried to obtain 20.0 g (77.3 mmol, 90%) of compound 2 as a mixture of cis- and trans-isomers.

Step B: A mixture of compound 2 (20.0 g, 77.3 mmol), obtained in the previous step, and $BF_3 \cdot Et_2O$ (50.0 g, 352 mmol) in acetic acid (125 mL) was refluxed for 18 h and evaporated under reduced pressure. The residue was mixed with water (100 mL) and extracted with MTBE (2×50 mL). The combined organic extracts were dried over $Na_2SO_4$ and evaporated under reduced pressure. The residue was purified by silica gel column chromatography to give 3.00 g (12.4 mmol, 16%) of compound 3.

Step C: A mixture of compound 3 (3.00 g, 12.4 mmol) and NaOH (0.500 g, 12.5 mmol) in ethanol (30 mL) was refluxed for 30 min and evaporated under reduced pressure. The residue was mixed with water (30 mL) and the insoluble material was filtered off. The filtrate was acidified with concentrated hydrochloric acid (5 mL). The precipitated solid was collected by filtration, washed with water (3 mL), and dried to obtain 2.41 g (11.3 mmol, 91%) of 4-chloro-7-fluoro-1H-indole-2-carboxylic acid.

Rt (Method G) 1.24 mins, m/z 212 [M−H]⁻

Preparation of 7-fluoro-4-methyl-1H-indole-2-carboxylic Acid

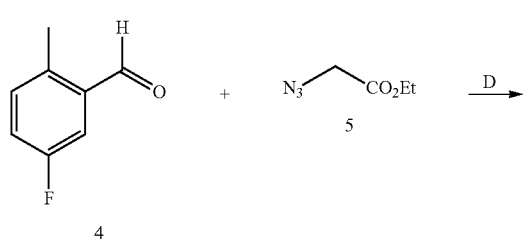

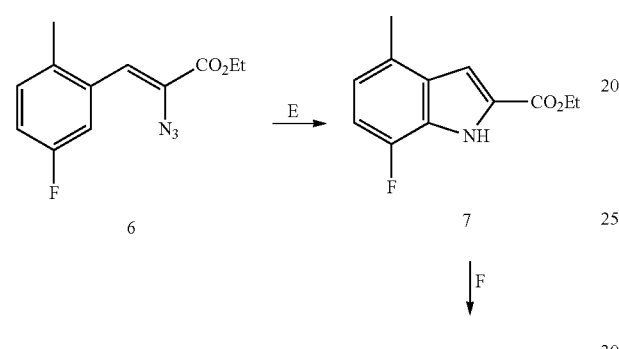

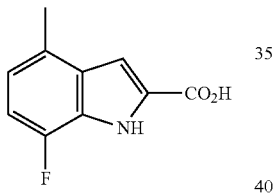

Preparation of 6,7-difluoro-1H-indole-2-carboxylic Acid

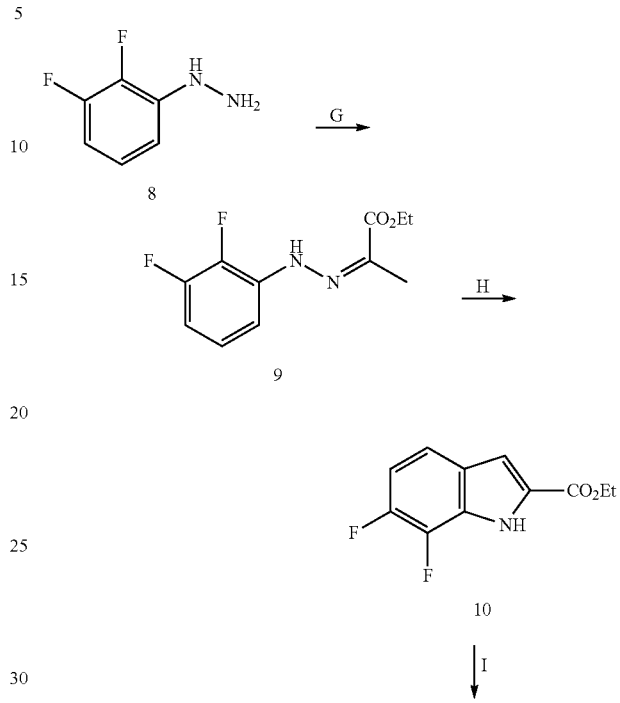

Step D: To a solution of sodium methoxide (21.6 g, 400 mmol) in methanol (300 mL) a solution of compound 4 (26.4 g, 183 mmol) and compound 5 (59.0 g, 457 mmol) in methanol (100 mL) was added dropwise at −10° C. The reaction mass was stirred for 3 h maintaining temperature below 5° C. and then quenched with ice water. The resulting mixture was stirred for 10 min, filtered, and washed with water to afford 35.0 g (156 mmol, 72%) of compound 6 as a white solid.

Step E: A solution of compound 6, obtained in the previous step, (35.0 g, 156 mmol) in xylene (250 mL) was refluxed for 1 h under an argon atmosphere and then evaporated under reduced pressure. The residue was recrystallized form hexane-ethyl acetate mixture (60:40) to give 21.0 g (103 mmol, 60%) of compound 7.

Step F: To a solution of compound 7 (21.0 g, 101 mmol) in ethanol (200 mL) was added 2 N aqueous sodium hydroxide solution (47 mL). The mixture was stirred for 2 h at 60° C. The solvent was evaporated and the residue was acidified with aqueous hydrochloric acid to pH 5-6. The resulting precipitate was filtered, washed with water, and dried to obtain 18.0 g (93.2 mmol, 92%) of 7-fluoro-4-methyl-1H-indole-2-carboxylic acid.

Rt (Method G) 1.12 mins, m/z 192 [M−H]−

Step G: A mixture of compound 8 (5.00 g, 34.7 mmol), acetic acid (1 mL), and ethyl pyruvate (5.00 g, 43.1 mmol) in ethanol (20 mL) was refluxed for 1 h, cooled to r.t., and diluted with water (20 mL). The precipitated solid was collected by filtration and dried to obtain 5.50 g (22.7 mmol, 66%) of compound 9 as a mixture of cis- and trans-isomers.

Step H: A mixture of compound 9 (5.50 g, 22.7 mmol), obtained in the previous step, and $BF_3 \cdot Et_2O$ (10.0 g, 70.5 mmol) in acetic acid (25 mL) was refluxed for 18 h and evaporated under reduced pressure. The residue was mixed with water (30 mL) and extracted with MTBE (2×30 mL). The combined organic extracts were dried over $Na_2SO_4$ and evaporated under reduced pressure. The residue was purified by silica gel column chromatography to give 0.460 g (2.04 mmol, 9%) of compound 10.

Step I: A mixture of compound 10 (0.450 g, 2.00 mmol) and NaOH (0.100 g, 2.50 mmol) in ethanol (10 mL) was refluxed for 30 min and evaporated under reduced pressure. The residue was mixed with water (10 mL) and the insoluble material was filtered off. The filtrate was acidified with concentrated hydrochloric acid (1 mL). The precipitated solid was collected by filtration, washed with water (3 mL), and dried to obtain 0.38 g (1.93 mmol, 95%) of 6,7-difluoro-1H-indole-2-carboxylic acid.

Rt (Method G) 1.10 mins, m/z 196 [M−H]−

Preparation of 4-cyano-1H-indole-2-carboxylic Acid

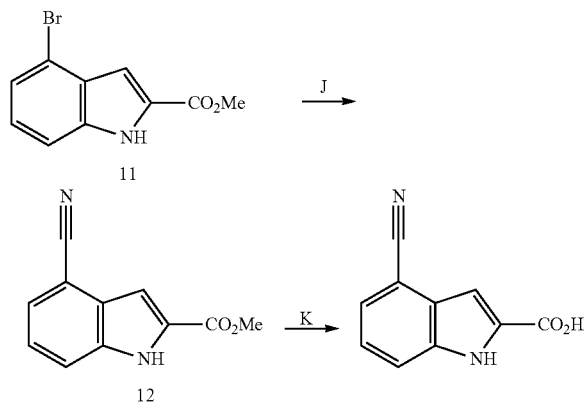

Step J: To a stirred solution of compound 11 (5.00 g, 19.7 mmol) in DMF (50 mL) was added CuCN (3.00 g, 33.5 mmol). The mixture was stirred for 4 h at 150° C. The mixture was then cooled to r.t., and water (100 mL) added. The resulting mixture was extracted with ethyl acetate (4×100 mL). The combined organic extracts were washed with water (50 mL) and brine (50 mL), dried over $Na_2SO_4$, and evaporated under reduced pressure to give 2.50 g (12.5 mmol, 63%) of compound 12, pure enough for the next step.

Step K: To a solution of compound 12 (2.50 g, 12.5 mmol) in ethanol (30 mL) was added $LiOH \cdot H_2O$ (0.600 g, 13.0 mmol). The mixture was refluxed for 10 h. The solvent was evaporated under reduced pressure and the residue diluted with water (50 mL). The aqueous layer was acidified to pH 6 with 10% aq. hydrochloric acid and the precipitated solid was collected by filtration. The residue was washed with water and dried under vacuum to afford 1.20 g (6.45 mmol, 52%) of 4-cyano-1H-indole-2-carboxylic acid as a white solid.

Rt (Method G) 1.00 mins, m/z 197 [M+H]$^+$

Preparation of 4-cyano-7-fluoro-1H-indole-2-carboxylic Acid

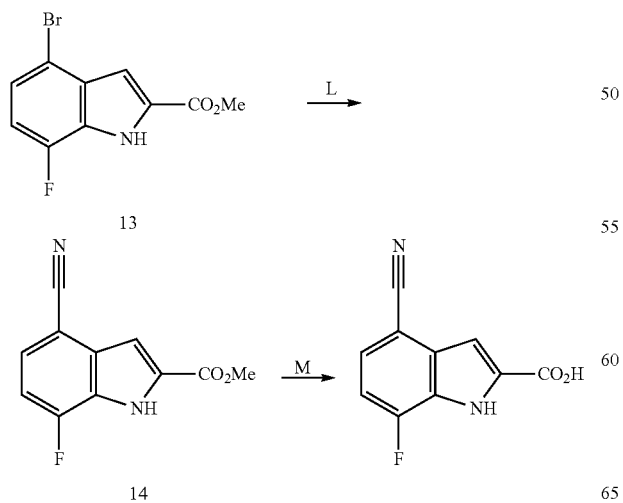

Step L: To a stirred solution of compound 13 (5.00 g, 18.4 mmol) in DMF (50 mL) was added CuCN (2.80 g, 31.2 mmol). The mixture was stirred for 4 h at 150° C. The mixture was then cooled to r.t., and water (100 mL) added. The resulting mixture was extracted with ethyl acetate (4×100 mL). The combined organic extracts were washed with water (50 mL) and brine (50 mL), dried over $Na_2SO_4$, and evaporated under reduced pressure to give 1.50 g (6.87 mmol, 37%) of compound 14, pure enough for the next step.

Step M: To a solution of compound 14 (1.50 g, 6.87 mmol) in ethanol (20 mL) was added $LiOH \cdot H_2O$ (0.400 g, 9.53 mmol). The mixture was refluxed for 10 h. The solvent was evaporated under reduced pressure and the residue diluted with water (40 mL). The aqueous layer was acidified to pH 6.0 with 10% aq. hydrochloric acid and the precipitate was collected by filtration. The residue was washed with water and dried under vacuum to afford 0.400 g (1.95 mmol, 28%) of 4-cyano-7-fluoro-1H-indole-2-carboxylic acid as a white solid.

Rt (Method G) 1.02 mins, m/z 203 [M−H]$^-$

Preparation of 4-cyano-5-fluoro-1H-indole-2-carboxylic Acid

Step N: To a solution of compound 15 (5.00 g, 19.4 mmol) in DMF (50 mL) was added $NaHCO_3$ (1.59 g, 18.9 mmol) and iodomethane (3 mL). The resulting mixture was stirred overnight at r.t., then diluted with water (50 mL) and extracted with diethyl ether (3×50 mL). The combined organic extracts were dried over $Na_2SO_4$, and evaporated under reduced pressure to obtain 4.90 g (18.0 mmol, 90%) of compound 16 as white solid.

Step O: To a stirred solution of compound 16 (4.80 g, 17.6 mmol) in DMF (50 mL) was added CuCN (2.70 g, 30.1 mmol). The mixture was stirred for 4 h at 150° C. The mixture was then cooled to r.t., water (100 mL) added. The resulting mixture was extracted with ethyl acetate (4×100 mL). The combined organic extracts were washed with water (50 mL) and brine (50 mL), dried over $Na_2SO_4$, and evaporated under reduced pressure to give 1.40 g (6.42 mmol, 36%) of compound 17, pure enough for the next step.

Step P: To a solution of compound 17 (1.40 g, 6.42 mmol) in ethanol (20 mL) was added $LiOH.H_2O$ (0.350 g, 8.34 mmol). The mixture was refluxed for 10 h. The solvent was evaporated under reduced pressure and the residue diluted with water (30 mL). The aqueous layer was acidified to pH 6.0 with 10% aq. hydrochloric acid and the precipitate collected by filtration. The residue was washed with water and dried under vacuum to afford 0.500 g (2.45 mmol, 38%) of 4-cyano-5-fluoro-1H-indole-2-carboxylic acid as a white solid.

Rt (Method G) 1.10 mins, m/z 203 [M–H]⁻

Preparation of
4,5,6-trifluoro-1H-indole-2-carboxylic Acid

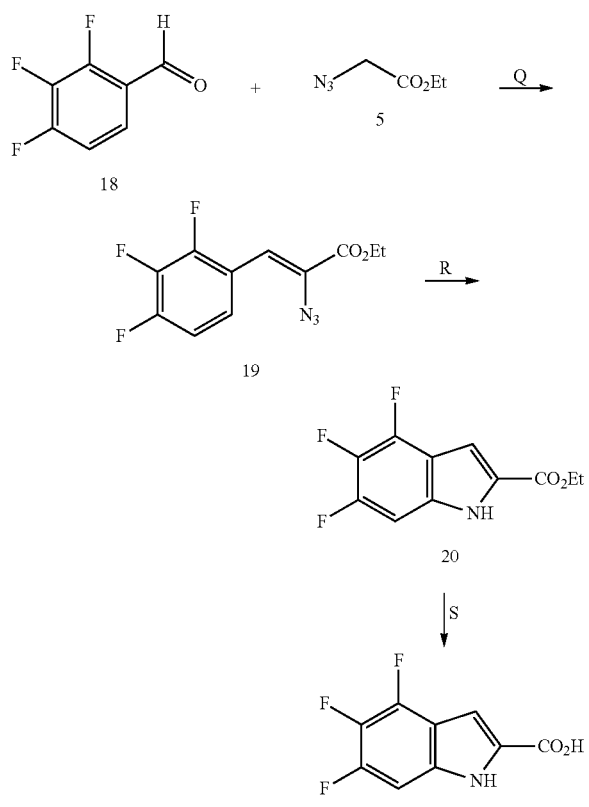

collected by filtration. The solid was washed with water and dried to afford 12.0 g (46.7 mmol, 72%) of compound 19 as a white solid.

Step R: A solution of compound 19, obtained in the previous step, (12.0 g, 46.7 mmol) in xylene (250 mL) was refluxed for 1 h under an argon atmosphere and then evaporated under reduced pressure. The residue was recrystallized form hexane-ethyl acetate mixture (60:40) to give 7.00 g (30.5 mmol, 65%) of compound 20.

Step S: To a solution of compound 20 (7.00 g, 30.5 mmol) in ethanol (50 mL) was added 2 N aqueous sodium hydroxide solution (18 mL). The mixture was stirred for 2 h at 60° C. The solvent was evaporated and the residue was acidified to pH 5-6 with aqueous hydrochloric acid. The resulting precipitate was collected by filtration, washed with water, and dried to obtain 5.00 g (23.2 mmol, 76%) 4,5,6-trifluoro-1H-indole-2-carboxylic acid.

¹H NMR (400 MHz, d6-dmso) 7.17 (1H, s), 7.22 (1H, dd), 12.3 (1H, br s), 13.3 (1H, br s)

Preparation of
4,6,7-trifluoro-1H-indole-2-carboxylic Acid

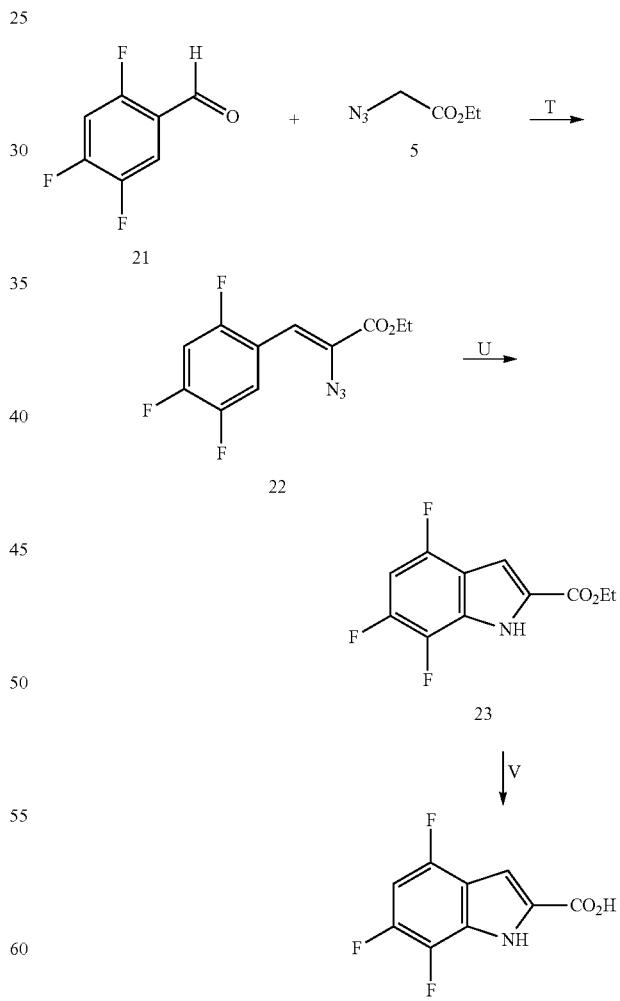

Step Q: To a solution of sodium methoxide (23.0 g, 426 mmol) in methanol (200 mL) at −10° C. was added dropwise a solution of compound 18 (15.0 g, 93.7 mmol) and compound 5 (26.0 g, 201 mmol) in methanol (100 mL). The reaction mixture was stirred for 3 h, maintaining the temperature below 5° C. and then quenched with ice water. The resulting mixture was stirred for 10 min, and the precipitate Step T: To a solution of sodium methoxide (23.0 g, 426 mmol) in methanol (200 mL) at −10° C. was added dropwise a solution of compound 21 (15.0 g, 90.3 mmol) and compound 5 (26.0 g, 201 mmol) in methanol (100 mL). The reaction mixture was stirred for 3 h maintaining the temperature below 5° C. and then quenched with ice water. The resulting mixture was stirred for 10 min. The precipitate was collected by filtration, washed with water and dried to afford 10.0 g (38.0 mmol, 42%) of compound 22 as a white solid.

Step U: A solution of compound 22, obtained in the previous step, (10.0 g, 38.0 mmol) in xylene (200 mL) was refluxed for 1 h under an argon atmosphere and then concentrated under reduced pressure. The residue was recrystallized form hexane-ethyl acetate mixture (60:40) to give 6.00 g (26.2 mmol, 69%) of compound 23.

Step V: To a solution of compound 23 (7.00 g, 30.5 mmol) in ethanol (40 mL) was added 2 N aqueous sodium hydroxide solution (16 mL). The mixture was stirred for 2 h at 60° C. The solvent was evaporated and the residue was acidified to pH 5-6 with aqueous hydrochloric acid. The resulting precipitate was collected by filtration, washed with water, and dried to obtain 4.10 g (19.1 mmol, 62%) of 4,6,7-trifluoro-1H-indole-2-carboxylic acid.

Rt (Method G) 1.16 mins, m/z 214 [M−H]⁻

Preparation of 4-cyano-6-fluoro-1H-indole-2-carboxylic Acid

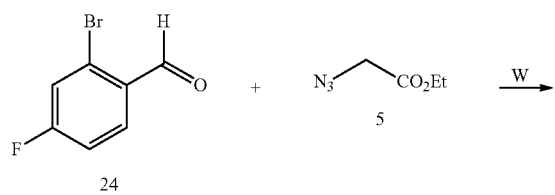

collected by filtration, washed with water and dried to afford 45.0 g (143 mmol, 48%) of compound 25.

Step X: A solution of compound 25, obtained in the previous step, (35.0 g, 111 mmol) in xylene (250 mL) was refluxed for 1 h under an argon atmosphere and then evaporated under reduced pressure. The residue was recrystallized form hexane-ethyl acetate mixture (60:40) to give 11.0 g (38.4 mmol, 35%) of compound 26.

Step Y: To a stirred solution of compound 26 (11.0 g, 38.4 mmol) in DMF (20 mL) was added CuCN (6.60 g, 73.7 mmol). The mixture was stirred for 4 h at 150° C. The mixture was then cooled to r.t., and water (70 mL) added. The mixture was extracted with ethyl acetate (4×50 mL). The combined organic extracts were washed with water (50 mL) and brine (50 mL), dried over Na$_2$SO$_4$, and evaporated under reduced pressure to give 2.40 g (10.3 mmol, 27%) of compound 27, pure enough for the next step.

Step Z: To a solution of compound 27 (2.40 g, 6.42 mmol) in ethanol (30 mL) was added LiOH.H$_2$O (0.600 g, 14.3 mmol). The mixture was refluxed for 10 h. The mixture was concentrated under reduced pressure and the residue diluted with water (50 mL). The aqueous layer was acidified to pH 6 with 10% aq. hydrochloric acid and the precipitate was collected by filtration. The solid was washed with water and dried under vacuum to afford 1.20 g (5.88 mmol, 57%) of 4-cyano-6-fluoro-1H-indole-2-carboxylic acid as a white solid.

Rt (Method G) 1.06 mins, m/z 203 [M−H]⁻

Preparation of 4-ethyl-1H-indole-2-carboxylic Acid

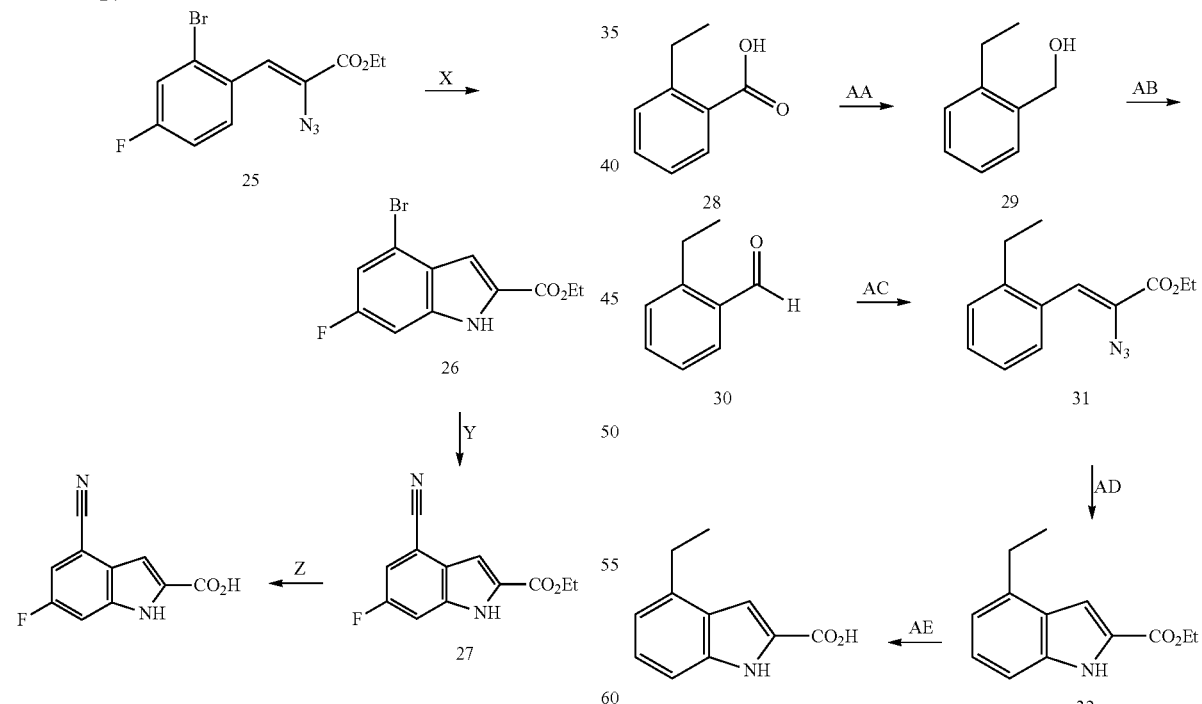

Step W: To a solution of sodium methoxide (65.0 g, 1203 mmol) in methanol (500 mL) at −10° C. was added dropwise a solution of compound 24 (60.0 g, 296 mmol) and compound 5 (85.0 g, 658 mmol) in methanol (200 mL). The reaction mixture was stirred for 3 h maintaining the temperature below 5° C. and then quenched with ice water. The resulting mixture was stirred for 10 min. The precipitate was Step AA: A solution of compound 28 (70.0 g, 466 mmol) in dry THF (500 mL) was treated with 10 M solution of BH$_3$ in THF (53 mL, 53.0 mmol of BH$_3$) at 0° C. The reaction mass was stirred at r.t. for 24 h before methanol (150 mL) was slowly added thereto. The resulting mixture was stirred for 45 min, and evaporated under reduced pressure to yield 55.0 g (404 mmol, 87%) of compound 29, pure enough for the next step.

Step AB: To a cooled (0° C.) solution of compound 29 (55.0 g, 404 mmol) in CH$_2$Cl2 (400 mL) was added Dess-Martin periodinane (177 g, 417 mmol) portionwise. After stirring for 1 h at r.t., the reaction mixture was quenched with saturated aqueous Na$_2$S$_2$O$_3$ (300 mL) and saturated aqueous NaHCO$_3$ (500 m). The mixture was extracted with CH$_2$Cl2 (3×300 mL). The combined organic extracts were washed with water and brine, dried over Na$_2$SO$_4$ and concentrated to yield 51.0 g of crude compound 30 as a yellow solid.

Step AC: To a solution of sodium methoxide (107 g, 1981 mmol) in methanol (600 mL) at −10° C. was added dropwise a solution of compound 30, obtained in the previous step, (51.0 g) and compound 5 (126 g, 976 mmol) in methanol (300 mL). The reaction mixture was stirred for 4 h maintaining temperature below 5° C., then quenched with ice water. The resulting mixture was stirred for 10 min, and the precipitate collected by filtration. The solid was washed with water and dried to afford 35.0 g (151 mmol, 37% over 2 steps) of compound 31.

Step AD: A solution of compound 31, obtained in the previous step, (35.0 g, 151 mmol) in xylene (500 mL) was refluxed for 1 h under an argon atmosphere and then concentrated under reduced pressure. The residue was recrystallized form hexane-ethyl acetate mixture (60:40) to give 21.0 g (103 mmol, 68%) of compound 32.

Step AE: To a solution of compound 32 (21.0 g, 103 mmol) in ethanol (200 mL) was added 2 N aqueous sodium hydroxide solution (47 mL). The mixture was stirred for 2 h at 60° C. The mixture was concentrated under reduced pressure, and the residue acidified to pH 5-6 with aqueous hydrochloric acid. The precipitate was collected by filtration, washed with water, and dried to obtain 19 g (100 mmol, 97%) of 4-ethyl-H-indole-2-carboxylic acid.

Rt (Method G) 1.20 mins, m/z 188 [M−H]$^-$ $^1$H NMR (400 MHz, d6-dmso) δ 1.25 (t, 3H), 2.88 (q, 2H), 6.86 (1H, d), 7.08-7.20 (2H, m), 7.26 (1H, d), 11.7 (1H, br s), 12.9 (1H, br s)

Preparation of
4-cyclopropyl-1H-indole-2-carboxylic Acid

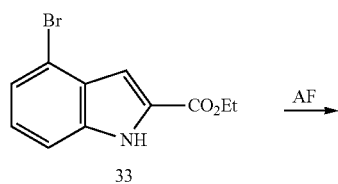

33

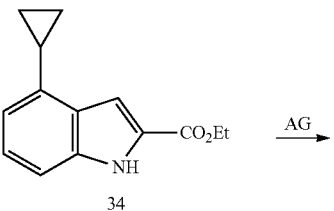

34

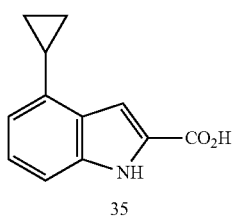

35

Step AF: To a degassed suspension of compound 33 (2.00 g, 7.80 mmol), cyclopropylboronic acid (0.754 g, 8.78 mmol), K$_3$PO$_4$ (5.02 g, 23.6 mmol), tricyclohexyl phosphine (0.189 g, 0.675 mmol), and water (2.0 mL) in toluene (60.0 mL) was added palladium (II) acetate (0.076 g, 0.340 mmol). The reaction mixture was stirred at 100° C. for 4 h. The reaction progress was monitored by diluting an aliquot of the reaction mixture with water and extracting with ethyl acetate. The organic layer was spotted over an analytical silica gel TLC plate and visualized using 254 nm UV light. The reaction progressed to completion with the formation of a polar spot. The R$_f$ values of the starting material and product were 0.3 and 0.2, respectively. The reaction mixture was allowed to cool to r.t. and filtered through a pad of celite. The filtrate was concentrated under reduced pressure and the crude product was purified by flash column using 230-400 mesh silica gel and eluted with 10% ethyl acetate in petroleum ether to afford 1.10 g (5.11 mmol, 63%) of compound 34 as a brown liquid. TLC system: 5% ethyl acetate in petroleum ether.

Step AG: A mixture of compound 34 (1.10 g, 5.11 mmol) in ethanol (40 mL) and 2 N aqueous sodium hydroxide (15 mL) was stirred for 2 h at 60° C. The mixture was concentrated under reduced pressure, and the residue acidified to pH 5-6 with aqueous hydrochloric acid. The precipitate was collected by filtration, washed with water, and dried to yield 1.01 g (5.02 mmol, 92%) of 4-cyclopropyl-1H-indole-2-carboxylic acid.

Rt (Method G) 1.17 mins, m/z 200 [M−H]$^-$

Preparation of
4-chloro-5-fluoro-1H-indole-2-carboxylic Acid

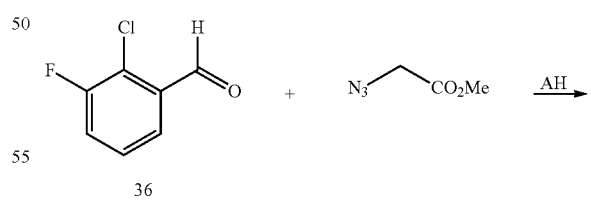

36

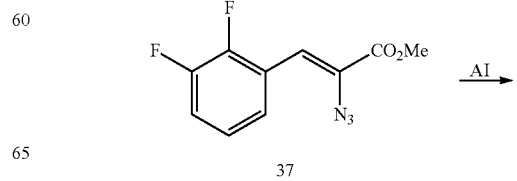

37

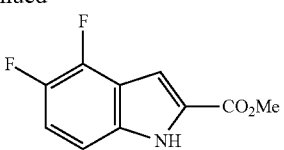

Step AH: To a solution of sodium methoxide (39.9 g, 738 mmol) in methanol (300 mL) at −10° C. was added dropwise a solution of compound 36 (28.8 g, 182 mmol) and methyl azidoacetate (52.1 g, 404 mmol) in methanol (150 mL). The reaction mixture was stirred for 3 h maintaining temperature below 5° C., then quenched with ice water. The resulting mixture was stirred for 10 min. The precipitate was collected by filtration, washed with water and dried to afford 20.0 g (78.2 mmol, 43%) of compound 37.

Step AI: A solution of compound 37 (19.4 g, 76.0 mmol) in xylene (250 mL) was refluxed for 1 h under an argon atmosphere and then concentrated under reduced pressure. The residue was recrystallized from hexane-ethyl acetate (50:50) to give 9.00 g (39.5 mmol, 52%) of compound 38.

Step AJ: To a solution of compound 38 (8.98 g, 39.4 mmol) in ethanol (100 mL) was added 2 N aqueous sodium hydroxide solution (18 mL). The mixture was stirred for 2 h at 60° C. The mixture was concentrated under reduced pressure, and the residue acidified to pH 5-6 with aqueous hydrochloric acid. The resulting precipitate was collected by filtration, washed with water, and dried to obtain 7.75 g (36.3 mmol, 92%) of 4-chloro-5-fluoro-1H-indole-2-carboxylic acid.

Rt (Method G) 1.15 mins, m/z 212 [M−H]$^-$ $^1$H NMR (400 MHz, d6-dmso) 7.08 (1H, s), 7.28 (1H, dd) 7.42 (1H, dd), 12.2 (1H, br s), 13.2 (1H, br s)

Preparation of
5-fluoro-4-(1-hydroxyethyl)-1H-indole-2-carboxylic Acid

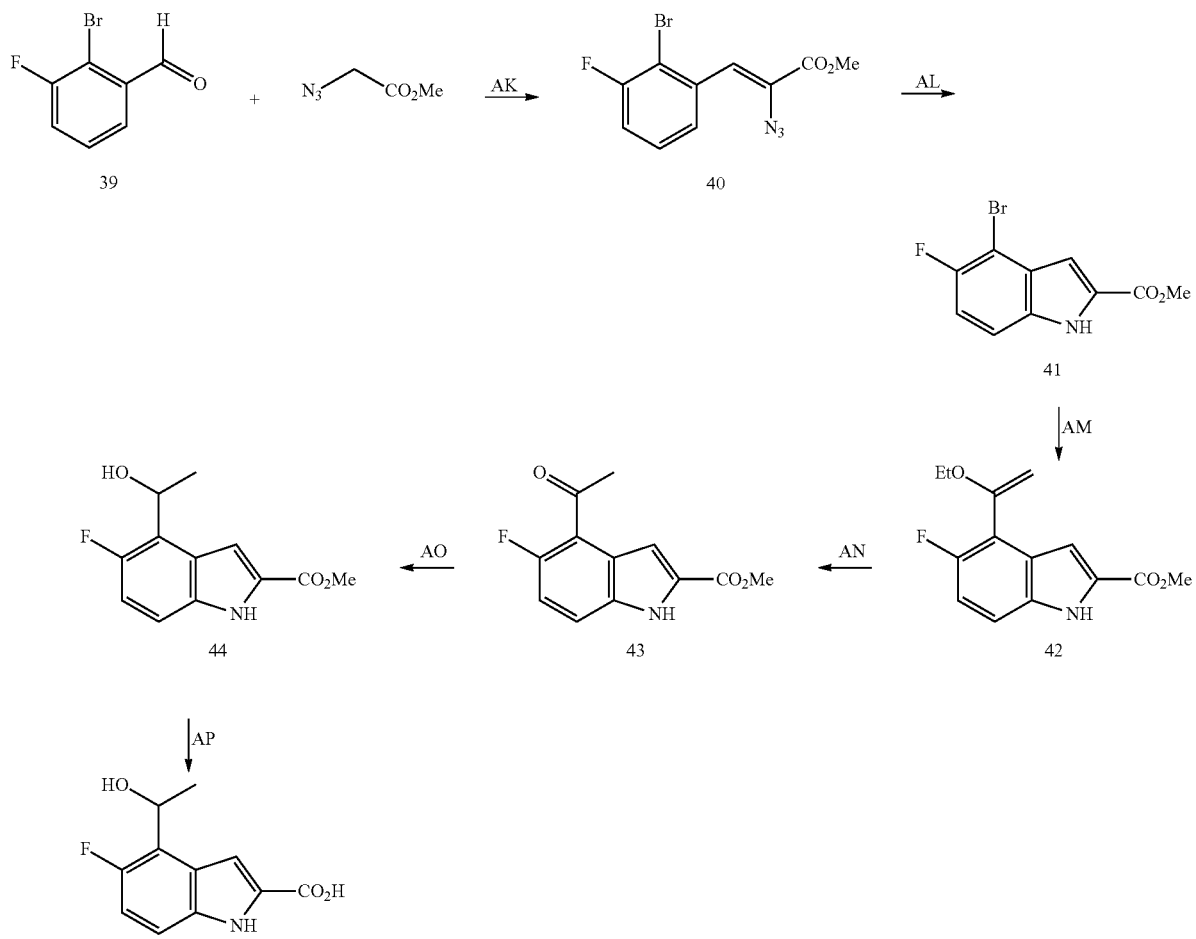

Step AK: To a solution of sodium methoxide (50.0 g, 926 mmol) in methanol (300 mL) at −10° C. was added dropwise a solution of compound 39 (45.0 g, 222 mmol) and methyl azidoacetate (59.0 g, 457 mmol) in methanol (100 mL). The reaction mixture was stirred for 3 h maintaining the temperature below 5° C., then quenched with ice water. The resulting mixture was stirred for 10 min. The precipitate was collected by filtration, washed with water and dried to afford 35.0 g (133 mmol, 60%) of compound 40 as a white solid.

Step AL: A solution of compound 40, obtained in the previous step, (35.0 g, 133 mmol) in xylene (250 mL) was refluxed for 1 h under an argon atmosphere and then evaporated under reduced pressure. The residue was recrystallized from hexane-ethyl acetate (60:40) to give 21.0 g (77.2 mmol, 58%) of compound 41.

Step AM: To a degassed solution of compound 41 (4.00 g, 14.7 mmol) and tributyl(1-ethoxyvinyl)stannane (5.50 g, 15.2 mmol) in toluene (50 mL) under nitrogen was added bis(triphenylphosphine) palladium(I) dichloride (1.16 g, 1.65 mmol). The reaction mixture was stirred at 60° C. for 20 h. The reaction mixture was cooled to room temperature and filtered. The filtrate was concentrated under reduced pressure and the residue purified by silica gel chromatography to afford 2.50 g (9.50 mmol, 65%) of compound 42 as a pale yellow solid.

Step AN: To a solution of compound 42 (2.40 g, 9.12 mmol) in 1,4-dioxane (30 mL) was added 2M hydrochloric acid (15 mL). The resulting mixture was stirred at room temperature for 30 min. The mixture was concentrated under vacuum and the residue partitioned between ethyl acetate and water. The organic extract was washed with water and brine, dried over sodium sulfate, filtered, and evaporated. The residue was triturated with 5% ether in isohexane and dried to afford 1.80 g (7.65 mmol, 84%) of compound 43 as a white solid.

Step AO: A suspension of compound 43 (1.70 g, 7.23 mmol) and NaBH$_4$ (2.50 g, 66.1 mmol) in ethanol (13 mL) was refluxed for 2 h, then cooled to room temperature, and filtered. The filtrate was concentrated under reduced pressure and the residue dissolved in ethyl acetate. The solution was washed with 1N hydrochloric acid and brine, dried over Na$_2$SO$_4$, and evaporated under reduced pressure to give 1.60 g (6.74 mmol, 93%) of compound 44 as a colourless oil.

Step AP: To a solution of compound 44 (1.50 g, 6.32 mmol) in methanol (40 mL) was added 2N aqueous NaOH (10 mL). The mixture was stirred for 2 h at 60° C. The mixture was concentrated under reduced pressure and the residue acidified to pH 5-6 with 10% hydrochloric acid. The precipitate was collected by filtration, washed with water (3×15 mL), and dried to obtain 1.30 g (5.82 mmol, 92%) of 5-fluoro-4-(1-hydroxyethyl)-1H-indole-2-carboxylic acid.

Rt (Method G) 1.00 mins, m/z 222 [M–H]$^-$

Preparation of
4-ethyl-5-fluoro-1H-indole-2-carboxylic Acid

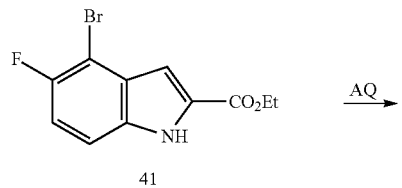

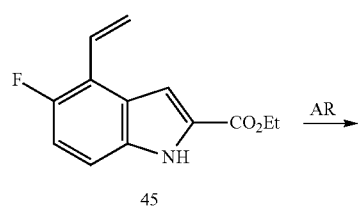

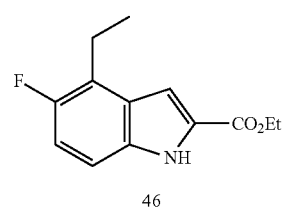

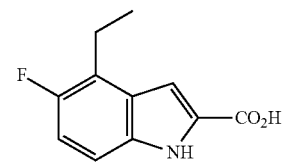

Step AQ: To a heated (90° C.) solution of compound 41 (4.00 g, 14.7 mmol) in anhydrous DMF under nitrogen (10 mL) were added tri-n-butyl(vinyl)tin (3.60 g, 11.4 mmol) and Pd(PPh$_3$)$_2$Cl$_2$ (0.301 g, 0.757 mmol). The resulting mixture was stirred at 90° C. for 1 h. The mixture was then cooled to room temperature and purified by silica gel column chromatography (60-80% ethyl acetate in hexane) to give 2.20 g (10.0 mmol, 68%) of compound 45 as yellow solid.

Step AR: A mixture of compound 45 (1.50 g, 6.84 mmol) and Pd/C (0.300 g, 10% wt.) in methanol (20 mL) was stirred under an atmosphere of hydrogen at room temperature for 16 h. The mixture was filtered, then concentrated under reduced pressure to give 1.45 g (6.55 mmol, 96%) of compound 46.

Step AS: To a solution of compound 46 (1.40 g, 6.33 mmol) in methanol (40 mL) was added 2N aqueous NaOH (10 mL). The mixture was stirred for 2 h at 60° C. The mixture was concentrated under vacuum, then the residue was acidified to pH 5-6 with 10% hydrochloric acid. The precipitate was collected by filtration, washed with water (3×15 mL), and dried to obtain 1.20 g (5.79 mmol, 91%) of target compound 4-ethyl-5-fluoro-1H-indole-2-carboxylic acid.

Rt (Method G) 1.33 mins, m/z 206 [M–H]$^-$

Preparation of
4-ethyl-6-fluoro-1H-indole-2-carboxylic Acid

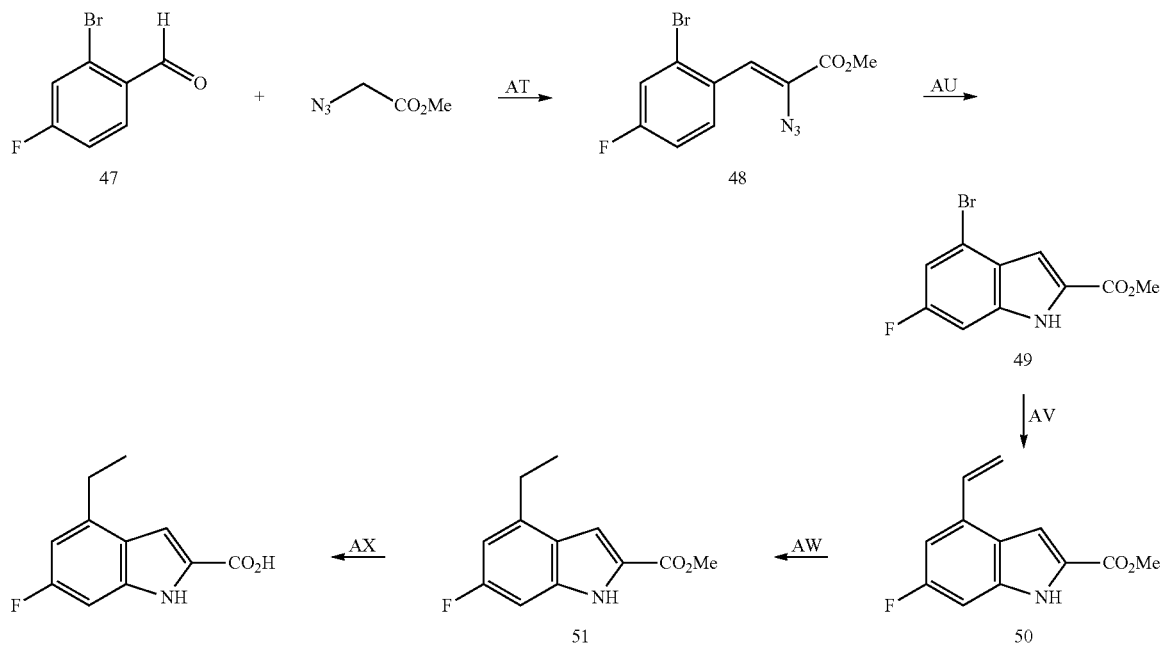

Step AT: To a solution of sodium methoxide (50.0 g, 926 mmol) in methanol (300 mL) at −10° C. was added dropwise a solution of compound 47 (45.0 g, 202 mmol) and methyl azidoacetate (59.0 g, 457 mmol) in methanol (100 mL). The reaction mixture was stirred for 3 h maintaining temperature below 5° C., then quenched with ice water. The resulting mixture was stirred for 10 min. The precipitate was collected by filtration, washed with water and dried to afford 38.5 g (128 mmol, 63%) of compound 48 as a white solid.

Step AU: A solution of compound 48, obtained in the previous step, (38.5 g, 128 mmol) in xylene (250 mL) was refluxed for 1 h under an argon atmosphere and then concentrated under reduced pressure. The residue was recrystallized hexane-ethyl acetate (60:40) to give 18.0 g (67.3 mmol, 53%) of compound 49.

Step AV: To a heated (90° C.) solution of compound 49 (4.00 g, 14.7 mmol) in anhydrous DMF under nitrogen (10 mL) were added tri-n-butyl(vinyl)tin (3.60 g, 11.4 mmol) and Pd(PPh$_3$)$_2$Cl$_2$ (0.301 g, 0.757 mmol). The resulting mixture was stirred at 90° C. for 1 h. The mixture was then cooled to room temperature and purified by silica gel column chromatography (60-80% ethyl acetate in hexane) to give 2.00 g (9.12 mmol, 62%) of compound 50 as yellow solid.

Step AW: A mixture of compound 50 (1.50 g, 6.84 mmol) and Pd/C (0.300 g, 10% wt.) in methanol (20 mL) was stirred under an atmosphere of hydrogen at room temperature for 16 h. The mixture was filtered and concentrated to give 1.40 g (6.33 mmol, 93%) of compound 51.

Step AX: To a solution of compound 51 (1.10 g, 4.97 mmol) in methanol (40 mL) was added 2N aqueous NaOH (10 mL). The mixture was stirred for 2 h at 60° C. The mixture was concentrated under reduced pressure, then acidified to pH 5-6 with 10% hydrochloric acid. The precipitate was collected by filtration, washed with water (3×15 mL), and dried to obtain 0.900 g (4.34 mmol, 87%) of target compound 4-ethyl-6-fluoro-1H-indole-2-carboxylic acid.

Rt (Method G) 1.29 mins, m/z 206 [M−H]⁻

Preparation of
6-fluoro-4-(1-hydroxyethyl)-1H-indole-2-carboxylic Acid

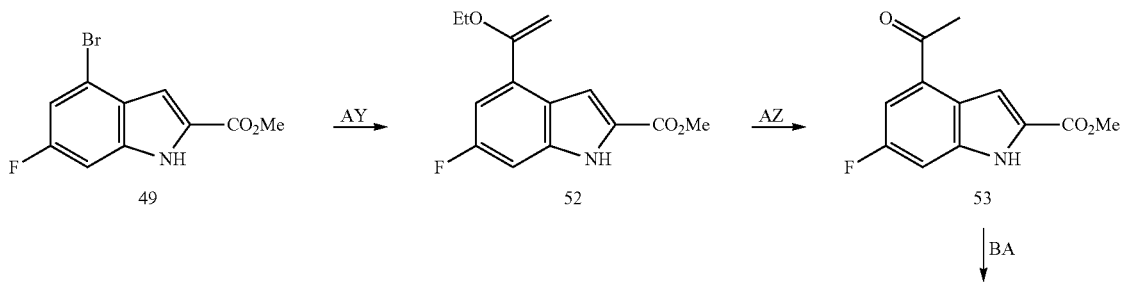

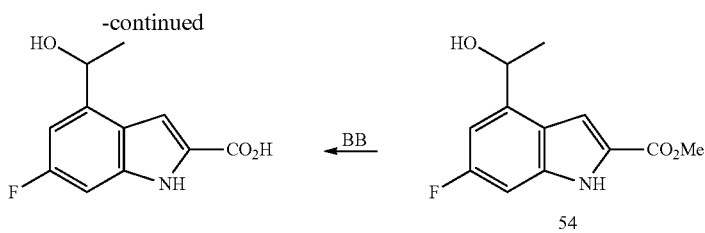

Step AY: To a degassed solution of compound 49 (4.00 g, 14.7 mmol) and tributyl(1-ethoxyvinyl)stannane (5.50 g, 15.2 mmol) in toluene (50 mL) under nitrogen were added bis(triphenylphosphine) palladium(II) dichloride (1.16 g, 1.65 mmol). The reaction mixture was stirred at 60° C. for 20 h. The reaction mixture was cooled to room temperature and filtered. The filtrate was concentrated under reduced pressure and the residue purified by silica gel chromatography to give 2.10 g (7.98 mmol, 54%) of compound 52 as a pale yellow solid.

Step AZ: To a solution of compound 52 (2.10 g, 7.98 mmol) in 1,4-dioxane (30 mL) was added 2M hydrochloric acid (15 mL). The resulting mixture was stirred at room temperature for 30 min. The mixture was concentrated under reduced pressure, and residue partitioned between ethyl acetate and water. The organic extract was washed with water and brine, dried over sodium sulfate, filtered, and concentrated. The residue was triturated with 5% ether in isohexane and dried to afford 1.70 g (7.23 mmol, 91%) of compound 53 as a white solid.

Step BA: A suspension of compound 53 (1.70 g, 7.23 mmol) and NaBH$_4$ (2.50 g, 66.1 mmol) in ethanol (13 mL) was refluxed for 2 h, cooled to room temperature, and filtered. The filtrate was concentrated under reduced pressure and the residue was dissolved in ethyl acetate. The solution was washed with 1N hydrochloric acid and brine, dried over Na$_2$SO$_4$, and concentrated under reduced pressure to give 1.60 g (6.74 mmol, 93%) of compound 54 as a colourless oil.

Step BB: To a solution of compound 54 (1.40 g, 5.90 mmol) in methanol (40 mL) was added 2N aqueous NaOH (10 mL). The mixture was stirred for 2 h at 60° C. The mixture was concentrated and the residue acidified to pH 5-6 with 10% hydrochloric acid. The precipitate was collected by filtration, washed with water (3×15 mL), and dried to obtain 1.10 g (4.93 mmol, 48%) of target compound 6-fluoro-4-(1-hydroxyethyl)-1H-indole-2-carboxylic acid.

Rt (Method G) 1.00 mins, m/z 222 [M–H]$^-$

Preparation of
4-ethyl-7-fluoro-1H-indole-2-carboxylic Acid

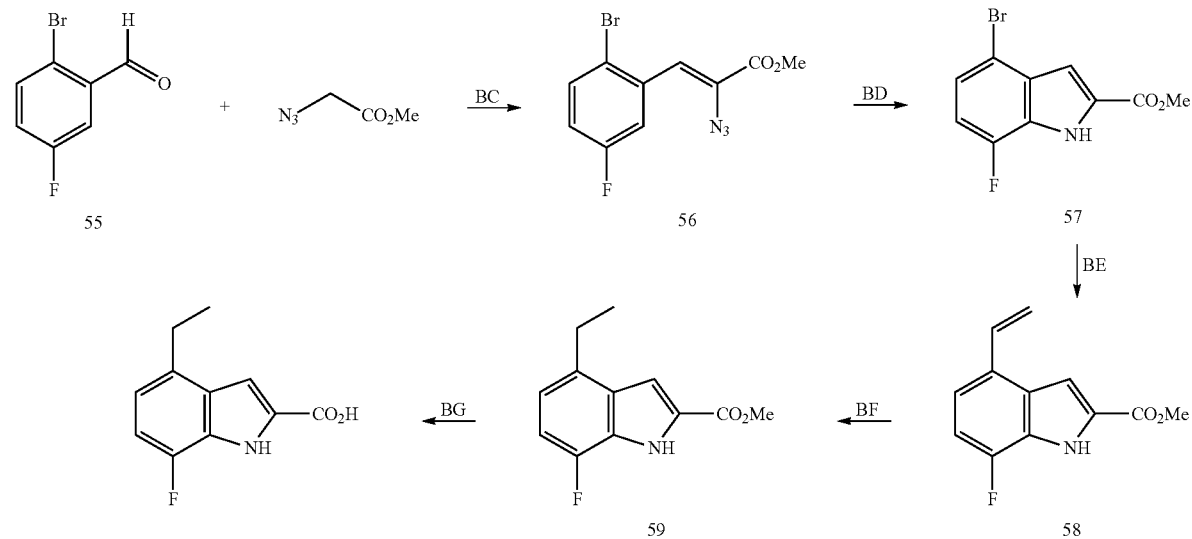

Step BC: To a solution of sodium methoxide (50.0 g, 926 mmol) in methanol (300 mL) –10° C. was added dropwise a solution of compound 55 (45.0 g, 222 mmol) and methyl azidoacetate (59.0 g, 457 mmol) in methanol (100 mL). The reaction mixture was stirred for 3 h maintaining temperature below 5° C., then quenched with ice water. The resulting mixture was stirred for 10 min. The precipitate was collected by filtration, washed with water and dried to afford 33.0 g (110 mmol, 50%) of compound 56 as a white solid.

Step BD: A solution of compound 56, obtained in the previous step, (33.0 g, 110 mmol) in xylene (250 mL) was refluxed for 1 h under an argon atmosphere and then concentrated under reduced pressure. The residue was recrystallized from hexane-ethyl acetate (60:40) to give 21.5 g (79.0 mmol, 72%) of compound 57.

Step BE: To a heated (90° C.) solution of compound 57 (4.00 g, 14.7 mmol) in anhydrous DMF under nitrogen (10 mL) were added tri-n-butyl(vinyl)tin (3.60 g, 11.4 mmol)

and Pd(PPh$_3$)$_2$Cl$_2$ (0.301 g, 0.757 mmol). The resulting mixture was stirred at 90° C. for 1 h. The mixture was cooled to room temperature and purified by silica gel column chromatography (60-80% EtOAc in hexane). The combined product fractions of the product were concentrated, washed with water (3×100 mL), dried over Na$_2$SO$_4$, and concentrated to give 1.80 g (8.21 mmol, 56%) of compound 58 as yellow solid.

Step BF: A mixture of compound 58 (1.50 g, 6.84 mmol) and Pd/C (0.300 g, 10% wt.) in methanol (20 mL) was stirred under atmosphere of hydrogen at room temperature for 16 h. The mixture was filtered and concentrated to give 1.25 g (5.65 mmol, 83%) of compound 59.

Step BG: To a solution of compound 59 (1.40 g, 6.33 mmol) in methanol (40 mL) was added 2N aqueous NaOH (10 mL). The mixture was stirred for 2 h at 60° C. The mixture was concentrated under reduced pressure, and the residue acidified to pH 5-6 with 10% hydrochloric acid. The precipitate was collected by filtration, washed with water (3×15 mL), and dried to obtain 1.25 g (6.03 mmol, 95%) of target compound 4-ethyl-7-fluoro-1H-indole-2-carboxylic acid.

Rt (Method G) 1.27 mins, m/z 206 [M–H]$^-$

Preparation of 7-fluoro-4-(1-hydroxyethyl)-1H-indole-2-carboxylic Acid

Step BH: To a degassed solution of compound 57 (4.00 g, 14.7 mmol) and tributyl(1-ethoxyvinyl)stannane (5.50 g, 15.2 mmol) in toluene (50 mL) under nitrogen was added bis(triphenylphosphine) palladium(I) dichloride (1.16 g, 1.65 mmol). The reaction mixture was stirred at 60° C. for 20 h. The mixture was cooled to room temperature and filtered. The filtrate was concentrated under reduced pressure and the residue purified by silica gel chromatography to afford 2.70 g (10.3 mmol, 70%) of compound 60 as a pale yellow solid.

Step BI: To a solution of compound 60 (2.40 g, 9.12 mmol) in 1,4-dioxane (30 mL) was added 2M hydrochloric acid (15 mL). The mixture was stirred at room temperature for 30 min. The majority of the solvent was evaporated and the residue was partitioned between ethyl acetate and water. The combined organic extracts were washed with water and brine, dried over sodium sulfate, filtered, and evaporated. The residue was triturated with 5% ether in isohexane and dried to afford 1.90 g (8.08 mmol, 86%) of compound 61 as a white solid.

Step BJ: A suspension of compound 61 (1.70 g, 7.23 mmol) and NaBH$_4$ (2.50 g, 66.1 mmol) in ethanol (13 mL) was refluxed for 2 h, cooled to room temperature, and filtered. The filtrate was evaporated under reduced pressure and the residue was dissolved in ethyl acetate. The solution was washed with 1N hydrochloric acid and brine, dried over Na$_2$SO$_4$, and evaporated under reduced pressure to give 1.50 g (6.32 mmol, 87%) of compound 62 as a colourless oil.

Step BK: To a solution of compound 62 (1.50 g, 6.32 mmol) in methanol (40 mL) was added 2N aqueous NaOH (10 mL). The mixture was stirred for 2 h at 60° C. The mixture was concentrated under reduced pressure and the residue acidified to pH 5-6 with 10% hydrochloric acid. The precipitate was collected by filtration, washed with water (3×15 mL), and dried to obtain 1.35 g (6.05 mmol, 96%) of target compound 7-fluoro-4-(1-hydroxyethyl)-1H-indole-2-carboxylic acid.

Rt (Method G) 0.90 mins, m/z 222 [M–H]$^-$

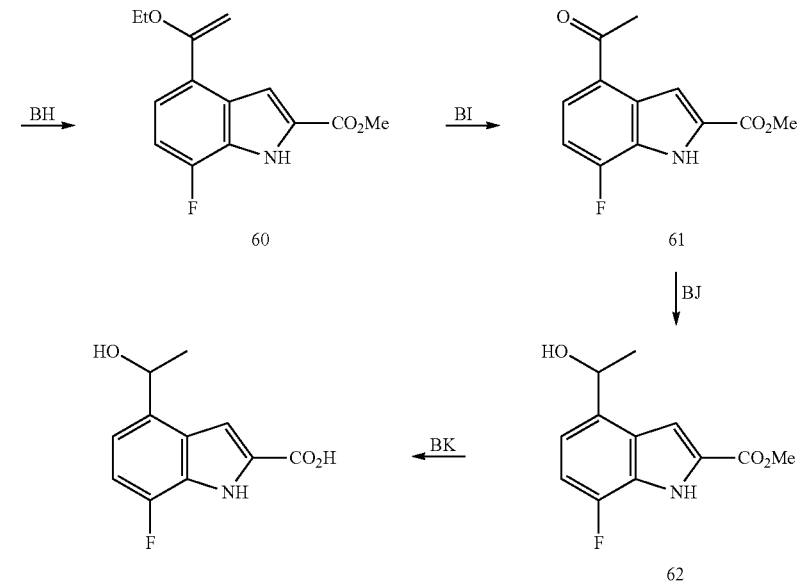

Preparation of 4-(hydroxymethyl)-1H-indole-2-carboxylic Acid

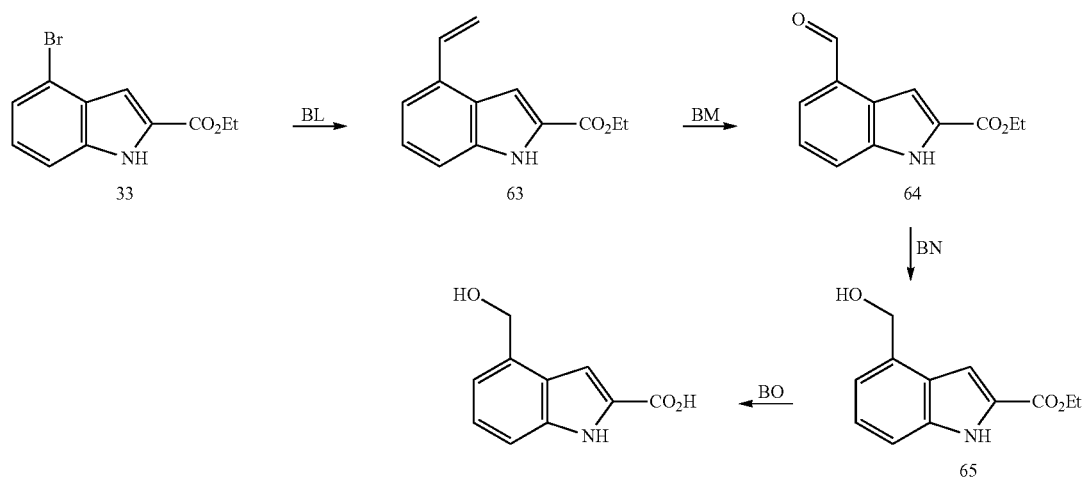

Step BL: To a solution of compound 33 (10.0 g, 39.4 mmol) in a mixture of dioxane (200 mL) and water (50 mL) were added potassium vinyltrifluoroborate (11.0 g, 82.1 mmol), triethylamine (30 mL, 248 mmol) and Pd(dppf)Cl$_2$ (1.00 g, 1.37 mmol). The mixture was stirred at 80° C. for 48 h. The mixture was concentrated under vacuum, and the residue was dissolved in ethyl acetate. The solution was washed with water and concentrated under reduced pressure. The obtained material was purified by silica gel column chromatography to give 2.50 g (12.4 mmol, 38%) of compound 63.

Step BM: To a mixture of compound 63 (2.50 g, 12.4 mmol), acetone (200 m), and water (40 mL) were added OsO$_4$ (0.100 g, 0.393 mmol) and NaIO$_4$ (13.4 g, 62.6 mmol). The reaction was stirred for 10 h at room temperature. The acetone was distilled off and the remaining aqueous solution extracted with dichloromethane. The organic layer was washed with saturated NaHCO$_3$ solution (2×50 mL) and brine (2×50 mL), dried over Na$_2$SO$_4$, and concentrated under reduced pressure to obtain 1.50 g (7.40 mmol, 60%) of compound 64.

Step BN: To a cooled (0° C.) solution of compound 64 (1.50 g, 7.38 mmol) in THF/methanol mixture (100 mL) was added NaBH$_4$ (0.491 g, 13.0 mmol). The reaction mixture was stirred for 12 h at room temperature. Then the mixture was cooled to 0° C., treated with 2N hydrochloric acid (40 mL), and concentrated. The residue was extracted with ethyl acetate. The organic extract was washed with water, dried over Na$_2$SO$_4$, and concentrated under reduced pressure to obtain 1.00 g (4.87 mmol, 65%) of compound 65, pure enough for the next step.

Step BO: To a solution of compound 65, obtained in the previous step, (1.00 g, 4.87 mmol) in THF (50 mL), was added 1N aqueous LiGH (9 mL). The resulting mixture was stirred for 48 h at room temperature, then concentrated and diluted with 1N aqueous NaHSO$_4$ (9 mL). The mixture was extracted with ethyl acetate. The organic extract was dried over Na$_2$SO$_4$, and concentrated under reduced pressure. The residue was recrystallized from MTBE to obtain 0.250 g (1.30 mmol, 27%) of target compound 4-(hydroxymethyl)-1H-indole-2-carboxylic acid.

Rt (Method G) 0.98 mins, m/z 190 [M–H]$^-$

Preparation of 4-(2-hydroxypropan-2-yl)-1H-indole-2-carboxylic Acid

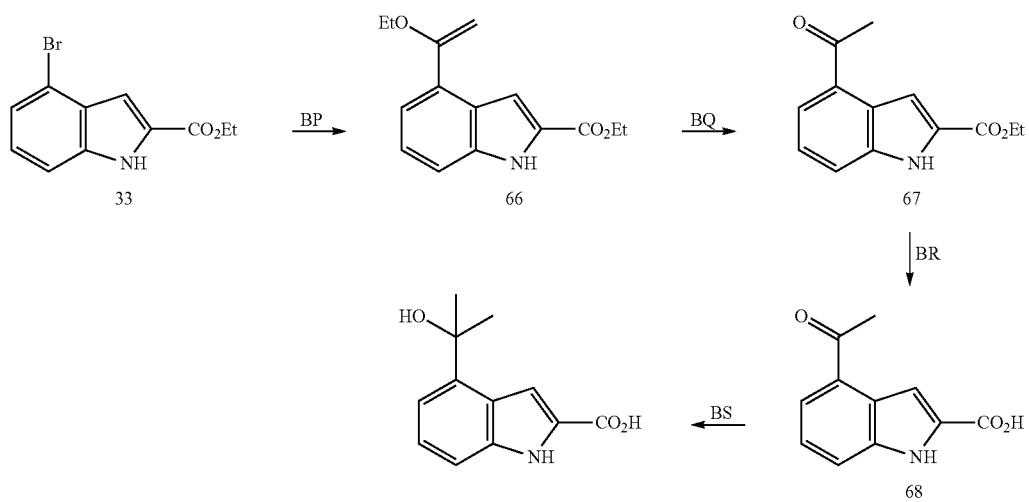

Steps BP and BQ: To a degassed solution of compound 33 (1.00 g, 3.94 mmol) and tributyl-(1-ethoxyvinyl)stannane (1.58 g, 4.37 mmol) in DMF (25 mL) under argon was added bis(triphenylphosphine)palladium(I) dichloride (0.100 g, 0.142 mmol). The reaction mixture was stirred at room temperature until TLC revealed completion of the reaction (approx. 7 days). The mixture was concentrated under reduced pressure and the residue partitioned between ethyl acetate and water. The organic layer was filtered through a plug of silica gel, dried over $MgSO_4$, and concentrated under reduced pressure. The resulting black oil was dissolved in methanol (100 mL), treated with 5N hydrochloric acid (100 mL), and stirred at room temperature overnight. The mixture was concentrated and the residue dissolved in ethyl acetate. The solution was washed with water, dried over $Na_2SO_4$, and concentrated under reduced pressure. The crude product was purified by silica gel column chromatography to give 0.500 g (2.30 mmol, 58%) of compound 66.

Step BR: To a solution of compound 66 (1.00 g, 4.60 mmol) in THF (50 mL), was added 1N aqueous LiOH (7 mL). The resulting mixture was stirred for 48 h at room temperature, then concentrated under reduced pressure and diluted with 1N aqueous $NaHSO_4$ (7 mL). The mixture was extracted with ethyl acetate. The organic extract was dried over $MgSO_4$, and concentrated under reduced pressure. The residue was recrystallized from MTBE to obtain 0.900 g (4.43 mmol, 96%) of compound 67.

Step BS: To a cooled (0° C.) solution of compound 67 (0.900 g, 4.43 mmol) in THF (50 mL) under argon was added a 1N solution of MeMgCl (16 mL) in hexane. The resulting mixture was stirred for 48 h at room temperature. The mixture was carefully quenched with 1N $NaHSO_4$ and extracted with ethyl acetate. The organic extract was dried over $Na_2SO_4$, and concentrated under reduced pressure. The residue was recrystallized from MTBE to obtain 0.250 g (1.14 mmol, 26%) of target compound 4-(2-hydroxypropan-2-yl)-1H-indole-2-carboxylic acid.

Rt (Method G) 0.99 mins, m/z 202 [M–H]⁻

Preparation of 4-(1-hydroxyethyl)-1H-indole-2-carboxylic Acid

Step BS: To a cooled (0° C.) solution of compound 66 (1.00 g, 4.60 mmol) in THF/methanol mixture (50 mL) was added $NaBH_4$ (0.385 g, 10.2 mmol). The reaction mixture was stirred for 12 h at room temperature. The mixture was cooled to 0° C., treated with 2N hydrochloric acid (20 mL), and concentrated. The residue was extracted with ethyl acetate. The organic extract was washed with water, dried over $Na_2SO_4$, and evaporated under reduced pressure to obtain 0.800 g (3.65 mmol, 79%) of compound 69, pure enough for the next step.

Step BT: To a solution of compound 69, obtained in the previous step, (0.800 g, 3.65 mmol) in THF (50 mL), was added 1N aqueous LiGH (6 mL). The resulting mixture was stirred for 48 h at room temperature, then concentrated and diluted with 1N aqueous $NaHSO_4$ (6 mL). The mixture was extracted with ethyl acetate. The organic extract was dried over $MgSO_4$, and concentrated under reduced pressure. The residue was recrystallized from MTBE to obtain 0.300 g (1.46 mmol, 40%) of target compound 4-(1-hydroxyethyl)-1H-indole-2-carboxylic acid.

Rt (Method G) 0.82 mins, m/z 204 [M–H]⁻

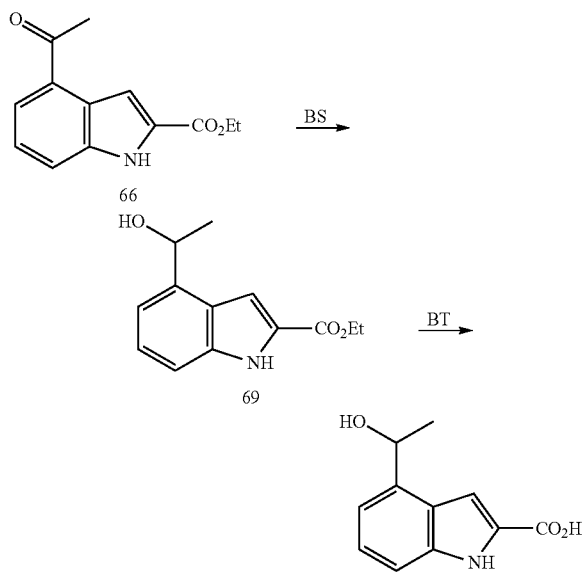

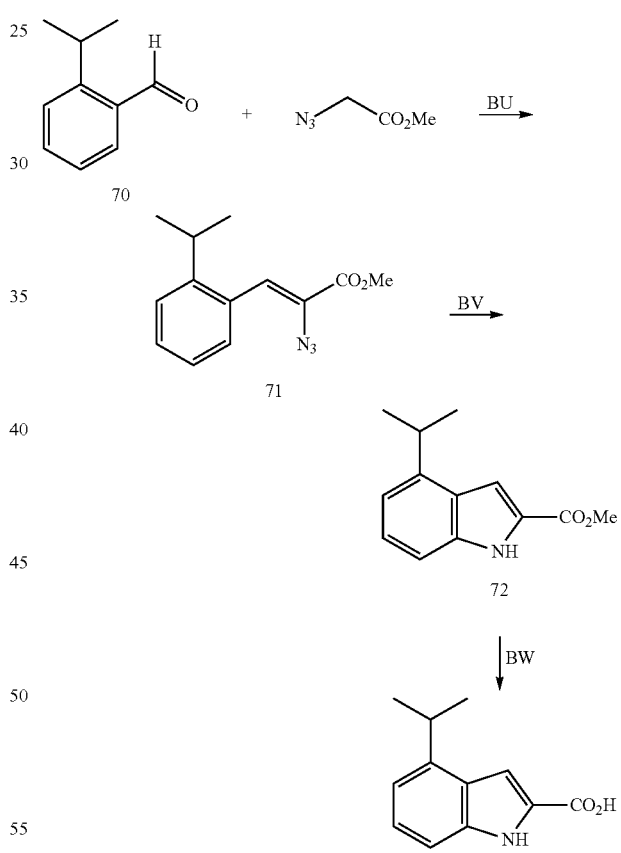

Step BU: To a solution of sodium methoxide (10.0 g, 185 mmol) in methanol (150 mL) at −10° C. was added dropwise a solution of compound 70 (15.0 g, 101 mmol) and methyl azidoacetate (12.0 g, 104 mmol) in methanol (100 mL). The reaction mixture was stirred for 3 h maintaining the temperature below 5° C., then quenched with ice water. The resulting mixture was stirred for 10 min. The precipitate was then collected by filtration, washed with water and dried to afford 7.00 g (23.3 mmol, 23%) of compound 71 as a white solid.

Step BV: A solution of compound 71, obtained in the previous step, (7.00 g, 23.3 mmol) in xylene (200 mL) was refluxed for 1 h under an argon atmosphere and then concentrated under reduced pressure. The residue was recrystallized from hexane-ethyl acetate (60:40) to give 3.50 g (16.1 mmol, 69%) of compound 72.

Step BW: To a solution of compound 72 (3.50 g, 16.1 mmol) in methanol (100 mL) was added 2N aqueous NaOH (40 mL). The mixture was stirred for 2 h at 60° C. The mixture was concentrated under reduced pressure, and then residue acidified to pH 5-6 with 10% hydrochloric acid. The precipitate was collected by filtration, washed with water (3×50 mL), and dried to obtain 2.70 g (13.3 mmol, 83%) of target compound 4-(propan-2-yl)-1H-indole-2-carboxylic acid.

Rt (Method G) 1.32 mins, m/z 202 [M–H]⁻

Preparation of 4-ethenyl-1H-indole-2-carboxylic Acid

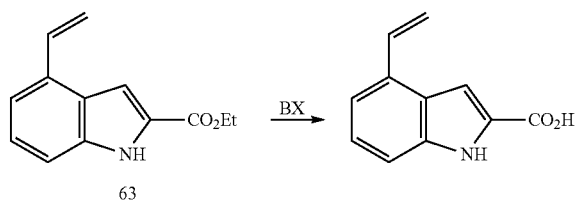

Step BX: To a solution of compound 63 (0.900 g, 4.47 mmol) in THF (50 mL), was added 1N aqueous LiOH (8 mL). The resulting mixture was stirred for 48 h at room temperature, then concentrated under reduced pressure and diluted with 1N aqueous NaHSO₄ (8 mL). The mixture was extracted with ethyl acetate. The organic extract was dried over MgSO₄ and concentrated under reduced pressure. The residue was recrystallized from MTBE to obtain 0.500 g (2.67 mmol, 59%) of target compound 4-ethenyl-1H-indole-2-carboxylic acid.

Rt (Method G) 1.14 mins, m/z 186 [M–H]⁻

Preparation of 4-ethynyl-1H-indole-2-carboxylic Acid

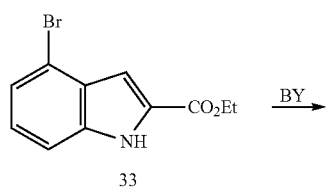

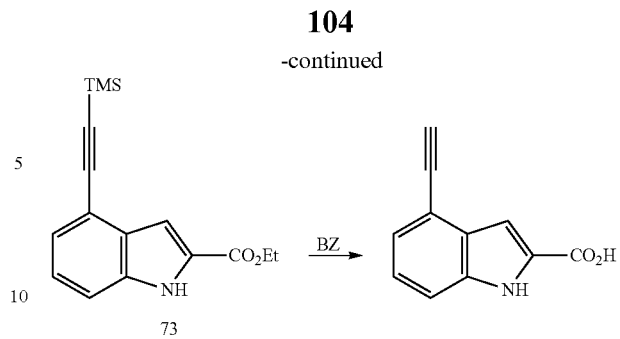

Step BY: To a solution of compound 33 (1.00 g, 3.94 mmol) in THF (50 mL) under argon were added TMS-acetylene (0.68 mL, 4.80 mmol), CuI (0.076 g, 0.399 mmol), triethylamine (2.80 mL, 20.0 mmol), and Pd(dppf)Cl₂ (0.100 g, 0.137 mmol). The mixture was stirred at 60° C. until TLC revealed completion of the reaction (approx. 5 days). The mixture was concentrated under reduced pressure, and the residue dissolved in ethyl acetate. The solution was washed with water, dried over Na₂SO₄, and concentrated under reduced pressure. The residue was purified by silica gel column chromatography to give 0.600 g (2.14 mmol, 56%) of compound 73.

Step BZ: To a solution of compound 73 (0.840 g, 3.10 mmol) in THF (50 mL), was added 1N aqueous LiOH (7 mL). The resulting mixture was stirred for 48 h at room temperature, then concentrated under reduced pressure and diluted with 1N aqueous NaHSO₄ (7 mL). The mixture was extracted with ethyl acetate. The organic extract was dried over MgSO₄ and concentrated under reduced pressure. The residue was recrystallized from MTBE to obtain 0.400 g (2.17 mmol, 70%) of target compound 4-ethynyl-1H-indole-2-carboxylic acid.

Rt (Method G) 1.12 mins, m/z 184 [M–H]⁻

Preparation of 4-(1,1-difluoroethyl)-1H-indole-2-carboxylic Acid

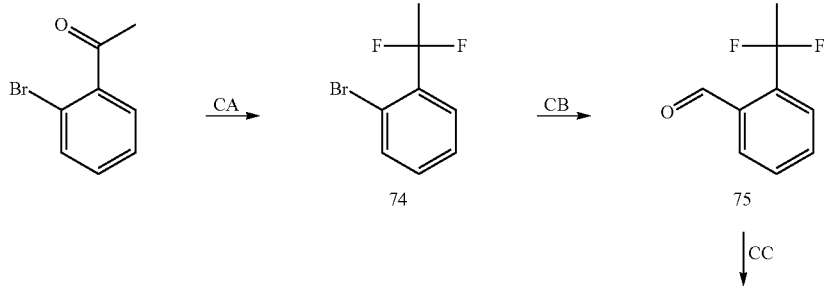

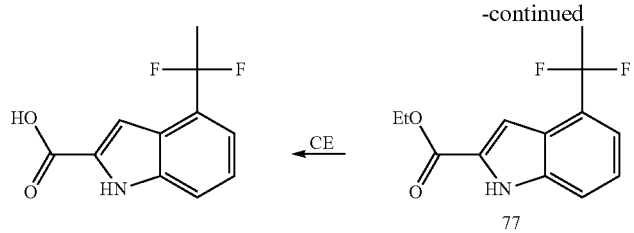
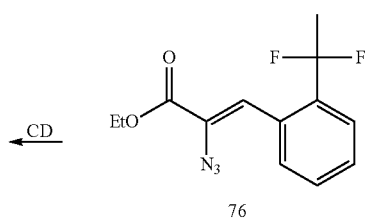

Step CA: To a mixture of 2-bromoacetophenone (63.0 g, 317 mmol), water (0.5 mL), and dichloromethane (100 mL) was added Morph-DAST (121 mL, 992 mmol). The resulting mixture was stirred for 28 days at room temperature. The reaction mixture was then poured into saturated aqueous $NaHCO_3$ (1000 mL) and extracted with ethyl acetate (2×500 mL). The organic layer was dried over $Na_2SO_4$ and concentrated under reduced pressure. The residue was purified by silica gel column chromatography to give 16.8 g (76.0 mmol, 12%) of compound 74.

Step CB: To a cooled (−85° C.) solution of compound 74 (16.8 g, 76.0 mmol) in THF (300 mL) under Ar was added 2.5M solution of n-BuLi in hexanes (36.5 mL, 91.5 mmol) over 30 min. The resulting mixture was stirred for 1 h at −85° C. DMF (8.80 mL, 114 mmol) was then added (maintaining temperature below −80° C.) and the reaction stirred for a further 45 min. The reaction was quenched with saturated aqueous $NH_4Cl$ (100 mL) and diluted with water (600 mL). The obtained mixture was extracted with ethyl acetate (2×500 mL). The combined organic extracts were dried over $Na_2SO_4$, and concentrated under reduced pressure to obtain 12.5 g (73.6 mmol, 97%) of compound 75 (sufficiently pure for the next step).

Step CC: To a cooled (−30° C.) mixture of compound 75 (12.5 g, 73.5 mmol), ethanol (500 mL), and ethyl azidoacetate (28.5 g, 221 mmol) was added a freshly prepared solution of sodium methoxide (prepared by mixing Na (5.00 g, 217 mmol) and methanol (100 mL)) portionwise under Ar (maintaining the temperature below −25° C.). The reaction mixture was warmed to 15° C. and stirred for 12 h. The obtained mixture was poured into saturated aqueous $NH_4Cl$ (2500 mL) and stirred for 20 min. The precipitate was collected by filtration, washed with water, and dried to obtain 10.0 g (35.6 mmol, 51%) of compound 76.

Step CD: A solution of compound 76 (10.0 g, 35.6 mmol) in xylene (500 mL) was refluxed until gas evolution ceased (approx. 2 h) and then concentrated under reduced pressure. The orange oil obtained was triturated with hexane/ethyl acetate (5:1), collected by filtration, and dried to obtain 1.53 g (6.04 mmol, 17%) of compound 77.

Step CE: To a solution of compound 77 (1.53 g, 6.04 mmol) in THF/water 9:1 mixture (100 mL) was added $LiOH \cdot H_2O$ (0.590 g, 14.1 mmol). The resulting mixture was stirred overnight at r.t. The volatiles were evaporated and the residue mixed with water (50 mL) and 1N hydrochloric acid (10 mL). The mixture was extracted with ethyl acetate (2×100 mL). The combined organic extracts were dried over $Na_2SO_4$, and concentrated under reduced pressure. The crude product was purified by silica gel column chromatography to give 0.340 g (1.33 mmol, 24%) of 4-(1,1-difluoroethyl)-1H-indole-2-carboxylic acid.

Rt (Method G) 1.16 mins, m/z 224 [M−H]$^-$

Preparation of 4-(trimethylsilyl)-H-indole-2-carboxylic Acid

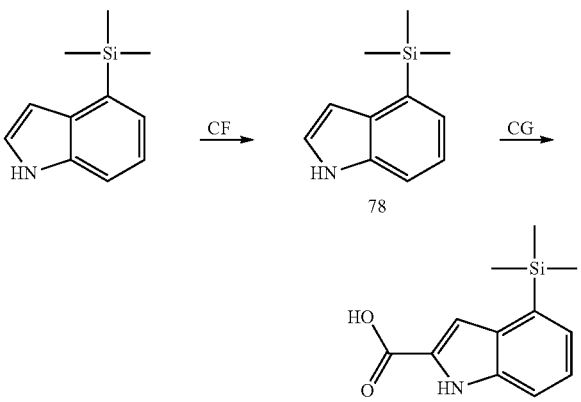

Step CF: To a cooled (−78° C.) solution of 4-bromo-1H-indole (5.00 g, 25.5 mmol) in THF (100 mL) under Ar was added a 2.5M solution of n-BuLi in hexanes (23 mL, 57.5 mmol). The resulting mixture was stirred for 30 min. TMSCl (16 mL, 126 mmol) was added and the reaction mixture warmed to room temperature. After 1 h the mixture was diluted with MTBE (250 mL), washed with water (2×200 mL) and brine (200 mL), then dried over $Na_2SO_4$, and concentrated under reduced pressure. The residue was refluxed in methanol (100 mL) for 1 h. The solvent was then distilled off to obtain 3.60 g (19.0 mmol, 74%) of compound 78.

Step CG: To a cooled (−78° C.) solution of compound 78 (1.50 g, 7.92 mmol) in THF (50 mL) under Ar was added a 2.5M solution of n-BuLi in hexanes (3.8 mL, 9.5 mmol). The resulting mixture was stirred for 20 min. $CO_2$ (2 L) was then bubbled through the mixture for 10 min, and the reaction mixture warmed to room temperature. The volatiles were evaporated and the residue dissolved in THF (50 mL). The solution was cooled to −78° C., and a 1.7M solution of t-BuLi (5.6 mL, 9.50 mmol) was added. The mixture was warmed to −30° C., then again cooled to −78° C. $CO_2$ (2 L) was bubbled through the solution for 10 min. The obtained solution was allowed to slowly warm to r.t. then concentrated under reduced pressure. The residue was dissolved in water (50 mL), washed with MTBE (2×50 mL), then acidified to pH 4, and extracted with ethyl acetate (2×50 mL). The organic extract was washed with water (2×50 mL), and brine (50 m), dried over $Na_2SO_4$, and evaporated under reduced pressure. The crude product was washed with hexane and dried to obtain 1.24 g (5.31 mmol, 67%) of target compound 4-(trimethylsilyl)-1H-indole-2-carboxylic acid.

Rt (Method G) 1.47 mins, m/z 232 [M−H]$^-$

Preparation of 6-chloro-5-fluoro-1H-indole-2-carboxylic Acid

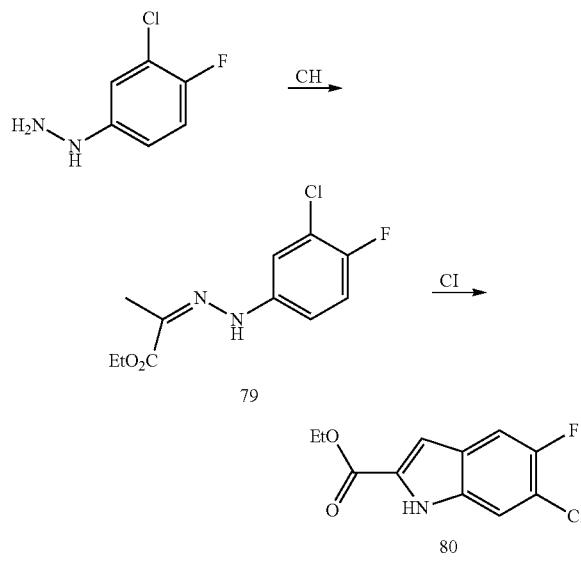

Step CH: To a solution of (3-chloro-4-fluorophenyl)hydrazine (80.0 g, 498 mmol) in ethanol (200 mL) was added ethyl pyruvate (58.0 g, 499 mmol). The mixture was refluxed for 1 h, then concentrated under reduced pressure, and diluted with water (300 mL). The solid was collected by filtration then dried to obtain 122 g (472 mmol, 95%) of compound 79.

Step CI: A suspension of compound 79 (122 g, 472 mmol) and pTSA (81.5 g, 473 mmol) in toluene (500 mL) was refluxed for 48 h, then cooled to room temperature. The precipitate was collected by filtration and purified by fractional crystallization from toluene to obtain 4.00 g (16.6 mmol, 4%) of compound 80.

Step CJ: To a refluxing solution of compound 80 (4.00 g, 16.6 mmol) in ethanol (30 mL) was added NaOH (0.660 g, 16.5 mmol). The mixture was refluxed for 1 h, then concentrated under reduced pressure. The residue was triturated with warm water (80° C., 50 mL) and the solution acidified (pH 2) with concentrated hydrochloric acid. The precipitate was collected by filtration, washed with water (2×10 mL), and dried to obtain 3.18 g (14.9 mmol, 90%) of target compound 6-chloro-5-fluoro-1H-indole-2-carboxylic acid.

Rt (Method G) 1.23 mins, m/z 212 [M–H]⁻

Preparation of 4-(difluoromethyl)-6-fluoro-1H-indole-2-carboxylic Acid

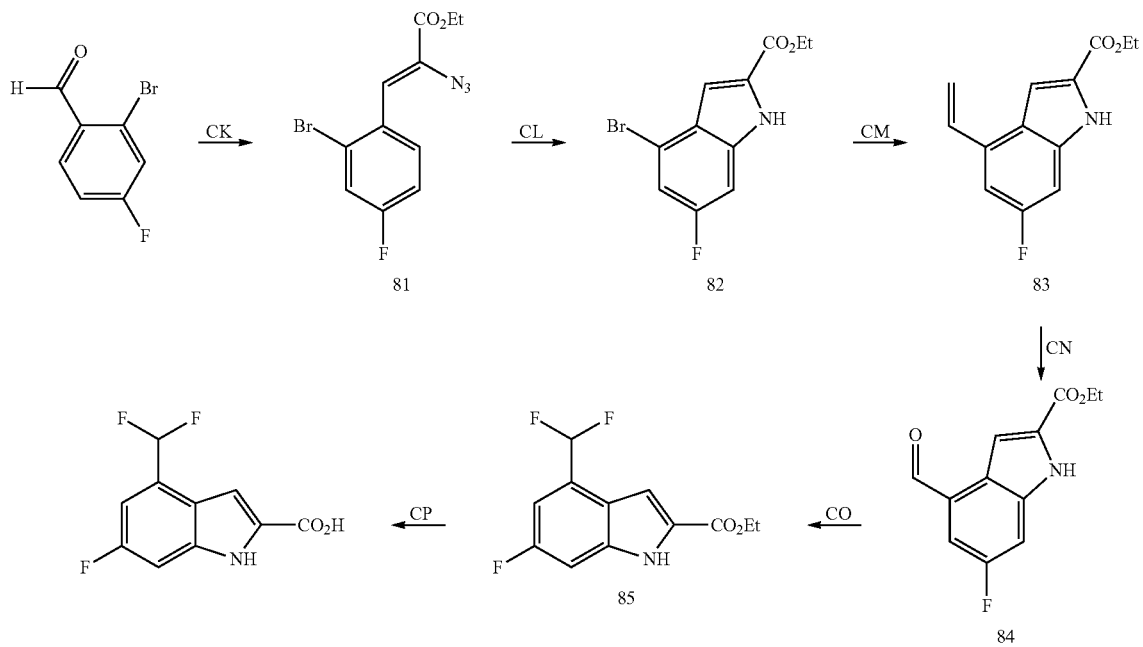

-continued

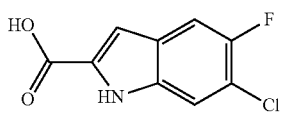

Step CK: To a solution of sodium methoxide (50.0 g, 926 mmol) in methanol (300 mL) at −10° C. was added dropwise a solution of 2-bromo-4-fluorobenzaldehyde (222 mmol) and methyl azidoacetate (59.0 g, 457 mmol) in methanol (100 mL). The reaction mixture was stirred for 3 h, maintaining the temperature below 5° C., then quenched with ice water. The resulting mixture was stirred for 10 min and the solid collected by filtration. The solid was washed with water to afford compound 81 as a white solid (62% yield).

Step CL: A solution of compound 81 (133 mmol) in xylene (250 mL) was refluxed for 1 h under an argon atmosphere and then concentrated under reduced pressure. The residue was recrystallized form hexane-ethyl acetate mixture (60:40) to give compound 82 (58% yield).

Step CM: To a heated (90° C.) solution of compound 82 (14.7 mmol) in anhydrous DMF (10 mL) tri-n-butyl(vinyl) tin (3.60 g, 11.4 mmol) and Pd(PPh3)2Cl2 (0.301 g, 0.757 mmol) were added under nitrogen and the resulting mixture was stirred at 90° C. for 1 h. The mixture was cooled to room temperature and purified by silica gel column chromatography (60-80% ethyl acetate in hexane). The combined product fractions were concentrated, washed with water (3×100 mL), dried over Na₂SO₄, and concentrated under reduced pressure to afford compound 83 as a yellow solid (60% yield).

Step CN: To a mixture of compound 83 (12.4 mmol), acetone (200 mL), and water (40 mL) OsO₄ (0.100 g, 0.393 mmol) and NaIO₄ (13.4 g, 62.6 mmol) were added and the reaction was stirred for 10 h at room temperature. Acetone was distilled off and the aqueous solution was extracted with dichloromethane. The combined organic layer was washed with saturated NaHCO₃ solution (2×50 mL) and brine (2×50 mL), dried over Na₂SO₄, and concentrated under reduced pressure to afford compound 84 (33% yield).

Step CO: To a solution of compound 85 (11.0 mmol) in dichloromethane (50 mL) was added Morph-DAST (4.10 mL, 33.6 mmol). The resulting mixture was stirred until NMR of an aliquot revealed completion of the reaction (2-5 days). The reaction mixture was added dropwise to a cold saturated NaHCO₃ solution (1000 mL). The mixture obtained was extracted with ethyl acetate. The organic layer was dried over MgSO₄ and concentrated. The residue was purified by column chromatography to give compound 86 as yellow solid (48% yield).

Step CP: To a solution of compound 87 (4.50 mmol) in THF (50 mL), was added 1N aqueous LiGH (8 mL). The resulting mixture was stirred for 48 h at room temperature then concentrated under reduced pressure and diluted with 1N aqueous NaHSO₄ (8 mL). The obtained mixture was extracted with ethyl acetate. The organic extract was dried over MgSO₄ and concentrated under reduced pressure. The residue was recrystallized from MTBE to obtain 4-(difluoromethyl)-6-fluoro-1H-indole-2-carboxylic acid (87%).

Rt (Method G) 1.22 mins, m/z 228 [M−H]⁻

Preparation of
4-(difluoromethyl)-7-fluoro-1H-indole-2-carboxylic
Acid

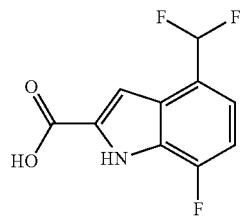 [SMILES: O=C(O)c1cc2c(C(F)F)ccc(F)c2[nH]1]

Prepared as described for 4-(difluoromethyl)-6-fluoro-1H-indole-2-carboxylic acid, starting from 2-bromo-5-fluorobenzaldehyde (2.5% overall yield).

Rt (Method G) 1.13 mins, m/z 228 [M−H]⁻

Preparation of
4-(difluoromethyl)-1H-indole-2-carboxylic Acid

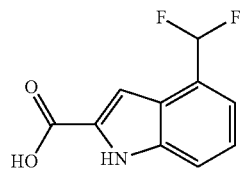 [SMILES: O=C(O)c1cc2c(C(F)F)cccc2[nH]1]

Prepared as described for 4-(difluoromethyl)-6-fluoro-1H-indole-2-carboxylic acid, starting from 4-bromo-1H-indole-2-carboxylic acid (11% overall yield).

Rt (Method G) 1.17 mins, m/z 210 [M−H]⁻

Preparation of 4-(1,1-difluoroethyl)-6-fluoro-1H-indole-2-carboxylic Acid

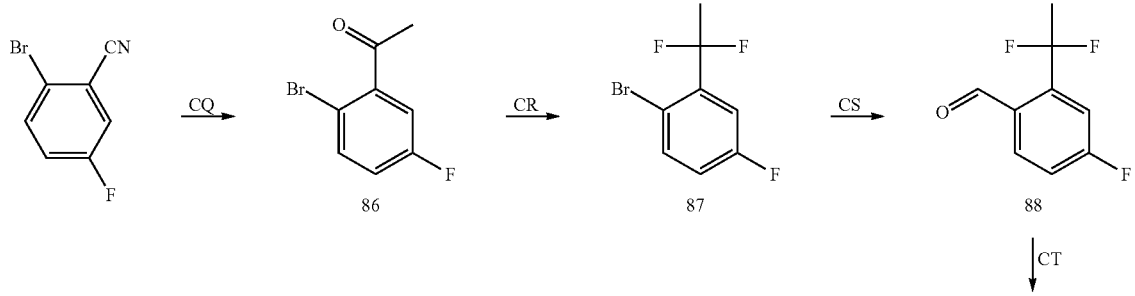

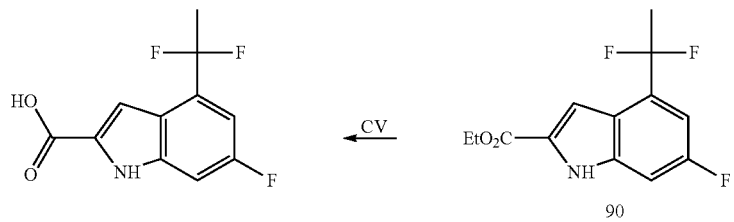

Step CQ: To a solution of 2-bromo-5-fluorobenzonitrile (10.0 g, 48.5 mmol) in anhydrous tetrahydrofuran (100 mL) under nitrogen was added methylmagnesium bromide (3.2M in ether, 19 mL, 60.0 mmol). The resulting mixture was heated to reflux for 4 h. The reaction mixture was then cooled, poured into 2N hydrochloric acid (100 mL), and diluted with methanol (100 mL). The organic solvents were removed and the crude product precipitated out. The reaction mixture was extracted with ethyl acetate, dried over MgSO$_4$, and concentrated. The residue was purified by column chromatography (heptane/dichloromethane) to give 4.88 g (21.9 mmol, 45%) of compound 86 as a pink oil.

Step CR: To a solution of compound 86 (110 mmol) in dichloromethane (50 mL) at room temperature was added Morph-DAST (41 mL, 336 mmol) and a few drops of water. The resulting mixture was stirred for 48 days at room temperature; every 7 days an additional portion of Morph-DAST (41 mL, 336 mmol) was added. After the reaction was complete, the mixture was carefully added dropwise to cold saturated aqueous NaHCO$_3$. The product was extracted with ethyl acetate and the organic extract dried over MgSO$_4$ and concentrated. The residue was purified by column chromatography to give 87 as a colorless liquid (37% yield).

Step CS: To a cooled (−80° C.) solution of compound 87 (21.0 mmol) in THF (150 mL) was added slowly a 2.5M solution of n-BuLi in hexanes (10.0 mL, 25.0 mmol of n-BuLi). The mixture was stirred for 1 h, then DMF (2.62 mL, 33.8 mmol) was added and the mixture stirred for a further 1 h. The reaction was quenched with saturated aqueous NH$_4$Cl (250 mL) and extracted with Et$_2$O (3×150 mL). The organic layer was dried over Na$_2$SO$_4$ and concentrated under reduced pressure. The residue was purified by silica gel chromatography (ethyl acetate/hexane 1:9) to give compound 88 (52% yield).

Step CT: To a solution of sodium methoxide (50.0 g, 926 mmol) in methanol (300 mL) at −10° C. was added dropwise a solution of compound 88 (222 mmol) and methyl azidoacetate (59.0 g, 457 mmol) in methanol (100 mL). The reaction mixture was stirred for 3 h, maintaining the temperature below 5° C., then quenched with ice water. The resulting mixture was stirred for 10 min. The solid obtained was collected by filtration, and washed with water to afford compound 89 as a white solid (66% yield).

Step CU: A solution of compound 89 (120 mmol) in xylene (250 mL) was refluxed for 1 h under an argon atmosphere and then concentrated under reduced pressure. The residue was recrystallized from hexane-ethyl acetate to give compound 90 (70% yield).

Step CV: To a solution of compound 90 (4.40 mmol) in THF (50 mL) was added 1N aqueous LiGH (8 mL). The resulting mixture was stirred for 48 h at room temperature, then concentrated under reduced pressure and diluted with 1N aqueous NaHSO$_4$ (8 mL). The residue obtained was extracted with ethyl acetate. The organic extract was dried over MgSO$_4$ and concentrated under reduced pressure. The residue was recrystallized from MTBE to obtain target compound 4-(1,1-difluoroethyl)-6-fluoro-1H-indole-2-carboxylic acid (95% yield).

Rt (Method G) 1.26 mins, m/z 242 [M−H]$^-$

Preparation of 4-(1,1-difluoroethyl)-7-fluoro-1H-indole-2-carboxylic Acid

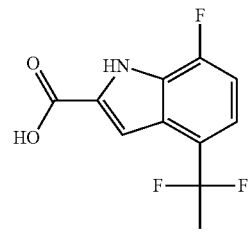 [SMILES: CC(F)(F)c1ccc(F)c2[nH]c(C(=O)O)cc12]

Prepared as described for 4-(1,1-difluoroethyl)-6-fluoro-1H-indole-2-carboxylic acid, starting from 2-bromo-4-fluoroacetophenone (3.6% overall yield).

Rt (Method G) 1.23 mins, m/z 242 [M−H]$^-$

Preparation of tert-butyl 2-bromo-4H,6H,7H-[1,3]thiazolo[5,4-c]pyridine-5-carboxylate and 2-bromo-4H,5H,6H,7H-[1,3]thiazolo[5,4-c]pyridine

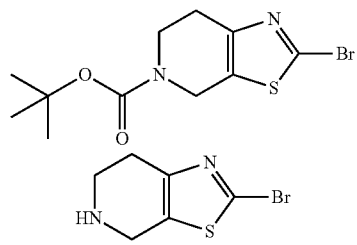

The syntheses of tert-butyl 2-bromo-4H,6H,7H-[1,3]thiazolo[5,4-c]pyridine-5-carboxylate and 2-bromo-4H,5H,6H,7H-[1,3]thiazolo[5,4-c]pyridine were performed as described in WO2008/085118, WO2007/106349, and WO2007/106349.

113

Preparation of tert-butyl 2-chloro-4H,5H,6H,7H-[1,3]thiazolo[5,4-c]pyridine-5-carboxylate

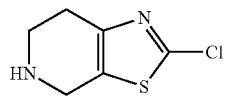

The synthesis of 2-chloro-4H,5H,6H,7H-[1,3]thiazolo[5,4-c]pyridine-5-carboxylate was performed as described in WO2010/04441.

Example 1

{[5-(1H-indole-2-carbonyl)-4H,5H,6H,7H-[1,3]thiazolo[5,4-c]pyridin-2-yl]methyl}[(oxolan-3-yl)methyl]amine

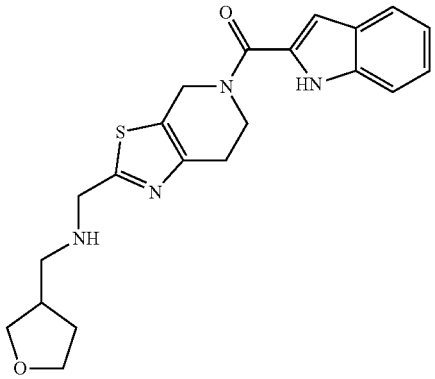 [SMILES: O=C(c1cc2ccccc2[nH]1)N1CCc2nc(CNCC3CCOC3)sc2C1]

Rt (Method D) 2.89 mins, m/z 397 [M+H]⁺.

1H NMR (400 MHz, DMSO-d6) δ 11.64 (s, 1H), 7.64 (d, J=8.0 Hz, 1H), 7.43 (d, J=8.2 Hz, 1H), 7.25-7.16 (m, 1H), 7.12-7.02 (m, 1H), 6.98-6.90 (m, 1H), 5.33-4.56 (m, 2H), 4.18-3.98 (m, 2H), 3.91 (s, 2H), 3.79-3.63 (m, 2H), 3.58 (q, J=7.6 Hz, 1H), 3.41 (dd, J=8.3, 6.0 Hz, 1H), 3.04-2.69 (m, 3H), 2.63-2.51 (m, 2H), 2.39-2.24 (m, 1H), 2.00-1.86 (m, 1H), 1.60-1.46 (m, 1H).

Example 2

N-[5-(1H-indole-2-carbonyl)-4H,5H,6H,7H-[1,3]thiazolo[5,4-c]pyridin-2-yl]oxane-4-carboxamide

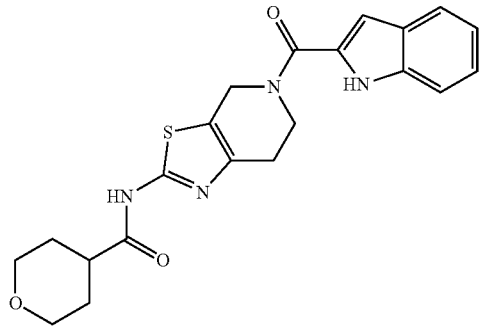 [SMILES: O=C(Nc1nc2c(s1)CN(C(=O)c1cc3ccccc3[nH]1)CC2)C1CCOCC1]

114

Rt (Method B) 3.02 mins, m/z 411 [M+H]⁺.

1H NMR (400 MHz, DMSO-d6) δ 12.04 (s, 1H), 11.78-11.44 (m, 1H), 7.64 (d, J=7.9 Hz, 1H), 7.43 (d, J=8.2 Hz, 1H), 7.20 (t, J=7.6 Hz, 1H), 7.06 (t, J=7.5 Hz, 1H), 6.93 (d, J=2.1 Hz, 1H), 4.91 (s, 2H), 4.05 (s, 2H), 3.96-3.80 (m, 2H), 2.83 (s, 2H), 2.78-2.64 (m, 1H), 1.80-1.52 (m, 4H).

Example 3

N-[5-(1H-indole-2-carbonyl)-4H,5H,6H,7H-[1,3]thiazolo[5,4-c]pyridin-2-yl]-2-methoxyacetamide

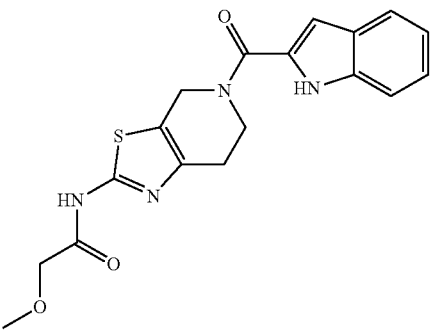 [SMILES: COCC(=O)Nc1nc2c(s1)CN(C(=O)c1cc3ccccc3[nH]1)CC2]

Rt (Method B) 2.99 mins, m/z 371 [M+H]⁺. 1H NMR (400 MHz, DMSO-d6) δ 11.97 (s, 1H), 11.64 (d, J=2.1 Hz, 1H), 7.64 (d, J=7.9 Hz, 1H), 7.43 (d, J=8.2 Hz, 1H), 7.20 (t, J=7.5 Hz, 1H), 7.06 (t, J=7.5 Hz, 1H), 6.94 (d, J=2.0 Hz, 1H), 4.92 (s, 2H), 4.24-3.91 (m, 4H), 3.33 (s, 3H), 2.84 (s, 2H).

Example 4

2-ethoxy-N-[5-(1H-indole-2-carbonyl)-4H,5H,6H,7H-[1,3]thiazolo[5,4-c]pyridin-2-yl]acetamide

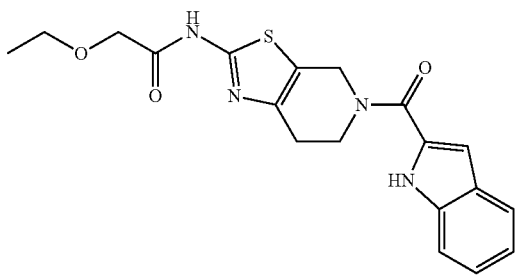 [SMILES: CCOCC(=O)Nc1nc2c(s1)CN(C(=O)c1cc3ccccc3[nH]1)CC2]

Rt (Method B) 3.14 mins, m/z 385 [M+H]⁺.

1H NMR (400 MHz, DMSO-d6) δ 11.92 (s, 1H), 11.64 (d, J=2.1 Hz, 1H), 7.64 (d, J=7.9 Hz, 1H), 7.43 (d, J=8.2 Hz, 1H), 7.20 (t, J=7.6 Hz, 1H), 7.06 (t, J=7.5 Hz, 1H), 6.94 (d, J=2.0 Hz, 1H), 4.92 (s, 2H), 4.16 (s, 2H), 4.05 (s, 2H), 3.53 (q, J=7.0 Hz, 2H), 2.84 (s, 2H), 1.15 (t, J=7.0 Hz, 3H).

Example 5

Ethyl 4-{[5-(1H-indole-2-carbonyl)-4H,5H,6H,7H-[1,3]thiazolo[5,4-c]pyridin-2-yl]amino}piperidine-1-carboxylate

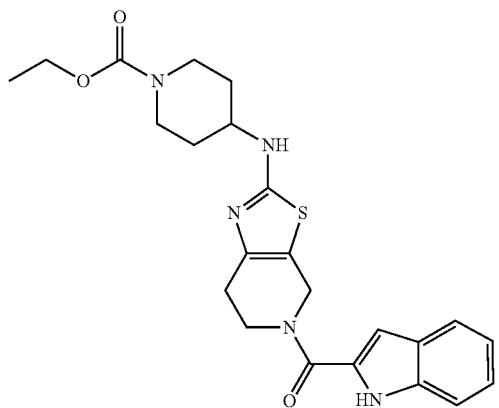 [SMILES: CCOC(=O)N1CCC(Nc2nc3c(s2)CN(C(=O)c2cc4ccccc4[nH]2)CC3)CC1]

Rt (Method A) 3.3 mins, m/z 454 [M+H]⁺.

1H NMR (400 MHz, DMSO-d6) δ 11.62 (s, 1H), 7.62 (d, J=8.0 Hz, 1H), 7.51 (d, J=7.3 Hz, 1H), 7.42 (d, J=8.3 Hz, 1H), 7.20 (t, J=7.5 Hz, 1H), 7.06 (t, J=7.4 Hz, 1H), 6.89 (s, 1H), 5.06-4.45 (m, 2H), 4.09-3.94 (m, 4H), 3.90-3.80 (m, 2H), 3.77-3.60 (m, 1H), 3.11-2.86 (m, 2H), 2.72-2.62 (m, 2H), 1.95-1.86 (m, 2H), 1.36-1.26 (m, 2H), 1.18 (t, J=7.1 Hz, 3H).

Example 6

N-[5-(1H-indole-2-carbonyl)-4H,5H,6H,7H-[1,3]thiazolo[5,4-c]pyridin-2-yl]cyclopropanesulfonamide

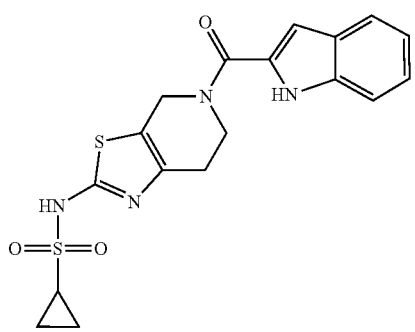 [SMILES: O=C(c1cc2ccccc2[nH]1)N1CCc2nc(NS(=O)(=O)C3CC3)sc2C1]

Rt (Method A) 2.48 mins, m/z 403 [M+H]⁺.

1H NMR (400 MHz, DMSO-d6) δ 12.49 (s, 1H), 11.64 (s, 1H), 7.63 (d, J=8.0 Hz, 1H), 7.43 (d, J=8.3 Hz, 1H), 7.20 (t, J=7.6 Hz, 1H), 7.06 (t, J=7.5 Hz, 1H), 6.92 (s, 1H), 4.99-4.39 (m, 2H), 4.06-3.96 (m, 2H), 2.72-2.62 (m, 2H), 2.61-2.53 (m, 1H), 0.93-0.83 (m, 4H).

Example 7

5-(4-ethyl-6-fluoro-1H-indole-2-carbonyl)-4H,5H,6H,7H-[1,3]thiazolo[5,4-c]pyridin-2-amine

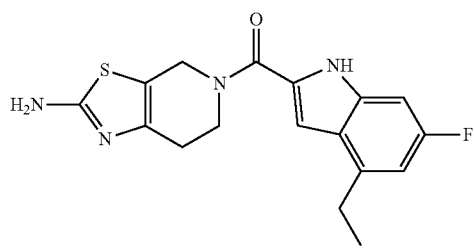 [SMILES: CCc1cc(F)cc2[nH]c(C(=O)N3CCc4nc(N)sc4C3)cc12]

Rt (Method D) 3.12 mins, m/z 345 [M+H]⁺.

1H NMR (400 MHz, DMSO-d6) δ 11.67 (s, 1H), 7.02-6.92 (m, 2H), 6.91-6.80 (m, 2H), 6.80-6.73 (m, 1H), 5.11-4.41 (m, 2H), 4.23-3.72 (m, 2H), 2.90 (q, J=7.4 Hz, 2H), 2.76-2.57 (m, 2H), 1.28 (t, J=7.5 Hz, 3H).

Example 8

5-(4-ethyl-7-fluoro-1H-indole-2-carbonyl)-4H,5H,6H,7H-[1,3]thiazolo[5,4-c]pyridin-2-amine

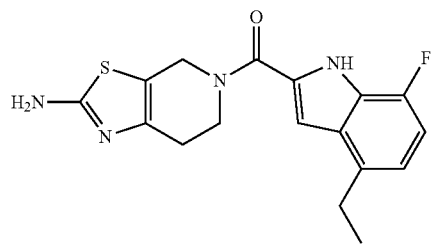 [SMILES: CCc1ccc(F)c2[nH]c(C(=O)N3CCc4nc(N)sc4C3)cc12]

Rt (Method D) 3.11 mins, m/z 345 [M+H]⁺.

Example 9

(2-{2-amino-4H,5H,6H,7H-[1,3]thiazolo[5,4-c]pyridine-5-carbonyl}-1H-indol-4-yl)methanol

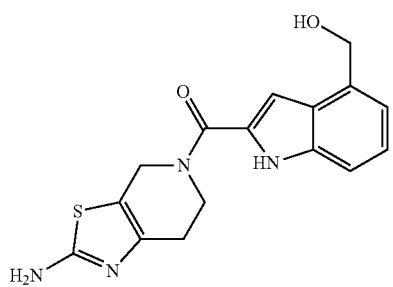 [SMILES: Nc1nc2c(s1)CN(C(=O)c1cc3c(CO)cccc3[nH]1)CC2]

Rt (Method D) 2.33 mins, m/z 329 [M+H]⁺.

Example 10

1-(2-{2-amino-4H,5H,6H,7H-[1,3]thiazolo[5,4-c]pyridine-5-carbonyl}-1H-indol-4-yl)ethan-1-ol

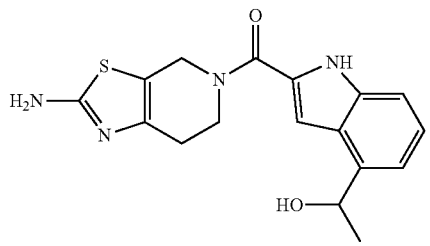 [SMILES: CC(O)c1cccc2[nH]c(C(=O)N3CCc4nc(N)sc4C3)cc12]

Rt (Method D) 2.42 mins, m/z 343 [M+H]⁺.

Example 11

2-(2-{2-amino-4H,5H,6H,7H-[1,3]thiazolo[5,4-c]pyridine-5-carbonyl}-1H-indol-4-yl)propan-2-ol

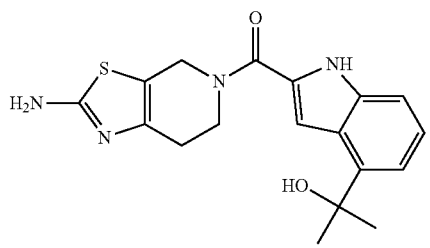 [SMILES: CC(C)(O)c1cccc2[nH]c(C(=O)N3CCc4nc(N)sc4C3)cc12]

Rt (Method D) 2.55 mins, m/z 357 [M+H]⁺.

1H NMR (400 MHz, DMSO-d6) δ 11.58 (s, 1H), 7.35-7.24 (m, 1H), 7.19-7.03 (m, 3H), 6.86 (s, 2H), 5.07 (s, 1H), 4.92-4.54 (m, 2H), 4.23-3.72 (m, 2H), 2.74-2.56 (m, 2H), 1.59 (s, 6H).

Example 12

5-[4-(propan-2-yl)-1H-indole-2-carbonyl]-4H,5H,6H,7H-[1,3]thiazolo[5,4-c]pyridin-2-amine

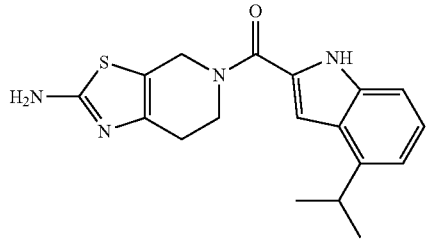 [SMILES: CC(C)c1cccc2[nH]c(C(=O)N3CCc4nc(N)sc4C3)cc12]

Rt (Method D) 3.17 mins, m/z 341 [M+H]⁺.

Example 13

5-(4-ethenyl-1H-indole-2-carbonyl)-4H,5H,6H,7H-[1,3]thiazolo[5,4-c]pyridin-2-amine

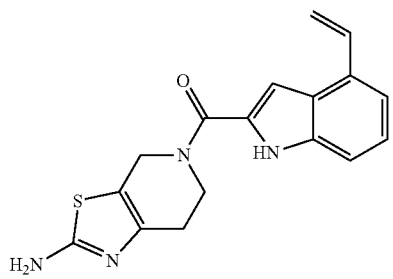 [SMILES: C=Cc1cccc2[nH]c(C(=O)N3CCc4nc(N)sc4C3)cc12]

Rt (Method D) 2.98 mins, m/z 325 [M+H]⁺.

Example 14

5-(4-ethynyl-1H-indole-2-carbonyl)-4H,5H,6H,7H-[1,3]thiazolo[5,4-c]pyridin-2-amine

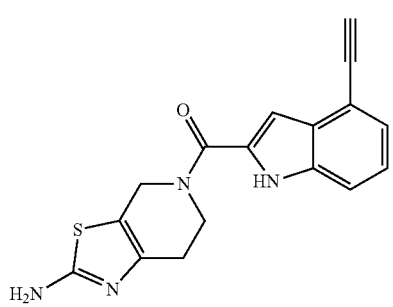 [SMILES: C#Cc1cccc2[nH]c(C(=O)N3CCc4nc(N)sc4C3)cc12]

Rt (Method D) 2.89 mins, m/z 323 [M+H]⁺.

Example 15

1-(2-{2-amino-4H,5H,6H,7H-[1,3]thiazolo[5,4-c]pyridine-5-carbonyl}-6-fluoro-1H-indol-4-yl)ethan-1-ol

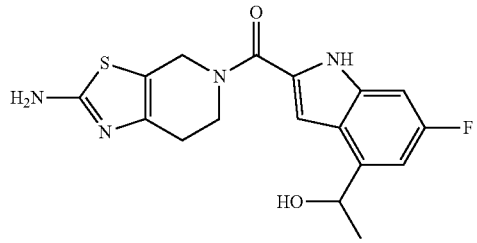 [SMILES: CC(O)c1cc(F)cc2[nH]c(C(=O)N3CCc4nc(N)sc4C3)cc12]

Rt (Method D) 2.55 mins, m/z 361 [M+H]⁺.

Example 16

1-(2-{2-amino-4H,5H,6H,7H-[1,3]thiazolo[5,4-c]pyridine-5-carbonyl}-7-fluoro-1H-indol-4-yl)ethan-1-ol

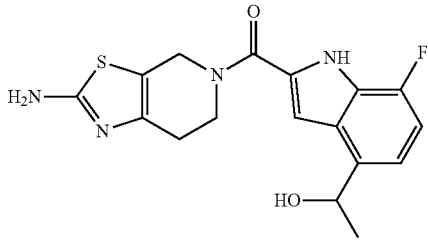 [SMILES: CC(O)c1ccc(F)c2[nH]c(C(=O)N3CCc4nc(N)sc4C3)cc12]

Rt (Method D) 2.5 mins, m/z 361 [M+H]⁺.

Example 17

2-{2-amino-4H,5H,6H,7H-[1,3]thiazolo[5,4-c]pyridine-5-carbonyl}-1H-indole-6-carbonitrile

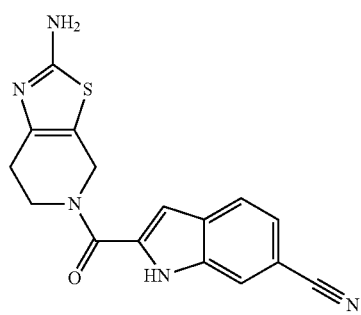 [SMILES: N#Cc1ccc2cc(C(=O)N3CCc4nc(N)sc4C3)[nH]c2c1]

Rt (Method D) 2.65 mins, m/z 324 [M+H]⁺.

Example 18

[5-(1H-indole-2-carbonyl)-4H,5H,6H,7H-[1,3]thiazolo[5,4-c]pyridin-2-yl]methanamine

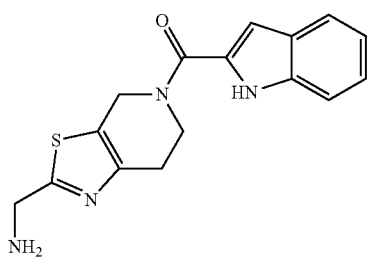 [SMILES: NCc1nc2c(s1)CN(C(=O)c1cc3ccccc3[nH]1)CC2]

Rt (Method D) 2.64 mins, m/z 313 [M+H]⁺.
1H NMR (400 MHz, DMSO-d6) δ 11.64 (s, 1H), 7.64 (d, J=7.9 Hz, 1H), 7.43 (d, J=8.1 Hz, 1H), 7.25-7.16 (m, 1H), 7.10-7.03 (m, 1H), 6.96-6.90 (m, 1H), 5.27-4.66 (m, 2H), 4.15-3.97 (m, 2H), 3.97-3.88 (m, 2H), 2.99-2.79 (m, 2H), 2.48-2.23 (m, 2H).

Example 19

N-[5-(1H-indole-2-carbonyl)-4H,5H,6H,7H-[1,3]thiazolo[5,4-c]pyridin-2-yl]-3-methoxypropanamide

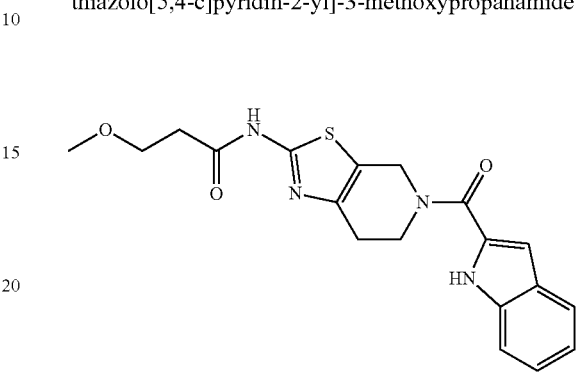

Rt (Method B) 2.99 mins, m/z 385 [M+H]⁺.
1H NMR (400 MHz, DMSO-d6) δ 12.05 (s, 1H), 11.64 (s, 1H), 7.64 (d, J=7.9 Hz, 1H), 7.43 (d, J=8.1 Hz, 1H), 7.20 (t, J=7.6 Hz, 1H), 7.06 (t, J=7.5 Hz, 1H), 6.93 (s, 1H), 4.91 (s, 2H), 4.05 (s, 2H), 3.62 (t, J=6.1 Hz, 2H), 3.22 (d, J=1.3 Hz, 3H), 2.83 (s, 2H), 2.65 (t, J=6.0 Hz, 2H).

Example 20

N-[5-(1H-indole-2-carbonyl)-4H,5H,6H,7H-[1,3]thiazolo[5,4-c]pyridin-2-yl]-2-(oxan-4-yl)acetamide

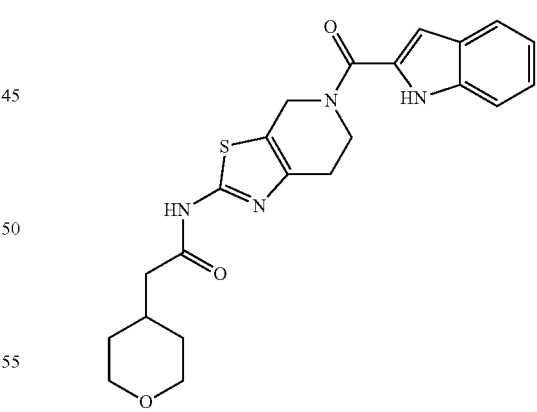

Rt (Method A) 3.08 mins, m/z 425 [M+H]⁺.
1H NMR (400 MHz, DMSO-d6) δ 12.03 (s, 1H), 11.64 (s, 1H), 7.64 (d, J=8.0 Hz, 1H), 7.43 (d, J=8.3 Hz, 1H), 7.20 (t, J=7.6 Hz, 1H), 7.06 (t, J=7.5 Hz, 1H), 6.93 (s, 1H), 5.12-4.66 (m, 2H), 4.16-3.96 (m, 2H), 3.89-3.74 (m, 2H), 3.30-3.22 (m, 2H), 2.94-2.74 (m, 2H), 2.35 (d, J=7.1 Hz, 2H), 2.05-1.88 (m, 1H), 1.54 (d, J=12.2 Hz, 2H), 1.29-1.15 (m, 3H).

Example 21—Intentionally Left Blank

Example 22

5-(1H-indole-2-carbonyl)-N-(1,1,1-trifluoropropan-2-yl)-4H,5H,6H,7H-[1,3]thiazolo[5,4-c]pyridin-2-amine

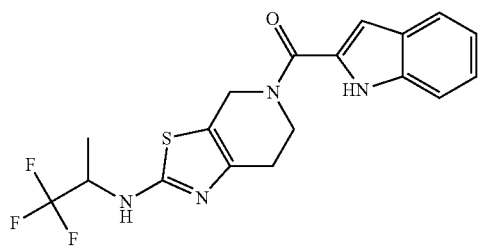 [SMILES: CC(Nc1nc2c(s1)CN(C(=O)c1cc3ccccc3[nH]1)CC2)C(F)(F)F]

Rt (Method A) 3.4 mins, m/z 395 [M+H]⁺.

1H NMR (400 MHz, DMSO-d6) δ 11.63 (s, 1H), 8.01 (d, J=8.7 Hz, 1H), 7.62 (d, J=8.0 Hz, 1H), 7.42 (d, J=8.4 Hz, 1H), 7.23-7.17 (m, 1H), 7.10-7.02 (m, 1H), 6.89 (d, J=1.4 Hz, 1H), 4.97-4.51 (m, 3H), 4.09-3.91 (m, 2H), 2.78-2.62 (m, 2H), 1.29 (d, J=6.9 Hz, 3H).

Example 23

5-(1H-indole-2-carbonyl)-N-[(4-methylmorpholin-2-yl)methyl]-4H,5H,6H,7H-[1,3]thiazolo[5,4-c]pyridin-2-amine

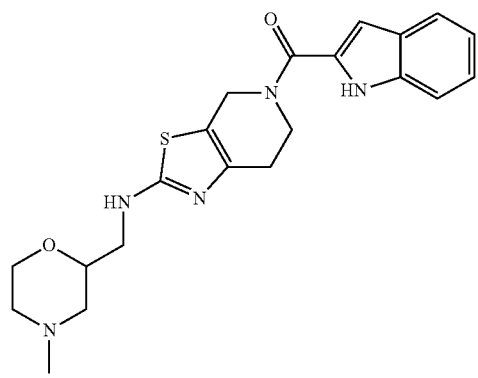 [SMILES: CN1CCOC(CNc2nc3c(s2)CN(C(=O)c2cc4ccccc4[nH]2)CC3)C1]

Rt (Method A) 2.95 mins, m/z 412 [M+H]⁺.

1H NMR (400 MHz, DMSO-d6) δ 11.63 (s, 1H), 7.62 (d, J=8.1 Hz, 1H), 7.58 (t, J=5.8 Hz, 1H), 7.42 (d, J=8.3 Hz, 1H), 7.19 (dd, J=7.4 Hz, 1H), 7.05 (dd, J=7.4 Hz, 1H), 6.94-6.84 (m, 1H), 5.12-4.33 (m, 2H), 4.12-3.87 (m, 2H), 3.82-3.71 (m, 1H), 3.64-3.55 (m, 1H), 3.47 (td, J=11.2, 2.6 Hz, 1H), 3.24 (t, J=5.8 Hz, 2H), 2.74-2.61 (m, 3H), 2.59-2.54 (m, 1H), 2.16 (s, 3H), 1.95 (td, J=11.3, 3.3 Hz, 1H), 1.70 (t, J=10.6 Hz, 1H).

Example 24

N-[5-(1H-indole-2-carbonyl)-4H,5H,6H,7H-[1,3]thiazolo[5,4-c]pyridin-2-yl]methanesulfonamide

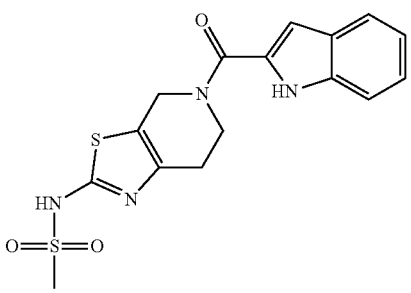 [SMILES: CS(=O)(=O)Nc1nc2c(s1)CN(C(=O)c1cc3ccccc3[nH]1)CC2]

Rt (Method A) 2.37 mins, m/z 377 [M+H]⁺.

1H NMR (400 MHz, DMSO-d6) δ 12.48 (s, 1H), 11.64 (s, 1H), 7.63 (d, J=7.9 Hz, 1H), 7.43 (d, J=8.2 Hz, 1H), 7.24-7.17 (m, 1H), 7.09-7.02 (m, 1H), 6.96-6.89 (m, 1H), 4.88-4.55 (m, 2H), 4.13-3.91 (m, 2H), 2.87 (s, 3H), 2.75-2.62 (m, 2H).

Example 25

6-(1H-indole-2-carbonyl)-4H,5H,6H,7H,8H-[1,3]thiazolo[4,5-d]azepin-2-amine

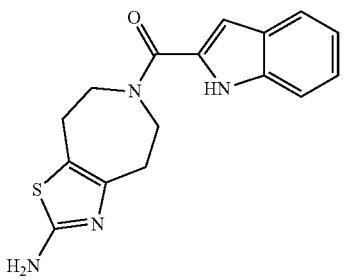 [SMILES: Nc1nc2c(s1)CCN(C(=O)c1cc3ccccc3[nH]1)CC2]

Rt (Method A) 2.88 mins, m/z 313 [M+H]⁺.

1H NMR (400 MHz, DMSO-d6) δ 11.57 (s, 1H), 7.62 (d, J=8.0 Hz, 1H), 7.42 (d, J=8.2 Hz, 1H), 7.18 (ddd, J=8.1, 6.8, 1.1 Hz, 1H), 7.04 (dd, J=7.5 Hz, 1H), 6.94-6.77 (m, 1H), 6.62 (s, 2H), 4.18-3.74 (m, 4H), 2.99-2.71 (m, 4H).

Example 26

N-[5-(1H-indole-2-carbonyl)-4H,5H,6H,7H-[1,3]thiazolo[5,4-c]pyridin-2-yl]-3,3-dimethylbutanamide

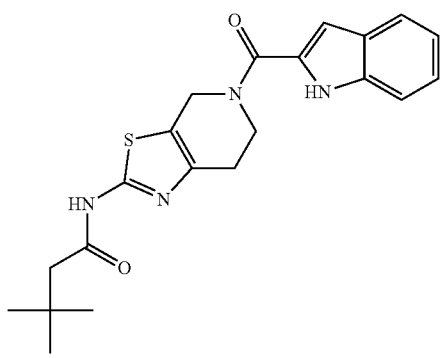 [SMILES: CC(C)(C)CC(=O)Nc1nc2c(s1)CN(C(=O)c1cc3ccccc3[nH]1)CC2]

Rt (Method A) 3.5 mins, m/z 397 [M+H]+.

1H NMR (400 MHz, DMSO-d6) δ 11.95 (s, 1H), 11.64 (s, 1H), 7.64 (d, J=8.0 Hz, 1H), 7.43 (d, J=8.2 Hz, 1H), 7.20 (dd, J=7.6 Hz, 1H), 7.06 (dd, J=7.5 Hz, 1H), 6.93 (s, 1H), 5.16-4.65 (m, 2H), 4.11-3.99 (m, 2H), 2.89-2.77 (m, 2H), 2.29 (s, 2H), 0.99 (s, 9H).

Example 27

[1-({[5-(1H-indole-2-carbonyl)-4H,5H,6H,7H-[1,3]thiazolo[5,4-c]pyridin-2-yl]amino}methyl)cyclobutyl]methanol

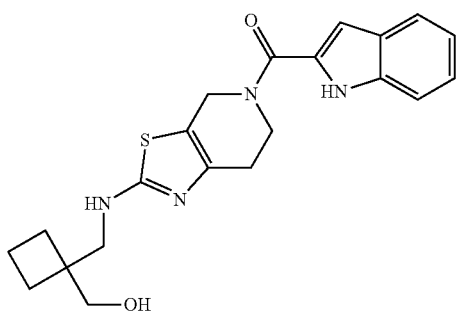 [SMILES: O=C(c1cc2ccccc2[nH]1)N1CCc2nc(NCC3(CO)CCC3)sc2C1]

Rt (Method A) 3.22 mins, m/z 397 [M+H]+.

1H NMR (400 MHz, DMSO-d6) δ 11.62 (s, 1H), 7.62 (d, J=7.9 Hz, 1H), 7.52 (t, J=5.9 Hz, 1H), 7.42 (d, J=8.1 Hz, 1H), 7.19 (ddd, J=8.3, 6.9, 1.2 Hz, 1H), 7.05 (ddd, J=8.1, 7.1, 1.0 Hz, 1H), 6.89 (d, J=1.5 Hz, 1H), 4.80 (t, J=5.8 Hz, 1H), 4.76-4.58 (m, 2H), 4.14-3.84 (m, 2H), 3.33-3.23 (m, 4H), 2.72-2.57 (m, 2H), 1.84-1.64 (m, 6H).

Example 28

1-[5-(1H-indole-2-carbonyl)-4H,5H,6H,7H-[1,3]thiazolo[5,4-c]pyridin-2-yl]-3-methylurea

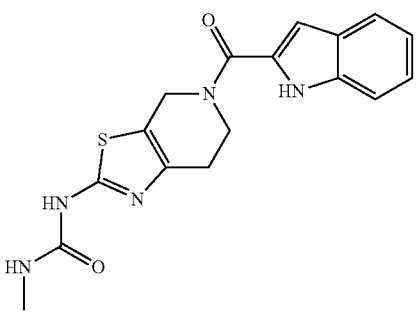 [SMILES: CNC(=O)Nc1nc2c(s1)CN(C(=O)c1cc3ccccc3[nH]1)CC2]

Rt (Method B) 2.82 mins, m/z 356 [M+H]+.

1H NMR (400 MHz, DMSO-d6) δ 11.63 (d, J=2.1 Hz, 1H), 10.40 (s, 1H), 7.63 (d, J=7.9 Hz, 1H), 7.43 (d, J=8.1 Hz, 1H), 7.26-7.15 (m, 1H), 7.06 (t, J=7.4 Hz, 1H), 6.92 (d, J=2.0 Hz, 1H), 6.52-6.34 (m, 1H), 4.85 (s, 2H), 4.02 (s, 2H), 2.89-2.62 (m, 5H).

Example 29—Intentionally Left Blank

Example 30—Intentionally Left Blank

Example 31

[5-(1H-indole-2-carbonyl)-4H,5H,6H,7H-[1,3]thiazolo[5,4-c]pyridin-2-yl]methanol

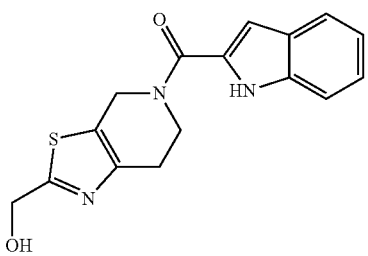 [SMILES: O=C(c1cc2ccccc2[nH]1)N1CCc2nc(CO)sc2C1]

Rt (Method D) 2.72 mins, m/z 314 [M+H]+.

1H NMR (400 MHz, DMSO-d6) δ 11.65 (s, 1H), 7.64 (d, J=8.0 Hz, 1H), 7.43 (d, J=8.1 Hz, 1H), 7.26-7.17 (m, 1H), 7.11-7.03 (m, 1H), 6.94 (s, 1H), 6.15-5.94 (m, 1H), 5.28-4.76 (m, 2H), 4.67 (s, 2H), 4.18-3.94 (m, 2H), 3.00-2.80 (m, 2H).

Example 32

Ethyl({[5-(1H-indole-2-carbonyl)-4H,5H,6H,7H-[1,3]thiazolo[5,4-c]pyridin-2-yl]methyl})amine

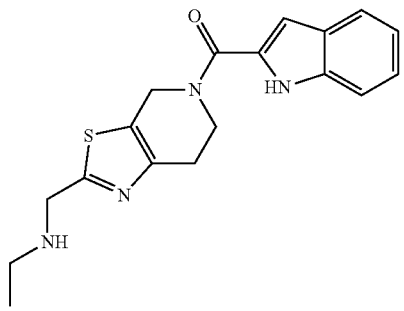 [SMILES: CCNCc1nc2c(s1)CN(C(=O)c1cc3ccccc3[nH]1)CC2]

Rt (Method D) 2.92 mins, m/z 341 [M+H]+.

1H NMR (400 MHz, DMSO-d6) δ 11.65 (s, 1H), 7.64 (d, J=8.0 Hz, 1H), 7.43 (d, J=8.2 Hz, 1H), 7.26-7.18 (m, 1H), 7.10-7.02 (m, 1H), 6.96-6.90 (m, 1H), 5.27-4.70 (m, 2H), 4.20-3.96 (m, 2H), 3.90 (s, 2H), 3.00-2.80 (m, 2H), 2.59 (q, J=7.1 Hz, 2H), 1.02 (t, J=7.0 Hz, 3H) (NH coincides with DMSO or water signal).

Example 33

(+/−)-trans-5-(1H-indole-2-carbonyl)-N-{[(1R,2S,4S)-7-oxabicyclo[2.2.1]heptan-2-yl]methyl}-4H,5H,6H,7H-[1,3]thiazolo[5,4-c]pyridin-2-amine

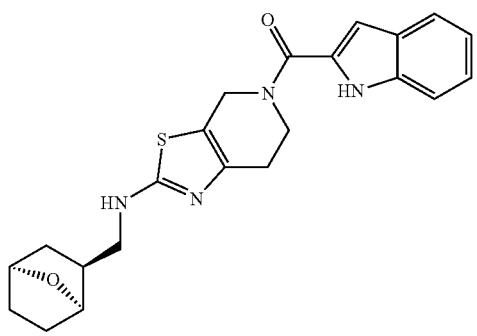 [SMILES: O=C(c1cc2ccccc2[nH]1)N1CCc2nc(NC[C@@H]3C[C@@H]4CC[C@H]3O4)sc2C1]

Rt (Method A) 3.14 mins, m/z 409 [M+H]+.

1H NMR (400 MHz, DMSO-d6) δ 11.63 (s, 1H), 7.62 (d, J=8.0 Hz, 1H), 7.51 (t, J=5.0 Hz, 1H), 7.42 (d, J=8.3 Hz, 1H), 7.19 (ddd, J=8.3, 7.0, 1.1 Hz, 1H), 7.06 (dd, J=7.4 Hz, 1H), 6.89 (d, J=2.1 Hz, 1H), 5.08-4.52 (m, 2H), 4.50-4.38 (m, 2H), 4.10-3.90 (m, 2H), 3.30-3.26 (m, 1H), 3.19-3.06 (m, 1H), 2.73-2.59 (m, 2H), 2.32-2.21 (m, 1H), 1.81 (tdd, J=11.4, 5.4, 2.6 Hz, 1H), 1.76-1.68 (m, 1H), 1.62-1.50 (m, 1H), 1.50-1.35 (m, 2H), 0.97 (dd, J=11.8, 5.2 Hz, 1H).

Example 34

(+/−)-cis-5-(1H-indole-2-carbonyl)-N-{1[(1R,2R,4S)-7-oxabicyclo[2.2.1]heptan-2-yl]methyl}-4H,5H,6H,7H-[1,3]thiazolo[5,4-c]pyridin-2-amine

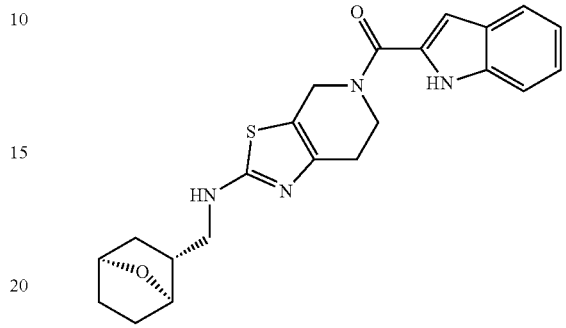

Rt (Method A) 3.21 mins, m/z 409 [M+H]+.

1H NMR (400 MHz, DMSO-d6) δ 11.62 (s, 1H), 7.74-7.56 (m, 2H), 7.42 (d, J=8.2 Hz, 1H), 7.19 (ddd, J=8.2, 6.9, 1.2 Hz, 1H), 7.05 (dd, J=7.5 Hz, 1H), 6.89 (d, J=1.9 Hz, 1H), 5.03-4.52 (m, 2H), 4.47 (t, J=4.9 Hz, 1H), 4.29 (d, J=5.0 Hz, 1H), 4.16-3.82 (m, 2H), 3.00 (ddd, J=14.3, 9.0, 5.5 Hz, 1H), 2.90 (dt, J=12.8, 6.1 Hz, 1H), 2.76-2.58 (m, 2H), 2.06-1.96 (m, 1H), 1.62-1.47 (m, 3H), 1.43-1.34 (m, 2H), 1.18-1.10 (m, 1H).

Example 35

5-(1H-indole-2-carbonyl)-N-[(oxan-2-yl)methyl]-4H,5H,6H,7H-[1,3]thiazolo[5,4-c]pyridin-2-amine

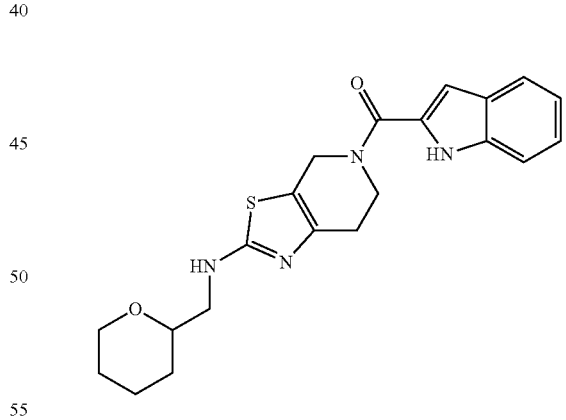

Rt (Method A) 3.32 mins, m/z 397 [M+H]+.

1H NMR (400 MHz, DMSO-d6) δ 11.62 (s, 1H), 7.62 (d, J=8.1 Hz, 1H), 7.55 (t, J=5.7 Hz, 1H), 7.42 (d, J=8.1 Hz, 1H), 7.23-7.16 (m, 1H), 7.09-7.02 (m, 1H), 6.89 (d, J=2.0 Hz, 1H), 4.95-4.54 (m, 2H), 4.08-3.91 (m, 2H), 3.91-3.83 (m, 1H), 3.45-3.37 (m, 2H), 3.27-3.11 (m, 2H), 2.70-2.62 (m, 2H), 1.81-1.71 (m, 1H), 1.64-1.53 (m, 1H), 1.49-1.37 (m, 3H), 1.21-1.09 (m, 1H).

Example 36

5-(1H-indole-2-carbonyl)-N-[2-(morpholin-4-yl)ethyl]-4H,5H,6H,7H-[1,3]thiazolo[5,4-c]pyridin-2-amine

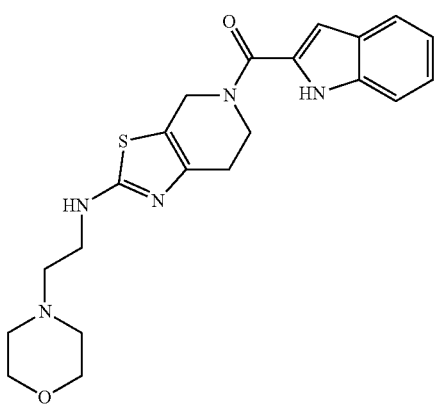 [SMILES: O=C(c1cc2ccccc2[nH]1)N1CCc2nc(NCCN3CCOCC3)sc2C1]

Rt (Method A) 2.96 mins, m/z 412 [M+H]⁺.

1H NMR (400 MHz, DMSO-d6) δ 11.63 (s, 1H), 7.62 (d, J=8.1 Hz, 1H), 7.46-7.37 (m, 2H), 7.25-7.16 (m, 1H), 7.09-7.02 (m, 1H), 6.89 (d, J=1.6 Hz, 1H), 4.97-4.50 (m, 2H), 4.08-3.89 (m, 2H), 3.64-3.51 (m, 4H), 3.32-3.26 (m, 2H), 2.72-2.62 (m, 2H), 2.46 (t, J=6.6 Hz, 2H), 2.42-2.34 (m, 4H).

Example 37

Propan-2-yl (2S)-2-[({1-({[5-(4,6-difluoro-1H-indole-2-carbonyl)-4H,5H,6H,7H-[1,3]thiazolo[5,4-c]pyridin-2-yl]amino}methyl)cyclopropyl]methoxy}(phenoxy)phosphoryl)amino]propanoate

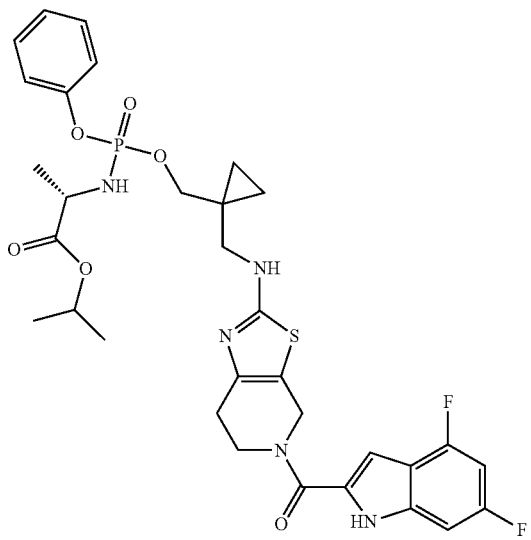 [SMILES: CC(C)OC(=O)[C@H](C)NP(=O)(OCC1(CNc2nc3c(s2)CN(C(=O)c2cc4c(F)cc(F)cc4[nH]2)CC3)CC1)Oc1ccccc1]

Rt (Method A) 3.78 mins, m/z 688 [M+H]⁺.

1H NMR (400 MHz, DMSO-d6) δ 12.06 (s, 1H), 7.53 (m, 1H), 7.33 (m, 2H), 7.15 (m, 3H), 7.04 (m, 1H), 6.99-6.86 (m, 2H), 5.84 (m, 1H), 4.84 (m, 3H), 4.02-3.88 (m, 3H), 3.88-3.70 (m, 2H), 3.30-3.16 (m, 2H), 2.67 (m, 2H), 1.23-1.10 (m, 9H), 0.61-0.46 (m, 4H)

Example 38

N-{[5-(1H-indole-2-carbonyl)-4H,5H,6H,7H-[1,3]thiazolo[5,4-c]pyridin-2-yl]methyl}cyclopropanamine

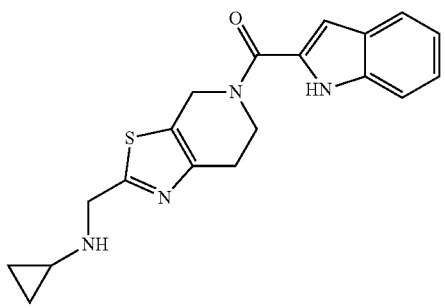 [SMILES: O=C(c1cc2ccccc2[nH]1)N1CCc2nc(CNC3CC3)sc2C1]

Rt (Method D) 3.08 mins, m/z 353 [M+H]⁺.

1H NMR (400 MHz, DMSO-d6) δ 11.65 (s, 1H), 7.64 (d, J=7.9 Hz, 1H), 7.43 (d, J=8.3 Hz, 1H), 7.24-7.16 (m, 1H), 7.09-7.03 (m, 1H), 6.96-6.90 (m, 1H), 5.20-4.79 (m, 2H), 4.16-3.99 (m, 2H), 3.99-3.91 (m, 2H), 3.16-3.03 (m, 1H), 2.99-2.82 (m, 2H), 2.22-2.13 (m, 1H), 0.41-0.33 (m, 2H), 0.32-0.24 (m, 2H).

Example 39

2-{2-[(morpholin-4-yl)methyl]-4H,5H,6H,7H-[1,3]thiazolo[5,4-c]pyridine-5-carbonyl}-1H-indole

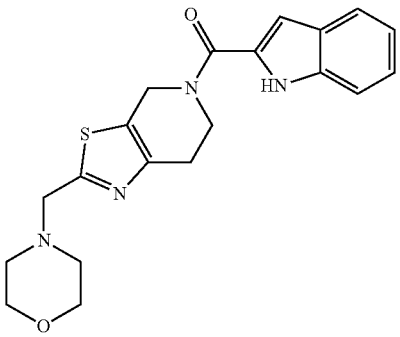 [SMILES: O=C(c1cc2ccccc2[nH]1)N1CCc2nc(CN3CCOCC3)sc2C1]

Rt (Method D) 2.96 mins, m/z 383 [M+H]⁺.

1H NMR (400 MHz, DMSO-d6) δ 11.65 (s, 1H), 7.64 (d, J=8.0 Hz, 1H), 7.43 (d, J=8.2 Hz, 1H), 7.24-7.17 (m, 1H), 7.10-7.03 (m, 1H), 6.93 (s, 1H), 5.34-4.61 (m, 2H), 4.18-3.94 (m, 2H), 3.76 (s, 2H), 3.67-3.51 (m, 4H), 3.04-2.80 (m, 2H), 2.50-2.46 (m, 4H).

Example 40

N-{[5-(1H-indole-2-carbonyl)-4H,5H,6H,7H-[1,3]thiazolo[5,4-c]pyridin-2-yl]methyl}oxolan-3-amine

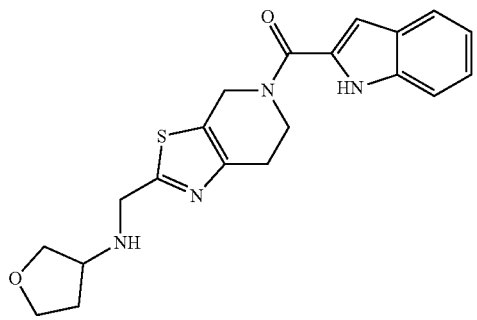 [SMILES: O=C(c1cc2ccccc2[nH]1)N1CCc2nc(CNC3CCOC3)sc2C1]

Rt (Method D) 2.82 mins, m/z 383 [M+H]$^+$.

1H NMR (400 MHz, DMSO-d6) δ 11.65 (s, 1H), 7.64 (d, J=8.0 Hz, 1H), 7.43 (d, J=8.2 Hz, 1H), 7.25-7.17 (m, 1H), 7.10-7.03 (m, 1H), 6.97-6.91 (m, 1H), 5.28-4.54 (m, 2H), 4.18-3.99 (m, 2H), 3.92 (s, 2H), 3.77 (q, J=7.4 Hz, 1H), 3.73-3.59 (m, 2H), 3.43 (dd, J=8.6, 4.1 Hz, 1H), 3.38-3.33 (m, 1H), 3.00-2.74 (m, 3H), 1.99-1.88 (m, 1H), 1.73-1.62 (m, 1H).

Example 41

{1-[({[5-(1H-indole-2-carbonyl)-4H,5H,6H,7H-[1,3]thiazolo[5,4-c]pyridin-2-yl]methyl}amino)methyl]cyclopropyl}methanol

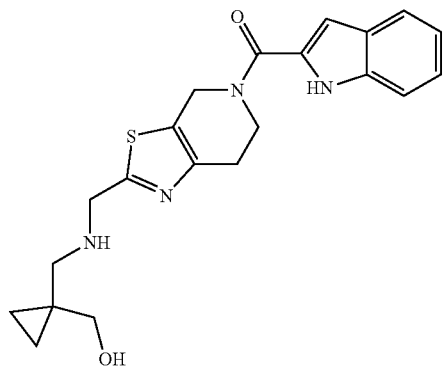 [SMILES: O=C(c1cc2ccccc2[nH]1)N1CCc2nc(CNCC3(CO)CC3)sc2C1]

Rt (Method D) 2.88 mins, m/z 397 [M+H]$^+$.

1H NMR (400 MHz, DMSO-d6) δ 11.64 (s, 1H), 7.64 (d, J=8.0 Hz, 1H), 7.43 (d, J=8.3 Hz, 1H), 7.23-7.17 (m, 1H), 7.09-7.03 (m, 1H), 6.96-6.91 (m, 1H), 5.22-4.79 (m, 2H), 4.65-4.32 (m, 1H), 4.16-3.95 (m, 2H), 3.92 (s, 2H), 3.41-3.34 (m, 2H), 2.99-2.79 (m, 2H), 2.56 (s, 2H), 0.38-0.27 (m, 4H).

Example 42

[1-(hydroxymethyl)-3-{[5-(1H-indole-2-carbonyl)-4H,5H,6H,7H-[1,3]thiazolo[5,4-c]pyridin-2-yl]amino}cyclobutyl]methanol

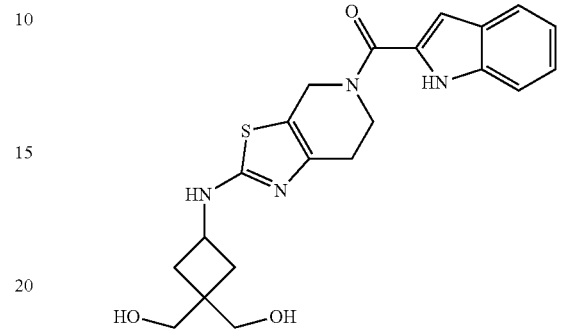

Rt (Method A) 2.8 mins, m/z 413 [M+H]$^+$.

1H NMR (400 MHz, DMSO-d6) δ 11.62 (s, 1H), 7.68 (d, J=7.0 Hz, 1H), 7.62 (d, J=8.0 Hz, 1H), 7.42 (d, J=8.2 Hz, 1H), 7.23-7.16 (m, 1H), 7.09-7.02 (m, 1H), 6.91-6.86 (m, 1H), 5.00-4.54 (m, 3H), 4.50 (t, J=5.3 Hz, 1H), 4.10-3.87 (m, 3H), 3.39 (d, J=5.4 Hz, 2H), 3.30 (d, J=5.3 Hz, 2H), 2.76-2.58 (m, 2H), 2.15-2.04 (m, 2H), 1.77-1.65 (m, 2H).

Example 43

2-{[5-(1H-indole-2-carbonyl)-4H,5H,6H,7H-[1,3]thiazolo[5,4-c]pyridin-2-yl]amino}propane-1,3-diol

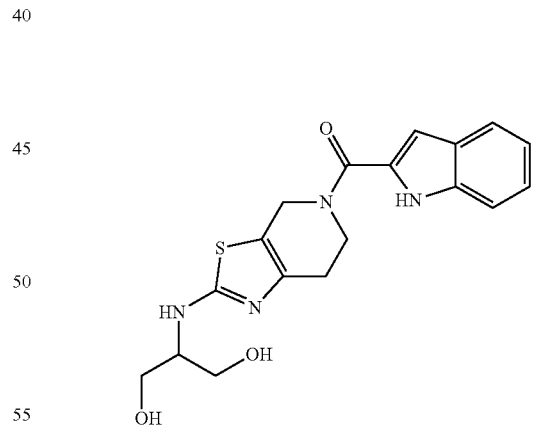

Rt (Method D) 2.61 mins, m/z 373 [M+H]$^+$.

1H NMR (400 MHz, DMSO-d6) δ 11.63 (s, 1H), 7.63 (d, J=8.0 Hz, 1H), 7.43 (d, J=8.2 Hz, 1H), 7.30 (d, J=7.7 Hz, 1H), 7.24-7.16 (m, 1H), 7.10-7.02 (m, 1H), 6.93-6.85 (m, 1H), 5.10-4.43 (m, 4H), 4.12-3.84 (m, 3H), 3.71-3.60 (m, 1H), 3.49 (t, J=5.3 Hz, 4H), 2.75-2.60 (m, 2H).

Example 44

3-({[5-(1H-indole-2-carbonyl)-4H,5H,6H,7H-[1,3]thiazolo[5,4-c]pyridin-2-yl]amino}methyl)oxetan-3-ol

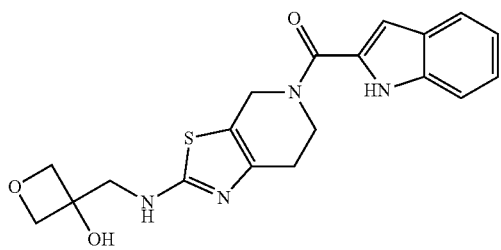 [SMILES: O=C(c1cc2ccccc2[nH]1)N1CCc2nc(NCC3(O)COC3)sc2C1]

Rt (Method A) 2.82 mins, m/z 385 [M+H]+.

1H NMR (400 MHz, DMSO-d6) δ 11.63 (s, 1H), 7.67 (t, J=5.7 Hz, 1H), 7.63 (d, J=8.0 Hz, 1H), 7.43 (d, J=8.2 Hz, 1H), 7.24-7.15 (m, 1H), 7.10-7.01 (m, 1H), 6.89 (s, 1H), 6.01 (s, 1H), 5.14-4.53 (m, 2H), 4.41 (q, J=6.4 Hz, 4H), 4.14-3.83 (m, 2H), 3.55 (d, J=5.7 Hz, 2H), 2.77-2.59 (m, 2H).

Example 45

(1s,4s)-4-{[5-(1H-indole-2-carbonyl)-4H,5H,6H,7H-[1,3]thiazolo[5,4-c]pyridin-2-yl]amino}cyclohexan-1-ol

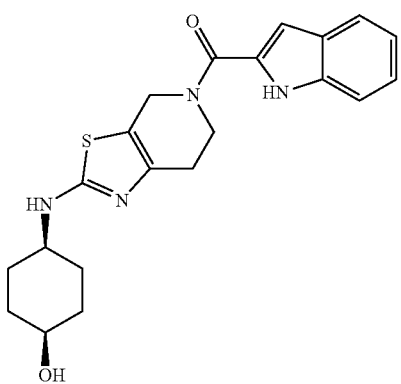 [SMILES: O=C(c1cc2ccccc2[nH]1)N1CCc2nc(N[C@H]3CC[C@@H](O)CC3)sc2C1]

Rt (Method B) 2.43 mins, m/z 397 [M+H]+.

1H NMR (400 MHz, DMSO-d6) δ 11.62 (s, 1H), 7.62 (d, J=8.0 Hz, 1H), 7.48-7.40 (m, 2H), 7.19 (t, J=7.6 Hz, 1H), 7.05 (t, J=7.5 Hz, 1H), 6.88 (d, J=1.5 Hz, 1H), 5.02-4.48 (m, 2H), 4.40 (d, J=2.9 Hz, 1H), 4.07-3.87 (m, 2H), 3.73-3.60 (m, 1H), 3.59-3.46 (m, 1H), 2.74-2.58 (m, 2H), 1.72-1.42 (m, 8H).

Example 46

1-({[5-(1H-indole-2-carbonyl)-4H,5H,6H,7H-[1,3]thiazolo[5,4-c]pyridin-2-yl]amino}methyl)cyclobutan-1-ol

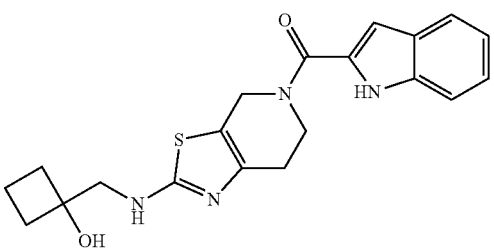 [SMILES: O=C(c1cc2ccccc2[nH]1)N1CCc2nc(NCC3(O)CCC3)sc2C1]

Step 1: To a solution of 1-(aminomethyl)cyclobutan-1-ol (3 g, 29.7 mmol) in THF (100 mL) was added dropwise benzoyl isothiocyanate (3.99 ml, 29.7 mmol). The mixture was stirred at room temperature for 4.5 hours then concentrated under reduced pressure. The yellow solid residue obtained was dissolved in methanol (100 ml) and water (100 ml) and potassium carbonate (4.30 g, 31.1 mmol) was added. The mixture was stirred at room temperature for 16 hours. Silica gel was added and the mixture was concentrated. Purification by flash chromatography (80 g silica, DCM/ammonia in methanol (0-10%) gave the desired product 1-((1-hydroxycyclobutyl)methyl)thiourea (3.49 g, 73% yield).

Step 2: To a suspension of 1-((1-hydroxycyclobutyl)methyl)thiourea (3.49 g, 21.78 mmol) in absolute ethanol (100 ml) was added tert-butyl 3-bromo-4-oxopiperidine-1-carboxylate (6.06 g, 21.78 mmol). Sodium bicarbonate (2.74 g, 32.7 mmol) was added and the mixture warmed to 80° C. After 2 h the mixture was cooled to room temperature and filtered. The filtrate was concentrated to give a light yellow solid. The crude material was dissolved in dichloromethane/methanol, silica gel was added and the solvents were evaporated. Purification by flash column chromatography (silica gel, 0 to 5% methanol in dichloromethane) gave the desired product tert-butyl 2-(((1-hydroxycyclobutyl)methyl)amino)-6,7-dihydrothiazolo[5,4-c]pyridine-5(4H)-carboxylate as a white solid (6.71 g, 91% yield).

Step 3: HCl in dioxane (50 ml, 200 mmol) was added to tert-butyl 2-(((1-hydroxycyclobutyl)methyl)amino)-6,7-dihydrothiazolo[5,4-c]pyridine-5(4H)-carboxylate (5.2 g, 15.32 mmol) and the resulting suspension was stirred at rt for 1 h. The mixture was filtered, the collected solid was washed with diethyl ether and added to a pre-stirred (10 min) solution of 1H-indole-2-carboxylic acid (2.469 g, 15.32 mmol), triethylamine (8.54 ml, 61.3 mmol), aza-HOBt (0.209 g, 1.532 mmol) and EDC (3.08 g, 16.08 mmol) in dichloromethane (80 ml). The mixture was stirred at rt for 19 h. The mixture was washed with sat. aq. Sodium bicarbonate solution and brine. The organic layer was concentrated to dryness, dissolved in ethyl acetate and ethanol and again concentrated to dryness. The residue was dissolved in ethyl acetate and ethanol, silica gel was added and the solvents were evaporated. The product was purified in two batches by flash chromatography to give the desired product as a light yellow solid (4.7 g). The solid was dissolved in ethanol and concentrated to dryness. The yellow solid residue was further purified by trituration from hot ethanol, collected by filtration and dried under vacuum to give the desired product (2-(((1-hydroxycyclobutyl)methyl)amino)-6,7-dihydrothiazolo[5,4-c]pyridin-5(4H)-yl)(1H-indol-2-yl)methanone as a white solid (3.35 g, 57% yield).

Rt (Method B) 2.5 mins, m/z 383 [M+H]⁺.

1H NMR (400 MHz, DMSO-d6) δ 11.62 (s, 1H), 7.62 (d, J=8.0 Hz, 1H), 7.47-7.39 (m, 2H), 7.23-7.16 (m, 1H), 7.09-7.02 (m, 1H), 6.89 (d, J=1.5 Hz, 1H), 5.28 (s, 1H), 4.73 (s, 2H), 4.09-3.82 (m, 2H), 2.77-2.56 (m, 2H), 2.05-1.85 (m, 4H), 1.62 (q, J=9.7 Hz, 1H), 1.46 (h, J=9.1 Hz, 1H).

Example 47

(1S,2S)-2-{[5-(1H-indole-2-carbonyl)-4H,5H,6H,7H-[1,3]thiazolo[5,4-c]pyridin-2-yl]amino}cyclohexan-1-ol

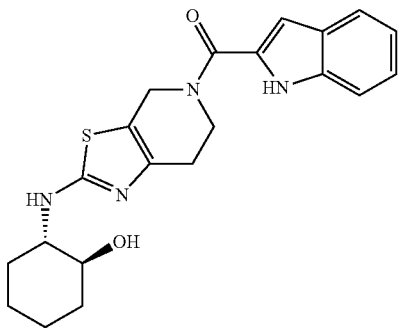 [SMILES: O=C(c1cc2ccccc2[nH]1)N1CCc2nc(N[C@H]3CCCC[C@@H]3O)sc2C1]

Rt (Method A) 2.51 mins, m/z 397 [M+H]⁺.

1H NMR (400 MHz, DMSO-d6) δ 11.64 (s, 1H), 7.63 (d, J=8.0 Hz, 1H), 7.46-7.34 (m, 2H), 7.20 (t, J=7.6 Hz, 1H), 7.06 (t, J=7.5 Hz, 1H), 6.89 (d, J=1.5 Hz, 1H), 5.04-4.42 (m, 3H), 4.07-3.88 (m, 2H), 3.33-3.24 (m, 2H), 2.75-2.59 (m, 2H), 2.04-1.94 (m, 1H), 1.89-1.79 (m, 1H), 1.67-1.50 (m, 2H), 1.31-1.07 (m, 4H).

Example 48

(1-{[5-(1H-indole-2-carbonyl)-4H,5H,6H,7H-[1,3]thiazolo[5,4-c]pyridin-2-yl]amino}cyclobutyl)methanol

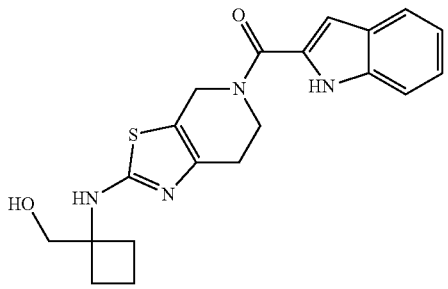 [SMILES: O=C(c1cc2ccccc2[nH]1)N1CCc2nc(NC3(CO)CCC3)sc2C1]

Rt (Method A) 3.14 mins, m/z 383 [M+H]⁺.

1H NMR (400 MHz, DMSO-d6) δ 11.62 (s, 1H), 7.65-7.57 (m, 2H), 7.42 (d, J=8.2 Hz, 1H), 7.23-7.16 (m, 1H), 7.09-7.02 (m, 1H), 6.89 (d, J=1.5 Hz, 1H), 4.96 (t, J=5.6 Hz, 1H), 4.91-4.58 (m, 2H), 4.02-3.93 (m, 2H), 3.62 (d, J=5.6 Hz, 2H), 2.73-2.58 (m, 2H), 2.17-2.03 (m, 4H), 1.87-1.63 (m, 2H).

Example 49

5-(1H-indole-2-carbonyl)-N-[(3-methyloxolan-3-yl)methyl]-4H,5H,6H,7H-[1,3]thiazolo[5,4-c]pyridin-2-amine

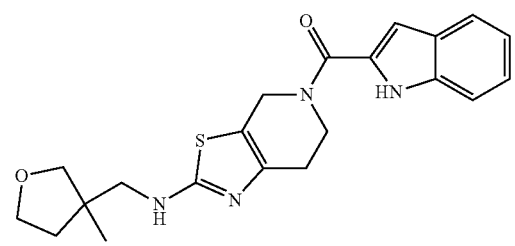 [SMILES: CC1(CNc2nc3c(s2)CN(C(=O)c2cc4ccccc4[nH]2)CC3)CCOC1]

Rt (Method A) 3.16 mins, m/z 397 [M+H]⁺.

1H NMR (400 MHz, DMSO-d6) δ 11.62 (s, 1H), 7.62 (d, J=8.0 Hz, 1H), 7.54 (t, J=5.8 Hz, 1H), 7.42 (d, J=8.2 Hz, 1H), 7.19 (t, J=7.6 Hz, 1H), 7.05 (t, J=7.4 Hz, 1H), 6.92-6.86 (m, 1H), 4.98-4.53 (m, 2H), 4.10-3.89 (m, 2H), 3.80-3.67 (m, 2H), 3.55 (d, J=8.4 Hz, 1H), 3.30-3.18 (m, 3H), 2.71-2.60 (m, 2H), 1.86-1.76 (m, 1H), 1.61-1.51 (m, 1H), 1.06 (s, 3H).

Examples 50 to 57—Intentionally left blank

Example 58

N'-[5-(1H-indole-2-carbonyl)-4H,5H,6H,7H-[1,3]thiazolo[5,4-c]pyridin-2-yl]acetohydrazide

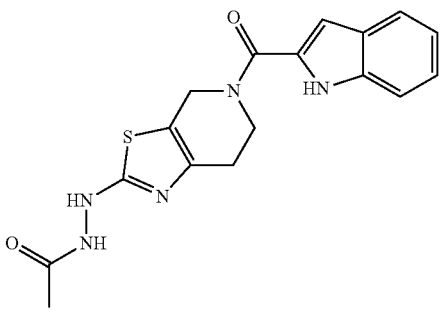 [SMILES: CC(=O)NNc1nc2c(s1)CN(C(=O)c1cc3ccccc3[nH]1)CC2]

Rt (Method A) 2.71 mins, m/z 356 [M+H]⁺.

1H NMR (400 MHz, DMSO-d6) δ 11.63 (s, 1H), 10.08 (s, 1H), 9.19 (s, 1H), 7.63 (d, J=7.9 Hz, 1H), 7.42 (d, J=8.3 Hz, 1H), 7.19 (ddd, J=8.3, 7.0, 1.2 Hz, 1H), 7.06 (dd, J=7.5 Hz, 1H), 6.89 (d, J=2.0 Hz, 1H), 5.11-4.54 (m, 2H), 4.32-3.70 (m, 2H), 2.85-2.67 (m, 2H), 1.87 (s, 3H).

Example 59

[1-({[5-(4,7-difluoro-1H-indole-2-carbonyl)-4H,5H,6H,7H-[1,3]thiazolo[5,4-c]pyridin-2-yl]amino}methyl)cyclopropyl]methanol

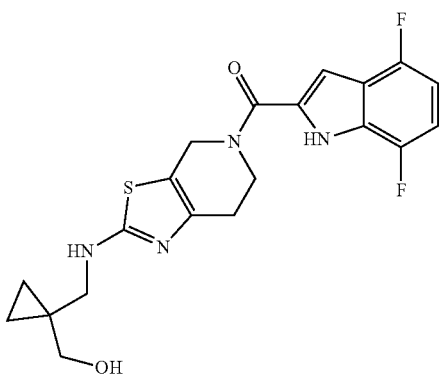 [SMILES: O=C(c1cc2c(F)ccc(F)c2[nH]1)N1CCc2nc(NCC3(CO)CC3)sc2C1]

Rt (Method B) 2.54 mins, m/z 419 [M+H]+.

1H NMR (400 MHz, DMSO-d6) δ 12.47 (s, 1H), 7.51 (s, 1H), 7.06-6.97 (m, 1H), 6.94 (d, J=2.8 Hz, 1H), 6.86-6.75 (m, 1H), 4.66 (s, 3H), 3.92 (t, J=5.7 Hz, 2H), 3.30-3.16 (m, 4H), 2.63 (s, 2H), 0.49-0.27 (m, 4H).

Example 60

[1-({[5-(4-chloro-6-fluoro-1H-indole-2-carbonyl)-4H,5H,6H,7H-[1,3]thiazolo[5,4-c]pyridin-2-yl]amino}methyl)cyclopropyl]methanol

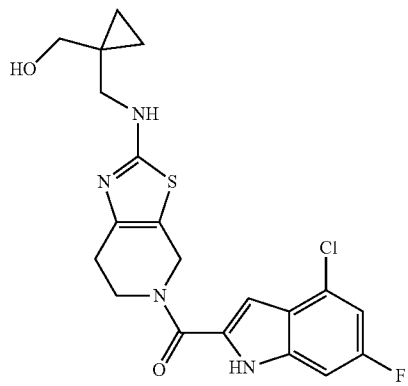 [SMILES: O=C(c1cc2c(Cl)cc(F)cc2[nH]1)N1CCc2nc(NCC3(CO)CC3)sc2C1]

Rt (Method B) 2.70 mins, m/z 435/437 [M+H]+.

1H NMR (400 MHz, DMSO-d6) δ 12.11 (s, 1H), 7.51 (s, 1H), 7.17 (d, J=9.5 Hz, 2H), 6.88 (s, 1H), 5.14-4.35 (m, 3H), 3.97 (s, 2H), 3.25 (dd, J=18.1, 3.9 Hz, 4H), 2.64 (s, 2H), 0.47-0.29 (m, 4H).

Example 61

3,3,3-trifluoro-N-[5-(1H-indole-2-carbonyl)-4H,5H,6H,7H-[1,3]thiazolo[5,4-c]pyridin-2-yl]propanamide

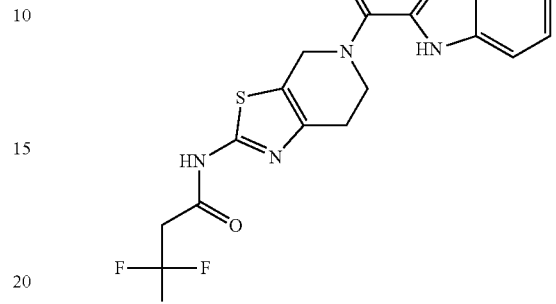

Rt (Method A) 3.19 mins, m/z 409 [M+H]+.

1H NMR (400 MHz, DMSO-d6) δ 12.44 (s, 1H), 11.64 (s, 1H), 7.64 (d, J=8.0 Hz, 1H), 7.43 (d, J=8.3 Hz, 1H), 7.20 (t, J=7.5 Hz, 1H), 7.06 (t, J=7.5 Hz, 1H), 6.93 (s, 1H), 5.09-4.74 (m, 2H), 4.05 (s, 2H), 3.63 (q, J=11.1 Hz, 2H), 2.84 (s, 2H).

Example 62

2-(dimethylamino)-N-[5-(1H-indole-2-carbonyl)-4H,5H,6H,7H-[1,3]thiazolo[5,4-c]pyridin-2-yl]acetamide

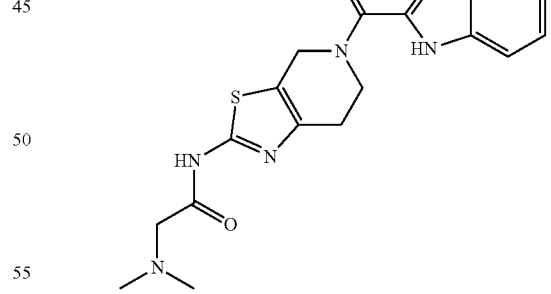

Rt (Method A) 3.00 mins, m/z 384 [M+H]+.

1H NMR (400 MHz, DMSO-d6) δ 11.93-11.67 (m, 1H), 11.64 (s, 1H), 7.64 (d, J=8.0 Hz, 1H), 7.43 (d, J=8.2 Hz, 1H), 7.20 (t, J=7.5 Hz, 1H), 7.06 (t, J=7.5 Hz, 1H), 6.93 (s, 1H), 5.11-4.74 (m, 2H), 4.19-3.91 (m, 2H), 3.20 (s, 2H), 2.92-2.76 (m, 2H), 2.25 (s, 6H).

Example 63

[1-({[5-(4-chloro-1H-indole-2-carbonyl)-4H,5H,6H,7H-[1,3]thiazolo[5,4-c]pyridin-2-yl]amino}methyl)cyclopropyl]methanol

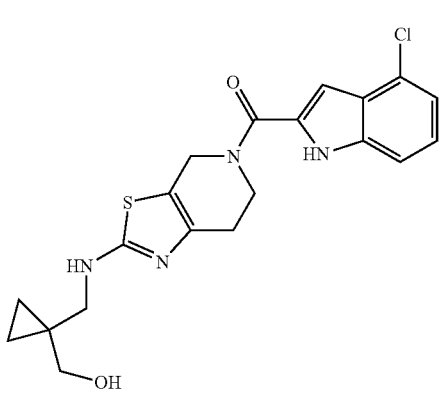 [SMILES: O=C(c1cc2c(Cl)cccc2[nH]1)N1CCc2nc(NCC3(CO)CC3)sc2C1]

Rt (Method B) 2.62 mins, m/z 417/419 [M+H]⁺.

1H NMR (400 MHz, DMSO-d6) δ 12.03 (d, J=2.3 Hz, 1H), 7.51 (t, J=5.7 Hz, 1H), 7.41 (d, J=8.0 Hz, 1H), 7.20 (t, J=7.8 Hz, 1H), 7.14 (d, J=7.4 Hz, 1H), 6.86 (d, J=2.0 Hz, 1H), 5.13-4.37 (m, 3H), 3.97 (s, 2H), 3.25 (dd, J=19.0, 5.7 Hz, 4H), 2.64 (s, 2H), 0.52-0.21 (m, 4H).

Example 64

[1-({[5-(4-methyl-1H-indole-2-carbonyl)-4H,5H,6H,7H-[1,3]thiazolo[5,4-c]pyridin-2-yl]amino}methyl)cyclopropyl]methanol

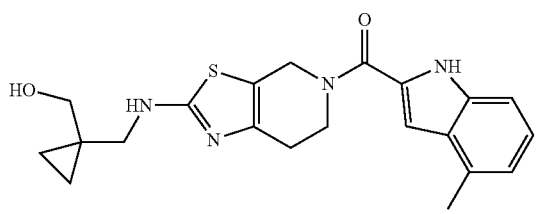 [SMILES: Cc1cccc2[nH]c(C(=O)N3CCc4nc(NCC5(CO)CC5)sc4C3)cc12]

Rt (Method B) 2.52 mins, m/z 397 [M+H]⁺.

1H NMR (400 MHz, DMSO-d6) δ 11.58 (d, J=2.2 Hz, 1H), 7.50 (t, J=5.6 Hz, 1H), 7.24 (d, J=8.2 Hz, 1H), 7.08 (t, J=7.6 Hz, 1H), 6.97-6.88 (m, 1H), 6.84 (d, J=7.0 Hz, 1H), 5.21-4.41 (m, 3H), 3.99 (s, 2H), 3.25 (dd, J=18.9, 5.7 Hz, 4H), 2.65 (s, 2H), 0.51-0.25 (m, 4H).

Example 65—Intentionally Left Blank

Example 66

N-[(1,4-dioxan-2-yl)methyl]-5-(1H-indole-2-carbonyl)-4H,5H,6H,7H-[1,3]thiazolo[5,4-c]pyridin-2-amine

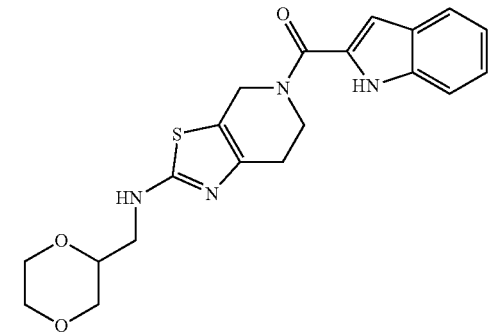 [SMILES: O=C(c1cc2ccccc2[nH]1)N1CCc2nc(NCC3COCCO3)sc2C1]

Rt (Method D) 2.94 mins, m/z 399 [M+H]⁺.

1H NMR (400 MHz, DMSO-d6) δ 11.62 (s, 1H), 7.62 (d, J=7.9 Hz, 1H), 7.58 (t, J=5.5 Hz, 1H), 7.42 (d, J=8.2 Hz, 1H), 7.26-7.14 (m, 1H), 7.10-6.99 (m, 1H), 6.93-6.84 (m, 1H), 5.12-4.37 (m, 2H), 4.18-3.84 (m, 2H), 3.77-3.52 (m, 5H), 3.45 (td, J=10.8, 2.4 Hz, 1H), 3.29-3.15 (m, 3H), 2.77-2.58 (m, 2H).

Example 67

4-{[5-(1H-indole-2-carbonyl)-4H,5H,6H,7H-[1,3]thiazolo[5,4-c]pyridin-2-yl]amino}cyclohexan-1-ol

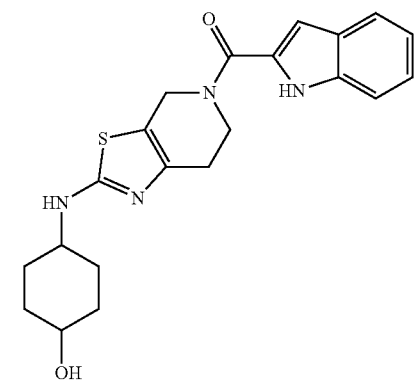 [SMILES: O=C(c1cc2ccccc2[nH]1)N1CCc2nc(NC3CCC(O)CC3)sc2C1]

Rt (Method A) 2.94 mins, m/z 397 [M+H]⁺.

1H NMR (400 MHz, DMSO-d6) δ 11.62 (s, 1H), 7.62 (d, J=8.0 Hz, 1H), 7.42 (d, J=8.2 Hz, 1H), 7.36 (d, J=7.5 Hz, 1H), 7.23-7.16 (m, 1H), 7.05 (t, J=7.5 Hz, 1H), 6.88 (d, J=1.6 Hz, 1H), 5.12-4.36 (m, 3H), 4.20-3.82 (m, 2H), 3.46-3.35 (m, 2H), 2.75-2.57 (m, 2H), 2.02-1.89 (m, 2H), 1.87-1.76 (m, 2H), 1.29-1.12 (m, 4H).

Example 68

2-{[5-(1H-indole-2-carbonyl)-4H,5H,6H,7H-[1,3]thiazolo[5,4-c]pyridin-2-yl]amino}-2-methylpropan-1-ol

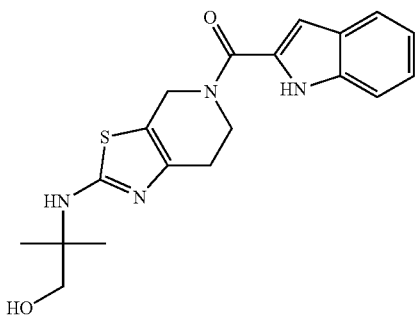 [SMILES: CC(C)(CO)Nc1nc2c(s1)CN(C(=O)c1cc3ccccc3[nH]1)CC2]

Rt (Method A) 3.14 mins, m/z 371 [M+H]⁺.

1H NMR (400 MHz, DMSO-d6) δ 11.62 (s, 1H), 7.62 (d, J=8.0 Hz, 1H), 7.42 (d, J=8.2 Hz, 1H), 7.24-7.15 (m, 2H), 7.05 (t, J=7.2 Hz, 1H), 6.93-6.86 (m, 1H), 5.09 (t, J=5.7 Hz, 1H), 4.87-4.59 (m, OH), 4.05-3.89 (m, 2H), 3.48 (d, J=5.6 Hz, 2H), 2.74-2.59 (m, 2H), 1.25 (s, 6H).

Example 69

5-(1H-indole-2-carbonyl)-N-(4-methyloxan-4-yl)-4H,5H,6H,7H-[1,3]thiazolo[5,4-c]pyridin-2-amine

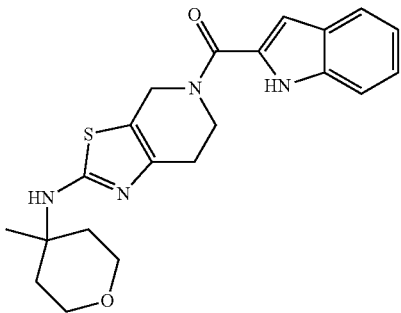 [SMILES: CC1(Nc2nc3c(s2)CN(C(=O)c2cc4ccccc4[nH]2)CC3)CCOCC1]

Rt (Method A) 3.28 mins, m/z 397 [M+H]⁺.

1H NMR (400 MHz, DMSO-d6) δ 11.62 (s, 1H), 7.62 (d, J=8.0 Hz, 1H), 7.43 (d, J=8.2 Hz, 1H), 7.27 (s, 1H), 7.19 (t, J=7.6 Hz, 1H), 7.05 (t, J=7.5 Hz, 1H), 6.92-6.86 (m, 1H), 5.05-4.56 (m, 2H), 4.07-3.85 (m, 2H), 3.62-3.49 (m, 4H), 2.75-2.57 (m, 2H), 2.19-2.06 (m, 2H), 1.60-1.47 (m, 2H), 1.37 (s, 3H).

Example 70

5-(1H-indole-2-carbonyl)-N-(1-methoxypropan-2-yl)-4H,5H,6H,7H-[1,3]thiazolo[5,4-c]pyridin-2-amine

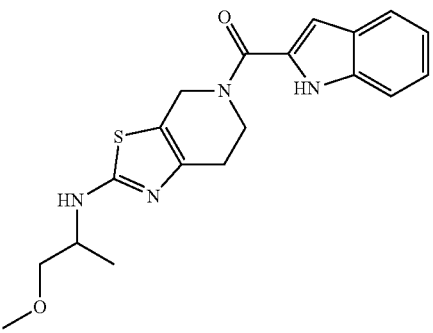 [SMILES: COCC(C)Nc1nc2c(s1)CN(C(=O)c1cc3ccccc3[nH]1)CC2]

Rt (Method A) 3.17 mins, m/z 371 [M+H]⁺.

1H NMR (400 MHz, DMSO-d6) δ 11.62 (s, 1H), 7.62 (d, J=8.0 Hz, 1H), 7.47-7.39 (m, 2H), 7.23-7.16 (m, 1H), 7.08-7.02 (m, 1H), 6.89 (d, J=1.5 Hz, 1H), 5.01-4.46 (m, 2H), 4.09-3.91 (m, 2H), 3.91-3.79 (m, 1H), 3.40-3.35 (m, 1H), 3.28-3.23 (m, 4H), 2.72-2.59 (m, 2H), 1.12 (d, J=6.6 Hz, 3H).

Example 71

N-tert-butyl-5-(1H-indole-2-carbonyl)-4H,5H,6H,7H-[1,3]thiazolo[5,4-c]pyridin-2-amine

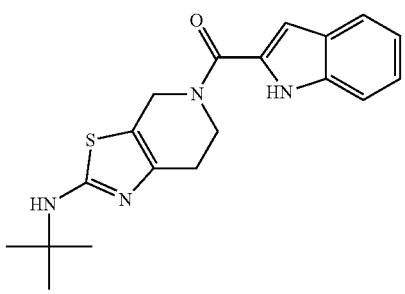 [SMILES: CC(C)(C)Nc1nc2c(s1)CN(C(=O)c1cc3ccccc3[nH]1)CC2]

Rt (Method A) 3.55 mins, m/z 355 [M+H]⁺.

1H NMR (400 MHz, DMSO-d6) δ 11.62 (s, 1H), 7.66 (d, J=8.3 Hz, 1H), 7.43 (d, J=8.2 Hz, 1H), 7.24 (s, 1H), 7.22-7.15 (m, 1H), 7.09-7.02 (m, 1H), 6.91-6.86 (m, 1H), 5.06-4.49 (m, 2H), 4.08-3.89 (m, 2H), 2.77-2.60 (m, 2H), 1.33 (s, 9H).

Example 72

5-(1H-indole-2-carbonyl)-N-[(oxolan-2-yl)methyl]-4H,5H,6H,7H-[1,3]thiazolo[5,4-c]pyridin-2-amine

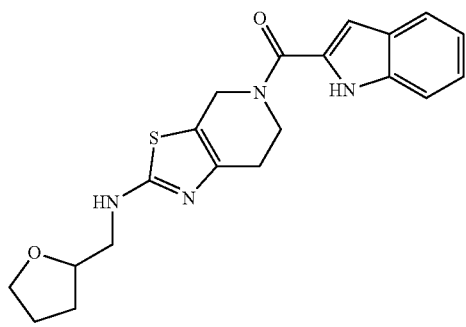 [SMILES: O=C(c1cc2ccccc2[nH]1)N1CCc2nc(NCC3CCCO3)sc2C1]

Rt (Method A) 3.14 mins, m/z 383 [M+H]⁺.

1H NMR (400 MHz, DMSO-d6) δ 11.62 (s, 1H), 7.62 (d, J=8.0 Hz, 1H), 7.57 (t, J=5.6 Hz, 1H), 7.42 (d, J=8.4 Hz, 1H), 7.19 (ddd, J=8.3, 6.9, 1.2 Hz, 1H), 7.08-7.01 (m, 1H), 6.89 (d, J=2.0 Hz, 1H), 5.09-4.38 (m, 2H), 4.08-3.88 (m, 3H), 3.80-3.72 (m, 1H), 3.62 (q, J=7.4 Hz, 1H), 3.25 (q, J=5.6 Hz, 2H), 2.75-2.59 (m, 2H), 1.95-1.86 (m, 1H), 1.86-1.71 (m, 2H), 1.59-1.49 (m, 1H).

Example 73

5-(1H-indole-2-carbonyl)-N-[3-(morpholin-4-yl)propyl]-4H,5H,6H,7H-[1,3]thiazolo[5,4-c]pyridin-2-amine

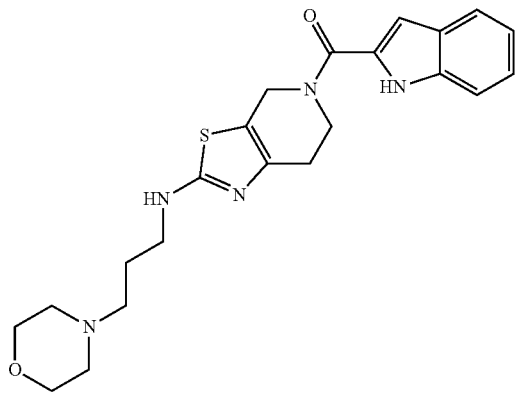 [SMILES: O=C(c1cc2ccccc2[nH]1)N1CCc2nc(NCCCN3CCOCC3)sc2C1]

Rt (Method D) 2.91 mins, m/z 426 [M+H]⁺.

1H NMR (400 MHz, DMSO-d6) δ 11.63 (s, 1H), 7.63 (d, J=8.0 Hz, 1H), 7.48 (t, J=5.3 Hz, 1H), 7.43 (d, J=8.2 Hz, 1H), 7.26-7.14 (m, 1H), 7.09-7.02 (m, 1H), 6.89 (s, 1H), 5.06-4.45 (m, 2H), 4.13-3.89 (m, 2H), 3.64-3.49 (m, 4H), 3.20 (q, J=6.6 Hz, 2H), 2.79-2.59 (m, 2H), 2.41-2.23 (m, 6H), 1.68 (p, J=6.9 Hz, 2H).

Example 74

Benzyl({[5-(1H-indole-2-carbonyl)-4H,5H,6H,7H-[1,3]thiazolo[5,4-c]pyridin-2-yl]methyl})amine

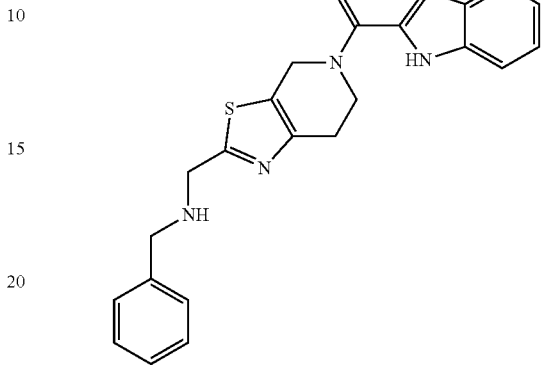

Rt (Method D) 3.42 mins, m/z 403 [M+H]⁺.

1H NMR (400 MHz, DMSO-d6) δ 11.65 (s, 1H), 7.64 (d, J=8.0 Hz, 1H), 7.43 (d, J=8.2 Hz, 1H), 7.39-7.29 (m, 4H), 7.28-7.17 (m, 2H), 7.10-7.03 (m, 1H), 6.94 (s, 1H), 5.32-4.66 (m, 2H), 4.15-3.96 (m, 2H), 3.95-3.85 (m, 2H), 3.82-3.70 (m, 2H), 3.26-3.09 (m, 1H), 3.00-2.80 (m, 2H).

Example 75

[1-({[5-(4,6-difluoro-1H-indole-2-carbonyl)-4H,5H,6H,7H-[1,3]thiazolo[5,4-c]pyridin-2-yl]amino}methyl)cyclopropyl]methanol

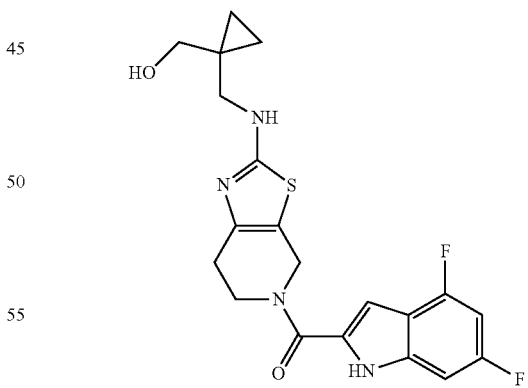

Rt (Method B) 2.58 mins, m/z 419 [M+H]⁺.

1H NMR (400 MHz, DMSO-d6) δ 12.06 (d, J=2.4 Hz, 1H), 7.50 (t, J=5.6 Hz, 1H), 7.04 (dd, J=9.3, 2.0 Hz, 1H), 7.00-6.83 (m, 2H), 5.15-4.32 (m, 3H), 3.96 (s, 2H), 3.25 (dd, J=19.1, 5.2 Hz, 4H), 2.72-2.57 (m, 2H), 0.47-0.30 (m, 4H).

Example 76

5-(4-methyl-1H-indole-2-carbonyl)-N-(oxolan-3-yl)-4H,5H,6H,7H-[1,3]thiazolo[5,4-c]pyridin-2-amine

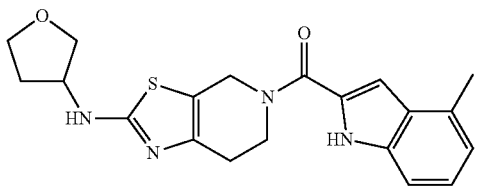 [SMILES: Cc1cccc2[nH]c(C(=O)N3CCc4nc(NC5CCOC5)sc4C3)cc12]

To (2-bromo-6,7-dihydrothiazolo[5,4-c]pyridin-5(4H)-yl)(4-methyl-1H-indol-2-yl)methanone (0.035 g, 0.093 mmol) was added tetrahydrofuran-3-amine (0.5 ml, 5.81 mmol). The mixture was stirred at r.t. overnight, then at 70° C. for 24 h. The mixture was concentrated under reduced pressure, purified by silica gel chromatography, then re-purified by basic reverse phase HPLC to give the desired product (0.003 g, 8% yield)

Rt (Method A) 3.09 mins, m/z 383 [M+H]⁺.

Example 77

2-{2-amino-4H,5H,6H,7H-[1,3]thiazolo[5,4-c]pyridine-5-carbonyl}-6-fluoro-1H-indole-4-carbonitrile

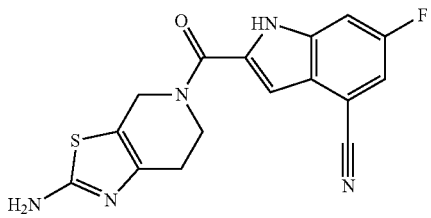 [SMILES: N#Cc1cc(F)cc2[nH]c(C(=O)N3CCc4nc(N)sc4C3)cc12]

To 4-cyano-6-fluoro-1H-indole-2-carboxylic acid (0.030 g, 0.147 mmol) in DMF (2 mL) was added HATU (0.0615 g, 0.162 mmol). The resulting clear yellow solution was stirred at r.t. for 5 min. 4,5,6,7-tetrahydrothiazolo[5,4-c]pyridin-2-amine dihydrochloride (0.0335 g, 0.147 mmol) in DMF (1 ml) and triethylamine (0.123 ml, 0.882 mmol) were then added. The mixture was stirred at r.t. for 1 h. Water (1 mL) was added. The resulting solution was purified by basic HPLC to give the desired product (0.032 g, 60% yield).

Rt (Method A) 2.89 mins, m/z 342 [M+H]⁺.

Example 78

5-(4,5,6-trifluoro-1H-indole-2-carbonyl)-4H,5H,6H,7H-[1,3]thiazolo[5,4-c]pyridin-2-amine

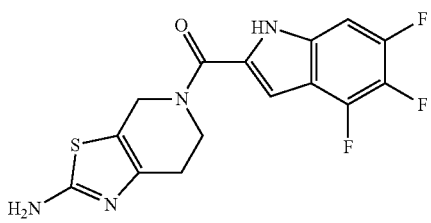 [SMILES: Nc1nc2c(s1)CN(C(=O)c1cc3c(F)c(F)c(F)cc3[nH]1)CC2]

To 4,5,6-trifluoro-1H-indole-2-carboxylic acid (0.030 g, 0.139 mmol) in DMF (2 mL) was added HATU (0.0583 g, 0.153 mmol). The resulting clear yellow solution was stirred at r.t. for 5 min. 4,5,6,7-tetrahydrothiazolo[5,4-c]pyridin-2-amine dihydrochloride (0.0318 g, 0.139 mmol) in DMF (1 ml) and triethylamine (0.117 ml, 0.837 mmol) were then added. The mixture was stirred at r.t. for 1 h. Water (1 mL) was added. The resulting solution was purified by basic HPLC to give the desired product (0.027 g, 55% yield).

Rt (Method A) 3.09 mins, m/z 353 [M+H]⁺.

Example 79

2-{2-amino-4H,5H,6H,7H-[1,3]thiazolo[5,4-c]pyridine-5-carbonyl}-7-fluoro-1H-indole-4-carbonitrile

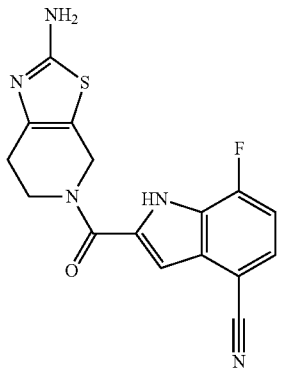 [SMILES: N#Cc1ccc(F)c2[nH]c(C(=O)N3CCc4nc(N)sc4C3)cc12]

To 4-cyano-7-fluoro-1H-indole-2-carboxylic acid (0.030 g, 0.147 mmol) in DMF (2 mL) was added HATU (0.0615 g, 0.162 mmol). The resulting clear yellow solution was stirred at r.t. for 5 min. 4,5,6,7-tetrahydrothiazolo[5,4-c]pyridin-2-amine dihydrochloride (0.0335 g, 0.147 mmol) in DMF (1 ml) and triethylamine (0.123 ml, 0.882 mmol) were then added. The mixture was stirred at r.t. for 1 h. Water (1 mL) was added. The resulting solution was purified by basic HPLC to give the desired product (0.029 g, 59% yield).

Rt (Method A) 2.80 mins, m/z 342 [M+H]⁺.

Example 80

5-(4-chloro-5-fluoro-1H-indole-2-carbonyl)-4H,5H,6H,7H-[1,3]thiazolo[5,4-c]pyridin-2-amine

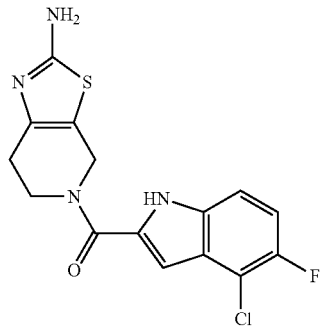 [SMILES: Nc1nc2c(s1)CN(C(=O)c1cc3c(Cl)c(F)ccc3[nH]1)CC2]

To 4-chloro-5-fluoro-1H-indole-2-carboxylic acid (0.030 g, 0.14 mmol) in DMF (2 mL) was added HATU (0.0587 g, 0.154 mmol). The resulting clear yellow solution was stirred at r.t. for 5 min. 4,5,6,7-tetrahydrothiazolo[5,4-c]pyridin-2-amine dihydrochloride (0.0320 g, 0.14 mmol) in DMF (1 ml) and triethylamine (0.117 ml, 0.843 mmol) were then added. The mixture was stirred at r.t. for 1 h. Water (1 mL) was added. The resulting solution was purified by basic HPLC to give the desired product (0.015 g, 49% yield).

Rt (Method A) 3.08 mins, m/z 351/353 [M+H]$^+$.

Example 81

5-(4-ethyl-1H-indole-2-carbonyl)-4H,5H,6H,7H-[1,3]thiazolo[5,4-c]pyridin-2-amine

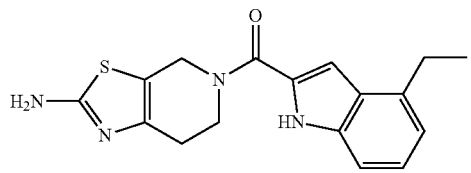 [SMILES: CCc1cccc2[nH]c(C(=O)N3CCc4nc(N)sc4C3)cc12]

To 4-ethyl-1H-indole-2-carboxylic acid (0.030 g, 0.159 mmol) in DMF (2 mL) was added HATU (0.0663 g, 0.174 mmol). The resulting clear yellow solution was stirred at r.t. for 5 min. 4,5,6,7-tetrahydrothiazolo[5,4-c]pyridin-2-amine dihydrochloride (0.0362 g, 0.159 mmol) in DMF (1 ml) and triethylamine (0.133 ml, 0.951 mmol) were then added. The mixture was stirred at r.t. for 1 h. Water (1 mL) was added. The resulting solution was purified by basic HPLC to give the desired product (0.031 g, 60% yield).

Rt (Method A) 3.11 mins, m/z 327 [M+H]$^+$.

Example 82

5-(4-cyclopropyl-1H-indole-2-carbonyl)-4H,5H,6H,7H-[1,3]thiazolo[5,4-c]pyridin-2-amine

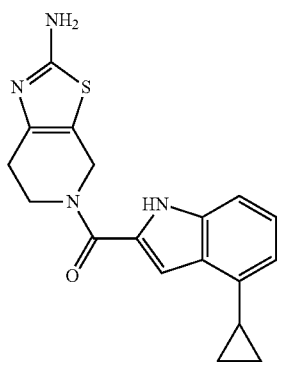 [SMILES: Nc1nc2c(s1)CN(C(=O)c1cc3c(C4CC4)cccc3[nH]1)CC2]

To 4-cyclopropyl-1H-indole-2-carboxylic acid (0.030 g, 0.149 mmol) in DMF (2 mL) was added HATU (0.0624 g, 0.164 mmol). The resulting clear yellow solution was stirred at r.t. for 5 min. 4,5,6,7-tetrahydrothiazolo[5,4-c]pyridin-2-amine dihydrochloride (0.0340 g, 0.149 mmol) in DMF (1 ml) and triethylamine (0.125 ml, 0.895 mmol) were then added. The mixture was stirred at r.t. for 1 h. Water (1 mL) was added. The resulting solution was purified by basic HPLC to give the desired product (0.031 g, 61% yield).

Rt (Method A) 3.11 mins, m/z 339 [M+H]$^+$.

Example 83

5-(4-cyano-1H-indole-2-carbonyl)-4H,5H,6H,7H-[1,3]thiazolo[5,4-c]pyridin-2-amine

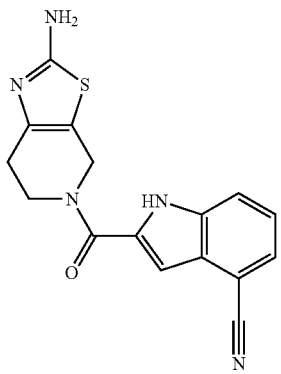 [SMILES: N#Cc1cccc2[nH]c(C(=O)N3CCc4nc(N)sc4C3)cc12]

To 4-cyano-1H-indole-2-carboxylic acid (0.030 g, 0.161 mmol) in DMF (2 mL) was added HATU (0.0674 g, 0.177 mmol). The resulting clear yellow solution was stirred at r.t. for 5 min. 4,5,6,7-tetrahydrothiazolo[5,4-c]pyridin-2-amine dihydrochloride (0.0368 g, 0.161 mmol) in DMF (1 ml) and triethylamine (0.135 ml, 0.967 mmol) were then added. The mixture was stirred at r.t. for 1 h. Water (1 mL) was added. The resulting solution was purified by basic HPLC to give the desired product (0.030 g, 58% yield).

Rt (Method A) 2.78 mins, m/z 324 [M+H]$^+$.

Example 84

5-(4,6,7-trifluoro-1H-indole-2-carbonyl)-4H,5H,6H,7H-[1,3]thiazolo[5,4-c]pyridin-2-amine

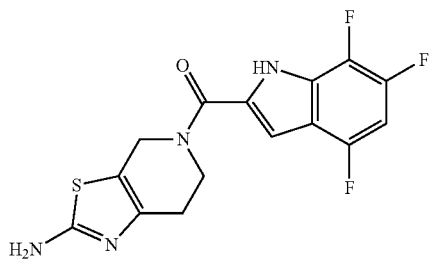 [SMILES: Nc1nc2c(s1)CN(C(=O)c1cc3c(F)cc(F)c(F)c3[nH]1)CC2]

To 4,6,7-trifluoro-1H-indole-2-carboxylic acid (0.030 g, 0.139 mmol) in DMF (2 mL) was added HATU (0.0583 g, 0.153 mmol). The resulting clear yellow solution was stirred at r.t. for 5 min. 4,5,6,7-tetrahydrothiazolo[5,4-c]pyridin-2-amine dihydrochloride (0.0318 g, 0.139 mmol) in DMF (1 ml) and triethylamine (0.117 ml, 0.837 mmol) were then added. The mixture was stirred at r.t. for 1 h. Water (1 mL) was added. The resulting solution was purified by basic HPLC to give the desired product (0.035 g, 71% yield).

Rt (Method A) 3.04 mins, m/z 353 [M+H]$^+$.

Example 85

5-(4-chloro-7-fluoro-1H-indole-2-carbonyl)-4H,5H,6H,7H-[1,3]thiazolo[5,4-c]pyridin-2-amine

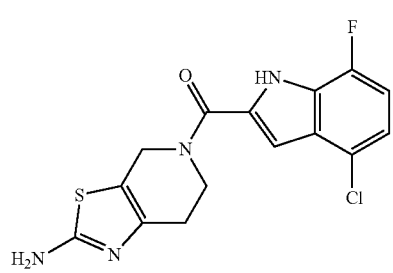

To 4-chloro-7-fluoro-1H-indole-2-carboxylic acid (0.030 g, 0.140 mmol) in DMF (2 mL) was added HATU (0.0587 g, 0.154 mmol). The resulting clear yellow solution was stirred at r.t. for 5 min. 4,5,6,7-tetrahydrothiazolo[5,4-c]pyridin-2-amine dihydrochloride (0.0320 g, 0.140 mmol) in DMF (1 ml) and triethylamine (0.117 ml, 0.837 mmol) were then added. The mixture was stirred at r.t. for 1 h. Water (1 mL) was added. The resulting solution was purified by basic HPLC to give the desired product (0.032 g, 66% yield).

Rt (Method A) 3.09 mins, m/z 351/353 [M+H]$^+$.

Example 86

5-(7-fluoro-4-methyl-1H-indole-2-carbonyl)-4H,5H,6H,7H-[1,3]thiazolo[5,4-c]pyridin-2-amine

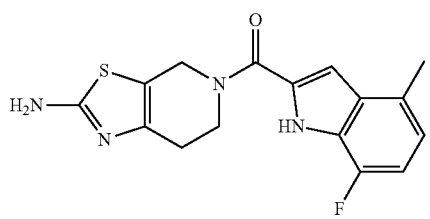 [SMILES: Cc1ccc(F)c2[nH]c(C(=O)N3CCc4nc(N)sc4C3)cc12]

To 7-fluoro-4-methyl-1H-indole-2-carboxylic acid (0.030 g, 0.155 mmol) in DMF (2 mL) was added HATU (0.0650 g, 0.171 mmol). The resulting clear yellow solution was stirred at r.t. for 5 min. 4,5,6,7-tetrahydrothiazolo[5,4-c]pyridin-2-amine dihydrochloride (0.0354 g, 0.155 mmol) in DMF (1 ml) and triethylamine (0.130 ml, 0.932 mmol) were then added. The mixture was stirred at r.t. for 1 h. Water (1 mL) was added. The resulting solution was purified by basic HPLC to give the desired product (0.032 g, 61% yield).

Rt (Method A) 3.01 mins, m/z 331 [M+H]$^+$.

Example 87

[1-({[5-(1H-indole-2-carbonyl)-4H,5H,6H,7H-[1,3]thiazolo[5,4-c]pyridin-2-yl]amino}methyl)cyclopropyl]methanol

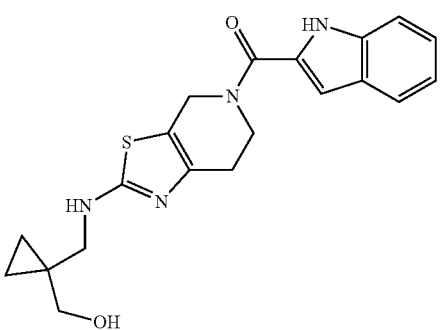 [SMILES: O=C(c1cc2ccccc2[nH]1)N1CCc2nc(NCC3(CO)CC3)sc2C1]

To (2-bromo-6,7-dihydrothiazolo[5,4-c]pyridin-5(4H)-yl)(1H-indol-2-yl)methanone (0.030 g, 0.083 mmol) was added (1-(aminomethyl)cyclopropyl)methanol (0.653 ml, 6.87 mmol). The mixture was stirred at 60° C. for 72 h. DMSO (2 mL) was added, and the mixture purified by acidic reverse phase HPLC (twice) to give the desired product (0.0149 g, 47% yield) Rt (Method A) 3.00 mins, m/z 383 [M+H]$^+$.

Example 88

N,N-dimethyl-5-(4-methyl-1H-indole-2-carbonyl)-4H,5H,6H,7H-[1,3]thiazolo[5,4-c]pyridin-2-amine

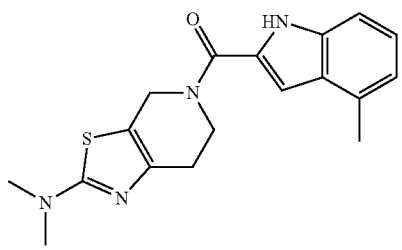 [SMILES: Cc1cccc2[nH]c(C(=O)N3CCc4nc(N(C)C)sc4C3)cc12]

To (2-bromo-6,7-dihydrothiazolo[5,4-c]pyridin-5(4H)-yl)(4-methyl-1H-indol-2-yl)methanone (0.035 g, 0.093 mmol) was added tetrahydrofuran-3-amine (0.500 ml, 5.81 mmol). The mixture was stirred at 70° C. for 72 h then concentrated under reduced pressure, and purified by silica gel chromatography to give the desired product (0.011 g, 33% yield) Rt (Method A) 3.32 mins, m/z 341 [M+H]$^+$.

Example 89

5-(1H-indole-2-carbonyl)-N-(2-methanesulfonyl-ethyl)-4H,5H,6H,7H-[1,3]thiazolo[5,4-c]pyridin-2-amine

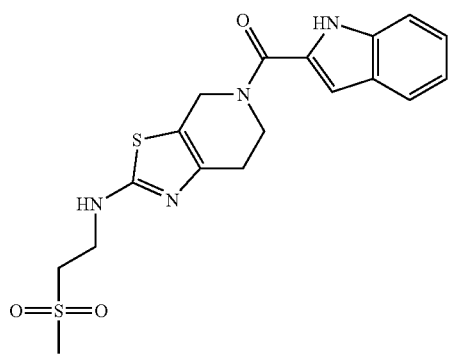 [SMILES: CS(=O)(=O)CCNc1nc2c(s1)CN(C(=O)c1cc3ccccc3[nH]1)CC2]

To (2-bromo-6,7-dihydrothiazolo[5,4-c]pyridin-5(4H)-yl)(1H-indol-2-yl)methanone (0.030 g, 0.083 mmol) was added 2-(methylsulfonyl)ethan-1-amine (1.001 mL, 9.94 mmol). The mixture was stirred at 80° C. for 7 days. DMSO (4 mL) was added, and the mixture purified by basic reverse phase HPLC to give the desired product (0.0051 g, 15% yield) Rt (Method A) 3.56 mins, m/z [M+H]$^+$ 405.

Example 90

5-(4-bromo-7-fluoro-1H-indole-2-carbonyl)-4H,5H,6H,7H-[1,3]thiazolo[5,4-c]pyridin-2-amine

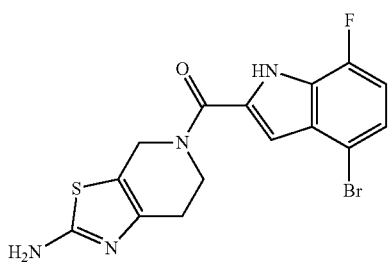

To 4-bromo-7-fluoro-1H-indole-2-carboxylic acid (0.0339 g, 0.132 mmol) in DMF (2 mL) was added triethylamine (0.110 mL, 0-789 mmol). HATU was then added (0.0550 g, 0.145 mmol) and the resulting solution stirred at 0° C. for 5 min. 4,5,6,7-tetrahydrothiazolo[5,4-c]pyridin-2-amine dihydrochloride (0.0300 g, 0.132 mmol) was then added. The mixture was stirred at r.t. for 1.5 h. Water (40 mL) was added and crude product collected by filtration. The residue was dissolved in DMSO (5 mL) and purified by basic HPLC to give the desired product (0.0176 g, 34% yield).

Rt (Method A) 3.37 mins, m/z 395/397 [M+H]$^+$.

Example 91

5-(1H-indole-2-carbonyl)-N-[(oxolan-3-yl)methyl]-4H,5H,6H,7H-[1,3]thiazolo[5,4-c]pyridin-2-amine

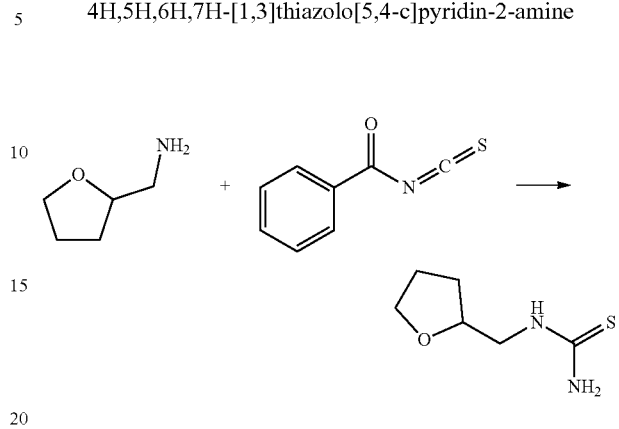

Step 1: To a cooled (ice bath) solution of (tetrahydrofuran-3-yl)methanamine (9.6 g, 95 mmol) in dry THF (150 ml) under argon was added benzoyl isothiocyanate (12.80 ml, 95 mmol). The mixture was warmed to room temperature and stirred overnight. The reaction mixture was concentrated under reduced pressure. The residue was suspended in methanol (150 ml) and water (150 ml) and potassium carbonate (13.77 g, 100 mmol) was added. The mixture was stirred overnight at room temperature, then concentrated under reduced pressure with co-evaporation with ethyl acetate. The solid obtained was suspended in 1:1 DCM/MeOH (150 ml) and filtered. The filtrate was concentrated and purified by silica gel flash chromatography (1%-10% methanol in DCM, 500 g silica gel) to yield the desired product as a white solid (7.20 g, 47% yield).

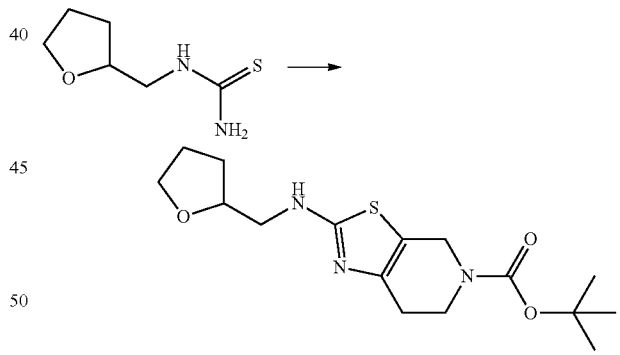

Step 2: To a solution of tert-butyl 3-bromo-4-oxopiperidine-1-carboxylate (12.50 g, 44.9 mmol), 1-((tetrahydrofuran-3-yl)methyl)thiourea (7.2 g, 44.9 mmol) in absoluted ethanol (250 ml) was added sodium bicarbonate (5.66 g, 67.4 mmol). The mixture was then heated to reflux and stirred for 2 h. The mixture was cooled and concentrated under reduced pressure. The crude product was partitioned between EtOAc (200 ml) and 5% citric acid (300 ml). The layers were separated and the aqueous phase was extracted with EtOAc (200 ml). The combined organic layer was washed with brine, dried (Na$_2$SO$_4$), filtered and concentrated under reduced pressure to give 12.79 g of the desired product (12-79 g, 79% yield).

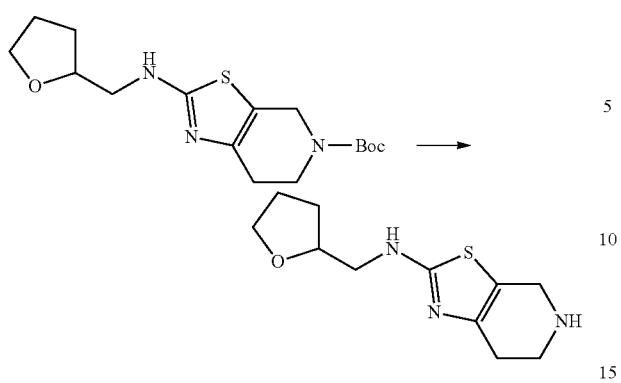

Step 3: To a solution of tert-butyl 2-(((tetrahydrofuran-3-yl)methyl)amino)-6,7-dihydrothiazolo[5,4-c]pyridine-5(4H)-carboxylate (12.79 g, 35.4 mmol) in dioxane (40 ml) was added HCl (40 ml, 4M solution in dioxane, 160 mmol). The mixture was stirred for 2 h at room temperature, then concentrated under reduced pressure. The solid obtained was triturated with DIPE (200 ml) and collected by filtration. The solid was washed with further DIPE then dried to give the desired product as the dihydrochloride salt (10.4 g, 94% yield).

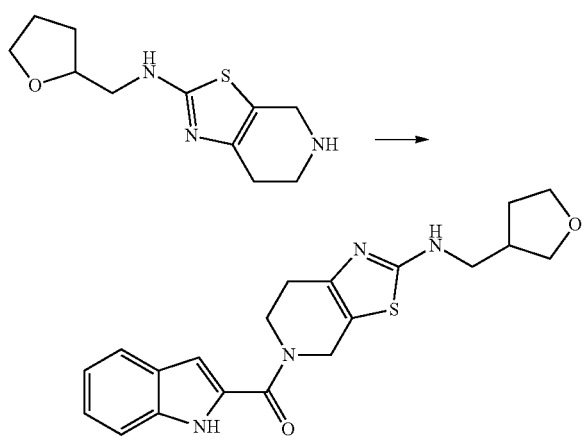

Step 4: To a suspension of N—((tetrahydrofuran-3-yl)methyl)-4,5,6,7-tetrahydrothiazolo[5,4-c]pyridin-2-amine dihydrochloride (10.4 g, 33.3 mmol) in dry DMF (40.0 ml) was added triethylamine (23.15 ml, 167 mmol). The mixture was stirred for 30 min.

Meanwhile, to a cooled (0° C.) solution of 1H-indole-2-carboxylic acid (5.37 g, 33.3 mmol) in dry DMF (40 ml) was added HATU (13.93 g, 36.6 mmol). The mixture was stirred for 15 minutes. The pre-formed mixture of amine and base was then added and the mixture stirred for a further 2 h at 0° C.

The reaction mixture was warmed to room temperature, poured into water (500 ml) and extracted twice with ethyl acetate (300 ml, then 200 ml). The combined organic extracts were washed with brine, dried (Na$_2$SO$_4$), filtered and concentrated, then purified by flash column chromatography (500 g silica, 2% to 10% ethanol in ethyl acetate) to yield the desired product as an off-white solid (9.5 g, containing 1.1 wt % EtOAc and 0.8 wt % DMF). Residual solvents were removed by dissolving the solid in boiling ethanol and pouring the mixture into cold water—the solid obtained crystallized on standing, and was collected by filtration then dried under vacuum (7.9 g, 62% yield).

Rt (Method A) 3.28 mins, m/z 383 [M+H]$^+$.

1H NMR (400 MHz, DMSO-d6) 11.74-11.54 (m, 1H), 7.79-7.52 (m, 2H), 7.43 (d, J=8.1 Hz, 1H), 7.20 (t, J=7.6 Hz, 1H), 7.06 (t, J=7.4 Hz, 1H), 6.89 (d, J=2.0 Hz, 1H), 5.02-4.46 (m, 2H), 4.06-3.95 (m, 2H), 3.89-3.51 (m, 3H), 3.27-3.09 (m, 2H), 2.73-2.65 (m, 2H), 2.59-2.39 (m, 1H), 2.04-1.86 (m, 1H), 1.62-1.48 (m, 1H).

Example 92

5-(6-bromo-1H-indole-2-carbonyl)-4H,5H,6H,7H-[1,3]thiazolo[5,4-c]pyridin-2-amine

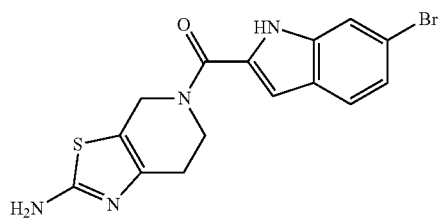

To 6-bromo-1H-indole-2-carboxylic acid (0.0316 g, 0.132 mmol) in DMF (2 mL) was added triethylamine (0.110 mL, 0.789 mmol). HATU was then added (0.0550 g, 0.145 mmol) and the resulting solution stirred at 0° C. for 5 min. 4,5,6,7-tetrahydrothiazolo[5,4-c]pyridin-2-amine dihydrochloride (0.0300 g, 0.132 mmol) was then added. The mixture was stirred at r.t. for 1.5 h. Water (40 mL) was added and crude product collected by filtration. The filtrate was extracted with EtOAc and brine; the organic layer was separated, and concentrated under reduced pressure. The residue was dissolved in DMSO (5 mL) and purified by basic HPLC to give the desired product (0.0124 g, 25% yield).

Rt (Method A) 3.38 mins, m/z 377/379 [M+H]$^+$.

Example 93

2-{2-amino-4H,5H,6H,7H-[1,3]thiazolo[5,4-c]pyridine-5-carbonyl}-4-bromo-1H-indol-7-ol

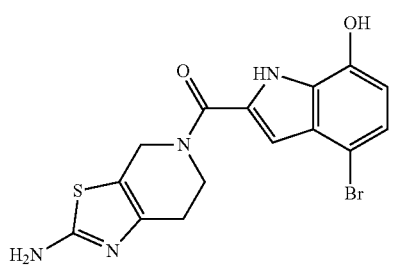

To a cooled (ice bath) solution of (2-amino-6,7-dihydrothiazolo[5,4-c]pyridin-5(4H)-yl)(4-bromo-7-methoxy-1H-indol-2-yl)methanone (0.020 g, 0.049 mmol) in dichloromethane (0.5 ml) was added dropwise BBr$_3$ (1M in DCM) (0.014 ml, 0.014 mmol) was added dropwise. After 5 min, the mixture was warmed, and then heated at reflux (~43° C.) for 2 h. A further portion of BBr$_3$ (1M in DCM) (0.014 ml, 0.014 mmol) was added and the solution heated for a further 24 h. A further portion of BBr₃ (1M in DCM) (0.147 ml, 0.147 mmol) was added and the solution heated for a further 2.5 h. The mixture was cooled and sat. NaHCO₃ (4 mL) was added. The precipitate was collected by filtration, then washed with DCM (4 mL), NaHCO₃ (8 mL) and brine (8 mL). The solid residue was dissolved in DMSO (5 mL) and purified by basic HPLC to give the desired product (0.0030 g, 15% yield).

Rt (Method A) 2.40 mins, m/z 393/395 [M+H]⁺.

Example 94

5-(4-bromo-7-methoxy-1H-indole-2-carbonyl)-4H,5H,6H,7H-[1,3]thiazolo[5,4-c]pyridin-2-amine

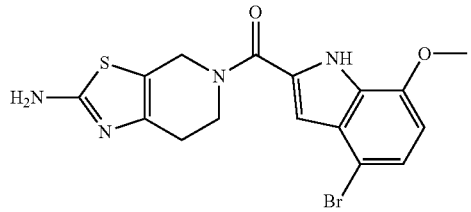 [SMILES: COc1ccc(Br)c2cc(C(=O)N3CCc4nc(N)sc4C3)[nH]c12]

To 6-bromo-1H-indole-2-carboxylic acid (0.0316 g, 0.132 mmol) in DMF (2 mL) was added triethylamine (0.110 mL, 0-789 mmol). HATU (0.0550 g, 0.145 mmol) was then added and the resulting solution stirred at 0° C. for 5 min. 4,5,6,7-tetrahydrothiazolo[5,4-c]pyridin-2-amine dihydrochloride (0.0300 g, 0.132 mmol) was then added. The mixture was stirred at r.t. for 1.5 h. Water (40 mL) was added and crude product collected by filtration. The filtrate was extracted with EtOAc and brine; the organic layer was separated, and concentrated under reduced pressure. The residue was dissolved in DMSO (5 mL) and purified by basic HPLC to give the desired product (0.0124 g, 25% yield).

Rt (Method A) 3.38 mins, m/z 377/379 [M+H]⁺.

Example 95

1-{[5-(1H-indole-2-carbonyl)-4H,5H,6H,7H-[1,3]thiazolo[5,4-c]pyridin-2-yl]amino}-2-methylpropan-2-ol

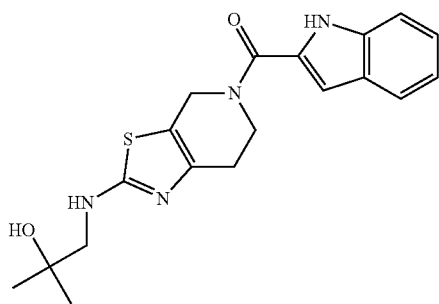 [SMILES: CC(C)(O)CNc1nc2c(s1)CN(C(=O)c1cc3ccccc3[nH]1)CC2]

To (2-bromo-6,7-dihydrothiazolo[5,4-c]pyridin-5(4H)-yl) (1H-indol-2-yl)methanone (0.030 g, 0.083 mmol) was added 1-amino-2-methylpropan-2-ol (1.003 mL, 10.77 mmol). The mixture was stirred at 80° C. for 40 h. DMSO (4 mL) was added, and the mixture purified by basic reverse phase HPLC to give the desired product (0.0145 g, 47% yield) Rt (Method A) 3.21 mins, m/z 371 [M+H]⁺.

Example 96

N-(cyclopropylmethyl)-5-(1H-indole-2-carbonyl)-4H,5H,6H,7H-[1,3]thiazolo[5,4-c]pyridin-2-amine

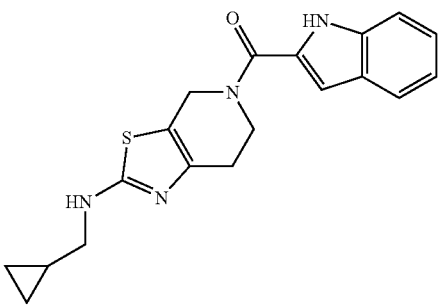 [SMILES: O=C(c1cc2ccccc2[nH]1)N1CCc2nc(NCC3CC3)sc2C1]

To (2-bromo-6,7-dihydrothiazolo[5,4-c]pyridin-5(4H)-yl)(1H-indol-2-yl)methanone (0.030 g, 0.083 mmol) was added cyclopropylmethanamine (1.006 mL, 11.59 mmol). The mixture was stirred at 80° C. for 20 h. DMSO (4 mL) was added, and the mixture purified by basic reverse phase HPLC to give the desired product (0.0169 g, 59% yield) Rt (Method A) 2.64 mins, m/z [M+H]⁺ 353.

Example 97

5-(1H-indole-2-carbonyl)-N-(2-methoxyethyl)-4H,5H,6H,7H-[1,3]thiazolo[5,4-c]pyridin-2-amine

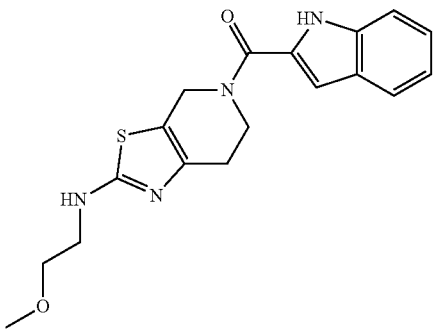 [SMILES: COCCNc1nc2c(s1)CN(C(=O)c1cc3ccccc3[nH]1)CC2]

To (2-bromo-6,7-dihydrothiazolo[5,4-c]pyridin-5(4H)-yl)(1H-indol-2-yl)methanone (0.030 g, 0.083 mmol) was added 2-methoxyethan-1-amine (0.871 mL, 11.59 mmol). The mixture was stirred at 80° C. for 23 h. DMSO (4 mL) was added, and the mixture purified by basic reverse phase HPLC to give the desired product (0.0146 g, 49% yield) Rt (Method A) 3.26 mins, m/z 357 [M+H]⁺.

Example 98

2-{2-amino-4H,5H,6H,7H-[1,3]thiazolo[5,4-c]pyridine-5-carbonyl}-1H-indol-7-ol

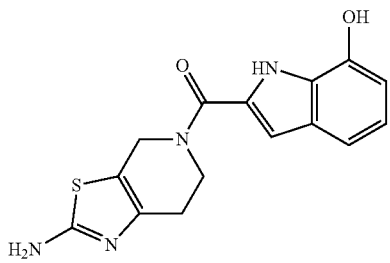 [SMILES: Nc1nc2c(s1)CN(C(=O)c1cc3cccc(O)c3[nH]1)CC2]

To a cooled (0° C.) solution of 7-hydroxy-1H-indole-2-carboxylic acid (0.0230 g, 0.132 mmol) and 4,5,6,7-tetrahydrothiazolo[5,4-c]pyridin-2-amine dihydrochloride (0.0300 g, 0.132 mmol) in DMF (1 mL) was added triethylamine (0.091 mL, 0.658 mmol). HATU (0.0550 g, 0.145 mmol) was added and the resulting solution stirred at for 1.5 h. Water (25 mL) was added and product extracted with EtOAc (3×25 mL). The combined organic extracts were washed with brine (5×25 mL) and dried ($Na_2SO_4$), filtered and concentrated. The residue was dissolved in DCM (~2 mL) and purified by silica gel chromatography (DCM:methanol) to give the desired product (0.0170 g, 37% yield).

Rt (Method A) 2.86 mins, m/z 315 [M+H]$^+$.

Example 99

(2S)-1-{[5-(1H-indole-2-carbonyl)-4H,5H,6H,7H-[1,3]thiazolo[5,4-c]pyridin-2-yl]amino}propan-2-ol

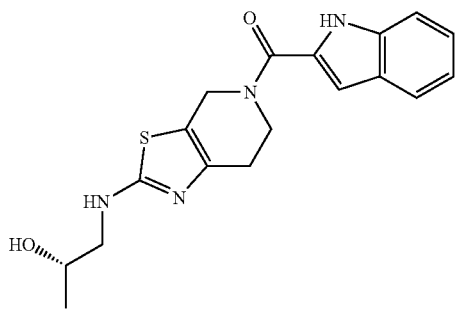 [SMILES: C[C@H](O)CNc1nc2c(s1)CN(C(=O)c1cc3ccccc3[nH]1)CC2]

To (2-bromo-6,7-dihydrothiazolo[5,4-c]pyridin-5(4H)-yl)(1H-indol-2-yl)methanone (0.030 g, 0.083 mmol) was added (S)-1-amino-2-propan-2-ol (0.062 mg, 0.083 mmol). The mixture was stirred at 80° C. for 20 h. DMSO (3 mL) was added, and the mixture purified by basic reverse phase HPLC to give the desired product (0.0157 g, 53% yield) LCMS Rt (Method A) 3.28 mins, m/z 357 [M+H]$^+$.

Example 100

Propan-2-yl (2S)-2-{[(2-{[5-(4,6-difluoro-1H-indole-2-carbonyl)-4H,5H,6H,7H-[1,3]thiazolo[5,4-c]pyridin-2-yl]amino}ethoxy)(phenoxy)phosphoryl]amino}propanoate

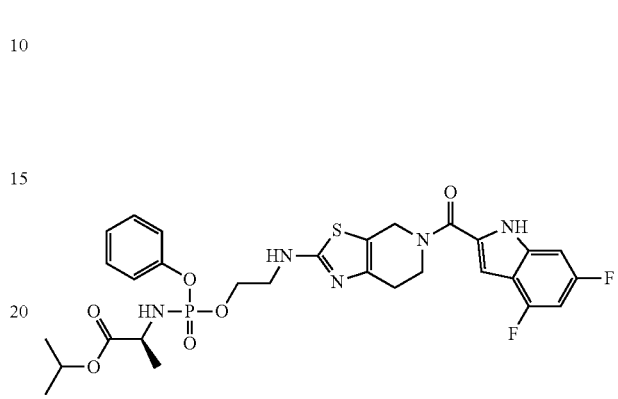

Rt (Method A) 3.61 mins, m/z 648 [M+H]$^+$.

1H NMR (400 MHz, d6-DMSO) 12.07 (m, 1H), 7.67 (m, 1H), 7.34 (m, 2H), 7.16 (m, 3H), 7.07-7.00 (m, 1H), 7.00-6.87 (m, 2H), 5.93 (m, 1H), 4.84 (m, 3H), 4.19-4.04 (m, 2H), 3.97 (m, 2H), 3.84-3.72 (m, 1H), 3.56-3.41 (m, 2H), 2.73-2.59 (m, 2H), 1.28-1.09 (m, 9H)

Example 101

5-(4-chloro-6-fluoro-1H-indole-2-carbonyl)-N-[(oxolan-3-yl)methyl]-4H,5H,6H,7H-[1,3]thiazolo[5,4-c]pyridin-2-amine

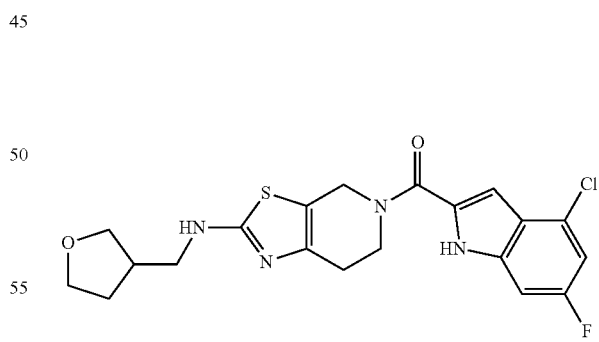

Rt (Method B) 2.77 mins, m/z 435/437 [M+H]$^+$.

1H NMR (400 MHz, d6-DMSO) 12.11 (s, 1H), 7.63 (t, J=5.2 Hz, 1H), 7.17 (d, J=9.5 Hz, 2H), 6.88 (s, 1H), 4.77 (s, 2H), 3.97 (s, 2H), 3.78-3.65 (m, 2H), 3.61 (q, J=7.7 Hz, 1H), 3.42 (dd, J=8.5, 5.5 Hz, 1H), 3.23-3.09 (m, 2H), 2.66 (s, 2H), 2.02-1.87 (m, 1H), 1.64-1.48 (m, 1H)

Example 102

2-{[5-(4,6-difluoro-1H-indole-2-carbonyl)-4H,5H,6H,7H-[1,3]thiazolo[5,4-c]pyridin-2-yl]oxy}ethan-1-ol

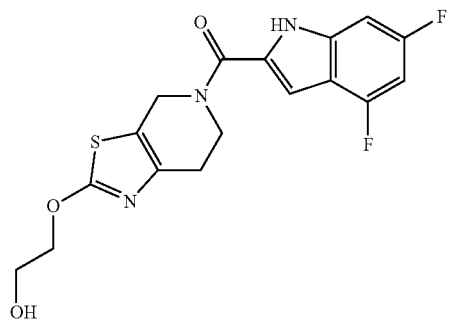 [SMILES: O=C(c1cc2c(F)cc(F)cc2[nH]1)N1CCc2nc(OCCO)sc2C1]

Rt (Method A) 3.08 mins, m/z 380 [M+H]+.

1H NMR (400 MHz, DMSO-d6) 7.08-7.01 (m, 1H), 6.99 (s, 1H), 6.96-6.87 (m, 1H), 4.86 (m, 3H), 4.40-4.29 (m, 2H), 4.01 (m, 2H), 3.77-3.66 (m, 2H), 2.75 (m, 2H)

Example 103

5-(4-cyano-6-fluoro-1H-indole-2-carbonyl)-N-[(oxolan-3-yl)methyl]-4H,5H,6H,7H-[1,3]thiazolo[5,4-c]pyridin-2-amine

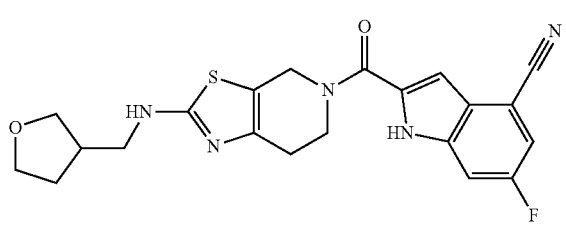 [SMILES: N#Cc1cc(F)cc2[nH]c(C(=O)N3CCc4nc(NCC5CCOC5)sc4C3)cc12]

Rt (Method B) 2.55 mins, m/z 426 [M+H]+.

1H NMR (400 MHz, DMSO-d6) 12.37 (s, 1H), 7.80-7.47 (m, 3H), 7.01 (s, 1H), 4.85 (s, 2H), 3.96 (s, 2H), 3.81-3.55 (m, 3H), 3.47-3.38 (m, 1H), 3.25-3.06 (m, 2H), 2.81-2.58 (m, 2H), 2.04-1.85 (m, 1H), 1.64-1.46 (m, 1H).

Example 104

5-(4-cyano-1H-indole-2-carbonyl)-N-[(oxolan-3-yl)methyl]-4H,5H,6H,7H-[1,3]thiazolo[5,4-c]pyridin-2-amine

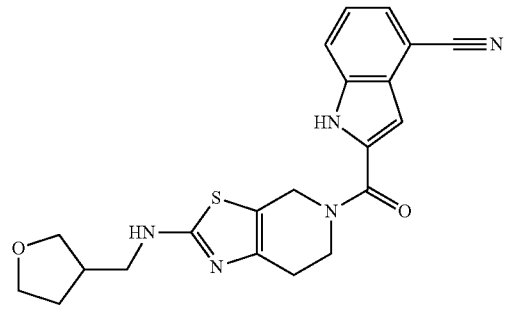 [SMILES: N#Cc1cccc2[nH]c(C(=O)N3CCc4nc(NCC5CCOC5)sc4C3)cc12]

Rt (Method B) 2.45 mins, m/z 408 [M+H]+.

1H NMR (400 MHz, DMSO-d6) 12.31 (s, 1H), 7.78 (d, J=8.3 Hz, 1H), 7.63 (d, J=7.2 Hz, 2H), 7.36 (t, J=7.8 Hz, 1H), 6.97 (s, 1H), 5.13-4.33 (m, 2H), 3.97 (s, 2H), 3.82-3.54 (m, 3H), 3.50-3.38 (m, 1H), 3.24-3.06 (m, 2H), 2.67 (s, 2H), 2.03-1.83 (m, 1H), 1.65-1.47 (m, 1H).

Example 105

5-(4,5,6-trifluoro-1H-indole-2-carbonyl)-N-[(oxolan-3-yl)methyl]-4H,5H,6H,7H-[1,3]thiazolo[5,4-c]pyridin-2-amine

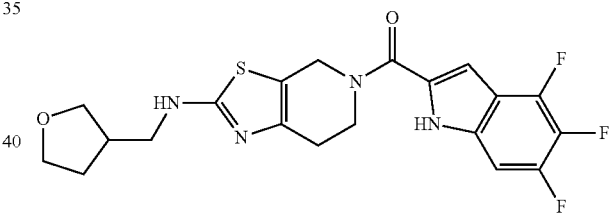

Rt (Method B) 2.74 mins, m/z 437 [M+H]+.

1H NMR (400 MHz, DMSO-d6) 12.17 (s, 1H), 7.63 (s, 1H), 7.41-7.17 (m, 1H), 7.05 (s, 1H), 5.17-4.33 (m, 2H), 3.96 (s, 2H), 3.83-3.55 (m, 3H), 3.52-3.39 (m, 1H), 3.17 (s, 2H), 2.67 (s, 2H), 2.12-1.83 (m, 1H), 1.70-1.45 (m, 1H).

Example 106

5-(4,6,7-trifluoro-1H-indole-2-carbonyl)-N-[(oxolan-3-yl)methyl]-4H,5H,6H,7H-[1,3]thiazolo[5,4-c]pyridin-2-amine

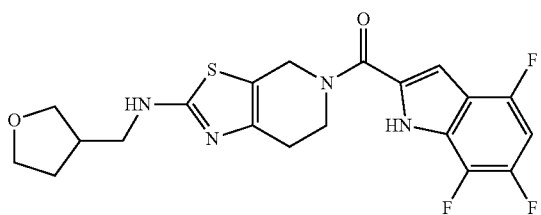 [SMILES: O=C(c1cc2c(F)cc(F)c(F)c2[nH]1)N1CCc2nc(NCC3CCOC3)sc2C1]

Rt (Method B) 2.69 mins, m/z 437 [M+H]+.

1H NMR (400 MHz, DMSO-d6) 12.70 (s, 1H), 7.63 (s, 1H), 7.23-7.06 (m, 1H), 7.06-6.85 (m, 1H), 4.68 (s, 2H), 3.92 (t, J=5.6 Hz, 2H), 3.82-3.55 (m, 3H), 3.47-3.39 (m, 1H), 3.23-3.09 (m, 2H), 2.65 (s, 2H), 2.06-1.83 (m, 1H), 1.67-1.43 (m, 1H).

Example 107

5-(1H-indole-2-carbonyl)-6-methyl-4H,5H,6H,7H-[1,3]thiazolo[5,4-c]pyridin-2-amine

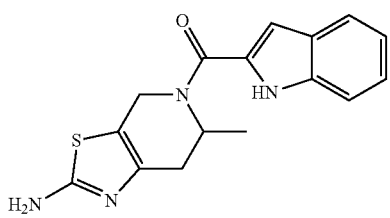 [SMILES: CC1Cc2nc(N)sc2CN1C(=O)c1cc2ccccc2[nH]1]

Rt (Method B) 2.29 mins, m/z 313 [M+H]+.

1H NMR (400 MHz, DMSO-d6) 11.60 (s, 1H), 7.62 (d, J=8.0 Hz, 1H), 7.42 (d, J=8.2 Hz, 1H), 7.24-7.14 (m, 1H), 7.11-7.00 (m, 1H), 6.85 (s, 3H), 5.24-4.93 (m, 2H), 4.28 (s, 1H), 3.00-2.75 (m, 1H), 2.45-2.34 (m, 1H), 1.25 (d, J=6.8 Hz, 3H).

Example 108—Intentionally Left Blank

Example 109

5-(1H-indole-2-carbonyl)-4-methyl-4H,5H,6H,7H-[1,3]thiazolo[5,4-c]pyridin-2-amine

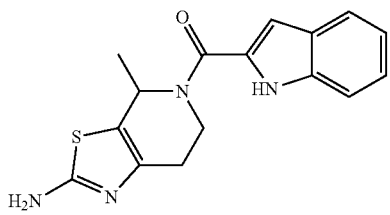 [SMILES: CC1c2sc(N)nc2CCN1C(=O)c1cc2ccccc2[nH]1]

Rt (Method A) 2.92 mins, m/z 341 [M+H]+.

1H NMR (400 MHz, DMSO-d6) 11.98 (s, 1H), 11.64 (s, 1H), 7.64 (d, J=8.0 Hz, 1H), 7.43 (d, J=8.2 Hz, 1H), 7.25-7.16 (m, 1H), 7.10-7.03 (m, 1H), 6.96-6.90 (m, 1H), 5.13-4.70 (m, 2H), 4.15-3.92 (m, 2H), 2.92-2.72 (m, 2H), 2.12 (s, 3H).

Example 110

5-(1H-indole-2-carbonyl)-N-methyl-N-[(oxolan-3-yl)methyl]-4H,5H,6H,7H-[1,3]thiazolo[5,4-c]pyridin-2-amine

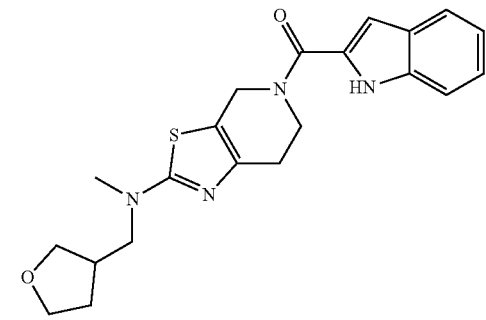 [SMILES: CN(CC1CCOC1)c1nc2c(s1)CN(C(=O)c1cc3ccccc3[nH]1)CC2]

Rt (Method A) 3.32 mins, m/z 397 [M+H]+.

1H NMR (400 MHz, DMSO-d6) Î' 11.63 (s, 1H), 7.63 (d, J=7.9 Hz, 1H), 7.43 (d, J=8.2 Hz, 1H), 7.20 (dd, J=7.2 Hz, 1H), 7.06 (dd, J=7.4 Hz, 1H), 6.90 (d, J=1.6 Hz, 1H), 5.16-4.42 (m, 2H), 4.11-3.91 (m, 2H), 3.81-3.72 (m, 1H), 3.71-3.65 (m, 1H), 3.65-3.57 (m, 1H), 3.47-3.37 (m, 3H), 2.99 (s, 3H), 2.76-2.60 (m, 3H), 1.98-1.86 (m, 1H), 1.61-1.50 (m, 1H).

Example 111

2-{[5-(4,6-difluoro-1H-indole-2-carbonyl)-4H,5H,6H,7H-[1,3]thiazolo[5,4-c]pyridin-2-yl]amino}ethan-1-ol

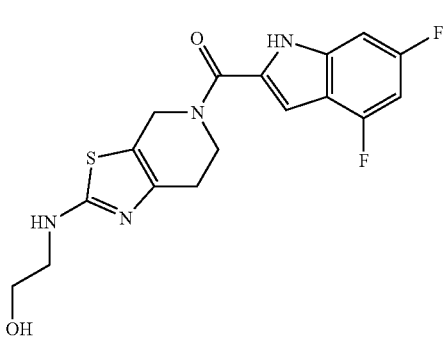

Rt (Method B) 3.08 mins, m/z 379 [M+H]+.

1H NMR (400 MHz, DMSO-d6) 12.06 (s, 1H), 7.51 (m, 1H), 7.04 (m, 1H), 6.99-6.87 (m, 2H), 4.74 (m, 3H), 3.97 (m, 2H), 3.51 (m, 2H), 3.26 (m, 2H), 2.66 (m, 2H)

Example 112

5-(4,5-difluoro-1H-indole-2-carbonyl)-N-[(oxolan-3-yl)methyl]-4H,5H,6H,7H-[1,3]thiazolo[5,4-c]pyridin-2-amine

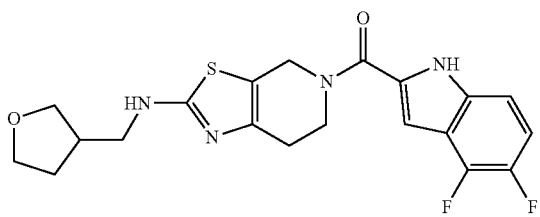 [SMILES: O=C(c1cc2c(F)c(F)ccc2[nH]1)N1CCc2nc(NCC3CCOC3)sc2C1]

Rt (Method B) 2.43 mins, m/z 379 [M+H]⁺.

1H NMR (400 MHz, DMSO-d6) 12.06 (s, 1H), 7.70-7.54 (m, 1H), 7.30-7.18 (m, 2H), 7.00 (s, 1H), 4.75 (s, 2H), 3.96 (s, 2H), 3.79-3.65 (m, 2H), 3.61 (q, J=7.8 Hz, 1H), 3.42 (dd, J=8.5, 5.5 Hz, 1H), 3.25-3.07 (m, 2H), 2.86-2.57 (m, 2H), 2.03-1.85 (m, 1H), 1.65-1.45 (m, 1H).

Example 113

5-(6-bromo-1H-indole-2-carbonyl)-N-[(oxolan-3-yl)methyl]-4H,5H,6H,7H-[1,3]thiazolo[5,4-c]pyridin-2-amine

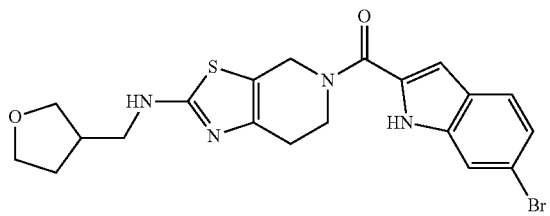 [SMILES: O=C(c1cc2ccc(Br)cc2[nH]1)N1CCc2nc(NCC3CCOC3)sc2C1]

Rt (Method B) 2.73 mins, m/z 460/462 [M+H]⁺.

1H NMR (400 MHz, DMSO-d6) 11.79 (s, 1H), 7.87-7.47 (m, 3H), 7.34-7.11 (m, 1H), 7.05-6.83 (m, 1H), 4.72 (s, 2H), 3.98 (s, 2H), 3.84-3.65 (m, 2H), 3.61 (q, J=7.8 Hz, 1H), 3.50-3.39 (m, 1H), 3.25-3.09 (m, 2H), 2.67 (s, 2H), 2.04-1.86 (m, 1H), 1.66-1.46 (m, 1H).

Example 114

5-(7-fluoro-4-methyl-1H-indole-2-carbonyl)-N-[(oxolan-3-yl)methyl]-4H,5H,6H,7H-[1,3]thiazolo[5,4-c]pyridin-2-amine

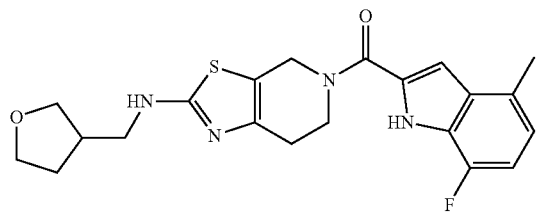 [SMILES: Cc1ccc(F)c2[nH]c(C(=O)N3CCc4nc(NCC5CCOC5)sc4C3)cc12]

Rt (Method B) 2.64 mins, m/z 415 [M+H]⁺.

1H NMR (400 MHz, DMSO-d6) 12.05 (s, 1H), 7.77-7.47 (m, 1H), 6.96-6.85 (m, 2H), 6.84-6.74 (m, 1H), 4.72 (s, 2H), 4.00-3.86 (m, 2H), 3.79-3.65 (m, 2H), 3.65-3.55 (m, 1H), 3.42 (dd, J=8.5, 5.4 Hz, 1H), 3.23-3.09 (m, 2H), 2.65 (s, 2H), 2.46 (s, 3H), 2.03-1.84 (m, 1H), 1.65-1.44 (m, 1H).

Example 115

5-(4-ethyl-1H-indole-2-carbonyl)-N-[(oxolan-3-yl)methyl]-4H,5H,6H,7H-[1,3]thiazolo[5,4-c]pyridin-2-amine

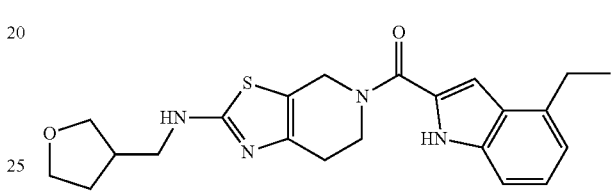

Rt (Method B) 2.72 mins, m/z 411 [M+H]⁺.

1H NMR (400 MHz, DMSO-d6) 11.59 (s, 1H), 7.71-7.56 (m, 1H), 7.25 (d, J=8.2 Hz, 1H), 7.17-7.07 (m, 1H), 6.93 (s, 1H), 6.87 (d, J=7.0 Hz, 1H), 4.77 (s, 2H), 3.99 (s, 2H), 3.80-3.66 (m, 2H), 3.61 (q, J=7.7 Hz, 1H), 3.42 (dd, J=8.5, 5.4 Hz, 1H), 3.23-3.10 (m, 2H), 2.89 (q, J=7.5 Hz, 2H), 2.67 (s, 2H), 2.04-1.85 (m, 1H), 1.66-1.47 (m, 1H), 1.28 (t, J=7.5 Hz, 3H).

Example 116

5-(4-chloro-7-fluoro-1H-indole-2-carbonyl)-N-[(oxolan-3-yl)methyl]-4H,5H,6H,7H-[1,3]thiazolo[5,4-c]pyridin-2-amine

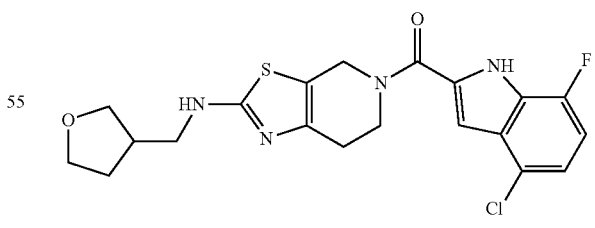

Rt (Method B) 2.72 mins, m/z 435/437 [M+H]⁺.

1H NMR (400 MHz, DMSO-d6) 12.55 (s, 1H), 7.63 (s, 1H), 7.25-6.99 (m, 2H), 6.99-6.75 (m, 1H), 4.72 (s, 2H), 4.05-3.84 (m, 2H), 3.84-3.54 (m, 3H), 3.53-3.38 (m, 1H), 3.27-3.07 (m, 3H), 2.77-2.59 (m, 2H), 2.05-1.84 (m, 1H), 1.66-1.41 (m, 1H).

Example 117

7-fluoro-2-(2-{[(oxolan-3-yl)methyl]amino}-4H,5H,6H,7H-[1,3]thiazolo[5,4-c]pyridine-5-carbonyl)-1H-indole-4-carbonitrile

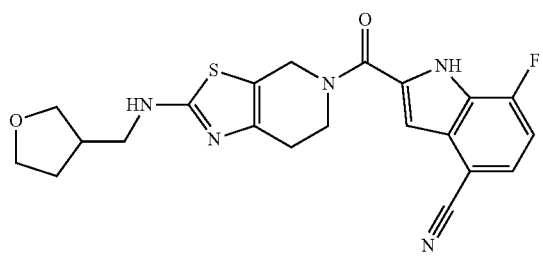 [SMILES: N#Cc1ccc(F)c2[nH]c(C(=O)N3CCc4nc(NCC5CCOC5)sc4C3)cc12]

Rt (Method B) 2.47 mins, m/z 426 [M+H]+.

1H NMR (400 MHz, DMSO-d6) 12.88 (s, 1H), 7.83-7.49 (m, 2H), 7.32-7.16 (m, 1H), 7.00 (s, 1H), 4.96-4.47 (m, 2H), 3.92 (s, 2H), 3.81-3.53 (m, 3H), 3.51-3.38 (m, 1H), 3.16 (s, 2H), 2.81-2.56 (m, 2H), 2.04-1.83 (m, 1H), 1.64-1.42 (m, 1H).

Example 118

5-(1H-indole-2-carbonyl)-N-(2,2,2-trifluoroethyl)-4H,5H,6H,7H-[1,3]thiazolo[5,4-c]pyridin-2-amine

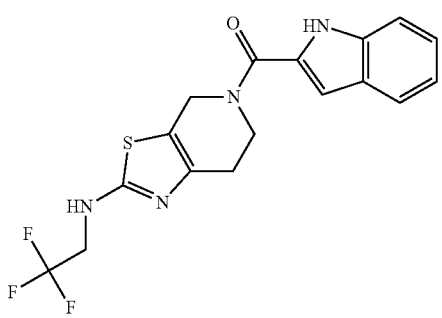 [SMILES: O=C(c1cc2ccccc2[nH]1)N1CCc2nc(NCC(F)(F)F)sc2C1]

Rt (Method A) 3.28 mins, m/z 381 [M+H]+.

1H NMR (400 MHz, DMSO-d6) 11.63 (s, 1H), 8.10 (t, J=6.4 Hz, 1H), 7.63 (d, J=7.9 Hz, 1H), 7.43 (d, J=8.2 Hz, 1H), 7.20 (dd, J=7.6 Hz, 1H), 7.06 (dd, J=7.5 Hz, 1H), 6.92-6.87 (m, 1H), 5.22-4.39 (m, 2H), 4.18-4.05 (m, 2H), 4.05-3.91 (m, 2H), 2.78-2.65 (m, 2H).

Example 119

5-(4,6-difluoro-1H-indole-2-carbonyl)-N-[(oxolan-3-yl)methyl]-4H,5H,6H,7H-[1,3]thiazolo[5,4-c]pyridin-2-amine

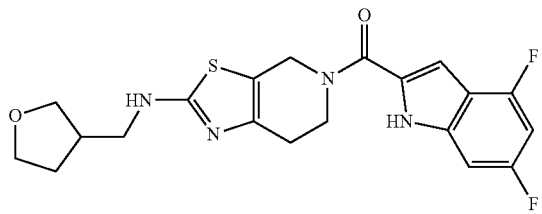 [SMILES: Cc1cc(F)cc2[nH]c(C(=O)N3CCc4nc(NCC5CCOC5)sc4C3)cc12]

Rt (Method B) 2.64 mins, m/z 419 [M+H]+.

1H NMR (400 MHz, d6-DMSO) 12.06 (s, 1H), 7.63 (t, J=5.0 Hz, 1H), 7.04 (d, J=9.3 Hz, 1H), 7.00-6.85 (m, 2H), 4.77 (s, 2H), 3.97 (s, 2H), 3.79-3.65 (m, 2H), 3.61 (q, J=7.7 Hz, 1H), 3.42 (dd, J=8.4, 5.5 Hz, 1H), 3.23-3.09 (m, 2H), 2.67 (s, 2H), 2.01-1.87 (m, 1H), 1.63-1.47 (m, 1H).

Example 120

5-(6-fluoro-4-methyl-1H-indole-2-carbonyl)-N-[(oxolan-3-yl)methyl]-4H,5H,6H,7H-[1,3]thiazolo[5,4-c]pyridin-2-amine

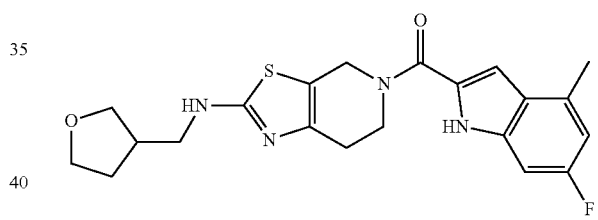

Rt (Method B) 2.66 mins, m/z 415 [M+H]+.

1H NMR (400 MHz, d6-DMSO) 11.76-11.51 (m, 1H), 7.62 (t, J=5.4 Hz, 1H), 7.05-6.86 (m, 2H), 6.83-6.67 (m, 1H), 4.77 (s, 2H), 3.98 (s, 2H), 3.78-3.65 (m, 2H), 3.61 (q, J=7.8 Hz, 1H), 3.42 (dd, J=8.5, 5.4 Hz, 1H), 3.23-3.10 (m, 2H), 2.80-2.58 (m, 2H), 2.01-1.86 (m, 1H), 1.63-1.44 (m, 1H).

Example 121

5-(4-chloro-1H-indole-2-carbonyl)-N-[(oxolan-3-yl)methyl]-4H,5H,6H,7H-[1,3]thiazolo[5,4-c]pyridin-2-amine

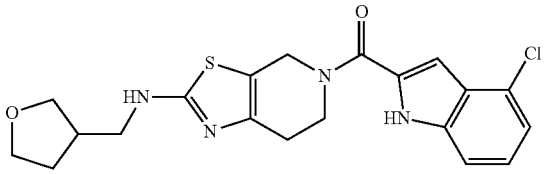 [SMILES: O=C(c1cc2c(Cl)cccc2[nH]1)N1CCc2nc(NCC3CCOC3)sc2C1]

Rt (Method B) 2.66 mins, m/z 417/419 [M+H]+.

1H NMR (400 MHz, d6-DMSO) 12.03 (s, 1H), 7.63 (t, J=5.1 Hz, 1H), 7.41 (d, J=8.0 Hz, 1H), 7.24-7.10 (m, 2H), 6.86 (s, 1H), 4.77 (s, 2H), 3.98 (s, 2H), 3.78-3.65 (m, 2H), 3.61 (q, J=7.8 Hz, 1H), 3.42 (dd, J=8.5, 5.4 Hz, 1H), 3.23-3.10 (m, 2H), 2.67 (s, 2H), 2.01-1.87 (m, 1H), 1.64-1.47 (m, 1H).

Example 122

5-(4,7-difluoro-1H-indole-2-carbonyl)-N-[(oxolan-3-yl)methyl]-4H,5H,6H,7H-[1,3]thiazolo[5,4-c]pyridin-2-amine

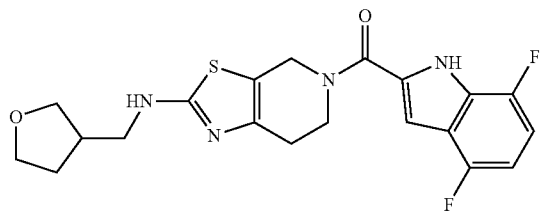

Rt (Method B) 2.59 mins, m/z 419 [M+H]+.

1H NMR (400 MHz, d6-DMSO) 12.47 (s, 1H), 7.63 (s, 1H), 7.08-6.88 (m, 2H), 6.87-6.74 (m, 1H), 4.68 (s, 2H), 3.92 (t, J=5.6 Hz, 2H), 3.79-3.65 (m, 2H), 3.61 (q, J=7.7 Hz, 1H), 3.42 (dd, J=8.3, 5.5 Hz, 1H), 3.16 (t, J=8.0 Hz, 2H), 2.65 (s, 2H), 2.04-1.87 (m, 1H), 1.65-1.46 (m, 1H).

Example 123

5-(4-(trifluoromethyl)-1H-indole-2-carbonyl)-N-[(oxolan-3-yl)methyl]-4H,5H,6H,7H-[1,3]thiazolo[5,4-c]pyridin-2-amine

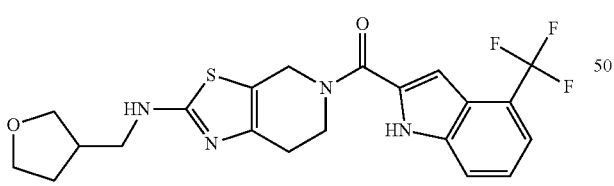

Rt (Method B) 2.78 mins, m/z 451 [M+H]+.

1H NMR (400 MHz, d6-DMSO) 12.23 (s, 1H), 7.73 (d, J=8.2 Hz, 1H), 7.64 (t, J=5.2 Hz, 1H), 7.46 (d, J=7.3 Hz, 1H), 7.43-7.31 (m, 1H), 6.86 (s, 1H), 4.97-4.50 (m, 2H), 3.96 (s, 2H), 3.81-3.65 (m, 2H), 3.60 (q, J=7.7 Hz, 1H), 3.42 (dd, J=8.5, 5.4 Hz, 1H), 3.24-3.09 (m, 2H), 2.78-2.61 (m, 2H), 2.01-1.86 (m, 1H), 1.63-1.49 (m, 1H).

Example 124

5-(4-methyl-1H-indole-2-carbonyl)-N-[(oxolan-3-yl)methyl]-4H,5H,6H,7H-[1,3]thiazolo[5,4-c]pyridin-2-amine

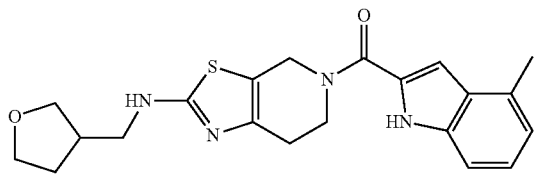 [SMILES: Cc1cccc2[nH]c(C(=O)N3CCc4nc(NCC5CCOC5)sc4C3)cc12]

Rt (Method B) 2.58 mins, m/z 397 [M+H]+.

1H NMR (400 MHz, d6-DMSO) 11.59 (s, 1H), 7.62 (t, J=5.4 Hz, 1H), 7.24 (d, J=8.2 Hz, 1H), 7.18-7.03 (m, 1H), 7.00-6.77 (m, 2H), 4.78 (s, 2H), 3.99 (s, 2H), 3.82-3.65 (m, 2H), 3.61 (q, J=7.8 Hz, 1H), 3.42 (dd, J=8.5, 5.4 Hz, 1H), 3.23-3.09 (m, 2H), 2.67 (s, 2H), 2.03-1.88 (m, 1H), 1.65-1.45 (m, 1H).

Example 125

5-(6-chloro-1H-indole-2-carbonyl)-N-[(oxolan-3-yl)methyl]-4H,5H,6H,7H-[1,3]thiazolo[5,4-c]pyridin-2-amine

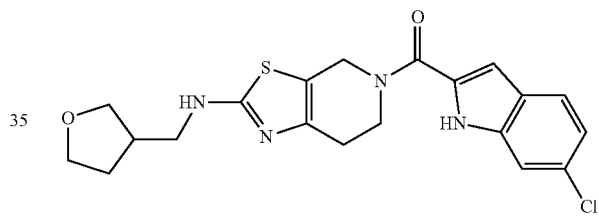

Rt (Method B) 2.69 mins, m/z 417/419 [M+H]+.

1H NMR (400 MHz, d6-DMSO) 11.78 (s, 1H), 7.77-7.55 (m, 2H), 7.44 (d, J=1.4 Hz, 1H), 7.08 (dd, J=8.5, 1.9 Hz, 1H), 6.94 (d, J=1.6 Hz, 1H), 4.74 (s, 2H), 3.98 (s, 2H), 3.80-3.65 (m, 2H), 3.61 (q, J=7.8 Hz, 1H), 3.42 (dd, J=8.5, 5.4 Hz, 1H), 3.24-3.07 (m, 2H), 2.80-2.61 (m, 2H), 2.02-1.87 (m, 1H), 1.64-1.46 (m, 1H).

Example 126

5-(1H-indole-2-carbonyl)-N-[(oxetan-3-yl)methyl]-4H,5H,6H,7H-[1,3]thiazolo[5,4-c]pyridin-2-amine

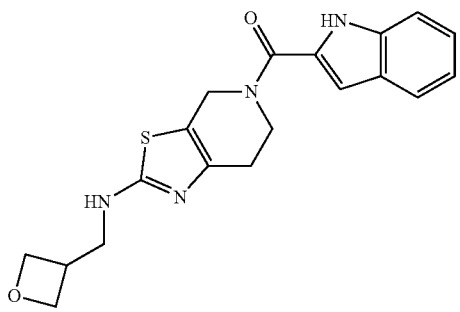 [SMILES: O=C(c1cc2ccccc2[nH]1)N1CCc2nc(NCC3COC3)sc2C1]

Rt (Method A) 2.69 mins, m/z 369 [M+H]⁺.

1H NMR (400 MHz, d6-DMSO) 11.63 (s, 1H), 7.66-7.60 (m, 2H), 7.42 (d, J=8.0 Hz, 1H), 7.20 (dd, 7.5 Hz, 1H), 7.06 (dd, J=7.5 Hz, 1H), 6.91-6.87 (m, 1H), 5.11-4.67 (m, 2H), 4.62 (dd, J=7.7, 6.1 Hz, 2H), 4.29 (dd, J=5.9 Hz, 2H), 4.13-3.80 (m, 2H), 3.52-3.45 (m, 2H), 3.22-3.13 (m, 1H), 2.70-2.64 (m, 2H).

Example 127

5-(1H-indole-2-carbonyl)-N-(oxetan-3-yl)-4H,5H, 6H,7H-[1,3]thiazolo[5,4-c]pyridin-2-amine

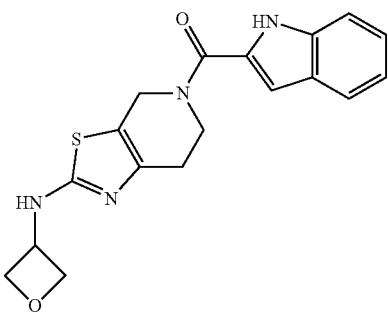 [SMILES: O=C(c1cc2ccccc2[nH]1)N1CCc2nc(NC3COC3)sc2C1]

To (2-bromo-6,7-dihydrothiazolo[5,4-c]pyridin-5(4H)-yl)(1H-indol-2-yl)methanone (0.030 g, 0.083 mmol) was added oxetan-3-amine (0.802 mL, 11.43 mmol). The mixture was stirred at 80° C. for 60 h. DMF (4 mL) was added, and the mixture purified by basic reverse phase HPLC to give the desired product (0.0129 g, 44% yield)

Rt (Method A) 3.24 mins, m/z 355 [M+H]⁺.

Example 128

5-(1H-indole-2-carbonyl)-N-(propan-2-yl)-4H,5H, 6H,7H-[1,3]thiazolo[5,4-c]pyridin-2-amine

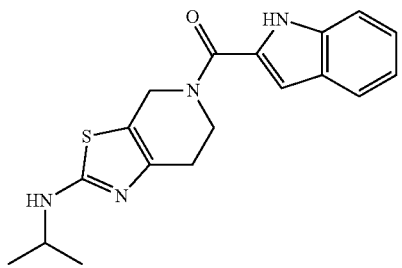 [SMILES: CC(C)Nc1nc2c(s1)CN(C(=O)c1cc3ccccc3[nH]1)CC2]

To (2-bromo-6,7-dihydrothiazolo[5,4-c]pyridin-5(4H)-yl)(1H-indol-2-yl)methanone (0.030 g, 0.083 mmol) was added propan-2-amine (1.002 mL, 11.76 mmol). A second portion of propan-2-amine (1.002 mL, 11.76 mmol) was added and the mixture stirred for a further 10 days. The residue was dissolved in a minimal volume of DMF then purified by silica gel chromatography (0-100% EtOAc: heptane) to give the desired product (0.0089 g, 32% yield)

Rt (Method A) 3.16 mins, m/z 341 [M+H]⁺.

Example 129

3-{[5-(1H-indole-2-carbonyl)-4H,5H,6H,7H-[1,3]thiazolo[5,4-c]pyridin-2-yl]amino}propan-1-ol

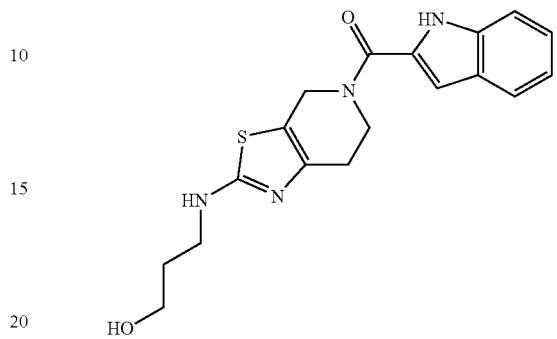

To (2-bromo-6,7-dihydrothiazolo[5,4-c]pyridin-5(4H)-yl)(1H-indol-2-yl)methanone (0.030 g, 0.083 mmol) was added 3-amino-propan-1-ol (1.001 mL, 13.09 mmol). The mixture was stirred at 80° C. for 20 h, then poured into DIPE (20 mL). The mixture was then concentrated under reduced pressure and the residue dissolved in a minimal volume of DCM. Purification by silica gel chromatography (DCM: MeOH 9:1) gave the desired product (0.0143 g, 48% yield)

Rt (Method A) 2.97 mins, m/z 357 [M+H]⁺.

Example 130

5-(4-bromo-5-fluoro-1H-indole-2-carbonyl)-4H,5H, 6H,7H-[1,3]thiazolo[5,4-c]pyridin-2-amine

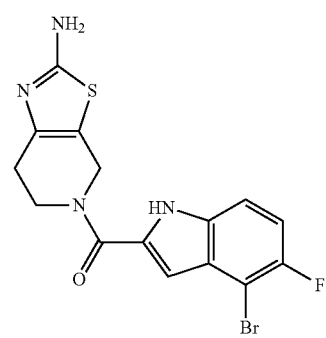

To a cooled (0° C.) solution of 4-bromo-5-fluoro-H-indole-2-carboxylic acid (0.0340 g, 0.132 mmol) and 4,5,6,7-tetrahydrothiazolo[5,4-c]pyridin-2-amine dihydrochloride (0.0300 g, 0.132 mmol) in DMF (1 mL) was added triethylamine (0.091 mL, 0.658 mmol). HATU (0.0550 g, 0.145 mmol) was added and the resulting solution stirred at for 1.5 h. Water (25 mL) was added and precipitate collected by filtration. The solid was washed with water (3×10 mL) and dried. The residue was dissolved in DCM (~2 mL) and purified by silica gel chromatography (DCM:methanol 9:1) to give the desired product (0.080 g, 15% yield).

Rt (Method A) 2.97 mins, m/z 357 [M+H]⁺.

Example 131

(2S)-1-{[5-(1H-indole-2-carbonyl)-4H,5H,6H,7H-[1,3]thiazolo[5,4-c]pyridin-2-yl]amino}propan-2-ol

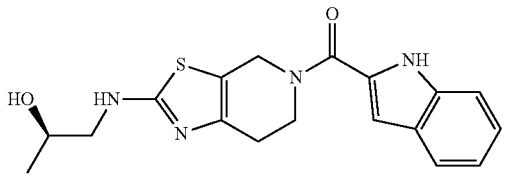 [SMILES: C[C@@H](O)CNc1nc2c(s1)CN(C(=O)c1cc3ccccc3[nH]1)CC2]

To (2-bromo-6,7-dihydrothiazolo[5,4-c]pyridin-5(4H)-yl)(1H-indol-2-yl)methanone (0.030 g, 0.083 mmol) was added (R)-1-amino-2-propan-2-ol (1.004 mL, 13.00 mmol). The mixture was stirred at 80° C. for 20 h. DMSO (3 mL) was added, and the mixture purified by basic reverse phase HPLC to give the desired product (0.0098 g, 33% yield)

Rt (Method A) 2.99 mins, m/z 357 [M+H]$^+$.

Example 132

5-(4,7-difluoro-1H-indole-2-carbonyl)-N-(oxolan-3-yl)-4H,5H,6H,7H-[1,3]thiazolo[5,4-c]pyridin-2-amine

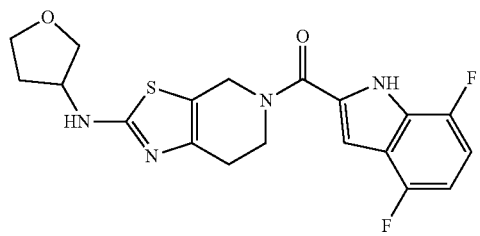 [SMILES: O=C(c1cc2c(F)ccc(F)c2[nH]1)N1CCc2nc(NC3CCOC3)sc2C1]

To (2-bromo-6,7-dihydrothiazolo[5,4-c]pyridin-5(4H)-yl)(4,7,difluoro-1H-indol-2-yl)methanone (0.030 g, 0.753 mmol) was added tetrahydrofuran-3-amine (1.0 ml, 5.81 mmol). The mixture was stirred at 80° C. for 7 days. The mixture was cooled, then purified directly by basic reverse phase HPLC to give the desired product (0.114 g, 35% yield)

Rt (Method A) 3.15 mins, m/z 405 [M+H]$^+$.

Also obtained Example 133

5-(4,7-difluoro-1H-indole-2-carbonyl)-N,N-dimethyl-4H,5H,6H,7H-[1,3]thiazolo[5,4-c]pyridin-2-amine (0.110 g, 39% yield)

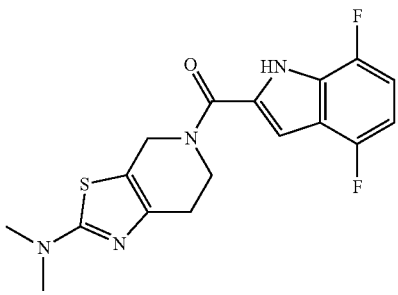 [SMILES: CN(C)c1nc2c(s1)CN(C(=O)c1cc3c(F)ccc(F)c3[nH]1)CC2]

Rt (Method A) 3.36 mins, m/z 363 [M+H]$^+$.

Example 134

5-(6-chloro-7-methyl-1H-indole-2-carbonyl)-4H,5H,6H,7H-[1,3]thiazolo[5,4-c]pyridin-2-amine

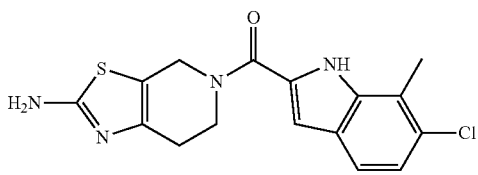 [SMILES: Cc1c(Cl)ccc2cc(C(=O)N3CCc4nc(N)sc4C3)[nH]c12]

To a cooled (0° C.) solution of 6-chloro-7-methyl-1H-indole-2-carboxylic acid (0.0276 g, 0.132 mmol) in DMF (2 mL) was added triethylamine (0.110 mL, 0.789 mmol). HATU was added (0.0550 g, 0.145 mmol) and the resulting solution stirred for 5 min. 4,5,6,7-tetrahydrothiazolo[5,4-c]pyridin-2-amine dihydrochloride (0.0300 g, 0.132 mmol) was then added. The mixture was stirred at r.t. for 1 h. The mixture was poured into water (40 mL) and crude product collected by filtration. The residue was dissolved in DMSO (4 mL) and purified by basic HPLC to give the desired product (0.0245 g, 54% yield).

Rt (Method A) 3.51 mins, m/z 347/349 [M+H]$^+$.

Example 135

5-(5,6-dichloro-1H-indole-2-carbonyl)-4H,5H,6H,7H-[1,3]thiazolo[5,4-c]pyridin-2-amine

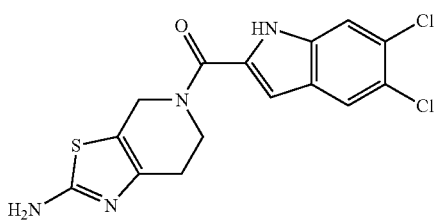 [SMILES: Nc1nc2c(s1)CN(C(=O)c1cc3cc(Cl)c(Cl)cc3[nH]1)CC2]

To a cooled (0° C.) solution of 5,6-dichloro-1H-indole-2-carboxylic acid (0.0303 g, 0.132 mmol) in DMF (2 mL) was added triethylamine (0.110 mL, 0.789 mmol). HATU was added (0.0550 g, 0.145 mmol) and the resulting solution stirred for 5 min. 4,5,6,7-tetrahydrothiazolo[5,4-c]pyridin-2-amine dihydrochloride (0.0300 g, 0.132 mmol) was then added. The mixture was stirred at r.t. for 1 h. The mixture was poured into water (40 mL) and crude product collected by filtration. The residue was dissolved in DMSO (4 mL) and purified by basic HPLC to give the desired product (0.0137 g, 28% yield).

Rt (Method A) 3.56 mins, m/z 367/369 [M+H]$^+$.

Example 136

5-(4,5-dimethyl-1H-indole-2-carbonyl)-4H,5H,6H,7H-[1,3]thiazolo[5,4-c]pyridin-2-amine

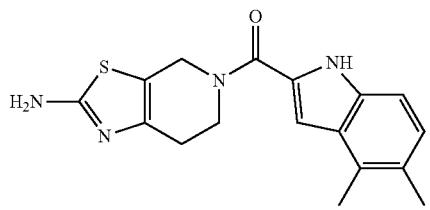 [SMILES: Cc1ccc2[nH]c(C(=O)N3CCc4nc(N)sc4C3)cc2c1C]

To a cooled (0° C.) solution of 4,5-dimethyl-1H-indole-2-carboxylic acid (0.0249 g, 0.132 mmol) in DMF (2 mL) was added triethylamine (0.110 mL, 0.789 mmol). HATU was added (0.0550 g, 0.145 mmol) and the resulting solution stirred for 5 min. 4,5,6,7-tetrahydrothiazolo[5,4-c]pyridin-2-amine dihydrochloride (0.0300 g, 0.132 mmol) was then added. The mixture was stirred at r.t. for 1 h. The mixture was poured into water (40 mL) and product (0.0358 g, 83% yield) collected by filtration.

Rt (Method A) 3.37 mins, m/z 327 [M+H]$^+$.

Example 137

5-(5,7-dimethyl-1H-indole-2-carbonyl)-4H,5H,6H,7H-[1,3]thiazolo[5,4-c]pyridin-2-amine

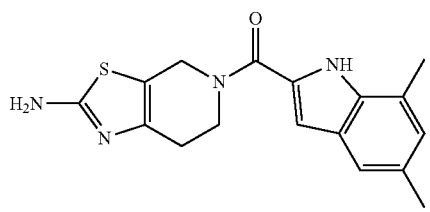 [SMILES: Cc1cc(C)c2[nH]c(C(=O)N3CCc4nc(N)sc4C3)cc2c1]

To a cooled (0° C.) solution of 5,7-dimethyl-1H-indole-2-carboxylic acid (0.0249 g, 0.132 mmol) in DMF (2 mL) was added triethylamine (0.110 mL, 0.789 mmol). HATU was added (0.0550 g, 0.145 mmol) and the resulting solution stirred for 5 min. 4,5,6,7-tetrahydrothiazolo[5,4-c]pyridin-2-amine dihydrochloride (0.0300 g, 0.132 mmol) was then added. The mixture was stirred at r.t. for 1 h. The mixture was poured into water (40 mL) then purified by basic HPLC to give the desired product (0.0231 g, 54% yield) collected by filtration.

Rt (Method A) 3.45 mins, m/z 327 [M+H]$^+$.

Example 138

5-(4,6-dimethyl-1H-indole-2-carbonyl)-4H,5H,6H,7H-[1,3]thiazolo[5,4-c]pyridin-2-amine

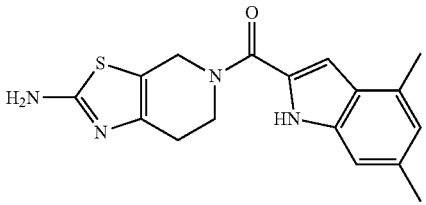 [SMILES: Cc1cc(C)c2cc(C(=O)N3CCc4nc(N)sc4C3)[nH]c2c1]

To a cooled (0° C.) solution of 4,6-dimethyl-1H-indole-2-carboxylic acid (0.0366 g, 0.193 mmol) in DMF (2 mL) was added triethylamine (0.162 mL, 1.16 mmol). HATU was added (0.0810 g, 0.213 mmol) and the resulting solution stirred for 5 min. 4,5,6,7-tetrahydrothiazolo[5,4-c]pyridin-2-amine dihydrochloride (0.0300 g, 0.132 mmol) was then added. The mixture was stirred at r.t. for 1 h. The mixture was poured into water (40 mL), collected by filtration and dried to give the desired product (0.0557 g, 88% yield).

Rt (Method A) 3.49 mins, m/z 327 [M+H]$^+$.

Example 139

5-(5-chloro-7-methyl-1H-indole-2-carbonyl)-4H,5H,6H,7H-[1,3]thiazolo[5,4-c]pyridin-2-amine

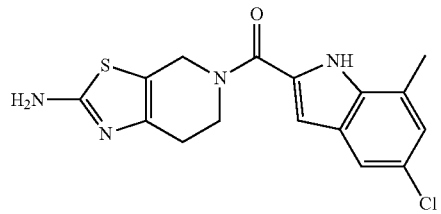 [SMILES: Cc1cc(Cl)cc2cc(C(=O)N3CCc4nc(N)sc4C3)[nH]c12]

To a cooled (0° C.) solution of 5-chloro-7-methyl-1H-indole-2-carboxylic acid (0.0405 g, 0.193 mmol) in DMF (2 mL) was added triethylamine (0.162 mL, 1.16 mmol). HATU was added (0.0810 g, 0.213 mmol) and the resulting solution stirred for 5 min. 4,5,6,7-tetrahydrothiazolo[5,4-c]pyridin-2-amine dihydrochloride (0.0300 g, 0.132 mmol) was then added. The mixture was stirred at r.t. for 1 h. The mixture was poured into water (40 mL), collected by filtration and dried to give the desired product (0.0515 g, 77% yield).

Rt (Method A) 3.58 mins, m/z 347 [M+H]$^+$.

Example 140

5-(4-chloro-6-fluoro-1H-indole-2-carbonyl)-N-(oxolan-3-yl)-4H,5H,6H,7H-[1,3]thiazolo[5,4-c]pyridin-2-amine

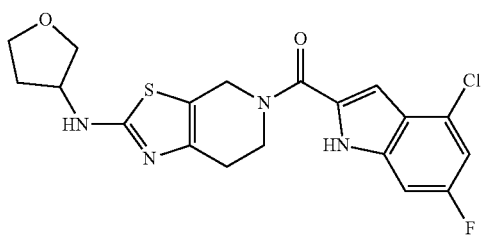 [SMILES: O=C(c1cc2c(Cl)cc(F)cc2[nH]1)N1CCc2nc(NC3CCOC3)sc2C1]

To (2-bromo-6,7-dihydrothiazolo[5,4-c]pyridin-5(4H)-yl)(4,7-difluoro-1H-indol-2-yl)methanone (0.250 g, 0.603 mmol) was added tetrahydrofuran-3-amine (1.038 ml, 12.1 mmol). The mixture was stirred at 80° C. for 72 hours. The mixture was cooled, diluted with DMSO (4 mL) then purified directly by basic reverse phase HPLC to give the desired product (0.0627 g, 25% yield)

Rt (Method A) 3.52 mins, m/z 421/423 [M+H]$^+$.

Also obtained Example 209
5-(4-chloro-6-fluoro-1H-indole-2-carbonyl)-N,N-dimethyl-4H,5H,6H,7H-[1,3]thiazolo[5,4-c]pyridin-2-amine (0.0657 g, 29% yield)

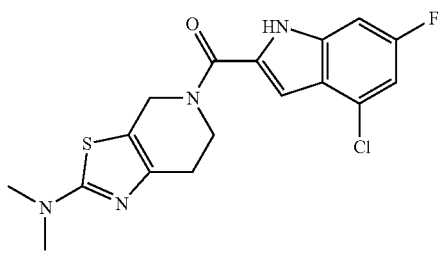 [SMILES: CN(C)c1nc2c(s1)CN(C(=O)c1cc3c(Cl)cc(F)cc3[nH]1)CC2]

Rt (Method A) 3.77 mins, m/z 379/381 [M+H]$^+$.

Example 141

5-(1H-indole-2-carbonyl)-4H,5H,6H,7H-[1,3]thiazolo[5,4-c]pyridin-2-ol

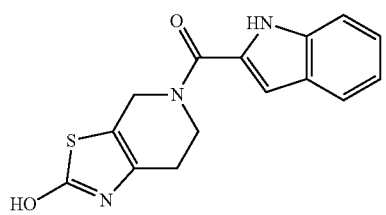 [SMILES: O=C(c1cc2ccccc2[nH]1)N1CCc2nc(O)sc2C1]

To a solution of (2-(benzyloxy)-6,7-dihydrothiazolo[5,4-c]pyridin-5(4H)-yl)(1H-indol-2-yl)methanone (0.0150 g, 0.039 mmol) under argon in absolute ethanol (15 ml) was added 10% palladium on activated carbon (2.049 mg, 1.926 µmol). The argon atmosphere was replaced by hydrogen (excess) and the reaction mixture stirred vigorously for 1.5 h. The reaction mixture was purged with nitrogen, and then filtered through a short plug of Kieselguhr. The reaction flask was rinsed with EtOH (5 mL), MeOH (5 mL) and DCM (5 ml), the washing being used to rinse the filter cake. The combined organic extracts were concentrated, dissolved in a minimal volume of DMSO and purified by basic HPLC to give the desired product (0.0027 g, 24% yield).

Rt (Method A) 2.86 mins, m/z 300 [M+H]$^+$

Example 142

1-{[5-(4-chloro-6-fluoro-1H-indole-2-carbonyl)-4H,5H,6H,7H-[1,3]thiazolo[5,4-c]pyridin-2-yl]amino}propan-2-ol

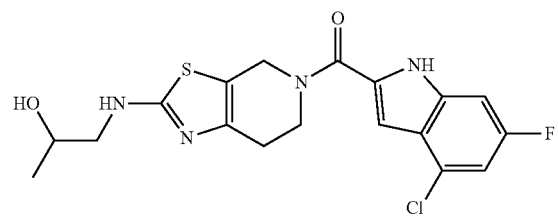 [SMILES: CC(O)CNc1nc2c(s1)CN(C(=O)c1cc3c(Cl)cc(F)cc3[nH]1)CC2]

To (2-bromo-6,7-dihydrothiazolo[5,4-c]pyridin-5(4H)-yl)(4-chloro-6-fluoro-1H-indol-2-yl)methanone (0.250 g, 0.603 mmol) was added 1-amino-propan-2-ol (0.943 ml, 12.06 mmol). The mixture was stirred at 80° C. for 20 hours. The mixture was cooled, diluted with DMSO (3 mL) then purified directly by basic reverse phase HPLC to give the desired product (0.124 g, 50% yield)

Rt (Method A) 3.40 mins, m/z 409/411 [M+H]$^+$.

Example 143

5-(6-bromo-4-fluoro-1H-indole-2-carbonyl)-4H,5H,6H,7H-[1,3]thiazolo[5,4-c]pyridin-2-amine

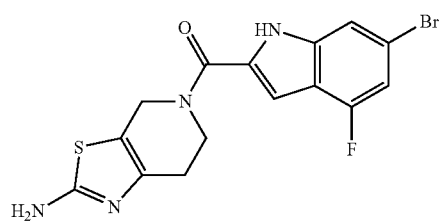

To a cooled (0° C.) solution of 6-bromo-4-fluoro-1H-indole-2-carboxylic acid (0.0499 g, 0.193 mmol) in DMF (2 mL) was added triethylamine (0.162 mL, 1.16 mmol). HATU was added (0.0810 g, 0.213 mmol) and the resulting solution stirred for 5 min. 4,5,6,7-tetrahydrothiazolo[5,4-c]pyridin-2-amine dihydrochloride (0.0300 g, 0.132 mmol) was then added. The mixture was stirred at 0° C. for 1 h, then for 2.5 h at r.t., then poured into water (40 mL), collected by filtration and dried to give the desired product (0.0540 g, 71% yield).

Rt (Method A) 3.66 mins, m/z 395/397 [M+H]$^+$.

Example 144

1-{[5-(4,7-difluoro-1H-indole-2-carbonyl)-4H,5H,
6H,7H-[1,3]thiazolo[5,4-c]pyridin-2-yl]
amino}propan-2-ol

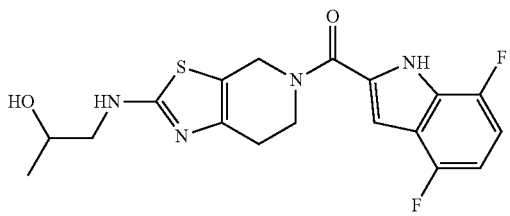 [SMILES: CC(O)CNc1nc2c(s1)CN(C(=O)c1cc3c(F)ccc(F)c3[nH]1)CC2]

To (2-bromo-6,7-dihydrothiazolo[5,4-c]pyridin-5(4H)-yl)(4,7-difluoro-1H-indol-2-yl)methanone (0.150 g, 0.377 mmol) was added 1-amino-propan-2-ol (1.000 ml, 12.78 mmol). The mixture was stirred at 80° C. for 24 hours. The mixture was concentrated, dissolved in a minimal volume of DCM, then purified by silica gel chromatography (DCM: methanol 9:1). The solid obtained was triturated with DIPE, then dried to give the desired product (0.089 g, 57% yield)

Rt (Method A) 3.41 mins, m/z 393 [M+H]$^+$.

Example 145

5-(4-nitro-1H-indole-2-carbonyl)-4H,5H,6H,7H-[1,
3]thiazolo[5,4-c]pyridin-2-amine

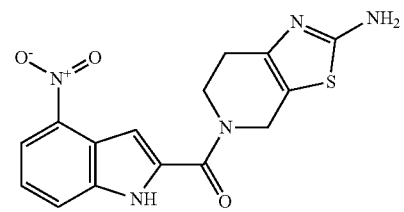 [SMILES: Nc1nc2c(s1)CN(C(=O)c1cc3c([N+](=O)[O-])cccc3[nH]1)CC2]

To a solution of 4-nitro-1H-indole-2-carboxylic acid (0.0418 g, 0.203 mmol) and 4,5,6,7-tetrahydrothiazolo[5,4-c]pyridin-2-amine dihydrochloride (0.0300 g, 0.132 mmol) in DMF (1 mL) was added triethylamine (0.134 mL, 0.96 mmol). The mixture was stirred for 15 mins, then cooled (ice bath). HATU (0.0810 g, 0.213 mmol) was added. The mixture was slowly warmed to r.t. and stirred for 24 h. The mixture was diluted with MeOH (1 mL) and MeCN (3 mL), filtered, and the filtrate purified by basic HPLC to give the desired product (0.0240 g, 32% yield).

Rt (Method A) 3.06 mins, m/z 344 [M+H]$^+$.

Example 146

5-(4-(trifluoromethyl)-1H-indole-2-carbonyl)-4H,
5H,6H,7H-[1,3]thiazolo[5,4-c]pyridin-2-amine

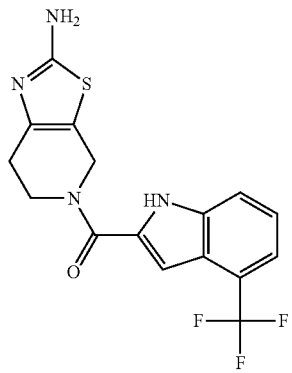 [SMILES: Nc1nc2c(s1)CN(C(=O)c1cc3c(C(F)(F)F)cccc3[nH]1)CC2]

To a solution of 4-(trifluoromethyl)-1H-indole-2-carboxylic acid (0.0465 g, 0.203 mmol) and 4,5,6,7-tetrahydrothiazolo[5,4-c]pyridin-2-amine dihydrochloride (0.0300 g, 0.132 mmol) in DMF (1 mL) was added triethylamine (0.134 mL, 0.96 mmol). The mixture was stirred for 15 mins, then cooled (ice bath). HATU (0.0810 g, 0.213 mmol) was added. The mixture was slowly warmed to r.t. and stirred for 24 h. The mixture was diluted with MeOH (1 mL) and MeCN (3 mL), filtered, and the filtrate purified by basic HPLC to give the desired product (0.0410 g, 52% yield).

Rt (Method A) 3.23 mins, m/z 367 [M+H]$^+$.

Example 147

5-(6-chloro-4-fluoro-1H-indole-2-carbonyl)-4H,5H,
6H,7H-[1,3]thiazolo[5,4-c]pyridin-2-amine

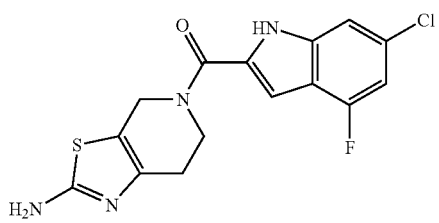 [SMILES: Nc1nc2c(s1)CN(C(=O)c1cc3c(F)cc(Cl)cc3[nH]1)CC2]

To a solution of 6-chloro-4-fluoro-1H-indole-2-carboxylic acid (0.0467 g, 0.203 mmol) and 4,5,6,7-tetrahydrothiazolo[5,4-c]pyridin-2-amine dihydrochloride (0.0300 g, 0.132 mmol) in DMF (1 mL) was added triethylamine (0.134 mL, 0.96 mmol). The mixture was stirred for 15 mins, then cooled (ice bath). EDCI (0.0408 g, 0.213 mmol) and HOAt (0.0026 mg, 0.019 mmol) were added. The mixture was slowly warmed to r.t. and stirred for 24 h. The mixture was diluted with MeOH (0.5 mL) and MeCN (2 mL), filtered, and the filtrate purified by basic HPLC to give the desired product (0.0180 g, 23% yield).

Rt (Method A) 3.22 mins, m/z 351/353 [M+H]$^+$.

Example 148

5-(6,7-dichloro-1H-indole-2-carbonyl)-4H,5H,6H,7H-[1,3]thiazolo[5,4-c]pyridin-2-amine

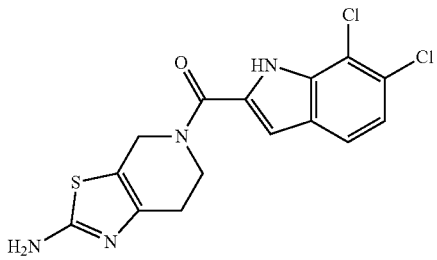 [SMILES: Nc1nc2c(s1)CN(C(=O)c1cc3ccc(Cl)c(Cl)c3[nH]1)CC2]

To a solution of 6,7-dichloro-1H-indole-2-carboxylic acid (0.0467 g, 0.203 mmol) and 4,5,6,7-tetrahydrothiazolo[5,4-c]pyridin-2-amine dihydrochloride (0.0300 g, 0.132 mmol) in DMF (1 mL) was added triethylamine (0.134 mL, 0.96 mmol). The mixture was stirred for 15 mins, then cooled (ice bath). EDCI (0.0408 g, 0.213 mmol) and HOAt (0.0026 mg, 0.019 mmol) were added. The mixture was slowly warmed to r.t. and stirred for 24 h. The mixture was diluted with MeOH (0.5 mL) and MeCN (2 mL), filtered, and the filtrate purified by basic HPLC to give the desired product (0.0160 g, 21% yield).

Rt (Method A) 3.25 mins, m/z 367/369 [M+H]$^+$.

Example 149

5-(4-methyl-1H-indole-2-carbonyl)-4H,5H,6H,7H-[1,3]thiazolo[5,4-c]pyridin-2-amine

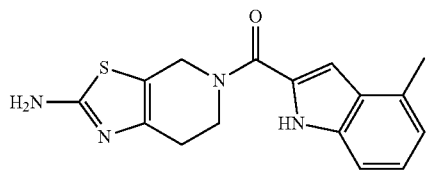 [SMILES: Cc1cccc2[nH]c(C(=O)N3CCc4nc(N)sc4C3)cc12]

To a solution of 4-methyl-1H-indole-2-carboxylic acid (0.0356 g, 0.203 mmol) and 4,5,6,7-tetrahydrothiazolo[5,4-c]pyridin-2-amine dihydrochloride (0.0300 g, 0.132 mmol) in DMF (1 mL) was added triethylamine (0.134 mL, 0.96 mmol). The mixture was stirred for 15 mins, then cooled (ice bath). EDCI (0.0408 g, 0.213 mmol) and HOAt (0.0026 mg, 0.019 mmol) were added. The mixture was slowly warmed to r.t. and stirred for 24 h. The mixture was diluted with MeOH (0.5 mL) and MeCN (2 mL), filtered, and the filtrate purified by basic HPLC to give the desired product (0.0110 g, 18% yield).

Rt (Method A) 3.02 mins, m/z 313 [M+H]$^+$.

Example 150

5-(6-methyl-1H-indole-2-carbonyl)-4H,5H,6H,7H-[1,3]thiazolo[5,4-c]pyridin-2-amine

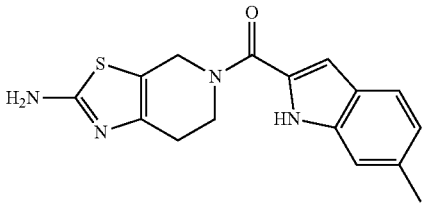 [SMILES: Cc1ccc2cc(C(=O)N3CCc4nc(N)sc4C3)[nH]c2c1]

To a solution of 6-methyl-1H-indole-2-carboxylic acid (0.0356 g, 0.203 mmol) and 4,5,6,7-tetrahydrothiazolo[5,4-c]pyridin-2-amine dihydrochloride (0.0300 g, 0.132 mmol) in DMF (1 mL) was added triethylamine (0.134 mL, 0.96 mmol). The mixture was stirred for 15 mins, then cooled (ice bath). EDCI (0.0408 g, 0.213 mmol) and HOAt (0.0026 mg, 0.019 mmol) were added. The mixture was slowly warmed to r.t. and stirred for 24 h. The mixture was diluted with MeOH (0.5 mL) and MeCN (2 mL), filtered, and the filtrate purified by basic HPLC to give the desired product (0.0120 g, 18% yield).

Rt (Method A) 3.02 mins, m/z 313 [M+H]$^+$.

Example 151

2-{2-methoxy-4H,5H,6H,7H-[1,3]thiazolo[5,4-c]pyridine-5-carbonyl}-1H-indole

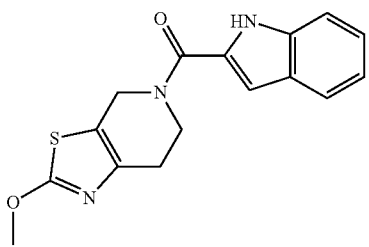 [SMILES: COc1nc2c(s1)CN(C(=O)c1cc3ccccc3[nH]1)CC2]

To a suspension of sodium hydride (0.0094 g, 0.248 mmol, 60% in oil) in THF (1 mL) was added dry methanol (0.0085 mL, 0.199 mmol) (microwave vial). The mixture was stirred for 15 mins, then (2-bromo-6,7-dihydrothiazolo[5,4-c]pyridin-5(4H)-yl)(4,7-difluoro-1H-indol-2-yl)methanone (0.030 g, 0.083 mmol) was added. The mixture was then heated in a microwave reactor at 120° C. for 1.5 h. The mixture was poured into saturated aqueous NH$_4$Cl, and extracted with EtOAc (3×25 mL). The combined extracts were dried (Na$_2$SO$_4$), filtered and concentrated, then purified by basic HPLC to give the desired product (0.0160 g, 55% yield).

Rt (Method A) 3.27 mins, m/z 314 [M+H]$^+$.

Example 152

2-{2-ethoxy-4H,5H,6H,7H-[1,3]thiazolo[5,4-c]pyridine-5-carbonyl}-1H-indole

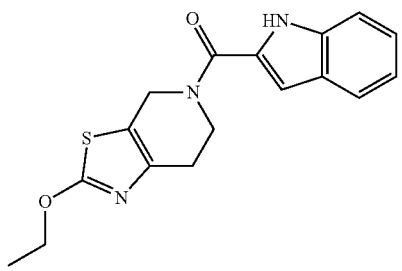 [SMILES: CCOc1nc2c(s1)CN(C(=O)c1cc3ccccc3[nH]1)CC2]

To a suspension of sodium hydride (0.0094 g, 0.248 mmol, 60% in oil) in THF (1 mL) was added dry ethanol (0.012 mL, 0.199 mmol) (microwave vial). The mixture was stirred for 15 mins, then (2-bromo-6,7-dihydrothiazolo[5,4-c]pyridin-5(4H)-yl)(4,7-difluoro-1H-indol-2-yl)methanone (0.030 g, 0.083 mmol) was added. The mixture was then heated in a microwave reactor at 120° C. for 1 h. The mixture was poured into saturated aqueous NH$_4$Cl, and extracted with EtOAc (3×25 mL). The combined extracts were washed with brine (25 mL), dried (Na$_2$SO$_4$), filtered and concentrated, then purified by basic HPLC to give the desired product (0.0090 g, 33% yield).

Rt (Method A) 3.48 mins, m/z 328 [M+H]$^+$.

Example 153

5-(7-methoxy-1H-indole-2-carbonyl)-4H,5H,6H,7H-[1,3]thiazolo[5,4-c]pyridin-2-amine

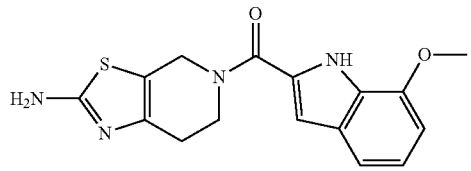 [SMILES: COc1cccc2cc(C(=O)N3CCc4nc(N)sc4C3)[nH]c12]

To a solution of 7-methoxy-1H-indole-2-carboxylic acid (0.0388 g, 0.203 mmol) and 4,5,6,7-tetrahydrothiazolo[5,4-c]pyridin-2-amine dihydrochloride (0.0300 g, 0.132 mmol) in DMF (1 mL) was added triethylamine (0.134 mL, 0.96 mmol). The mixture was stirred for 15 mins, then cooled (ice bath). EDCI (0.0408 g, 0.213 mmol) and HOAt (0.0026 mg, 0.019 mmol) were added. The mixture was slowly warmed to r.t. and stirred for 24 h. The mixture was diluted with MeOH (0.5 mL) and MeCN (2 mL), filtered, and the filtrate purified by basic HPLC to give the desired product (0.0120 g, 18% yield).

Rt (Method A) 2.87 mins, m/z 329 [M+H]$^+$.

Example 154

5-(7-chloro-1H-indole-2-carbonyl)-4H,5H,6H,7H-[1,3]thiazolo[5,4-c]pyridin-2-amine

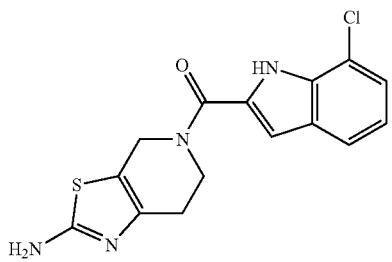

To a solution of 7-chloro-1H-indole-2-carboxylic acid (0.0283 g, 0.145 mmol) in DMF (0.8 mL) was HATU (0.0525 g, 0.138 mmol) and the resulting solution stirred for 4 min. 4,5,6,7-tetrahydrothiazolo[5,4-c]pyridin-2-amine dihydrochloride (0.0300 g, 0.132 mmol) and triethylamine (0.110 mL, 0.789 mmol) were then added. The mixture was stirred at r.t. for 20 h. The mixture diluted with DMSO (2 mL), filtered, and the filtrate purified by basic HPLC to give the desired product (0.0065 g, 15% yield).

Rt (Method A) 3.02 mins, m/z 333/335 [M+H]$^+$.

Example 155

5-(5-chloro-1H-indole-2-carbonyl)-4H,5H,6H,7H-[1,3]thiazolo[5,4-c]pyridin-2-amine

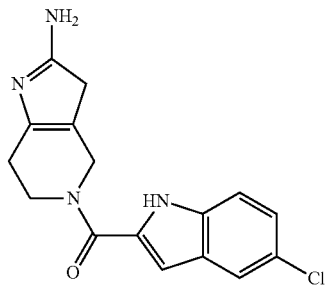 [SMILES: NC1=NC2=C(C1)CN(C(=O)c1cc3cc(Cl)ccc3[nH]1)CC2]

To a solution of 5-chloro-1H-indole-2-carboxylic acid (0.0283 g, 0.145 mmol) in DMF (0.8 mL) was HATU (0.0525 g, 0.138 mmol) and the resulting solution stirred for 4 min. 4,5,6,7-tetrahydrothiazolo[5,4-c]pyridin-2-amine dihydrochloride (0.0300 g, 0.132 mmol) and triethylamine (0.110 mL, 0.789 mmol) were then added. The mixture was stirred at r.t. for 72 h. The mixture diluted with DMSO (2 mL), filtered, and the filtrate purified by basic HPLC to give the desired product (0.0290 g, 66% yield).

Rt (Method A) 3.08 mins, m/z 333/335 [M+H]$^+$.

Example 156

5-(6-chloro-1H-indole-2-carbonyl)-4H,5H,6H,7H-[1,3]thiazolo[5,4-c]pyridin-2-amine

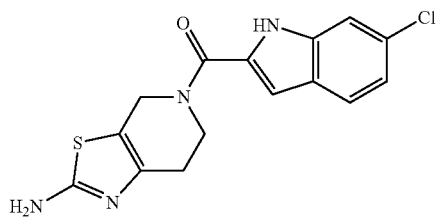 [SMILES: Nc1nc2c(s1)CN(C(=O)c1cc3ccc(Cl)cc3[nH]1)CC2]

To a solution of 6-chloro-1H-indole-2-carboxylic acid (0.0283 g, 0.145 mmol) in DMF (0.8 mL) was HATU (0.0525 g, 0.138 mmol) and the resulting solution stirred for 4 min. 4,5,6,7-tetrahydrothiazolo[5,4-c]pyridin-2-amine dihydrochloride (0.0300 g, 0.132 mmol) and triethylamine (0.110 mL, 0.789 mmol) were then added. The mixture was stirred at r.t. for 72 h. The mixture diluted with DMSO (2 mL), filtered, and the filtrate purified by basic HPLC to give the desired product (0.0161 g, 37% yield).

Rt (Method B) 2.54 mins, m/z 333/335 [M+H]$^+$.

Example 157

2-{[5-(1H-indole-2-carbonyl)-4H,5H,6H,7H-[1,3]thiazolo[5,4-c]pyridin-2-yl]amino}ethan-1-ol

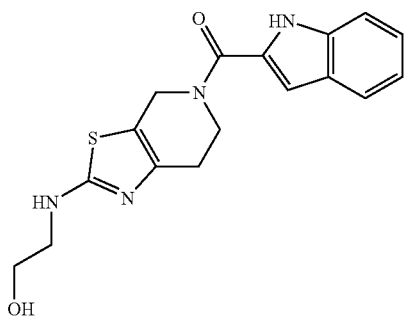 [SMILES: O=C(c1cc2ccccc2[nH]1)N1CCc2nc(NCCO)sc2C1]

To (2-bromo-6,7-dihydrothiazolo[5,4-c]pyridin-5(4H)-yl)(1H-indol-2-yl)methanone (0.030 g, 0.083 mmol) was added 2-amino-ethan-1-ol (1.500 ml, 24.85 mmol). The mixture was stirred at 70° C. for 20 hours. The mixture was then purified directly by basic reverse phase HPLC to give the desired product (0.0119 g, 42% yield)

Rt (Method A) 2.82 mins, m/z 343 [M+H]$^+$.

Example 158

2-[2-(benzyloxy)-4H,5H,6H,7H-[1,3]thiazolo[5,4-c]pyridine-5-carbonyl]-1H-indole

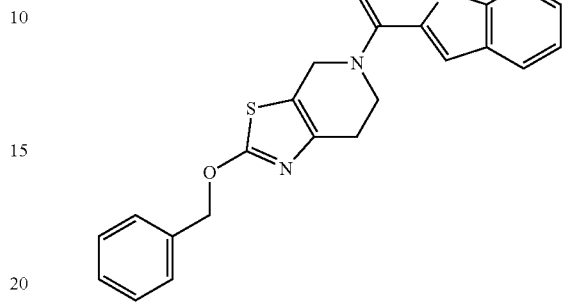

To a suspension of sodium hydride (0.0050 g, 0.1 mmol, 60% in oil) in THF (1 mL) was added benzyl alcohol (0.0102 mL, 0.099 mmol) (microwave vial). The mixture was stirred for 15 mins, then (2-bromo-6,7-dihydrothiazolo[5,4-c]pyridin-5(4H)-yl)(1H-indol-2-yl)methanone (0.030 g, 0.083 mmol) was added. The mixture was then heated in a microwave reactor at 120° C. for 1 h. The mixture was poured into saturated aqueous NH$_4$Cl, and extracted with EtOAc (3×25 mL). The combined extracts washed with brine (25 mL), dried (Na$_2$SO$_4$), filtered and concentrated, then purified by basic HPLC to give the desired product (0.0100 g, 30% yield).

Rt (Method A) 3.86 mins, m/z 390 [M+H]$^+$.

Example 159

5-(5,6-difluoro-1H-indole-2-carbonyl)-4H,5H,6H,7H-[1,3]thiazolo[5,4-c]pyridin-2-amine

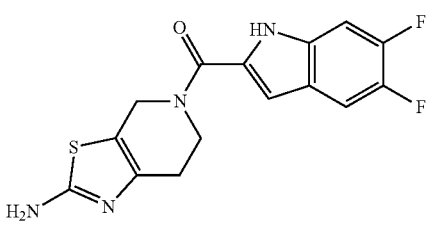 [SMILES: Nc1nc2c(s1)CN(C(=O)c1cc3cc(F)c(F)cc3[nH]1)CC2]

To a solution of 5,6-difluoro-1H-indole-2-carboxylic acid (0.0270 g, 0.138 mmol) and 4,5,6,7-tetrahydrothiazolo[5,4-c]pyridin-2-amine dihydrochloride (0.0300 g, 0.132 mmol) in DMF (1.5 mL) was added triethylamine (0.091 mL, 0.658 mmol). EDCI (0.0280 g, 0.213 mmol) and HOAt (0.0018 mg, 0.013 mmol) were added. The mixture was stirred for 24 h. The mixture was diluted with MeCN (1.5 mL) and purified by basic HPLC to give the desired product (0.0070 g, 14% yield).

Rt (Method B) 2.44 mins, m/z 335 [M+H]$^+$.

Example 160

5-(5,7-difluoro-1H-indole-2-carbonyl)-4H,5H,6H,7H-[1,3]thiazolo[5,4-c]pyridin-2-amine

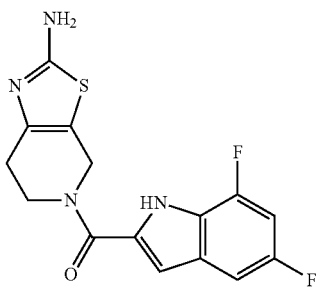 [SMILES: Nc1nc2c(s1)CN(C(=O)c1cc3cc(F)cc(F)c3[nH]1)CC2]

To a solution of 5,7-difluoro-1H-indole-2-carboxylic acid (0.0270 g, 0.138 mmol) and 4,5,6,7-tetrahydrothiazolo[5,4-c]pyridin-2-amine dihydrochloride (0.0300 g, 0.132 mmol) in DMF (1.5 mL) was added triethylamine (0.091 mL, 0.658 mmol). EDCI (0.0280 g, 0.213 mmol) and HOAt (0.0018 mg, 0.013 mmol) were added. The mixture was stirred for 24 h. The mixture was diluted with MeCN (1.5 mL) and purified by basic HPLC to give the desired product (0.0070 g, 14% yield).

Rt (Method B) 2.40 mins, m/z 335 [M+H]$^+$.

Example 161

5-chloro-2-{2-methyl-4H,5H,6H,7H-[1,3]thiazolo[5,4-c]pyridine-5-carbonyl}-1H-indole

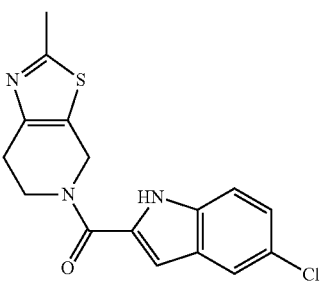 [SMILES: Cc1nc2c(s1)CN(C(=O)c1cc3cc(Cl)ccc3[nH]1)CC2]

To 5-chloro-1H-indole-2-carboxylic acid (0.0283 g, 0.145 mmol) was added HATU (0.0509 g, 0.134 mmol) as a solution in DMF (0.4 mL), followed by triethylamine (0.089 ml, 0.638 mmol) as a solution in DMF (0.4 mL). The mixture was stirred for 30 min, then 2-methyl-4,5,6,7-tetrahydrothiazolo[5,4-c]pyridine hydrobromide (0.0300 g, 0.128 mmol) was added. The mixture was stirred at r.t. for 48 h. The mixture was filtered, rinsing with MeOH and the filtrate purified by basic HPLC to give the desired product.

Rt (Method A) 3.34 mins, m/z 332/334 [M+H]$^+$.

Example 162

5-(6-chloro-1H-indole-2-carbonyl)-4H,5H,6H,7H-[1,3]thiazolo[5,4-c]pyridin-2-amine

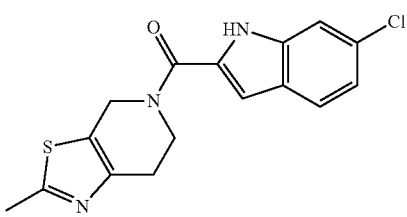 [SMILES: Cc1nc2c(s1)CN(C(=O)c1cc3ccc(Cl)cc3[nH]1)CC2]

Rt (Method A) 3.35 mins, m/z 332/334 [M+H]$^+$.

Example 163

5-(5,7-difluoro-1H-indole-2-carbonyl)-4H,5H,6H,7H-[1,3]thiazolo[5,4-c]pyridin-2-amine

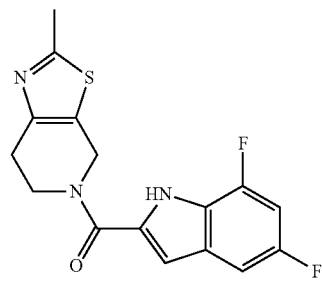 [SMILES: Cc1nc2c(s1)CN(C(=O)c1cc3cc(F)cc(F)c3[nH]1)CC2]

Rt (Method A) 3.22 mins, m/z 334 [M+H]$^+$.

Example 164

5-(5,6-difluoro-1H-indole-2-carbonyl)-4H,5H,6H,7H-[1,3]thiazolo[5,4-c]pyridin-2-amine

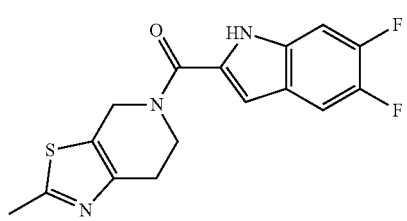 [SMILES: Cc1nc2c(s1)CN(C(=O)c1cc3cc(F)c(F)cc3[nH]1)CC2]

Rt (Method A) 3.24 mins, m/z 334 [M+H]$^+$.

Example 165

5-(4-fluoro-6-chloro-1H-indole-2-carbonyl)-4H,5H,6H,7H-[1,3]thiazolo[5,4-c]pyridin-2-amine

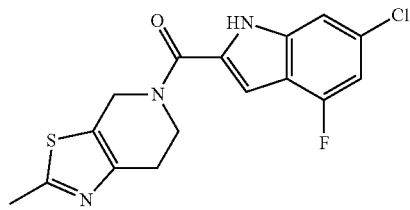 [SMILES: Cc1nc2c(s1)CN(C(=O)c1cc3c(F)cc(Cl)cc3[nH]1)CC2]

Rt (Method A) 3.47 mins, m/z 350/352 [M+H]$^+$.

Example 166

2-[2-(morpholin-4-yl)-4H,5H,6H,7H-[1,3]thiazolo[5,4-c]pyridine-5-carbonyl]-1H-indole

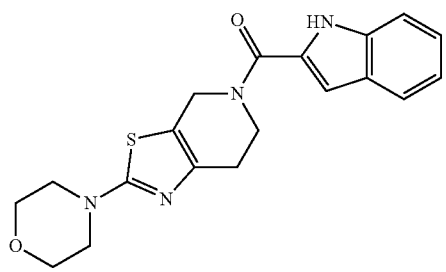 [SMILES: O=C(c1cc2ccccc2[nH]1)N1CCc2nc(N3CCOCC3)sc2C1]

To (2-bromo-6,7-dihydrothiazolo[5,4-c]pyridin-5(4H)-yl)(1H-indol-2-yl)methanone (0.030 g, 0.083 mmol) was added morpholine (0.500 ml, 5.72 mmol). The mixture was stirred at 60° C. for 5 hours. The mixture was cooled, diluted with MeCN (2 mL) then purified directly by acidic reverse phase HPLC to give the desired product (0.016 g, 50% yield)

Rt (Method B) 3.01 mins, m/z 369 [M+H]$^+$.

Example 167

5-(4-chloro-6-fluoro-1H-indole-2-carbonyl)-4H,5H,6H,7H-[1,3]thiazolo[5,4-c]pyridin-2-amine

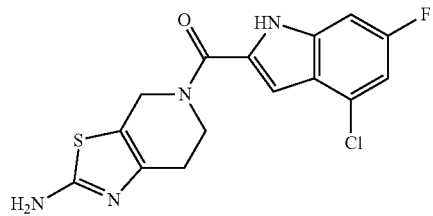 [SMILES: Nc1nc2c(s1)CN(C(=O)c1cc3c(Cl)cc(F)cc3[nH]1)CC2]

To (4-chloro-6-fluoro)-1H-indole-2-carboxylic acid (0.0310 g, 0.145 mmol) was added HATU (0.0526 g, 0.138 mmol) as a solution in DMF (0.4 mL), followed by 4,5,6,7-tetrahydrothiazolo[5,4-c]pyridin-2-amine dihydrochloride (0.0300 g, 0.132 mmol). Triethylamine (0.110 ml, 0.791 mmol) as a solution in DMF (0.4 mL) was then added and the mixture stirred for 72 h. The mixture was purified by basic HPLC to give the desired product.

Rt (Method A) 3.14 mins, m/z 351/353 [M+H]$^+$.

Example 168

5-(4,6-dichloro-1H-indole-2-carbonyl)-4H,5H,6H,7H-[1,3]thiazolo[5,4-c]pyridin-2-amine

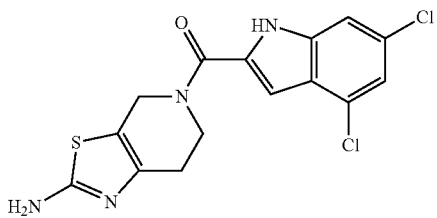 [SMILES: Nc1nc2c(s1)CN(C(=O)c1cc3c(Cl)cc(Cl)cc3[nH]1)CC2]

Rt (Method A) 3.32 mins, m/z 367/369 [M+H]$^+$.

Example 169

5-(6-fluoro-4-methyl-1H-indole-2-carbonyl)-4H,5H,6H,7H-[1,3]thiazolo[5,4-c]pyridin-2-amine

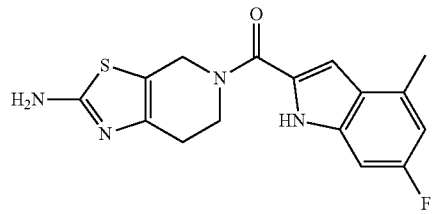 [SMILES: Cc1cc(F)cc2[nH]c(C(=O)N3CCc4nc(N)sc4C3)cc12]

Rt (Method A) 3.04 mins, m/z 331 [M+H]$^+$.

Example 170

5-(4,7-difluoro-1H-indole-2-carbonyl)-4H,5H,6H,7H-[1,3]thiazolo[5,4-c]pyridin-2-amine

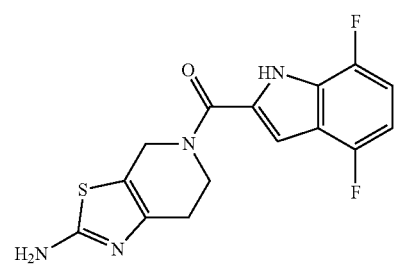

Rt (Method A) 2.96 mins, m/z 335 [M+H]$^+$.

Example 171

5-(7-bromo-1H-indole-2-carbonyl)-4H,5H,6H,7H-[1,3]thiazolo[5,4-c]pyridin-2-amine

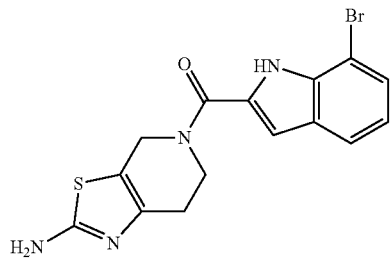 [SMILES: Nc1nc2c(s1)CN(C(=O)c1cc3cccc(Br)c3[nH]1)CC2]

Rt (Method A) 3.08 mins, m/z 378/380 [M+H]$^+$.

Example 172

5-(4,5-difluoro-1H-indole-2-carbonyl)-4H,5H,6H,7H-[1,3]thiazolo[5,4-c]pyridin-2-amine

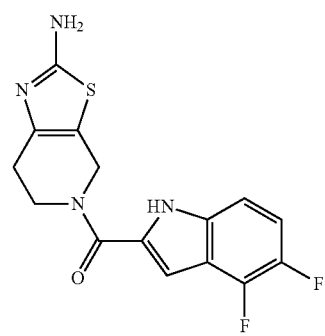 [SMILES: Nc1nc2c(s1)CN(C(=O)c1cc3c(F)c(F)ccc3[nH]1)CC2]

Rt (Method A) 2.99 mins, m/z 335 [M+H]$^+$.

Example 173

5-(7-(difluoromethoxy)-1H-indole-2-carbonyl)-4H,5H,6H,7H-[1,3]thiazolo[5,4-c]pyridin-2-amine

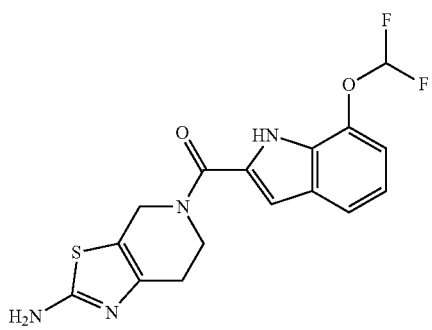 [SMILES: Nc1nc2c(s1)CN(C(=O)c1cc3cccc(OC(F)F)c3[nH]1)CC2]

Rt (Method A) 3.00 mins, m/z 365 [M+H]$^+$.

Example 174

5-(7-(trifluoromethoxy)-1H-indole-2-carbonyl)-4H,5H,6H,7H-[1,3]thiazolo[5,4-c]pyridin-2-amine

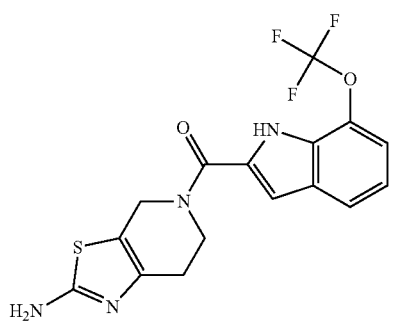 [SMILES: Nc1nc2c(s1)CN(C(=O)c1cc3cccc(OC(F)(F)F)c3[nH]1)CC2]

Rt (Method A) 3.21 mins, m/z 383 [M+H]$^+$.

Example 175

5-(7-methyl-1H-indole-2-carbonyl)-4H,5H,6H,7H-[1,3]thiazolo[5,4-c]pyridin-2-amine

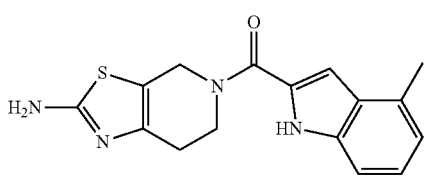 [SMILES: Cc1cccc2[nH]c(C(=O)N3CCc4nc(N)sc4C3)cc12]

Rt (Method A) 2.98 mins, m/z 313 [M+H]$^+$.

Example 176

5-(4,5-dichloro-1H-indole-2-carbonyl)-4H,5H,6H,7H-[1,3]thiazolo[5,4-c]pyridin-2-amine

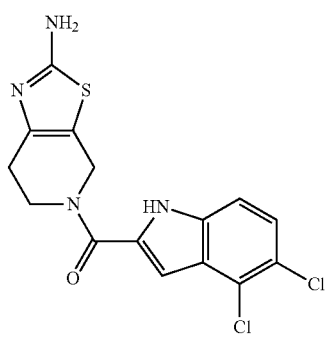 [SMILES: Nc1nc2c(s1)CN(C(=O)c1cc3c(Cl)c(Cl)ccc3[nH]1)CC2]

Rt (Method A) 3.24 mins, m/z 367/369 [M+H]$^+$.

Example 177

5-(4,7-dichloro-1H-indole-2-carbonyl)-4H,5H,6H,7H-[1,3]thiazolo[5,4-c]pyridin-2-amine

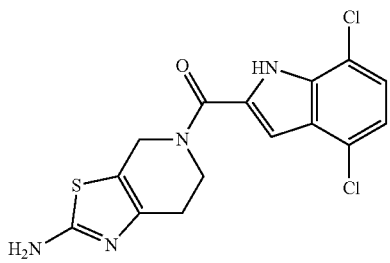 [SMILES: Nc1nc2c(s1)CN(C(=O)c1cc3c(Cl)ccc(Cl)c3[nH]1)CC2]

Rt (Method A) 3.23 mins, m/z 367/369 [M+H]⁺.

Example 178

1-{[5-(1H-indole-2-carbonyl)-4H,5H,6H,7H-[1,3]thiazolo[5,4-c]pyridin-2-yl]amino}propan-2-ol

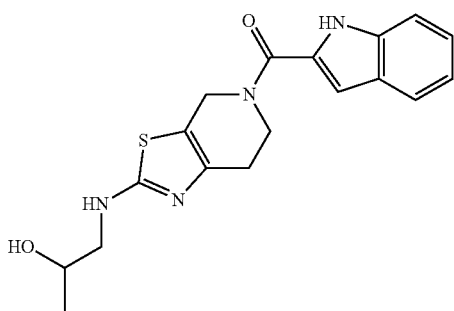

To (2-bromo-6,7-dihydrothiazolo[5,4-c]pyridin-5(4H)-yl)(1H-indol-2-yl)methanone (0.030 g, 0.083 mmol) was added 1-amino-propan-2-ol (1.503 ml, 19.21 mmol). The mixture was stirred at 50° C. for 20 hours. The mixture was then purified directly by basic reverse phase HPLC to give the desired product (0.0300 g, 36% yield)

Rt (Method A) 3.11 mins, m/z 357 [M+H]⁺.

Example 179

N1-[5-(1H-indole-2-carbonyl)-4H,5H,6H,7H-[1,3]thiazolo[5,4-c]pyridin-2-yl]ethane-1,2-diamine

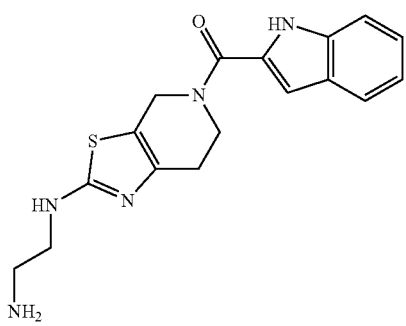 [SMILES: NCCNc1nc2c(s1)CN(C(=O)c1cc3ccccc3[nH]1)CC2]

To (2-bromo-6,7-dihydrothiazolo[5,4-c]pyridin-5(4H)-yl)(1H-indol-2-yl)methanone (0.030 g, 0.083 mmol) was added ethane-1,2-diamine (1.552 ml, 23.19 mmol). The mixture was stirred at 36° C. for 20 hours. The mixture was then purified directly by basic reverse phase HPLC to give the desired product (0.0225 g, 79% yield)

Rt (Method B) 2.06 mins, m/z 342 [M+H]⁺.

Example 180

5-(1H-indole-2-carbonyl)-N-(oxolan-3-yl)-4H,5H,6H,7H-[1,3]thiazolo[5,4-c]pyridin-2-amine

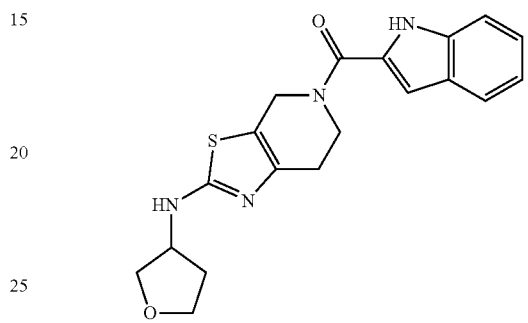

To (2-bromo-6,7-dihydrothiazolo[5,4-c]pyridin-5(4H)-yl)(1H-indol-2-yl)methanone (0.030 g, 0.083 mmol) was added tetrahydrofuran-3-amine (0.250 mL, 2.90 mmol). The mixture was stirred at 60° C. for 96 hours. The mixture was then purified directly by basic reverse phase HPLC to give the desired product (0.0023 g, 7% yield)

Rt (Method A) 3.22 mins, m/z 369 [M+H]⁺.

Example 181

5-(1H-indole-2-carbonyl)-N-[2-(4-methylpiperazin-1-yl)ethyl]-4H,5H,6H,7H-[1,3]thiazolo[5,4-c]pyridin-2-amine

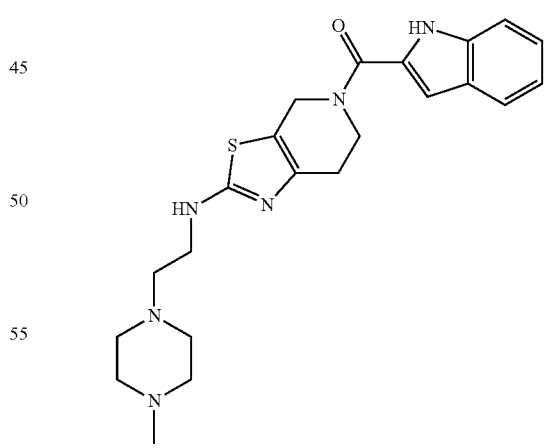

To (2-bromo-6,7-dihydrothiazolo[5,4-c]pyridin-5(4H)-yl)(1H-indol-2-yl)methanone (0.030 g, 0.083 mmol) was added 2-(4-methylpiperizan-1-yl)ethan-1-amine (0.248 mL, 1.656 mmol). The mixture was stirred at 60° C. for 48 hours. The mixture was purified directly by basic reverse phase HPLC to give the desired product (0.0053 g, 15% yield)

Rt (Method A) 2.90 mins, m/z 425 [M+H]⁺.

Example 182

7-(difluoromethoxy)-2-{2-methyl-4H,5H,6H,7H-[1,3]thiazolo[5,4-c]pyridine-5-carbonyl}-1H-indole

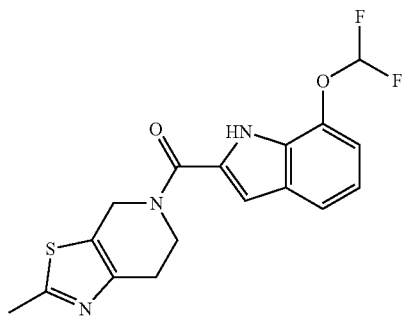 [SMILES: Cc1nc2c(s1)CN(C(=O)c1cc3cccc(OC(F)F)c3[nH]1)CC2]

To (7-difluoromethoxy)-1H-indole-2-carboxylic acid (0.0320 g, 0.141 mmol) was added HATU (0.0509 g, 0.134 mmol) as a solution in DMF (0.4 mL), followed by 2-methyl-4,5,6,7-tetrahydrothiazolo[5,4-c]pyridine hydrobromide (30 mg, 0.128 mmol). Triethylamine (0.071 ml, 0.51 mmol) as a solution in DMF (0.4 mL) was then added and the mixture stirred for 24 h. Water (1 drop) was added, the mixture filtered and the filtrate purified by basic HPLC to give the desired product.

Rt (Method A) 3.25 mins, m/z 364 [M+H]$^+$.

Example 183

2-{2-methyl-4H,5H,6H,7H-[1,3]thiazolo[5,4-c]pyridine-5-carbonyl}-7-(trifluoromethoxy)-1H-indole

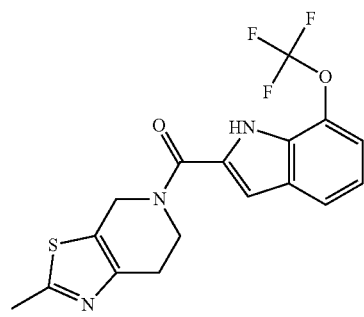 [SMILES: Cc1nc2c(s1)CN(C(=O)c1cc3cccc(OC(F)(F)F)c3[nH]1)CC2]

Rt (Method A) 3.49 mins, m/z 382 [M+H]$^+$.

Example 184

4-methyl-2-{2-methyl-4H,5H,6H,7H-[1,3]thiazolo[5,4-c]pyridine-5-carbonyl}-1H-indole

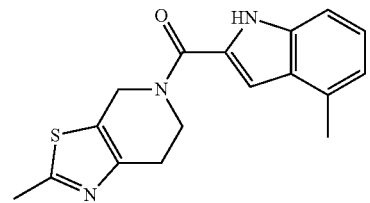 [SMILES: Cc1nc2c(s1)CN(C(=O)c1cc3c(C)cccc3[nH]1)CC2]

Rt (Method A) 3.24 mins, m/z 312 [M+H]$^+$.

Example 185

4,5-dichloro-2-{2-methyl-4H,5H,6H,7H-[1,3]thiazolo[5,4-c]pyridine-5-carbonyl}-1H-indole

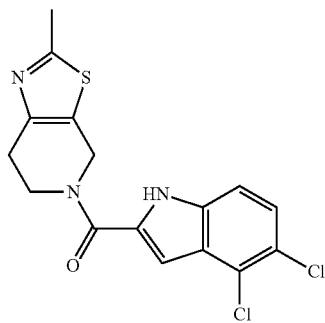 [SMILES: Cc1nc2c(s1)CN(C(=O)c1cc3c(Cl)c(Cl)ccc3[nH]1)CC2]

Rt (Method A) 3.53 mins, m/z 366/368 [M+H]$^+$.

Example 186

4,7-dichloro-2-{2-methyl-4H,5H,6H,7H-[1,3]thiazolo[5,4-c]pyridine-5-carbonyl}-1H-indole

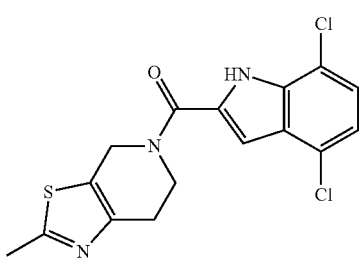 [SMILES: Cc1nc2c(s1)CN(C(=O)c1cc3c(Cl)ccc(Cl)c3[nH]1)CC2]

Rt (Method A) 3.53 mins, m/z 366/368 [M+H]$^+$.

Example 187

4-chloro-6-fluoro-2-{2-methyl-4H,5H,6H,7H-[1,3]
thiazolo[5,4-c]pyridine-5-carbonyl}-1H-indole

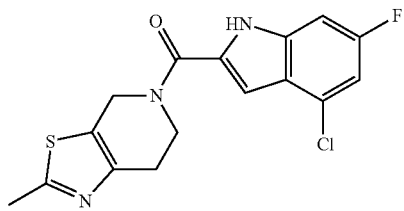 [SMILES: Cc1nc2c(s1)CN(C(=O)c1cc3c(Cl)cc(F)cc3[nH]1)CC2]

Rt (Method A) 3.44 mins, m/z 350/352 [M+H]$^+$.

Example 188

4,6-dichloro-2-{2-methyl-4H,5H,6H,7H-[1,3]thi-
azolo[5,4-c]pyridine-5-carbonyl}-1H-indole

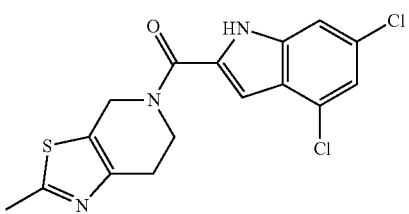 [SMILES: Cc1nc2c(s1)CN(C(=O)c1cc3c(Cl)cc(Cl)cc3[nH]1)CC2]

Rt (Method A) 3.64 mins, m/z 366/368 [M+H]$^+$.

Example 189

7-chloro-2-{2-methyl-4H,5H,6H,7H-[1,3]thiazolo[5,
4-c]pyridine-5-carbonyl}-1H-indole

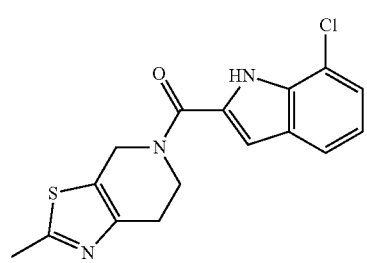 [SMILES: Cc1nc2c(s1)CN(C(=O)c1cc3cccc(Cl)c3[nH]1)CC2]

Rt (Method A) 3.29 mins, m/z 332/334 [M+H]$^+$.

Example 190

6-fluoro-4-methyl-2-{2-methyl-4H,5H,6H,7H-[1,3]
thiazolo[5,4-c]pyridine-5-carbonyl}-1H-indole

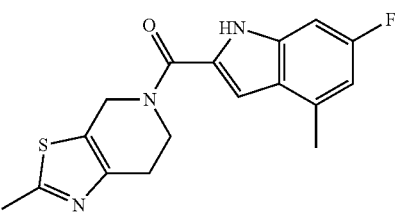 [SMILES: Cc1nc2c(s1)CN(C(=O)c1cc3c(C)cc(F)cc3[nH]1)CC2]

Rt (Method A) 3.31 mins, m/z 330 [M+H]$^+$.

Example 191

4,7-difluoro-2-{2-methyl-4H,5H,6H,7H-[1,3]thi-
azolo[5,4-c]pyridine-5-carbonyl}-1H-indole

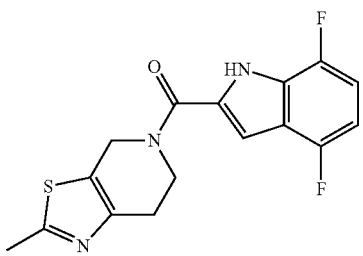

Rt (Method A) 3.23 mins, m/z 334 [M+H]$^+$.

Example 192

7-bromo-2-{2-methyl-4H,5H,6H,7H-[1,3]thiazolo[5,
4-c]pyridine-5-carbonyl}-1H-indole

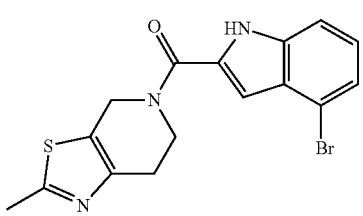 [SMILES: Cc1nc2c(s1)CN(C(=O)c1cc3c(Br)cccc3[nH]1)CC2]

Rt (Method A) 3.38 mins, m/z 377/379 [M+H]$^+$.

Example 193

4,5-difluoro-2-{2-methyl-4H,5H,6H,7H-[1,3]thiazolo[5,4-c]pyridine-5-carbonyl}-1H-indole

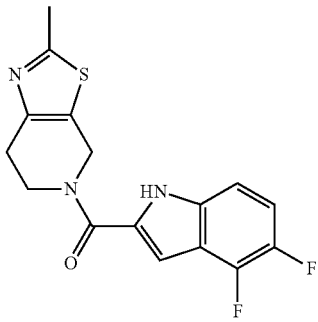 [SMILES: Cc1nc2c(s1)CN(C(=O)c1cc3c(F)c(F)ccc3[nH]1)CC2]

Rt (Method A) 3.26 mins, m/z 334 [M+H]⁺.

Example 194

4-methoxy-2-{2-methyl-4H,5H,6H,7H-[1,3]thiazolo[5,4-c]pyridine-5-carbonyl}-1H-indole

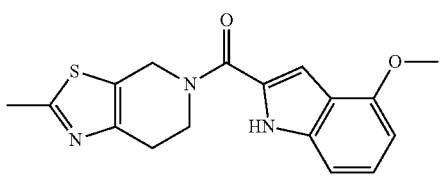

Rt (Method A) 3.10 mins, m/z 328 [M+H]⁺.

Example 195

5-(4-fluoro-1H-indole-2-carbonyl)-4H,5H,6H,7H-[1,3]thiazolo[5,4-c]pyridin-2-amine

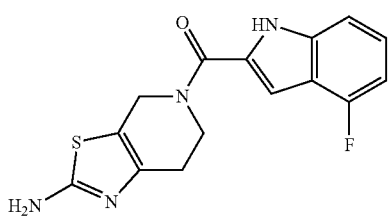 [SMILES: Nc1nc2c(s1)CN(C(=O)c1cc3c(F)cccc3[nH]1)CC2]

Rt (Method B) 2.37 mins, m/z 317 [M+H]⁺.

Example 196

5-(5-fluoro-1H-indole-2-carbonyl)-4H,5H,6H,7H-[1,3]thiazolo[5,4-c]pyridin-2-amine

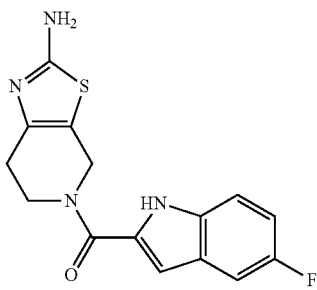 [SMILES: Nc1nc2c(s1)CN(C(=O)c1cc3cc(F)ccc3[nH]1)CC2]

Rt (Method B) 2.33 mins, m/z 317 [M+H]⁺.

Example 197

5-(6-fluoro-1H-indole-2-carbonyl)-4H,5H,6H,7H-[1,3]thiazolo[5,4-c]pyridin-2-amine

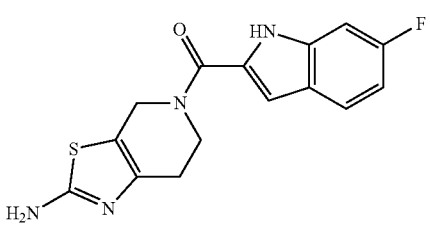 [SMILES: Nc1nc2c(s1)CN(C(=O)c1cc3ccc(F)cc3[nH]1)CC2]

Rt (Method B) 2.34 mins, m/z 317 [M+H]⁺.

Example 198—Intentionally Left Blank

Example 199

5-[6-(trifluoromethyl)-1H-indole-2-carbonyl]-4H,5H,6H,7H-[1,3]thiazolo[5,4-c]pyridin-2-amine

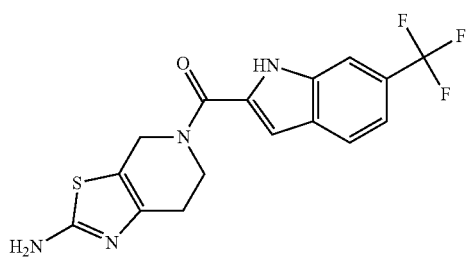 [SMILES: Nc1nc2c(s1)CN(C(=O)c1cc3ccc(C(F)(F)F)cc3[nH]1)CC2]

Rt (Method B) 2.49 mins, m/z 368 [M+H]⁺.

Example 200

2-{4H,5H,6H,7H-[1,3]thiazolo[5,4-c]pyridine-5-carbonyl}-1H-indole

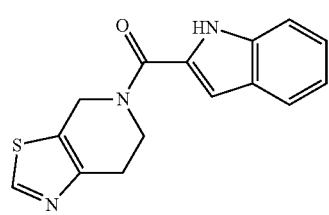 [SMILES: O=C(c1cc2ccccc2[nH]1)N1CCc2ncsc2C1]

To 1H-indole-2-carboxylic acid (0.0230 g, 0.141 mmol) in DMF (0.3 mL) was added triethylamine (0.150 mL, 1.079 mmol) and HATU (0.0560 g, 0.148 mmol). The mixture was stirred for 30 min, then 4,5,6,7-tetrahydrothiazolo[5,4-c]pyridine dihydrochloride (0.030 g, 0.141 mmol) was added. The mixture was stirred for 2 h then filtered and the filtrate purified by basic HPLC to give the desired product (0.015 g, 37% yield).

Rt (Method A) 2.98 mins, m/z 284 [M+H]$^+$.

Example 201

5-(1H-indole-2-carbonyl)-4H,5H,6H,7H-[1,3]thiazolo[5,4-c]pyridine-2-carboxamide

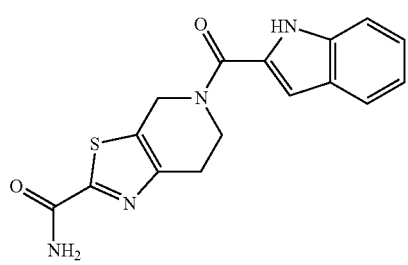 [SMILES: NC(=O)c1nc2c(s1)CN(C(=O)c1cc3ccccc3[nH]1)CC2]

To a cooled (0° C.) solution of 1H-indole-2-carboxylic acid (0.0130 g, 0.078 mmol), 4,5,6,7-tetrahydrothiazolo[5,4-c]pyridine-2-carboxamide 2,2,2-trifluoroacetate (0.022 g, 0.074 mmol) and triethylamine (0.051 mL, 0.7 mmol) in DMF (2 mL) was added EDCI (0.0160 g, 0.081 mmol) and HOAt (0.001 g, 0.007 mmol). The mixture was slowly warmed to r.t. and stirred for 20 h. The mixture was diluted with MeCN (2 mL) and purified by basic HPLC to give the desired product (0.010 g, 40% yield).

Rt (Method A) 2.85 mins, m/z 327 [M+H]$^+$.

Example 202

2-[2-(pyrimidin-2-yl)-4H,5H,6H,7H-[1,3]thiazolo[5,4-c]pyridine-5-carbonyl]-1H-indole

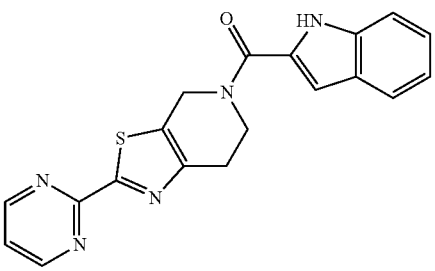 [SMILES: O=C(c1cc2ccccc2[nH]1)N1CCc2nc(-c3ncccn3)sc2C1]

To a cooled (0° C.) solution of 1H-indole-2-carboxylic acid (0.0170 g, 0.104 mmol), 2-(pyrimidin-2-yl)-4,5,6,7-tetrahydrothiazolo[5,4-c]pyridine 2,2,2-trifluoroacetate (0.033 g, 0.099 mmol) and triethylamine (0.069 mL, 0.7 mmol) in DMF (2 mL) was added EDCI (0.0210 g, 0.109 mmol) and HOAt (0.0013 g, 0.010 mmol). The mixture was slowly warmed to r.t. and stirred for 48 h. The mixture was diluted with MeCN (2 mL) and purified by basic HPLC to give the desired product (0.025 g, 66% yield).

Rt (Method A) 3.04 mins, m/z 362 [M+H]$^+$.

Example 203

5-(1H-indole-2-carbonyl)-4H,5H,6H,7H-[1,3]thiazolo[5,4-c]pyridine-2-carbonitrile

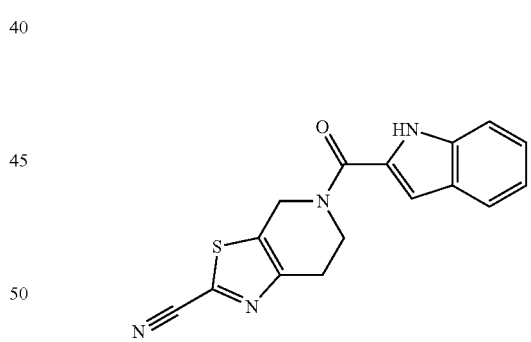

To a cooled (0° C.) solution of 1H-indole-2-carboxylic acid (0.0072 g, 0.045 mmol), 4,5,6,7-tetrahydrothiazolo[5,4-c]pyridine-2-carbonitrile 2,2,2-trifluoroacetate (0.012 g, 0.043 mmol) and triethylamine (0.030 mL, 0.21 mmol) in DMF (2 mL) was added EDCI (0.0091 g, 0.047 mmol) and HOAt (0.0006 g, 0.047 mmol). The mixture was slowly warmed to r.t. and stirred for 20 h. The mixture was diluted with MeCN (2 mL) and purified by basic HPLC to give the desired product (0.005 g, 36% yield).

Rt (Method A) 3.29 mins, m/z 309 [M+H]$^+$.

Example 204

5-(1H-indole-2-carbonyl)-N,N-dimethyl-4H,5H,6H,7H-[1,3]thiazolo[5,4-c]pyridin-2-amine

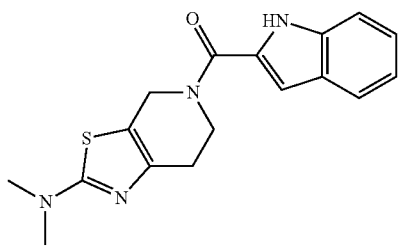 [SMILES: CN(C)c1nc2c(s1)CN(C(=O)c1cc3ccccc3[nH]1)CC2]

To a cooled (0° C.) solution of 1H-indole-2-carboxylic acid (0.0160 g, 0.100 mmol), N,N-dimethyl-4,5,6,7-tetrahydrothiazolo[5,4-c]pyridine-2-amine bis(2,2,2-trifluoroacetate) (0.039 g, 0.095 mmol) and triethylamine (0.066 mL, 0.47 mmol) in DMF (2 mL) was added EDCI (0.020 g, 0.104 mmol) and HOAt (0.0012 g, 0.094 mmol). The mixture was slowly warmed to r.t. and stirred for 48 h. The mixture was diluted with MeCN (2 mL) and purified by basic HPLC to give the desired product (0.004 g, 12% yield).

Rt (Method A) 3.19 mins, m/z 327 [M+H]$^+$.

Example 205

N-[(2,2-dimethyl-1,3-dioxolan-4-yl)methyl]-5-(1H-indole-2-carbonyl)-4H,5H,6H,7H-[1,3]thiazolo[5,4-c]pyridin-2-amine

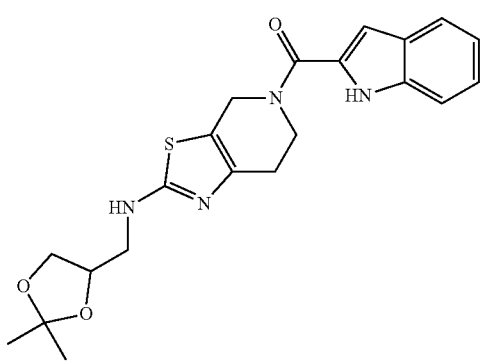 [SMILES: CC1(C)OCC(CNc2nc3c(s2)CN(C(=O)c2cc4ccccc4[nH]2)CC3)O1]

Rt (Method A) 3.17 mins, m/z 413 [M+H]$^+$.

$^1$H NMR (400 MHz, Chloroform-d) δ 9.11 (s, 1H), 7.70 (d, J=8.0 Hz, 1H), 7.45 (d, J=8.1 Hz, 1H), 7.32 (dd, J=7.2 Hz, 1H), 7.18 (dd, J=7.5 Hz, 1H), 6.89 (s, 1H), 5.21 (t, J=5.3 Hz, 2H), 5.15-4.67 (m, 2H), 4.44-4.35 (m, 1H), 4.34-4.14 (m, 2H), 4.11 (dd, J=8.3, 6.5 Hz, 1H), 3.77 (dd, J=8.3, 6.2 Hz, 1H), 3.64-3.55 (m, 1H), 3.43-3.33 (m, 1H), 2.97-2.81 (m, 2H), 1.48 (s, 3H), 1.39 (s, 3H).

Example 206

5-(1H-indole-2-carbonyl)-N-(oxan-4-yl)-4H,5H,6H,7H-[1,3]thiazolo[5,4-c]pyridin-2-amine

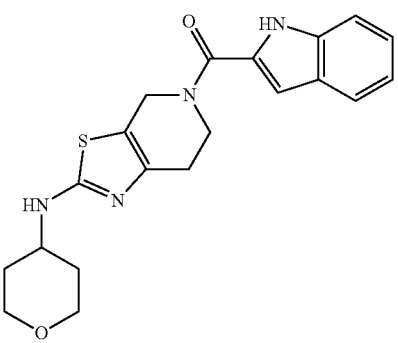 [SMILES: O=C(c1cc2ccccc2[nH]1)N1CCc2nc(NC3CCOCC3)sc2C1]

Rt (Method A) 3.03 mins, m/z 383 [M+H]$^+$.

$^1$H NMR (400 MHz, d6-DMSO) δ 11.62 (s, 1H), 7.62 (d, J=8.0 Hz, 1H), 7.52 (d, J=7.3 Hz, 1H), 7.42 (d, J=8.2 Hz, 1H), 7.19 (dd, J=7.3 Hz, 1H), 7.06 (dd, J=7.4 Hz, 1H), 6.92-6.86 (m, 1H), 5.17-4.29 (m, 2H), 4.05-3.91 (m, 2H), 3.88-3.78 (m, 2H), 3.75-3.63 (m, 1H), 3.44-3.36 (m, 2H), 2.73-2.61 (m, 2H), 1.94-1.83 (m, 2H), 1.48-1.34 (m, 2H).

Example 207

2-{2-chloro-4H,5H,6H,7H-[1,3]thiazolo[5,4-c]pyridine-5-carbonyl}-1H-indole

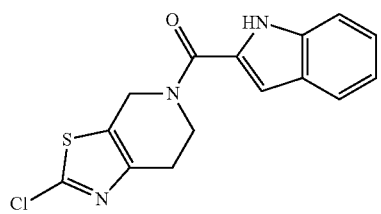 [SMILES: O=C(c1cc2ccccc2[nH]1)N1CCc2nc(Cl)sc2C1]

Rt (Method A) 3.36 mins, m/z 318 [M+H]$^+$.

$^1$H NMR (400 MHz, d6-DMSO) δ 11.65 (s, 1H), 7.63 (d, J=7.9 Hz, 1H), 7.43 (d, J=8.2 Hz, 1H), 7.21 (dd, J=7.3 Hz, 1H), 7.06 (dd, J=7.4 Hz, 1H), 6.96-6.91 (m, 1H), 5.29-4.65 (m, 2H), 4.28-3.83 (m, 2H), 3.08-2.79 (m, 2H).

Example 208

3-{[5-(1H-indole-2-carbonyl)-4H,5H,6H,7H-[1,3]thiazolo[5,4-c]pyridin-2-yl]amino}propane-1,2-diol

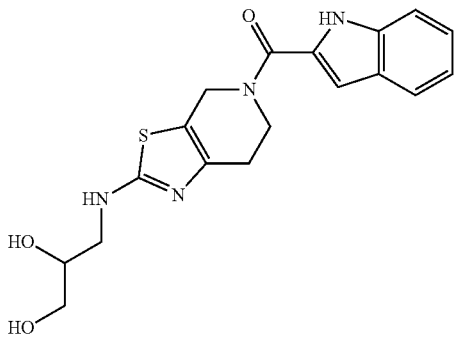 [SMILES: O=C(c1cc2ccccc2[nH]1)N1CCc2nc(NCC(O)CO)sc2C1]

Rt (Method A) 2.69 mins, m/z 373 [M+H]+.

$^1$H NMR (400 MHz, d6-DMSO) δ 11.63 (s, 1H), 7.62 (d, J=8.0 Hz, 1H), 7.49 (t, J=5.6 Hz, 1H), 7.42 (d, J=8.2 Hz, 1H), 7.23-7.16 (m, 1H), 7.05 (dd, J=7.4 Hz, 1H), 6.92-6.85 (m, 1H), 4.85 (d, J=4.9 Hz, 1H), 4.95-4.55 (m, 2H), 4.65 (t, J=5.8 Hz, 1H), 4.13-3.81 (m, 2H), 3.68-3.56 (m, 1H), 3.19-3.08 (m, 1H), 2.79-2.58 (m, 2H)—one signal (3H) coincides with H$_2$O signal.

Example 209

5-(4-chloro-6-fluoro-1H-indole-2-carbonyl)-N,N-dimethyl-4H,5H,6H,7H-[1,3]thiazolo[5,4-c]pyridin-2-amine

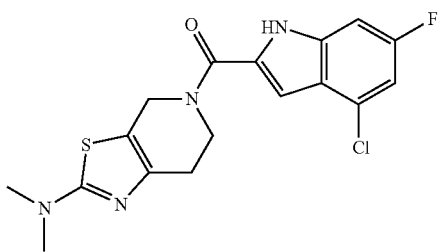 [SMILES: CN(C)c1nc2c(s1)CN(C(=O)c1cc3c(Cl)cc(F)cc3[nH]1)CC2]

Rt (Method A) 3.77 mins, m/z 379/381 [M+H]+.

Example 210

5-(4-chloro-1H-indole-2-carbonyl)-4H,5H,6H,7H-[1,3]thiazolo[5,4-c]pyridin-2-amine

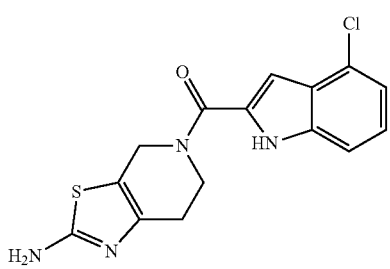 [SMILES: Nc1nc2c(s1)CN(C(=O)c1cc3c(Cl)cccc3[nH]1)CC2]

A solution of 4,5,6,7-tetrahydrothiazolo[5,4-c]pyridin-2-amine dihydrochloride (0.030 g, 0.132 mmol) and triethylamine (0.080 g, 0.789 mmol, 0.110 ml) in dry DMF (1 mL) was added 4-chloro-1H-indole-2-carboxylic acid (0.0257 g, 0.132 mmol) was added and the mixture stirred at room temperature for 90 mins. DMSO (2 mL) was added to the reaction mixture and the mixture filtered. The solution was purified by basic reversed phase chromatography (Reveleris, X select prep column, water/acetonitrile/NH$_4$HCO$_3$) to give the desired product (0.031 g, 67% yield).

Rt (Method B) 3.06 mins, m/z 333/335 [M+H]+.

Example 211

4-chloro-2-{2-methyl-4H,5H,6H,7H-[1,3]thiazolo[5,4-c]pyridine-5-carbonyl}-1H-indole

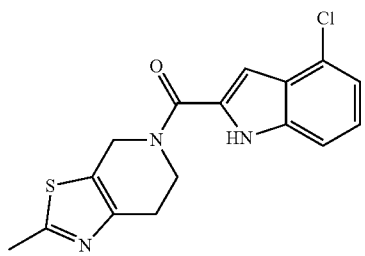 [SMILES: Cc1nc2c(s1)CN(C(=O)c1cc3c(Cl)cccc3[nH]1)CC2]

A solution of 2-methyl4,5,6,7-tetrahydrothiazolo[5,4-c]pyridine (0.030 g, 0.195 mmol) and triethylamine (0.0591 g, 0.584 mmol, 0.081 ml) in dry DMF (1 mL) was added 4-chloro-1H-indole-2-carboxylic acid (0.038 g, 0.195 mmol) was added and the mixture stirred at room temperature for 90 mins. DMSO (2 mL) was added to the reaction mixture and the mixture filtered. The solution was purified by basic reversed phase chromatography (Reveleris, X select prep column, water/acetonitrile/NH$_4$HCO$_3$) to give the desired product (0.023 g, 34% yield).

Rt (Method C) 1.981 mins, m/z 332 [M+H]+.

Examples 212 to 214—Intentionally left blank

Example 215

4-({[5-(1H-indole-2-carbonyl)-4H,5H,6H,7H-[1,3]thiazolo[5,4-c]pyridin-2-yl]amino}methyl)piperidin-4-ol

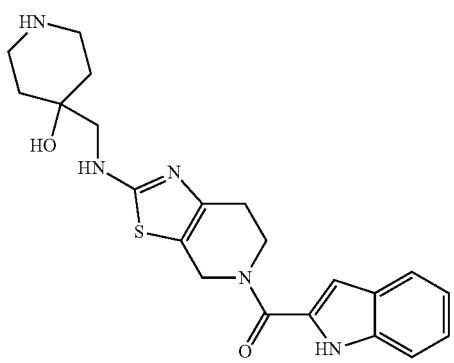 [SMILES: O=C(c1cc2ccccc2[nH]1)N1CCc2nc(NCC3(O)CCNCC3)sc2C1]

Rt (Method B) 1.95 mins, m/z 412 [M+H]+

1H NMR (400 MHz, DMSO-d6) δ 11.68-11.63 (m, 1H), 8.85-8.65 (m, 1H), 8.65-8.41 (m, 1H), 7.63 (d, J=8.1 Hz, 1H), 7.44 (d, J=8.3 Hz, 1H), 7.25-7.16 (m, 1H), 7.11-7.02 (m, 1H), 6.94-6.88 (m, 1H), 5.00 (d, J=190.2 Hz, 3H), 4.01 (s, 2H), 3.15 (d, J=12.3 Hz, 2H), 3.02 (d, J=10.9 Hz, 2H), 2.73 (s, 2H), 1.71 (d, J=12.1 Hz, 4H)—one signal (4H) coincides with H2O signal Example 216

2-({[5-(1H-indole-2-carbonyl)-4H,5H,6H,7H-[1,3]thiazolo[5,4-c]pyridin-2-yl]amino}methyl)-2-methylbutan-1-ol

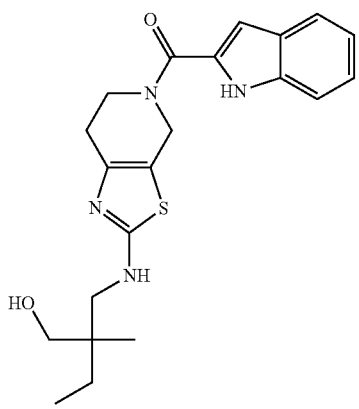 [SMILES: CCC(C)(CO)CNc1nc2c(s1)CN(C(=O)c1cc3ccccc3[nH]1)CC2]

Rt (Method A) 3.37 mins, m/z 399 [M+H]+

1H NMR (400 MHz, DMSO-d6) δ 11.62 (s, 1H), 7.62 (m, 1H) 7.49 (m, 1H), 7.42 (m, 1H), 7.19 (m, 1H), 7.05 (m, 1H), 6.89 (m, 1H), 4.86 (t, J=6.1 Hz, 1H), 4.73 (m, 2H), 3.98 (m, 2H), 3.16-3.06 (m, 4H), 2.64 (m, 2H), 1.26-1.20 (m, 2H), 0.81-0.75 (m, 6H)

Example 217

3-{[5-(1H-indole-2-carbonyl)-4H,5H,6H,7H-[1,3]thiazolo[5,4-c]pyridin-2-yl]amino}-2-methylpropan-1-ol

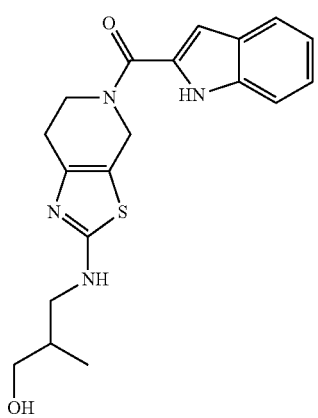 [SMILES: CC(CO)CNc1nc2c(s1)CN(C(=O)c1cc3ccccc3[nH]1)CC2]

Rt (Method A) 3 mins, m/z 371 [M+H]+

1H NMR (400 MHz, DMSO-d6) δ 11.62 (s, 1H), 7.62 (d, J=8.1 Hz, 1H), 7.49 (t, J=5.7 Hz, 1H), 7.42 (d, J=8.2 Hz, 1H), 7.19 (dd, J=7.5 Hz, 1H), 7.05 (dd, J=7.5 Hz, 1H), 6.92-6.87 (m, 1H), 4.91-4.62 (m, 2H), 4.57 (t, J=5.4 Hz, 1H), 4.07-3.90 (m, 2H), 3.29-3.24 (m, 2H), 3.24-3.17 (m, 1H), 3.07-2.97 (m, 1H), 2.71-2.60 (m, 2H), 1.86-1.76 (m, 1H), 0.86 (d, J=6.8 Hz, 3H).

Example 218

(1-{[5-(4,6-difluoro-1H-indole-2-carbonyl)-4H,5H,6H,7H-[1,3]thiazolo[5,4-c]pyridin-2-yl]amino}cyclobutyl)methanol

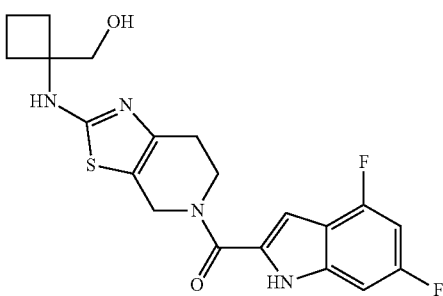 [SMILES: O=C(c1cc2c(F)cc(F)cc2[nH]1)N1CCc2nc(NC3(CO)CCC3)sc2C1]

Rt (Method A) 3.31 mins, m/z 419 [M+H]+

1H NMR (400 MHz, DMSO-d6) δ 12.05 (s, 1H), 7.59 (s, 1H), 7.05 (m, 1H), 6.96 (m, 1H), 6.91 (m, 1H), 4.95 (m, 1H), 4.75 (m, 2H), 3.96 (m, 2H), 3.62 (m, 2H), 2.64 (m, 2H), 2.11 (m, 4H), 1.86-1.67 (m, 2H)

Example 219 tert-butyl 4-hydroxy-4-({[5-(1H-indole-2-carbonyl)-4H,5H,6H,7H-[1,3]thiazolo[5,4-c]pyridin-2-yl]amino}methyl)piperidine-1-carboxylate

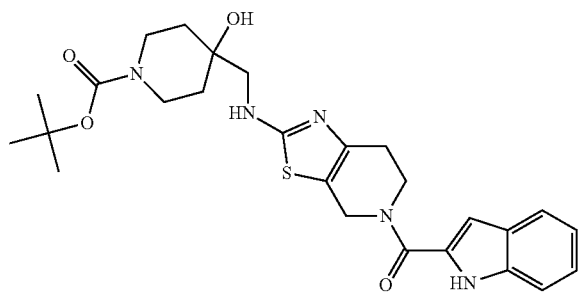 [SMILES: CC(C)(C)OC(=O)N1CCC(O)(CNc2nc3c(s2)CN(C(=O)c2cc4ccccc4[nH]2)CC3)CC1]

Rt (Method A) 3.37 mins, m/z 512 [M+H]+

1H NMR (400 MHz, DMSO-d6) δ 11.62 (s, 1H), 7.62 (d, J=7.8 Hz, 1H), 7.48 (t, J=5.8 Hz, 1H), 7.42 (d, J=8.3 Hz, 1H), 7.19 (ddd, J=8.1, 6.9, 1.2 Hz, 1H), 7.05 (ddd, J=8.1, 6.9, 1.0 Hz, 1H), 6.90-6.87 (m, 1H), 5.19-4.40 (m, 3H), 4.09-3.85 (m, 2H), 3.73-3.58 (m, 2H), 3.23 (d, J=5.8 Hz, 2H), 3.17-2.92 (m, 2H), 2.74-2.59 (m, 2H), 1.48-1.40 (m, 4H), 1.38 (s, 9H).

Example 220

5-(3-fluoro-1H-indole-2-carbonyl)-4H,5H,6H,7H-[1,3]thiazolo[5,4-c]pyridin-2-amine

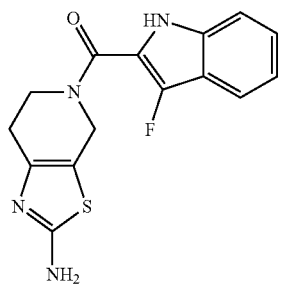 [SMILES: Nc1nc2c(s1)CN(C(=O)c1[nH]c3ccccc3c1F)CC2]

Rt (Method A) 2.96 mins, m/z 317 [M+H]+

1H NMR (400 MHz, DMSO-d6) δ 11.47 (s, 1H), 7.61 (d, J=8.1 Hz, 1H), 7.42-7.35 (m, 1H), 7.27 (dd, J=7.6 Hz, 1H), 7.12 (dd, J=7.5 Hz, 1H), 6.84 (s, 2H), 4.67-4.58 (m, 2H), 3.91-3.83 (m, 2H), 2.66-2.58 (m, 2H).

Example 221

3-{[5-(1H-indole-2-carbonyl)-4H,5H,6H,7H-[1,3]thiazolo[5,4-c]pyridin-2-yl]amino}-2,2-dimethylpropan-1-ol

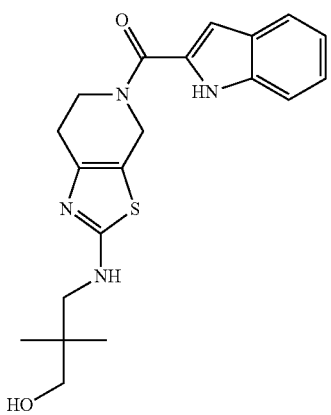 [SMILES: CC(C)(CO)CNc1nc2c(s1)CN(C(=O)c1cc3ccccc3[nH]1)CC2]

Rt (Method A) 3.2 mins, m/z 385 [M+H]+

1H NMR (400 MHz, DMSO-d6) δ 11.63 (s, 1H), 7.62 (d, J=8.0 Hz, 1H), 7.53 (t, J=5.9 Hz, 1H), 7.42 (d, J=8.0 Hz, 1H), 7.23-7.16 (m, 1H), 7.09-7.02 (m, 1H), 6.89 (s, 1H), 4.87 (t, J=6.0 Hz, 1H), 4.84-4.57 (m, 2H), 4.06-3.91 (m, 2H), 3.13-3.05 (m, 4H), 2.71-2.58 (m, 2H), 0.82 (s, 6H).

Example 222

(1-{[5-(4,5-difluoro-1H-indole-2-carbonyl)-4H,5H,6H,7H-[1,3]thiazolo[5,4-c]pyridin-2-yl]amino}cyclobutyl)methanol

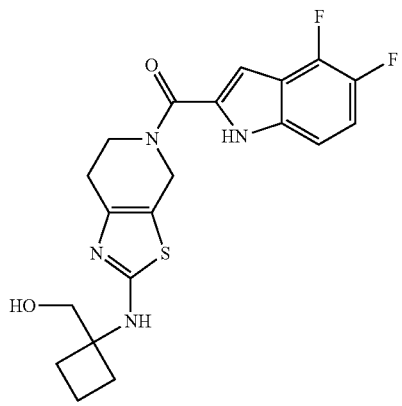 [SMILES: O=C(c1cc2c(F)c(F)ccc2[nH]1)N1CCc2nc(NC3(CO)CCC3)sc2C1]

Rt (Method A) 3.28 mins, m/z 419 [M+H]+

1H NMR (400 MHz, DMSO-d6) δ 12.05 (s, 1H), 7.59 (s, 1H), 7.23 (m, 2H), 6.99 (m, 1H), 4.95 (t, J=5.3 Hz, 1H), 4.75 (m, 2H), 3.95 (m, 2H), 3.62 (d, J=5.6 Hz, 2H), 2.64 (m, 2H), 2.12-2.08 (m, 4H), 1.87-1.67 (m, 2H)

Example 223

(1-{[5-(4-chloro-6-fluoro-1H-indole-2-carbonyl)-4H,5H,6H,7H-[1,3]thiazolo[5,4-c]pyridin-2-yl]amino}cyclobutyl)methanol

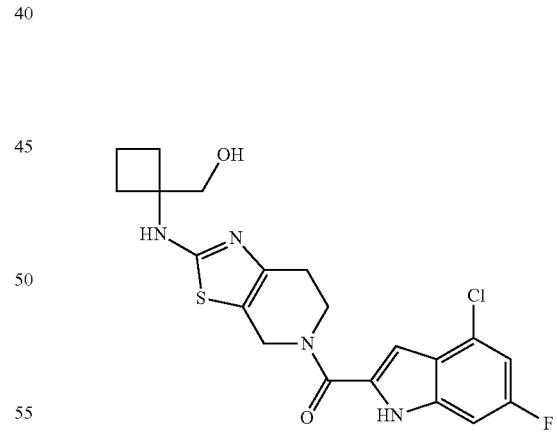

Rt (Method A) 3.45 mins, m/z 435/437 [M+H]+

1H NMR (400 MHz, DMSO-d6) δ 7.59 (s, 1H), 7.17 (d, J=9.5 Hz, 2H), 6.88 (s, 1H), 4.96 (t, J=5.3 Hz, 1H), 4.76 (m, 2H), 3.96 (m, 2H), 3.62 (d, J=5.6 Hz, 2H), 2.64 (m, 2H), 2.15-2.05 (m, 4H), 1.87-1.67 (m, 2H) (Indole NH not visible)

Example 224

(1-{[5-(4-chloro-1H-indole-2-carbonyl)-4H,5H,6H,7H-[1,3]thiazolo[5,4-c]pyridin-2-yl]amino}cyclobutyl)methanol

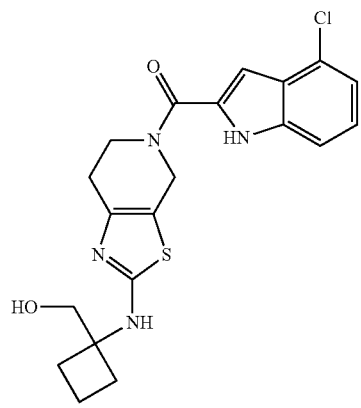 [SMILES: O=C(c1cc2c(Cl)cccc2[nH]1)N1CCc2nc(NC3(CO)CCC3)sc2C1]

Rt (Method A) 3.36 mins, m/z 417/419 [M+H]+

1H NMR (400 MHz, DMSO-d6) δ 12.02 (s, 1H), 7.60 (s, 1H), 7.39 (m, 1H), 7.20 (t, J=7.6 Hz, 1H), 7.14 (m, 1H), 6.86 (m, 1H), 4.96 (t, J=5.3 Hz, 1H), 4.76 (m, 2H), 3.97 (m, 2H), 3.62 (d, J=5.6 Hz, 2H), 2.64 (m, 2H), 2.13-2.08 (m, 4H), 1.84-1.67 (m, 2H)

Example 225

2,2-difluoro-3-{[5-(1H-indole-2-carbonyl)-4H,5H,6H,7H-[1,3]thiazolo[5,4-c]pyridin-2-yl]amino}propan-1-ol

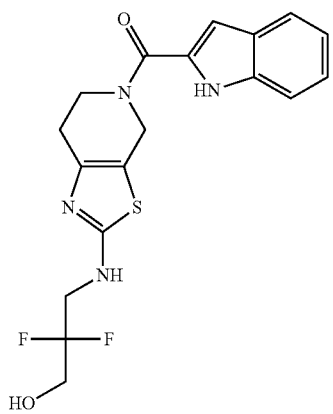 [SMILES: O=C(c1cc2ccccc2[nH]1)N1CCc2nc(NCC(F)(F)CO)sc2C1]

Rt (Method A) 3.07 mins, m/z 393 [M+H]+

1H NMR (400 MHz, DMSO-d6) δ 11.63 (s, 1H), 7.89 (t, J=5.9 Hz, 1H), 7.63 (d, J=7.9 Hz, 1H), 7.43 (d, J=8.2 Hz, 1H), 7.25-7.15 (m, 1H), 7.10-7.02 (m, 1H), 6.93-6.85 (m, 1H), 5.66 (t, J=6.5 Hz, 1H), 5.03-4.42 (m, 2H), 4.17-3.89 (m, 2H), 3.75 (td, J=14.6, 5.9 Hz, 2H), 3.61 (td, J=13.3, 6.3 Hz, 2H), 2.79-2.58 (m, 2H).

Example 226

3-{[5-(1H-indole-2-carbonyl)-4H,5H,6H,7H-[1,3]thiazolo[5,4-c]pyridin-2-yl]amino}-2-[(oxan-4-yl)methyl]propan-1-ol

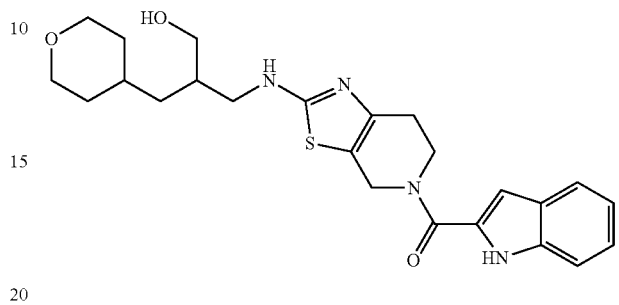

Rt (Method A) 3.08 mins, m/z 455 [M+H]+

1H NMR (400 MHz, DMSO-d6) δ 11.62 (s, 1H), 7.63 (d, J=7.9 Hz, 1H), 7.53-7.39 (m, 2H), 7.25-7.15 (m, 1H), 7.10-7.02 (m, 1H), 6.89 (s, 1H), 4.99-4.53 (m, 3H), 4.12-3.89 (m, 2H), 3.88-3.73 (m, 2H), 3.32-3.21 (m, 4H), 3.17 (t, J=5.7 Hz, 2H), 2.72-2.59 (m, 2H), 1.83-1.70 (m, 1H), 1.68-1.46 (m, 3H), 1.29-1.03 (m, 4H).

Example 227

2-(cyclobutylmethyl)-3-{[5-(1H-indole-2-carbonyl)-4H,5H,6H,7H-[1,3]thiazolo[5,4-c]pyridin-2-yl]amino}propan-1-ol

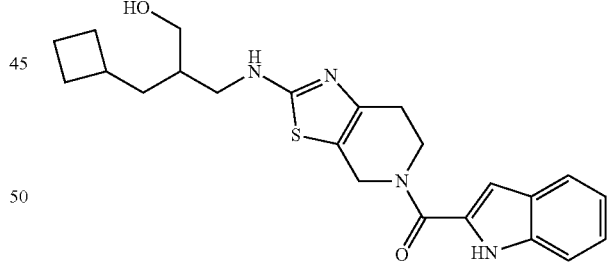

Rt (Method A) 3.52 mins, m/z 425 [M+H]+

1H NMR (400 MHz, DMSO-d6) δ 11.62 (s, 1H), 7.63 (d, J=8.0 Hz, 1H), 7.52-7.39 (m, 2H), 7.26-7.15 (m, 1H), 7.11-7.02 (m, 1H), 6.89 (s, 1H), 5.18-4.50 (m, 3H), 4.10-3.85 (m, 2H), 3.31-3.21 (m, 2H), 3.15 (dp, J=13.0, 7.2, 6.4 Hz, 2H), 2.78-2.58 (m, 2H), 2.42-2.30 (m, 1H), 2.06-1.91 (m, 2H), 1.88-1.67 (m, 2H), 1.64-1.48 (m, 3H), 1.45-1.28 (m, 2H).

Example 228

{1-[5-(1H-indole-2-carbonyl)-4H,5H,6H,7H-[1,3]thiazolo[5,4-c]pyridin-2-yl]-3-methylazetidin-3-yl}methanol

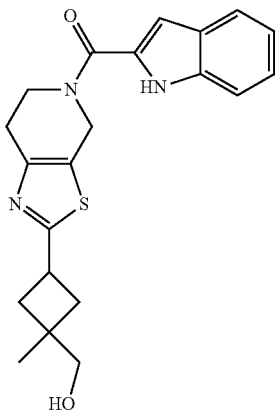 [SMILES: CC1(CO)CC(c2nc3c(s2)CN(C(=O)c2cc4ccccc4[nH]2)CC3)C1]

Rt (Method D) 2.86 mins, m/z 383 [M+H]+

1H NMR (400 MHz, DMSO-d6) 11.64 (s, 1H), 7.62 (d, J=8.0 Hz, 1H), 7.43 (d, J=8.3 Hz, 1H), 7.24-7.17 (m, 1H), 7.10-7.02 (m, 1H), 6.93-6.88 (m, 1H), 4.80 (t, J=5.3 Hz, 1H), 4.69-4.31 (m, 2H), 4.10-3.89 (m, 2H), 3.50 (d, J=11.2 Hz, 1H), 3.27-3.05 (m, 4H), 2.97 (d, J=14.8 Hz, 1H), 2.64-2.51 (m, 2H), 0.87 (s, 3H).

Example 229

[1-({[5-(4-chloro-6-fluoro-1H-indole-2-carbonyl)-4H,5H,6H,7H-[1,3]thiazolo[5,4-c]pyridin-2-yl]amino}methyl)cyclopropyl]methyl (2S)-2-amino-3-methylbutanoate

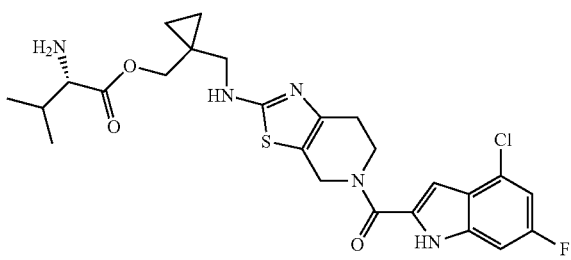 [SMILES: CC(C)[C@H](N)C(=O)OCC1(CNc2nc3c(s2)CN(C(=O)c2cc4c(Cl)cc(F)cc4[nH]2)CC3)CC1]

Rt (Method A) 3.59 mins, m/z 534/536 [M+H]+

1H NMR (400 MHz, DMSO-d6) δ 12.08 (s, 1H), 7.56 (m, 1H), 7.16 (m, 2H), 6.88 (m, 1H), 4.75 (m, 2H), 4.03-3.89 (m, 4H) 3.25 (m, 2H), 3.14 (d, J=5.2 Hz, 1H), 2.63 (m, 2H), 1.87 (m, 2H), 0.87 (d, J=6.8 Hz, 3H), 0.81 (d, J=6.8 Hz, 3H), 0.57-0.50 (m, 4H)

Example 230

(1-{[5-(1H-indole-2-carbonyl)-4H,5H,6H,7H-[1,3]thiazolo[5,4-c]pyridin-2-yl]amino}cyclopropyl)methanol

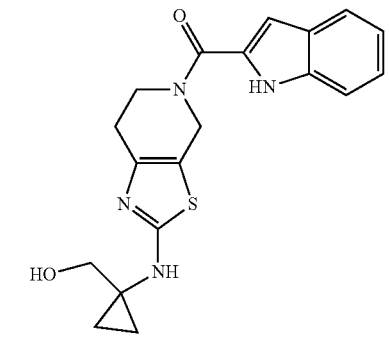 [SMILES: O=C(c1cc2ccccc2[nH]1)N1CCc2nc(NC3(CO)CC3)sc2C1]

Rt (Method A) 2.96 mins, m/z 369 [M+H]+

1H NMR (400 MHz, DMSO-d6) 11.62 (s, 1H), 7.83 (s, 1H), 7.63 (d, J=7.9 Hz, 1H), 7.43 (d, J=8.2 Hz, 1H), 7.20 (t, J=7.6 Hz, 1H), 7.06 (t, J=7.4 Hz, 1H), 6.89 (s, 1H), 5.05-4.46 (m, 3H), 4.14-3.81 (m, 2H), 3.49 (d, J=5.2 Hz, 2H), 2.76-2.59 (m, 2H), 0.82-0.62 (m, 4H).

Example 231

5-(1H-indole-2-carbonyl)-N-(3-methoxyoxan-4-yl)-4H,5H,6H,7H-[1,3]thiazolo[5,4-c]pyridin-2-amine

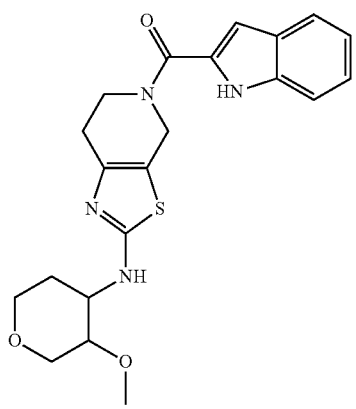 [SMILES: COC1COCCC1Nc1nc2c(s1)CN(C(=O)c1cc3ccccc3[nH]1)CC2]

Rt (Method A) 3.02 mins, m/z 413 [M+H]+

1H NMR (400 MHz, DMSO-d6) δ 11.63 (s, 1H), 7.66-7.58 (m, 1.3H), 7.55-7.47 (m, 0.7H), 7.43 (d, J=8.2 Hz, 1H), 7.24-7.15 (m, 1H), 7.06 (t, J=7.4 Hz, 1H), 6.89 (s, 1H), 4.97-4.47 (m, 2H), 4.09-3.88 (m, 3.6H), 3.80-3.56 (m, 1.4H), 3.47-3.35 (m, 2H), 3.31 (s, 1H), 3.27 (m, 2.3H), 3.19-3.07 (m, 0.7H), 2.75-2.59 (m, 2H), 2.08-1.95 (m, 0.3H), 1.84-1.70 (m, 0.7H), 1.66-1.55 (m, 0.7H), 1.52-1.37 (m, 0.3H).

Example 232

1-[3-({[5-(1H-indole-2-carbonyl)-4H,5H,6H,7H-[1,3]thiazolo[5,4-c]pyridin-2-yl]amino}methyl)morpholin-4-yl]ethan-1-one

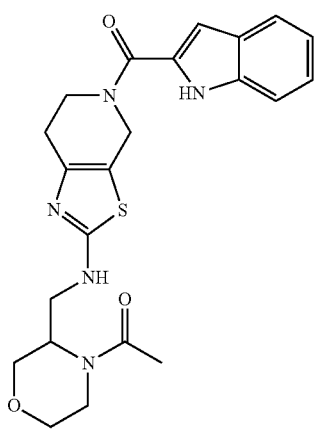 [SMILES: CC(=O)N1CCOCC1CNc1nc2c(s1)CN(C(=O)c1cc3ccccc3[nH]1)CC2]

Rt (Method A) 2.88 mins, m/z 440 [M+H]+

1H NMR (400 MHz, DMSO-d6) δ 11.61 (s, 1H), 7.80 (t, J=5.5 Hz, 0.66H), 7.63 (d, J=8.0 Hz, 1H), 7.48 (t, J=5.5 Hz, 0.33H), 7.43 (d, J=8.2 Hz, 1H), 7.20 (dd, J=7.6 Hz, 1H), 7.06 (dd, J=7.5 Hz, 1H), 6.92-6.86 (m, 1H), 5.03-4.55 (m, 2H), 4.50-4.40 (m, 0.33H), 4.09 (d, J=13.6 Hz, 0.66H), 4.06-3.86 (m, 3H), 3.81 (t, J=13.3 Hz, 2H), 3.56-3.46 (m, 3H), 3.22-3.07 (m, 1.33H), 2.94-2.82 (m, 0.66H), 2.76-2.60 (m, 2H), 2.01 (s, 2H), 1.96 (s, 1H)—A ~2:1 mixture of conformers observed.

Example 233

2-{[5-(1H-indole-2-carbonyl)-4H,5H,6H,7H-[1,3]thiazolo[5,4-c]pyridin-2-yl]amino}-1-(piperidin-1-yl)ethan-1-one

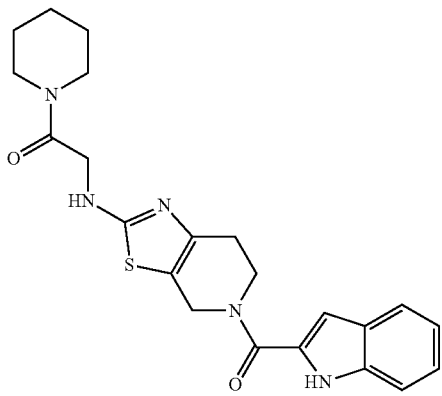 [SMILES: O=C(CNc1nc2c(s1)CN(C(=O)c1cc3ccccc3[nH]1)CC2)N1CCCCC1]

Rt (Method A) 3.19 mins, m/z 424 [M+H]+

1H NMR (400 MHz, DMSO-d6) 11.61 (s, 1H), 7.63 (d, J=8.1 Hz, 1H), 7.55 (t, J=5.3 Hz, 1H), 7.43 (d, J=8.1 Hz, 1H), 7.19 (dd, J=7.7 Hz, 1H), 7.06 (dd, J=7.5 Hz, 1H), 6.91-6.85 (m, 1H), 5.10-4.39 (m, 2H), 4.09 (d, J=5.4 Hz, 2H), 4.04-3.82 (m, 2H), 3.46-3.37 (m, 4H), 2.77-2.58 (m, 2H), 1.66-1.55 (m, 2H), 1.55-1.47 (m, 2H), 1.47-1.34 (m, 2H).

Example 234

[1-({[5-(6-chloro-5-fluoro-1H-indole-2-carbonyl)-4H,5H,6H,7H-[1,3]thiazolo[5,4-c]pyridin-2-yl]amino}methyl)cyclopropyl]methanol

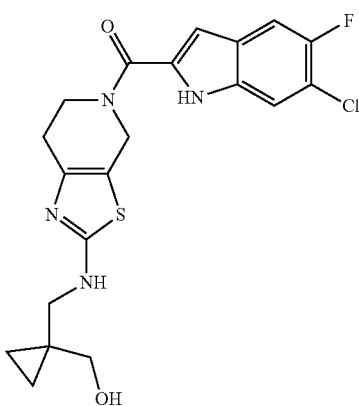 [SMILES: O=C(c1cc2cc(F)c(Cl)cc2[nH]1)N1CCc2nc(NCC3(CO)CC3)sc2C1]

Rt (Method A) 3.27 mins, m/z 435/437 [M+H]+

1H NMR (400 MHz, DMSO-d6) δ 11.87 (s, 1H), 7.62 (d, J=9.9 Hz, 1H), 7.52 (m, 2H), 6.92 (s, 1H), 4.65 (m, 3H), 3.96 (m, 2H), 3.27 (d, J=5.7 Hz, 2H), 3.23 (d, J=5.6 Hz, 2H), 2.65 (m, 2H), 0.41 (m, 2H), 0.36 (m, 2H)

Example 235

[1-({[5-(1H-indole-2-carbonyl)-4H,5H,6H,7H-[1,3]thiazolo[5,4-c]pyridin-2-yl]amino}methyl)cyclopropyl]methyl (2S)-2-amino-3-methylbutanoate Rt (Method A) 3.29 mins, m/z 482 [M+H]+

1H NMR (400 MHz, DMSO-d6) δ 11.62 (s, 1H), 7.62 (d, J=7.9 Hz, 1H), 7.57 (t, J=5.6 Hz, 1H), 7.42 (d, J=8.2 Hz, 1H), 7.19 (m, 1H), 7.05 (m, 1H), 6.89 (s, 1H), 4.73 (m, 2H), 4.03-3.90 (m, 4H) 3.25 (m, 2H), 3.13 (d, J=5.2 Hz, 1H), 2.64 (m, 2H), 1.85 (m, 2H), 0.88 (d, J=6.8 Hz, 3H), 0.82 (d, J=6.8 Hz, 3H), 0.57 (m, 2H), 0.51 (m, 2H)

Example 236

[1-({[5-(4-ethyl-7-fluoro-1H-indole-2-carbonyl)-4H,5H,6H,7H-[1,3]thiazolo[5,4-c]pyridin-2-yl]amino}methyl)cyclopropyl]methanol

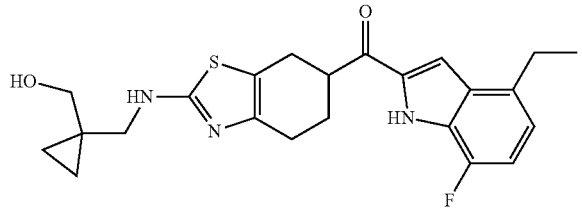 [SMILES: CCc1ccc(F)c2[nH]c(C(=O)C3CCc4nc(NCC5(CO)CC5)sc4C3)cc12]

Rt (Method A) 3.35 mins, m/z 429 [M+H]+

1H NMR (400 MHz, DMSO-d6) δ 12.03 (s, 1H), 7.50 (t, J=5.6 Hz, 1H), 6.92 (m, 2H), 6.81 (m, 1H), 4.71-4.64 (m, 3H), 3.93 (m, 2H), 3.28 (d, J=5.6 Hz, 2H), 3.23 (d, J=5.6 Hz, 2H), 2.85 (q, J=7.6 Hz, 2H), 2.64 (m, 2H), 1.26 (t, J=7.6 Hz, 3H), 0.41 (m, 2H), 0.36 (m, 2H)

Example 237

[4-({[5-(1H-indole-2-carbonyl)-4H,5H,6H,7H-[1,3]thiazolo[5,4-c]pyridin-2-yl]amino}methyl)oxan-4-yl]methanol

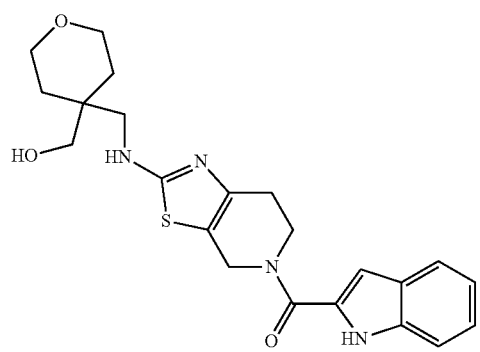 [SMILES: O=C(c1cc2ccccc2[nH]1)N1CCc2nc(NCC3(CO)CCOCC3)sc2C1]

Rt (Method A) 3.00 mins, m/z 427 [M+H]+

1H NMR (400 MHz, DMSO-d6) δ 11.62 (s, 1H), 7.62 (d, J=8.0 Hz, 1H), 7.56 (t, J=6.1 Hz, 1H), 7.42 (d, J=8.2 Hz, 1H), 7.23-7.16 (m, 1H), 7.09-7.02 (m, 1H), 6.89 (d, J=1.8 Hz, 1H), 4.97-4.50 (m, 3H), 4.11-3.88 (m, 2H), 3.62-3.48 (m, 4H), 3.30-3.21 (m, 4H), 2.72-2.56 (m, 2H), 1.43-1.29 (m, 4H).

Example 238 tert-butyl 3-({[5-(1H-indole-2-carbonyl)-4H,5H,6H,7H-[1,3]thiazolo[5,4-c]pyridin-2-yl]amino}methyl)morpholine-4-carboxylate

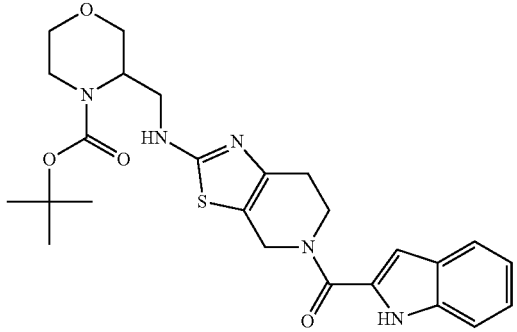 [SMILES: CC(C)(C)OC(=O)N1CCOCC1CNc1nc2c(s1)CN(C(=O)c1cc3ccccc3[nH]1)CC2]

Rt (Method A) 3.33 mins, m/z 498 [M+H]+

1H NMR (400 MHz, Chloroform-d) δ 9.13 (s, 1H), 7.68 (d, J=8.2 Hz, 1H), 7.43 (d, J=8.2 Hz, 1H), 7.30 (ddd, J=8.2, 7.0, 1.1 Hz, 1H), 7.16 (dd, J=7.5 Hz, 1H), 6.89-6.83 (m, 1H), 5.85-5.17 (m, 1H), 5.17-4.64 (m, 2H), 4.30-4.21 (m, 1H), 4.21-4.05 (m, 2H), 3.87 (d, J=11.9 Hz, 2H), 3.83-3.65 (m, 2H), 3.61 (dd, J=12.0, 3.5 Hz, 1H), 3.53-3.42 (m, 2H), 3.24-3.10 (m, 1H), 2.92-2.81 (m, 2H), 1.44 (s, 9H).

Example 239

5-(6-chloro-5-fluoro-1H-indole-2-carbonyl)-N-[(oxolan-3-yl)methyl]-4H,5H,6H,7H-[1,3]thiazolo[5,4-c]pyridin-2-amine

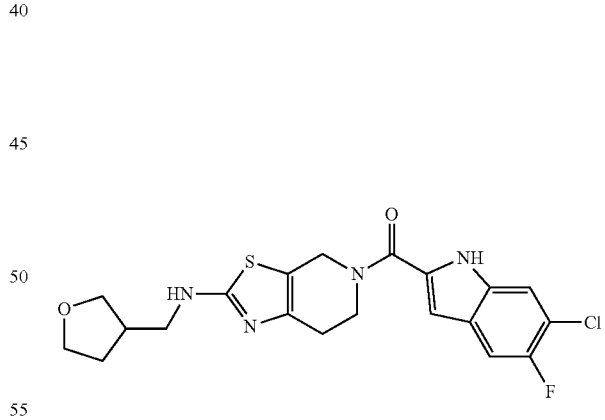

Rt (Method A) 3.31 mins, m/z 435/437 [M+H]+

1H NMR (400 MHz, DMSO-d6) δ 11.87 (s, 1H), 7.69-7.59 (m, 2H), 7.54 (d, J=6.5 Hz, 1H), 6.91 (s, 1H), 4.98-4.51 (m, 2H), 4.03-3.90 (m, 2H), 3.77-3.65 (m, 2H), 3.61 (q, J=7.8 Hz, 1H), 3.42 (dd, J=8.5, 5.4 Hz, 1H), 3.24-3.09 (m, 2H), 2.75-2.59 (m, 2H), 2.49-2.42 (m, 1H), 2.01-1.87 (m, 1H), 1.61-1.47 (m, 1H).

Example 240—Intentionally Left Blank

Example 241

(3R,4R)-4-({[5-(1H-indole-2-carbonyl)-4H,5H,6H,7H-[1,3]thiazolo[5,4-c]pyridin-2-yl]amino}methyl)oxolan-3-ol

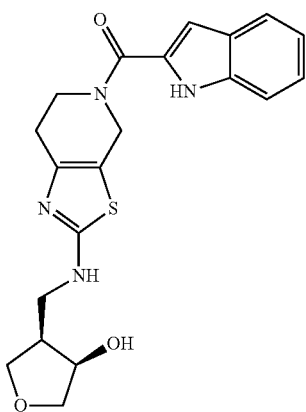 [SMILES: O=C(c1cc2ccccc2[nH]1)N1CCc2nc(NC[C@@H]3COC[C@@H]3O)sc2C1]

Rt (Method A) 2.87 mins, m/z 399 [M+H]+

1H NMR (400 MHz, DMSO-d6) δ 11.62 (s, 1H), 7.63 (d, J=7.9 Hz, 1H), 7.57 (t, J=5.5 Hz, 1H), 7.43 (d, J=8.3 Hz, 1H), 7.20 (t, J=7.6 Hz, 1H), 7.06 (t, J=7.5 Hz, 1H), 6.89 (d, J=1.5 Hz, 1H), 5.19 (d, J=4.0 Hz, 1H), 5.01-4.49 (m, 2H), 4.22-4.14 (m, 1H), 4.10-3.89 (m, 2H), 3.86-3.75 (m, 2H), 3.62-3.55 (m, 1H), 3.46-3.38 (m, 2H), 3.31-3.15 (m, 1H), 2.77-2.59 (m, 2H), 2.40-2.26 (m, 1H).

Example 242

1-[2-({[5-(1H-indole-2-carbonyl)-4H,5H,6H,7H-[1,3]thiazolo[5,4-c]pyridin-2-yl]amino}methyl)morpholin-4-yl]ethan-1-one

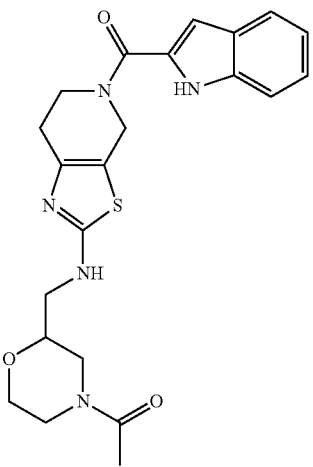 [SMILES: CC(=O)N1CCOC(CNc2nc3c(s2)CN(C(=O)c2cc4ccccc4[nH]2)CC3)C1]

Rt (Method A) 2.88 mins, m/z 440 [M+H]+

1H NMR (400 MHz, Chloroform-d) δ 9.11 (s, 1H), 7.68 (d, J=8.0 Hz, 1H), 7.43 (d, J=8.3 Hz, 1H), 7.30 (dd, J=7.6 Hz, 1H), 7.16 (dd, J=7.5 Hz, 1H), 6.90-6.83 (m, 1H), 5.39-5.16 (m, 1H), 5.13-4.65 (m, 2H), 4.55-4.45 (m, 0.5H), 4.45-4.37 (m, 0.5H), 4.29-4.06 (m, 2H), 3.96 (dd, J=10.9, 3.4 Hz, 1H), 3.72-3.45 (m, 4H), 3.41-3.22 (m, 1.5H), 3.13-3.03 (m, 0.5H), 2.95-2.83 (m, 2H), 2.83-2.74 (m, 0.5H), 2.65-2.54 (m, 0.5H), 2.10 (s, 3H)—An ~1:1 mixture of conformers observed.

Example 243

N-[5-(4-chloro-6-fluoro-1H-indole-2-carbonyl)-4H,5H,6H,7H-[1,3]thiazolo[5,4-c]pyridin-2-yl]-3,3-dimethylbutanamide

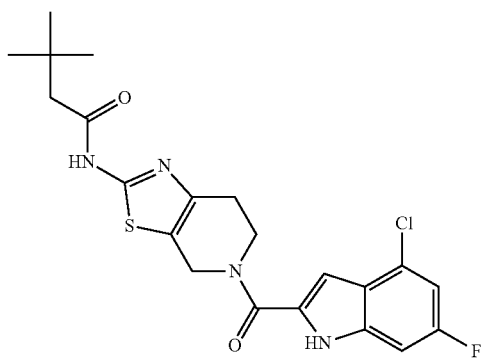 [SMILES: CC(C)(C)CC(=O)Nc1nc2c(s1)CN(C(=O)c1cc3c(Cl)cc(F)cc3[nH]1)CC2]

Rt (Method A) 3.82 mins, m/z 449/451 [M+H]+

1H NMR (400 MHz, DMSO-d6) δ 12.27-11.79 (m, 2H), 7.21-7.14 (m, 2H), 6.92 (s, 1H), 5.20-4.60 (m, 2H), 4.12-3.98 (m, 2H), 2.90-2.76 (m, 2H), 2.29 (s, 2H), 0.99 (s, 9H).

Example 244

1-[2-(2-{[(oxolan-3-yl)methyl]amino}-4H,5H,6H,7H-[1,3]thiazolo[5,4-c]pyridine-5-carbonyl)-1H-indol-4-yl]ethan-1-ol

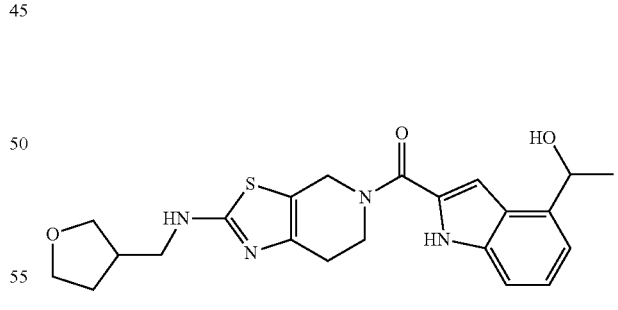

Rt (Method A) 2.72 mins, m/z 427 [M+H]+

1H NMR (400 MHz, DMSO-d6) δ 11.60 (s, 1H), 7.63 (t, J=5.5 Hz, 1H), 7.29 (d, J=8.1 Hz, 1H), 7.19-7.12 (m, 1H), 7.08 (d, J=7.1 Hz, 1H), 7.02-6.97 (m, 1H), 5.20-5.09 (m, 2H), 3.77-3.66 (m, 2H), 3.66-3.57 (m, 1H), 3.42 (dd, J=8.6, 5.5 Hz, 1H), 3.21-3.12 (m, 2H), 2.02-1.87 (m, 1H), 1.63-1.49 (m, 1H), 1.44 (d, J=6.2 Hz, 3H).

Example 245

[2-(2-{[(oxolan-3-yl)methyl]amino}-4H,5H,6H,7H-[1,3]thiazolo[5,4-c]pyridine-5-carbonyl)-1H-indol-4-yl]methanol

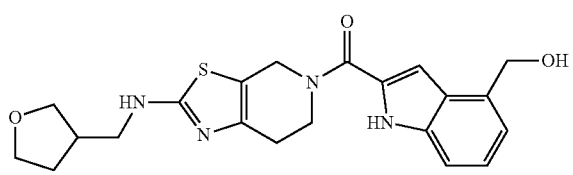 [SMILES: O=C(c1cc2c(CO)cccc2[nH]1)N1CCc2nc(NCC3CCOC3)sc2C1]

Rt (Method A) 2.65 mins, m/z 413 [M+H]+

1H NMR (400 MHz, DMSO-d6) δ 11.62 (s, 1H), 7.63 (t, J=5.5 Hz, 1H), 7.31 (d, J=8.2 Hz, 1H), 7.21-7.11 (m, 1H), 7.05 (d, J=6.7 Hz, 1H), 6.96 (d, J=1.4 Hz, 1H), 5.16 (t, J=5.7 Hz, 1H), 4.87-4.65 (m, 4H), 4.08-3.89 (m, 2H), 3.79-3.65 (m, 2H), 3.65-3.55 (m, 1H), 3.42 (dd, J=8.5, 5.5 Hz, 1H), 3.20-3.13 (m, 2H), 2.72-2.60 (m, 2H), 2.49-2.43 (m, 1H), 2.02-1.87 (m, 1H), 1.62-1.48 (m, 1H).

Example 246

5-(1H-indole-2-carbonyl)-N-[(3-methoxyoxolan-3-yl)methyl]-4H,5H,6H,7H-[1,3]thiazolo[5,4-c]pyridin-2-amine

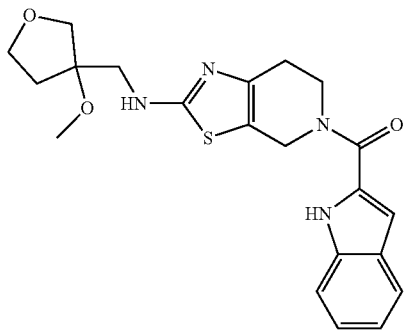 [SMILES: COC1(CNc2nc3c(s2)CN(C(=O)c2cc4ccccc4[nH]2)CC3)CCOC1]

Rt (Method A) 3.02 mins, m/z 413 [M+H]+

1H NMR (400 MHz, DMSO-d6) δ 11.62 (s, 1H), 7.63 (d, J=8.0 Hz, 1H), 7.51 (t, J=5.4 Hz, 1H), 7.43 (d, J=8.2 Hz, 1H), 7.20 (dd, J=15.2, 0.9 Hz, 1H), 7.06 (t, J=7.4 Hz, 1H), 6.89 (d, J=1.6 Hz, 1H), 4.92-4.56 (m, 2H), 4.12-3.88 (m, 2H), 3.83-3.65 (m, 3H), 3.61-3.45 (m, 3H), 3.17 (s, 3H), 2.78-2.57 (m, 2H), 2.08-1.95 (m, 1H), 1.90-1.75 (m, 1H).

Example 247

5-(1H-indole-2-carbonyl)-N-[1-(oxolan-3-yl)ethyl]-4H,5H,6H,7H-[1,3]thiazolo[5,4-c]pyridin-2-amine

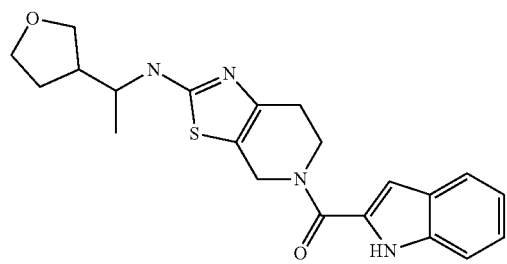

Rt (Method A) 3.14 mins, m/z 397 [M+H]+

1H NMR (400 MHz, DMSO-d6) δ 11.62 (s, 1H), 7.62 (d, J=8.0 Hz, 1H), 7.52-7.40 (m, 2H), 7.23-7.16 (m, 1H), 7.06 (t, J=7.5 Hz, 1H), 6.89 (d, J=1.7 Hz, 1H), 4.91-4.55 (m, 2H), 4.14-3.87 (m, 2H), 3.78-3.55 (m, 4H), 3.45-3.38 (m, 1H), 2.75-2.58 (m, 2H), 2.37-2.23 (m, 1H), 1.99-1.85 (m, 1H), 1.70-1.49 (m, 1H), 1.17-1.04 (m, 3H).

Example 248

[1-({[5-(4-ethyl-6-fluoro-1H-indole-2-carbonyl)-4H,5H,6H,7H-[1,3]thiazolo[5,4-c]pyridin-2-yl]amino}methyl)cyclopropyl]methanol

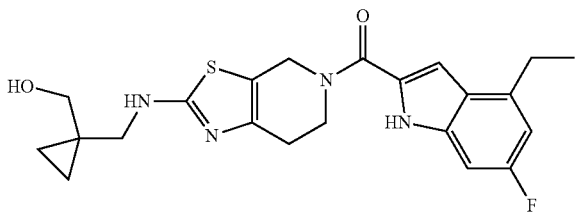 [SMILES: CCc1cc(F)cc2[nH]c(C(=O)N3CCc4nc(NCC5(CO)CC5)sc4C3)cc12]

Rt (Method A) 3.35 mins, m/z 429 [M+H]+

1H NMR (400 MHz, DMSO-d6) δ 11.66 (s, 1H), 7.49 (t, J=5.6 Hz, 1H), 6.96 (m, 2H), 6.77 (m, 1H), 4.75-4.64 (m, 3H), 3.98 (m, 2H), 3.29 (d, J=5.4 Hz, 2H), 3.23 (d, J=5.6 Hz, 2H), 2.90 (q, J=7.6 Hz, 2H), 2.65 (m, 2H), 1.28 (t, J=7.5 Hz, 3H), 0.41 (m, 2H), 0.36 (m, 2H)

Example 249

1-{6-fluoro-2-[2-({[1-(hydroxymethyl)cyclopropyl]methyl}amino)-4H,5H,6H,7H-[1,3]thiazolo[5,4-c]pyridine-5-carbonyl]-1H-indol-4-yl}ethan-1-ol

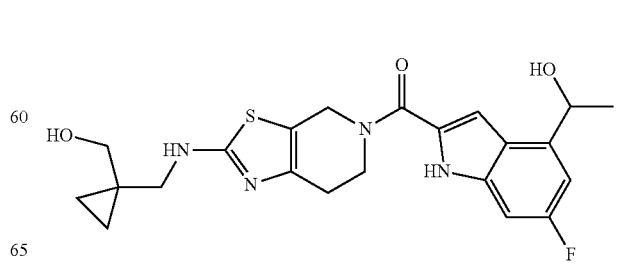

Rt (Method A) 2.82 mins, m/z 445 [M+H]+

1H NMR (400 MHz, DMSO-d6) δ 11.68 (s, 1H), 7.50 (t, J=5.7 Hz, 1H), 6.99 (m, 2H), 6.93 (m, 1H), 5.31 (d, J=4.3 Hz, 1H), 5.19-5.13 (m, 1H), 4.74-4.64 (m, 3H), 4.04-3.94 (m, 2H), 3.28 (d, J=5.4 Hz, 2H), 3.23 (d, J=5.6 Hz, 2H), 2.65 (m, 2H), 1.43 (d, J=6.4 Hz, 3H), 0.41 (m, 2H), 0.36 (m, 2H)

Example 250

1-{2-[2-({[1-(hydroxymethyl)cyclopropyl]methyl}amino)-4H,5H,6H,7H-[1,3]thiazolo[5,4-c]pyridine-5-carbonyl]-1H-indol-4-yl}ethan-1-ol

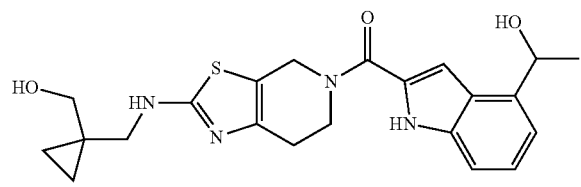 [SMILES: CC(O)c1cccc2[nH]c(C(=O)N3CCc4nc(NCC5(CO)CC5)sc4C3)cc12]

Rt (Method A) 2.71 mins, m/z 427 [M+H]+

1H NMR (400 MHz, DMSO-d6) δ 11.59 (s, 1H), 7.50 (m, 1H), 7.28 (d, J=8.1 Hz, 1H), 7.15 (m, 1H), 7.07 (d, J=7.0 Hz, 1H), 6.98 (s, 1H), 5.16-5.11 (m, 2H), 4.75-4.64 (m, 3H), 3.99 (m, 2H), 3.28 (d, J=5.5 Hz, 2H), 3.23 (d, J=5.6 Hz, 2H), 2.65 (m, 2H), 1.43 (d, J=6.1 Hz, 3H), 0.41 (m, 2H), 0.36 (m, 2H)

Example 251

[1-({[5-(4-chloro-5-fluoro-1H-indole-2-carbonyl)-4H,5H,6H,7H-[1,3]thiazolo[5,4-c]pyridin-2-yl]amino}methyl)cyclopropyl]methanol

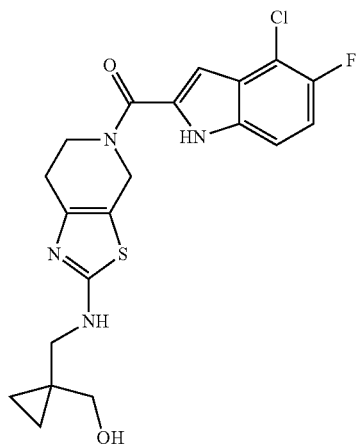 [SMILES: O=C(c1cc2c(Cl)c(F)ccc2[nH]1)N1CCc2nc(NCC3(CO)CC3)sc2C1]

Rt (Method A) 3.26 mins, m/z 435/437 [M+H]+

1H NMR (400 MHz, DMSO-d6) δ 12.11 (s, 1H), 7.51 (m, 1H), 7.42 (m, 1H), 7.27-7.22 (m, 1H), 6.89 (s, 1H), 4.81-4.64 (m, 3H), 3.96 (m, 2H), 3.28 (d, J=5.8 Hz, 2H), 3.23 (d, J=5.6 Hz, 2H), 2.64 (m, 2H), 0.41 (m, 2H), 0.36 (m, 2H)

Example 252

[1-({[5-(4,5-difluoro-1H-indole-2-carbonyl)-4H,5H,6H,7H-[1,3]thiazolo[5,4-c]pyridin-2-yl]amino}methyl)cyclopropyl]methanol

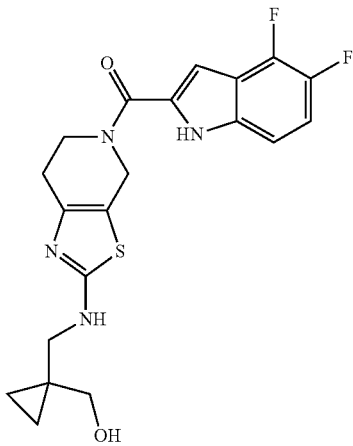 [SMILES: O=C(c1cc2c(F)c(F)ccc2[nH]1)N1CCc2nc(NCC3(CO)CC3)sc2C1]

Rt (Method A) 3.17 mins, m/z 419 [M+H]+

1H NMR (400 MHz, DMSO-d6) δ 12.05 (s, 1H), 7.49 (m, 1H), 7.28-7.22 (m, 2H), 6.99 (s, 1H), 4.81-4.64 (m, 3H), 3.96 (m, 2H), 3.28 (d, J=5.8 Hz, 2H), 3.23 (d, J=5.6 Hz, 2H), 2.65 (m, 2H), 0.41 (m, 2H), 0.36 (m, 2H)

Example 253

3-({[5-(1H-indole-2-carbonyl)-4H,5H,6H,7H-[1,3]thiazolo[5,4-c]pyridin-2-yl]amino}methyl)oxolan-3-ol

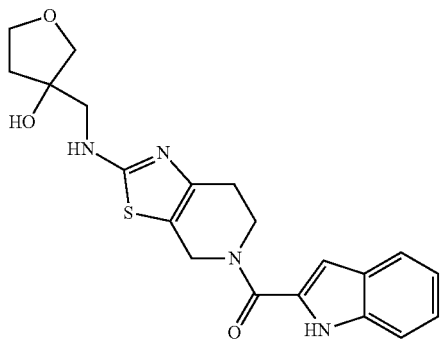 [SMILES: O=C(c1cc2ccccc2[nH]1)N1CCc2nc(NCC3(O)CCOC3)sc2C1]

Rt (Method A) 2.84 mins, m/z 399 [M+H]+

1H NMR (400 MHz, DMSO-d6) δ 11.62 (s, 1H), 7.62 (d, J=8.0 Hz, 1H), 7.57 (t, J=5.7 Hz, 1H), 7.42 (d, J=8.4 Hz, 1H), 7.23-7.15 (m, 1H), 7.10-7.02 (m, 1H), 6.91-6.87 (m, 1H), 5.11 (s, 1H), 5.04-4.45 (m, 2H), 4.08-3.90 (m, 2H), 3.86-3.70 (m, 2H), 3.61 (d, J=8.9 Hz, 1H), 3.47 (d, J=9.0 Hz, 1H), 3.43-3.37 (m, 2H), 2.75-2.57 (m, 2H), 1.96-1.85 (m, 1H), 1.82-1.72 (m, 1H).

Example 254

5-(4-ethyl-7-fluoro-1H-indole-2-carbonyl)-N-[(oxolan-3-yl)methyl]-4H,5H,6H,7H-[1,3]thiazolo[5,4-c]pyridin-2-amine

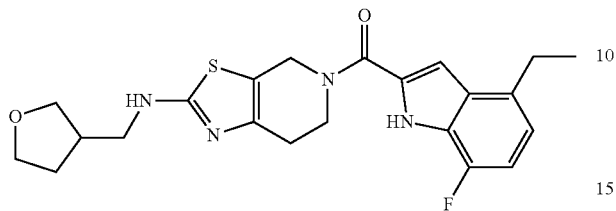

Rt (Method A) 3.38 mins, m/z 429 [M+H]+

1H NMR (400 MHz, DMSO-d6) δ 12.04 (s, 1H), 7.63 (t, J=5.2 Hz, 1H), 6.96-6.88 (m, 2H), 6.81 (dd, J=7.9, 4.3 Hz, 1H), 4.84-4.60 (m, 2H), 3.97-3.89 (m, 3H), 3.76-3.65 (m, 2H), 3.64-3.56 (m, 1H), 3.42 (dd, J=8.6, 5.4 Hz, 1H), 3.20-3.13 (m, 2H), 2.85 (q, J=7.5 Hz, 2H), 2.70-2.59 (m, 2H), 2.49-2.43 (m, 1H), 2.00-1.90 (m, 1H), 1.61-1.49 (m, 1H), 1.26 (t, J=7.5 Hz, 3H).

Example 255

5-(4-ethyl-6-fluoro-1H-indole-2-carbonyl)-N-[(oxolan-3-yl)methyl]-4H,5H,6H,7H-[1,3]thiazolo[5,4-c]pyridin-2-amine

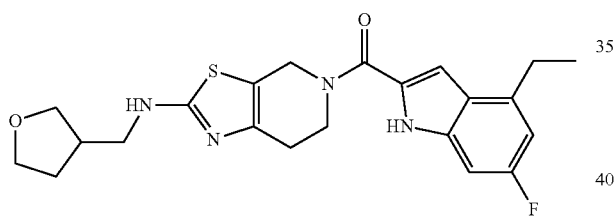

Rt (Method A) 3.38 mins, m/z 429 [M+H]+

1H NMR (400 MHz, DMSO-d6) δ 11.67 (s, 1H), 7.62 (t, J=5.7 Hz, 1H), 6.99-6.93 (m, 2H), 6.77 (dd, J=10.9, 2.2 Hz, 1H), 4.91-4.50 (m, 2H), 4.04-3.90 (m, 2H), 3.77-3.65 (m, 2H), 3.65-3.55 (m, 1H), 3.42 (dd, J=8.6, 5.4 Hz, 1H), 3.23-3.10 (m, 2H), 2.90 (q, J=7.5 Hz, 2H), 2.72-2.61 (m, 2H), 2.49-2.41 (m, 1H), 2.01-1.88 (m, 1H), 1.61-1.49 (m, 1H), 1.28 (t, J=7.5 Hz, 3H).

Example 256

5-(4-ethyl-5-fluoro-1H-indole-2-carbonyl)-N-[(oxolan-3-yl)methyl]-4H,5H,6H,7H-[1,3]thiazolo[5,4-c]pyridin-2-amine

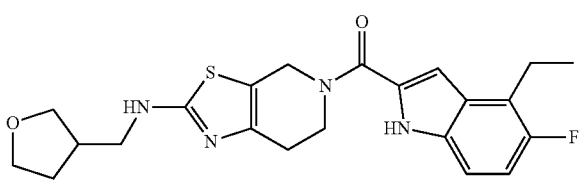 [SMILES: CCc1c(F)ccc2[nH]c(C(=O)N3CCc4nc(NCC5CCOC5)sc4C3)cc12]

Rt (Method A) 3.44 mins, m/z 429 [M+H]+

1H NMR (400 MHz, DMSO-d6) δ 11.82 (s, 1H), 7.62 (t, J=5.4 Hz, 1H), 7.18 (d, J=8.4 Hz, 1H), 7.14-7.04 (m, 1H), 6.86 (s, 1H), 5.04-4.45 (m, 2H), 4.03-3.88 (m, 2H), 3.77-3.66 (m, 2H), 3.65-3.55 (m, 1H), 3.42 (dd, J=8.5, 5.5 Hz, 1H), 3.20-3.11 (m, 2H), 2.74-2.59 (m, 4H), 2.49-2.42 (m, 1H), 2.00-1.88 (m, 1H), 1.61-1.49 (m, 1H), 1.19 (t, J=7.5 Hz, 3H).

Example 257

1-[7-fluoro-2-(2-{[(oxolan-3-yl)methyl]amino}-4H,5H,6H,7H-[1,3]thiazolo[5,4-c]pyridine-5-carbonyl)-1H-indol-4-yl]ethan-1-ol

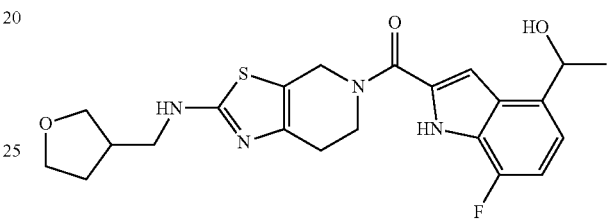

Rt (Method A) 2.78 mins, m/z 445 [M+H]+

1H NMR (400 MHz, DMSO-d6) δ 12.05 (s, 1H), 7.63 (t, J=5.5 Hz, 1H), 7.06-6.90 (m, 3H), 5.19 (d, J=3.8 Hz, 1H), 5.15-5.03 (m, 1H), 4.82-4.55 (m, 2H), 4.03-3.83 (m, 2H), 3.78-3.64 (m, 2H), 3.65-3.55 (m, 1H), 3.42 (dd, J=8.5, 5.4 Hz, 1H), 3.22-3.11 (m, 2H), 2.71-2.59 (m, 2H), 2.49-2.43 (m, 1H), 2.00-1.89 (m, 1H), 1.60-1.49 (m, 1H), 1.41 (d, J=6.4 Hz, 3H).

Example 258

1-[6-fluoro-2-(2-{[(oxolan-3-yl)methyl]amino}-4H,5H,6H,7H-[1,3]thiazolo[5,4-c]pyridine-5-carbonyl)-1H-indol-4-yl]ethan-1-ol

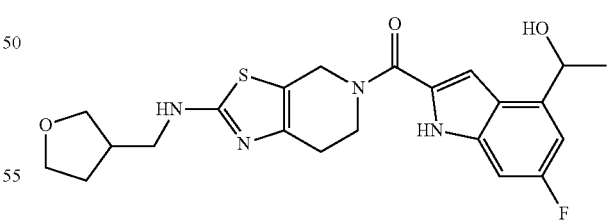

Rt (Method A) 2.83 mins, m/z 445 [M+H]+

1H NMR (400 MHz, DMSO-d6) δ 11.69 (s, 1H), 7.63 (t, J=5.6 Hz, 1H), 7.03-6.96 (m, 2H), 6.93 (dd, J=11.0, 2.2 Hz, 1H), 5.32 (d, J=4.1 Hz, 1H), 5.21-5.12 (m, 1H), 4.88-4.60 (m, 2H), 4.06-3.86 (m, 2H), 3.76-3.65 (m, 2H), 3.65-3.56 (m, 1H), 3.42 (dd, J=8.6, 5.4 Hz, 1H), 3.21-3.12 (m, 2H), 2.72-2.60 (m, 2H), 2.49-2.43 (m, 1H), 2.01-1.88 (m, 1H), 1.61-1.49 (m, 1H), 1.42 (d, J=6.4 Hz, 3H).

Example 259

1-[5-fluoro-2-(2-{[(oxolan-3-yl)methyl]amino}-4H,5H,6H,7H-[1,3]thiazolo[5,4-c]pyridine-5-carbonyl)-1H-indol-4-yl]ethan-1-ol

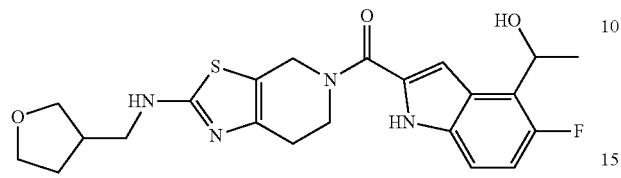

Rt (Method A) 2.83 mins, m/z 445 [M+H]+

1H NMR (400 MHz, DMSO-d6) δ 11.86 (s, 1H), 7.62 (t, J=5.5 Hz, 1H), 7.34 (dd, J=8.4, 7.0 Hz, 1H), 7.23 (d, J=8.5 Hz, 1H), 6.88 (s, 1H), 5.23-5.04 (m, 2H), 4.97-4.49 (m, 2H), 4.06-3.88 (m, 2H), 3.78-3.65 (m, 2H), 3.64-3.54 (m, 1H), 3.42 (dd, J=8.5, 5.4 Hz, 1H), 3.21-3.10 (m, 2H), 2.75-2.58 (m, 2H), 2.49-2.42 (m, 1H), 2.00-1.86 (m, 1H), 1.63-1.48 (m, 1H), 1.36 (d, J=6.2 Hz, 3H).

Example 260

5-(1H-indole-2-carbonyl)-N—[(morpholin-2-yl)methyl]-4H,5H,6H,7H-[1,3]thiazolo[5,4-c]pyridin-2-amine

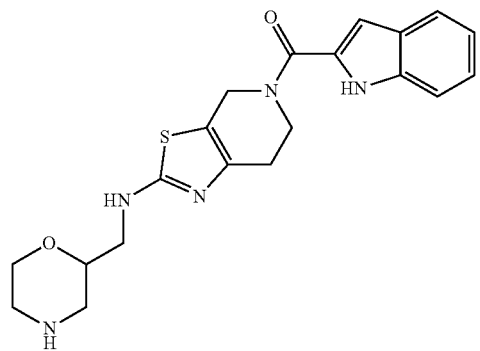 [SMILES: O=C(c1cc2ccccc2[nH]1)N1CCc2nc(NCC3CNCCO3)sc2C1]

Rt (Method A) 3.01 mins, m/z 398 [M+H]+

1H NMR (400 MHz, Chloroform-d) δ 9.14 (s, 1H), 7.68 (d, J=8.0 Hz, 1H), 7.43 (d, J=8.3 Hz, 1H), 7.30 (dd, J=7.6 Hz, 1H), 7.16 (dd, J=7.5 Hz, 1H), 6.93-6.79 (m, 1H), 5.43-5.18 (m, 1H), 5.17-4.59 (m, 2H), 4.37-3.99 (m, 2H), 3.94-3.84 (m, 1H), 3.76-3.66 (m, 1H), 3.62 (td, J=10.9, 3.4 Hz, 1H), 3.49-3.37 (m, 1H), 3.31-3.18 (m, 1H), 3.01-2.76 (m, 5H), 2.68 (t, J=11.1 Hz, 1H).

Example 261

3-cyclopropyl-N-[5-(1H-indole-2-carbonyl)-4H,5H,6H,7H-[1,3]thiazolo[5,4-c]pyridin-2-yl]-3-methylbutanamide

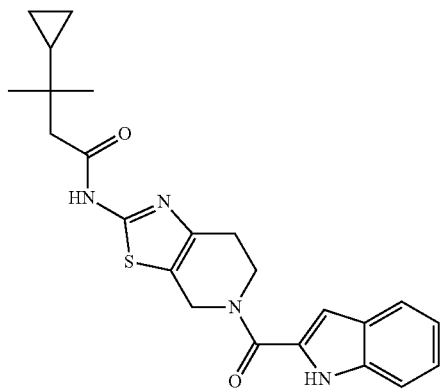 [SMILES: CC(C)(CC(=O)Nc1nc2c(s1)CN(C(=O)c1cc3ccccc3[nH]1)CC2)C1CC1]

Rt (Method A) 3.66 mins, m/z 423 [M+H]+

1H NMR (400 MHz, DMSO-d6) δ 11.95 (s, 1H), 11.64 (s, 1H), 7.64 (d, J=8.0 Hz, 1H), 7.43 (d, J=8.3 Hz, 1H), 7.20 (t, J=7.6 Hz, 1H), 7.06 (t, J=7.5 Hz, 1H), 6.93 (s, 1H), 5.03-4.81 (m, 2H), 4.13-3.98 (m, 2H), 2.90-2.76 (m, 2H), 2.33 (s, 2H), 0.88-0.77 (m, 7H), 0.26-0.13 (m, 4H).

Example 262

N-[5-(1H-indole-2-carbonyl)-4H,5H,6H,7H-[1,3]thiazolo[5,4-c]pyridin-2-yl]-3,3-dimethylpentanamide

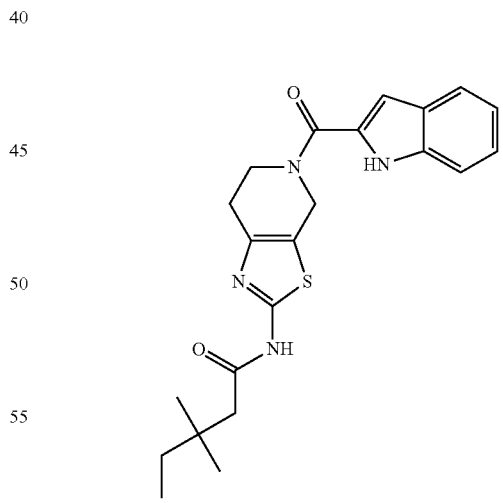

Rt (Method A) 3.68 mins, m/z 411 [M+H]+

1H NMR (400 MHz, DMSO-d6) δ 11.96 (s, 1H), 11.64 (s, 1H), 7.64 (d, J=7.9 Hz, 1H), 7.43 (d, J=8.3 Hz, 1H), 7.23-7.17 (m, 1H), 7.09-7.03 (m, 1H), 6.96-6.90 (m, 1H), 5.08-4.74 (m, 2H), 4.13-3.95 (m, 2H), 2.90-2.75 (m, 2H), 2.28 (s, 2H), 1.31 (q, J=7.5 Hz, 2H), 0.93 (s, 6H), 0.82 (t, J=7.5 Hz, 3H).

Example 263

N-[5-(4-chloro-1H-indole-2-carbonyl)-4H,5H,6H,7H-[1,3]thiazolo[5,4-c]pyridin-2-yl]-3,3-dimethylbutanamide

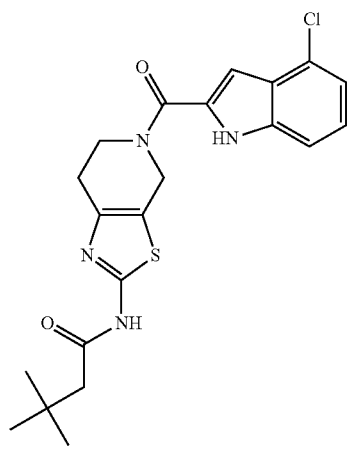 [SMILES: CC(C)(C)CC(=O)Nc1nc2c(s1)CN(C(=O)c1cc3c(Cl)cccc3[nH]1)CC2]

Rt (Method A) 3.73 mins, m/z 431/433 [M+H]+

1H NMR (400 MHz, DMSO-d6) δ 12.21-11.75 (m, 2H), 7.41 (d, J=8.0 Hz, 1H), 7.20 (t, J=7.8 Hz, 1H), 7.15 (d, J=7.0 Hz, 1H), 6.89 (s, 1H), 5.23-4.60 (m, 2H), 4.10-3.97 (m, 2H), 2.89-2.76 (m, 2H), 2.29 (s, 2H), 0.99 (s, 9H).

Example 264

3-tert-butyl-1-[5-(1H-indole-2-carbonyl)-4H,5H,6H,7H-[1,3]thiazolo[5,4-c]pyridin-2-yl]urea

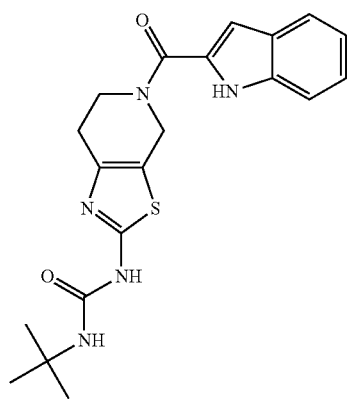 [SMILES: CC(C)(C)NC(=O)Nc1nc2c(s1)CN(C(=O)c1cc3ccccc3[nH]1)CC2]

Rt (Method A) 3.35 mins, m/z 398 [M+H]+

1H NMR (400 MHz, DMSO-d6) δ 11.64 (s, 1H), 9.93 (s, 1H), 7.63 (d, J=8.0 Hz, 1H), 7.43 (d, J=8.2 Hz, 1H), 7.23-7.16 (m, 1H), 7.09-7.03 (m, 1H), 6.93-6.89 (m, 1H), 6.47 (s, 1H), 5.09-4.61 (m, 2H), 4.06-3.98 (m, 2H), 2.79-2.72 (m, 2H), 1.29 (s, 9H).

Example 265

3-tert-butyl-1-[5-(4-chloro-6-fluoro-1H-indole-2-carbonyl)-4H,5H,6H,7H-[1,3]thiazolo[5,4-c]pyridin-2-yl]urea

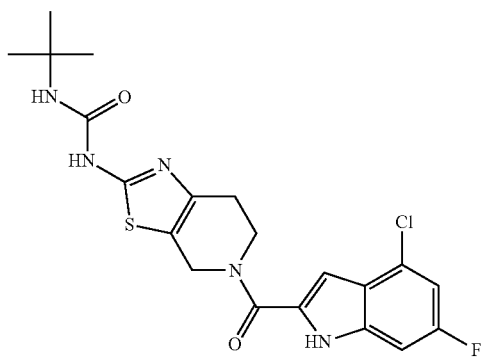 [SMILES: CC(C)(C)NC(=O)Nc1nc2c(s1)CN(C(=O)c1cc3c(Cl)cc(F)cc3[nH]1)CC2]

Rt (Method A) 3.64 mins, m/z 450/452 [M+H]+

1H NMR (400 MHz, DMSO-d6) δ 12.80-11.37 (m, 1H), 10.54-9.55 (m, 1H), 7.19-7.12 (m, 2H), 6.90 (s, 1H), 6.48 (s, 1H), 5.07-4.60 (m, 2H), 4.11-3.88 (m, 2H), 2.79-2.70 (m, 2H), 1.29 (s, 9H).

Example 266

1-[5-(4-chloro-6-fluoro-1H-indole-2-carbonyl)-4H,5H,6H,7H-[1,3]thiazolo[5,4-c]pyridin-2-yl]-3-methylurea

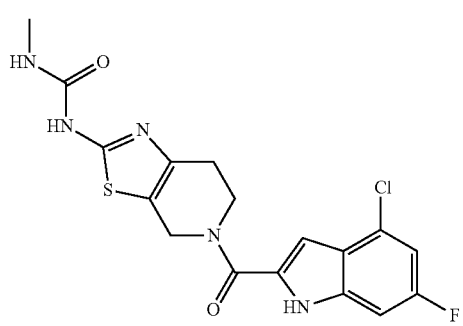 [SMILES: CNC(=O)Nc1nc2c(s1)CN(C(=O)c1cc3c(Cl)cc(F)cc3[nH]1)CC2]

Rt (Method A) 3.20 mins, m/z 408/410 [M+H]+

1H NMR (400 MHz, DMSO-d6) δ 12.11 (s, 1H), 10.45 (s, 1H), 7.22-7.14 (m, 2H), 6.91 (s, 1H), 6.53-6.43 (m, 1H), 5.19-4.63 (m, 2H), 4.17-3.89 (m, 2H), 2.85-2.62 (m, 5H).

Example 267

N-[5-(1H-indole-2-carbonyl)-4H,5H,6H,7H-[1,3]thiazolo[5,4-c]pyridin-2-yl]-2,2-dimethylcyclopropane-1-carboxamide

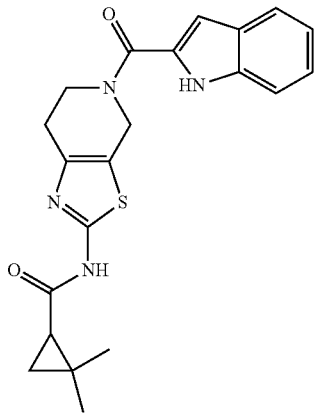 [SMILES: CC1(C)CC1C(=O)Nc1nc2c(s1)CN(C(=O)c1cc3ccccc3[nH]1)CC2]

Rt (Method A) 3.48 mins, m/z 395 [M+H]+

1H NMR (400 MHz, DMSO-d6) δ 12.15 (s, 1H), 11.64 (s, 1H), 7.63 (d, J=7.9 Hz, 1H), 7.43 (d, J=8.2 Hz, 1H), 7.24-7.16 (m, 1H), 7.10-7.02 (m, 1H), 6.93 (d, J=1.3 Hz, 1H), 5.07-4.71 (m, 2H), 4.15-3.94 (m, 2H), 2.93-2.76 (m, 2H), 1.79 (dd, J=7.8, 5.5 Hz, 1H), 1.15 (s, 3H), 1.12 (s, 3H), 1.07-1.02 (m, 1H), 0.90 (dd, J=7.8, 4.0 Hz, 1H).

Example 268

N-[5-(1H-indole-2-carbonyl)-4H,5H,6H,7H-[1,3]thiazolo[5,4-c]pyridin-2-yl]-2-methylcyclopropane-1-carboxamide

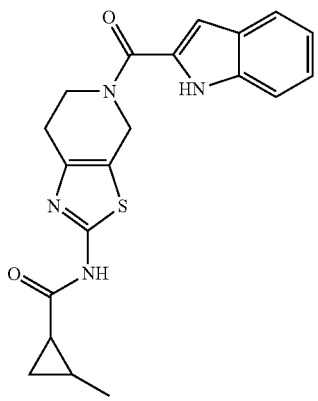 [SMILES: CC1CC1C(=O)Nc1nc2c(s1)CN(C(=O)c1cc3ccccc3[nH]1)CC2]

Rt (Method A) 3.31 mins, m/z 381 [M+H]+

1H NMR (400 MHz, DMSO-d6) δ 12.23 (s, 1H), 11.64 (s, 1H), 7.63 (d, J=7.9 Hz, 1H), 7.43 (d, J=8.1 Hz, 1H), 7.24-7.16 (m, 1H), 7.10-7.03 (m, 1H), 6.93 (d, J=1.6 Hz, 1H), 5.06-4.71 (m, 2H), 4.15-3.95 (m, 2H), 2.92-2.76 (m, 2H), 1.70-1.59 (m, 1H), 1.35-1.26 (m, 1H), 1.12-1.03 (m, 4H), 0.79-0.72 (m, 1H).

Example 269

(1R,2R)-2-{[5-(1H-indole-2-carbonyl)-4H,5H,6H,7H-[1,3]thiazolo[5,4-c]pyridin-2-yl]amino}cyclohexan-1-ol

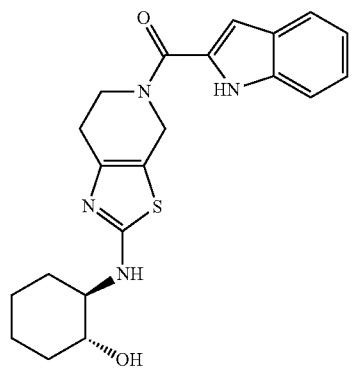 [SMILES: O=C(c1cc2ccccc2[nH]1)N1CCc2nc(N[C@@H]3CCCC[C@H]3O)sc2C1]

Rt (Method B) 2.51 mins, m/z 397 [M+H]+

1H NMR (400 MHz, DMSO-d6) δ 11.62 (s, 1H), 7.62 (d, J=8.0 Hz, 1H), 7.42 (d, J=8.2 Hz, 1H), 7.36 (d, J=6.6 Hz, 1H), 7.23-7.16 (m, 1H), 7.05 (t, J=7.5 Hz, 1H), 6.89 (d, J=1.6 Hz, 1H), 4.92-4.50 (m, 3H), 4.08-3.88 (m, 2H), 3.32-3.26 (m, 2H), 2.74-2.57 (m, 2H), 2.03-1.94 (m, 1H), 1.89-1.80 (m, 1H), 1.67-1.53 (m, 2H), 1.30-1.08 (m, 4H).

Example 270

5-(1H-indole-2-carbonyl)-N-[(oxan-3-yl)methyl]-4H,5H,6H,7H-[1,3]thiazolo[5,4-c]pyridin-2-amine

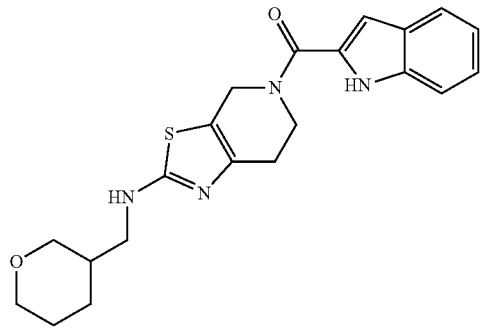 [SMILES: O=C(c1cc2ccccc2[nH]1)N1CCc2nc(NCC3CCCOC3)sc2C1]

Rt (Method B) 2.60 mins, m/z 397 [M+H]+

1H NMR (400 MHz, DMSO-d6) δ 11.62 (s, 1H), 7.62 (d, J=8.0 Hz, 1H), 7.51 (t, J=5.5 Hz, 1H), 7.42 (d, J=8.3 Hz, 1H), 7.23-7.16 (m, 1H), 7.09-7.02 (m, 1H), 6.89 (d, J=1.6 Hz, 1H), 4.88-4.59 (m, 2H), 4.11-3.88 (m, 2H), 3.81-3.66 (m, 2H), 3.31-3.25 (m, 1H), 3.15-3.03 (m, 3H), 2.71-2.62 (m, 2H), 1.87-1.73 (m, 2H), 1.60-1.51 (m, 1H), 1.51-1.40 (m, 1H), 1.29-1.16 (m, 1H).

Example 271

[1-({[5-(6-fluoro-4-methyl-1H-indole-2-carbonyl)-4H,5H,6H,7H-[1,3]thiazolo[5,4-c]pyridin-2-yl]amino}methyl)cyclopropyl]methanol

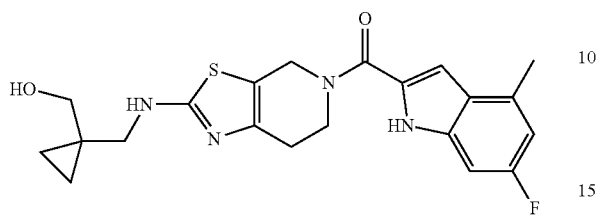

Rt (Method A) 3.22 mins, m/z 415 [M+H]+
1H-NMR (400 MHz, DMSO-d6) δ 11.66 (s, 1H), 7.50 (m, 1H), 6.95 (m, 2H), 6.75 (m, 1H), 4.76-4.65 (m, 3H), 3.98 (m, 2H), 3.27 (d, J=5.8 Hz, 2H), 3.23 (d, J=5.6 Hz, 2H), 2.66 (m, 2H), 2.51 (s, 3H), 0.41 (m, 2H), 0.36 (m, 2H)

Example 272

[1-({[5-(4-ethyl-1H-indole-2-carbonyl)-4H,5H,6H,7H-[1,3]thiazolo[5,4-c]pyridin-2-yl]amino}methyl)cyclopropyl]methanol

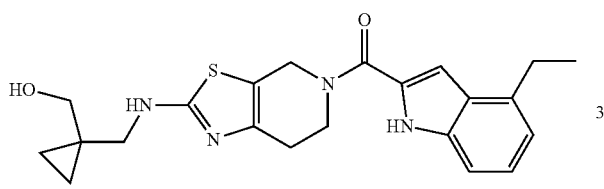

Rt (Method A) 3.28 mins, m/z 411 [M+H]+
1H NMR (400 MHz, DMSO-d6) δ 11.58 (s, 1H), 7.50 (m, 1H), 7.25 (d, J=8.2 Hz, 1H), 7.11 (m, 1H), 6.92 (m, 1H), 6.87 (m, 1H) 4.76-4.65 (m, 3H), 3.98 (m, 2H), 3.27 (d, J=5.8 Hz, 2H), 3.23 (d, J=5.6 Hz, 2H), 2.89 (m, 2H), 2.66 (m, 2H), 1.28 (t, J=7.5 Hz, 3H), 0.41 (m, 2H), 0.36 (m, 2H)

Example 273 tert-butyl 2-({[5-(1H-indole-2-carbonyl)-4H,5H,6H,7H-[1,3]thiazolo[5,4-c]pyridin-2-yl]amino}methyl)morpholine-4-carboxylate

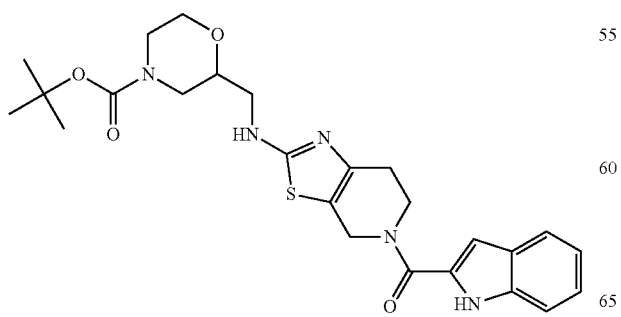

Rt (Method A) 3.48 mins, m/z 498 [M+H]+
1H NMR (400 MHz, Chloroform-d) δ 9.16 (s, 1H), 7.68 (d, J=8.0 Hz, 1H), 7.43 (d, J=8.1 Hz, 1H), 7.30 (ddd, J=8.2, 6.9, 1.2 Hz, 1H), 7.16 (ddd, J=7.9, 6.9, 1.0 Hz, 1H), 6.90-6.84 (m, 1H), 5.42-5.21 (m, 1H), 5.18-4.52 (m, 2H), 4.31-4.06 (m, 2H), 4.06-3.71 (m, 3H), 3.63 (ddd, J=13.5, 6.6, 2.9 Hz, 1H), 3.59-3.44 (m, 2H), 3.28 (dd, J=13.1, 7.7 Hz, 1H), 3.08-2.90 (m, 1H), 2.90-2.80 (m, 2H), 2.80-2.59 (m, 1H), 1.46 (s, 9H).

Example 274

N-[5-(1H-indole-2-carbonyl)-4H,5H,6H,7H-[1,3]thiazolo[5,4-c]pyridin-2-yl]-1-methylcyclopropane-1-carboxamide

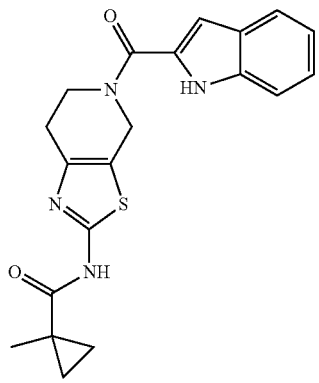 [SMILES: CC1(C(=O)Nc2nc3c(s2)CN(C(=O)c2cc4ccccc4[nH]2)CC3)CC1]

Rt (Method A) 3.33 mins, m/z 381 [M+H]+
1H NMR (400 MHz, DMSO-d6) δ 11.64 (s, 1H), 11.52 (s, 1H), 7.63 (d, J=7.9 Hz, 1H), 7.43 (d, J=8.3 Hz, 1H), 7.23-7.16 (m, 1H), 7.10-7.02 (m, 1H), 6.93 (d, J=1.5 Hz, 1H), 5.08-4.73 (m, 2H), 4.14-3.95 (m, 2H), 2.97-2.76 (m, 2H), 1.38 (s, 3H), 1.22-1.11 (m, 2H), 0.77-0.65 (m, 2H).

Example 275

N-[5-(1H-indole-2-carbonyl)-4H,5H,6H,7H-[1,3]thiazolo[5,4-c]pyridin-2-yl]-2,2-dimethylpropanamide

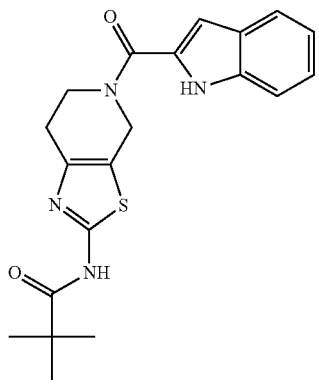 [SMILES: CC(C)(C)C(=O)Nc1nc2c(s1)CN(C(=O)c1cc3ccccc3[nH]1)CC2]

Rt (Method A) 3.42 mins, m/z 383 [M+H]+
1H NMR (400 MHz, DMSO-d6) δ 11.72 (s, 1H), 11.64 (s, 1H), 7.64 (d, J=8.0 Hz, 1H), 7.43 (d, J=8.4 Hz, 1H), 7.24-7.16 (m, 1H), 7.10-7.03 (m, 1H), 6.96-6.91 (m, 1H), 5.17-4.66 (m, 2H), 4.21-3.91 (m, 2H), 2.96-2.75 (m, 2H), 1.22 (s, 9H).

Example 276

5-[4-(trimethylsilyl)-1H-indole-2-carbonyl]-4H,5H,6H,7H-[1,3]thiazolo[5,4-c]pyridin-2-amine

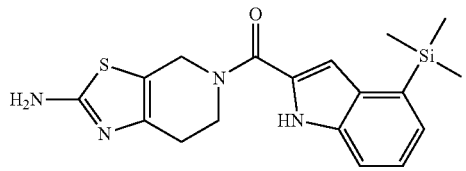 [SMILES: C[Si](C)(C)c1cccc2[nH]c(C(=O)N3CCc4nc(N)sc4C3)cc12]

Rt (Method A) 3.48 mins, m/z 371 [M+H]+

1H NMR (400 MHz, DMSO-d6) δ 11.70 (s, 1H), 7.49-7.40 (m, 1H), 7.22-7.12 (m, 2H), 6.92-6.78 (m, 3H), 4.86-4.49 (m, 2H), 4.13-3.80 (m, 2H), 2.72-2.56 (m, 2H), 0.36 (s, 9H).

Example 277

5-(6-chloro-5-fluoro-1H-indole-2-carbonyl)-4H,5H,6H,7H-[1,3]thiazolo[5,4-c]pyridin-2-amine

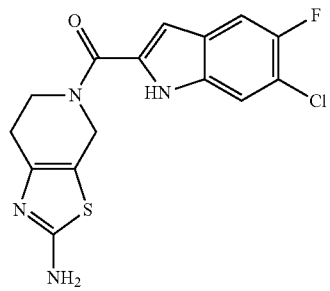 [SMILES: Nc1nc2c(s1)CN(C(=O)c1cc3cc(F)c(Cl)cc3[nH]1)CC2]

Rt (Method A) 3.12 mins, m/z 351/353 [M+H]+

1H NMR (400 MHz, DMSO-d6) δ 11.87 (s, 1H), 7.62 (d, J=10.0 Hz, 1H), 7.55 (d, J=6.4 Hz, 1H), 6.95-6.90 (m, 1H), 6.86 (s, 2H), 4.98-4.49 (m, 2H), 4.12-3.79 (m, 2H), 2.77-2.54 (m, 2H).

Example 278

2-{[5-(1H-indole-2-carbonyl)-4H,5H,6H,7H-[1,3]thiazolo[5,4-c]pyridin-2-yl]amino}acetamide

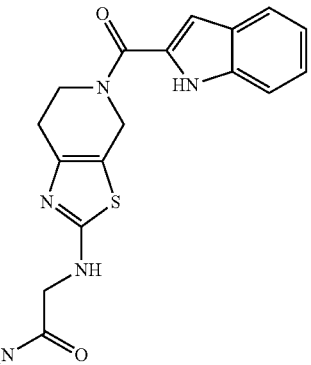

Rt (Method A) 2.71 mins, m/z 356 [M+H]+

1H NMR (400 MHz, DMSO-d6) δ 11.63 (s, 1H), 7.73-7.58 (m, 2H), 7.42 (d, J=8.2 Hz, 1H), 7.39-7.30 (m, 1H), 7.23-7.15 (m, 1H), 7.11-6.99 (m, 2H), 6.92-6.86 (m, 1H), 5.04-4.48 (m, 2H), 4.14-3.86 (m, 2H), 3.79 (d, J=5.8 Hz, 2H), 2.79-2.57 (m, 2H).

Example 279

5-(4,6-difluoro-1H-indole-2-carbonyl)-4H,5H,6H-pyrrolo[3,4-d][1,3]thiazol-2-amine

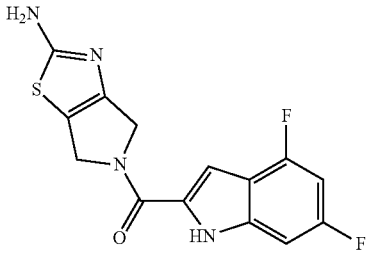 [SMILES: Nc1nc2c(s1)CN(C(=O)c1cc3c(F)cc(F)cc3[nH]1)C2]

Rt (Method B) 2.92 mins, m/z 321 [M+H]+

1H NMR (400 MHz, DMSO-d6) δ 12.04 (d, J=6.9 Hz, 1H), 7.25-7.12 (m, 3H), 7.06 (d, J=9.3 Hz, 1H), 6.92 (td, J=10.4, 2.0 Hz, 1H), 5.11-5.01 (m, 1H), 4.95-4.83 (m, 1H), 4.76-4.66 (m, 1H), 4.58-4.49 (m, 1H).

Example 280

5-(1H-indole-2-carbonyl)-4H,5H,6H-pyrrolo[3,4-d][1,3]thiazol-2-amine

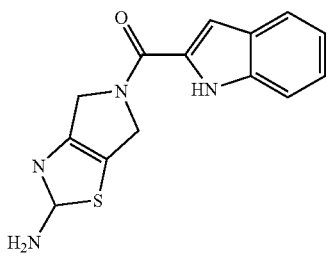 [SMILES: NC1NC2=C(CN(C(=O)c3cc4ccccc4[nH]3)C2)S1]

Rt (Method B) 2.67 mins, m/z 285 [M+H]+
1H NMR (400 MHz, DMSO-d6) δ 11.62 (d, J=7.9 Hz, 1H), 7.65 (t, J=8.6 Hz, 1H), 7.47 (d, J=8.2 Hz, 1H), 7.24-7.03 (m, 5H), 5.10-5.01 (m, 1H), 4.92-4.84 (m, 1H), 4.74-4.67 (m, 1H), 4.57-4.49 (m, 1H).

Example 281

5-(1H-indole-2-carbonyl)-5,7-dihydro-4H-spiro[[1,3]thiazolo[5,4-c]pyridine-6,1'-cyclopropan]-2-amine

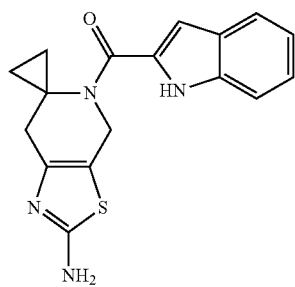 [SMILES: Nc1nc2c(s1)CN(C(=O)c1cc3ccccc3[nH]1)C1(CC1)C2]

Rt (Method B) 2.36 mins, m/z 325 [M+H]+
1H NMR (400 MHz, DMSO-d6) δ 11.76-11.36 (m, 1H), 7.63 (d, J=8.0 Hz, 1H), 7.42 (d, J=8.2 Hz, 1H), 7.19 (t, J=7.5 Hz, 1H), 7.05 (t, J=7.5 Hz, 1H), 7.00-6.73 (m, 3H), 4.76 (s, 2H), 1.29-0.32 (m, 4H).

Example 282

2-(cyclopropylmethyl)-3-{[5-(1H-indole-2-carbonyl)-4H,5H,6H,7H-[1,3]thiazolo[5,4-c]pyridin-2-yl]amino}propan-1-ol

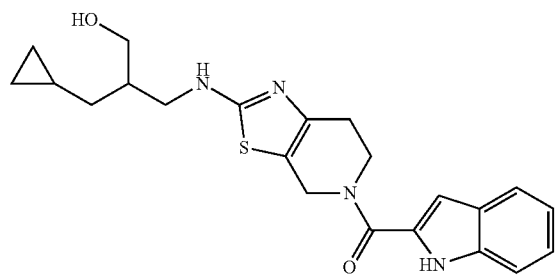 [SMILES: O=C(c1cc2ccccc2[nH]1)N1CCc2nc(NCC(CO)CC3CC3)sc2C1]

Rt (Method A) 3.33 mins, m/z 411 [M+H]+
1H NMR (400 MHz, Chloroform-d) δ 9.13 (s, 1H), 7.68 (d, J=7.9 Hz, 1H), 7.43 (d, J=8.3 Hz, 1H), 7.33-7.28 (m, 1H), 7.19-7.12 (m, 1H), 6.88-6.83 (m, 1H), 5.47-5.12 (m, 1H), 5.08-4.58 (m, 2H), 4.39-3.94 (m, 2H), 3.70 (dd, J=11.6, 3.9 Hz, 1H), 3.66-3.58 (m, 1H), 3.50 (dd, J=11.6, 7.0 Hz, 1H), 3.47-3.39 (m, 1H), 2.98-2.66 (m, 2H), 1.90-1.83 (m, 1H), 1.32-1.16 (m, 2H), 0.75-0.63 (m, 1H), 0.52-0.45 (m, 2H), 0.06 (d, J=5.8 Hz, 2H)—one signal (1H) coincides with H2O signal.

Example 283

3-{[5-(1H-indole-2-carbonyl)-4H,5H,6H,7H-[1,3]thiazolo[5,4-c]pyridin-2-yl]amino}-2-methoxy-2-methylpropan-1-ol

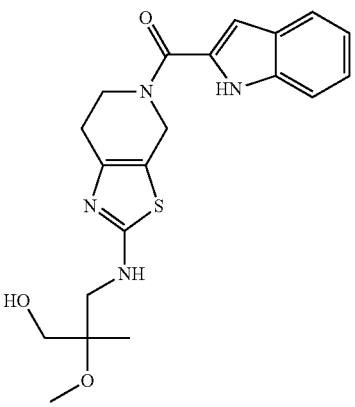

Rt (Method A) 2.96 mins, m/z 401 [M+H]+
1H NMR (400 MHz, Chloroform-d) δ 9.11 (s, 1H), 7.68 (d, J=8.0 Hz, 1H), 7.46-7.40 (m, 1H), 7.30 (ddd, J=8.2, 6.9, 1.0 Hz, 1H), 7.19-7.12 (m, 1H), 6.88-6.83 (m, 1H), 5.41-5.17 (m, 1H), 5.13-4.63 (m, 2H), 4.32-3.92 (m, 3H), 3.58 (d, J=14.5 Hz, 1H), 3.51 (d, J=11.8 Hz, 1H), 3.42-3.33 (m, 2H), 3.28 (s, 3H), 2.87-2.79 (m, 2H), 1.21 (s, 3H).

Example 284

2-cyclopropyl-3-{[5-(1H-indole-2-carbonyl)-4H,5H,6H,7H-[1,3]thiazolo[5,4-c]pyridin-2-yl]amino}propan-1-ol

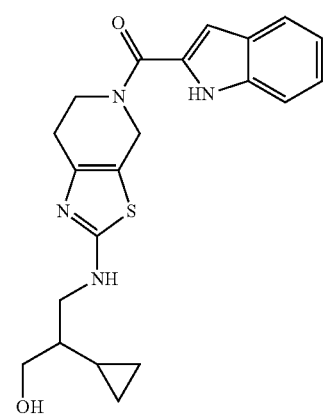 [SMILES: O=C(c1cc2ccccc2[nH]1)N1CCc2nc(NCC(CO)C3CC3)sc2C1]

Rt (Method A) 3.19 mins, m/z 397 [M+H]+

1H NMR (400 MHz, DMSO-d6) δ 11.62 (s, 1H), 7.62 (d, J=7.9 Hz, 1H), 7.46 (t, J=5.7 Hz, 1H), 7.42 (d, J=8.2 Hz, 1H), 7.19 (dd, J=7.6 Hz, 1H), 7.05 (dd, J=7.5 Hz, 1H), 6.89 (s, 1H), 5.03-4.66 (m, 2H), 4.64 (t, J=5.4 Hz, 1H), 4.09-3.86 (m, 2H), 3.52-3.38 (m, 2H), 3.30-3.25 (m, 2H), 2.73-2.59 (m, 2H), 0.96-0.81 (m, 1H), 0.68-0.56 (m, 1H), 0.47-0.31 (m, 2H), 0.21-0.04 (m, 2H).

Example 285

5-(1H-indole-2-carbonyl)-N-[2-(1H-pyrazol-1-yl)ethyl]-4H,5H,6H,7H-[1,3]thiazolo[5,4-c]pyridin-2-amine

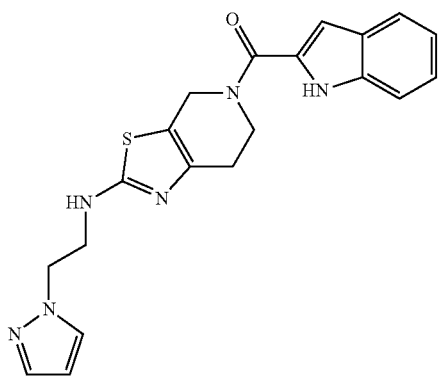 [SMILES: O=C(c1cc2ccccc2[nH]1)N1CCc2nc(NCCn3cccn3)sc2C1]

Rt (Method A) 3.05 mins, m/z 393 [M+H]+

1H NMR (400 MHz, DMSO-d6) δ 11.63 (s, 1H), 7.68 (d, J=2.1 Hz, 1H), 7.66-7.57 (m, 2H), 7.47-7.40 (m, 2H), 7.23-7.16 (m, 1H), 7.09-7.02 (m, 1H), 6.89 (d, J=1.6 Hz, 1H), 6.22 (t, J=2.0 Hz, 1H), 4.93-4.54 (m, 2H), 4.29 (t, J=6.1 Hz, 2H), 4.04-3.94 (m, 2H), 3.60 (q, J=5.9 Hz, 2H), 2.74-2.65 (m, 2H).

Example 286

N-[2-(1H-imidazol-4-yl)ethyl]-5-(1H-indole-2-carbonyl)-4H,5H,6H,7H-[1,3]thiazolo[5,4-c]pyridin-2-amine

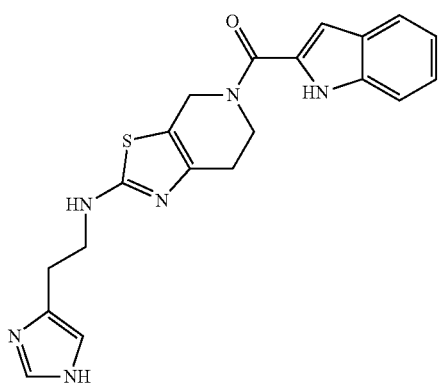 [SMILES: O=C(c1cc2ccccc2[nH]1)N1CCc2nc(NCCc3c[nH]cn3)sc2C1]

Rt (Method A) 2.9 mins, m/z 393 [M+H]+

1H NMR (400 MHz, DMSO-d6) δ 12.04-11.68 (m, 1H), 11.63 (s, 1H), 7.63 (d, J=8.0 Hz, 1H), 7.59-7.48 (m, 2H), 7.42 (d, J=8.2 Hz, 1H), 7.23-7.16 (m, 1H), 7.10-7.00 (m, 1H), 6.92-6.60 (m, 2H), 5.00-4.55 (m, 2H), 4.13-3.88 (m, 2H), 3.41 (q, J=6.8 Hz, 2H), 2.89-2.59 (m, 4H).

Example 287

2-({[5-(1H-indole-2-carbonyl)-4H,5H,6H,7H-[1,3]thiazolo[5,4-c]pyridin-2-yl]amino}methyl)-4-methylpentan-1-ol

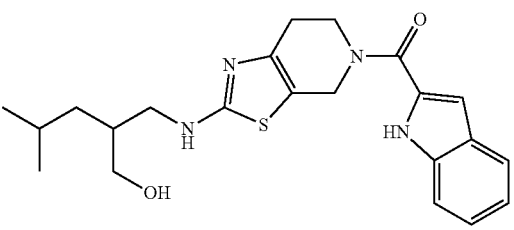 [SMILES: CC(C)CC(CO)CNc1nc2c(s1)CN(C(=O)c1cc3ccccc3[nH]1)CC2]

Rt (Method A) 3.45 mins, m/z 413 [M+H]+

1H NMR (400 MHz, DMSO-d6) δ 11.62 (m, 1H), 7.62 (m, 1H) 7.45 (m, 2H), 7.19 (m, 1H), 7.05 (m, 1H), 6.89 (m, 1H), 4.74 (m, 2H), 4.57 (t, J=5.5 Hz, 1H), 3.98 (m, 2H), 3.39-3.28 (m, 2H), 3.16 (t, J=5.9 Hz, 2H), 2.65 (m, 2H), 1.75-1.61 (m, 2H), 1.21-1.04 (m, 2H), 0.86 (t, J=6.1 Hz, 6H)

Example 288

(1S,2R)-2-({[5-(1H-indole-2-carbonyl)-4H,5H,6H,7H-[1,3]thiazolo[5,4-c]pyridin-2-yl]amino}methyl)cyclohexan-1-ol

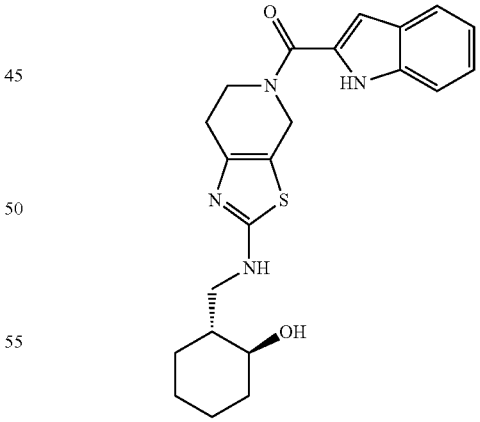

Rt (Method A) 3.31 mins, m/z 411 [M+H]+

1H NMR (400 MHz, DMSO-d6) δ 11.62 (s, 1H), 7.62 (d, J=7.9 Hz, 1H) 7.43 (m, 2H), 7.19 (m, 1H), 7.05 (m, 1H), 6.89 (m, 1H), 4.86 (d, J=4.9 Hz, 1H), 4.73 (m, 2H), 3.98 (m, 2H), 3.44 (m, 1H), 3.18-3.06 (m, 2H), 2.65 (m, 2H), 1.82-1.73 (m, 2H), 1.68-1.55 (m, 2H), 1.36 (m, 1H), 1.25-0.93 (m, 4H)

Example 289

Methyl (2S,4S)-4-{[5-(1H-indole-2-carbonyl)-4H,5H,6H,7H-[1,3]thiazolo[5,4-c]pyridin-2-yl]amino}pyrrolidine-2-carboxylate

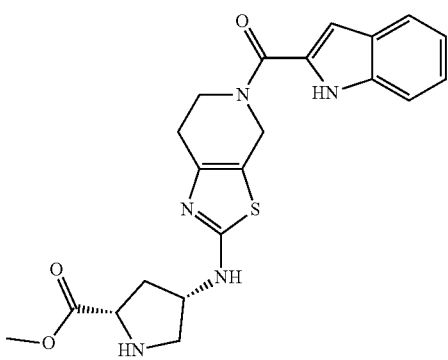 [SMILES: COC(=O)[C@@H]1C[C@H](Nc2nc3c(s2)CN(C(=O)c2cc4ccccc4[nH]2)CC3)CN1]

Rt (Method B) 2.34 mins, m/z 426 [M+H]+

1H NMR (400 MHz, DMSO-d6) δ 11.62 (s, 1H), 7.62 (d, J=7.9 Hz, 1H), 7.57 (d, J=6.3 Hz, 1H), 7.43 (d, J=8.3 Hz, 1H), 7.20 (dd, J=7.6 Hz, 1H), 7.06 (dd, J=7.5 Hz, 1H), 6.89 (d, J=1.6 Hz, 1H), 5.19-4.46 (m, 2H), 4.10-3.90 (m, 3H), 3.71 (dd, J=8.9, 6.9 Hz, 1H), 3.63 (s, 3H), 3.03 (dd, J=10.8, 6.2 Hz, 1H), 2.74 (dd, J=10.8, 5.4 Hz, 1H), 2.71-2.60 (m, 2H), 2.45-2.35 (m, 1H), 1.73 (dt, J=13.1, 6.4 Hz, 1H)—one signal coincides with H2O signal.

Example 290

5-[4-(1,1-difluoroethyl)-6-fluoro-1H-indole-2-carbonyl]-4H,5H,6H,7H-[1,3]thiazolo[5,4-c]pyridin-2-amine

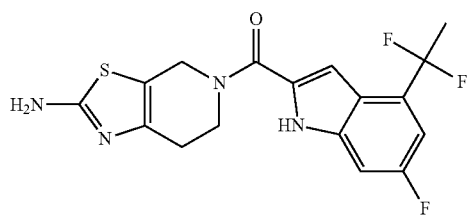 [SMILES: CC(F)(F)c1cc(F)cc2[nH]c(C(=O)N3CCc4nc(N)sc4C3)cc12]

Rt (Method A) 3.16 mins, m/z 381 [M+H]+

1H NMR (400 MHz, DMSO-d6) δ 12.06 (s, 1H), 7.34-7.25 (m, 1H), 7.11 (dd, J=10.3, 2.3 Hz, 1H), 6.98-6.75 (m, 3H), 5.01-4.47 (m, 2H), 4.12-3.88 (m, 2H), 2.66-2.56 (m, 2H), 2.09 (t, J=19.0 Hz, 3H).

Example 291

5-[4-(1,1-difluoroethyl)-1H-indole-2-carbonyl]-4H,5H,6H,7H-[1,3]thiazolo[5,4-c]pyridin-2-amine

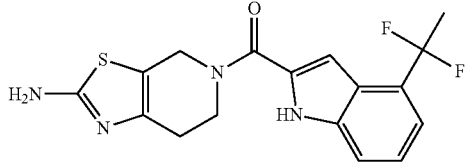 [SMILES: CC(F)(F)c1cccc2[nH]c(C(=O)N3CCc4nc(N)sc4C3)cc12]

Rt (Method A) 3.08 mins, m/z 363 [M+H]+

1H NMR (400 MHz, DMSO-d6) δ 11.97 (s, 1H), 7.55 (d, J=7.9 Hz, 1H), 7.31-7.17 (m, 2H), 6.95-6.77 (m, 3H), 4.92-4.48 (m, 2H), 4.09-3.84 (m, 2H), 2.66-2.56 (m, 2H), 2.08 (t, J=18.9 Hz, 3H).

Example 292

5-[4-(difluoromethyl)-6-fluoro-1H-indole-2-carbonyl]-4H,5H,6H,7H-[1,3]thiazolo[5,4-c]pyridin-2-amine

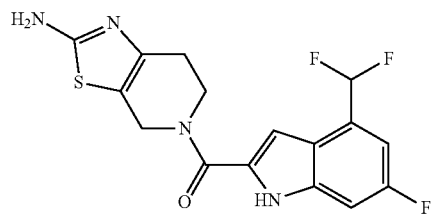 [SMILES: Nc1nc2c(s1)CN(C(=O)c1cc3c(C(F)F)cc(F)cc3[nH]1)CC2]

Rt (Method A) 3.05 mins, m/z 367 [M+H]+

1H NMR (400 MHz, DMSO-d6) δ 12.08 (s, 1H), 7.51-7.16 (m, 3H), 7.01 (s, 1H), 6.86 (s, 2H), 4.86-4.61 (m, 2H), 4.01-3.93 (m, 2H), 2.65-2.60 (m, 2H).

Example 293

5-[4-(difluoromethyl)-1H-indole-2-carbonyl]-4H,5H,6H,7H-[1,3]thiazolo[5,4-c]pyridin-2-amine

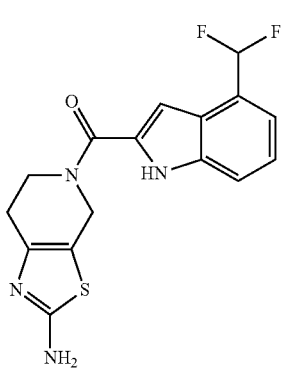 [SMILES: Nc1nc2c(s1)CN(C(=O)c1cc3c(C(F)F)cccc3[nH]1)CC2]

Rt (Method A) 2.97 mins, m/z 349 [M+H]+ 1H NMR (400 MHz, DMSO-d6) δ 12.00 (s, 1H), 7.64-7.55 (m, 1H), 7.48-7.17 (m, 3H), 6.98 (s, 1H), 6.86 (s, 2H), 5.00-4.52 (m, 2H), 4.08-3.89 (m, 2H), 2.72-2.59 (m, 2H).

Example 294

5-(1H-indole-2-carbonyl)-N-[(4-methylmorpholin-3-yl)methyl]-4H,5H,6H,7H-[1,3]thiazolo[5,4-c]pyridin-2-amine

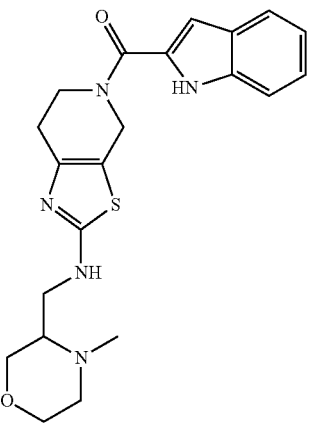 [SMILES: CN1CCOCC1CNc1nc2c(s1)CN(C(=O)c1cc3ccccc3[nH]1)CC2]

Rt (Method A) 2.96 mins, m/z 412 [M+H]+
1H NMR (400 MHz, DMSO-d6) δ 11.62 (s, 1H), 7.62 (d, J=7.9 Hz, 1H), 7.47-7.38 (m, 2H), 7.19 (ddd, J=8.2, 7.0, 1.2 Hz, 1H), 7.05 (ddd, J=7.9, 6.9, 1.0 Hz, 1H), 6.92-6.86 (m, 1H), 5.06-4.45 (m, 2H), 4.09-3.88 (m, 2H), 3.76-3.60 (m, 2H), 3.51-3.39 (m, 2H), 3.25 (dd, J=11.2, 9.5 Hz, 1H), 3.20-3.11 (m, 1H), 2.78-2.65 (m, 2H), 2.63 (dt, J=11.9, 2.3 Hz, 1H), 2.25 (s, 3H), 2.23-2.12 (m, 2H)."

Example 295

2-(2-{hexahydro-1H-imidazo[4,3-c][1,4]oxazin-2-yl}-4H,5H,6H,7H-[1,3]thiazolo[5,4-c]pyridine-5-carbonyl)-1H-indole

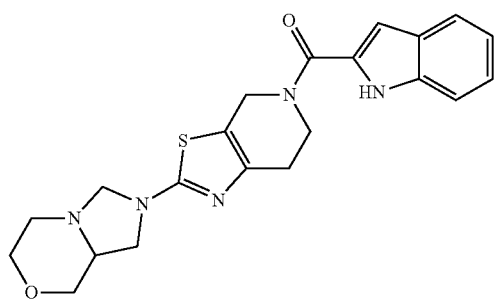 [SMILES: O=C(c1cc2ccccc2[nH]1)N1CCc2nc(N3CC4COCCN4C3)sc2C1]

Rt (Method A) 2.96 mins, m/z 410 [M+H]+
1H NMR (400 MHz, DMSO-d6) δ 11.64 (s, 1H), 7.63 (d, J=8.0 Hz, 1H), 7.44 (d, J=8.2 Hz, 1H), 7.20 (dd, J=7.6 Hz, 1H), 7.06 (dd, J=7.4 Hz, 1H), 6.95-6.86 (m, 1H), 5.03-4.64 (m, 2H), 4.36 (d, J=7.0 Hz, 1H), 4.11-3.98 (m, 2H), 3.97 (d, J=7.1 Hz, 1H), 3.84 (d, J=11.7, 3.1 Hz, 1H), 3.69-3.55 (m, 3H), 3.34-3.29 (m, 1H), 3.22 (t, J=9.3 Hz, 1H), 3.10-3.01 (m, 1H), 2.81-2.70 (m, 2H), 2.70-2.59 (m, 1H), 2.59-2.52 (m, 1H).

Example 296—Intentionally Left Blank

Example 297

2-{[5-(1H-indole-2-carbonyl)-4H,5H,6H,7H-[1,3]thiazolo[5,4-c]pyridin-2-yl]amino}-2-(oxolan-3-yl)ethan-1-ol

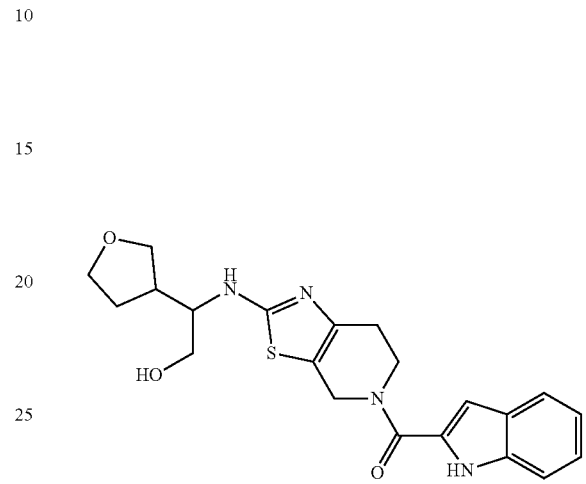

Rt (Method A) 2.84 mins, m/z 413 [M+H]+
1H NMR (400 MHz, DMSO-d6) δ 11.62 (s, 1H), 7.62 (d, J=7.9 Hz, 1H), 7.50-7.36 (m, 2H), 7.19 (t, J=7.6 Hz, 1H), 7.05 (t, J=7.5 Hz, 1H), 6.88 (d, J=6.3 Hz, 1H), 5.00-4.46 (m, 3H), 4.06-3.91 (m, 2H), 3.80-3.50 (m, 4H), 3.48-3.34 (m, 3H), 2.75-2.56 (m, 2H), 2.48-2.36 (m, 1H), 2.01-1.86 (m, 1H), 1.70-1.55 (m, 1H).

Example 298

(1-{[5-(6-fluoro-4-methyl-1H-indole-2-carbonyl)-4H,5H,6H,7H-[1,3]thiazolo[5,4-c]pyridin-2-yl]amino}cyclobutyl)methanol

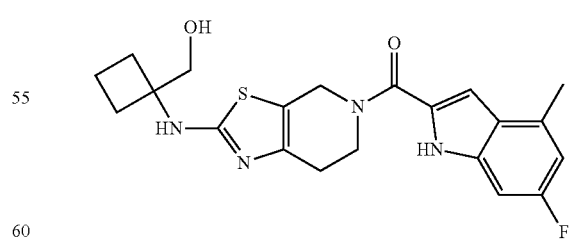

Rt (Method A) 3.33 mins, m/z 415 [M+H]+
1H NMR (400 MHz, DMSO-d6) δ 11.66 (s, 1H), 7.60 (s, 1H), 7.00-6.89 (m, 2H), 6.76 (d, 1H), 5.10-4.45 (m, 3H), 4.19-3.82 (m, 2H), 3.63 (d, J=4.6 Hz, 2H), 2.78-2.56 (m, 2H), 2.51 (s, 3H), 2.19-2.03 (m, 4H), 1.87-1.64 (m, 2H).

Example 299

(1-{[5-(6-chloro-1H-indole-2-carbonyl)-4H,5H,6H,7H-[1,3]thiazolo[5,4-c]pyridin-2-yl]amino}cyclobutyl)methanol

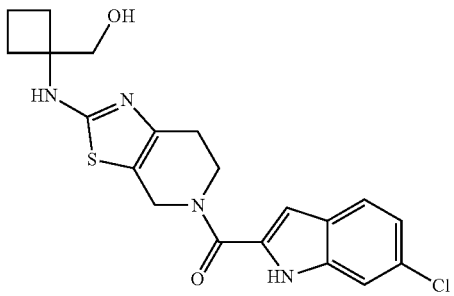 [SMILES: O=C(c1cc2ccc(Cl)cc2[nH]1)N1CCc2nc(NC3(CO)CCC3)sc2C1]

Rt (Method A) 3.36 mins, m/z 417/419 [M+H]+

1H NMR (400 MHz, DMSO-d6) δ 11.78 (s, 1H), 7.69-7.56 (m, 2H), 7.43 (d, J=1.7 Hz, 1H), 7.08 (dd, J=8.5, 1.9 Hz, 1H), 6.94 (s, 1H), 4.96 (t, J=5.5 Hz, 3H), 4.08-3.84 (m, 2H), 3.62 (d, J=5.4 Hz, 2H), 2.74-2.56 (m, 2H), 2.17-2.00 (m, 4H), 1.87-1.61 (m, 2H).

Example 300

(1-{[5-(4-ethyl-1H-indole-2-carbonyl)-4H,5H,6H,7H-[1,3]thiazolo[5,4-c]pyridin-2-yl]amino}cyclobutyl)methanol

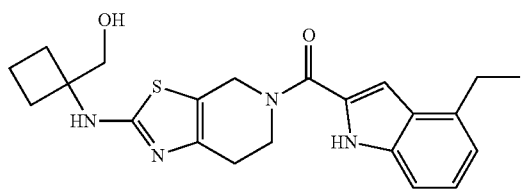 [SMILES: CCc1cccc2[nH]c(C(=O)N3CCc4nc(NC5(CO)CCC5)sc4C3)cc12]

Rt (Method A) 3.41 mins, m/z 411 [M+H]+

1H NMR (400 MHz, DMSO-d6) δ 11.58 (s, 1H), 7.59 (s, 1H), 7.25 (d, J=8.2 Hz, 1H), 7.16-7.07 (m, 1H), 6.93 (s, 1H), 6.87 (d, J=7.1 Hz, 1H), 5.12-4.49 (m, 3H), 4.08-3.87 (m, 2H), 3.62 (d, J=5.3 Hz, 2H), 2.89 (q, J=7.5 Hz, 2H), 2.74-2.56 (m, 2H), 2.19-2.03 (m, 4H), 1.87-1.64 (m, 2H), 1.28 (t, J=7.5 Hz, 3H).

Example 301

(1s,4s)-4-{[5-(6-chloro-1H-indole-2-carbonyl)-4H,5H,6H,7H-[1,3]thiazolo[5,4-c]pyridin-2-yl]amino}cyclohexan-1-ol

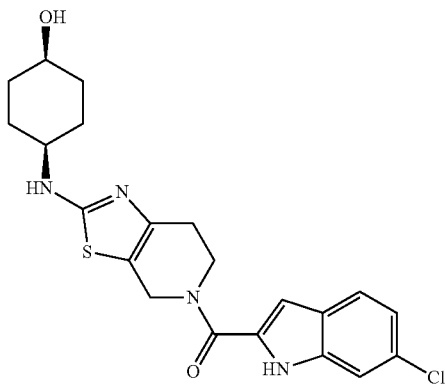 [SMILES: O=C(c1cc2ccc(Cl)cc2[nH]1)N1CCc2nc(N[C@H]3CC[C@@H](O)CC3)sc2C1]

Rt (Method A) 3.21 mins, m/z 431/433 [M+H]+

1H NMR (400 MHz, DMSO-d6) δ 11.78 (s, 1H), 7.65 (d, J=8.5 Hz, 1H), 7.47-7.39 (m, 2H), 7.08 (dd, J=8.5, 1.9 Hz, 1H), 6.93 (s, 1H), 5.01-4.52 (m, 2H), 4.39 (d, J=3.0 Hz, 1H), 4.07-3.87 (m, 2H), 3.69-3.61 (m, 1H), 3.57-3.47 (m, 1H), 2.74-2.58 (m, 2H), 1.74-1.42 (m, 8H).

Example 302

(1s,4s)-4-{[5-(4-chloro-1H-indole-2-carbonyl)-4H,5H,6H,7H-[1,3]thiazolo[5,4-c]pyridin-2-yl]amino}cyclohexan-1-ol

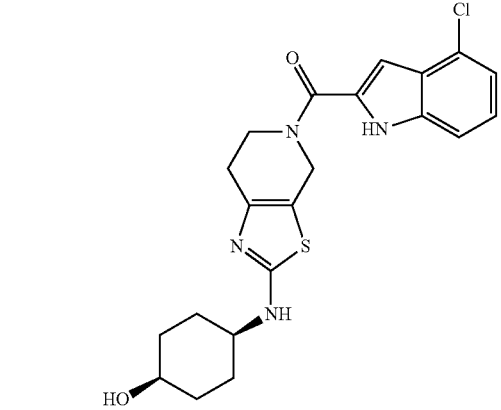 [SMILES: O=C(c1cc2c(Cl)cccc2[nH]1)N1CCc2nc(N[C@H]3CC[C@@H](O)CC3)sc2C1]

Rt (Method A) 3.2 mins, m/z 431/433 [M+H]+

1H NMR (400 MHz, DMSO-d6) δ 12.02 (s, 1H), 7.48-7.38 (m, 2H), 7.25-7.11 (m, 2H), 6.85 (s, 1H), 4.99-4.51 (m, 2H), 4.45-4.34 (m, 1H), 4.12-3.84 (m, 2H), 3.70-3.61 (m, 1H), 3.58-3.48 (m, 1H), 2.74-2.57 (m, 2H), 1.72-1.43 (m, 8H).

Example 303

(1s,4s)-4-{[5-(6-fluoro-4-methyl-1H-indole-2-carbonyl)-4H,5H,6H,7H-[1,3]thiazolo[5,4-c]pyridin-2-yl]amino}cyclohexan-1-ol

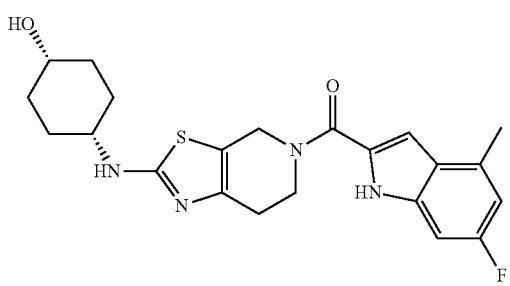 [SMILES: Cc1cc(F)cc2[nH]c(C(=O)N3CCc4nc(N[C@H]5CC[C@@H](O)CC5)sc4C3)cc12]

Rt (Method A) 3.18 mins, m/z 429 [M+H]+

1H NMR (400 MHz, DMSO-d6) δ 11.66 (s, 1H), 7.43 (d, J=7.3 Hz, 1H), 6.98-6.93 (m, 2H), 6.78-6.72 (m, 1H), 5.10-4.50 (m, 2H), 4.39 (d, J=3.0 Hz, 1H), 4.13-3.81 (m, 2H), 3.70-3.59 (m, 1H), 3.58-3.47 (m, 1H), 2.71-2.58 (m, 2H), 2.53-2.51 (m, 3H), 1.72-1.42 (m, 8H).

Example 304

N-[5-(6-chloro-5-fluoro-1H-indole-2-carbonyl)-4H,5H,6H,7H-[1,3]thiazolo[5,4-c]pyridin-2-yl]-1-methylcyclopropane-1-carboxamide

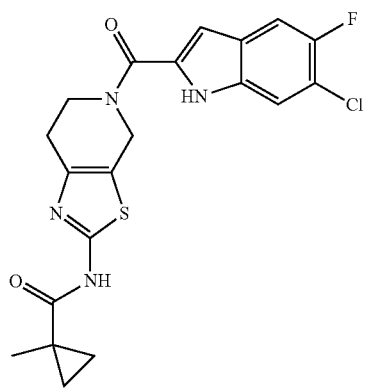 [SMILES: CC1(C(=O)Nc2nc3c(s2)CN(C(=O)c2cc4cc(F)c(Cl)cc4[nH]2)CC3)CC1]

Rt (Method A) 3.65 mins, m/z 433/435 [M+H]+

1H NMR (400 MHz, DMSO-d6) δ 11.89 (s, 1H), 11.64-11.46 (m, 1H), 7.63 (d, J=10.0 Hz, 1H), 7.55 (d, J=6.4 Hz, 1H), 6.96 (s, 1H), 5.05-4.67 (m, 2H), 4.09-3.96 (m, 2H), 2.90-2.75 (m, 2H), 1.37 (s, 3H), 1.19-1.13 (m, 2H), 0.74-0.67 (m, 2H).

Example 305

N-[5-(4-chloro-6-fluoro-1H-indole-2-carbonyl)-4H,5H,6H,7H-[1,3]thiazolo[5,4-c]pyridin-2-yl]-1-methylcyclopropane-1-carboxamide

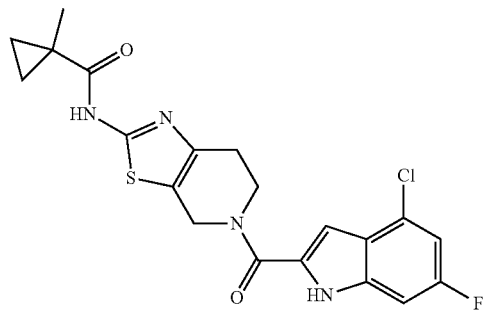 [SMILES: CC1(C(=O)Nc2nc3c(s2)CN(C(=O)c2cc4c(Cl)cc(F)cc4[nH]2)CC3)CC1]

Rt (Method A) 3.66 mins, m/z 433/435 [M+H]+

1H NMR (400 MHz, DMSO-d6) δ 12.24-11.97 (m, 1H), 11.77-11.41 (m, 1H), 7.19 (s, 1H), 7.16 (s, 1H), 6.92 (s, 1H), 4.90 (s, 2H), 4.12-3.97 (m, 2H), 2.87-2.78 (m, 2H), 1.37 (s, 3H), 1.19-1.13 (m, 2H), 0.73-0.67 (m, 2H).

Example 306

N-[5-(4-ethyl-6-fluoro-1H-indole-2-carbonyl)-4H,5H,6H,7H-[1,3]thiazolo[5,4-c]pyridin-2-yl]-1-methylcyclopropane-1-carboxamide

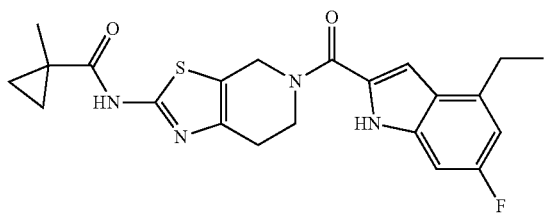 [SMILES: CCc1cc(F)cc2[nH]c(C(=O)N3CCc4nc(NC(=O)C5(C)CC5)sc4C3)cc12]

Rt (Method A) 3.67 mins, m/z 427 [M+H]+

1H NMR (400 MHz, DMSO-d6) δ 11.70-11.65 (m, 1H), 11.63-11.42 (m, 1H), 7.03-6.94 (m, 2H), 6.77 (dd, J=10.8, 2.3 Hz, 1H), 5.10-4.71 (m, 2H), 4.12-3.98 (m, 2H), 2.91 (q, J=7.6 Hz, 2H), 2.87-2.79 (m, 2H), 1.38 (s, 3H), 1.28 (t, J=7.5 Hz, 3H), 1.17 (q, J=3.8 Hz, 2H), 0.71 (q, J=4.0 Hz, 2H).

Example 307

N-[5-(6-fluoro-4-methyl-1H-indole-2-carbonyl)-4H,5H,6H,7H-[1,3]thiazolo[5,4-c]pyridin-2-yl]-1-methylcyclopropane-1-carboxamide

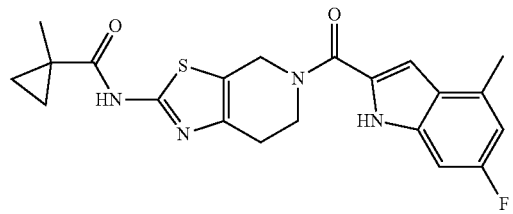 [SMILES: Cc1cc(F)cc2[nH]c(C(=O)N3CCc4nc(NC(=O)C5(C)CC5)sc4C3)cc12]

Rt (Method A) 3.54 mins, m/z 413 [M+H]+

1H NMR (400 MHz, DMSO-d6) δ 11.70-11.65 (m, 1H), 11.60-11.42 (m, 1H), 7.02-6.93 (m, 1H), 6.76 (dd, J=11.0, 2.2 Hz, 1H), 5.11-4.73 (m, 2H), 4.11-4.00 (m, 2H), 2.90-2.78 (m, 2H), 2.53 (s, 3H), 1.38 (s, 3H), 1.17 (q, J=3.8 Hz, 2H), 0.72 (q, J=4.0 Hz, 2H).

Example 308

N-[5-(4-chloro-1H-indole-2-carbonyl)-4H,5H,6H,7H-[1,3]thiazolo[5,4-c]pyridin-2-yl]-1-methylcyclopropane-1-carboxamide

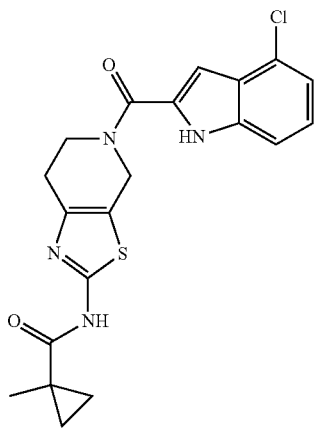 [SMILES: CC1(C(=O)Nc2nc3c(s2)CN(C(=O)c2cc4c(Cl)cccc4[nH]2)CC3)CC1]

Rt (Method A) 3.56 mins, m/z 415/417 [M+H]+

1H NMR (400 MHz, DMSO-d6) δ 12.04 (s, 1H), 11.64-11.43 (m, 1H), 7.41 (d, J=8.0 Hz, 1H), 7.20 (t, J=7.8 Hz, 1H), 7.15 (d, J=7.4 Hz, 1H), 6.93-6.87 (m, 1H), 5.20-4.66 (m, 2H), 4.09-4.01 (m, 2H), 2.91-2.76 (m, 2H), 1.38 (s, 3H), 1.17 (q, J=3.8 Hz, 2H), 0.72 (q, J=4.0 Hz, 2H).

Example 309—Intentionally Left Blank

Example 310

5-(1H-indole-2-carbonyl)-N-(4-methoxycyclohexyl)-4H,5H,6H,7H-[1,3]thiazolo[5,4-c]pyridin-2-amine

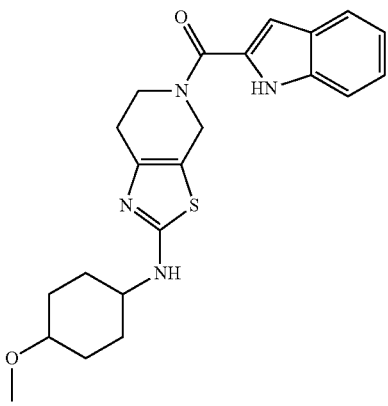 [SMILES: COC1CCC(Nc2nc3c(s2)CN(C(=O)c2cc4ccccc4[nH]2)CC3)CC1]

Rt (Method A) 3.27 mins, m/z 411 [M+H]+

1H NMR (400 MHz, DMSO-d6) δ 11.62 (s, 1H), 7.62 (d, J=8.0 Hz, 1H), 7.46-7.38 (m, 2H), 7.19 (t, J=7.2 Hz, 1H), 7.06 (t, J=7.4 Hz, 1H), 6.88 (d, J=1.5 Hz, 1H), 4.95-4.50 (m, 2H), 4.09-3.86 (m, 2H), 3.52-3.40 (m, 1H), 3.22 (s, 3H), 3.16-3.05 (m, 1H), 2.75-2.58 (m, 2H), 2.02-1.92 (m, 4H), 1.26-1.16 (m, 4H).

Example 311

1-({[5-(4-chloro-1H-indole-2-carbonyl)-4H,5H,6H,7H-[1,3]thiazolo[5,4-c]pyridin-2-yl]amino}methyl)cyclobutan-1-ol

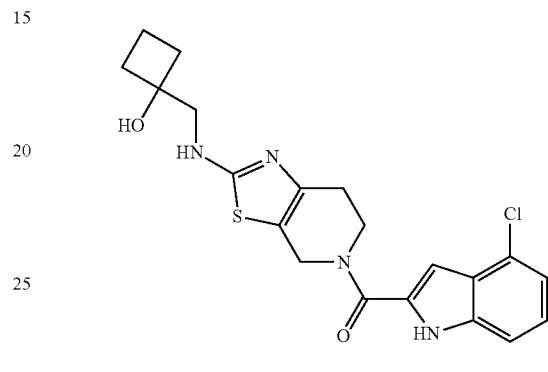

Rt (Method A) 3.29 mins, m/z 417/419 [M+H]+

1H NMR (400 MHz, DMSO-d6) δ 12.02 (s, 1H), 7.49-7.37 (m, 2H), 7.23-7.12 (m, 2H), 6.86 (s, 1H), 5.27 (s, 1H), 5.06-4.35 (m, 2H), 4.17-3.74 (m, 2H), 3.36-3.33 (m, 2H), 2.74-2.57 (m, 2H), 2.05-1.86 (m, 4H), 1.68-1.57 (m, 1H), 1.53-1.39 (m, 1H).

Example 312

1-({[5-(6-fluoro-4-methyl-1H-indole-2-carbonyl)-4H,5H,6H,7H-[1,3]thiazolo[5,4-c]pyridin-2-yl]amino}methyl)cyclobutan-1-ol

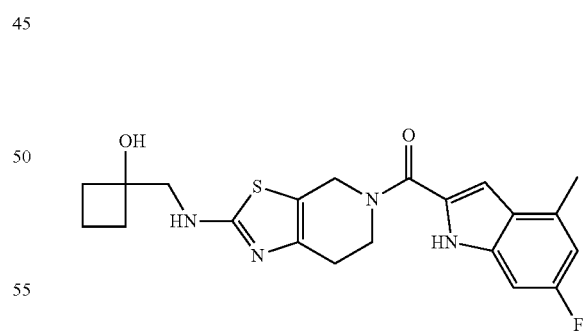

Rt (Method A) 3.27 mins, m/z 415 [M+H]+

1H NMR (400 MHz, DMSO-d6) δ 11.66 (s, 1H), 7.44 (t, J=5.6 Hz, 1H), 6.99-6.90 (m, 2H), 6.79-6.72 (m, 1H), 5.28 (s, 1H), 5.05-4.45 (m, 2H), 4.14-3.79 (m, 2H), 3.36-3.33 (m, 2H), 2.77-2.59 (m, 2H), 2.53-2.51 (m, 3H), 2.06-1.84 (m, 4H), 1.69-1.56 (m, 1H), 1.53-1.38 (m, 1H).

Example 313

1-({[5-(4-chloro-6-fluoro-1H-indole-2-carbonyl)-4H, 5H,6H,7H-[1,3]thiazolo[5,4-c]pyridin-2-yl] amino}methyl)cyclobutan-1-ol

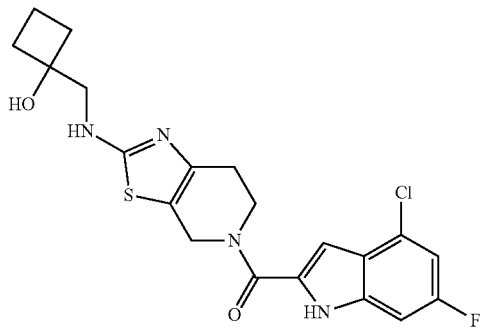 [SMILES: O=C(c1cc2c(Cl)cc(F)cc2[nH]1)N1CCc2nc(NCC3(O)CCC3)sc2C1]

Rt (Method A) 3.39 mins, m/z 435/437 [M+H]+

1H NMR (400 MHz, DMSO-d6) δ 12.10 (s, 1H), 7.44 (t, J=5.4 Hz, 1H), 7.17 (d, J=9.6 Hz, 2H), 6.88 (s, 1H), 5.27 (s, 1H), 5.07-4.46 (m, 2H), 4.14-3.82 (m, 2H), 2.72-2.58 (m, 2H), 2.05-1.85 (m, 4H), 1.68-1.56 (m, 1H), 1.53-1.39 (m, 1H).

Example 314

1-({[5-(4,6-difluoro-1H-indole-2-carbonyl)-4H,5H, 6H,7H-[1,3]thiazolo[5,4-c]pyridin-2-yl] amino}methyl)cyclobutan-1-ol

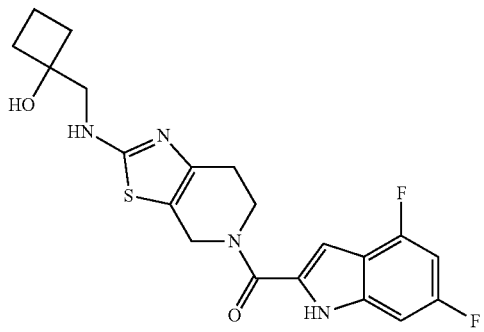 [SMILES: O=C(c1cc2c(F)cc(F)cc2[nH]1)N1CCc2nc(NCC3(O)CCC3)sc2C1]

Rt (Method A) 3.26 mins, m/z 419 [M+H]+ 1H NMR (400 MHz, DMSO-d6) δ 12.06 (s, 1H), 7.43 (t, J=5.5 Hz, 1H), 7.04 (dd, J=9.1, 2.1 Hz, 1H), 7.00-6.86 (m, 2H), 5.27 (s, 1H), 4.08-3.84 (m, 2H), 3.35-3.33 (m, 2H), 2.76-2.56 (m, 2H), 2.05-1.85 (m, 4H), 1.70-1.56 (m, 1H), 1.53-1.37 (m, 1H).

Example 315

N-[5-(1H-indole-2-carbonyl)-4H,5H,6H,7H-[1,3] thiazolo[5,4-c]pyridin-2-yl]oxane-2-carboxamide

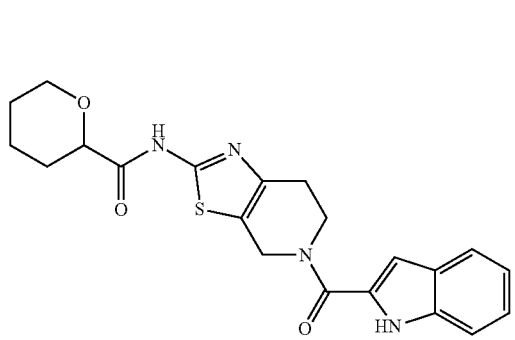 [SMILES: O=C(Nc1nc2c(s1)CN(C(=O)c1cc3ccccc3[nH]1)CC2)C1CCCCO1]

Rt (Method A) 3.37 mins, m/z 411 [M+H]+

1H NMR (400 MHz, DMSO-d6) δ 11.67-11.61 (m, 2H), 7.63 (d, J=8.0 Hz, 1H), 7.43 (d, J=8.0 Hz, 1H), 7.23-7.17 (m, 1H), 7.09-7.03 (m, 1H), 6.95-6.91 (m, 1H), 5.38-4.44 (m, 2H), 4.13-3.89 (m, 4H), 3.51-3.41 (m, 1H), 2.84 (s, 2H), 1.82 (d, J=8.6 Hz, 2H), 1.52 (d, J=7.1 Hz, 4H).

Example 316

N-[5-(4-chloro-1H-indole-2-carbonyl)-4H,5H,6H, 7H-[1,3]thiazolo[5,4-c]pyridin-2-yl]oxane-4-carboxamide

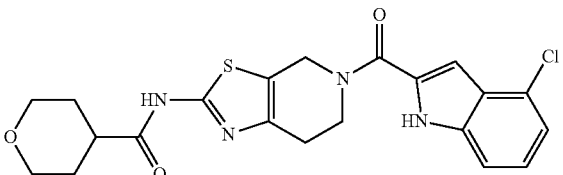

Rt (Method A) 3.25 mins, m/z 445/447 [M+H]+

1H NMR (400 MHz, DMSO-d6) δ 12.03 (s, 2H), 7.41 (d, J=8.1 Hz, 1H), 7.20 (t, J=7.8 Hz, 1H), 7.15 (d, J=7.3 Hz, 1H), 6.90 (s, 1H), 4.93 (s, 1H), 4.04 (s, 2H), 3.88 (d, J=10.7 Hz, 2H), 3.31-3.28 (m, 2H), 2.82 (s, 2H), 2.70 (s, 1H), 1.78-1.55 (m, 4H), 1.32-1.21 (m, 1H).

Example 317

Ethyl 1-({[5-(1H-indole-2-carbonyl)-4H,5H,6H,7H-[1,3]thiazolo[5,4-c]pyridin-2-yl]amino}methyl)cyclopropane-1-carboxylate

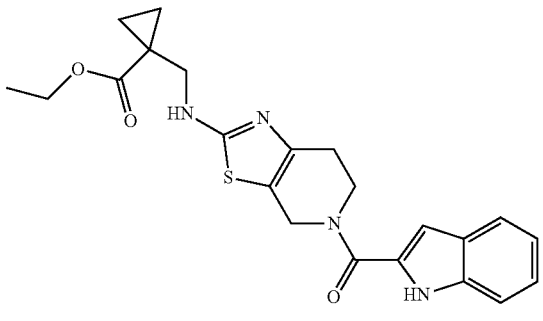 [SMILES: CCOC(=O)C1(CNc2nc3c(s2)CN(C(=O)c2cc4ccccc4[nH]2)CC3)CC1]

Rt (Method A) 3.44 mins, m/z 425 [M+H]+
1H NMR (400 MHz, Chloroform-d) δ 9.08 (s, 1H), 7.68 (d, J=8.0 Hz, 1H), 7.43 (d, J=8.1 Hz, 1H), 7.30 (ddd, J=8.2, 7.0, 1.2 Hz, 1H), 7.18-7.13 (m, 1H), 6.88-6.84 (m, 1H), 5.58-5.51 (m, 1H), 5.09-4.69 (m, 2H), 4.26-4.05 (m, 4H), 3.48 (d, J=5.5 Hz, 2H), 2.91-2.77 (m, 2H), 1.29 (q, J=4.3 Hz, 2H), 1.24 (t, J=7.1 Hz, 3H), 1.00 (q, J=4.3 Hz, 2H).

Example 318

N-[5-(6-chloro-1H-indole-2-carbonyl)-4H,5H,6H,7H-[1,3]thiazolo[5,4-c]pyridin-2-yl]oxane-4-carboxamide

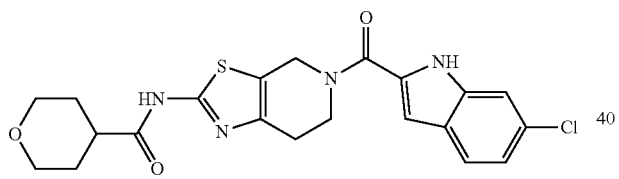

Rt (Method A) 3.23 mins, m/z 445/447 [M+H]+
1H NMR (400 MHz, DMSO-d6) δ 12.11-11.71 (m, 2H), 7.66 (d, J=8.6 Hz, 1H), 7.48-7.39 (m, 1H), 7.08 (dd, J=8.5, 1.9 Hz, 1H), 6.98 (s, 1H), 5.03-4.72 (m, 2H), 4.13-3.98 (m, 2H), 3.88 (d, J=11.4 Hz, 2H), 3.21-3.12 (m, 2H), 2.90-2.77 (m, 2H), 2.74-2.69 (m, 1H), 1.77-1.56 (m, 4H).

Example 319

N-[5-(4,6-difluoro-1H-indole-2-carbonyl)-4H,5H,6H,7H-[1,3]thiazolo[5,4-c]pyridin-2-yl]oxane-4-carboxamide

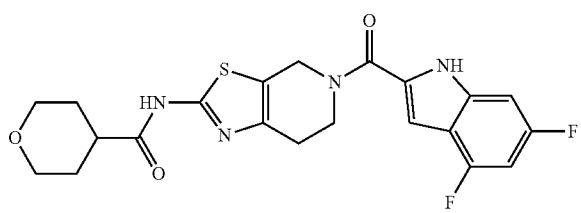 [SMILES: O=C(Nc1nc2c(s1)CN(C(=O)c1cc3c(F)cc(F)cc3[nH]1)CC2)C1CCOCC1]

Rt (Method A) 3.21 mins, m/z 447 [M+H]+
1H NMR (400 MHz, DMSO-d6) δ 12.12-11.99 (m, 2H), 7.07-6.99 (m, 2H), 6.92 (td, J=10.4, 2.1 Hz, 1H), 5.18-4.68 (m, 2H), 4.07-3.98 (m, 2H), 3.92-3.85 (m, 2H), 3.34 (s, 2H), 2.90-2.77 (m, 2H), 2.77-2.68 (m, 1H), 1.76-1.57 (m, 4H).

Example 320

N-[5-(4-chloro-6-fluoro-1H-indole-2-carbonyl)-4H,5H,6H,7H-[1,3]thiazolo[5,4-c]pyridin-2-yl]oxane-4-carboxamide

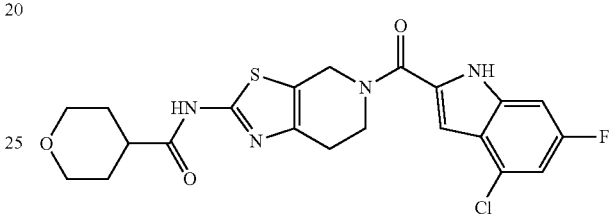

Rt (Method A) 3.33 mins, m/z 463/465 [M+H]+
1H NMR (400 MHz, DMSO-d6) δ 12.27-11.90 (m, 2H), 7.21-7.15 (m, 2H), 6.92 (s, 1H), 5.18-4.75 (m, 2H), 4.11-3.95 (m, 2H), 3.94-3.84 (m, 2H), 3.52-3.11 (m, 2H), 2.89-2.76 (m, 2H), 2.76-2.68 (m, 1H), 1.76-1.57 (m, 4H).

Example 321

N-[5-(6-fluoro-4-methyl-1H-indole-2-carbonyl)-4H,5H,6H,7H-[1,3]thiazolo[5,4-c]pyridin-2-yl]oxane-4-carboxamide

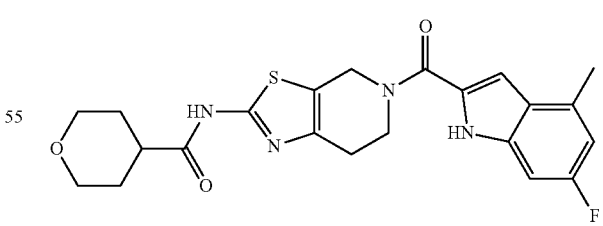

Rt (Method A) 3.23 mins, m/z 443 [M+H]+
1H NMR (400 MHz, DMSO-d6) δ 12.14-11.91 (m, 1H), 11.70-11.65 (m, 1H), 7.01-6.92 (m, 2H), 6.76 (d, J=10.6 Hz, 1H), 5.05-4.81 (m, 2H), 4.09-4.01 (m, 2H), 3.93-3.85 (m, 2H), 3.36-3.28 (m, 2H), 2.87-2.78 (m, 2H), 2.75-2.65 (m, 1H), 2.53 (s, 3H), 1.76-1.57 (m, 4H).

Example 322

5-[4-(difluoromethyl)-7-fluoro-1H-indole-2-carbonyl]-N-[(oxolan-3-yl)methyl]-4H,5H,6H,7H-[1,3]thiazolo[5,4-c]pyridin-2-amine

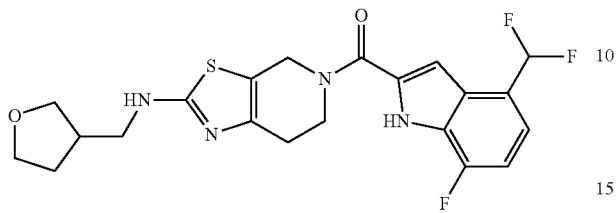

Rt (Method A) 3.18 mins, m/z 451 [M+H]+
1H NMR (400 MHz, DMSO-d6) δ 12.51 (s, 1H), 7.71-7.57 (m, 1H), 7.45-7.10 (m, 3H), 6.99 (s, 1H), 4.89-4.49 (m, 2H), 3.92 (t, J=5.8 Hz, 2H), 3.78-3.65 (m, 2H), 3.61 (q, J=7.7 Hz, 1H), 3.42 (dd, J=8.6, 5.4 Hz, 1H), 3.24-3.09 (m, 2H), 2.70-2.55 (m, 2H), 2.49-2.41 (m, 1H), 2.01-1.89 (m, 1H), 1.61-1.50 (m, 1H).

Example 323

5-[4-(1,1-difluoroethyl)-7-fluoro-1H-indole-2-carbonyl]-N-[(oxolan-3-yl)methyl]-4H,5H,6H,7H-[1,3]thiazolo[5,4-c]pyridin-2-amine

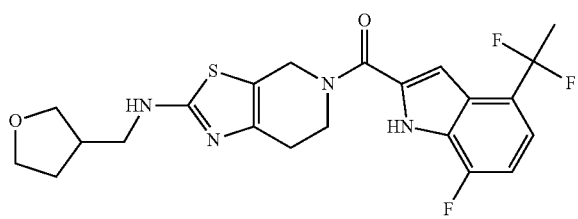 [SMILES: CC(F)(F)c1ccc(F)c2[nH]c(C(=O)N3CCc4nc(NCC5CCOC5)sc4C3)cc12]

Rt (Method A) 3.29 mins, m/z 465 [M+H]+
1H NMR (400 MHz, DMSO-d6) δ 12.46 (s, 1H), 7.63 (s, 1H), 7.25-7.17 (m, 1H), 7.15-7.05 (m, 1H), 6.91-6.84 (m, 1H), 4.87-4.54 (m, 2H), 3.97-3.86 (m, 2H), 3.76-3.65 (m, 2H), 3.65-3.56 (m, 1H), 3.42 (dd, J=8.6, 5.4 Hz, 1H), 3.16 (q, J=6.2, 5.4 Hz, 2H), 2.70-2.57 (m, 2H), 2.49-2.41 (m, 1H), 2.07 (t, J=18.8 Hz, 3H), 1.99-1.88 (m, 1H), 1.60-1.50 (m, 1H).

Example 324

5-[4-(1,1-difluoroethyl)-1H-indole-2-carbonyl]-N-[(oxolan-3-yl)methyl]-4H,5H,6H,7H-[1,3]thiazolo[5,4-c]pyridin-2-amine

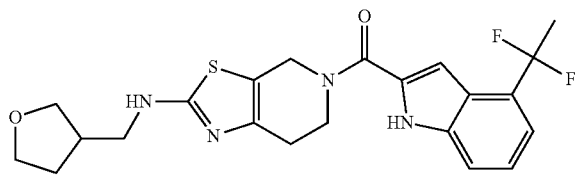 [SMILES: CC(F)(F)c1cccc2[nH]c(C(=O)N3CCc4nc(NCC5CCOC5)sc4C3)cc12]

Rt (Method A) 3.24 mins, m/z 447 [M+H]+
1H NMR (400 MHz, DMSO-d6) δ 11.97 (s, 1H), 7.63 (t, J=5.6 Hz, 1H), 7.55 (d, J=7.9 Hz, 1H), 7.31-7.20 (m, 2H), 6.86 (s, 1H), 4.96-4.53 (m, 2H), 4.05-3.88 (m, 2H), 3.78-3.65 (m, 2H), 3.60 (q, J=7.8 Hz, 1H), 3.42 (dd, J=8.6, 5.4 Hz, 1H), 3.23-3.10 (m, 2H), 2.71-2.60 (m, 2H), 2.49-2.43 (m, 1H), 2.08 (t, J=18.8 Hz, 3H), 2.00-1.90 (m, 1H), 1.60-1.50 (m, 1H).

Example 325

5-[4-(difluoromethyl)-1H-indole-2-carbonyl]-N-[(oxolan-3-yl)methyl]-4H,5H,6H,7H-[1,3]thiazolo[5,4-c]pyridin-2-amine

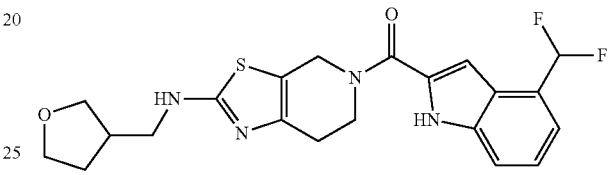

Rt (Method A) 3.14 mins, m/z 433 [M+H]+
1H NMR (400 MHz, DMSO-d6) δ 12.01 (s, 1H), 7.69-7.56 (m, 2H), 7.48-7.17 (m, 3H), 6.99 (s, 1H), 5.06-4.49 (m, 2H), 4.13-3.88 (m, 2H), 3.77-3.65 (m, 2H), 3.61 (q, J=7.7 Hz, 1H), 3.42 (dd, J=8.6, 5.4 Hz, 1H), 3.24-3.09 (m, 2H), 2.74-2.58 (m, 2H), 2.49-2.43 (m, 1H), 1.99-1.89 (m, 1H), 1.60-1.50 (m, 1H).

Example 326

5-[4-(difluoromethyl)-6-fluoro-1H-indole-2-carbonyl]-N-[(oxolan-3-yl)methyl]-4H,5H,6H,7H-[1,3]thiazolo[5,4-c]pyridin-2-amine

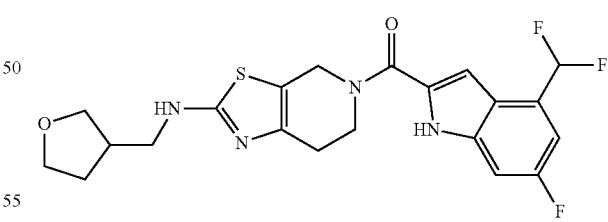

Rt (Method A) 3.23 mins, m/z 451 [M+H]+
1H NMR (400 MHz, DMSO-d6) δ 12.09 (s, 1H), 7.64 (t, J=5.6 Hz, 1H), 7.51-7.18 (m, 3H), 7.02 (s, 1H), 5.04-4.44 (m, 2H), 4.09-3.83 (m, 2H), 3.77-3.65 (m, 2H), 3.61 (q, J=7.7 Hz, 1H), 3.42 (dd, J=8.6, 5.5 Hz, 1H), 3.23-3.09 (m, 2H), 2.76-2.58 (m, 2H), 2.49-2.41 (m, 1H), 2.00-1.88 (m, 1H), 1.60-1.49 (m, 1H).

Example 327

5-[4-(1,1-difluoroethyl)-6-fluoro-1H-indole-2-carbonyl]-N-[(oxolan-3-yl)methyl]-4H,5H,6H,7H-[1,3]thiazolo[5,4-c]pyridin-2-amine

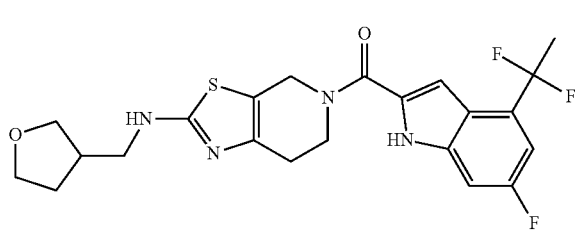 [SMILES: CC(F)(F)c1cc(F)cc2[nH]c(C(=O)N3CCc4nc(NCC5CCOC5)sc4C3)cc12]

Rt (Method A) 3.34 mins, m/z 465 [M+H]+

1H NMR (400 MHz, DMSO-d6) δ 12.07 (s, 1H), 7.63 (t, J=5.6 Hz, 1H), 7.30 (dd, J=9.4, 2.2 Hz, 1H), 7.11 (dd, J=10.4, 2.2 Hz, 1H), 6.91-6.85 (m, 1H), 4.94-4.49 (m, 2H), 4.08-3.84 (m, 2H), 3.76-3.65 (m, 2H), 3.61 (q, J=7.7 Hz, 1H), 3.42 (dd, J=8.6, 5.4 Hz, 1H), 3.23-3.09 (m, 2H), 2.70-2.58 (m, 2H), 2.49-2.43 (m, 1H), 2.09 (t, J=19.0 Hz, 3H), 2.01-1.88 (m, 1H), 1.62-1.49 (m, 1H).

Example 328

5-(4-ethyl-6-fluoro-1H-indole-2-carbonyl)-N-{[(3S)-oxolan-3-yl]methyl}-4H,5H,6H,7H-[1,3]thiazolo[5,4-c]pyridin-2-amine

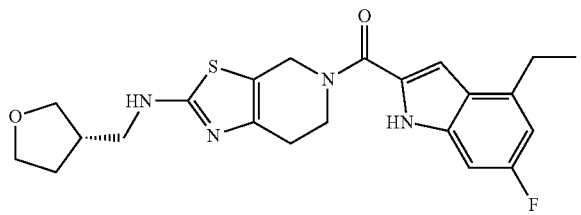 [SMILES: CCc1cc(F)cc2[nH]c(C(=O)N3CCc4nc(NC[C@@H]5CCOC5)sc4C3)cc12]

Rt (Method A) 3.38 mins, m/z 429 [M+H]+

1H NMR (400 MHz, DMSO-d6) δ 11.66 (s, 1H), 7.62 (t, J=5.5 Hz, 1H), 7.00-6.93 (m, 2H), 6.76 (dd, J=10.8, 2.2 Hz, 1H), 4.98-4.58 (m, 2H), 4.08-3.88 (m, 2H), 3.77-3.65 (m, 2H), 3.61 (q, J=7.8 Hz, 1H), 3.42 (dd, J=8.5, 5.4 Hz, 1H), 3.23-3.11 (m, 2H), 2.90 (q, J=7.5 Hz, 2H), 2.74-2.59 (m, 2H), 2.49-2.43 (m, 1H), 2.00-1.88 (m, 1H), 1.60-1.49 (m, 1H), 1.28 (t, J=7.5 Hz, 3H).

Example 329

5-(4-ethyl-6-fluoro-1H-indole-2-carbonyl)-N-{[(3R)-oxolan-3-yl]methyl}-4H,5H,6H,7H-[1,3]thiazolo[5,4-c]pyridin-2-amine

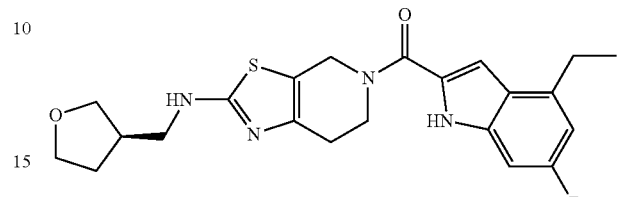

Rt (Method A) 3.38 mins, m/z 429 [M+H]+

1H NMR (400 MHz, DMSO-d6) δ 11.66 (s, 1H), 7.62 (t, J=5.5 Hz, 1H), 7.01-6.91 (m, 2H), 6.76 (dd, J=10.8, 2.1 Hz, 1H), 5.06-4.49 (m, 2H), 4.10-3.87 (m, 2H), 3.77-3.66 (m, 2H), 3.61 (q, J=7.8 Hz, 1H), 3.42 (dd, J=8.5, 5.4 Hz, 1H), 3.23-3.10 (m, 2H), 2.90 (q, J=7.5 Hz, 2H), 2.74-2.58 (m, 2H), 2.47-2.38 (m, 1H), 2.00-1.87 (m, 1H), 1.61-1.49 (m, 1H), 1.28 (t, J=7.5 Hz, 3H).

Example 330

N-[5-(1H-indole-2-carbonyl)-4H,5H,6H,7H-[1,3]thiazolo[5,4-c]pyridin-2-yl]-1-(methoxymethyl)cyclopropane-1-carboxamide

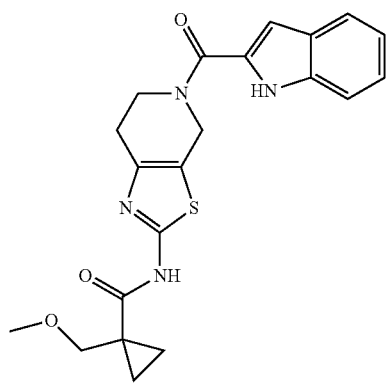 [SMILES: COCC1(C(=O)Nc2nc3c(s2)CN(C(=O)c2cc4ccccc4[nH]2)CC3)CC1]

Rt (Method A) 3.34 mins, m/z 411 [M+H]+

1H NMR (400 MHz, DMSO-d6) δ 11.66-11.61 (m, 1H), 11.39-11.14 (m, 1H), 7.64 (d, J=8.0 Hz, 1H), 7.45-7.40 (m, 1H), 7.23-7.17 (m, 1H), 7.09-7.03 (m, 1H), 6.95-6.91 (m, 1H), 4.90 (s, 2H), 4.05 (s, 2H), 3.62 (s, 2H), 3.31 (s, 3H), 2.96-2.73 (m, 2H), 1.18 (q, J=4.1 Hz, 2H), 0.86 (q, J=4.2 Hz, 2H).

Example 331

1-({[5-(6-chloro-1H-indole-2-carbonyl)-4H,5H,6H,7H-[1,3]thiazolo[5,4-c]pyridin-2-yl]amino}methyl)cyclobutan-1-ol

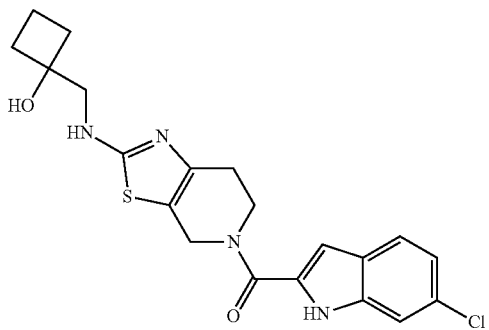 [SMILES: O=C(c1cc2ccc(Cl)cc2[nH]1)N1CCc2nc(NCC3(O)CCC3)sc2C1]

Rt (Method A) 3.13 mins, m/z 417/419 [M+H]+

1H NMR (400 MHz, DMSO-d6) δ 11.78 (s, 1H), 7.65 (d, J=8.6 Hz, 1H), 7.47-7.38 (m, 2H), 7.08 (dd, J=8.4, 1.9 Hz, 1H), 6.96-6.92 (m, 1H), 5.27 (s, 1H), 4.93-4.50 (m, 2H), 4.05-3.90 (m, 2H), 2.72-2.60 (m, 2H), 2.54 (s, 1H), 2.04-1.96 (m, 2H), 1.96-1.86 (m, 2H), 1.68-1.57 (m, 1H), 1.53-1.40 (m, 1H).

Example 332—Intentionally Left Blank

Example 333

N-[5-(4-ethyl-1H-indole-2-carbonyl)-4H,5H,6H,7H-[1,3]thiazolo[5,4-c]pyridin-2-yl]-1-methylcyclopropane-1-carboxamide

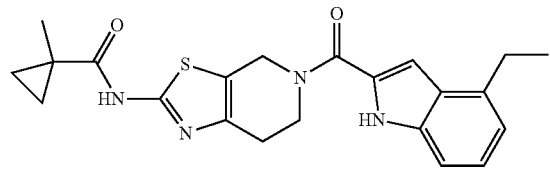 [SMILES: CCc1cccc2[nH]c(C(=O)N3CCc4nc(NC(=O)C5(C)CC5)sc4C3)cc12]

Rt (Method A) 3.61 mins, z 409 [M+H]+

1H NMR (400 MHz, DMSO-d6) δ 11.63-11.57 (m, 1H), 11.57-11.49 (m, 1H), 7.25 (d, J=8.2 Hz, 1H), 7.15-7.08 (m, 1H), 6.99-6.94 (m, 1H), 6.88 (d, J=7.0 Hz, 1H), 5.15-4.71 (m, 2H), 4.16-3.96 (m, 2H), 2.95-2.78 (m, 4H), 1.38 (s, 3H), 1.29 (t, J=7.5 Hz, 3H), 1.17 (q, J=3.8 Hz, 2H), 0.72 (q, J=4.0 Hz, 2H).

Example 334

N-[5-(4-ethyl-1H-indole-2-carbonyl)-4H,5H,6H,7H-[1,3]thiazolo[5,4-c]pyridin-2-yl]oxane-4-carboxamide

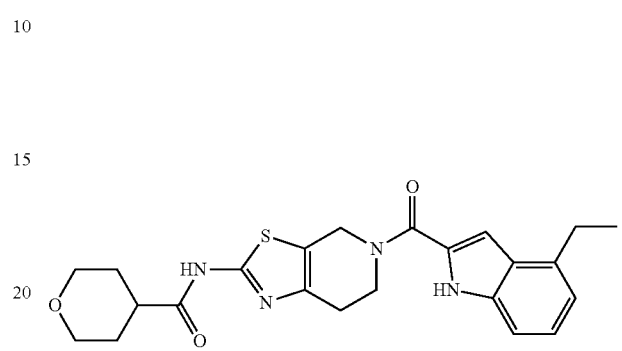

Rt (Method A) 3.30 mins, m/z 439 [M+H]+

1H NMR (400 MHz, DMSO-d6) δ 12.12-11.93 (m, 1H), 11.62-11.58 (m, 1H), 7.25 (d, J=8.2 Hz, 1H), 7.15-7.09 (m, 1H), 6.99-6.95 (m, 1H), 6.88 (d, J=7.0 Hz, 1H), 5.14-4.72 (m, 2H), 4.12-3.98 (m, 2H), 3.93-3.84 (m, 2H), 3.37-3.29 (m, 2H), 2.90 (q, J=7.5 Hz, 2H), 2.87-2.79 (m, 2H), 2.76-2.69 (m, 1H), 1.76-1.57 (m, 4H), 1.29 (t, J=7.6 Hz, 3H).

Example 335

(1s,4s)-4-{[5-(4-ethyl-1H-indole-2-carbonyl)-4H,5H,6H,7H-[1,3]thiazolo[5,4-c]pyridin-2-yl]amino}cyclohexan-1-ol

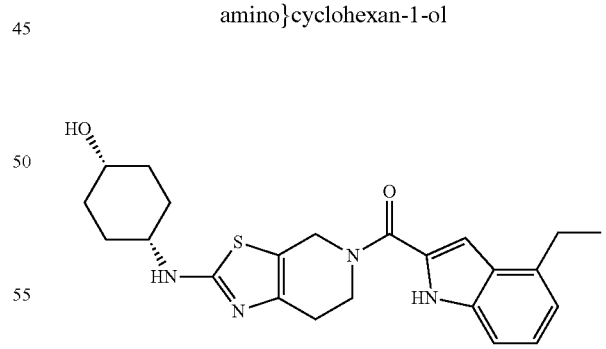

Rt (Method A) 3.26 mins, m/z 425 [M+H]+

1H NMR (400 MHz, DMSO-d6) δ 11.60-11.55 (m, 1H), 7.43 (d, J=7.2 Hz, 1H), 7.25 (d, J=8.1 Hz, 1H), 7.15-7.08 (m, 1H), 6.92 (d, J=2.1 Hz, 1H), 6.87 (d, J=7.1 Hz, 1H), 4.96-4.55 (m, 2H), 4.39 (d, J=3.1 Hz, 1H), 4.07-3.89 (m, 2H), 3.69-3.62 (m, 1H), 3.58-3.47 (m, 1H), 2.89 (q, J=7.5 Hz, 2H), 2.69-2.61 (m, 2H), 1.71-1.43 (m, 8H), 1.28 (t, J=7.5 Hz, 3H).

Example 336

1-cyano-N-[5-(1H-indole-2-carbonyl)-4H,5H,6H,7H-[1,3]thiazolo[5,4-c]pyridin-2-yl]cyclopropane-1-carboxamide

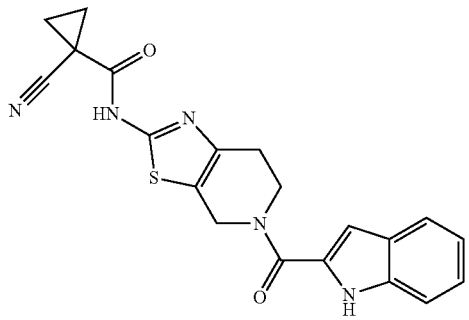 [SMILES: N#CC1(C(=O)Nc2nc3c(s2)CN(C(=O)c2cc4ccccc4[nH]2)CC3)CC1]

Rt (Method B) 3.15 mins, m/z 392 [M+H]+

1H NMR (400 MHz, DMSO-d6) δ 13.58-12.13 (m, 1H), 11.68-11.61 (m, 1H), 7.63 (d, J=8.1 Hz, 1H), 7.46-7.40 (m, 1H), 7.23-7.17 (m, 1H), 7.10-7.03 (m, 1H), 6.95-6.92 (m, 1H), 5.08-4.61 (m, 2H), 4.13-3.96 (m, 2H), 2.91-2.71 (m, 2H), 1.73-1.47 (m, 4H).

Example 337

1-fluoro-N-[5-(1H-indole-2-carbonyl)-4H,5H,6H,7H-[1,3]thiazolo[5,4-c]pyridin-2-yl]cyclopropane-1-carboxamide

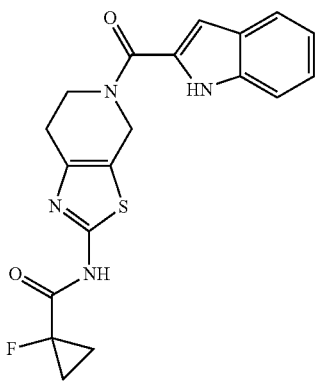 [SMILES: O=C(c1cc2ccccc2[nH]1)N1CCc2nc(NC(=O)C3(F)CC3)sc2C1]

Rt (Method A) 3.24 mins, m/z 385 [M+H]+

1H NMR (400 MHz, DMSO-d6) δ 12.60-12.28 (m, 1H), 11.64 (s, 1H), 7.64 (d, J=8.0 Hz, 1H), 7.46-7.40 (m, 1H), 7.23-7.17 (m, 1H), 7.09-7.03 (m, 1H), 6.97-6.91 (m, 1H), 5.23-4.66 (m, 2H), 4.19-3.94 (m, 2H), 2.92-2.80 (m, 2H), 1.53-1.32 (m, 4H).

Example 338

1-({[5-(4-ethyl-1H-indole-2-carbonyl)-4H,5H,6H,7H-[1,3]thiazolo[5,4-c]pyridin-2-yl]amino}methyl)cyclobutan-1-ol

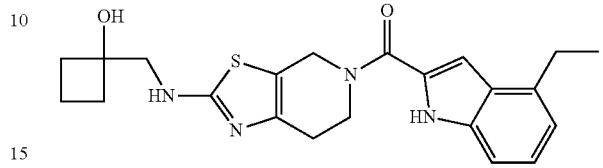

Rt (Method A) 3.36 mins, m/z 411 [M+H]+

1H NMR (400 MHz, DMSO-d6) δ 11.61-11.54 (m, 1H), 7.43 (t, J=5.6 Hz, 1H), 7.25 (d, J=8.3 Hz, 1H), 7.14-7.09 (m, 1H), 6.94-6.90 (m, 1H), 6.87 (d, J=7.1 Hz, 1H), 5.27 (s, 1H), 5.04-4.48 (m, 2H), 4.10-3.88 (m, 2H), 3.35-3.32 (m, 2H), 2.89 (q, J=7.5 Hz, 2H), 2.70-2.60 (m, 2H), 2.05-1.86 (m, 4H), 1.69-1.56 (m, 1H), 1.53-1.40 (m, 1H), 1.28 (t, J=7.5 Hz, 3H).

Example 339

(±)-3-{[5-(1H-indole-2-carbonyl)-4H,5H,6H,7H-[1,3]thiazolo[5,4-c]pyridin-2-yl]amino}oxan-4-ol

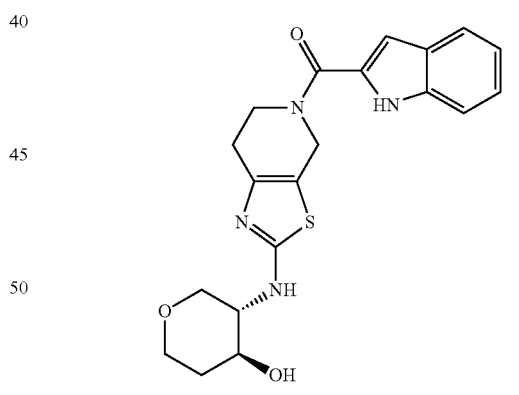

Rt (Method A) 2.84 mins, m/z 399 [M+H]+

1H NMR (400 MHz, DMSO-d6) δ 11.62 (s, 1H), 7.63 (d, J=7.9 Hz, 1H), 7.50 (d, J=7.2 Hz, 1H), 7.43 (d, J=8.3 Hz, 1H), 7.24-7.17 (m, 1H), 7.10-7.03 (m, 1H), 6.89 (d, J=1.5 Hz, 1H), 4.99 (d, J=4.9 Hz, 1H), 4.94-4.49 (m, 2H), 4.10-3.86 (m, 3H), 3.83-3.72 (m, 1H), 3.59-3.42 (m, 2H), 3.36-3.29 (m, 1H), 3.10-2.99 (m, 1H), 2.79-2.56 (m, 2H), 1.95-1.85 (m, 1H), 1.54-1.38 (m, 1H).

Example 340

5-(1H-indole-2-carbonyl)-N-{[1-(methoxymethyl)cyclopropyl]methyl}-4H,5H,6H,7H-[1,3]thiazolo[5,4-c]pyridin-2-amine

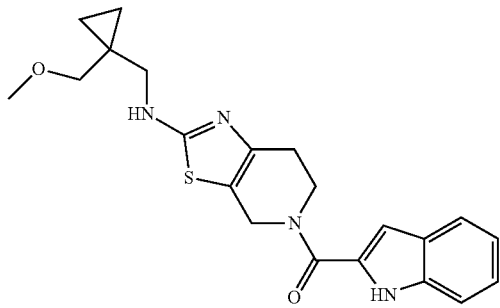 [SMILES: COCC1(CNc2nc3c(s2)CN(C(=O)c2cc4ccccc4[nH]2)CC3)CC1]

Rt (Method A) 3.29 mins, m/z 397 [M+H]+

1H NMR (400 MHz, DMSO-d6) δ 11.62 (s, 1H), 7.63 (d, J=8.0 Hz, 1H), 7.51-7.39 (m, 2H), 7.24-7.15 (m, 1H), 7.11-7.01 (m, 1H), 6.89 (s, 1H), 5.03-4.43 (m, 2H), 4.10-3.87 (m, 2H), 3.25-3.18 (m, 7H), 2.77-2.56 (m, 2H), 0.52-0.44 (m, 2H), 0.41-0.32 (m, 2H).

Example 341

5-[4-(difluoromethyl)-7-fluoro-1H-indole-2-carbonyl]-4H,5H,6H,7H-[1,3]thiazolo[5,4-c]pyridin-2-amine

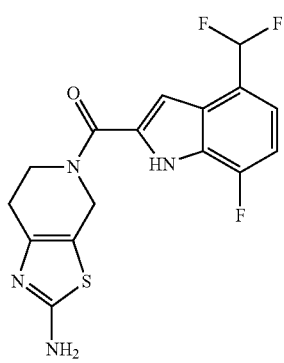 [SMILES: Nc1nc2c(s1)CN(C(=O)c1cc3c(C(F)F)ccc(F)c3[nH]1)CC2]

Rt (Method A) 3 mins, m/z 367 [M+H]+

1H NMR (400 MHz, DMSO-d6) δ 12.51 (s, 1H), 7.48-7.08 (m, 3H), 6.99 (d, J=3.1 Hz, 1H), 6.86 (s, 2H), 4.93-4.43 (m, 2H), 3.92 (t, J=5.8 Hz, 2H), 2.69-2.55 (m, 2H).

Example 342

5-[4-(1,1-difluoroethyl)-7-fluoro-1H-indole-2-carbonyl]-4H,5H,6H,7H-[1,3]thiazolo[5,4-c]pyridin-2-amine

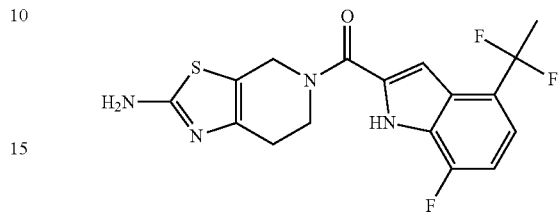

Rt (Method A) 3.12 mins, m/z 381 [M+H]+

1H NMR (400 MHz, DMSO-d6) δ 12.46 (s, 1H), 7.26-7.18 (m, 1H), 7.15-7.05 (m, 1H), 6.97-6.77 (m, 3H), 4.94-4.44 (m, 2H), 3.91 (t, J=5.8 Hz, 2H), 2.66-2.54 (m, 2H), 2.07 (t, J=18.9 Hz, 3H).

Example 343

(1s,4s)-4-{[5-(4-chloro-6-fluoro-1H-indole-2-carbonyl)-4H,5H,6H,7H-[1,3]thiazolo[5,4-c]pyridin-2-yl]amino}cyclohexan-1-ol

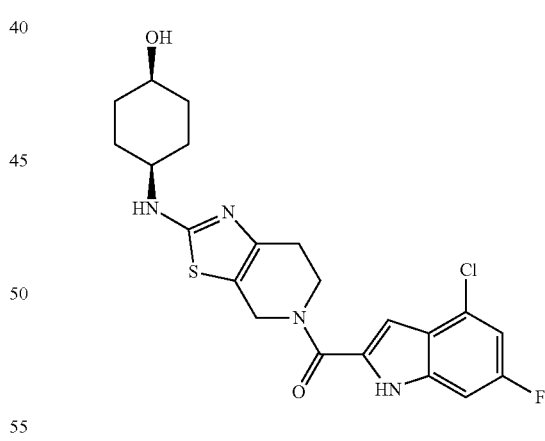

Rt (Method A) 3.29 mins, m/z 449/451 [M+H]+

1H NMR (400 MHz, DMSO-d6) δ 12.15-12.06 (m, 1H), 7.44 (d, J=7.3 Hz, 1H), 7.18 (s, 1H), 7.16 (s, 1H), 6.91-6.85 (m, 1H), 5.05-4.48 (m, 2H), 4.39 (s, 1H), 4.09-3.84 (m, 2H), 3.72-3.61 (m, 1H), 3.57-3.48 (m, 1H), 2.71-2.59 (m, 2H), 1.71-1.54 (m, 6H), 1.53-1.43 (m, 2H).

Example 344

(1s,4s)-4-{[5-(4,6-difluoro-1H-indole-2-carbonyl)-4H,5H,6H,7H-[1,3]thiazolo[5,4-c]pyridin-2-yl]amino}cyclohexan-1-ol

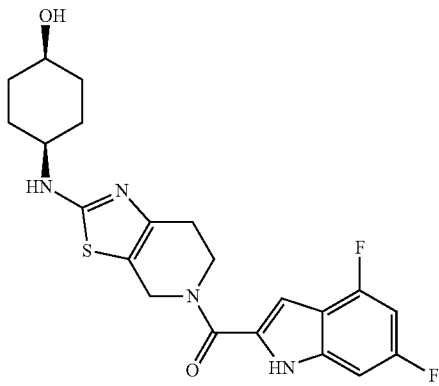 [SMILES: O=C(c1cc2c(Cl)cc(F)cc2[nH]1)N1CCc2nc(N[C@H]3CC[C@@H](O)CC3)sc2C1]

Rt (Method A) 3.17 mins, m/z 433 [M+H]+

1H NMR (400 MHz, DMSO-d6) δ 12.06 (s, 1H), 7.43 (d, J=7.3 Hz, 1H), 7.06-7.01 (m, 1H), 6.98-6.87 (m, 2H), 4.95-4.56 (m, 2H), 4.38 (d, J=3.2 Hz, 1H), 4.03-3.90 (m, 2H), 3.69-3.62 (m, 1H), 3.57-3.48 (m, 1H), 2.71-2.59 (m, 2H), 1.69-1.44 (m, 8H).

Example 345

1-({[5-(1H-indole-2-carbonyl)-4H,5H,6H,7H-[1,3]thiazolo[5,4-c]pyridin-2-yl]amino}methyl)cyclopropane-1-carboxylic acid

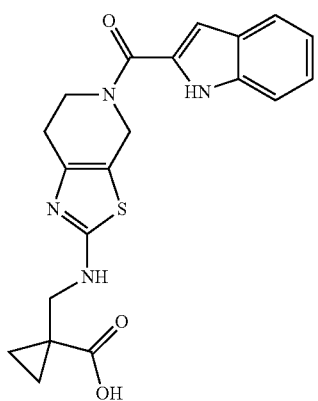 [SMILES: O=C(c1cc2ccccc2[nH]1)N1CCc2nc(NCC3(C(=O)O)CC3)sc2C1]

Rt (Method A) 2.51 mins, m/z 397 [M+H]+

1H NMR (400 MHz, DMSO-d6) δ 11.62 (s, 1H), 7.62 (d, J=8.0 Hz, 1H), 7.52 (t, J=4.9 Hz, 1H), 7.42 (d, J=8.2 Hz, 1H), 7.19 (dd, J=7.5 Hz, 1H), 7.05 (dd, J=7.5 Hz, 1H), 6.89 (d, J=1.7 Hz, 1H), 5.04-4.42 (m, 2H), 4.10-3.85 (m, 2H), 3.46-3.44 (m, 2H), 2.76-2.60 (m, 2H), 1.06-1.00 (m, 2H), 0.96-0.87 (m, 2H)—one signal (1H) coincides with H2O signal.

Example 346

1-hydroxy-N-[5-(1H-indole-2-carbonyl)-4H,5H,6H,7H-[1,3]thiazolo[5,4-c]pyridin-2-yl]cyclopropane-1-carboxamide

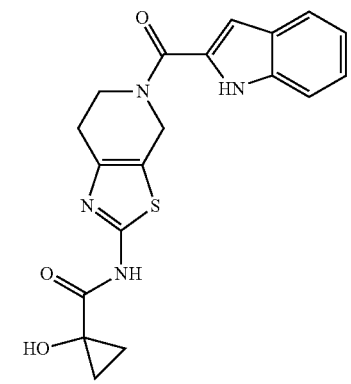 [SMILES: O=C(c1cc2ccccc2[nH]1)N1CCc2nc(NC(=O)C3(O)CC3)sc2C1]

Rt (Method A) 3.03 mins, m/z 383 [M+H]+

1H NMR (400 MHz, DMSO-d6) δ 11.64 (s, 1H), 11.31 (s, 1H), 7.64 (d, J=7.8 Hz, 1H), 7.43 (d, J=8.2 Hz, 1H), 7.23-7.17 (m, 1H), 7.09-7.03 (m, 1H), 6.96-6.91 (m, 1H), 6.58 (s, 1H), 5.29-4.53 (m, 2H), 4.17-3.95 (m, 2H), 2.96-2.76 (m, 2H), 1.20 (q, J=4.4, 3.9 Hz, 2H), 1.05 (q, J=4.8, 4.4 Hz, 2H).

Example 347

5-(1H-indole-2-carbonyl)-N-[1-(methoxymethyl)cyclobutyl]-4H,5H,6H,7H-[1,3]thiazolo[5,4-c]pyridin-2-amine

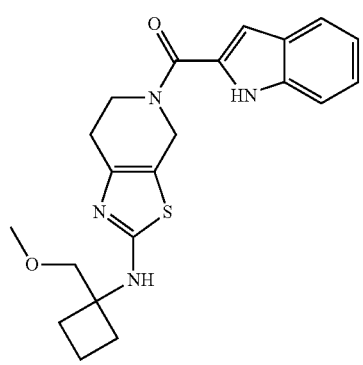 [SMILES: COCC1(Nc2nc3c(s2)CN(C(=O)c2cc4ccccc4[nH]2)CC3)CCC1]

Rt (Method A) 3.46 mins, m/z 397 [M+H]+

1H NMR (400 MHz, DMSO-d6) δ 11.61 (s, 1H), 7.71-7.56 (m, 2H), 7.43 (d, J=8.2 Hz, 1H), 7.20 (t, J=7.6 Hz, 1H), 7.06 (t, J=7.5 Hz, 1H), 6.94-6.85 (m, 1H), 5.03-4.36 (m, 2H), 4.08-3.85 (m, 2H), 3.60 (s, 2H), 3.27 (s, 3H), 2.79-2.58 (m, 2H), 2.34-2.01 (m, 4H), 1.92-1.66 (m, 2H).

Example 348

(1S,2R)-2-{[5-(1H-indole-2-carbonyl)-4H,5H,6H,7H-[1,3]thiazolo[5,4-c]pyridin-2-yl]amino}cyclohexan-1-ol

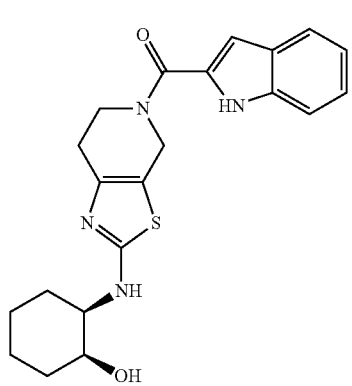 [SMILES: O=C(c1cc2ccccc2[nH]1)N1CCc2nc(N[C@@H]3CCCC[C@@H]3O)sc2C1]

Rt (Method A) 3.21 mins, m/z 397 [M+H]+

1H NMR (400 MHz, DMSO-d6) δ 11.62 (s, 1H), 7.63 (d, J=7.9 Hz, 1H), 7.43 (d, J=8.2 Hz, 1H), 7.27-7.15 (m, 2H), 7.06 (t, J=7.5 Hz, 1H), 6.93-6.86 (m, 1H), 5.11-4.33 (m, 3H), 4.13-3.81 (m, 3H), 3.66-3.58 (m, 1H), 2.74-2.56 (m, 2H), 1.73-1.17 (m, 8H).

Example 349

N-[2-(1H-imidazol-1-yl)ethyl]-5-(1H-indole-2-carbonyl)-4H,5H,6H,7H-[1,3]thiazolo[5,4-c]pyridin-2-amine

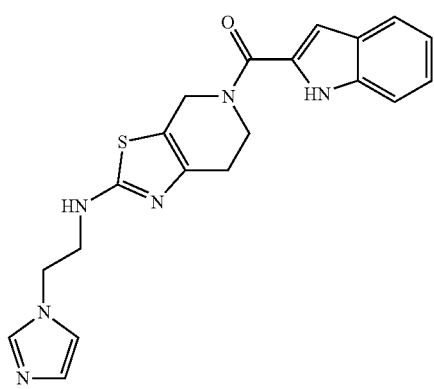 [SMILES: O=C(c1cc2ccccc2[nH]1)N1CCc2nc(NCCn3ccnc3)sc2C1]

Rt (Method A) 2.88 mins, m/z 393 [M+H]+

1H NMR (400 MHz, DMSO-d6) δ 11.70-11.56 (m, 1H), 7.73-7.53 (m, 3H), 7.43 (d, J=8.1 Hz, 1H), 7.25-7.13 (m, 2H), 7.09-7.00 (m, 1H), 6.94-6.82 (m, 2H), 5.17-4.38 (m, 2H), 4.15 (t, J=5.8 Hz, 2H), 4.09-3.85 (m, 2H), 3.53 (q, J=5.7 Hz, 2H), 2.80-2.57 (m, 2H).

Example 350

(1R,3S)-3-{[5-(1H-indole-2-carbonyl)-4H,5H,6H,7H-[1,3]thiazolo[5,4-c]pyridin-2-yl]amino}cyclohexan-1-ol

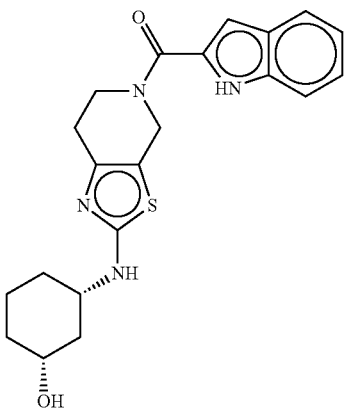

Rt (Method A) 3.02 mins, m/z 397 [M+H]+ 1H NMR (400 MHz, DMSO-d6) δ 11.63 (s, 1H), 7.62 (d, J=8.0 Hz, 1H), 7.49-7.36 (m, 2H), 7.19 (ddd, J=8.3, 6.9, 1.2 Hz, 1H), 7.05 (ddd, J=8.0, 7.0, 1.0 Hz, 1H), 6.89 (s, 1H), 5.17-4.40 (m, 3H), 4.20-3.74 (m, 2H), 3.51-3.37 (m, 2H), 2.75-2.57 (m, 2H), 2.21-2.10 (m, 1H), 1.97-1.84 (m, 1H), 1.84-1.73 (m, 1H), 1.73-1.59 (m, 1H), 1.31-1.15 (m, 1H), 1.12-0.92 (m, 3H).

Example 351

N-[5-(1H-indole-2-carbonyl)-4H,5H,6H,7H-[1,3]thiazolo[5,4-c]pyridin-2-yl]-2-(oxolan-3-yl)acetamide

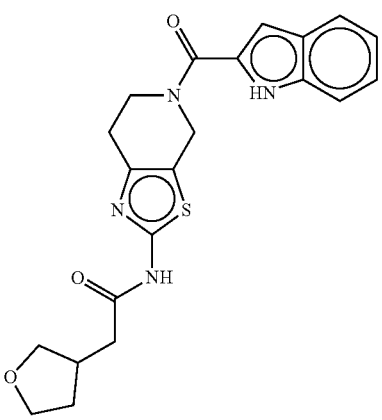

Rt (Method A) 3.04 mins, m/z 411 [M+H]+

1H NMR (400 MHz, DMSO-d6) δ 12.03 (s, 1H), 11.68-11.60 (m, 1H), 7.63 (d, J=7.9 Hz, 1H), 7.43 (d, J=8.2 Hz, 1H), 7.23-7.16 (m, 1H), 7.06 (t, J=7.4 Hz, 1H), 6.95-6.91 (m, 1H), 5.29-4.58 (m, 2H), 4.14-3.96 (m, 2H), 3.79 (dd, J=8.4, 6.4 Hz, 1H), 3.73 (td, J=8.1, 5.3 Hz, 1H), 3.63 (q, J=7.6 Hz, 1H), 3.31-3.26 (m, 1H), 2.93-2.75 (m, 2H), 2.60-2.51 (m, 3H), 2.05-1.94 (m, 1H), 1.57-1.45 (m, 1H).

Examples 352 and 353—Intentionally left blank

Example 354

(2S)-2-amino-4-{[5-(1H-indole-2-carbonyl)-4H,5H,6H,7H-[1,3]thiazolo[5,4-c]pyridin-2-yl]carbamoyl}butanoic acid

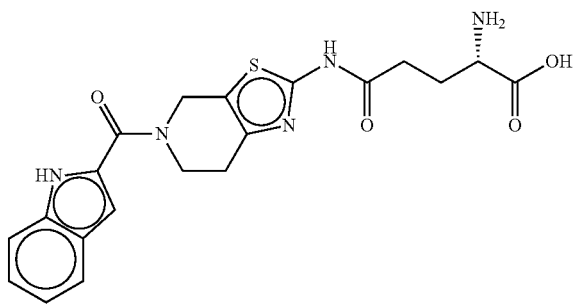

Rt (Method A) 0.89 mins, m/z 426 [M+H]+

1H NMR (400 MHz, DMSO-d6) δ 11.63 (s, 1H), 8.34 (s, 1H), 7.63 (d, J=8.0 Hz, 1H), 7.43 (d, J=8.3 Hz, 1H), 7.20 (t, J=7.5 Hz, 1H), 7.06 (t, J=7.5 Hz, 1H), 6.93 (d, J=1.6 Hz, 1H), 4.90 (s, 2H), 4.04 (s, 2H), 3.21 (t, J=6.9 Hz, 1H), 2.82 (s, 2H), 2.69-2.56 (m, 2H), 2.54 (s, 1H), 1.93 (hept, J=6.4 Hz, 2H).

Example 355

(1r,3r)-3-{[5-(4-chloro-5-fluoro-1H-indole-2-carbonyl)-4H,5H,6H,7H-[1,3]thiazolo[5,4-c]pyridin-2-yl]amino}cyclobutan-1-ol

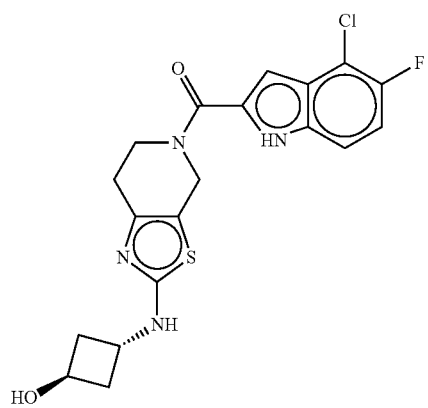

Rt (Method H) 0.99 mins, m/z 421.1 [M+H]+

1H NMR (400 MHz, DMSO-d6) δ 12.10 (s, 1H), 7.76 (d, J=6.2 Hz, 1H), 7.41 (dd, J=8.9, 4.0 Hz, 1H), 7.24 (dd, J=10.0, 8.9 Hz, 1H), 6.89 (s, 1H), 5.03 (d, J=5.6 Hz, 1H), 4.76 (s, 2H), 4.27 (h, J=5.9 Hz, 1H), 4.09-3.87 (m, 3H), 2.73-2.60 (m, 2H), 2.14 (t, J=6.1 Hz, 4H).

Example 356

(1r,3r)-3-{[5-(4-chloro-6-fluoro-1H-indole-2-carbonyl)-4H,5H,6H,7H-[1,3]thiazolo[5,4-c]pyridin-2-yl]amino}cyclobutan-1-ol

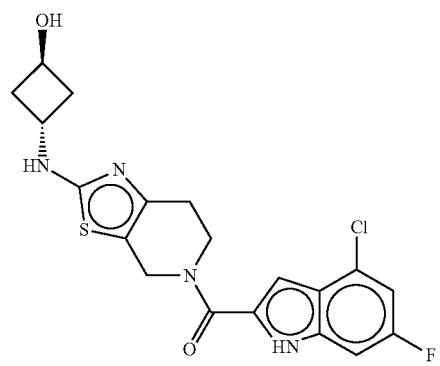

Rt (Method B) 2.63 mins, m/z 421 [M+H]+

1H NMR (400 MHz, DMSO-d6) δ 12.09 (s, 1H), 7.76 (d, J=6.2 Hz, 1H), 7.17 (d, J=9.4 Hz, 2H), 6.88 (s, 1H), 5.03 (d, J=5.5 Hz, 1H), 4.77 (s, 2H), 4.26 (p, J=5.9 Hz, 1H), 4.07-3.87 (m, 3H), 2.66 (d, J=9.1 Hz, 2H), 2.14 (t, J=6.1 Hz, 4H).

Example 357

(1r,3r)-3-{[5-(6-chloro-1H-indole-2-carbonyl)-4H,5H,6H,7H-[1,3]thiazolo[5,4-c]pyridin-2-yl]amino}cyclobutan-1-ol

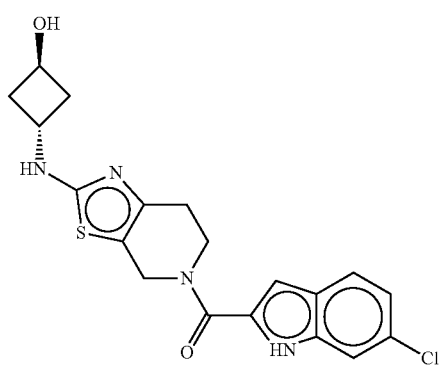

Rt (Method H) 0.97 mins, m/z 403 [M+H]+

1H NMR (400 MHz, DMSO-d6) δ 11.77 (s, 1H), 7.76 (d, J=6.2 Hz, 1H), 7.65 (d, J=8.6 Hz, 1H), 7.43 (d, J=1.9 Hz, 1H), 7.08 (dd, J=8.5, 1.9 Hz, 1H), 6.93 (s, 1H), 5.03 (d, J=5.4 Hz, 1H), 4.74 (s, 2H), 4.27 (q, J=5.9 Hz, 1H), 4.04-3.83 (m, 3H), 2.67 (s, 2H), 2.14 (t, J=6.1 Hz, 4H).

Example 358

(1R,5S,6R)—N-[5-(1H-indole-2-carbonyl)-4H,5H,6H,7H-[1,3]thiazolo[5,4-c]pyridin-2-yl]-3-oxabicyclo[3.1.0]hexane-6-carboxamide

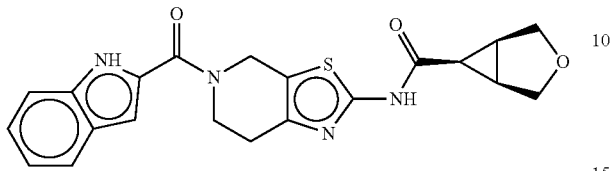

Rt (Method A) 1.18 mins, m/z 409 [M+H]+

1H NMR (400 MHz, DMSO-d6) δ 11.96 (s, 1H), 11.73-11.55 (m, 1H), 7.64 (d, J=8.0 Hz, 1H), 7.50-7.35 (m, 1H), 7.20 (ddd, J=8.2, 6.9, 1.2 Hz, 1H), 7.06 (ddd, J=8.1, 6.9, 1.0 Hz, 1H), 6.92 (d, J=2.1 Hz, 1H), 4.89 (s, 2H), 4.05 (s, 2H), 3.89 (d, J=8.6 Hz, 2H), 3.62 (dd, J=8.8, 1.9 Hz, 2H), 2.83 (s, 2H), 1.94 (s, 3H).

Example 359

(1R,5S,6R)—N-[5-(1H-indole-2-carbonyl)-4H,5H,6H,7H-[1,3]thiazolo[5,4-c]pyridin-2-yl]-3-azabicyclo[3.1.0]hexane-6-carboxamide

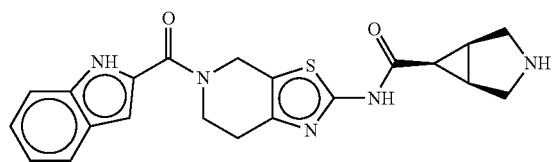

Rt (Method B) 0.80 mins, m/z 408 [M+H]+

1H NMR (400 MHz, DMSO-d6) δ 11.63 (d, J=2.2 Hz, 1H), 7.63 (d, J=8.0 Hz, 1H), 7.43 (d, J=8.2 Hz, 1H), 7.20 (t, J=7.6 Hz, 1H), 7.06 (t, J=7.5 Hz, 1H), 6.92 (d, J=1.8 Hz, 1H), 4.88 (s, 2H), 4.04 (s, 2H), 3.09 (s, 4H), 2.80 (s, 2H), 1.96 (d, J=8.0 Hz, 2H), 1.77 (t, J=8.1 Hz, 1H).

Example 360

(1R,5S,6S)—N-[5-(1H-indole-2-carbonyl)-4H,5H,6H,7H-[1,3]thiazolo[5,4-c]pyridin-2-yl]-3-azabicyclo[3.1.0]hexane-6-carboxamide

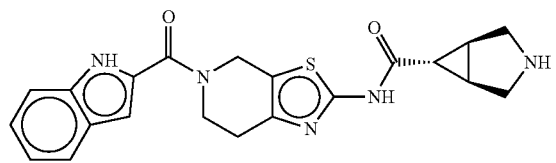

Rt (Method B) 0.84 mins, m/z 408 [M+H]+

1H NMR (400 MHz, DMSO-d6) δ 12.19 (s, 1H), 11.63 (d, J=2.2 Hz, 1H), 8.24 (s, 1H), 7.63 (d, J=7.9 Hz, 1H), 7.43 (d, J=8.2 Hz, 1H), 7.20 (t, J=7.6 Hz, 1H), 7.06 (t, J=7.5 Hz, 1H), 6.93 (d, J=2.0 Hz, 1H), 4.89 (s, 2H), 3.00 (d, J=11.2 Hz, 2H), 2.94-2.73 (m, 4H), 1.96 (t, J=2.2 Hz, 2H), 1.88 (t, J=3.0 Hz, 1H).

Example 361

(1R,5S,6S)—N-[5-(1H-indole-2-carbonyl)-4H,5H,6H,7H-[1,3]thiazolo[5,4-c]pyridin-2-yl]-3-oxabicyclo[3.1.0]hexane-6-carboxamide

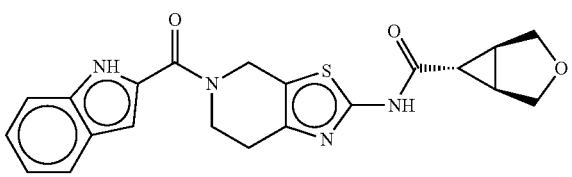

Rt (Method A) 1.27 mins, m/z 409 [M+H]+

1H NMR (400 MHz, DMSO-d6) δ 12.22 (s, 1H), 11.63 (d, J=1.9 Hz, 1H), 7.63 (d, J=8.1 Hz, 1H), 7.43 (d, J=8.2 Hz, 1H), 7.20 (ddd, J=8.3, 7.0, 1.2 Hz, 1H), 7.06 (ddd, J=8.0, 7.0, 1.0 Hz, 1H), 6.93 (d, J=2.2 Hz, 1H), 4.90 (s, 2H), 4.05 (s, 2H), 3.83 (d, J=8.8 Hz, 2H), 3.66 (d, J=8.4 Hz, 2H), 2.83 (s, 2H), 2.54 (s, 1H), 2.20-2.13 (m, 2H), 1.81 (t, J=3.2 Hz, 1H).

Example 362

1-({[5-(4-chloro-5-fluoro-1H-indole-2-carbonyl)-4H,5H,6H,7H-[1,3]thiazolo[5,4-c]pyridin-2-yl]amino}methyl)cyclobutan-1-ol

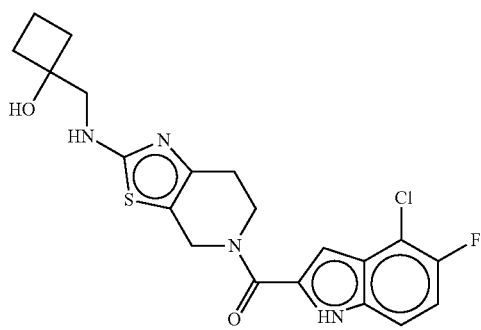

Rt (Method H) 1.04 mins, m/z 435/437 [M+H]+
No NMR available

Example 363

1-({[5-(4-ethyl-6-fluoro-1H-indole-2-carbonyl)-4H, 5H,6H,7H-[1,3]thiazolo[5,4-c]pyridin-2-yl] amino}methyl)cyclobutan-1-ol

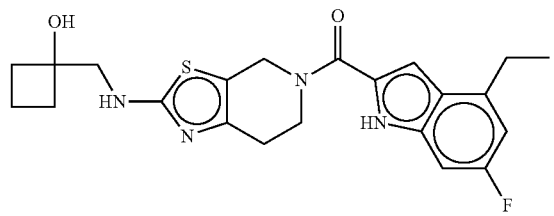

Rt (Method H) 1.08 mins, m/z 429 [M+H]+
No NMR available

Example 364

1-({[5-(4-bromo-1H-indole-2-carbonyl)-4H,5H,6H, 7H-[1,3]thiazolo[5,4-c]pyridin-2-yl]amino}methyl) cyclobutan-1-ol

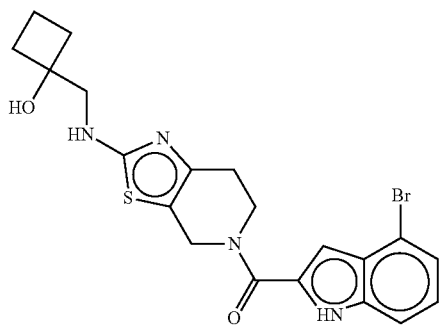

Rt (Method H) 1.03 mins, m/z 461/463 [M+H]+
1H NMR (400 MHz, DMSO-d6) δ 12.04 (s, 1H), 7.48-7.40 (m, 2H), 7.30 (d, J=7.5 Hz, 1H), 7.14 (t, J=7.9 Hz, 1H), 6.76 (s, 1H), 5.26 (s, 1H), 4.75 (br s, 2H), 3.97 (br s, 2H), 2.65 (br s, 2H), 2.05-1.96 (m, 2H), 1.96-1.85 (m, 2H), 1.68-1.57 (m, 1H), 1.46 (q, J=9.5 Hz, 1H).

Example 365

1-({[5-(6-bromo-1H-indole-2-carbonyl)-4H,5H,6H, 7H-[1,3]thiazolo[5,4-c]pyridin-2-yl]amino}methyl) cyclobutan-1-ol

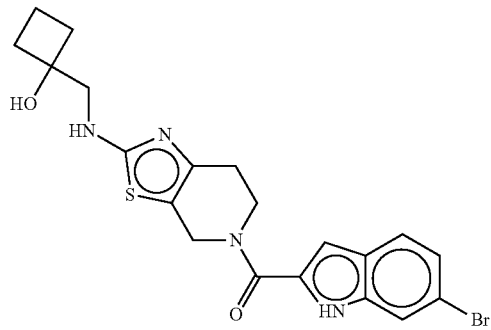

Rt (Method H) 1.04 mins, m/z 461/463 [M+H]+
No NMR available

Example 366

1-[({5-[6-fluoro-4-(1-hydroxyethyl)-1H-indole-2-carbonyl]-4H,5H,6H,7H-[1,3]thiazolo[5,4-c]pyridin-2-yl}amino)methyl]cyclobutan-1-ol

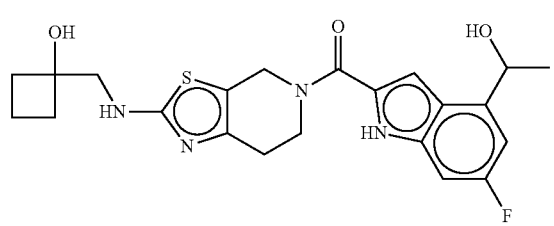

Rt (Method H) 0.8 mins, m/z 445 [M+H]+
No NMR available

Example 367

1-[({5-[4-(hydroxymethyl)-1H-indole-2-carbonyl]-4H,5H,6H,7H-[1,3]thiazolo[5,4-c]pyridin-2-yl}amino)methyl]cyclobutan-1-ol

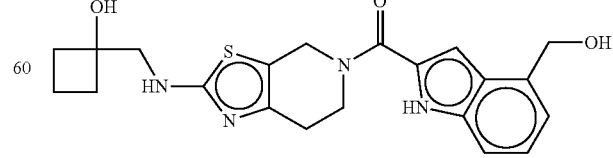

Rt (Method H) 0.7 mins, m/z 413 [M+H]+
No NMR available

Example 368

1-[({5-[4-(propan-2-yl)-1H-indole-2-carbonyl]-4H, 5H,6H,7H-[1,3]thiazolo[5,4-c]pyridin-2-yl}amino) methyl]cyclobutan-1-ol

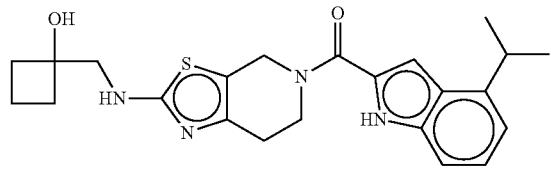

Rt (Method H) 1.1 mins, m/z 425 [M+H]+
1H NMR (400 MHz, DMSO-d6) δ 11.58 (d, J=2.2 Hz, 1H), 7.43 (t, J=5.6 Hz, 1H), 7.25 (d, J=8.2 Hz, 1H), 7.13 (t, J=7.7 Hz, 1H), 6.95 (d, J=2.0 Hz, 1H), 6.91 (d, J=7.2 Hz, 1H), 5.27 (s, 1H), 4.76 (br s, 2H), 3.98 (br s, 2H), 3.42-3.35 (m, 1H), 2.66 (br s, 2H), 2.05-1.96 (m, 2H), 1.96-1.86 (m, 2H), 1.68-1.57 (m, 1H), 1.53-1.39 (m, 1H), 1.32 (d, J=6.9 Hz, 6H).

Example 369

1-({[5-(5,6-difluoro-1H-indole-2-carbonyl)-4H,5H, 6H,7H-[1,3]thiazolo[5,4-c]pyridin-2-yl] amino}methyl)cyclobutan-1-ol

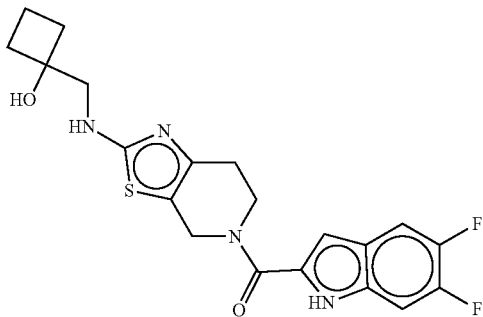

Rt (Method H) 0.96 mins, m/z 419 [M+H]+
No NMR available

Example 370

1-({[5-(4-methyl-1H-indole-2-carbonyl)-4H,5H,6H, 7H-[1,3]thiazolo[5,4-c]pyridin-2-yl]amino}methyl) cyclobutan-1-ol

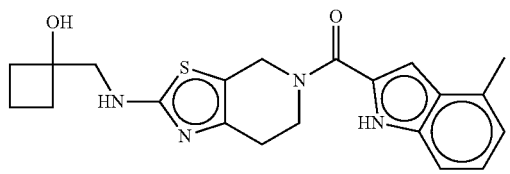

Rt (Method H) 0.96 mins, m/z 397 [M+H]+
No NMR available

Example 371

1-[({5-[4-(1,1-difluoroethyl)-6-fluoro-1H-indole-2-carbonyl]-4H,5H,6H,7H-[1,3]thiazolo[5,4-c]pyridin-2-yl}amino)methyl]cyclobutan-1-ol

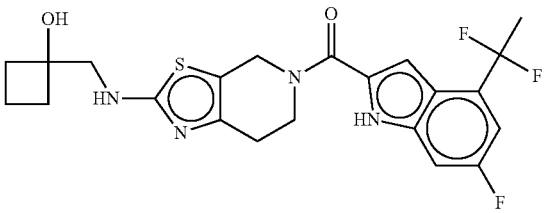

Rt (Method H) 1.07 mins, m/z 465 [M+H]+
No NMR available

Example 372

1-[({5-[4-(1,1-difluoroethyl)-1H-indole-2-carbonyl]-4H,5H,6H,7H-[1,3]thiazolo[5,4-c]pyridin-2-yl}amino)methyl]cyclobutan-1-ol

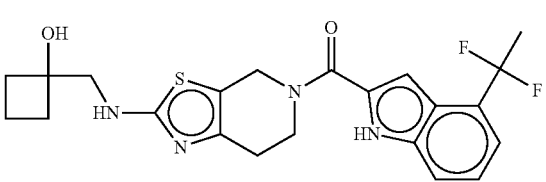

Rt (Method H) 1.01 mins, m/z 447 [M+H]+
No NMR available

Example 373

1-({[5-(6-chloro-5-fluoro-1H-indole-2-carbonyl)-4H, 5H,6H,7H-[1,3]thiazolo[5,4-c]pyridin-2-yl] amino}methyl)cyclobutan-1-ol

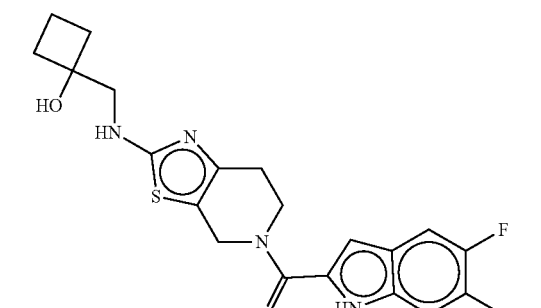

Rt (Method H) 1.03 mins, m/z 435/437 [M+H]+
1H NMR (400 MHz, DMSO-d6) δ 11.86 (s, 1H), 7.62 (d, J=10.0 Hz, 1H), 7.54 (d, J=6.4 Hz, 1H), 7.43 (t, J=5.6 Hz, 1H), 6.92 (s, 1H), 5.26 (s, 1H), 4.71 (br s, 2H), 3.96 (br s, 2H), 2.65 (br s, 2H), 2.05-1.96 (m, 2H), 1.96-1.85 (m, 2H), 1.68-1.57 (m, 1H), 1.51-1.40 (m, 1H).

Example 374

1-[({5-[4-(trifluoromethyl)-1H-indole-2-carbonyl]-4H,5H,6H,7H-[1,3]thiazolo[5,4-c]pyridin-2-yl}amino)methyl]cyclobutan-1-ol

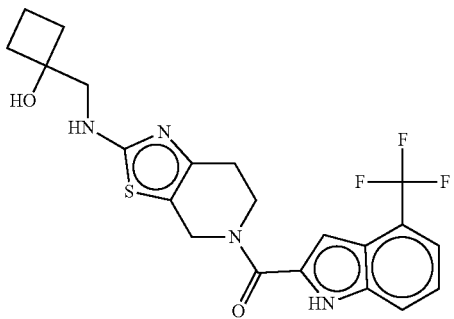

Rt (Method H) 1.06 mins, m/z 451 [M+H]+
No NMR available

Example 375

1-({[5-(4,5-difluoro-1H-indole-2-carbonyl)-4H,5H,6H,7H-[1,3]thiazolo[5,4-c]pyridin-2-yl]amino}methyl)cyclobutan-1-ol

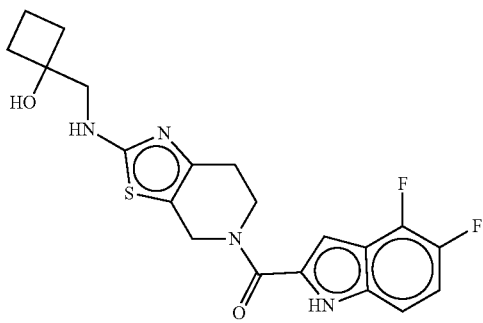

Rt (Method H) 0.98 mins, m/z 419 [M+H]+
No NMR available

Example 376

(1r,3r)-3-{[5-(4-ethyl-6-fluoro-1H-indole-2-carbonyl)-4H,5H,6H,7H-[1,3]thiazolo[5,4-c]pyridin- 2-yl]amino}cyclobutan-1-ol

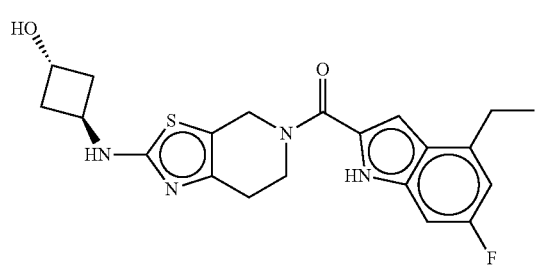

Rt (Method A) 3.22 mins, m/z 415 [M+H]+

1H NMR (400 MHz, DMSO-d6) δ 11.66 (d, J=2.2 Hz, 1H), 7.75 (d, J=6.3 Hz, 1H), 6.96 (m, 2H), 6.76 (dd, J=10.9, 2.3 Hz, 1H), 5.03 (d, J=5.5 Hz, 1H), 4.76 (m, 2H), 4.28 (m, 1H), 4.00 (m, 3H), 2.90 (q, J=7.5 Hz, 2H), 2.66 (m, 2H), 2.14 (m, 4H), 1.28 (t, J=7.6 Hz, 3H).

Example 377

(1r,3r)-3-{[5-(4,5-difluoro-1H-indole-2-carbonyl)-4H,5H,6H,7H-[1,3]thiazolo[5,4-c]pyridin-2-yl]amino}cyclobutan-1-ol

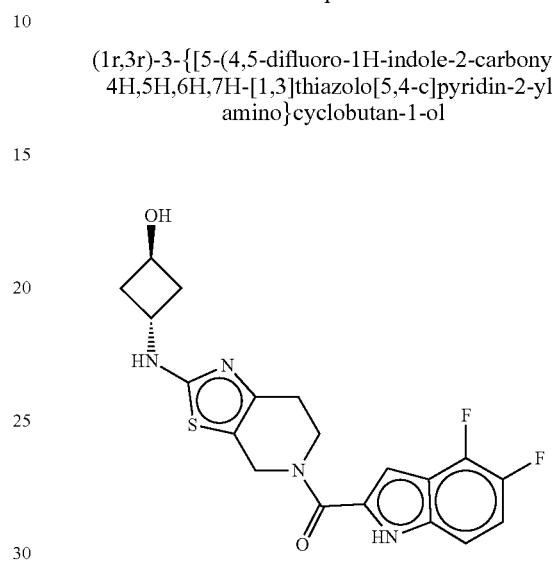

Rt (Method A) 3.06 mins, m/z 405 [M+H]+

1H NMR (400 MHz, DMSO-d6) δ 12.04 (s, 1H), 7.76 (d, J=6.2 Hz, 1H), 7.29-7.18 (m, 2H), 6.99 (s, 1H), 5.03 (d, J=5.4 Hz, 1H), 4.72 (m, 2H), 4.27 (m, 1H), 4.07-3.92 (m, 3H), 2.67 (m, 2H), 2.14 (m, 4H).

Example 378

(1r,3r)-3-{[5-(4,6-difluoro-1H-indole-2-carbonyl)-4H,5H,6H,7H-[1,3]thiazolo[5,4-c]pyridin-2-yl]amino}cyclobutan-1-ol

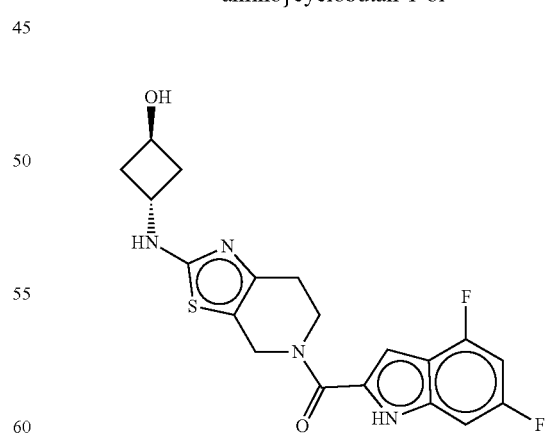

Rt (Method A) 3.08 mins, m/z 405 [M+H]+

1H NMR (400 MHz, DMSO-d6) δ 12.05 (s, 1H), 7.75 (d, J=6.2 Hz, 1H), 7.04 (dd, J=9.5, 2.0 Hz, 1H), 6.98-6.86 (m, 2H), 5.03 (d, J=5.5 Hz, 1H), 4.76 (m, 2H), 4.27 (m, 1H), 4.05-3.91 (m, 3H), 2.66 (m, 2H), 2.14 (m, 4H).

Example 379

(1r,3r)-3-{[5-(6-fluoro-4-methyl-1H-indole-2-carbonyl)-4H,5H,6H,7H-[1,3]thiazolo[5,4-c]pyridin-2-yl]amino}cyclobutan-1-ol

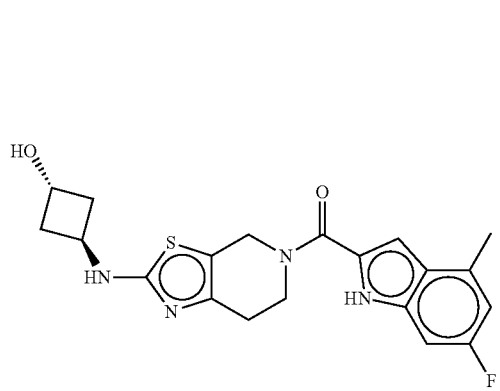

Rt (Method A) 3.1 mins, m/z 401 [M+H]+

1H NMR (400 MHz, DMSO-d6) δ 11.65 (s, 1H), 7.75 (d, J=6.2 Hz, 1H), 6.95 (m, 2H), 6.78-6.71 (m, 1H), 5.03 (d, J=5.5 Hz, 1H), 4.77 (m, 2H), 4.27 (m, 1H), 4.01 (m, 3H), 2.66 (m, 2H), 2.14 (m, 4H).

Example 380

(1r,3r)-3-{[5-(4-ethyl-1H-indole-2-carbonyl)-4H,5H,6H,7H-[1,3]thiazolo[5,4-c]pyridin-2-yl]amino}cyclobutan-1-ol

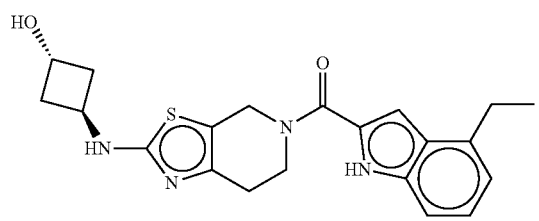

Rt (Method A) 3.16 mins, m/z 397 [M+H]+

1H NMR (400 MHz, DMSO-d6) δ 11.57 (d, J=2.2 Hz, 1H), 7.75 (d, J=6.3 Hz, 1H), 7.25 (d, J=8.3 Hz, 1H), 7.14-7.05 (m, 1H), 6.97-6.78 (m, 2H), 5.03 (d, J=5.6 Hz, 1H), 4.77 (m, 2H), 4.27 (m, 1H), 4.01 (m, 3H), 2.89 (q, J=7.6 Hz, 2H), 2.67 (m, 2H), 2.14 (m, 4H), 1.28 (t, J=7.5 Hz, 3H).

Example 381

(1r,3r)-3-{[5-(4-chloro-1H-indole-2-carbonyl)-4H,5H,6H,7H-[1,3]thiazolo[5,4-c]pyridin-2-yl]amino}cyclobutan-1-ol

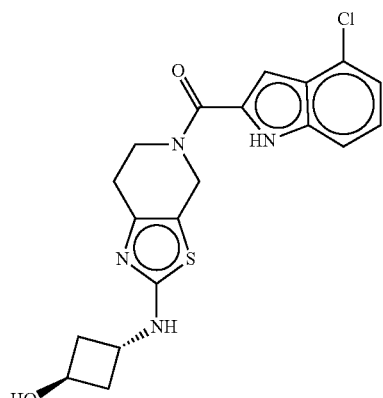

Rt (Method A) 3.1 mins, m/z 403/405 [M+H]+

1H NMR (400 MHz, DMSO-d6) δ 12.01 (s, 1H), 7.76 (d, J=6.3 Hz, 1H), 7.41 (d, J=8.1 Hz, 1H), 7.23-7.11 (m, 2H), 6.85 (s, 1H), 5.03 (d, J=5.6 Hz, 1H), 4.77 (m, 2H), 4.26 (m, 1H), 4.05-3.92 (m, 3H), 2.66 (m, 2H), 2.14 (m, 4H).

Example 382

1-acetyl-N-[5-(1H-indole-2-carbonyl)-4H,5H,6H,7H-[1,3]thiazolo[5,4-c]pyridin-2-yl]azetidine-3-carboxamide

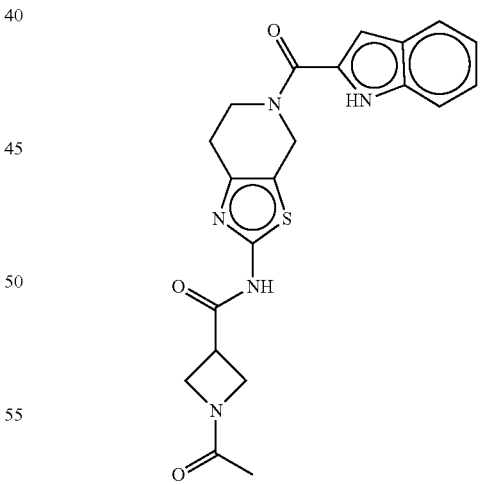

Rt (Method B) 2.85 mins, m/z 422 [M+H]+

1H NMR (400 MHz, DMSO-d6) δ 12.19 (s, 1H), 11.63 (d, J=1.8 Hz, 1H), 7.64 (d, J=7.9 Hz, 1H), 7.43 (d, J=8.3 Hz, 1H), 7.20 (ddd, J=8.2, 7.0, 1.1 Hz, 1H), 7.06 (ddd, J=7.9, 6.9, 1.0 Hz, 1H), 6.94 (d, J=2.5 Hz, 1H), 5.12-4.68 (m, 2H), 4.28 (t, J=8.6 Hz, 1H), 4.20 (dd, J=8.4, 5.7 Hz, 1H), 4.03 (m, 2H), 3.98 (d, J=9.1 Hz, 1H), 3.91 (dd, J=9.5, 5.8 Hz, 1H), 3.61 (tt, J=9.0, 5.7 Hz, 1H), 2.84 (m, 2H), 1.75 (s, 3H).

Example 383

N-[5-(1H-indole-2-carbonyl)-4H,5H,6H,7H-[1,3]thiazolo[5,4-c]pyridin-2-yl]-1-methylazetidine-3-carboxamide

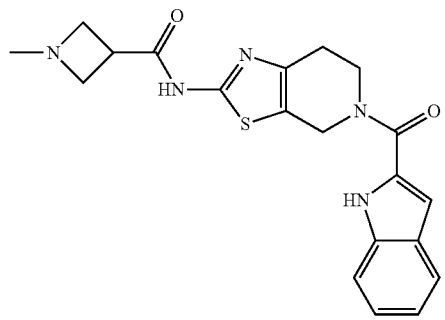 [SMILES: CN1CC(C(=O)Nc2nc3c(s2)CN(C(=O)c2cc4ccccc4[nH]2)CC3)C1]

Rt (Method B) 2.34 mins, m/z 394 [M+H]+

1H NMR (400 MHz, DMSO-d6) δ 12.02 (s, 1H), 11.63 (s, 1H), 7.63 (d, J=7.9 Hz, 1H), 7.43 (d, J=8.2 Hz, 1H), 7.26-7.12 (m, 1H), 7.06 (t, J=7.4 Hz, 1H), 6.93 (d, J=2.0 Hz, 1H), 5.11-4.68 (m, 2H), 4.05 (m, 2H), 3.55-3.37 (m, 4H), 3.22 (m, 1H), 2.83 (m, 2H), 2.23 (s, 3H).

Example 384 tert-butyl 4-{[5-(1H-indole-2-carbonyl)-4H,5H,6H,7H-[1,3]thiazolo[5,4-c]pyridin-2-yl]carbamoyl}piperidine-1-carboxylate

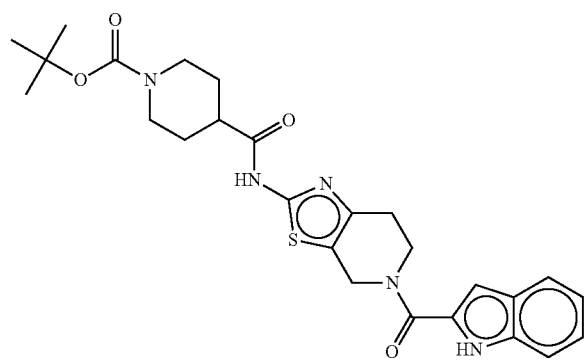

Rt (Method B) 3.47 mins, m/z 508 [M+H]+

1H NMR (400 MHz, DMSO-d6) δ 12.06 (s, 1H), 11.63 (d, J=2.3 Hz, 1H), 7.63 (d, J=8.0 Hz, 1H), 7.43 (d, J=8.2 Hz, 1H), 7.20 (t, J=7.7 Hz, 1H), 7.06 (t, J=7.5 Hz, 1H), 6.93 (d, J=2.1 Hz, 1H), 4.90 (m, 2H), 4.10-3.89 (m, 4H), 2.90-2.55 (m, 5H), 1.83-1.71 (m, 2H), 1.52-1.29 (m, 11H).

Example 385

N-[5-(1H-indole-2-carbonyl)-4H,5H,6H,7H-[1,3]thiazolo[5,4-c]pyridin-2-yl]piperidine-4-carboxamide hydrochloride

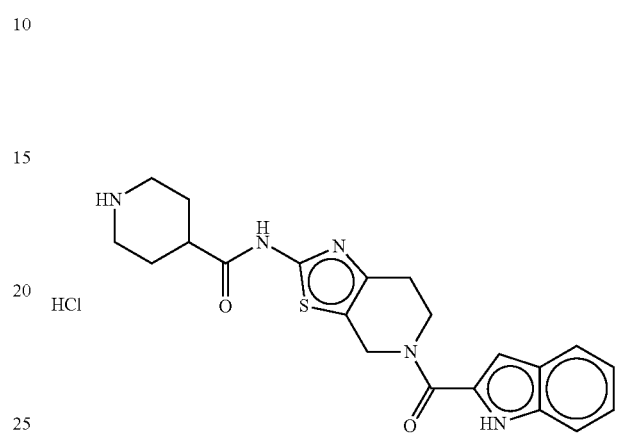

Rt (Method B) 2.37 mins, m/z 408 [M+H]+

1H NMR (400 MHz, DMSO-d6) δ 12.21 (s, 1H), 11.65 (d, J=2.2 Hz, 1H), 9.21-8.90 (m, 1H), 8.87-8.64 (m, 1H), 7.64 (d, J=8.0 Hz, 1H), 7.43 (d, J=8.2 Hz, 1H), 7.20 (t, J=7.5 Hz, 1H), 7.06 (t, J=7.5 Hz, 1H), 6.97-6.89 (m, 1H), 5.28-4.50 (m, 2H), 4.19-3.92 (m, 2H), 3.37-3.24 (m, 2H), 2.99-2.71 (m, 5H), 2.06-1.92 (m, 2H), 1.90-1.73 (m, 2H).

Example 386

N-[5-(1H-indole-2-carbonyl)-4H,5H,6H,7H-[1,3]thiazolo[5,4-c]pyridin-2-yl]azetidine-3-carboxamide hydrochloride

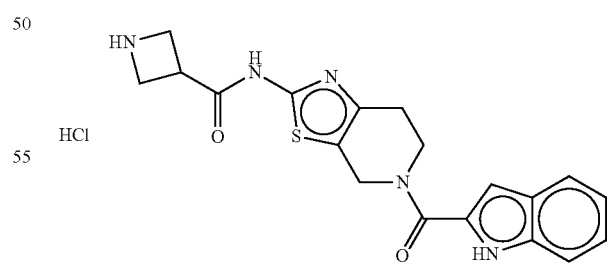

Rt (Method B) 2.32 mins, m/z 382 [M+H]+

1H NMR (400 MHz, DMSO-d6) δ 12.29 (s, 1H), 11.66 (d, J=2.2 Hz, 1H), 9.28 (s, 1H), 8.95 (s, 1H), 7.64 (d, J=8.1 Hz, 1H), 7.44 (d, J=8.3 Hz, 1H), 7.20 (t, J=7.7 Hz, 1H), 7.06 (t, J=7.5 Hz, 1H), 6.96-6.91 (m, 1H), 5.66-4.74 (m, 7H), 3.93-3.83 (m, 1H), 2.97-2.72 (m, 2H)

Example 387 tert-butyl 3-{[5-(1H-indole-2-carbonyl)-4H,5H,6H,7H-[1,3]thiazolo[5,4-c]pyridin-2-yl]carbamoyl}azetidine-1-carboxylate

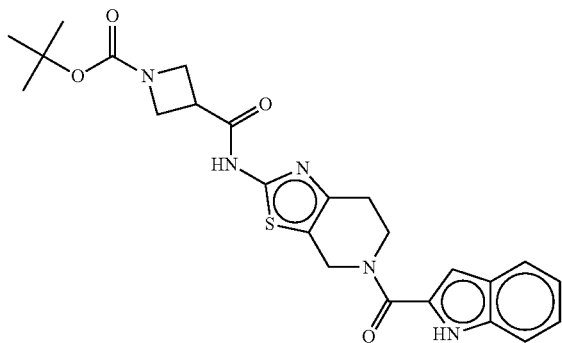

Rt (Method A) 3.5 mins, m/z 480 [M+H]+ 1H NMR (400 MHz, DMSO-d6) δ 12.17 (s, 1H), 11.79-11.52 (m, 1H), 7.64 (d, J=7.9 Hz, 1H), 7.43 (d, J=8.2 Hz, 1H), 7.20 (t, J=7.7 Hz, 1H), 7.06 (t, J=7.4 Hz, 1H), 7.00-6.87 (m, 1H), 5.26-4.67 (m, 2H), 4.16-3.82 (m, 6H), 3.65-3.51 (m, 1H), 2.99-2.72 (m, 2H), 1.38 (s, 9H).

Example 388

(1s,3s)-3-{[5-(1H-indole-2-carbonyl)-4H,5H,6H,7H-[1,3]thiazolo[5,4-c]pyridin-2-yl]amino}cyclobutan-1-ol

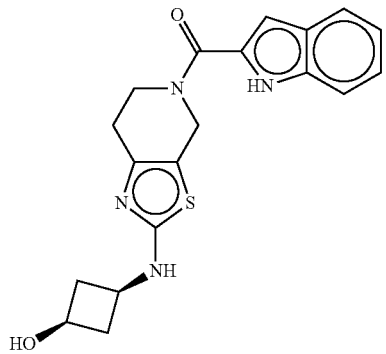

Rt (Method A) 2.89 mins, m/z 369 [M+H]+

1H NMR (400 MHz, DMSO-d6) δ 11.62 (s, 1H), 7.70 (d, J=7.0 Hz, 1H), 7.62 (d, J=8.1 Hz, 1H), 7.42 (d, J=8.2 Hz, 1H), 7.19 (t, J=7.6 Hz, 1H), 7.05 (t, J=7.2 Hz, 1H), 6.88 (d, J=1.6 Hz, 1H), 5.09 (d, J=5.9 Hz, 1H), 4.99-4.38 (m, 2H), 4.08-3.90 (m, 2H), 3.87-3.75 (m, 1H), 3.55-3.47 (m, 1H), 2.73-2.55 (m, 4H), 1.77-1.65 (m, 2H).

Example 389

5-(1H-indole-2-carbonyl)-N—[(pyrrolidin-3-yl)methyl]-4H,5H,6H,7H-[1,3]thiazolo[5,4-c]pyridin-2-amine

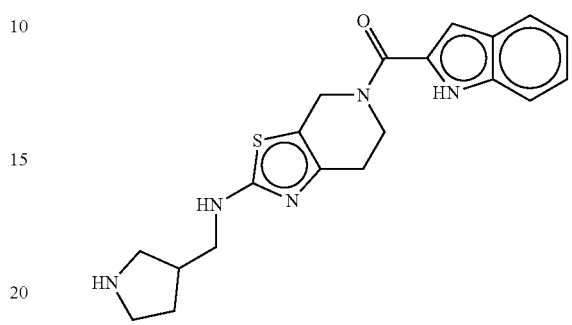

Rt (Method A) 3.09 mins, m/z 382 [M+H]+

1H NMR (400 MHz, DMSO-d6) δ 11.65 (d, J=1.9 Hz, 1H), 8.91 (s, 1H), 7.63 (d, J=8.0 Hz, 1H), 7.43 (d, J=8.2 Hz, 1H), 7.21 (t, J=7.6 Hz, 1H), 7.06 (t, J=7.5 Hz, 1H), 6.91 (d, J=2.0 Hz, 1H), 4.76 (m, 2H), 4.01 (m, 2H), 3.41-3.34 (m, 2H), 3.32-3.20 (m, 2H), 3.17-3.05 (m, 1H), 2.94-2.81 (m, 1H), 2.77-2.63 (m, 2H), 2.64-2.53 (m, 1H), 2.14-1.97 (m, 1H), 1.71-1.56 (m, 1H).

Example 390

3-(cyclopropanesulfonyl)-1-[5-(1H-indole-2-carbonyl)-4H,5H,6H,7H-[1,3]thiazolo[5,4-c]pyridin-2-yl]urea

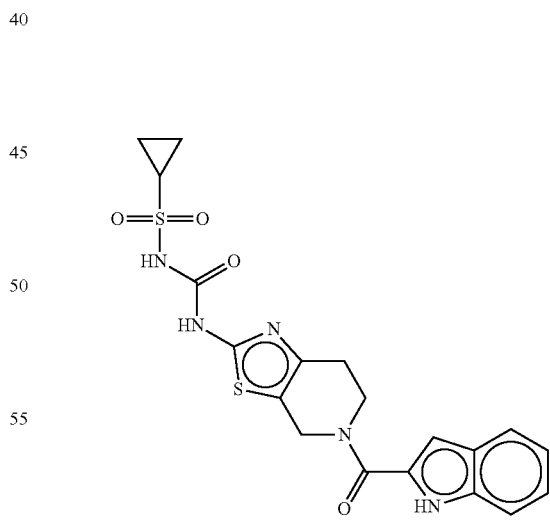

Rt (Method B) 3.05 mins, m/z 446 [M+H]+

1H NMR (400 MHz, DMSO-d6) δ 11.99 (s, 1H), 4.75-4.61 (m, 4H), 4.49 (s, 2H), 4.11-3.93 (m, 1H), 3.63 (t, J=5.8 Hz, 2H), 2.65-2.58 (m, 2H), 1.42 (s, 9H).

Example 391

1-[3-({[5-(1H-indole-2-carbonyl)-4H,5H,6H,7H-[1,3]thiazolo[5,4-c]pyridin-2-yl]amino}methyl)pyrrolidin-1-yl]ethan-1-one

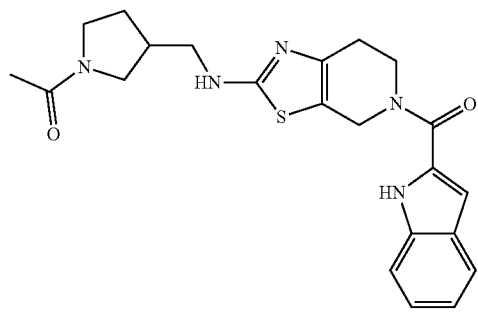 [SMILES: CC(=O)N1CCC(CNc2nc3c(s2)CN(C(=O)c2cc4ccccc4[nH]2)CC3)C1]

Rt (Method A) 2.92 mins, m/z 424 [M+H]+

1H NMR (400 MHz, DMSO-d6) δ 11.63 (s, 1H), 7.68-7.58 (m, 2H), 7.42 (d, J=8.2 Hz, 1H), 7.20 (t, J=7.7 Hz, 1H), 7.06 (t, J=7.5 Hz, 1H), 6.89 (s, 1H), 4.75 (m, 2H), 3.99 (m, 2H), 3.26-3.11 (m, 3H), 3.05-2.92 (m, 1H), 2.67 (m, 2H), 2.47-2.39 (m, 1H), 2.05-1.96 (m, 1H), 1.91 (s, 3H), 1.76-1.49 (m, 1H).

Example 392 tert-butyl 3-({[5-(1H-indole-2-carbonyl)-4H,5H,6H,7H-[1,3]thiazolo[5,4-c]pyridin-2-yl]amino}methyl)pyrrolidine-1-carboxylate

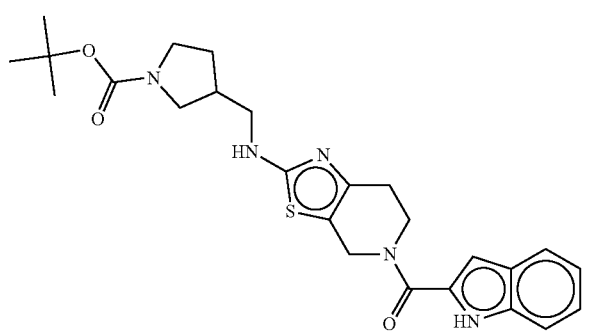

Rt (Method A) 3.56 mins, m/z 482 [M+H]+

1H NMR (400 MHz, DMSO-d6) δ 11.62 (d, J=2.1 Hz, 1H), 7.66-7.58 (m, 2H), 7.42 (d, J=8.1 Hz, 1H), 7.19 (dd, J=7.4 Hz, 1H), 7.05 (t, J=7.4 Hz, 1H), 6.89 (d, J=1.9 Hz, 1H), 4.95-4.54 (m, 2H), 4.07-3.89 (m, 2H), 3.25-3.12 (m, 4H), 2.96 (t, J=9.1 Hz, 1H), 2.76-2.60 (m, 2H), 2.47-2.38 (m, 1H), 1.98-1.85 (m, 1H), 1.65-1.51 (m, 1H), 1.39 (s, 9H).

Example 393

1-[5-(1H-indole-2-carbonyl)-4H,5H,6H,7H-[1,3]thiazolo[5,4-c]pyridin-2-yl]-3-methanesulfonylurea

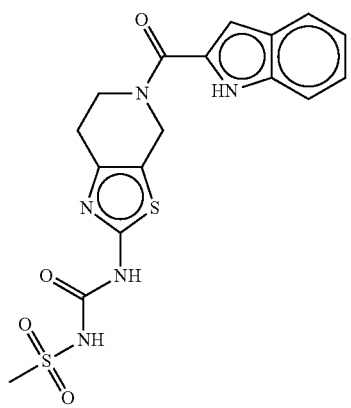

Rt (Method B) 2.91 mins, m/z 420 [M+H]+

1H NMR (400 MHz, DMSO-d6) δ 11.64 (d, J=2.2 Hz, 1H), 10.56 (s, 1H), 7.64 (d, J=7.9 Hz, 1H), 7.43 (d, J=8.1 Hz, 1H), 7.20 (dd, J=8.2, 6.7 Hz, 1H), 7.06 (t, J=7.5 Hz, 1H), 6.93 (d, J=1.9 Hz, 1H), 5.06-4.67 (m, 2H), 4.08-3.99 (m, 2H), 3.24 (s, 3H), 2.84-2.74 (m, 2H).

Example 394

(1s,4s)-4-{[5-(4-ethyl-6-fluoro-1H-indole-2-carbonyl)-4H,5H,6H,7H-[1,3]thiazolo[5,4-c]pyridin-2-yl]amino}cyclohexan-1-ol

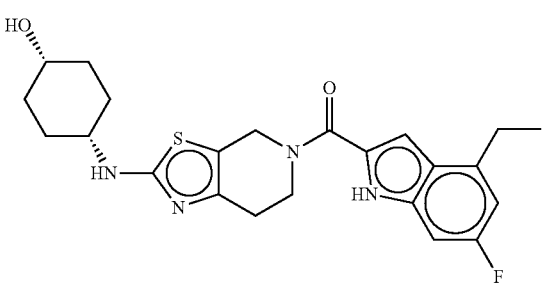

Rt (Method A) 3.33 mins, m/z 443 [M+H]+

1H NMR (400 MHz, DMSO-d6) δ 11.78-11.58 (m, 1H), 7.58-7.37 (m, 1H), 7.00-6.93 (m, 2H), 6.76 (dd, J=10.8, 2.2 Hz, 1H), 4.94-4.54 (m, 2H), 4.39 (s, 1H), 4.13-3.79 (m, 2H), 3.74-3.45 (m, 2H), 2.90 (q, J=7.6 Hz, 2H), 2.75-2.57 (m, 2H), 1.75-1.37 (m, 8H), 1.28 (t, J=7.5 Hz, 3H).

Example 395

(1s,4s)-4-{[5-(4,5-difluoro-1H-indole-2-carbonyl)-4H,5H,6H,7H-[1,3]thiazolo[5,4-c]pyridin-2-yl]amino}cyclohexan-1-ol

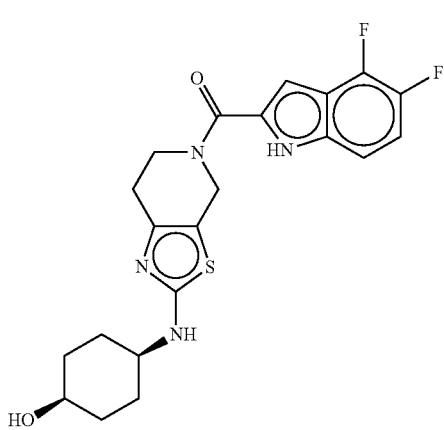

Rt (Method B) 2.59 mins, m/z 433 [M+H]+

1H NMR (400 MHz, DMSO-d6) δ 12.05 (s, 1H), 7.49-7.36 (m, 1H), 7.32-7.15 (m, 2H), 6.99 (s, 1H), 5.09-4.48 (m, 2H), 4.50-4.25 (m, 1H), 4.14-3.80 (m, 2H), 3.77-3.45 (m, 2H), 2.80-2.56 (m, 2H), 1.87-1.29 (m, 8H).

Example 396

(1R,3S)-3-{[5-(1H-indole-2-carbonyl)-4H,5H,6H,7H-[1,3]thiazolo[5,4-c]pyridin-2-yl]amino}cyclopentan-1-ol

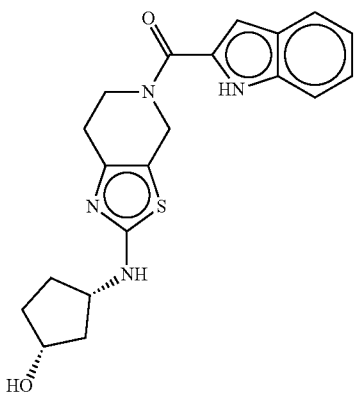

Rt (Method B) 2.4 mins, m/z 383 [M+H]+

1H NMR (400 MHz, DMSO-d6) δ 11.62 (s, 1H), 7.62 (d, J=8.0 Hz, 1H), 7.49 (d, J=7.2 Hz, 1H), 7.43 (d, J=8.2 Hz, 1H), 7.24-7.16 (m, 1H), 7.05 (t, J=7.5 Hz, 1H), 6.91-6.84 (m, 1H), 5.01-4.44 (m, 3H), 4.12-3.92 (m, 3H), 3.92-3.80 (m, 1H), 2.76-2.59 (m, 2H), 2.27-2.16 (m, 1H), 1.96-1.84 (m, 1H), 1.73-1.50 (m, 3H), 1.43-1.32 (m, 1H).

Example 397

(1r,3r)-3-{[5-(1H-indole-2-carbonyl)-4H,5H,6H,7H-[1,3]thiazolo[5,4-c]pyridin-2-yl]amino}cyclobutan-1-ol

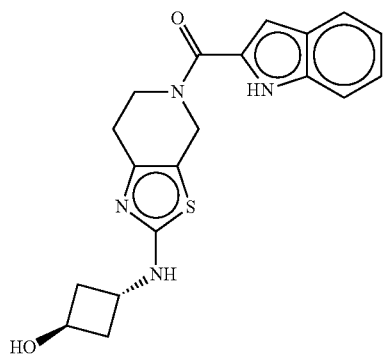

Rt (Method A) 2.88 mins, m/z 369 [M+H]+

1H NMR (400 MHz, DMSO-d6) δ 11.62 (s, 1H), 7.76 (d, J=6.2 Hz, 1H), 7.62 (d, J=8.0 Hz, 1H), 7.43 (d, J=8.2 Hz, 1H), 7.23-7.15 (m, 1H), 7.06 (t, J=7.5 Hz, 1H), 6.91-6.86 (m, 1H), 5.19-4.93 (m, 1H), 4.92-4.48 (m, 2H), 4.27 (p, J=6.0 Hz, 1H), 4.08-3.88 (m, 3H), 2.78-2.57 (m, 2H), 2.14 (t, J=6.1 Hz, 4H).

Example 398

N-[5-(4,5-difluoro-1H-indole-2-carbonyl)-4H,5H,6H,7H-[1,3]thiazolo[5,4-c]pyridin-2-yl]oxane-4-carboxamide

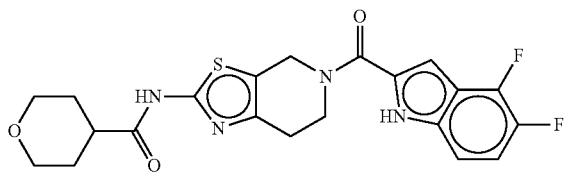

Rt (Method A) 3.2 mins, m/z 447 [M+H]+

1H NMR (400 MHz, DMSO-d6) δ 12.16-11.96 (m, 2H), 7.28-7.22 (m, 2H), 7.04 (s, 1H), 5.33-4.63 (m, 2H), 4.08-3.96 (m, 2H), 3.93-3.84 (m, 2H), 3.39-3.27 (m, 2H), 2.94-2.77 (m, 2H), 2.77-2.69 (m, 1H), 1.76-1.56 (m, 4H).

Example 399

N-{5-[4-(1,1-difluoroethyl)-1H-indole-2-carbonyl]-4H,5H,6H,7H-[1,3]thiazolo[5,4-c]pyridin-2-yl}oxane-4-carboxamide

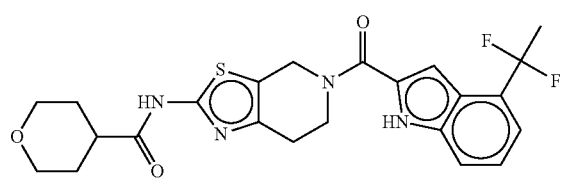

Rt (Method A) 3.24 mins, m/z 473 [M+H]+

1H NMR (400 MHz, DMSO-d6) δ 12.19-11.86 (m, 2H), 7.56 (d, J=8.1 Hz, 1H), 7.31-7.21 (m, 2H), 6.90 (s, 1H), 5.13-4.72 (m, 2H), 4.10-3.97 (m, 2H), 3.92-3.84 (m, 2H), 2.90-2.77 (m, 2H), 2.75-2.68 (m, 1H), 2.09 (t, J=18.8 Hz, 3H), 1.78-1.58 (m, 4H).

Example 400

N-{5-[4-(difluoromethyl)-1H-indole-2-carbonyl]-4H,5H,6H,7H-[1,3]thiazolo[5,4-c]pyridin-2-yl}oxane-4-carboxamide

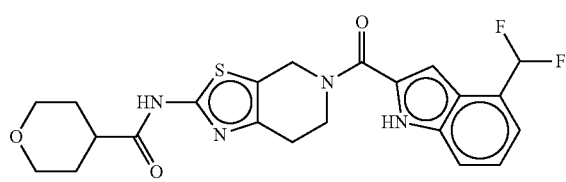

Rt (Method A) 3.15 mins, m/z 461 [M+H]+

1H NMR (400 MHz, DMSO-d6) δ 12.18-11.96 (m, 2H), 7.64-7.57 (m, 1H), 7.48-7.19 (m, 3H), 7.03 (s, 1H), 5.20-4.69 (m, 2H), 4.16-3.98 (m, 2H), 3.94-3.82 (m, 2H), 3.39-3.27 (m, 2H), 2.89-2.79 (m, 2H), 2.78-2.66 (m, 1H), 1.77-1.57 (m, 4H).

Example 401

N-{5-[4-(1,1-difluoroethyl)-6-fluoro-1H-indole-2-carbonyl]-4H,5H,6H,7H-[1,3]thiazolo[5,4-c]pyridin-2-yl}oxane-4-carboxamide

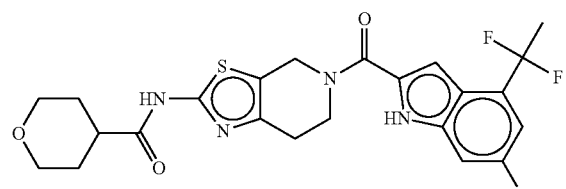

Rt (Method A) 3.33 mins, m/z 493 [M+H]+

1H NMR (400 MHz, DMSO-d6) δ 12.71-9.97 (m, 2H), 7.34-7.27 (m, 1H), 7.16-7.09 (m, 1H), 6.92 (s, 1H), 5.23-4.63 (m, 2H), 4.08-3.98 (m, 2H), 3.93-3.84 (m, 2H), 3.39-3.27 (m, 2H), 2.86-2.77 (m, 2H), 2.76-2.65 (m, 1H), 2.10 (t, J=18.9 Hz, 3H), 1.78-1.56 (m, 4H).

Example 402

N-{5-[4-(difluoromethyl)-6-fluoro-1H-indole-2-carbonyl]-4H,5H,6H,7H-[1,3]thiazolo[5,4-c]pyridin-2-yl}oxane-4-carboxamide

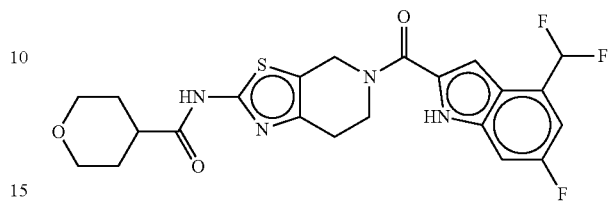

Rt (Method A) 3.24 mins, m/z 479 [M+H]+

1H NMR (400 MHz, DMSO-d6) δ 12.31-11.75 (m, 2H), 7.53-7.19 (m, 3H), 7.06 (s, 1H), 5.45-4.58 (m, 2H), 4.17-3.97 (m, 2H), 3.94-3.82 (m, 2H), 3.39-3.26 (m, 2H), 2.94-2.78 (m, 2H), 2.77-2.65 (m, 1H), 1.79-1.56 (m, 4H).

Example 403

N-[5-(4-ethyl-6-fluoro-1H-indole-2-carbonyl)-4H,5H,6H,7H-[1,3]thiazolo[5,4-c]pyridin-2-yl]oxane-4-carboxamide

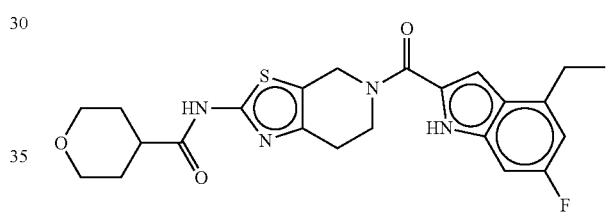

Rt (Method A) 3.38 mins, m/z 457 [M+H]+

1H NMR (400 MHz, DMSO-d6) δ 12.05 (s, 1H), 11.80-11.60 (m, 1H), 7.05-6.99 (m, 1H), 6.97 (dd, J=9.7, 2.2 Hz, 1H), 6.77 (dd, J=10.8, 2.4 Hz, 1H), 5.31-4.57 (m, 2H), 4.19-3.96 (m, 2H), 3.93-3.84 (m, 2H), 2.91 (q, J=7.6 Hz, 2H), 2.87-2.77 (m, 2H), 2.77-2.65 (m, 1H), 1.77-1.56 (m, 4H), 1.28 (t, J=7.5 Hz, 3H).

Example 404

5-({[5-(1H-indole-2-carbonyl)-4H,5H,6H,7H-[1,3]thiazolo[5,4-c]pyridin-2-yl]amino}methyl)pyrrolidin-2-one

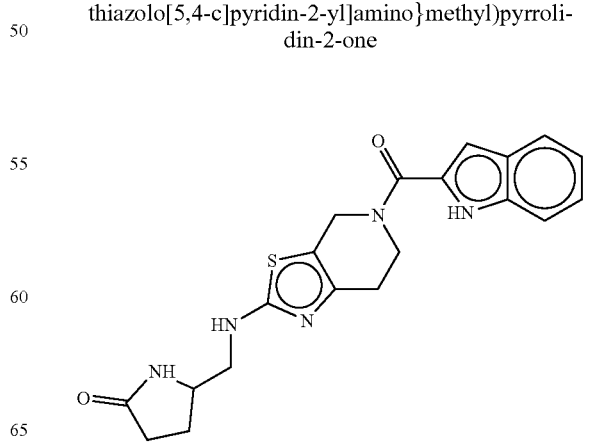

Rt (Method A) 1.08 mins, m/z 396.1 [M+H]+

1H NMR (400 MHz, DMSO-d6) δ 11.62 (d, J=2.3 Hz, 1H), 7.62 (m, 2H), 7.58 (t, J=5.8 Hz, 1H), 7.43 (d, J=8.2 Hz, 1H), 7.20 (dd, J=8.2, 6.9 Hz, 1H), 7.05 (t, J=7.5 Hz, 1H), 6.89 (d, J=2.0 Hz, 1H), 3.98 (m, 2H), 3.73 (q, J=6.1 Hz, 1H), 3.36 (d, J=5.8 Hz, 1H), 3.16 (dt, J=12.8, 6.0 Hz, 1H), 2.67 (m, 2H), 2.20-2.00 (m, 3H), 1.81-1.67 (m, 1H).

Example 405

1-({[5-(1H-indole-2-carbonyl)-4H,5H,6H,7H-[1,3]thiazolo[5,4-c]pyridin-2-yl]amino}methyl)cyclopropan-1-ol

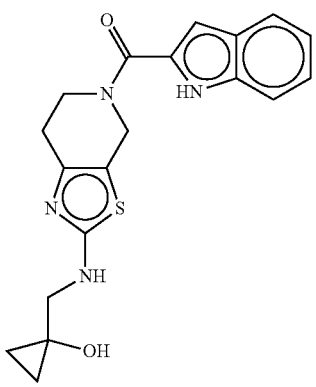

Rt (Method A) 1.18 mins, m/z 369.1 [M+H]+

1H NMR (400 MHz, DMSO-d6) δ 11.61 (s, 1H), 7.62 (d, J=8.0 Hz, 1H), 7.53 (t, J=5.6 Hz, 1H), 7.43 (d, J=8.1 Hz, 1H), 7.19 (ddd, J=8.3, 6.9, 1.2 Hz, 1H), 7.05 (ddd, J=8.0, 6.9, 1.0 Hz, 1H), 6.89 (d, J=2.2 Hz, 1H), 5.42 (s, 1H), 4.65 (m, 2H), 3.98 (m, 2H), 3.35 (m, 2H), 2.65 (m, 2H), 0.54 (m, 4H).

Example 406—Intentionally Left Blank

Example 407

5-(6-chloro-7-fluoro-1H-indole-2-carbonyl)-4H,5H,6H,7H-[1,3]thiazolo[5,4-c]pyridin-2-amine

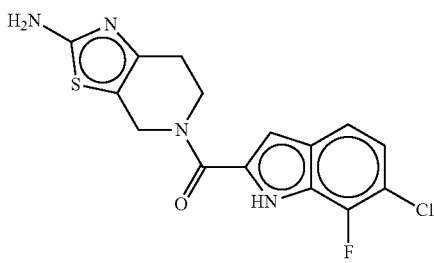

Rt (Method B) 2.49 mins, m/z 351/353 [M+H]+

1H NMR (400 MHz, DMSO-d6) δ 12.35 (s, 1H), 7.47 (d, J=8.5 Hz, 1H), 7.15 (dd, J=8.5, 6.4 Hz, 1H), 6.95 (d, J=3.1 Hz, 1H), 6.84 (s, 2H), 4.81-4.57 (m, 2H), 3.92 (t, J=5.8 Hz, 2H), 2.67-2.57 (s, 2H).

Example 408

1-[({5-[4-(difluoromethyl)-1H-indole-2-carbonyl]-4H,5H,6H,7H-[1,3]thiazolo[5,4-c]pyridin-2-yl}amino)methyl]cyclobutan-1-ol

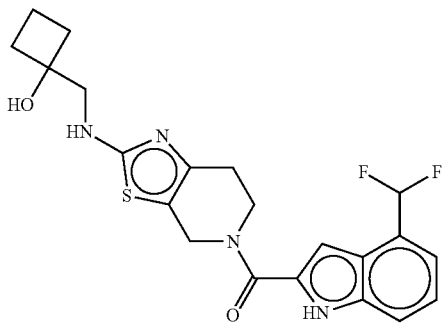

Rt (Method B) 2.58 mins, m/z 433 [M+H]+

1H NMR (400 MHz, DMSO-d6) δ 11.99 (m, 1H), 7.64-7.56 (m, 1H), 7.47-7.17 (m, 4H), 6.99 (s, 1H), 5.26 (s, 1H), 4.86-4.62 (m, 2H), 4.03-3.93 (m, 2H), 2.70-2.60 (m, 2H), 2.05-1.96 (m, 2H), 1.96-1.86 (m, 2H), 1.68-1.57 (m, 1H), 1.53-1.39 (m, 1H).

Example 409

N-[5-(1H-indole-2-carbonyl)-4H,5H,6H,7H-[1,3]thiazolo[5,4-c]pyridin-2-yl]-1-methylpiperidine-4-carboxamide

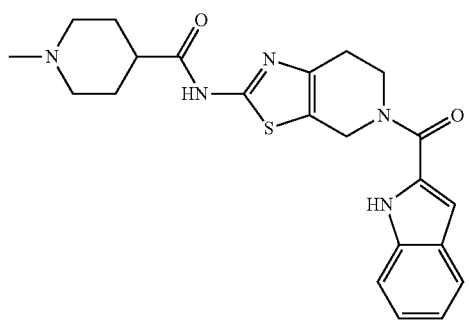 [SMILES: CN1CCC(C(=O)Nc2nc3c(s2)CN(C(=O)c2cc4ccccc4[nH]2)CC3)CC1]

Rt (Method B) 2.3 mins, m/z 424 [M+H]+ 1H NMR (400 MHz, DMSO-d6) δ 11.98 (s, 1H), 11.63 (s, 1H), 7.63 (d, J=7.9 Hz, 1H), 7.43 (d, J=8.3 Hz, 1H), 7.23-7.17 (m, 1H), 7.09-7.03 (m, 1H), 6.93 (d, J=2.1 Hz, 1H), 5.04-4.78 (m, 2H), 4.09-4.00 (m, 2H), 2.88-2.73 (m, 4H), 2.40 (tt, J=11.6, 4.1 Hz, 1H), 2.14 (s, 3H), 1.84 (td, J=11.6, 2.5 Hz, 2H), 1.78-1.70 (m, 2H), 1.68-1.56 (m, 2H).

Example 410

1-acetyl-N-[5-(1H-indole-2-carbonyl)-4H,5H,6H,7H-[1,3]thiazolo[5,4-c]pyridin-2-yl]piperidine-4-carboxamide

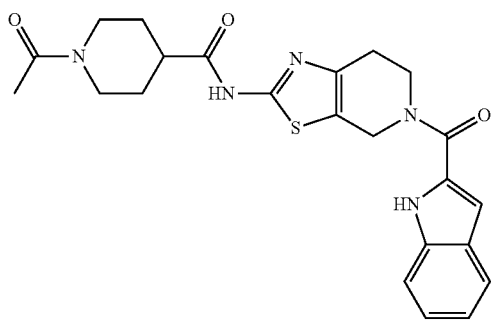 [SMILES: CC(=O)N1CCC(C(=O)Nc2nc3c(s2)CN(C(=O)c2cc4ccccc4[nH]2)CC3)CC1]

Rt (Method B) 2.86 mins, m/z 452 [M+H]+

1H NMR (400 MHz, DMSO-d6) δ 12.06 (s, 1H), 11.62 (d, J=2.2 Hz, 1H), 7.63 (d, J=7.9 Hz, 1H), 7.43 (d, J=8.2 Hz, 1H), 7.23-7.17 (m, 1H), 7.06 (t, J=7.4 Hz, 1H), 6.95-6.90 (m, 1H), 5.03-4.77 (m, 2H), 4.36 (d, J=13.0 Hz, 1H), 4.11-3.98 (m, 2H), 3.84 (d, J=13.6 Hz, 1H), 3.11-3.00 (m, 1H), 2.90-2.76 (m, 2H), 2.76-2.65 (m, 1H), 2.64-2.53 (m, 2H), 2.00 (s, 3H), 1.87-1.75 (m, 2H), 1.61-1.52 (m, 1H), 1.48-1.35 (m, 1H).

Example 411

4-hydroxy-N-[5-(1H-indole-2-carbonyl)-4H,5H,6H,7H-[1,3]thiazolo[5,4-c]pyridin-2-yl]cyclohexane-1-carboxamide

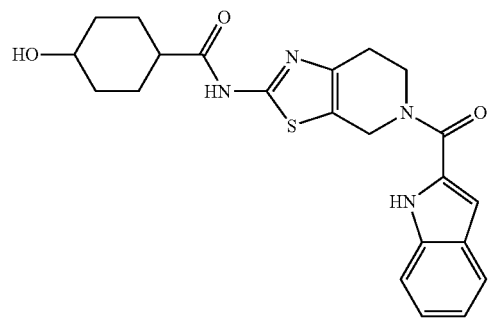 [SMILES: O=C(Nc1nc2c(s1)CN(C(=O)c1cc3ccccc3[nH]1)CC2)C1CCC(O)CC1]

Rt (Method B) 2.88 mins, m/z 425 [M+H]+ 1H NMR (400 MHz, DMSO-d6) δ 11.92 (s, 1H), 11.62 (s, 1H), 7.63 (d, J=8.0 Hz, 1H), 7.43 (d, J=8.2 Hz, 1H), 7.23-7.17 (m, 1H), 7.06 (t, J=7.5 Hz, 1H), 6.95-6.90 (m, 1H), 5.08-4.73 (m, 2H), 4.60-4.30 (m, 1H), 4.11-3.96 (m, 2H), 3.81-3.33 (m, 1H), 2.89-2.76 (m, 2H), 2.49-2.29 (m, 1H), 1.92-1.74 (m, 3H), 1.70-1.61 (m, 1H), 1.56-1.37 (m, 3H), 1.20-1.08 (m, 1H).

Example 412

N-[5-(1H-indole-2-carbonyl)-4H,5H,6H,7H-[1,3]thiazolo[5,4-c]pyridin-2-yl]-2-oxopiperidine-4-carboxamide

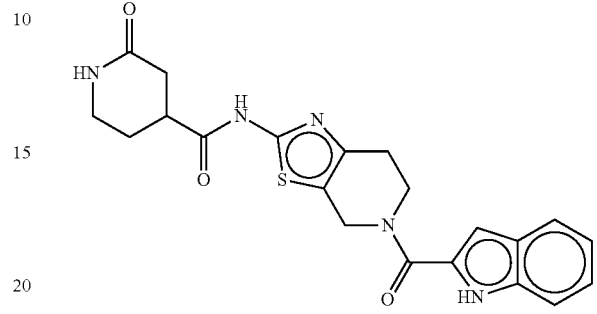

Rt (Method B) 2.74 mins, m/z 424 [M+H]+

1H NMR (400 MHz, DMSO-d6) δ 12.13 (s, 1H), 11.63 (s, 1H), 7.64 (d, J=7.9 Hz, 1H), 7.52 (s, 1H), 7.43 (d, J=8.2 Hz, 1H), 7.20 (ddd, J=8.3, 6.9, 1.1 Hz, 1H), 7.06 (t, J=7.4 Hz, 1H), 6.93 (d, J=2.1 Hz, 1H), 5.06-4.70 (m, 2H), 4.11-3.99 (m, 2H), 3.20-3.09 (m, 2H), 3.04-2.91 (m, 1H), 2.89-2.78 (m, 2H), 2.38-2.25 (m, 2H), 2.03-1.92 (m, 1H), 1.83-1.68 (m, 1H).

Example 413

5-(1H-indole-2-carbonyl)-N-{[1-(propan-2-yloxy)cyclobutyl]methyl}-4H,5H,6H,7H-[1,3]thiazolo[5,4-c]pyridin-2-amine

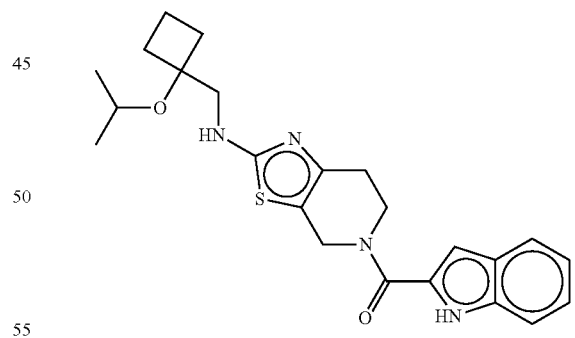

Rt (Method A) 3.58 mins, m/z 425 [M+H]+

1H NMR (400 MHz, DMSO-d6) δ 11.62 (s, 1H), 7.63 (d, J=7.9 Hz, 1H), 7.43 (d, J=8.2 Hz, 1H), 7.29 (t, J=5.3 Hz, 1H), 7.20 (t, J=7.6 Hz, 1H), 7.06 (t, J=7.5 Hz, 1H), 6.96-6.83 (m, 1H), 5.07-4.41 (m, 2H), 4.17-3.82 (m, 2H), 3.73 (hept, J=6.1 Hz, 1H), 3.45 (d, J=5.2 Hz, 2H), 2.81-2.58 (m, 2H), 2.12-1.88 (m, 4H), 1.75-1.62 (m, 1H), 1.62-1.46 (m, 1H), 1.06 (d, J=6.1 Hz, 6H)

Example 414

5-(1H-indole-2-carbonyl)-N-[(1-methoxycyclobutyl)methyl]-4H,5H,6H,7H-[1,3]thiazolo[5,4-c]pyridin-2-amine

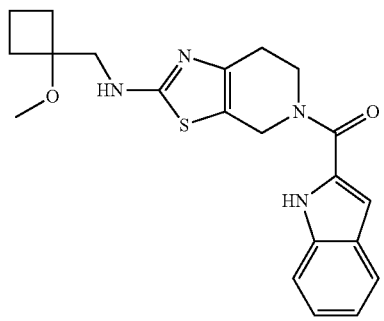 [SMILES: COC1(CNc2nc3c(s2)CN(C(=O)c2cc4ccccc4[nH]2)CC3)CCC1]

Rt (Method A) 3.27 mins, m/z 597 [M+H]+

1H NMR (400 MHz, DMSO-d6) δ 11.61 (s, 1H), 7.63 (d, J=8.0 Hz, 1H), 7.43 (d, J=8.3 Hz, 1H), 7.39 (t, J=5.6 Hz, 1H), 7.20 (t, J=7.6 Hz, 1H), 7.06 (t, J=7.5 Hz, 1H), 6.92-6.85 (m, 1H), 4.95-4.53 (m, 2H), 4.09-3.89 (m, 2H), 3.48 (d, J=5.5 Hz, 2H), 3.09 (s, 3H), 2.75-2.61 (m, 2H), 2.08-1.95 (m, 2H), 1.94-1.84 (m, 2H), 1.74-1.61 (m, 1H), 1.62-1.48 (m, 1H).

Example 415—Intentionally Left Blank

Example 416

N-(3,3-difluorocyclobutyl)-5-(1H-indole-2-carbonyl)-4H,5H,6H,7H-[1,3]thiazolo[5,4-c]pyridin-2-amine

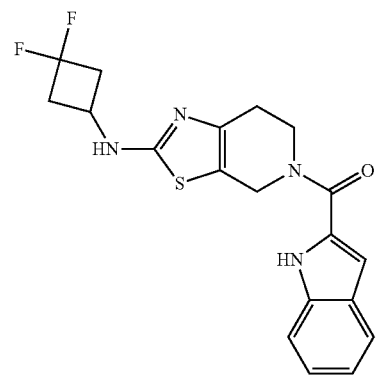 [SMILES: O=C(c1cc2ccccc2[nH]1)N1CCc2nc(NC3CC(F)(F)C3)sc2C1]

Rt (Method A) 3.3 mins, m/z 389 [M+H]+

1H NMR (400 MHz, DMSO-d6) δ 11.62 (s, 1H), 7.97 (d, J=6.1 Hz, 1H), 7.63 (d, J=7.9 Hz, 1H), 7.43 (d, J=8.2 Hz, 1H), 7.24-7.15 (m, 1H), 7.10-7.01 (m, 1H), 6.89 (s, 1H), 5.07-4.46 (m, 2H), 4.26-3.73 (m, 3H), 3.07-2.90 (m, 2H), 2.78-2.63 (m, 2H), 2.61-2.52 (m, 2H).

Example 417

N-ethyl-1-({[5-(1H-indole-2-carbonyl)-4H,5H,6H,7H-[1,3]thiazolo[5,4-c]pyridin-2-yl]amino}methyl)cyclobutane-1-carboxamide

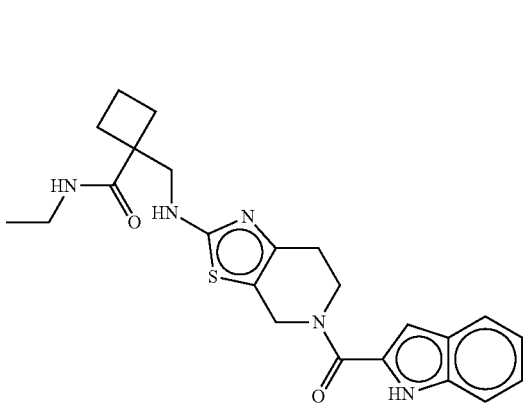

Rt (Method B) 2.54 mins, m/z 438 [M+H]+

1H NMR (400 MHz, DMSO-d6) δ 11.61 (s, 1H), 7.69-7.50 (m, 2H), 7.48-7.29 (m, 2H), 7.19 (t, J=7.6 Hz, 1H), 7.05 (t, J=7.5 Hz, 1H), 6.89 (d, J=2.1 Hz, 1H), 4.74 (m, 2H), 3.98 (m, 2H), 3.56 (d, J=5.9 Hz, 2H), 3.16-2.95 (m, 2H), 2.66 (m, 2H), 2.21 (m, 2H), 2.02-1.75 (m, 3H), 1.69 (m, 1H), 0.98 (t, J=7.2 Hz, 3H).

Example 418

N-(cyclobutylmethyl)-5-(1H-indole-2-carbonyl)-4H,5H,6H,7H-[1,3]thiazolo[5,4-c]pyridin-2-amine

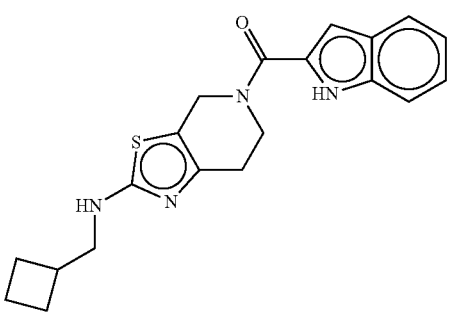

Rt (Method B) 2.73 mins, m/z 367 [M+H]+

1H NMR (400 MHz, DMSO-d6) δ 11.62 (s, 1H), 7.62 (d, J=8.0 Hz, 1H), 7.53-7.36 (m, 2H), 7.29-7.13 (m, 1H), 7.05 (t, J=7.5 Hz, 1H), 6.88 (d, J=2.2 Hz, 1H), 4.73 (m, 2H), 3.98 (m, 2H), 3.21 (m, 2H), 2.66 (m, 2H), 2.58-2.51 (m, 1H), 1.99 (m, 2H), 1.90-1.74 (m, 2H), 1.74-1.56 (m, 2H).

Example 419

5-(1H-indole-2-carbonyl)-N-(1-phenylcyclopropyl)-4H,5H,6H,7H-[1,3]thiazolo[5,4-c]pyridin-2-amine

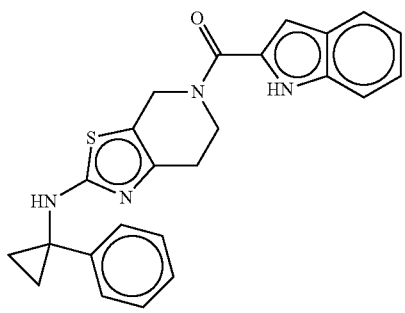

Rt (Method B) 3.06 mins, m/z 415 [M+H]+

1H NMR (400 MHz, DMSO-d6) δ 11.59 (s, 1H), 8.51 (s, 1H), 7.61 (d, J=8.0 Hz, 1H), 7.41 (d, J=8.3 Hz, 1H), 7.35-7.10 (m, 6H), 7.07-6.98 (m, 1H), 6.86 (d, J=2.0 Hz, 1H), 4.71 (m, 2H), 3.96 (m, 2H), 2.67 (m, 2H), 1.26 (m, 4H).

Example 420

N-[(3,3-difluorocyclobutyl)methyl]-5-(1H-indole-2-carbonyl)-4H,5H,6H,7H-[1,3]thiazolo[5,4-c]pyridin-2-amine

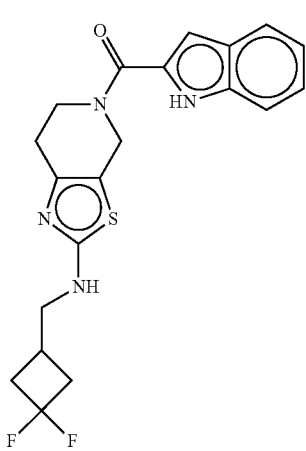

Rt (Method A) 3.38 mins, m/z 403 [M+H]+

1H NMR (400 MHz, DMSO-d6) δ 11.62 (s, 1H), 7.68-7.59 (m, 2H), 7.42 (d, J=8.2 Hz, 1H), 7.19 (t, J=7.7 Hz, 1H), 7.05 (t, J=7.4 Hz, 1H), 6.89 (s, 1H), 5.04-4.45 (m, 2H), 4.11-3.86 (m, 2H), 3.30 (s, 2H), 2.72-2.56 (m, 4H), 2.44-2.25 (m, 3H)—one signal (2H) coincides with H2O signal.

Example 421

N-[3-(difluoromethoxy)cyclobutyl]-5-(1H-indole-2-carbonyl)-4H,5H,6H,7H-[1,3]thiazolo[5,4-c]pyridin-2-amine

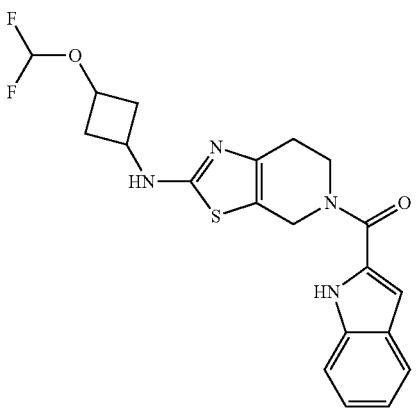 [SMILES: O=C(c1cc2ccccc2[nH]1)N1CCc2nc(NC3CC(OC(F)F)C3)sc2C1]

Rt (Method A) 3.37 mins, m/z 419 [M+H]+

1H NMR (400 MHz, DMSO-d6) δ 11.62 (s, 1H), 7.87 (d, J=6.2 Hz, 0.2H), 7.79 (d, J=7.6 Hz, 0.8H), 7.62 (d, J=7.9 Hz, 1H), 7.42 (d, J=8.2 Hz, 1H), 7.19 (t, J=7.6 Hz, 1H), 7.05 (t, J=7.5 Hz, 1H), 6.91-6.86 (m, 1H), 6.64 (t, J=75.9 Hz, 0.2H), 6.62 (t, J=75.7 Hz, 0.8H), 5.09-4.57 (m, 2H), 4.41-4.29 (m, 1H), 4.03-3.93 (m, 2H), 3.82-3.67 (m, 1H), 2.79-2.68 (m, 1.6H), 2.69-2.59 (m, 2H), 2.46-2.37 (m, 0.4H), 2.35-2.24 (m, 0.4H), 2.05-1.93 (m, 1.6H)—mixture of cis/trans isomers in 4:1 ratio.

Example 422

5-(1H-indole-2-carbonyl)-N-[1-(trifluoromethyl)cyclopropyl]-4H,5H,6H,7H-[1,3]thiazolo[5,4-c]pyridin-2-amine

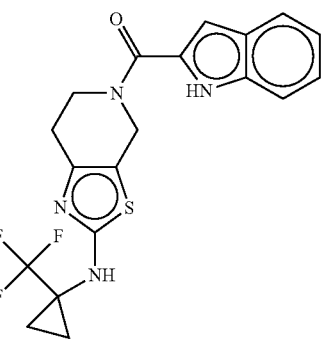

Rt (Method A) 3.37 mins, m/z 407 [M+H]+

1H NMR (400 MHz, DMSO-d6) δ 11.62 (s, 1H), 8.44 (s, 1H), 7.63 (d, J=8.0 Hz, 1H), 7.43 (d, J=8.2 Hz, 1H), 7.20 (t, J=7.6 Hz, 1H), 7.06 (t, J=7.5 Hz, 1H), 6.92-6.87 (m, 1H), 5.22-4.36 (m, 2H), 4.05-3.94 (m, 2H), 2.75-2.64 (m, 2H), 1.35-1.27 (m, 2H), 1.22-1.13 (m, 2H).

Example 423

5-(1H-indole-2-carbonyl)-N-[1-(methoxymethyl)cyclopropyl]-4H,5H,6H,7H-[1,3]thiazolo[5,4-c]pyridin-2-amine

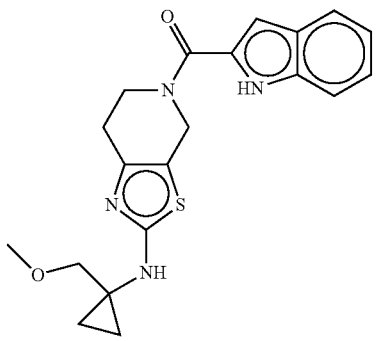

Rt (Method A) 3.14 mins, m/z 383 [M+H]+

1H NMR (400 MHz, DMSO-d6) δ 11.62 (s, 1H), 7.91 (s, 1H), 7.63 (d, J=8.0 Hz, 1H), 7.43 (d, J=8.2 Hz, 1H), 7.20 (t, J=7.5 Hz, 1H), 7.06 (t, J=7.4 Hz, 1H), 6.92-6.87 (m, 1H), 5.14-4.38 (m, 2H), 4.25-3.80 (m, 2H), 3.41 (s, 2H), 3.24 (s, 3H), 2.83-2.59 (m, 2H), 0.84-0.67 (m, 4H).

Example 424

N-(2,2-difluorocyclobutyl)-5-(1H-indole-2-carbonyl)-4H,5H,6H,7H-[1,3]thiazolo[5,4-c]pyridin-2-amine

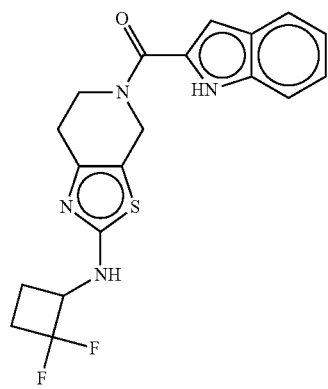

Rt (Method A) 3.28 mins, m/z 389 [M+H]+

1H NMR (400 MHz, DMSO-d6) δ 11.62 (s, 1H), 8.04 (d, J=8.3 Hz, 1H), 7.63 (d, J=8.1 Hz, 1H), 7.43 (d, J=8.2 Hz, 1H), 7.20 (t, J=7.6 Hz, 1H), 7.06 (t, J=7.5 Hz, 1H), 6.93-6.80 (m, 1H), 5.05-4.53 (m, 3H), 4.19-3.85 (m, 2H), 2.79-2.60 (m, 2H), 2.41-2.26 (m, 2H), 2.26-2.12 (m, 1H), 1.73-1.49 (m, 1H).

Example 425

N-(3,3-difluoro-1-methylcyclobutyl)-5-(1H-indole-2-carbonyl)-4H,5H,6H,7H-[1,3]thiazolo[5,4-c]pyridin-2-amine

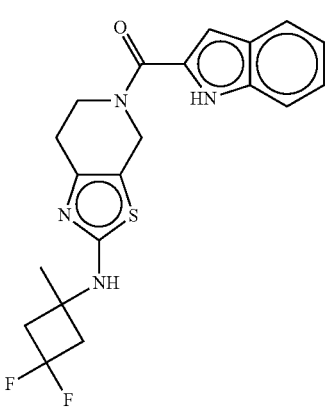

Rt (Method A) 3.5 mins, m/z 403 [M+H]+

1H NMR (400 MHz, DMSO-d6) δ 11.62 (s, 1H), 7.89 (s, 1H), 7.62 (d, J=8.1 Hz, 1H), 7.43 (d, J=8.1 Hz, 1H), 7.20 (t, J=7.6 Hz, 1H), 7.06 (t, J=7.5 Hz, 1H), 6.93-6.87 (m, 1H), 5.16-4.43 (m, 2H), 4.18-3.85 (m, 2H), 2.92 (q, J=13.6 Hz, 2H), 2.78-2.56 (m, 4H), 1.53 (s, 3H).

Example 426

5-(1H-indole-2-carbonyl)-N-[1-(trifluoromethyl)cyclobutyl]-4H,5H,6H,7H-[1,3]thiazolo[5,4-c]pyridin-2-amine

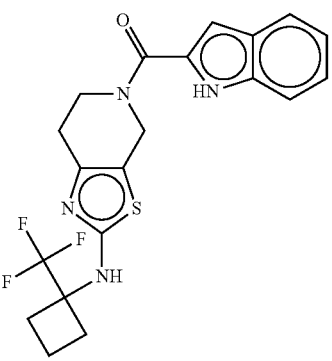

Rt (Method A) 3.58 mins, m/z 421 [M+H]+

1H NMR (400 MHz, DMSO-d6) δ 11.62 (s, 1H), 8.08 (s, 1H), 7.62 (d, J=8.0 Hz, 1H), 7.43 (d, J=8.2 Hz, 1H), 7.19 (t, J=7.7 Hz, 1H), 7.05 (t, J=7.4 Hz, 1H), 6.89 (s, 1H), 5.05-4.52 (m, 2H), 4.10-3.87 (m, 2H), 2.79-2.58 (m, 2H), 2.52-2.35 (m, 4H), 2.05-1.94 (m, 1H), 1.93-1.83 (m, 1H)—one signal (4H) coincides partially with DMSO signal.

Example 427—Intentionally Left Blank

Example 428

1-({[5-(1H-indole-2-carbonyl)-4H,5H,6H,7H-[1,3]thiazolo[5,4-c]pyridin-2-yl]amino}methyl)-N-methylcyclobutane-1-carboxamide

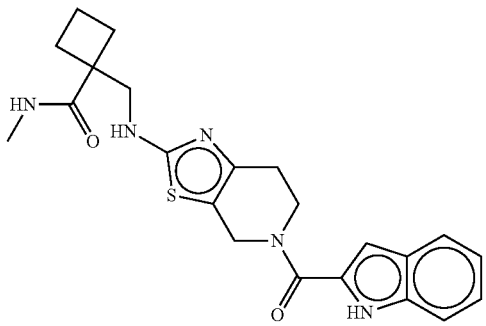

Rt (Method A) 2.93 mins, m/z 424 [M+H]+

1H NMR (400 MHz, DMSO-d6) δ 11.62 (s, 1H), 7.62 (d, J=8.1 Hz, 1H), 7.61-7.54 (m, 1H), 7.42 (d, J=8.3 Hz, 1H), 7.37 (t, J=5.8 Hz, 1H), 7.19 (t, J=7.6 Hz, 1H), 7.05 (t, J=7.5 Hz, 1H), 6.91-6.87 (m, 1H), 5.02-4.48 (m, 2H), 4.13-3.86 (m, 2H), 3.55 (d, J=6.0 Hz, 2H), 2.73-2.62 (m, 2H), 2.57 (d, J=4.5 Hz, 3H), 2.27-2.14 (m, 2H), 2.01-1.90 (m, 2H), 1.90-1.77 (m, 1H), 1.78-1.61 (m, 1H).

Example 429

N-cyclobutyl-5-(1H-indole-2-carbonyl)-4H,5H,6H,7H-[1,3]thiazolo[5,4-c]pyridin-2-amine

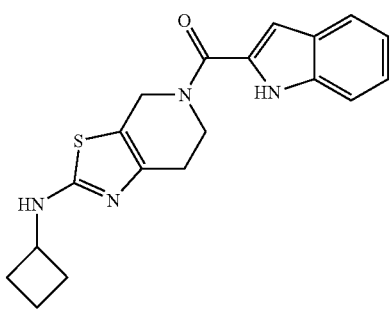

Rt (Method B) 2.63 mins, m/z 353 [M+H]+

1H NMR (400 MHz, DMSO-d6) δ 11.61 (s, 1H), 7.75 (d, J=7.4 Hz, 1H), 7.62 (d, J=7.9 Hz, 1H), 7.42 (d, J=8.3 Hz, 1H), 7.19 (t, J=7.6 Hz, 1H), 7.05 (t, J=7.5 Hz, 1H), 6.88 (s, 1H), 4.74 (m, 2H), 4.01 (m, J=15.5, 7.6 Hz, 3H), 2.66 (s, 2H), 2.35-2.10 (m, 2H), 1.95-1.75 (m, 2H), 1.75-1.53 (m, 2H).

Example 430

N-[3,3-difluoro-1-(1H-1,2,3-triazol-4-yl)cyclobutyl]-5-(1H-indole-2-carbonyl)-4H,5H,6H,7H-[1,3]thiazolo[5,4-c]pyridin-2-amine

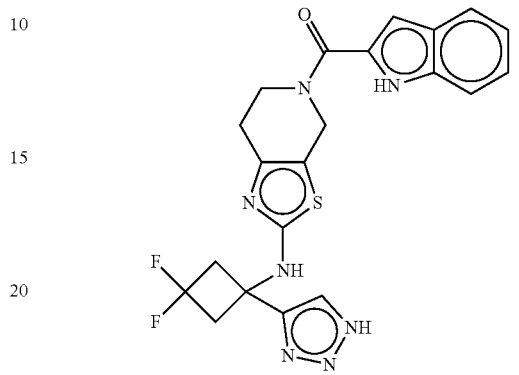

Rt (Method B) 2.95 mins, m/z 456 [M+H]+

1H NMR (400 MHz, DMSO-d6) δ 14.71 (s, 1H), 11.59 (s, 1H), 8.51 (s, 1H), 7.72 (s, 1H), 7.61 (d, J=8.1 Hz, 1H), 7.42 (d, J=8.2 Hz, 1H), 7.19 (t, J=7.6 Hz, 1H), 7.05 (t, J=7.5 Hz, 1H), 6.87 (d, J=2.1 Hz, 1H), 4.73 (s, 2H), 3.94 (s, 2H), 3.21 (t, J=12.3 Hz, 4H), 2.62 (s, 2H).

Example 431

N-{bicyclo[1.1.1]pentan-1-yl}-5-(1H-indole-2-carbonyl)-4H,5H,6H,7H-[1,3]thiazolo[5,4-c]pyridin-2-amine

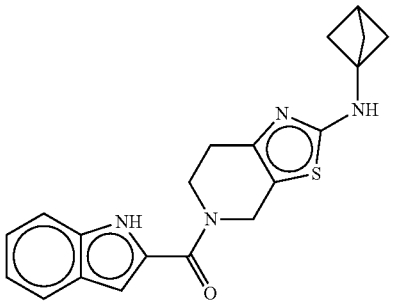

Rt (Method A) 3.42 mins, m/z 365 [M+H]+

1H NMR (400 MHz, DMSO-d6) δ 11.62 (s, 1H), 8.21 (s, 1H), 7.62 (d, J=8.0 Hz, 1H), 7.42 (d, J=8.2 Hz, 1H), 7.19 (t, J=7.7 Hz, 1H), 7.05 (t, J=7.5 Hz, 1H), 6.89 (s, 1H), 5.18-4.47 (m, 2H), 4.14-3.83 (m, 2H), 2.80-2.58 (m, 2H), 2.44 (s, 1H), 2.02 (s, 6H).

Example 432

5-(1H-indole-2-carbonyl)-N-{[1-(pyridin-2-yl)cyclobutyl]methyl}-4H,5H,6H,7H-[1,3]thiazolo[5,4-c]pyridin-2-amine

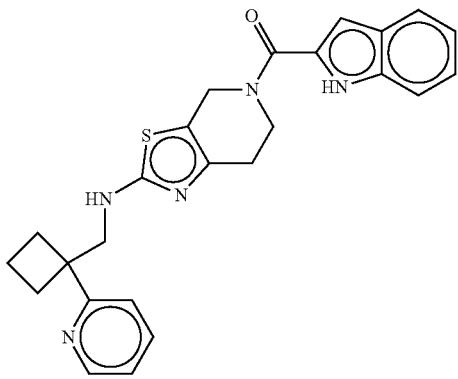

Rt (Method B) 2.48 mins, m/z 444 [M+H]+

1H NMR (400 MHz, DMSO-d6) δ 11.60 (s, 1H), 8.56-8.43 (m, 1H), 7.71 (m, 1H), 7.62 (d, J=8.0 Hz, 1H), 7.46-7.34 (m, 2H), 7.31 (d, J=7.9 Hz, 1H), 7.25-7.12 (m, 2H), 7.05 (t, J=7.6 Hz, 1H), 6.87 (d, J=2.1 Hz, 1H), 4.70 (m, 2H), 3.96 (m, 2H), 3.65 (d, J=5.8 Hz, 2H), 2.62 (m, 2H), 2.42-2.30 (m, 2H), 2.29-2.16 (m, 2H), 2.01 (m, 1H), 1.79 (m, 1H).

Example 433

N-{[1-(dimethylamino)cyclobutyl]methyl}-5-(1H-indole-2-carbonyl)-4H,5H,6H,7H-[1,3]thiazolo[5,4-c]pyridin-2-amine

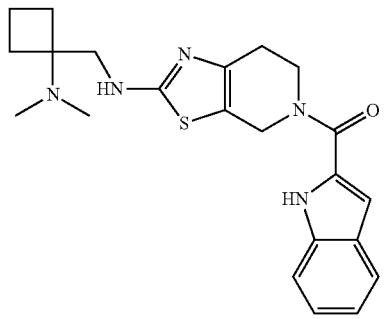 [SMILES: CN(C)C1(CNc2nc3c(s2)CN(C(=O)c2cc4ccccc4[nH]2)CC3)CCC1]

Rt (Method B) 2.31 mins, m/z 410 [M+H]+

1H NMR (400 MHz, DMSO-d6) δ 11.61 (s, 1H), 7.62 (d, J=8.0 Hz, 1H), 7.43 (d, J=8.2 Hz, 1H), 7.27 (t, J=5.6 Hz, 1H), 7.19 (m, J=8.3, 6.9, 1.1 Hz, 1H), 7.05 (t, J=7.5 Hz, 1H), 6.89 (s, 1H), 4.74 (m, 2H), 3.99 (m, 2H), 3.46 (d, J=5.6 Hz, 2H), 2.67 (m, 2H), 2.15 (s, 6H), 1.97 (m, 2H), 1.87-1.55 (m, 4H).

Example 434

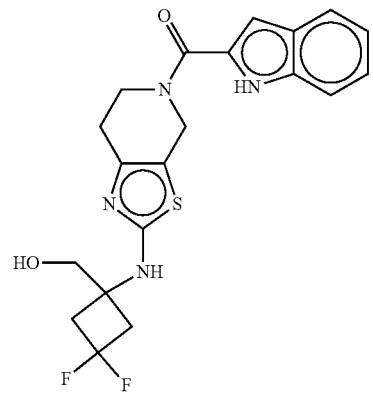

Rt (Method A) 3.17 mins, m/z 419 [M+H]+

1H NMR (400 MHz, DMSO-d6) δ 11.62 (s, 1H), 7.93 (s, 1H), 7.62 (d, J=8.0 Hz, 1H), 7.42 (d, J=8.2 Hz, 1H), 7.19 (t, J=7.5 Hz, 1H), 7.05 (t, J=7.6 Hz, 1H), 6.89 (s, 1H), 5.15 (t, J=5.6 Hz, 1H), 4.98-4.55 (m, 2H), 4.07-3.89 (m, 2H), 3.64 (d, J=5.4 Hz, 2H), 2.87-2.61 (m, 6H).

Example 435

3-{[5-(1H-indole-2-carbonyl)-4H,5H,6H,7H-[1,3]thiazolo[5,4-c]pyridin-2-yl]amino}bicyclo[1.1.1]pentane-1-carbonitrile

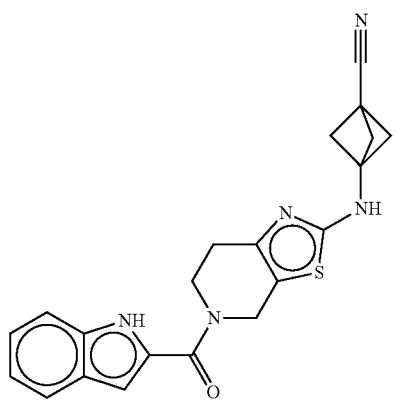

Rt (Method A) 3.27 mins, m/z 390 [M+H]+

1H NMR (400 MHz, DMSO-d6) δ 11.67-11.53 (m, 1H), 8.43 (s, 1H), 7.62 (d, J=8.0 Hz, 1H), 7.43 (d, J=8.3 Hz, 1H), 7.20 (t, J=7.7 Hz, 1H), 7.06 (t, J=7.5 Hz, 1H), 6.89 (d, J=2.1 Hz, 1H), 5.13-4.41 (m, 2H), 4.13-3.86 (m, 2H), 2.81-2.61 (m, 2H), 2.56-2.51 (m, 6H).

Example 436

N-(2-cyclopropyl-2,2-difluoroethyl)-5-(1H-indole-2-carbonyl)-4H,5H,6H,7H-[1,3]thiazolo[5,4-c]pyridin-2-amine

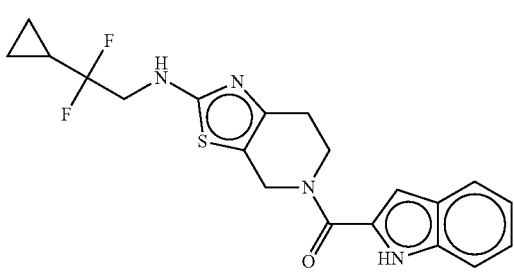

Rt (Method B) 3.12 mins, m/z 403 [M+H]+

1H NMR (400 MHz, DMSO-d6) δ 11.62 (s, 1H), 7.85 (t, J=6.4 Hz, 1H), 7.62 (d, J=8.0 Hz, 1H), 7.43 (d, J=8.2 Hz, 1H), 7.19 (t, J=7.5 Hz, 1H), 7.06 (t, J=7.4 Hz, 1H), 6.89 (d, J=1.9 Hz, 1H), 4.98-4.45 (m, 2H), 4.08-3.90 (m, 2H), 3.79 (td, J=14.3, 6.2 Hz, 2H), 2.76-2.60 (m, 2H), 1.41 (dt, J=13.3, 7.4 Hz, 1H), 0.61-0.53 (m, 4H).

Example 437

5-(5-fluoro-4-methyl-1H-indole-2-carbonyl)-4H,5H,6H,7H-[1,3]thiazolo[5,4-c]pyridin-2-amine

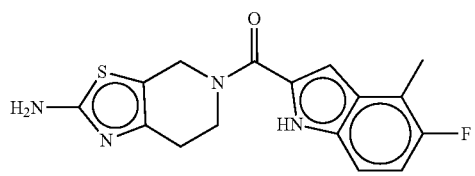

Rt (Method A) 3 mins, m/z 331 [M+H]+

1H NMR (400 MHz, DMSO-d6) δ 11.67 (d, J=2.2 Hz, 1H), 7.23 (dd, J=8.9, 4.2 Hz, 1H), 7.05-6.92 (m, 2H), 6.89-6.78 (m, 2H), 5.02-4.48 (m, 2H), 4.06-3.86 (m, 2H), 2.72-2.57 (m, 2H), 2.42 (d, J=1.9 Hz, 3H).

Example 438—Intentionally Left Blank

Example 439

N-[3,3-difluoro-1-(methoxymethyl)cyclobutyl]-5-(1H-indole-2-carbonyl)-4H,5H,6H,7H-[1,3]thiazolo[5,4-c]pyridin-2-amine

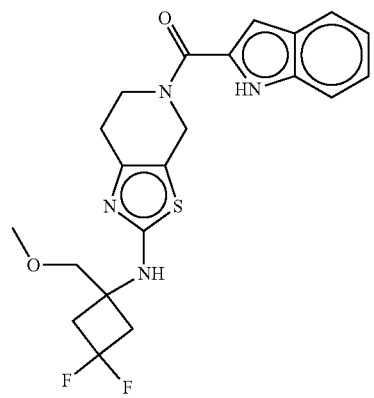

Rt (Method A) 3.47 mins, m/z 433 [M+H]+

1H NMR (400 MHz, DMSO-d6) δ 11.61 (s, 1H), 7.98 (s, 1H), 7.62 (d, J=7.9 Hz, 1H), 7.43 (d, J=8.3 Hz, 1H), 7.20 (t, J=7.6 Hz, 1H), 7.06 (t, J=7.5 Hz, 1H), 6.89 (d, J=2.0 Hz, 1H), 5.11-4.44 (m, 2H), 4.15-3.86 (m, 2H), 3.62 (s, 2H), 3.28 (s, 3H), 2.85-2.57 (m, 6H).

Example 440

3,3-difluoro-1-({[5-(1H-indole-2-carbonyl)-4H,5H,6H,7H-[1,3]thiazolo[5,4-c]pyridin-2-yl]amino}methyl)cyclobutan-1-ol

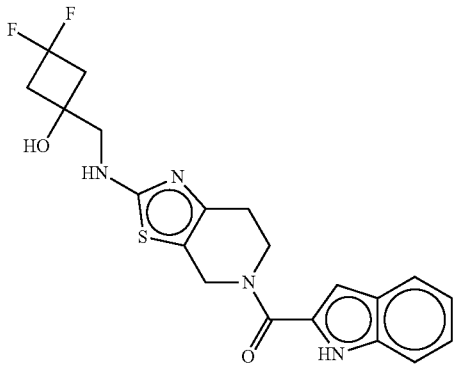

Rt (Method A) 3.16 mins, m/z 419 [M+H]+

1H NMR (400 MHz, DMSO-d6) δ 11.62 (s, 1H), 7.69-7.59 (m, 2H), 7.43 (d, J=8.2 Hz, 1H), 7.20 (t, J=7.6 Hz, 1H), 7.06 (t, J=7.5 Hz, 1H), 6.89 (d, J=2.0 Hz, 1H), 5.81 (s, 1H), 4.95-4.52 (m, 2H), 4.07-3.87 (m, 2H), 3.41 (d, J=5.9 Hz, 2H), 2.82-2.60 (m, 4H), 2.58-2.52 (m, 1H), 2.49-2.42 (m, 1H).

Example 441

N-[5-(6-chloro-5-fluoro-1H-indole-2-carbonyl)-4H,5H,6H,7H-[1,3]thiazolo[5,4-c]pyridin-2-yl]-1-methylpiperidine-4-carboxamide

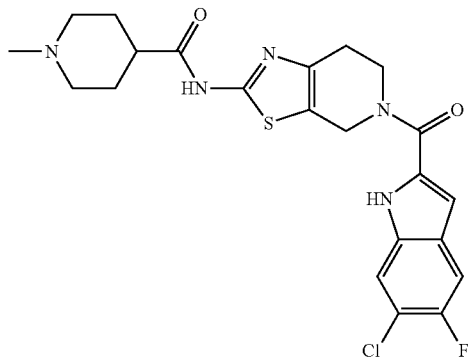 [SMILES: CN1CCC(C(=O)Nc2nc3c(s2)CN(C(=O)c2cc4cc(F)c(Cl)cc4[nH]2)CC3)CC1]

Rt (Method H) 1.01 mins, m/z 476/478 [M+H]+

1H NMR (400 MHz, DMSO-d6) δ 11.93 (m, 2H), 7.63 (d, J=10.0 Hz, 1H), 7.55 (d, J=6.4 Hz, 1H), 6.96 (s, 1H), 4.88 (m, 2H), 4.02 (m, 2H), 2.94-2.69 (m, 4H), 2.40 (m, 1H), 2.14 (s, 3H), 1.84 (m, 2H), 1.78-1.68 (m, 2H), 1.62 (m, 2H).

Example 442

N-[5-(6-fluoro-4-methyl-1H-indole-2-carbonyl)-4H,5H,6H,7H-[1,3]thiazolo[5,4-c]pyridin-2-yl]-1-methylpiperidine-4-carboxamide

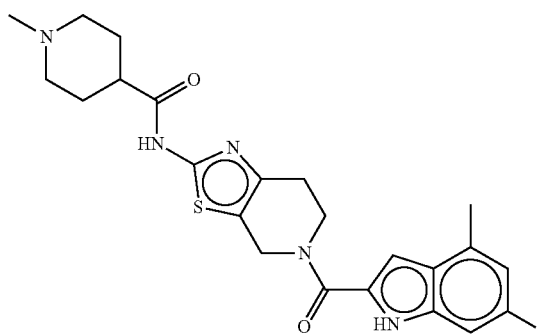

Rt (Method H) 0.97 mins, m/z 456 [M+H]+

1H NMR (400 MHz, DMSO-d6) δ 11.99 (s, 1H), 11.67 (d, J=2.1 Hz, 1H), 7.17-6.82 (m, 2H), 6.76 (dd, J=10.7, 2.3 Hz, 1H), 4.92 (m, 2H), 4.04 (m, 2H), 2.99-2.69 (m, 4H), 2.53 (s, 3H), 2.40 (m, 1H), 2.14 (s, 3H), 1.84 (m, 2H), 1.79-1.69 (m, 2H), 1.62 (m, 2H).

Example 443

N-[5-(4,6-difluoro-1H-indole-2-carbonyl)-4H,5H,6H,7H-[1,3]thiazolo[5,4-c]pyridin-2-yl]-1-methylpiperidine-4-carboxamide

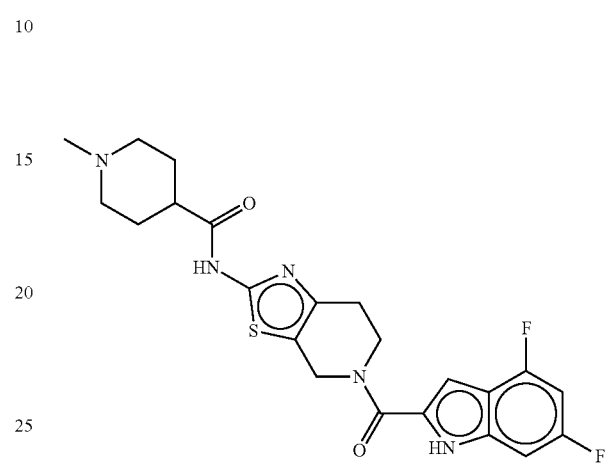

Rt (Method H) 0.96 mins, m/z 460 [M+H]+

1H NMR (400 MHz, DMSO-d6) δ 12.03 (s, 2H), 7.10-6.96 (m, 2H), 6.91 (dt, J=10.4, 2.1 Hz, 1H), 4.91 (m, 2H), 4.03 (m, 2H), 2.79 (m, 4H), 2.40 (m, 1H), 2.14 (s, 3H), 1.97-1.43 (m, 6H).

Example 444

(2S)-2-amino-3-{[5-(1H-indole-2-carbonyl)-4H,5H,6H,7H-[1,3]thiazolo[5,4-c]pyridin-2-yl]carbamoyl}propanoic acid

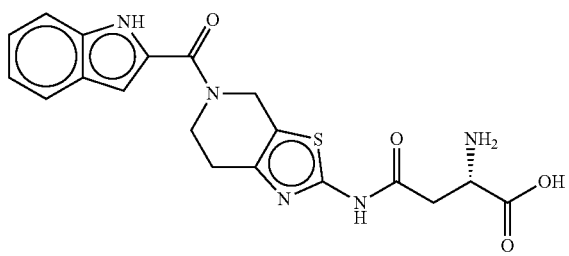

Rt (Method A) 0.85 mins, m/z 412 [M+H]+

1H NMR (400 MHz, DMSO-d6) δ 11.64 (d, J=2.1 Hz, 1H), 7.64 (d, J=8.0 Hz, 1H), 7.43 (d, J=8.2 Hz, 1H), 7.20 (t, J=7.5 Hz, 1H), 7.06 (t, J=7.5 Hz, 1H), 6.93 (d, J=1.8 Hz, 1H), 4.91 (s, 2H), 4.05 (s, 2H), 3.60 (t, J=6.5 Hz, 1H), 3.02 (dd, J=16.4, 6.8 Hz, 1H), 2.83 (s, 2H), 2.62 (dd, J=16.4, 6.3 Hz, 1H).

Example 445

(2S)-2-amino-4-{[5-(4-chloro-6-fluoro-1H-indole-2-carbonyl)-4H,5H,6H,7H-[1,3]thiazolo[5,4-c]pyridin-2-yl]carbamoyl}butanoic acid

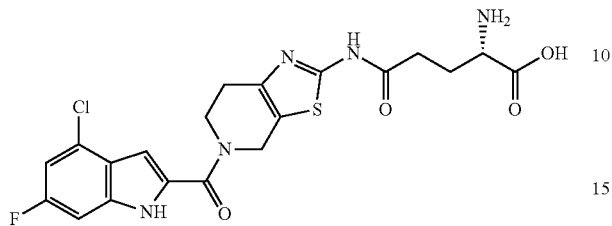

Rt (Method A) 2.73 mins, m/z 478/480 [M+H]+
1H NMR (400 MHz, DMSO-d6) δ 7.21-7.15 (m, 2H), 6.92 (s, 1H), 5.18-4.65 (m, 2H), 4.13-3.94 (m, 2H), 3.22-3.16 (m, 1H), 2.87-2.76 (m, 2H), 2.69-2.55 (m, 2H), 1.98-1.85 (m, 2H). Four signals, amide N—H, indole N—H, amine N—H2 and acid O—H (5H) are not observed.

Example 446

(2S)-2-amino-4-{[5-(4-chloro-1H-indole-2-carbonyl)-4H,5H,6H,7H-[1,3]thiazolo[5,4-c]pyridin-2-yl]carbamoyl}butanoic acid

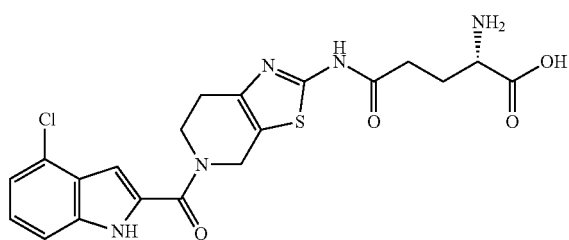 [SMILES: N[C@@H](CCC(=O)Nc1nc2c(s1)CN(C(=O)c1cc3c(Cl)cccc3[nH]1)CC2)C(=O)O]

Rt (Method A) 2.64 mins, m/z 460/462 [M+H]+
1H NMR (400 MHz, DMSO-d6) δ 12.43-11.67 (m, 1H), 7.41 (d, J=8.0 Hz, 1H), 7.20 (t, J=7.8 Hz, 1H), 7.15 (d, J=7.2 Hz, 1H), 6.90 (s, 1H), 5.29-4.57 (m, 2H), 4.11-3.97 (m, 2H), 3.21 (t, J=6.8 Hz, 1H), 2.89-2.74 (m, 2H), 2.69-2.52 (m, 2H), 2.01-1.83 (m, 2H). Three signals (4H) are not observed.

Example 447

(2S)-2-amino-4-{[5-(4,6-difluoro-1H-indole-2-carbonyl)-4H,5H,6H,7H-[1,3]thiazolo[5,4-c]pyridin-2-yl]carbamoyl}butanoic acid

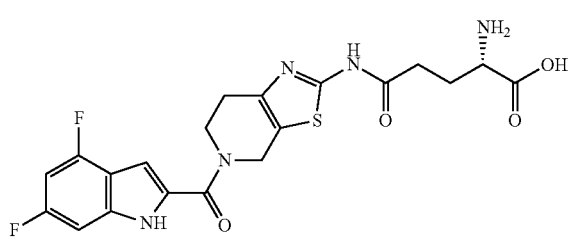 [SMILES: N[C@@H](CCC(=O)Nc1nc2c(s1)CN(C(=O)c1cc3c(F)cc(F)cc3[nH]1)CC2)C(=O)O]

Rt (Method A) 2.63 mins, m/z 462 [M+H]+ 1H NMR (400 MHz, DMSO-d6) δ 12.08 (s, 1H), 7.09-6.98 (m, 2H), 6.97-6.87 (m, 1H), 5.27-4.60 (m, 2H), 4.14-3.92 (m, 2H), 3.21 (t, J=6.6 Hz, 1H), 2.93-2.73 (m, 2H), 2.71-2.56 (m, 2H), 2.04-1.83 (m, 2H). Three signals, amide N—H, amine N—H2 and acid O—H (4H) are not observed.

Example 448

(2S)-2-amino-4-{[5-(4,6-difluoro-1H-indole-2-carbonyl)-4H,5H,6H,7H-[1,3]thiazolo[5,4-c]pyridin-2-yl]carbamoyl}butanoic acid

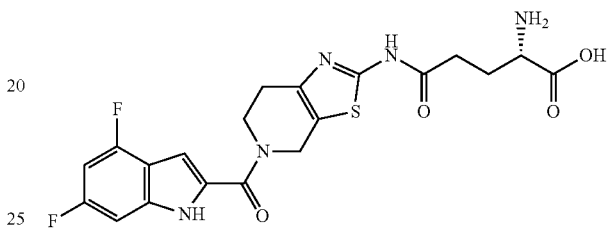

Rt (Method A) 2.77 mins, m/z 472 [M+H]+
1H NMR (400 MHz, DMSO-d6) δ 11.68 (s, 1H), 7.01 (s, 1H), 6.97 (dd, J=9.7, 1.9 Hz, 1H), 6.77 (dd, J=10.8, 2.2 Hz, 1H), 5.16-4.70 (m, 2H), 4.16-3.93 (m, 2H), 3.19 (t, J=6.9 Hz, 1H), 2.91 (q, J=7.6 Hz, 2H), 2.87-2.76 (m, 2H), 2.69-2.55 (m, 2H), 2.02-1.84 (m, 2H), 1.28 (t, J=7.5 Hz, 3H). Three signals, amide N—H, amine N—H2 and acid O—H (4H) are not observed.

Example 449

1-({[5-(4-chloro-6-fluoro-1H-indole-2-carbonyl)-4H,5H,6H,7H-[1,3]thiazolo[5,4-c]pyridin-2-yl]amino}methyl)-3,3-difluorocyclobutan-1-ol

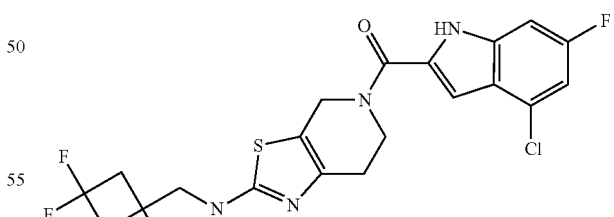

Rt (Method A) 3.44 mins, m/z 471/473 [M+H]+
1H NMR (400 MHz, DMSO-d6) δ 12.11 (s, 1H), 7.65 (s, 1H), 7.22-7.13 (m, 2H), 6.89 (s, 1H), 5.80 (s, 1H), 5.04-4.46 (m, 2H), 4.07-3.87 (m, 2H), 3.43-3.36 (m, 4H), 2.84-2.58 (m, 4H).

Example 450 tert-butyl 1-({[5-(1H-indole-2-carbonyl)-4H,5H,6H,7H-[1,3]thiazolo[5,4-c]pyridin-2-yl]amino}methyl)cyclobutane-1-carboxylate

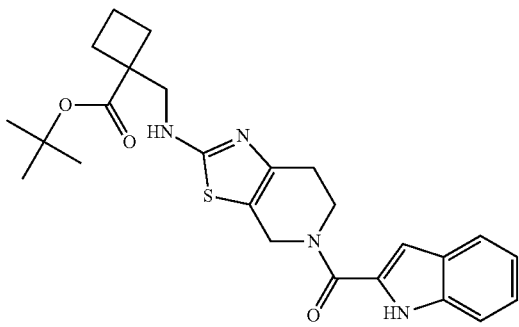 [SMILES: CC(C)(C)OC(=O)C1(CNc2nc3c(s2)CN(C(=O)c2cc4ccccc4[nH]2)CC3)CCC1]

Rt (Method A) 3.68 mins, z 467 [M+H]+

1H NMR (400 MHz, DMSO-d6) δ 11.63 (s, 1H), 7.62 (d, J=8.0 Hz, 1H), 7.50 (t, J=5.9 Hz, 1H), 7.42 (d, J=8.2 Hz, 1H), 7.19 (t, J=7.6 Hz, 1H), 7.05 (t, J=7.5 Hz, 1H), 6.91-6.86 (m, 1H), 5.29-4.22 (m, 2H), 4.11-3.88 (m, 2H), 3.60 (d, J=5.9 Hz, 2H), 2.74-2.57 (m, 2H), 2.28-2.17 (m, 2H), 2.03-1.72 (m, 4H), 1.37 (s, 9H).

Example 451

N-[(furan-2-yl)methyl]-5-(1H-indole-2-carbonyl)-4H,5H,6H,7H-[1,3]thiazolo[5,4-c]pyridin-2-amine

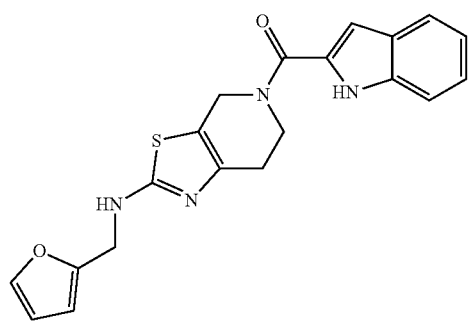 [SMILES: O=C(c1cc2ccccc2[nH]1)N1CCc2nc(NCc3ccco3)sc2C1]

Rt (Method H) 1.17 mins, m/z 379 [M+H]+

1H NMR (400 MHz, DMSO-d6) δ 11.63 (s, 1H), 7.90 (t, J=5.7 Hz, 1H), 7.62 (d, J=7.9 Hz, 1H), 7.59 (d, J=1.8 Hz, 1H), 7.42 (d, J=8.2 Hz, 1H), 7.23-7.15 (m, 1H), 7.09-7.02 (m, 1H), 6.89 (d, J=2.0 Hz, 1H), 6.39 (dd, J=3.2, 1.9 Hz, 1H), 6.29 (d, J=3.3 Hz, 1H), 5.03-4.50 (m, 2H), 4.40 (d, J=5.6 Hz, 2H), 4.04-3.93 (m, 2H), 2.76-2.63 (m, 2H).

Example 452

N-benzyl-5-(1H-indole-2-carbonyl)-4H,5H,6H,7H-[1,3]thiazolo[5,4-c]pyridin-2-amine

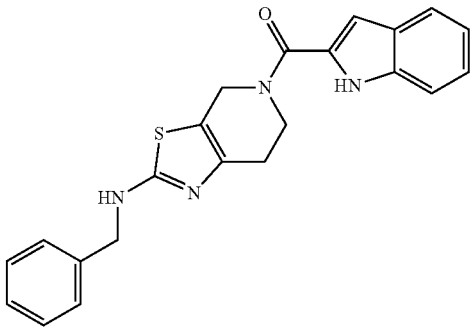 [SMILES: O=C(c1cc2ccccc2[nH]1)N1CCc2nc(NCc3ccccc3)sc2C1]

Rt (Method H) 1.23 mins, m/z 389 [M+H]+

1H NMR (400 MHz, DMSO-d6) δ 11.62 (s, 1H), 8.01 (t, J=5.9 Hz, 1H), 7.62 (d, J=8.0 Hz, 1H), 7.42 (d, J=8.2 Hz, 1H), 7.36-7.28 (m, 4H), 7.28-7.15 (m, 2H), 7.05 (t, J=7.5 Hz, 1H), 6.88 (d, J=2.0 Hz, 1H), 5.01-4.52 (m, 2H), 4.42 (d, J=5.9 Hz, 2H), 4.04-3.91 (m, 2H), 2.72-2.60 (m, 2H).

Example 453

N-{1-[(difluoromethoxy)methyl]cyclopropyl}-5-(1H-indole-2-carbonyl)-4H,5H,6H,7H-[1,3]thiazolo[5,4-c]pyridin-2-amine

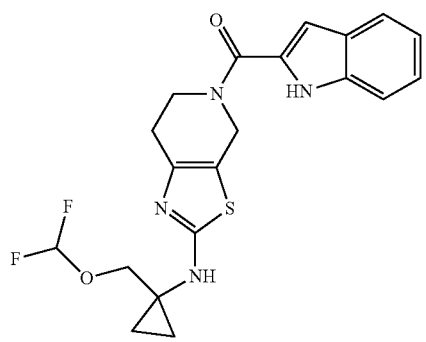 [SMILES: O=C(c1cc2ccccc2[nH]1)N1CCc2nc(NC3(COC(F)F)CC3)sc2C1]

Rt (Method H) 1.19 mins, m/z 419 [M+H]+

1H NMR (400 MHz, DMSO-d6) δ 11.65-11.60 (m, 1H), 8.02 (s, 1H), 7.63 (d, J=7.9 Hz, 1H), 7.43 (d, J=8.2 Hz, 1H), 7.20 (ddd, J=8.3, 7.0, 1.2 Hz, 1H), 7.09-7.02 (m, 1H), 6.89 (d, J=2.0 Hz, 1H), 6.66 (t, J=76.2 Hz, 1H), 5.10-4.47 (m, 2H), 4.04-3.95 (m, 2H), 3.95-3.90 (m, 2H), 2.74-2.65 (m, 2H), 0.90-0.77 (m, 4H).

Example 454

1-({[5-(5-fluoro-4-methyl-1H-indole-2-carbonyl)-4H,5H,6H,7H-[1,3]thiazolo[5,4-c]pyridin-2-yl]amino}methyl)cyclobutan-1-ol

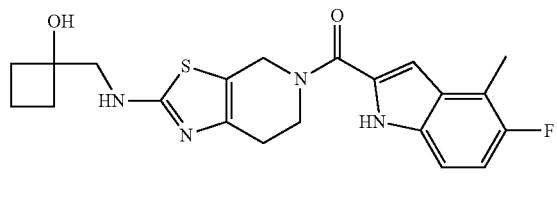 [SMILES: Cc1c(F)ccc2[nH]c(C(=O)N3CCc4nc(NCC5(O)CCC5)sc4C3)cc12]

Rt (Method B) 2.69 mins, m/z 415 [M+H]+

1H NMR (400 MHz, DMSO-d6) δ 11.68 (d, J=2.2 Hz, 1H), 7.44 (t, J=5.5 Hz, 1H), 7.23 (dd, J=8.9, 4.2 Hz, 1H), 7.01 (dd, J=10.2, 8.8 Hz, 1H), 6.97-6.93 (m, 1H), 5.28 (s, 1H), 5.07-4.39 (m, 2H), 4.02-3.93 (m, 2H), 3.40-3.34 (m, 2H), 2.76-2.58 (m, 2H), 2.46-2.38 (m, 3H), 2.05-1.85 (m, 4H), 1.68-1.57 (m, 1H), 1.51-1.40 (m, 1H).

Example 455

Ammonium 1-({[5-(1H-indole-2-carbonyl)-4H,5H,6H,7H-[1,3]thiazolo[5,4-c]pyridin-2-yl]amino}methyl)cyclobutane-1-carboxylate

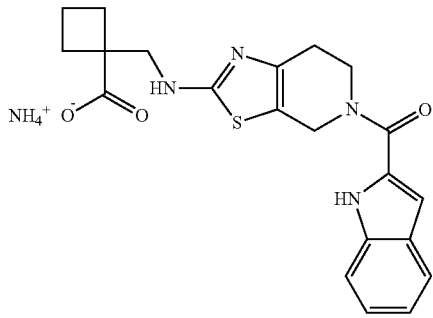 [SMILES: [NH4+] ; O=C(c1cc2ccccc2[nH]1)N1CCc2nc(NCC3(C(=O)O)CCC3)sc2C1]

Rt (Method A) 2.49 mins, m/z 411 [M+H]+

1H NMR (400 MHz, DMSO-d6) δ 11.63 (s, 1H), 7.62 (d, J=8.0 Hz, 1H), 7.58-7.47 (m, 1H), 7.42 (d, J=8.3 Hz, 1H), 7.23-7.16 (m, 1H), 7.09-7.02 (m, 1H), 6.91-6.87 (m, 1H), 5.04-4.42 (m, 2H), 4.12-3.85 (m, 2H), 3.62-3.49 (m, 2H), 2.75-2.60 (m, 2H), 2.31-2.18 (m, 2H), 2.02-1.74 (m, 4H), one signal (4H) coincides with water signal.

Example 456

1-({[5-(1H-indole-2-carbonyl)-4H,5H,6H,7H-[1,3]thiazolo[5,4-c]pyridin-2-yl]amino}methyl)cyclobutane-1-carboxamide

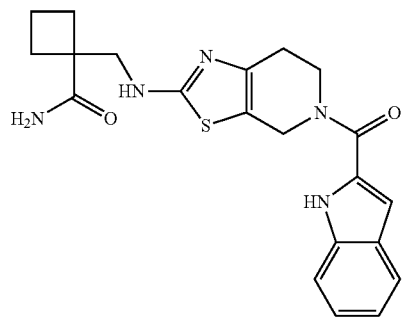 [SMILES: NC(=O)C1(CNc2nc3c(s2)CN(C(=O)c2cc4ccccc4[nH]2)CC3)CCC1]

Rt (Method A) 2.88 mins, m/z 410 [M+H]+

1H NMR (400 MHz, DMSO-d6) δ 11.61 (s, 1H), 7.62 (d, J=7.8 Hz, 1H), 7.42 (d, J=8.2 Hz, 1H), 7.36 (t, J=5.3 Hz, 1H), 7.23-7.12 (m, 2H), 7.05 (t, J=7.5 Hz, 1H), 6.91-6.84 (m, 2H), 4.98-4.44 (m, 2H), 4.11-3.89 (m, 2H), 3.56 (d, J=5.7 Hz, 2H), 2.70-2.62 (m, 2H), 2.27-2.17 (m, 2H), 1.99-1.64 (m, 4H).

Selected compounds of the invention were assayed in capsid assembly and HBV replication assays, as described below and a representative group of these active compounds is shown in Table 1.

Biochemical Capsid Assembly Assay

The screening for assembly effector activity was done based on a fluorescence quenching assay published by Zlotnick et al. (2007). The C-terminal truncated core protein containing 149 amino acids of the N-terminal assembly domain was fused to a unique cysteine residue at position 150 and was expressed in E. coli using the pET expression system (Merck Chemicals, Darmstadt). Purification of core dimer protein was performed using a sequence of size exclusion chromatography steps. In brief, the cell pellet from 1 L BL21 (DE3) Rosetta2 culture expressing the coding sequence of core protein cloned NdeI/XhoI into expression plasmid pET21b was treated for 1 h on ice with a native lysis buffer (Qproteome Bacterial Protein Prep Kit; Qiagen, Hilden). After a centrifugation step the supernatant was precipitated during 2 h stirring on ice with 0.23 g/ml of solid ammonium sulfate. Following further centrifugation the resulting pellet was resolved in buffer A (100 mM Tris, pH 7.5; 100 mM NaCl; 2 mM DTT) and was subsequently loaded onto a buffer A equilibrated CaptoCore 700 column (GE HealthCare, Frankfurt). The column flow through containing the assembled HBV capsid was dialyzed against buffer N (50 mM NaHCO$_3$ pH 9.6; 5 mM DTT) before urea was added to a final concentration of 3M to dissociate the capsid into core dimers for 1.5 h on ice. The protein solution was then loaded onto a 1 L Sephacryl S300 column. After elution with buffer N core dimer containing fractions were identified by SDS-PAGE and subsequently pooled and dialyzed against 50 mM HEPES pH 7.5; 5 mM DTT. To improve the assembly capacity of the purified core dimers a second round of assembly and disassembly starting with the addition of 5 M NaCl and including the size exclusion chromatography steps described above was performed. From the last chromatography step core dimer containing fractions were pooled and stored in aliquots at concentrations between 1.5 to 2.0 mg/ml at −80° C.

Immediately before labelling the core protein was reduced by adding freshly prepared DTT in a final concentration of 20 mM. After 40 min incubation on ice storage buffer and DTT was removed using a Sephadex G-25 column (GE HealthCare, Frankfurt) and 50 mM HEPES, pH 7.5. For labelling 1.6 mg/ml core protein was incubated at 4° C. and darkness overnight with BODIPY-FL maleimide (Invitrogen, Karlsruhe) in a final concentration of 1 mM. After labelling the free dye was removed by an additional desalting step using a Sephadex G-25 column. Labelled core dimers were stored in aliquots at 4° C. In the dimeric state the fluorescence signal of the labelled core protein is high and is quenched during the assembly of the core dimers to high molecular capsid structures. The screening assay was performed in black 384 well microtiter plates in a total assay volume of 10 µl using 50 mM HEPES pH 7.5 and 1.0 to 2.0 µM labelled core protein. Each screening compound was added in 8 different concentrations using a 0.5 log-unit serial dilution starting at a final concentration of 100 µM, 31.6 µM or 10 µM. In any case the DMSO concentration over the entire microtiter plate was 0.5%. The assembly reaction was started by the injection of NaCl to a final concentration of 300 µM which induces the assembly process to approximately 25% of the maximal quenched signal. 6 min after starting the reaction the fluorescence signal was measured using a Clariostar plate reader (BMG Labtech, Ortenberg) with an excitation of 477 nm and an emission of 525 nm. As 100% and 0% assembly control HEPES buffer containing 2.5 M and 0 M NaCl was used. Experiments were performed thrice in triplicates. $EC_{50}$ values were calculated by non-linear regression analysis using the Graph Pad Prism 6 software (GraphPad Software, La Jolla, USA).

Determination of HBV DNA from the Supernatants of HepAD38 Cells

The anti-HBV activity was analysed in the stable transfected cell line HepAD38, which has been described to secrete high levels of HBV virion particles (Ladner et al., 1997). In brief, HepAD38 cells were cultured at 37° C. at 5% $CO_2$ and 95% humidity in 200 µl maintenance medium, which was Dulbecco's modified Eagle's medium/Nutrient Mixture F-12 (Gibco, Karlsruhe), 10% fetal bovine serum (PAN Biotech Aidenbach) supplemented with 50 µg/ml penicillin/streptomycin (Gibco, Karlsruhe), 2 mM L-glutamine (PAN Biotech, Aidenbach), 400 µg/ml G418 (AppliChem, Darmstadt) and 0.3 µg/ml tetracycline. Cells were subcultured once a week in a 1:5 ratio, but were usually not passaged more than ten times. For the assay 60,000 cells were seeded in maintenance medium without any tetracycline into each well of a 96-well plate and treated with serial half-log dilutions of test compound. To minimize edge effects the outer 36 wells of the plate were not used but were filled with assay medium. On each assay plate six wells for the virus control (untreated HepAD38 cells) and six wells for the cell control (HepAD38 cells treated with 0.3 µg/ml tetracycline) were allocated, respectively. In addition, one plate set with reference inhibitors like BAY 41-4109, entecavir, and lamivudine instead of screening compounds were prepared in each experiment. In general, experiments were performed thrice in triplicates. At day 6 HBV DNA from 100 µl filtrated cell culture supernatant (AcroPrep Advance 96 Filter Plate, 0.45 µM Supor membran, PALL GmbH, Dreieich) was automatically purified on the MagNa Pure LC instrument using the MagNA Pure 96 DNA and Viral NA Small Volume Kit (Roche Diagnostics, Mannheim) according to the instructions of the manufacturer. EC50 values were calculated from relative copy numbers of HBV DNA. In brief, 5 µl of the 100 µl eluate containing HBV DNA were subjected to PCR LC480 Probes Master Kit (Roche) together with 1 µM antisense primer tgcagaggt-gaagcgaagtgcaca, 0.5 µM sense primer gacgtcctttgtt-tacgtcccgtc, 0.3 µM hybprobes acggggcgcacctctctttacgcgg-FL and LC640-ctcccgtctgtgccttctcatctgc-PH (TIBMolBiol, Berlin) to a final volume of 12.5 µl. The PCR was performed on the Light Cycler 480 real time system (Roche Diagnostics, Mannheim) using the following protocol: Pre-incubation for 1 min at 95° C., amplification: 40 cycles×(10 sec at 95° C., 50 sec at 60° C., 1 sec at 70° C.), cooling for 10 sec at 40° C. Viral load was quantitated against known standards using HBV plasmid DNA of pCH-9/3091 (Nassal et al., 1990, Cell 63: 1357-1363) and the LightCycler 480 SW 1.5 software (Roche Diagnostics, Mannheim) and $EC_{50}$ values were calculated using non-linear regression with GraphPad Prism 6 (GraphPad Software Inc., La Jolla, USA).

Cell Viability Assay

Using the AlamarBlue viability assay cytotoxicity was evaluated in HepAD38 cells in the presence of 0.3 µg/ml tetracycline, which blocks the expression of the HBV genome. Assay condition and plate layout were in analogy to the anti-HBV assay, however other controls were used. On each assay plate six wells containing untreated HepAD38 cells were used as the 100% viability control, and six wells filled with assay medium only were used as 0% viability control. In addition, a geometric concentration series of cycloheximide starting at 60 µM final assay concentration was used as positive control in each experiment. After six days incubation period Alamar Blue Presto cell viability reagent (ThermoFisher, Dreieich) was added in 1/11 dilution to each well of the assay plate. After an incubation for 30 to 45 min at 37° C. the fluorescence signal, which is proportional to the number of living cells, was read using a Tecan Spectrafluor Plus plate reader with an excitation filter 550 nm and emission filter 595 nm, respectively. Data were normalized into percentages of the untreated control (100% viability) and assay medium (0% viability) before CC50 values were calculated using non-linear regression and the GraphPad Prism 6.0 (GraphPad Software, La Jolla, USA). Mean $EC_{50}$ and $CC_{50}$ values were used to calculate the selectivity index ($SI=CC_{50}/EC_{50}$) for each test compound.

In Vivo Efficacy Models

HBV research and preclinical testing of antiviral agents are limited by the narrow species- and tissue-tropism of the virus, the paucity of infection models available and the restrictions imposed by the use of chimpanzees, the only animals fully susceptible to HBV infection. Alternative animal models are based on the use of HBV-related hepadnaviruses and various antiviral compounds have been tested in woodchuck hepatitis virus (WHV) infected woodchucks or in duck hepatitis B virus (DHBV) infected ducks or in woolly monkey HBV (WM-HBV) infected tupaia (overview in Dandri et al., 2017, Best Pract Res Clin Gastroenterol 31, 273-279). However, the use of surrogate viruses has several limitations. For example is the sequence homology between the most distantly related DHBV and HBV is only about 40% and that is why core protein assembly modifiers of the HAP family appeared inactive on DHBV and WHV but efficiently suppressed HBV (Campagna et al., 2013, J. Virol. 87, 6931-6942). Mice are not HBV permissive but major efforts have focused on the development of mouse models of HBV replication and infection, such as the generation of mice transgenic for the human HBV (HBV tg mice), the hydrodynamic injection (HDI) of HBV genomes in mice or the generation of mice having humanized livers and/or humanized immune systems and the intravenous injection of viral vectors based on adenoviruses containing HBV genomes (Ad-HBV) or the adenoassociated virus (AAV-HBV) into immune competent mice (overview in Dandri et al., 2017, Best Pract Res Clin Gastroenterol 31, 273-279). Using mice transgenic for the full HBV genome the ability of murine hepatocytes to produce infectious HBV virions could be demonstrated (Guidotti et al., 1995, J. Virol., 69: 6158-6169). Since transgenic mice are immunological tolerant to viral proteins and no liver injury was observed in HBV-producing mice, these studies demonstrated that HBV itself is not cytopathic. HBV transgenic mice have been employed to test the efficacy of several anti-HBV agents like the polymerase inhibitors and core protein assembly modifiers (Weber et al., 2002, Antiviral Research 54 69-78; Julander et al., 2003, Antivir. Res., 59: 155-161), thus proving that HBV transgenic mice are well suitable for many type of preclinical antiviral testing in vivo.

As described in Paulsen et al., 2015, PLOSone, 10: e0144383 HBV-transgenic mice (Tg [HBV1.3 fsX-3'5']) carrying a frameshift mutation (GC) at position 2916/2917 could be used to demonstrate antiviral activity of core protein assembly modifiers in vivo. In brief, The HBV-transgenic mice were checked for HBV-specific DNA in the serum by qPCR prior to the experiments (see section "Determination of HBV DNA from the supernatants of HepAD38 cells"). Each treatment group consisted of five male and five female animals approximately 10 weeks age with a titer of above $3 \times 10^6$ virions per ml serum. Compounds were formulated as a suspension in a suitable vehicle such as 2% DMSO/98% tylose (0.5% Methylcellulose/99.5% PBS) or 50% PEG400 and administered per os to the animals one to three times/day for a 10 day period. The vehicle served as negative control, whereas 1 µg/kg entecavir in a suitable vehicle was the positive control. Blood was obtained by retro bulbar blood sampling using an Isoflurane Vaporizer. For collection of terminal heart puncture six hours after the last treatment blood or organs, mice were anaesthetized with isoflurane and subsequently sacrificed by $CO_2$ exposure. Retro bulbar (100-150 µl) and heart puncture (400-500 µl) blood samples were collected into a Microvette 300 LH or Microvette 500 LH, respectively, followed by separation of plasma via centrifugation (10 min, 2000 g, 4° C.). Liver tissue was taken and snap frozen in liquid N2. All samples were stored at −80° C. until further use. Viral DNA was extracted from 50 µl plasma or 25 mg liver tissue and eluted in 50 µl AE buffer (plasma) using the DNeasy 96 Blood & Tissue Kit (Qiagen, Hilden) or 320 µl AE buffer (liver tissue) using the DNeasy Tissue Kit (Qiagen, Hilden) according to the manufacturer's instructions. Eluted viral DNA was subjected to qPCR using the LightCycler 480 Probes Master PCR kit (Roche, Mannheim) according to the manufacturer's instructions to determine the HBV copy number. HBV specific primers used included the forward primer 5'-CTG TAC CAA ACC TTC GGA CGG-3', the reverse primer 5'-AGG AGA AAC GGG CTG AGG C-3' and the FAM labelled probe FAM-CCA TCA TCC TGG GCT TTC GGA AAA TT-BBQ. One PCR reaction sample with a total volume of 20 µl contained 5 µl DNA eluate and 15 µl master mix (comprising 0.3 µM of the forward primer, 0.3 µM of the reverse primer, 0.15 µM of the FAM labelled probe). qPCR was carried out on the Roche LightCycler1480 using the following protocol: Pre-incubation for 1 min at 95° C., amplification: (10 sec at 95° C., 50 sec at 60° C., 1 sec at 70° C.)×45 cycles, cooling for 10 sec at 40° C. Standard curves were generated as described above. All samples were tested in duplicate. The detection limit of the assay is ~50 HBV DNA copies (using standards ranging from $250\text{-}2.5 \times 10^7$ copy numbers). Results are expressed as HBV DNA copies/10 µl plasma or HBV DNA copies/100 ng total liver DNA (normalized to negative control).

It has been shown in multiple studies that not only transgenic mice are a suitable model to proof the antiviral activity of new chemical entities in vivo the use of hydrodynamic injection of HBV genomes in mice as well as the use of immune deficient human liver chimeric mice infected with HBV positive patient serum have also frequently used to profile drugs targeting HBV (Li et al., 2016, Hepat. Mon. 16: e34420; Qiu et al., 2016, J. Med. Chem. 59: 7651-7666; Lutgehetmann et al., 2011, Gastroenterology, 140: 2074-2083). In addition chronic HBV infection has also been successfully established in immunecompetent mice by inoculating low doses of adenovirus-(Huang et al., 2012, Gastroenterology 142: 1447-1450) or adeno-associated virus (AAV) vectors containing the HBV genome (Dion et al., 2013, J Virol. 87: 5554-5563). This models could also be used to demonstrate the in vivo antiviral activity of novel anti-HBV agents.

TABLE 1

Biochemical and antiviral activities

| Example | $CC_{50}$ (µM) | Cell Activity | Assembly Activity |
|---|---|---|---|
| Example 1 | >100 | ++ | C |
| Example 2 | >32 | +++ | A |
| Example 3 | >100 | +++ | A |
| Example 4 | >100 | +++ | A |
| Example 5 | >32 | +++ | B |
| Example 6 | >32 | +++ | C |
| Example 7 | 92.0 | +++ | A |
| Example 8 | >100 | +++ | A |
| Example 9 | >100 | ++ | B |
| Example 10 | >100 | ++ | C |
| Example 11 | NT | NT | NT |
| Example 12 | 68.0 | +++ | A |
| Example 13 | >10 | ++ | B |
| Example 14 | >10 | ++ | C |
| Example 15 | >10 | ++ | B |
| Example 16 | NT | NT | NT |
| Example 17 | >10 | ++ | C |
| Example 18 | >10 | ++ | C |
| Example 19 | >10 | +++ | A |
| Example 20 | >32 | +++ | A |
| Example 21 | | Example not included | |
| Example 22 | >100 | +++ | C |
| Example 23 | >32 | ++ | B |
| Example 24 | >100 | ++ | C |
| Example 25 | >100 | + | C |
| Example 26 | 66.0 | +++ | B |
| Example 27 | >32 | +++ | A |
| Example 28 | >100 | +++ | A |
| Example 29 | | Example not included | |
| Example 30 | | Example not included | |
| Example 31 | >32 | ++ | B |
| Example 32 | >100 | + | C |
| Example 33 | >32 | +++ | A |
| Example 34 | >32 | +++ | A |
| Example 35 | >32 | +++ | B |
| Example 36 | >100 | ++ | B |
| Example 37 | >32 | +++ | C |
| Example 38 | 92.0 | +++ | A |
| Example 39 | >100 | +++ | A |
| Example 40 | >32 | ++ | B |
| Example 41 | >32 | ++ | C |
| Example 42 | >32 | +++ | A |
| Example 43 | >100 | +++ | A |
| Example 44 | >100 | +++ | A |
| Example 45 | >100 | +++ | A |
| Example 46 | 99.0 | +++ | A |
| Example 47 | >100 | +++ | A |

TABLE 1-continued

Biochemical and antiviral activities

| Example | CC$_{50}$ (μM) | Cell Activity | Assembly Activity |
|---|---|---|---|
| Example 48 | >100 | +++ | A |
| Example 49 | >100 | +++ | A |
| Example 50 | | Example not included | |
| Example 51 | | Example not included | |
| Example 52 | | Example not included | |
| Example 53 | | Example not included | |
| Example 54 | | Example not included | |
| Example 55 | | Example not included | |
| Example 56 | | Example not included | |
| Example 57 | | Example not included | |
| Example 58 | >32 | ++ | B |
| Example 59 | >32 | +++ | A |
| Example 60 | 60.0 | +++ | A |
| Example 61 | >100 | +++ | B |
| Example 62 | >32 | +++ | B |
| Example 63 | >32 | +++ | A |
| Example 64 | 86.0 | +++ | A |
| Example 65 | | Example not included | |
| Example 66 | >100 | +++ | A |
| Example 67 | >100 | +++ | A |
| Example 68 | >100 | +++ | A |
| Example 69 | >100 | +++ | A |
| Example 70 | >100 | +++ | A |
| Example 71 | 82.0 | +++ | A |
| Example 72 | >100 | +++ | A |
| Example 73 | >100 | +++ | A |
| Example 74 | >32 | ++ | C |
| Example 75 | 10.0 | +++ | A |
| Example 76 | >32 | +++ | A |
| Example 77 | >100 | +++ | A |
| Example 78 | >100 | +++ | A |
| Example 79 | >100 | ++ | C |
| Example 80 | >100 | +++ | A |
| Example 81 | >100 | +++ | A |
| Example 82 | >100 | ++ | B |
| Example 83 | >100 | ++ | A |
| Example 84 | >100 | +++ | A |
| Example 85 | >100 | +++ | A |
| Example 86 | >100 | +++ | A |
| Example 87 | >100 | +++ | A |
| Example 88 | >100 | ++ | C |
| Example 89 | >32 | +++ | A |
| Example 90 | >100 | +++ | A |
| Example 91 | >100 | +++ | A |
| Example 92 | >100 | +++ | A |
| Example 93 | >32 | + | C |
| Example 94 | NT | NT | NT |
| Example 95 | >100 | +++ | A |
| Example 96 | 95.0 | +++ | A |
| Example 97 | 100.0 | +++ | A |
| Example 98 | 78.0 | + | C |
| Example 99 | >100 | +++ | A |
| Example 100 | >32 | ++ | C |
| Example 101 | >32 | +++ | A |
| Example 102 | >100 | ++ | B |
| Example 103 | >32 | +++ | B |
| Example 104 | >32 | ++ | B |
| Example 105 | >32 | +++ | A |
| Example 106 | 98.0 | +++ | A |
| Example 107 | >100 | +++ | A |
| Example 108 | | Example not included | |
| Example 109 | >100 | + | C |
| Example 110 | >32 | ++ | C |
| Example 111 | >100 | +++ | A |
| Example 112 | >32 | +++ | A |
| Example 113 | >32 | +++ | A |
| Example 114 | >32 | +++ | B |
| Example 115 | >32 | +++ | A |
| Example 116 | 88.0 | +++ | B |
| Example 117 | >32 | ++ | C |
| Example 118 | >100 | +++ | C |
| Example 119 | 70.0 | +++ | A |
| Example 120 | 86.0 | +++ | A |
| Example 121 | 57.0 | +++ | A |
| Example 122 | 62.0 | +++ | A |
| Example 123 | >32 | +++ | B |
| Example 124 | >32 | +++ | A |
| Example 125 | >32 | +++ | A |
| Example 126 | >32 | ++ | B |
| Example 127 | >100 | +++ | A |
| Example 128 | >100 | +++ | A |
| Example 129 | >100 | +++ | A |
| Example 130 | 96.0 | ++ | C |
| Example 131 | >100 | +++ | A |
| Example 132 | >100 | +++ | A |
| Example 133 | >100 | ++ | C |
| Example 134 | >100 | +++ | A |
| Example 135 | >100 | ++ | B |
| Example 136 | >100 | ++ | B |
| Example 137 | >100 | + | C |
| Example 138 | >100 | ++ | A |
| Example 139 | >100 | + | C |
| Example 140 | >100 | +++ | A |
| Example 141 | >100 | ++ | C |
| Example 142 | >100 | +++ | A |
| Example 143 | >100 | +++ | A |
| Example 144 | >32 | +++ | A |
| Example 145 | >100 | +++ | A |
| Example 146 | >100 | +++ | A |
| Example 147 | >100 | +++ | A |
| Example 148 | >100 | ++ | A |
| Example 149 | >100 | ++ | A |
| Example 150 | >100 | +++ | A |
| Example 151 | >100 | ++ | C |
| Example 152 | >100 | ++ | C |
| Example 153 | >100 | + | C |
| Example 154 | >100 | +++ | A |
| Example 155 | 82.0 | ++ | A |
| Example 156 | 93.0 | +++ | A |
| Example 157 | >100 | +++ | A |
| Example 158 | >100 | ++ | C |
| Example 159 | >100 | +++ | A |
| Example 160 | >100 | +++ | A |
| Example 161 | >100 | ++ | B |
| Example 162 | >100 | +++ | A |
| Example 163 | >100 | +++ | A |
| Example 164 | >100 | +++ | A |
| Example 165 | 75.0 | ++ | A |
| Example 166 | 99.0 | ++ | C |
| Example 167 | >100 | +++ | A |
| Example 168 | 65.0 | +++ | A |
| Example 169 | >100 | +++ | A |
| Example 170 | >100 | +++ | A |
| Example 171 | >100 | +++ | A |
| Example 172 | 99.0 | +++ | A |
| Example 173 | >100 | ++ | A |
| Example 174 | 65.0 | ++ | A |
| Example 175 | >100 | +++ | A |
| Example 176 | 68.0 | ++ | B |
| Example 177 | >100 | + | C |
| Example 178 | >100 | +++ | A |
| Example 179 | 62.76 | ++ | B |
| Example 180 | >32 | +++ | A |
| Example 181 | >32 | ++ | A |
| Example 182 | >100 | ++ | C |
| Example 183 | >100 | + | C |
| Example 184 | >100 | +++ | A |
| Example 185 | >96 | + | C |
| Example 186 | 67.0 | + | C |
| Example 187 | >100 | +++ | A |
| Example 188 | >100 | ++ | B |
| Example 189 | >100 | ++ | B |
| Example 190 | >100 | +++ | A |
| Example 191 | >89 | +++ | B |
| Example 192 | 100.0 | +++ | A |
| Example 193 | >99 | +++ | A |
| Example 194 | >100 | + | C |
| Example 195 | 99.0 | ++ | B |
| Example 196 | >100 | ++ | A |
| Example 197 | >100 | +++ | A |
| Example 199 | 85.0 | +++ | A |
| Example 198 | | Example not included | |

TABLE 1-continued

Biochemical and antiviral activities

| Example | CC$_{50}$ (μM) | Cell Activity | Assembly Activity |
|---|---|---|---|
| Example 200 | >100 | ++ | A |
| Example 201 | >100 | ++ | C |
| Example 202 | >100 | ++ | B |
| Example 203 | >100 | + | C |
| Example 204 | >32 | ++ | C |
| Example 205 | >32 | +++ | B |
| Example 206 | >100 | +++ | A |
| Example 207 | >100 | + | NT |
| Example 208 | >100 | +++ | A |
| Example 209 | >100 | ++ | B |
| Example 210 | 99.0 | +++ | A |
| Example 211 | 94.0 | +++ | A |
| Example 212 | | Example not included | |
| Example 213 | | Example not included | |
| Example 214 | | Example not included | |
| Example 215 | NT | NT | NT |
| Example 216 | >10 | +++ | B |
| Example 217 | >10 | +++ | A |
| Example 218 | >10 | +++ | B |
| Example 219 | >10 | +++ | B |
| Example 220 | >10 | ++ | C |
| Example 221 | >10 | +++ | A |
| Example 222 | >10 | +++ | A |
| Example 223 | >10 | +++ | A |
| Example 224 | >10 | +++ | A |
| Example 225 | >10 | +++ | A |
| Example 226 | >10 | +++ | A |
| Example 227 | >10 | +++ | C |
| Example 228 | NT | NT | NT |
| Example 229 | >32 | +++ | A |
| Example 230 | >32 | +++ | A |
| Example 231 | >10 | +++ | B |
| Example 232 | >32 | +++ | B |
| Example 233 | >32 | ++ | C |
| Example 234 | >32 | +++ | A |
| Example 235 | >32 | +++ | A |
| Example 236 | 85.0 | +++ | A |
| Example 237 | >32 | +++ | A |
| Example 238 | >32 | ++ | C |
| Example 239 | >32 | +++ | A |
| Example 240 | | Example not included | |
| Example 241 | >100 | +++ | A |
| Example 242 | >32 | +++ | B |
| Example 243 | NT | NT | NT |
| Example 244 | >10 | +++ | C |
| Example 245 | >100 | +++ | C |
| Example 246 | >10 | +++ | A |
| Example 247 | >100 | +++ | A |
| Example 248 | >10 | +++ | A |
| Example 249 | >32 | +++ | B |
| Example 250 | >32 | +++ | C |
| Example 251 | 56.0 | +++ | A |
| Example 252 | 63.0 | +++ | A |
| Example 253 | >32 | +++ | A |
| Example 254 | >32 | +++ | A |
| Example 255 | 61.0 | +++ | A |
| Example 256 | >32 | + | NT |
| Example 257 | >32 | + | NT |
| Example 258 | >100 | ++ | C |
| Example 259 | NT | NT | NT |
| Example 260 | >32 | ++ | A |
| Example 261 | >32 | +++ | C |
| Example 262 | >100 | +++ | C |
| Example 263 | >32 | +++ | B |
| Example 264 | >100 | +++ | B |
| Example 265 | >32 | +++ | C |
| Example 266 | >100 | +++ | A |
| Example 267 | >100 | +++ | B |
| Example 268 | >32 | +++ | B |
| Example 269 | >100 | +++ | A |
| Example 270 | 70.0 | +++ | A |
| Example 271 | >100 | +++ | A |
| Example 272 | >100 | +++ | A |
| Example 273 | >10 | +++ | B |
| Example 274 | >100 | +++ | A |
| Example 275 | >100 | +++ | B |
| Example 276 | NT | NT | NT |
| Example 277 | >100 | +++ | A |
| Example 278 | >100 | ++ | C |
| Example 279 | NT | NT | NT |
| Example 280 | NT | NT | NT |
| Example 281 | NT | NT | NT |
| Example 282 | >10 | +++ | B |
| Example 283 | >10 | +++ | B |
| Example 284 | >10 | +++ | A |
| Example 285 | >10 | +++ | A |
| Example 286 | >10 | +++ | A |
| Example 287 | >10 | +++ | NT |
| Example 288 | >10 | +++ | B |
| Example 289 | 10.0 | + | A |
| Example 290 | >10 | +++ | A |
| Example 291 | NT | NT | NT |
| Example 292 | NT | +++ | A |
| Example 293 | >10 | +++ | A |
| Example 294 | NT | +++ | A |
| Example 295 | NT | ++ | C |
| Example 296 | | Example not included | |
| Example 297 | >10 | +++ | A |
| Example 298 | >10 | +++ | A |
| Example 299 | >10 | +++ | A |
| Example 300 | >10 | +++ | A |
| Example 301 | >10 | +++ | A |
| Example 302 | >10 | +++ | A |
| Example 303 | >10 | +++ | A |
| Example 304 | >10 | +++ | NT |
| Example 305 | >10 | +++ | NT |
| Example 306 | >10 | +++ | NT |
| Example 307 | >10 | +++ | NT |
| Example 308 | >10 | +++ | NT |
| Example 309 | | Example not included | |
| Example 310 | >10 | +++ | B |
| Example 311 | >10 | +++ | A |
| Example 312 | >10 | +++ | A |
| Example 313 | >10 | +++ | A |
| Example 314 | >10 | +++ | A |
| Example 315 | >10 | +++ | B |
| Example 316 | >10 | +++ | A |
| Example 317 | >10 | ++ | NT |
| Example 318 | >10 | +++ | A |
| Example 319 | >10 | +++ | A |
| Example 320 | >10 | +++ | B |
| Example 321 | >10 | +++ | A |
| Example 322 | >10 | +++ | A |
| Example 323 | NT | NT | NT |
| Example 324 | NT | NT | NT |
| Example 325 | >10 | +++ | A |
| Example 326 | >10 | +++ | A |
| Example 327 | >10 | +++ | A |
| Example 328 | >10 | +++ | A |
| Example 329 | >10 | +++ | A |
| Example 330 | >10 | +++ | B |
| Example 331 | >10 | +++ | B |
| Example 332 | | Example not included | |
| Example 333 | >10 | +++ | A |
| Example 334 | >10 | +++ | A |
| Example 335 | >10 | +++ | A |
| Example 336 | >10 | +++ | B |
| Example 337 | >10 | +++ | NT |
| Example 338 | >10 | +++ | A |
| Example 339 | >10 | +++ | B |
| Example 340 | >10 | +++ | A |
| Example 341 | >10 | ++ | A |
| Example 342 | NT | NT | NT |
| Example 343 | >10 | +++ | B |
| Example 344 | >10 | +++ | B |
| Example 345 | >10 | ++ | NT |
| Example 346 | >10 | +++ | NT |
| Example 347 | >10 | +++ | NT |
| Example 348 | >10 | +++ | NT |
| Example 349 | >10 | +++ | NT |
| Example 350 | >10 | +++ | NT |
| Example 351 | >10 | +++ | NT |

TABLE 1-continued

Biochemical and antiviral activities

| Example | CC$_{50}$ (μM) | Cell Activity | Assembly Activity |
|---|---|---|---|
| Example 352 | | Example not included | |
| Example 353 | | Example not included | |
| Example 354 | >10 | +++ | A |
| Example 355 | >10 | +++ | A |
| Example 356 | >10 | +++ | A |
| Example 357 | >10 | +++ | A |
| Example 358 | >10 | +++ | A |
| Example 359 | >10 | +++ | A |
| Example 360 | >10 | +++ | A |
| Example 361 | >10 | +++ | NT |
| Example 362 | >10 | +++ | A |
| Example 363 | >10 | +++ | A |
| Example 364 | >10 | +++ | A |
| Example 365 | >10 | +++ | A |
| Example 366 | >10 | +++ | C |
| Example 367 | >10 | +++ | C |
| Example 368 | >10 | +++ | NT |
| Example 369 | >10 | +++ | NT |
| Example 370 | >10 | +++ | A |
| Example 371 | >10 | +++ | A |
| Example 372 | >10 | ++ | A |
| Example 373 | >10 | +++ | NT |
| Example 374 | >10 | +++ | NT |
| Example 375 | >10 | +++ | A |
| Example 376 | >10 | +++ | NT |
| Example 377 | >10 | +++ | NT |
| Example 378 | >10 | +++ | NT |
| Example 379 | >10 | +++ | NT |
| Example 380 | >10 | +++ | NT |
| Example 381 | >10 | +++ | NT |
| Example 382 | >10 | +++ | NT |
| Example 383 | >10 | ++ | NT |
| Example 384 | >10 | +++ | NT |
| Example 385 | >10 | +++ | NT |
| Example 386 | >10 | ++ | NT |
| Example 387 | >10 | +++ | NT |
| Example 388 | >10 | +++ | NT |
| Example 389 | >10 | ++ | A |
| Example 390 | >10 | + | A |
| Example 391 | >10 | +++ | A |
| Example 392 | >10 | +++ | A |
| Example 393 | >10 | ++ | B |
| Example 394 | >10 | +++ | A |
| Example 395 | >10 | +++ | A |
| Example 396 | >10 | +++ | A |
| Example 397 | >10 | +++ | A |
| Example 398 | >10 | +++ | NT |
| Example 399 | >10 | ++ | A |
| Example 400 | >10 | +++ | A |
| Example 401 | >10 | +++ | A |
| Example 402 | >10 | +++ | A |
| Example 403 | >10 | +++ | A |
| Example 404 | >10 | +++ | A |
| Example 405 | >10 | +++ | A |
| Example 406 | | Example not included | |
| Example 407 | >10 | +++ | A |
| Example 408 | >10 | +++ | A |
| Example 409 | >10 | +++ | A |
| Example 410 | >10 | +++ | A |
| Example 411 | >10 | +++ | A |
| Example 412 | >10 | +++ | A |
| Example 413 | >10 | +++ | A |
| Example 414 | >10 | +++ | A |
| Example 415 | | Example not included | |
| Example 416 | >10 | +++ | B |
| Example 417 | >10 | +++ | A |
| Example 418 | >10 | +++ | B |
| Example 419 | >10 | +++ | B |
| Example 420 | NT | NT | NT |
| Example 421 | NT | NT | NT |
| Example 422 | NT | NT | NT |
| Example 423 | NT | NT | NT |
| Example 424 | NT | NT | NT |
| Example 425 | NT | NT | NT |
| Example 426 | NT | NT | NT |
| Example 427 | | Example not included | |
| Example 428 | >10 | +++ | A |
| Example 429 | >10 | +++ | A |
| Example 430 | >10 | +++ | A |
| Example 431 | >10 | +++ | NT |
| Example 432 | >10 | +++ | A |
| Example 433 | >10 | +++ | A |
| Example 434 | >10 | +++ | NT |
| Example 435 | >10 | +++ | NT |
| Example 436 | >10 | +++ | NT |
| Example 437 | >10 | +++ | NT |
| Example 438 | | Example not included | |
| Example 439 | NT | NT | NT |
| Example 440 | >10 | +++ | NT |
| Example 441 | NT | NT | NT |
| Example 442 | NT | NT | NT |
| Example 443 | NT | NT | NT |
| Example 444 | >10 | +++ | B |
| Example 445 | NT | NT | NT |
| Example 446 | NT | NT | NT |
| Example 447 | NT | NT | NT |
| Example 448 | NT | NT | NT |
| Example 449 | NT | NT | NT |
| Example 450 | NT | NT | NT |
| Example 451 | NT | NT | NT |
| Example 452 | NT | NT | NT |
| Example 453 | NT | NT | NT |
| Example 454 | NT | NT | NT |
| Example 455 | NT | NT | NT |
| Example 456 | NT | NT | NT |

In Table 1, "+++" represents an EC$_{50}$<1 μM; "++" represents 1 μM<EC$_{50}$<10 μM; "+" represents EC$_{50}$<100 μM (Cell activity assay), NT=inactive/no data In Table 1, "A" represents an IC$_{50}$<5 μM; "B" represents 5 μM<IC$_{50}$<10 μM; "C" represents IC$_{50}$<100 μM (Assembly assay activity), NT=inactive/no data

The invention claimed is:

1. A compound of Formula I

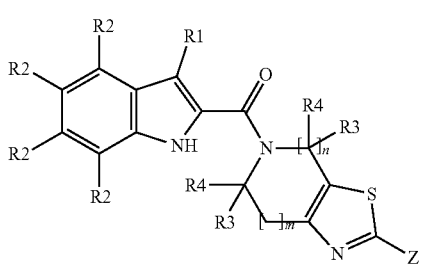

in which

Z is H, D, O(R5), $CH_3$, C≡N, Cl, C(=O)$NH_2$, N(R5)(R6), N(R5)C(=O)(R6), NHC(=O)N(R5)(R6), N(R5)$SO_2$(R6), NHC(=O)C(=O)O(R5), NHC(=O)C(=O)N(R5)(R6), NHC(=O)NH$SO_2$R5, $CH_2$—N(R5)(R6), or heteroaryl R1 is H, D, F, Cl, Br, or $NH_2$ R2 is for each position independently selected from the group consisting of H, $CF_2H$, $CF_3$, $CF_2CH_3$, F, Cl, Br, $CH_3$, Et, i-Pr, c-Pr, D, $CH_2OH$, $CH(CH_3)OH$, $CH_2F$, C(F)$CH_3$, I, C=C, C≡C, C≡N, $C(CH_3)_2OH$, $Si(CH_3)_3$, SMe, OH, and $OCH_3$ R3 and R4 are for each position independently selected from the group consisting of H, methyl and ethyl R3 and R4 are optionally connected to form a C3-C5-cycloalkyl ring R5 and R6 are independently selected from the group consisting of H, D, C1-C6-alkyl, C3-C6-cycloalkyl, C4-C7-heterocycloalkyl, C2-C6-aminoalkyl, and C2-C6-hydroxyalkyl, optionally substituted with 1, 2, or 3 groups each independently selected from the group consisting of OH, halo, C≡N, acyl, SO$_2$Me, carboxy, carboxyl ester, carbamoyl, substituted carbamoyl, C6-aryl, heteroaryl, C1-C6-alkyl, C3-C6-cycloalkyl, C3-C7-heterocycloalkyl, C3-C7-heterocycloalkyl substituted with acyl or carboxyl ester, C1-C6-haloalkyl, C1-C6-alkoxy, C1-C6-alkyl-O-C1-C6-alkyl, C1-C6-hydroxyalkyl, C1-C6-alkylamino and C2-C6-alkenyloxy R5 and R6 are optionally connected to form a C4-C7-heterocyclic ring containing 1 or 2 nitrogen or oxygen atoms, optionally substituted with 1, 2, or 3 groups each independently selected from the group consisting of OH, halo, acyl, SO$_2$Me, carboxy, carboxyl ester, carbamoyl, substituted carbamoyl, C6-aryl, heteroaryl, C1-C6-alkyl, C3-C6-cycloalkyl, C3-C7-heterocycloalkyl, C1-C6-haloalkyl, C1-C6-alkoxy, C1-C6-hydroxyalkyl, and C2-C6-alkenyloxy n is 1 or 2 m is 0 or 1 with the proviso that when Z is NHC(═O)N(R5)(R6), neither R5, nor R6 is cyclopentyl or isopropyl, and when Z is N(R5)C(═O)(R6) and R5 is H, R6 is not unsubstituted cyclopropyl, unsubstituted cyclobutyl, CH$_3$, or tetrahydrofuranyl, or a pharmaceutically acceptable salt, solvate or prodrug thereof.

2. The compound of Formula I according to claim 1 that is a compound of Formula II

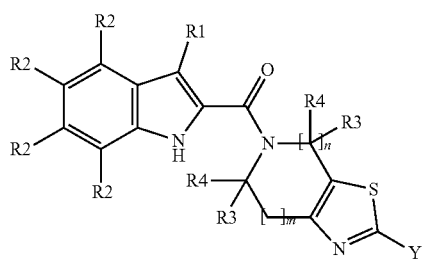

II in which

Y is N(R5)SO$_2$(R6), N(R5)(R6), or N(R5)C(═O)(R6)

R1 is H

R2 is for each position independently selected from the group consisting of H, CF$_2$H, CF$_3$, CF$_2$CH$_3$, F, Cl, Br, CH$_3$, Et, and i-Pr R3 and R4 are for each position independently selected from the group consisting of H and methyl R5 and R6 are independently selected from the group consisting of H, D, C1-C6-alkyl, C3-C6-cycloalkyl, C4-C7-heterocycloalkyl, C2-C6-aminoalkyl, and C2-C6-hydroxyalkyl, optionally substituted with 1, 2, or 3 groups each independently selected from the group consisting of OH, halo, acyl, SO$_2$Me, carboxy, carboxyl ester, carbamoyl, substituted carbamoyl, C6-aryl, heteroaryl, C1-C6-alkyl, C3-C6-cycloalkyl, C3-C7-heterocycloalkyl, C3-C7-heterocycloalkyl substituted with acyl or carboxyl ester, C1-C6-haloalkyl, C1-C6-alkoxy, C1-C6-alkyl-O-C1-C6-alkyl, C1-C6-hydroxyalkyl, and C2-C6-alkenyloxy R5 and R6 are optionally connected to form a C4-C7-heterocyclic ring containing 1 or 2 nitrogen or oxygen atoms, optionally substituted with 1, 2, or 3 groups each independently selected from the group consisting of OH, halo, acyl, SO$_2$Me, carboxy, carboxyl ester, carbamoyl, substituted carbamoyl, C6-aryl, heteroaryl, C1-C6-alkyl, C3-C6-cycloalkyl, C3-C7-heterocycloalkyl, C1-C6-haloalkyl, C1-C6-alkoxy, C1-C6-hydroxyalkyl, and C2-C6-alkenyloxy n is 1 or 2 m is 0 or 1 with the proviso that when Y is N(R5)C(═O)(R6) and R5 is H, R6 is not unsubstituted cyclopropyl, unsubstituted cyclobutyl, CH$_3$, or tetrahydrofuranyl, or a pharmaceutically acceptable salt, solvate or prodrug thereof.

3. The compound of Formula I according to claim 1 that is a compound of Formula III

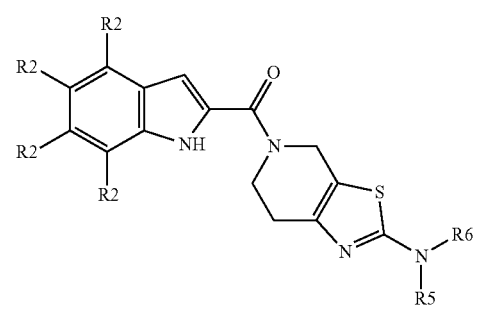

III in which

R2 is for each position independently selected from the group consisting of H, CF$_2$H, CF$_3$, CF$_2$CH$_3$, F, Cl, Br, CH$_3$, Et, and i-Pr R5 and R6 are independently selected from the group consisting of H, D, C1-C6-alkyl, C3-C6-cycloalkyl, C4-C7-heterocycloalkyl, C2-C6-aminoalkyl, and C2-C6-hydroxyalkyl, optionally substituted with 1, 2, or 3 groups each independently selected from the group consisting of OH, halo, acyl, SO$_2$Me, carboxy, carboxyl ester, carbamoyl, substituted carbamoyl, C6-aryl, heteroaryl, C1-C6-alkyl, C3-C6-cycloalkyl, C3-C7-heterocycloalkyl, C3-C7-heterocycloalkyl substituted with acyl or carboxyl ester, C1-C6-haloalkyl, C1-C6-alkoxy, C1-C6-alkyl-O-C1-C6-alkyl, C1-C6-hydroxyalkyl, and C2-C6-alkenyloxy or a pharmaceutically acceptable salt, solvate or prodrug thereof.

4. The compound of Formula I according to claim 1 that is a compound of Formula IVa or IVb

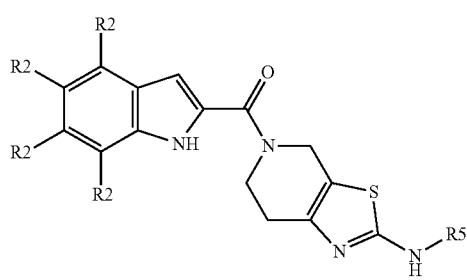

IVa

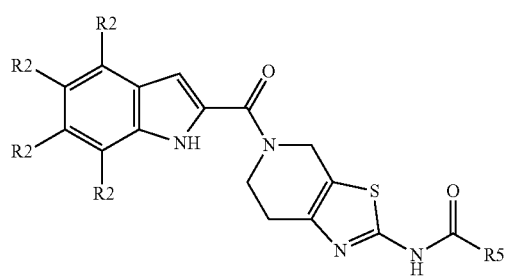

IVb in which

R2 is for each position independently selected from the group consisting of H, CH₂F, CF₂H, CF₃, C(F)CH₃, CF₂CH₃, F, Cl, Br, CH₃, and Et R5 is selected from the group consisting of H, D, C1-C6-alkyl, C3-C6-cycloalkyl, C4-C7-heterocycloalkyl, C2-C6-aminoalkyl, and C2-C6-hydroxyalkyl, optionally substituted with 1, 2, or 3 groups each independently selected from the group consisting of OH, halo, acyl, SO₂Me, carboxy, carboxyl ester, carbamoyl, substituted carbamoyl, C6-aryl, heteroaryl, C1-C6-alkyl, C3-C6-cycloalkyl, C3-C7-heterocycloalkyl, C1-C6-haloalkyl, C1-C6-alkoxy, C1-C6-hydroxyalkyl, and C2-C6-alkenyloxy, with the proviso that when the said compound is a compound of Formula IVb, R5 is not unsubstituted cyclopropyl, unsubstituted cyclobutyl, CH₃, or tetrahydrofuranyl, or a pharmaceutically acceptable salt, solvate or prodrug thereof.

5. A method for the treatment of an HBV infection in a subject, comprising administering to the subject a therapeutically effective amount of a compound according to claim 1 or a pharmaceutically acceptable salt, solvate or prodrug thereof.

6. A pharmaceutical composition comprising a compound according to claim 1 or a pharmaceutically acceptable salt, solvate or prodrug thereof together with a pharmaceutically acceptable carrier.

7. A method of treating an HBV infection in an individual in need thereof, comprising administering to the individual a therapeutically effective amount of a compound according to claim 1 or a pharmaceutically acceptable salt thereof.

8. A method for the preparation of a compound of Formula I according to claim 1

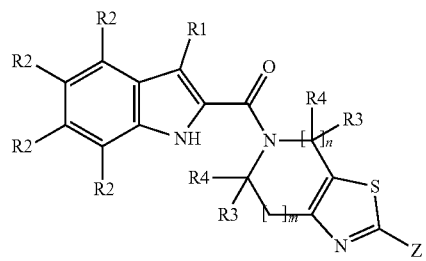

I comprising reacting a compound of Formula V

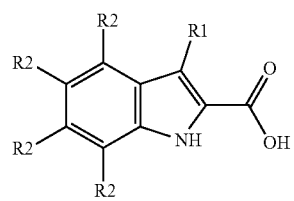

V in which R1 and R2 are as defined for the compound of formula I, with a compound of Formula VI

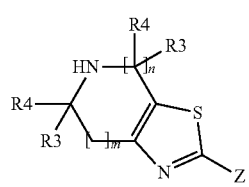

VI in which n, m, Z, R3 and R4 are as defined for the compound of formula I.

9. The compound of Formula I according to claim 1 that is a compound of Formula IVa or IVb

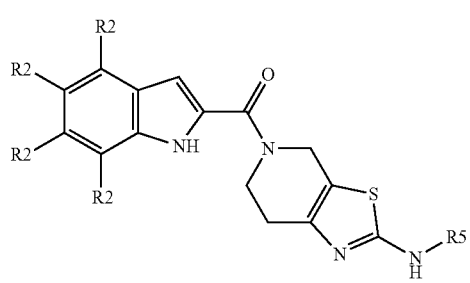

IVa

-continued

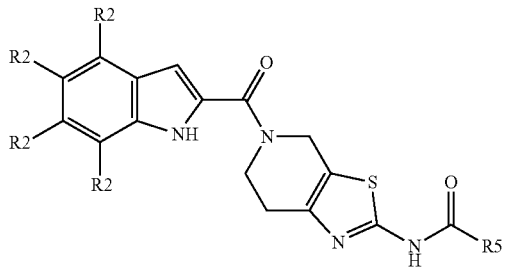

IVb in which
R2 is for each position independently selected from the group consisting of H, $CH_2F$, $CF_2H$, $CF_3$, $C(F)CH_3$, $CF_2CH_3$, F, Cl, Br, $CH_3$, and Et R5 is selected from the group consisting of C1-C6-alkyl, C3-C6-cycloalkyl, C4-C7-heterocycloalkyl and C2-C6-hydroxyalkyl optionally substituted with OH, C1-C6-alkoxy, C1-C6-hydroxylalkyl or C3-C7-heterocycloalkyl with the proviso that
when the said compound is a compound of Formula IVb, R5 is not unsubstituted cyclopropyl, unsubstituted cyclobutyl, $CH_3$, or tetrahydrofuranyl,
or a pharmaceutically acceptable salt, solvate or prodrug thereof.

10. The compound of Formula I according to claim 1 or a pharmaceutically acceptable salt thereof.

11. The compound of Formula I according to claim 2 that is a compound of Formula II or a pharmaceutically acceptable salt thereof.

12. The compound of Formula I according to claim 3 that is a compound of Formula III or a pharmaceutically acceptable salt thereof.

13. The compound of Formula I according to claim 4 that is a compound of Formula IVa or a pharmaceutically acceptable salt thereof.

14. The compound of Formula I according to claim 4 that is a compound of Formula IVb or a pharmaceutically acceptable salt thereof.

15. The compound of Formula I according to claim 9 that is a compound of Formula IVa or a pharmaceutically acceptable salt thereof.

16. The compound of Formula I according to claim 9 that is a compound of Formula IVb or a pharmaceutically acceptable salt thereof.

17. A pharmaceutical composition comprising a compound according to claim 1 or a pharmaceutically acceptable salt thereof together with a pharmaceutically acceptable carrier.

18. A method of treating an HBV infection in an individual in need thereof, comprising administering to the individual a therapeutically effective amount of a compound according to claim 2 or a pharmaceutically acceptable salt thereof.

19. A method of treating an HBV infection in an individual in need thereof, comprising administering to the individual a therapeutically effective amount of a compound according to claim 3 or a pharmaceutically acceptable salt thereof.

20. A method of treating an HBV infection in an individual in need thereof, comprising administering to the individual a therapeutically effective amount of a compound according to claim 4 or a pharmaceutically acceptable salt thereof.

* * * * *